United States Patent
Hunter et al.

(10) Patent No.: US 7,241,736 B2
(45) Date of Patent: Jul. 10, 2007

(54) COMPOSITIONS AND METHODS FOR TREATING DIVERTICULAR DISEASE

(75) Inventors: William L Hunter, Vancouver (CA); Philip M Toleikis, Vancouver (CA); David M Gravett, Vancouver (CA); Rui Avelar, Vancouver (CA); Dechi Guan, Vancouver (CA)

(73) Assignee: Angiotech International AG, Zug (CH)

( * ) Notice: Subject to any disclaimer, the term of this patent is extended or adjusted under 35 U.S.C. 154(b) by 0 days.

(21) Appl. No.: 11/129,763

(22) Filed: May 12, 2005

(65) Prior Publication Data

US 2005/0277577 A1     Dec. 15, 2005

Related U.S. Application Data

(63) Continuation-in-part of application No. 10/986,230, filed on Nov. 10, 2004.

(60) Provisional application No. 60/586,861, filed on Jul. 9, 2004, provisional application No. 60/578,471, filed on Jun. 9, 2004, provisional application No. 60/523,908, filed on Nov. 20, 2003, provisional application No. 60/524,023, filed on Nov. 20, 2003, provisional application No. 60/518,785, filed on Nov. 10, 2003.

(51) Int. Cl.
*A61K 38/00* (2006.01)
*A61K 38/17* (2006.01)
*C12P 21/02* (2006.01)

(52) U.S. Cl. ................ 514/2; 530/353; 435/69.5
(58) Field of Classification Search ............. 514/2; 600/114, 140; 530/353
See application file for complete search history.

(56) References Cited

U.S. PATENT DOCUMENTS

| | | | |
|---|---|---|---|
| 5,290,552 A | 3/1994 | Sierra et al. | 424/94.64 |
| 5,614,587 A | 3/1997 | Rhee et al. | 525/54.1 |
| 5,693,341 A | 12/1997 | Schroeder et al. | 424/488 |
| 5,752,974 A | 5/1998 | Rhee et al. | 606/214 |
| 5,874,500 A | 2/1999 | Rhee et al. | 525/54.1 |
| 6,096,309 A | 8/2000 | Prior et al. | 424/94.63 |
| 6,149,581 A * | 11/2000 | Klingenstein | 600/114 |
| 6,310,036 B1 | 10/2001 | Browdie | 514/2 |
| 6,312,725 B1 | 11/2001 | Wallace et al. | 424/484 |
| 6,458,147 B1 | 10/2002 | Cruise et al. | 606/214 |

(Continued)

FOREIGN PATENT DOCUMENTS

GB    2 326 344 A    12/1998

(Continued)

OTHER PUBLICATIONS

Robbs, J.V. 1977 Surgery, Gynecology & Obstetrics 145(2): abstract.*

(Continued)

*Primary Examiner*—Maryam Monshipouri
*Assistant Examiner*—Marsha Tsay
(74) *Attorney, Agent, or Firm*—Seed IP Law Group PLLC

(57) ABSTRACT

Agents, compositions, and implants are provided herein for treating diverticular disease (e.g., diverticulosis and diverticulitis). In particular, fibrosis-inducing agents, hemostatic agents, and/or anti-infective agents, or compositions containing one or more of these agents are provided for use in methods for treating diverticular disease.

26 Claims, 15 Drawing Sheets

Cyclosporin A activates proliferation of human smooth muscle cells.

U.S. PATENT DOCUMENTS

| | | | |
|---|---|---|---|
| 6,495,127 B1 | 12/2002 | Wallace et al. | 424/78.03 |
| 2003/0104026 A1 | 6/2003 | Wironen et al. | 424/422 |
| 2003/0124197 A1 | 7/2003 | Signore et al. | 424/499 |
| 2004/0043052 A1 | 3/2004 | Hunter et al. | 424/426 |
| 2004/0219214 A1 | 11/2004 | Gravett et al. | 424/484 |
| 2004/0225077 A1 | 11/2004 | Gravett et al. | 525/418 |

FOREIGN PATENT DOCUMENTS

| | | |
|---|---|---|
| WO | WO 97/22372 A1 | 6/1997 |
| WO | WO 98/57586 A1 | 12/1998 |
| WO | WO 00/50016 A2 | 8/2000 |
| WO | WO 01/78754 A2 | 10/2001 |
| WO | WO 02/15913 A1 | 2/2002 |
| WO | WO 2004/060424 A2 | 7/2004 |

OTHER PUBLICATIONS

Capon, A. and Mordon, S., "Can Thermal Lasers Promote Skin Wound Healing?" *Am. J. Clin. Dermatol.*, 4(1):1-12, 2003.

Lehmann, J. and King, C. R., "Wire or coated balloon? Searching for an optimal source for intravascular brachtherapy with β emitters using $^{32}$P as an example," *Journal of Applied Clinical Medical Physics*, 4(1):58-65, Winter 2003.

Nath, R. and Yue, N., "Effects of off-centering on dose uniformity along and around blood vessels undergoing catheter-based intravascular brachytherapy," *Cardiovascular Radiation Medicine*, 5(2):88-96, Apr.-Jun. 2004.

Qureshi, A. I. et al., "Endovascular treatment of intracranial aneurysms by using Guglielmi detachable coils in awake patients: safety and feasibility," *Neurosurg. Focus*, 10(5):880-885, Preview of J. Neurosurg., pp. 1-6, May 2001.

Reddy, G. K., "Photobiological Basis and Clinical Role of Low-Intensity Lasers in Biology and Medicine," *Journal of Clinical Laser Medicine & Surgery*, 22(2):141-150, Apr. 2004.

Rodemann, H. P. and Bamberg, M., "Cellular basis of radiation-induced fibrosis," *Radiotherapy and Oncology*, 35:83-90, 1995.

Vladimirov, Y. A. et al., "Photobiological Principles of Therapeutic Applications of Laser Radiation," *Biochemistry* (Moscow), 69(1):81-90, Jan. 2004, Translated from Biokhimiya, 69(1):103-113, 2004.

von Neumann-Cosel, P., "Electron capture radioactive sources for intravascular brachytherapy: a feasibility study," *Physics in Medicine and Biology*, 48(12):1855-1862, Jun. 21, 2003.

Yue, N. et al., "Effects of vessel curvature on dose distributions in catheter-based intravascular brachytherapy for various radionuclides," *Cardiovascular Radiation Medicine*, 5(3):142-150, Jul.-Sep. 2004.

"Catheter-Directed Cryoablation: An Emerging Therapy Cardiac Dysrhythmias," *Medcompare—Cardiovascular Technology Spotlight*, URL: http://www.medcompare.com/spotlight.asp?spotlightid=13, downloaded on May 5, 2005.

"Rf Ablation" *Boston Scientific*, URL: http://www.bostonscientific.com/common_templates/procedureOverview.jsp?task=tskProc, downloaded on May 5, 2005.

Stollman, N. and Raskin, J. B., "Diverticular disease of the colon," *The Lancet*, 363:631-639, Feb. 21, 2004.

* cited by examiner

Cyclosporin A activates proliferation of human smooth muscle cells.

COMPOSITIONS AND METHODS FOR TREATING DIVERTICULAR DISEASE

CROSS REFERENCE TO RELATED APPLICATIONS

This application is a continuation-in-part of U.S. patent application Ser. No. 10/986,230 filed Nov. 10, 2004, which claims the benefit of U.S. Provisional Application Nos. 60/518,785 filed Nov. 10, 2003; 60/523,908 filed Nov. 20, 2003; 60/524,023 filed Nov. 20, 2003; 60/578,471 filed Jun. 9, 2004, and 60/586,861 filed Jul. 9, 2004, which applications are incorporated herein by reference in their entireties.

BACKGROUND OF THE INVENTION

1. Field of the Invention

The present invention relates generally to pharmaceutical compositions, methods and implants, and more specifically, to compositions, implants, and methods for treating diverticular disease (e.g., diverticulitis).

2. Description of the Related Art

Diverticular disease is a condition whereby there is herniation of the mucosa and submucosa of a hollow organ, such as the gastrointestinal (GI) tract, urinary tract, or repiratory tract, which produces outpouchings through the muscular wall of the body passageway. Although diverticula can occur in any tubular organ, diverticular disease is of greatest clinical relevance in the lower GI tract (large bowel or colon), where it can cause life threatening inflammation and infection (diverticulitis) or bleeding (lower GI hemorrhage). Typically this condition is treated medically or through open surgical removal of the diverticula and/or complete resection of the segment of the bowel that contains them.

Diverticular disease (which encompasses diseases such as diverticulosis and diverticulitis) is an important medical condition and is the most common cause of large bleeds in the colon, accounting for 30% to 50% of massive GI hemorrhage. Diverticular disease results when a small pouch (referred to as a diverticulum) in the colon bulges outward through weak spot. About 10% of Americans over the age 40 have diverticulosis (i.e., the condition of having diverticula), and the condition becomes more common as people age (33% of the population over the age of 60 and 50% of people over 80 have diverticular disease). In many patients, diverticulosis remains asymptomatic. However, in about 10–25% of people with diverticulosis, the pouches become infected or inflamed. This condition, referred to as diverticulitis, can cause abdominal pain (in particular around the left side of the lower abdomen), peritonitis, abscess formation, and lower GI bleeding. Perhaps the most serious consequence of diverticular disease is lower intestinal hemorrhage (blood passed via the rectum). As many as 15% to 40% of diverticulosis patients experience an episode of bleeding, and 25% of those patients will have a recurrent bleeding episode. After a second hemorrhage, the chance of a third bleed is approximately 50%. The combined mortality and significant morbidity rate associated with diverticular hemorrhage is 10% to 20%, in part due to patient age and comorbidity with other conditions such as cardiac, pulmonary, or renal dysfunction.

Generally, diverticular bleeds are massive, painless, and self limiting. In 5% of diverticular patients, however, the bleed is substantial enough to cause cardiovascular instability and may require transfusion. Treatment of diverticular disease generally involves resuscitation, which includes large bore intravenous access, placement of a foley catheter, placement of a nasogastric tube to rule out upper gastrointestinal bleed, and administration of intravenous fluids. Patients are most frequently treated supportively with volume resuscitation, correction of coagulation abnormatlities and blood transfusion, if required. Most active lower GI bleeds will stop spontaneously. However, 18% to 25% of patients with diverticular bleed will become hemodynamically unstable as a result of the hemorrhage and continue to be unstable despite aggressive resuscitation. In cases of massive or severe bleeding, urgent surgery (e.g., segmented colectomy, blind segment resection, abdominal colectomy, total abdominal colectomy, and subtotal colectomy) may be required to attempt to stop the bleeding.

Although several pharmacological approaches for treating diverticulitis are described (see, e.g., U.S. Pat. Nos. 4,837,229; 6,297,214; 6,114,304; and 4,455,305), none have proven to be particularly effective. For example, hemodynamically stable, actively bleeding patients can be treated with vasospastic substances such as vasopressin. Risks associated with vasospastic substances include a re-bleed rate of 50% in patients after withdrawl of the medication, decreased coronary perfusion, hypertension, and cardiac arrythmias. Alternately, embolization (clogging the arteries that supply the bleeding bowel segment with small, locally injected particles) can sometimes stop the bleeding but is associated with colon infarctions and is preferably reserved only for patients who present a poor surgical risk.

Currently no reliable way exists to acutely treat diverticulitis, other than supportive measures, or urgent surgery in severe cases. Even for patients in whom symptoms spontaneously resolve (i.e., bleeding ceases), currently no reliable nonsurgical interventions can be employed to prevent recurrent bleeding. Also, many patients who would benefit from surgical resection of their diverticula are often not surgical candidates because of age, frailty as a result of blood loss, or other concurrent medical conditions. Therefore, a significant unmet medical need remains to develop nonsurgical, minimally invasive interventions that can eliminate diverticula and the morbidity and mortality associated with them.

BRIEF SUMMARY OF THE INVENTION

Briefly stated, the present invention provides agents, implants, compositions, and methods, for minimally invasive delivery of selected therapeutic, fibrosis-inducing agents, implants, and compositions directly into diverticula for the treatment of patients with diverticular disease. Compositions and implants, including devices, are provided herein for delivery of selected therapeutic agents into diverticula, as well as methods for making and using these agents, compositions, and implants. In certain embodiments, therapeutic agents or drug-impregnated implants (or biomaterials) are provided that induce adhesion or fibrosis in the walls of the diverticula or facilitate "filling" of the diverticula in situ; thus obliterating the lumen of the diverticula and relieving symptoms or reducing the risk that subsequent complications will develop. Within various embodiments, fibrosis is induced within the diverticula by local (intraluminal) or regional release of specific pharmacological agents delivered to the site via endoscopy or catheter-based interventions.

In one aspect, the present invention provides a composition comprising (a) a fibrosing agent and (b) a polymer or a compound that forms a crosslinked polymer in situ.

In another aspect, the present invention provides a composition comprising a composition comprising a fibrosing agent and a bulking agent.

In another aspect, the present invention provides a method for treating a diverticular disease that comprises introducing into a diverticulum in a host, a therapeutically effective amount of a fibrosing agent or a composition comprising a fibrosing agent, wherein the fibrosing agent induces a fibrotic response within the diverticulum, thereby treating diverticular disease in the host.

In another related aspect, the present invention provides a method for inducing fibrosis in a diverticulum of a host in need thereof that comprises introducing a composition into the diverticulum of the host, said composition comprising a fibrosing agent, wherein the agent induces fibrosis within the diverticulum.

In another aspect, the present invention provides a method for treating a diverticular disease that comprises introducing into a diverticulum in a host a composition, said composition comprising (a) fibrosing agent and (b) a polymer or a compound that forms a crosslinked polymer in situ, wherein the compostion induces a fibrotic response within the diverticulum, thereby treating diverticular disease in the host.

In another related aspect, the present invention provides a method for inducing fibrosis in a diverticulum of a host, comprising inserting a composition into the host, said composition comprising (a) a fibrosing agent and (b) a polymer or a compound that forms a crosslinked polymer in situ, wherein the composition induces fibrosis in the host.

In another aspect, the present invention provides a method for making an implant comprising combining (a) a fibrosing agent; (b) a polymer, or a composition comprising a polymer; and (c) an anti-infective agent, wherein the fibrosing agent induces a fibrotic response within a diveriticulum.

In another aspect, the present invention provides a kit for use in treating a diverticular disease, comprising: (a) a dry powder composition that comprises (i) a first component having a core substituted with m nucleophilic groups, where $m \geq 2$; and (ii) a second component having a core substituted with n electrophilic groups, where $n \geq 2$ and $m+n>4$; wherein the nucleophilic and electrophilic groups are non-reactive in a dry environment but are rendered reactive upon exposure to an aqueous environment such that the componenets inter-react in the aqueous environment to form a three-dimensional composition; (b) a first buffer solution having a pH within the range of about 1.0 to 5.5; and (c) a second buffer solution having a pH within the range of about 6.0 to 11.0; and (d) a third component comprising a fibrosing agent, wherein each component is packaged separately and admixed immediately prior to use.

In each of the above-mentioned aspects, the fibrosing agent may be one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, polylysine, fibronectin, bleomycin or an analogue or derivative thereof, a fibrosing agent that connective tissue growth factor (CTGF), metallic beryllium or an oxide thereof, copper, saracin, silica, crystalline silicates, quartz dust, talcum powder, ethanol, a component of extracellular matrix, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, poly(alkylcyanoacrylate), activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, an inhibitor of matrix metalloproteinase, a tissue inhibitor of matrix metalloproteinase, methotrexate, carbon tetrachloride, and thioacetamide. Additional fibrosing agents may also be used in the present invention are also disclosed in the detailed description below.

In each of the above-mentioned aspect, one or more of the following polymer may be used alone (as a fibrosing agent) or in combination with each of the fibrosing agents listed above or otherwise described herein: a copolymer, a block copolymer, a random copolymer, a biodegradable polymer, a non-biodegradable polymer, a hydrophilic polymer, a hydrophobic polymer, a polymer having hydrophilic domains, a polymer having hydrophobic domains, a non-conductive polymer, an elastomer, a hydrogel, a silicone polymer, a hydrocarbon polymer, a styrene-derived polymer, a butadiene-derived polymer, a macromer, a poly(ethylene glycol), a collagen or a derivative thereof, a methylated collagen, a combination of a collagen or a derivative thereof and a fibrinogen, a combination of a collagen or a derivative thereof and a thrombin, a combination of (a) a collagen or a derivative thereof; (b) a fibrinogen; and (c) a thrombin, a combination of a methylated collagen and a poly(ethylene glycol) or a derivative thereof, CT3, COSTASIS, a poly(ethylene glycol), COSEAL, TISSEAL, FLOSEAL, fibrin, an amorphous polymer, a cyanoacrylate, methyl cyanoacrylate, ethyl cyanoacrylate, butyl cyanoacrylate, octyl cyanoacrylate, methoxypropyl cyanoacrylate, a poly(alkylcyanoacrylate), poly(methylcyanoacrylate), poly(ethylcyanoacrylate), poly(butylcyanoacrylate), poly(isobutylcyanoacrylate), poly(hexylcyanoacrylate), poly(octylcyanoacrylate), a poly(carboxyalkylcyanoacrylate), poly(methoxypropylcyanoacrylate), a crosslinked polymer, a polymer reacts with mammalian tissue, a naturally occurring polymer, a protein, a carbohydrate, a both crosslinked and biodegradable polymer, a nonbiodegradable polymer, a methylated collagen, fibrinogen, thrombin, albumin, plasminogen, von Willebrands factor, Factor VIII, hypoallergenic collagen, atelopeptidic collagen, telopeptide collagen, crosslinked collagen, aprotinin, Gelatin, a protein conjugate, a gelatin conjugate, hyaluronic acid, a hyaluronic acid derivative, a synthetic polymer, a polymer formed from reactants comprising a synthetic isocyanate-containing compound, a synthetic isocyanate-containing compound, a polymer formed from reactants comprising a synthetic thiol-containing compound, a synthetic thiol-containing compound, a polymer formed from reactants comprising a synthetic compound containing at least two thiol groups, a synthetic compound containing at least two thiol groups, a polymer formed from reactants comprising a synthetic compound containing at least three thiol groups, a synthetic compound containing at least three thiol groups, a polymer formed from reactants comprising a synthetic compound containing at least four thiol groups, a synthetic compound containing at least four thiol groups, a polymer formed from reactants comprising a synthetic amino-containing compound, a synthetic amino-containing compound, a polymer formed from reactants comprising a synthetic compound containing at least two amino groups, a synthetic compound containing at least two amino groups, a polymer formed from reactants comprising a synthetic compound containing at least three amino groups, a synthetic compound containing at least three amino groups, a polymer formed from reactants comprising a synthetic compound containing at least four amino groups, a synthetic compound containing at least four amino groups, a polymer formed from reactants comprising a synthetic compound comprising a carbonyl-oxygen-succinimidyl group, a synthetic compound comprising a carbonyl-oxygen-succinimidyl group, a polymer formed from reactants comprising a synthetic compound comprising at least two carbonyl-oxygen-succinimidyl groups, a synthetic compound comprising at least two carbonyl-oxygen-succinimidyl groups, a polymer formed from reactants comprising a synthetic compound comprising at least three carbonyl-oxygen-succinimidyl groups, a synthetic compound comprising at least three carbonyl-oxygen-succinimidyl groups, a polymer formed from reactants comprising a synthetic compound comprising at least four carbonyl-oxygen-succinimidyl groups, a synthetic compound comprising at least four carbonyl-oxygen-succinimidyl groups, a polymer formed from reactants comprising a synthetic polyalkylene oxide-containing compound, a synthetic polyalkylene oxide-containing compound, a polymer formed from reactants comprising a synthetic compound comprising both polyalkylene oxide and biodegradable polyester blocks, a synthetic compound comprising both polyalkylene oxide and biodegradable polyester blocks, a polymer formed from reactants comprising a synthetic polyalkylene oxide-containing compound having reactive amino groups, a synthetic polyalkylene oxide-containing compound having reactive amino groups, a polymer formed from reactants comprising a synthetic polyalkylene oxide-containing compound having reactive thiol groups, a synthetic polyalkylene oxide-containing compound having reactive thiol groups, a polymer formed from reactants comprising a synthetic polyalkylene oxide-containing compound having reactive carbonyl-oxygen-succinimidyl groups, a synthetic polyalkylene oxide-containing compound having reactive carbonyl-oxygen-succinimidyl groups, a polymer formed from reactants comprising a synthetic compound comprising a biodegradable polyester block, a synthetic compound comprising a biodegradable polyester block, a polymer formed from reactants comprising a synthetic polymer formed in whole or part from lactic acid or lactideA synthetic polymer formed in whole or part from lactic acid or lactide, a polymer formed from reactants comprising a synthetic polymer formed in whole or part from glycolic acid or glycolide, a synthetic polymer formed in whole or part from glycolic acid or glycolide, a polymer formed from reactants comprising polylysine, Polylysine, a polymer formed from reactants comprising (a) protein and (b) a compound comprising a polyalkylene oxide portion, a polymer formed from reactants comprising (a) protein and (b) polylysine, a polymer formed from reactants comprising (a) protein and (b) a compound having at least four thiol groups, a polymer formed from reactants comprising (a) protein and (b) a compound having at least four amino groups, a polymer formed from reactants comprising (a) protein and (b) a compound having at least four carbonyl-oxygen-succinimide groups, a polymer formed from reactants comprising (a) protein and (b) a compound having a biodegradable region formed from reactants selected from lactic acid, lactide, glycolic acid, glycolide, and epsilon-caprolactone, a polymer formed from reactants comprising (a) collagen and (b) a compound comprising a polyalkylene oxide portion, a polymer formed from reactants comprising (a) collagen and (b) polylysine, a polymer formed from reactants comprising (a) collagen and (b) a compound having at least four thiol groups, a polymer formed from reactants comprising (a) collagen and (b) a compound having at least four amino groups, a polymer formed from reactants comprising (a) collagen and (b) a compound having at least four carbonyl-oxygen-succinimide groups, a polymer formed from reactants comprising (a) collagen and (b) a compound having a biodegradable region formed from reactants selected from lactic acid, lactide, glycolic acid, glycolide, and epsilon-caprolactone, a polymer formed from reactants comprising (a) methylated collagen and (b) a compound comprising a polyalkylene oxide portion, a polymer formed from reactants comprising (a) methylated collagen and (b) polylysine, a polymer formed from reactants comprising (a) methylated collagen and (b) a compound having at least four thiol groups, a polymer formed from reactants comprising (a) methylated collagen and (b) a compound having at least four amino groups, a polymer formed from reactants comprising (a) methylated collagen and (b) a compound having at least four carbonyl-oxygen-succinimide groups, a polymer formed from reactants comprising (a) methylated collagen and (b) a compound having a biodegradable region formed from reactants selected from lactic acid, lactide, glycolic acid, glycolide, and epsilon-caprolactone, a polymer formed from reactants comprising hyaluronic acid, a polymer formed from reactants comprising a hyaluronic acid derivative, a polymer formed from reactants comprising pentaerythritol poly(ethylene glycol) ether tetra-sulfhydryl of number average molecular weight between 3,000 and 30,000, Pentaerythritol poly(ethylene glycol)ether tetra-sulfhydryl of number average molecular weight between 3,000 and 30,000; a polymer formed from reactants comprising pentaerythritol poly(ethylene glycol) ether tetra-amino of number average molecular weight between 3,000 and 30,000; pentaerythritol poly(ethylene glycol)ether tetra-amino of number average molecular weight between 3,000 and 30,000; a polymer formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups; a mixture of (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups. Additional polymers that may be used in the present invention are also disclosed in the detailed description below.

In each of the above-mentioned aspect, one or more of the following anti-infective agents may be used alone (if capable of functioning as a fibrosing agent), with each of the fibrosing agents listed above (or otherwise described herein), with each of the polymers listed above (or otherwise described herein), or with each of the combination of the fibrosing agents listed above (or otherwise described herein) and the polymers listed above (or otherwise described herein): an anthracycline, doxorubicin, mitoxantrone, a fluoropyrimidine, 5-fluorouracil (5-FU), a folic acid antagonist, methotrexate, a podophylotoxin, etoposide, camptothecin, a hydroxyurea, a platinum complex, cisplatin, an antibiotic, doxycycline, metronidazole, trimethoprim-sulfamethoxazole, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), a quinolone (e.g., ciprofloxacin, ofloxacin, gatifloxacin, moxifloxacin, levofloxacin, and trovafloxacin), a DNA synthesis inhibitor (e.g., metronidazole), and a sulfonamide (e.g. trimethoprim, including cefixime, spectinomycin, tetracycline, nitrofurantoin, polymyxin B, and neomycin sulfate).

In each of the above-mentioned aspect, one or more of the following bulking agents may be used alone (if capable of functioning as a fibrosing agent), with each of the fibrosing agents listed above (or otherwise described herein), with each of the polymers listed above (or otherwise described herein), with each of the combination of the fibrosing agents listed above (or otherwise described herein) and the polymers listed above (or otherwise described herein), with each of the combination of the polymers listed above (or otherwise described herein) and the anti-infective agents listed above (or otherwise described herein), with each of the combination of the fibrosing agents listed above (or otherwise described herein) and the anti-infective agents listed above (or otherwise described herein): an agent or a composition that comprises microspheres, an agent or a composition that comprises a hydroxyapatite loaded gel, an agent or a composition that comprises a micronized alloderm acellular matrix, an agent or a composition that comprises hyaluronic acid, an agent or a composition that comprises micro-beads in a hydrogel, an agent or a composition that comprises a hylan polymer, and an agent or a composition that comprises a silicon microballoon and biocompatible polymer. Additional bulking agents that may be used in the present invention are described in the detailed description below.

One aspect of the invention relates to a homogeneous dry powder composition comprised of: a first component having a core substituted with m nucleophilic groups, where m=2; and a second component having a core substituted with n electrophilic groups, where n=2 and m+n>4; wherein the nucleophilic and electrophilic groups are non-reactive in a dry environment but are rendered reactive upon exposure to an aqueous environment such that the components interreact in the aqueous environment to form a three-dimensional matrix. A pharmaceutically acceptable carrier may also be included.

In one embodiment of the homogeneous dry powder composition, the nucleophilic and electrophilic groups undergo a nucleophilic substitution reaction, a nucleophilic addition reaction, or both. The nucleophilic groups may be selected from —NH$_2$, —NHR$^1$, —N(R$^1$)$_2$, —SH, —OH, —COOH, —C$_6$H$_4$—OH, —H, —PH$_2$, —PHR$^1$, —P(R$^1$)$_2$, —NH—NH$_2$, —CO—NH—NH$_2$, and —C$_5$H$_4$N, where R$^1$ is a hydrocarbyl group, and each R$^1$ may be the same or different. The electrophilic groups may be selected from —CO—Cl, —(CO)—O—(CO)—R (where R is an alkyl group), —CH=CH—CH=O and —CH=CH—C(CH$_3$)=O, halo, —N=C=O, —N=C=S, —SO$_2$CH=CH$_2$, —O(CO)—C=CH$_2$, —O(CO)—C(CH$_3$)=CH$_2$, —S—S—(C$_5$H$_4$N), —O(CO)—C(CH$_2$CH$_3$)=CH$_2$, —CH=CH—C=NH, —COOH, —(CO)O—N(COCH$_2$)$_2$, —CHO, —(CO)O—N(COCH$_2$)$_2$—S(O)$_2$OH, and —N(COCH)$_2$.

In another embodiment of the homogeneous dry powder composition, the nucleophilic groups are amino groups and the electrophilic groups are amine-reactive groups. The amine-reactive groups may contain an electrophilically reactive carbonyl group susceptible to nucleophilic attack by a primary or secondary amine. The amine-reactive groups may be selected from carboxylic acid esters, acid chloride groups, anhydrides, ketones, aldehydes, halo, isocyanato, thioisocyanato, epoxides, activated hydroxyl groups, olefins, carboxyl, succinimidyl ester, sulfosuccinimidyl ester, maleimido, epoxy, and ethenesulfonyl.

In yet another embodiment of the homogeneous dry powder composition, the nucleophilic groups are sulfhydryl groups and the electrophilic groups are sulfhydryl-reactive groups. The sulfhydryl-reactive groups may be selected so as to form a thioester, imido-thioester, thioether, or disulfide linkage upon reaction with the sulfhydryl groups. Where the sulfhydryl-reactive groups form a disulfide linkage, they may have the structure —S—S—Ar where Ar is a substituted or unsubstituted nitrogen-containing heteroaromatic moiety or a non-heterocyclic aromatic group substituted with an electron-withdrawing moiety. Where the sulfhydryl-reactive groups form a thioether linkage, they may be selected from maleimido, substituted maleimido, haloalkyl, epoxy, imino, aziridino, olefins, and a,β-unsaturated aldehydes and ketones. The sulfhydryl-reactive groups may be selected from mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates.

In still another embodiment of the homogeneous dry powder composition, the number of nucleophilic groups in the mixture is approximately equal to the number of electrophilic groups in the mixture. For example, the ratio of moles of nucleophilic groups to moles of electrophilic groups may be about 2:1 to 1:2, with a ratio of 1:1 preferred.

In a further embodiment of the homogeneous dry powder composition, the core is selected from hydrophilic polymers, hydrophobic polymers, amphiphilic polymers, C$_{2-14}$ hydrocarbyls, and heteroatom-containing C$_{2-14}$ hydrocarbyls.

Where the core is a hydrophilic polymer, the core may be a synthetic or naturally occurring hydrophilic polymer. The hydrophilic polymer may be a linear, branched, dendrimeric, hyperbranched, or star polymer. The hydrophilic polymer may be selected from polyalkylene oxides; polyols; poly(oxyalkylene)-substituted diols and polyols; polyoxyethylated sorbitol; polyoxyethylated glucose; poly(acrylic acids) and analogs and copolymers thereof; polymaleic acids; polyacrylamides; poly(olefinic alcohols); poly(N-vinyl lactams); polyoxazolines; polyvinylamines; and copolymers thereof. The hydrophilic polymer may also be selected from proteins, carboxylated polysaccharides, aminated polysaccharides, and activated polysaccharides, such as, for example, collagen and glycosaminoglycans.

Where the hydrophilic polymer is a polyalkylene oxide or polyols, the hydrophilic polymer may be selected from polyethylene glycol and poly(ethylene oxide)-poly(propylene oxide) copolymers. Where the hydrophilic polymer is a polyols, the hydrophilic polymer may be selected from glycerol, polyglycerol and propylene glycol. Where the hydrophilic polymer is a poly(oxyalkylene)-substituted polyol, the hydrophilic polymer may be selected from mono-, di- and tri-polyoxyethylated glycerol, mono- and di-polyoxyethylated propylene glycol, and mono- and di-polyoxyethylated trimethylene glycol. Where the hydrophilic polymer is a poly(acrylic acid), analog or copolymer thereof, the hydrophilic polymer may be selected from poly(acrylic acid), poly(methacrylic acid), poly(hydroxyethylmethacrylate), poly(hydroxyethylacrylate), poly(methylalkylsulfoxide acrylates), and poly(methylalkylsulfoxide methacrylates). Where the hydrophilic polymer is a polyacrylamide, the hydrophilic polymer may be selected from polyacrylamide, poly(methacrylamide), poly(dimethylacrylamide), poly(N-isopropylacrylamide), and copolymers thereof. Where the hydrophilic polymer is a poly(olefinic alcohol), the hydrophilic polymer may be selected from poly(vinyl alcohols) and copolymers thereof. Where the hydrophilic polymer is a poly(N-vinyl lactam), the hydrophilic polymer may be selected from poly(vinyl pyrrolidones), poly(vinyl caprolactams), and copolymers thereof. Where the hydrophilic polymer is a polyoxazoline, the hydrophilic polymer may be selected from poly(methyloxazoline) and poly(ethyloxazoline).

Where the core is a hydrophobic polymer selected, the core may be selected from polylactic acid and polyglycolic acid.

Where the core is a $C_{2-14}$ hydrocarbyl, the core may be selected from alkanes, diols, polyols, and polyacids.

Where the core is a heteroatom-containing $C_{2-14}$ hydrocarbyl, the core may be selected from di- and poly-electrophiles.

In another embodiment of the homogeneous dry powder composition, the first component has the structure of formula (I)

$$[X—(L^1)_p]_m—R, \qquad (I)$$

and the second component has the structure of formula (II)

$$[Y—(L^2)_q]_n—R', \qquad (II)$$

wherein m and n are integers from 2–12 and m+n>4; R and R' are independently selected from hydrophilic polymers, hydrophobic polymers, amphiphilic polymers, $C_{2-14}$ hydrocarbyls, and heteroatom-containing $C_{2-14}$ hydrocarbyls; X is a nucleophilic group; Y is an electrophilic group; $L^1$ and $L^2$ are linking groups; and p and q are integers from 0–1. The components may inter-react to form covalent bonds, noncovalent bonds, or both. Noncovalent bonds include ionic bonds, hydrogen bonds, or the association of hydrophobic molecular segments. In one preferred embodiment, all of the molecular segments are the same.

The homogeneous dry powder composition may further comprise a biologically active agent with or without a pharmaceutically acceptable carrier. The pharmaceutically acceptable carrier may be a micelle, a microsphere, or a nanosphere.

Where the pharmaceutically acceptable carrier is a microsphere or a nanosphere, the pharmaceutically acceptable carrier may be a degradable polymer, such as a polyester, and the polyester may be a glycolide/lactide copolymer. The degradable polymer may also be comprised of residues of one or more monomers selected from the group consisting of lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2one.).

The homogeneous dry powder composition may further comprise a biologically active agent. In one embodiment, the biologically active agent is a fibrosing agent or a composition comprising a fibrosis agent. In certain specific embodiments, the fibrosing agent is in another embodiment of the invention, the homogeneous dry powder composition further comprises a biologically active agent that is a fibrosing agent. As used in the homogeneous dry powder composition, the anti-fibrotic agent may be used to promote any of the following: regeneration; angiogenesis; fibroblast migration; fibroblast proliferation; deposition of extracellular matrix (ECM); and tissue remodeling. The fibrosing agent may also be used as a diverticular wall irritant.

Fibrosing agents that may be used in the homogeneous dry powder composition may be or may be comprised of silk; silkworm silk; spider silk; recombinant silk; raw silk; hydrolyzed silk; acid-treated silk; acylated silk; mineral particles; talc; chitosan; polylysine; fibronectin; bleomycin; or CTGF. The fibrosing agent may also be in the form of a particulate, which may be a biodegradable particulate or a non-biodegradable particulate. Biodegradable particulates may be comprised of a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester. Non-biodegradable particulates may be comprised of a material selected from the group consisting of polyester, polyurethane, silicone, polyethylene, polypropylene, polystyrene, polyacrylate, polymethacrylate, and silk. Examples of preferred particulates may be a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

In a further embodiment of the homogeneous dry powder composition, the biologically active agent promotes bone growth. Within this embodiment, the fibrosing agent may promote the bone growth. Fibrosing agents that may promote bone growth may include a bone morphogenic protein and an osteogenic growth factor, the latter which may be selected from transforming growth factor, platelet-derived growth factor, and fibroblast growth factor.

In another embodiment of the invention, the homogeneous dry powder composition with a fibrosing agent further comprises a pharmaceutical agent that induces sclerosis (a sclerosant), wherein the sclerosant may be a surfactant or it may be selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol.

In a further embodiment of the invention, the homogeneous dry powder composition with a fibrosing agent further comprises an inflammatory cytokine, which may be selected from the group consisting of TGFβ, PDGF, VEGF, bFGF, TNFα, NGF, GM-CSF, IGF-a, IL-1, IL-1-β, IL-8, IL-6, and growth hormone.

In still another embodiment of the invention, the homogeneous dry powder composition with a fibrosing agent further comprises an agent that stimulates cell proliferation, which may be selected from the group consisting of dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

In a further embodiment of the homogeneous dry powder composition, the biologically active agent is mixed with the first and second components to form a mixture.

In another embodiment of the homogeneous dry powder composition, the biologically active agent is chemically coupled to the first component or to the second component.

Another aspect of the invention relates to a crosslinkable composition comprised of: (a) a first crosslinkable component having m nucleophilic groups, wherein $m=2$; and (b) a second crosslinkable component having n electrophilic groups capable of reaction with the m nucleophilic groups to form covalent bonds, wherein $n=2$ and $m+n=5$, the first component comprises two or more amino acid residues selected from the group consisting of amino acids comprising primary amine groups and amino acids comprising thiol groups, the second component comprises a polyethylene glycol moiety, and each of the first and second crosslinkable components is biocompatible, synthetic, and nonimmunogenic, and further wherein crosslinking of the composition results in a biocompatible, nonimmunogenic, crosslinked matrix.

Any of the following are preferred embodiments of the crosslinkable composition described immediately above: $m>3$, $m=3$, $m=4$, $n=4$, the electrophilic groups are succinimidyl moieties, all n are identical, and all m are identical.

In one preferred embodiment, the selected amino acid residues are lysine. Within this embodiment, any of the following is preferred: $m>3$, $m=3$, $m=4$, $n=4$, the electrophilic groups are succinimidyl moieties, all n are identical, and all m are identical.

In another preferred embodiment, the selected amino acid residues are cysteine. Within this embodiment, any of the following is preferred: $m>3$, $m=3$, $m=4$, $n=4$, the electrophilic groups are succinimidyl moieties, all n are identical, and all m are identical.

Yet another aspect of the invention relates to a crosslinkable composition comprised of: (a) a first crosslinkable component having m nucleophilic groups, wherein $m=2$; and (b) a second crosslinkable component having n electrophilic groups capable of reaction with the m nucleophilic groups to form covalent bonds, wherein $n=2$ and $m+n=5$, the first component comprises two or more amino acid residues selected from the group consisting of amino acids comprising primary amine groups and amino acids comprising thiol groups, the second component comprises a polyethylene glycol moiety, the electrophilic groups are succinimidyl moieties, and each of the first and second crosslinkable components is biocompatible, synthetic, and nonimmunogenic, and further whererin crosslinking of the composition results in a biocompatible, nonimmunogenic, crosslinked matrix.

Any of the following are preferred embodiments of the crosslinkable composition described immediately above: $m>3$, $m=3$, $m=4$, $n=4$, the electrophilic groups are succinimidyl moieties, all n are identical, and all m are identical.

In one preferred embodiment, the selected amino acid residues are lysine. Within this embodiment, any of the following is preferred: $m>3$, $m=3$, $m=4$, $n=4$, the electrophilic groups are succinimidyl moieties, all n are identical, and all m are identical.

In another preferred embodiment, the selected amino acid residues are cysteine. Within this embodiment, any of the following is preferred: $m>3$, $m=3$, $m=4$, $n=4$, the electrophilic groups are succinimidyl moieties, all n are identical, and all m are identical.

Still another aspect of the invention relates to a crosslinkable composition comprised of: (a) a first crosslinkable component having m nucleophilic groups, wherein $m=2$; and (b) a second crosslinkable component having n electrophilic groups capable of reaction with the m nucleophilic groups to form covalent bonds, wherein $n=2$ and $m+n=5$, the first component comprises two or more amino acid residues selected from the group consisting of amino acids comprising primary amine groups and amino acids comprising thiol groups, the second component comprises a multifunctionally activated polyethylene glycol, and each of the first and second crosslinkable components is biocompatible, synthetic, and nonimmunogenic, and further wherein crosslinking of the composition results in a biocompatible, nonimmunogenic, crosslinked matrix.

Any of the following are preferred embodiments of the crosslinkable composition described immediately above: $m>3$, $m=3$, $m=4$, $n=4$, the electrophilic groups are succinimidyl moieties, all n are identical, all m are identical, the multifunctionally activated polyethylene glycol is tetrafunctionally activated polyethylene glycol, and the multifunctionally activated polyethylene glycol is a star-branched polyethylene glycol.

In one preferred embodiment, the selected amino acid residues are lysine. Within this embodiment, any of the following is preferred: $m>3$, $m=3$, $m=4$, $n=4$, the electrophilic groups are succinimidyl moieties, all n are identical, all m are identical, and the multifunctionally activated polyethylene glycol is tetrafunctionally activated polyethylene glycol or the multifunctionally activated polyethylene glycol is a star-branched polyethylene glycol.

In another preferred embodiment, the selected amino acid residues are cysteine. Within this embodiment, any of the following is preferred: $m>3$, $m=3$, $m=4$, $n=4$, the electrophilic groups are succinimidyl moieties, all n are identical, all m are identical, and the multifunctionally activated polyethylene glycol is tetrafunctionally activated polyethylene glycol or the multifunctionally activated polyethylene glycol is a star-branched polyethylene glycol.

Another aspect of the invention relates to a method of forming a three-dimensional matrix comprising the steps of: (a) providing a composition of the invention; and (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution; and (c) allowing a three-dimensional matrix to form. A preferred composition for use in this method is the homogeneous dry powder composition. The three-dimensional matrix of the invention described immediately above may be formed without input of any external energy or by polymerization.

In a preferred embodiment, the pH of the first buffer solution is selected to retard the reactivity of the nucleophilic groups on the first component by rendering the nucleophilic groups relatively non-nucleophilic. In this preferred embodiment, the second buffer solution neutralizes the effect of the first buffer solution, so that the nucleophilic groups of the first component regain their nucleophilic character and inter-react with the electrophilic groups of the second component.

In another preferred embodiment, the composition, first buffer solution and second buffer solution are housed separately in a multiple-compartment syringe system having a multiple barrels, a mixing head, and an exit orifice; step (b)(i) comprises adding the first buffer solution to the barrel housing the composition to dissolve the composition and form a homogeneous solution, and extruding the homogeneous solution into the mixing head; step (b)(ii) comprises simultaneously extruding the second buffer solution into the mixing head; and step (c) further comprises extruding the resulting composition through the orifice onto a surface.

Yet another aspect of the invention relates to a method of sealing tissue of a patient comprising the steps of: (a) providing a composition of the invention; (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution to form a mixture; and (c) placing the mixture into contact with tissue and allowing a three-dimensional matrix to form and seal the tissue. A preferred composition for use in this method is the homogeneous dry powder composition.

A further aspect of the invention relates to a method of forming a three-dimensional matrix on a surface of a device comprising the steps of: (a) providing a composition of the invention; and (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution; and applying the homogeneous solution to a surface of a device; and allowing the three-dimensional matrix to form. A preferred composition for use in this method is the homogeneous dry powder composition.

Yet another aspect of the invention relates to a method of promoting scarring in the vicinity of a medical implant comprising the steps of: (a) providing a composition of the invention; (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution; and (c) applying the mixture to a surface of a medical implant and allowing a three-dimensional matrix to form on the surface of the medical implant; and (d) placing the medical implant into an animal host, wherein release of the fibrotic agent from the matrix inhibits scarring in the animal host. In a preferred embodiment, the the fibrotic agent is released into tissue in the vicinity of the implant after deployment of the implant.

A preferred composition for use in this method is the homogeneous dry powder composition with a fibrosing agent.

A further aspect of the invention relates to a kit for use in medical applications, comprising: (a) a homogeneous dry powder composition comprised of: (i) a first component having a core substituted with m nucleophilic groups, where m=2; and (ii) a second component having a core substituted with n electrophilic groups, where n=2 and m+n>4; wherein the nucleophilic and electrophilic groups are non-reactive in a dry environment but are rendered reactive upon exposure to an aqueous environment such that the components inter-react in the aqueous environment to form a three-dimensional matrix; (b) a first buffer solution having a pH within the range of about 1.0 to 5.5; and (c) a second buffer solution having a pH within the range of about 6.0 to 11.0; wherein each component is packaged separately and admixed immediately prior to use. It is preferred of course that prior to use, each component is in a separate sterile package.

Another aspect of the invention relates to a kit for use in medical applications, comprising: (a) a composition of the invention; (b) a first buffer solution having a pH within the range of about 1.0 to 5.5; and (c) a second buffer solution having a pH within the range of about 6.0 to 11.0, wherein each component is packaged separately and admixed immediately prior to use. A preferred composition of the invention for use in this kit is the homogeneous dry powder composition. It is preferred that each component of the kit is in a separate sterile package.

The kit may further comprise a delivery device, which in one embodiment, may be a multi-compartment device. A preferred multi-compartment device of the invention is a multiple-compartment syringe system having multiple barrels, a mixing head, and an exit orifice. Where the kit is a multiple-compartment syringe system, the homogeneous dry powder composition, the first buffer solution, and the second buffer solution are housed separately in the multiple-compartment syringe system.

In another embodiment of the invention, the delivery device is a pressurized delivery system. A preferred pressurized delivery system comprises: a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet. Within this embodiment, a preferred pressurized carrier fluid is pressurized air and the preferred fluid components are the first buffer solution and the second buffer solution of the invention.

Another embodiment of the kit for use in medical applications further comprises a biologically active agent and the medical application involves delivering the biologically active agent. The biologically active agent may be packaged with the homogeneous dry powder composition and may further comprise a pharmaceutically acceptable carrier packaged with the biologically active agent and the homogeneous dry powder composition. The biologically active agent may also be packaged as a solution with the first buffer or as a solution with the second buffer. The kit may further comprise a pharmaceutically acceptable carrier as a fourth component. The biologically active agent is packaged with the pharmaceutically acceptable carrier.

These and other aspects of the present invention will become evident upon reference to the following detailed description and the attached drawings. All references disclosed herein are hereby incorporated by reference in their entireties as if each was incorporated individually.

DETAILED DESCRIPTION OF THE INVENTION

Figure 1:
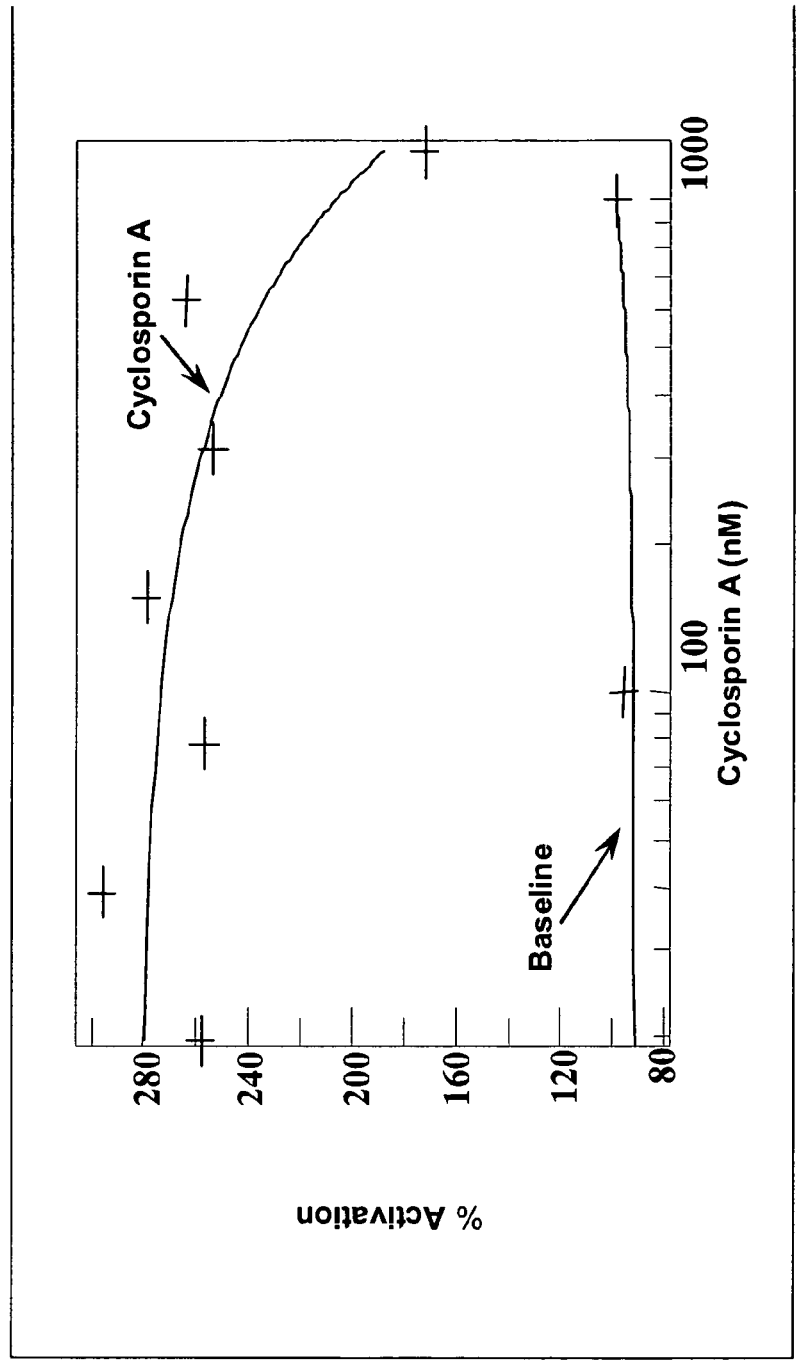
FIG. 1 is a graph showing the effect of cyclosporine A on proliferation of human smooth muscle cells.
Figure 2:
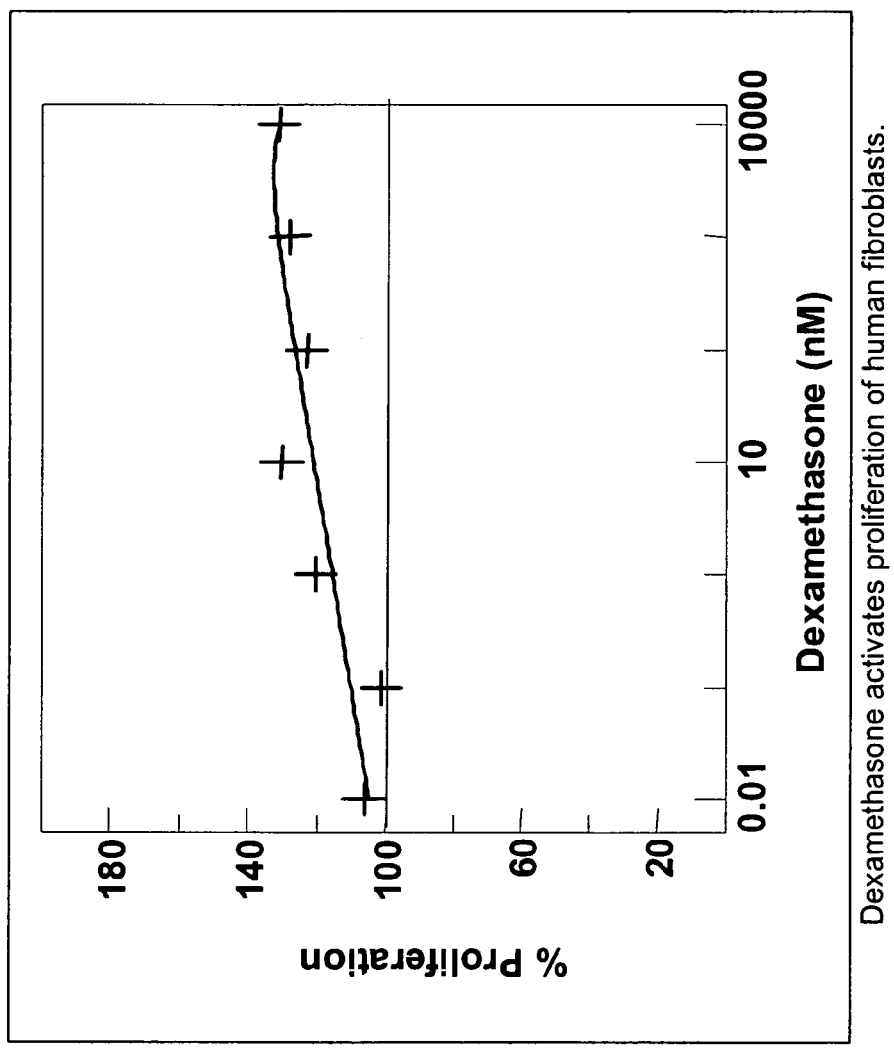
FIG. 2 is a graph showing the effect of dexamethasone on proliferation of human fibroblasts.
Figure 3:
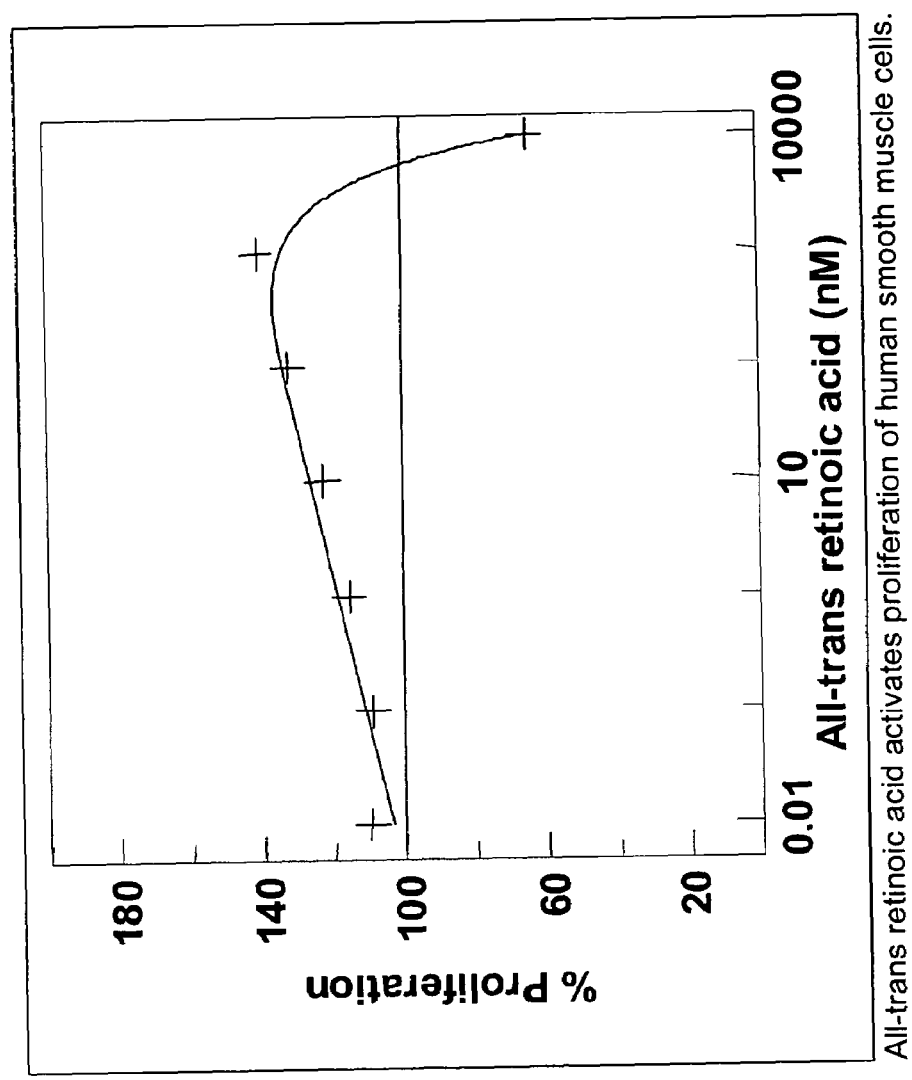
FIG. 3 is a graph showing the effect of all-trans retinoic acid (ATRA) on proliferation of human smooth muscle cells.
Figure 4:
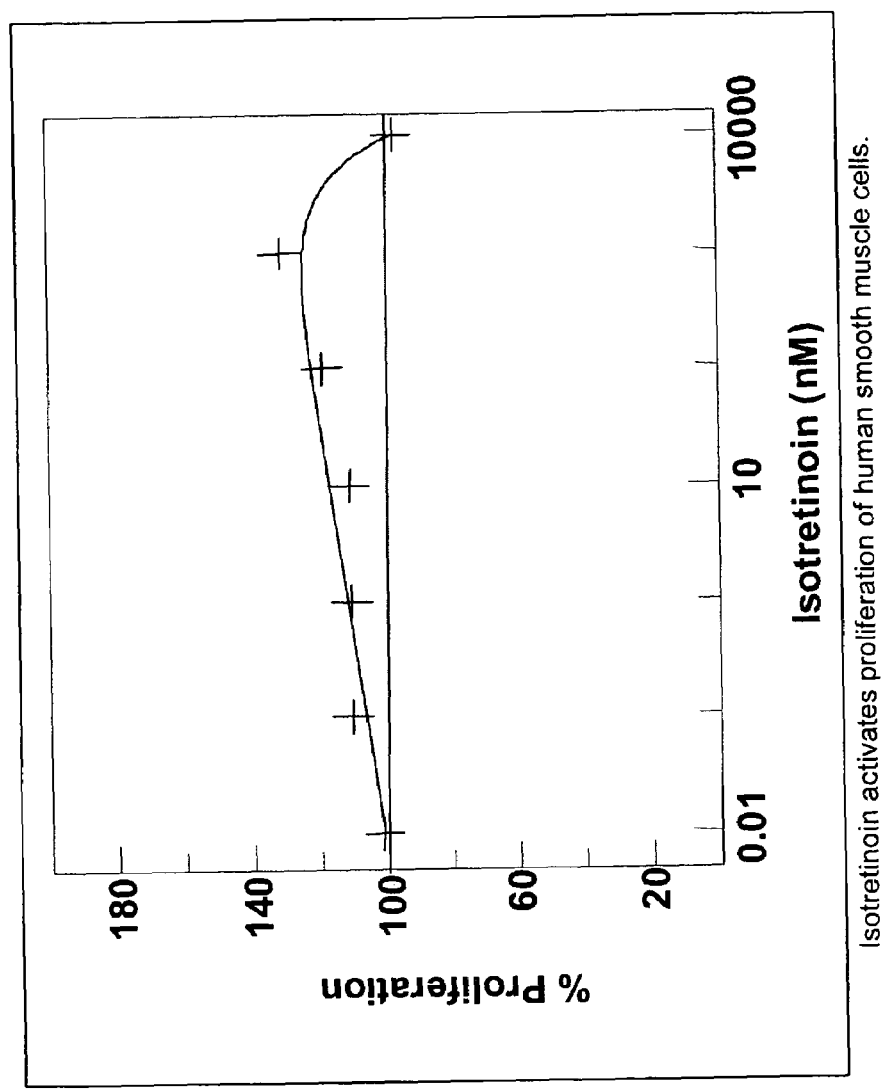
FIG. 4 is a graph showing the effect of isotretinoin on proliferation of human smooth muscle cells.
Figure 5:
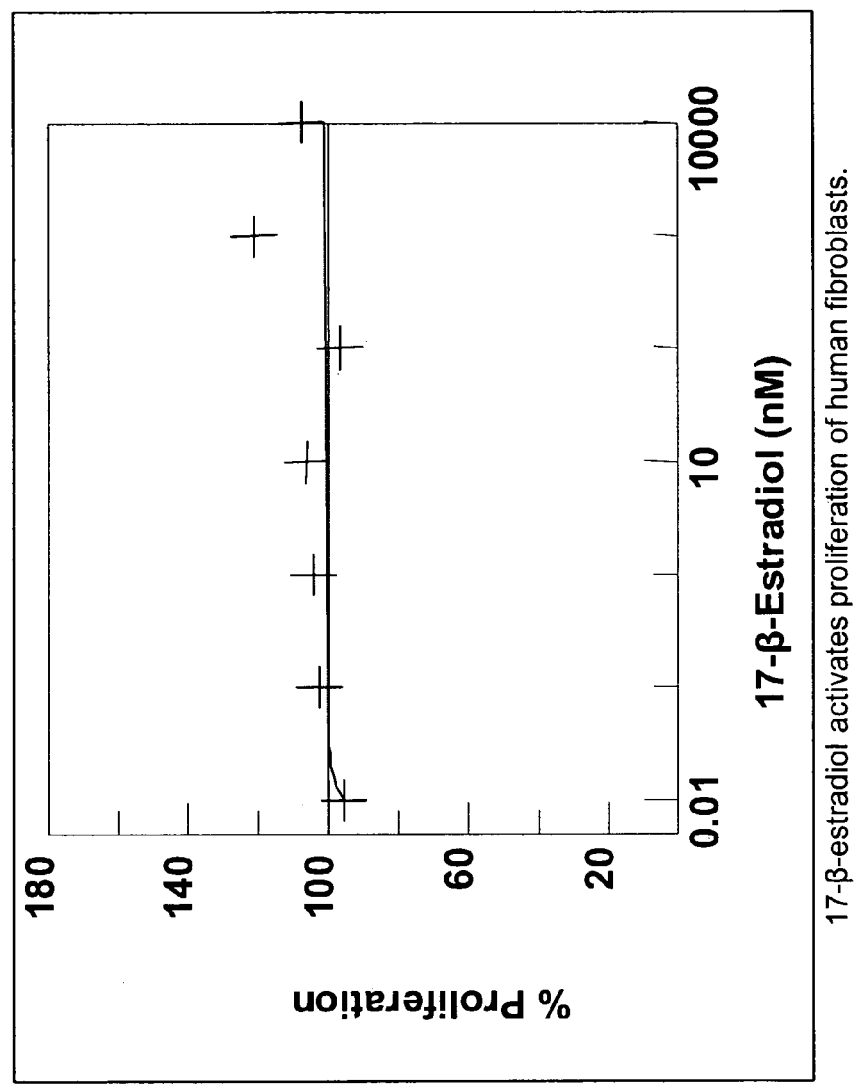
FIG. 5 is a graph showing the effect of 17-β-estradiol on proliferation of human fibroblasts.

The present invention provides minimally invasive, endoluminal, and endoscopic procedures that can be used to close, temporarily or permanently, diverticula through the administration of pharmacological compositions that induce scarring of the lumen of the diverticula and elimination of the diverticular sac.

As described herein, implants, procedures, and therapeutic compositions are provided for treatment of diverticula using endoscopic and imaging-guided interventions. For example, described herein are pharmaceutical agents that promote one or more aspects of the production of fibrous (scar) tissue or tissue regeneration. Furthermore, compositions and methods are described for administering fibrosis-inducing agents and drug-delivery compositions such that the pharmaceutical agent is delivered in therapeutic levels over a time period sufficient for fibrosis and healing to occur. Numerous specific implants are described that produce superior clinical outcomes by promotion of scarring and healing of diverticula.

Definitions

Prior to setting forth the invention, it may be helpful to an understanding thereof to first set forth definitions of certain terms that are used hereinafter.

"Medical implant" refers to a device or object or composition that is implanted (completely or partially) or inserted into a body. Accordingly, an implant refers to any object or composition placed in the body for the purpose of restoring physiological function, reducing/alleviating symptoms associated with disease, and/or repairing/replacing damaged or diseased organs and tissues.

"Diverticulitis" refers to diseases such as diverticulosis and diverticulitis. Diverticular disease results when a small pouch (referred to as a diverticulum) in the colon bulges outward through weak spot. The condition of having diverticula is called diverticulosis. When the pouches become infected or inflamed, the condition is called diverticulitis. Diverticulitis can cause abdominal pain, in particular, around the left side of the lower abdomen, and lower GI bleeding. Often the site of the herniations is the same site of penetration for a nutrient artery, leading to the approximation of the neck of the sack and arterial supply.

"Fibrosis," "scarring," or "fibrotic response" refers to the formation of fibrous tissue in response to injury or medical intervention. Four general components to the process of fibrosis (or scarring) include (1) formation of new blood vessels (angiogenesis); (2) migration and proliferation of fibroblasts; (3) deposition of extracellular matrix (ECM); and (4) remodeling (maturation and organization of the fibrous tissue). Therapeutic agents which promote (also referred to interchangeably herein as induce, stimulate, cause, increase, accelerate, and the like) fibrosis or scarring are referred to interchangeably herein as "fibrosis-inducing agents," "scarring agents," "fibrosing agents," "adhesion-inducing agents," and the like. These agents promote fibrosis through one or more mechanisms including, for example, inducing or promoting angiogenesis, stimulating migration or proliferation of connective tissue cells (such as fibroblasts, smooth muscle cells, vascular smooth muscle cells), inducing extracellular matrix (ECM) production, and promoting tissue remodeling. In addition, numerous therapeutic agents described herein can have the additional benefit of promoting tissue regeneration (the replacement of injured cells by cells of the same type).

"Sclerosing" refers to a tissue reaction in which an irritant is applied locally to a tissue that results in an inflammatory reaction and is followed by scar tissue formation at the site of irritation. A pharmaceutical agent that induces or promotes sclerosis is referred to as a "sclerosant," or a "sclerosing agent." Representative examples of sclerosants include ethanol, dimethyl sulfoxide, surfactants (e.g., Triton X, sorbitan monolaurate, sorbitan sesquioleate, glycerol monostearate and polyoxyethylene, polyoxyethylene cetyl ether, etc.), sucrose, sodium chloride, dextrose, glycerin, minocycline, tetracycline, doxycycline, polidocanol, sodium tetradecyl sulfate, sodium morrhuate, ethanolamine, phenol, sarapin and sotradecol.

"Radiographic guidance" refers to the placement of a drug delivery cathether, medical device, implant, biomaterial, therapeutic agent, access port or device and the like using medical imaging for guidance and to confirm accurate placement. Imaging technology is used to allow manipulation and intervention in a minimally invasive fashion (i.e., so as not to require open surgery). Any imaging technology can be used depending on the tissue being treated, but includes, for example, x-ray, angiography, MRI, CT scanning, ultrasound, PET scanning, and nuclear medicine scanning.

"Endoscopic guidance" refers to the placement of a drug delivery cathether, medical device, implant, biomaterial, therapeutic agent, access port or device and the like using endoscopy for direct visualization of the target tissue for guidance and to confirm accurate placement. Endoscopes are used to allow direct visualization in a minimally invasive fashion (i.e., so as not to require open surgery) by inserting a small camera into the body via an orifice (mouth, anus) or a small incision. Any endoscopic technology can be used depending on the tissue being treated, but includes, for example, flexible endoscopes, rigid endoscopes, gastroscopes, ERCP, bronchoscopes, proctoscopes, angioscopes, and colonoscopes.

The terms "inter-react" and "inter-reaction" as used herein refer to the formation of covalent bonds, noncovalent bonds, or both. The term thus includes crosslinking, which involves both intermolecular crosslinks and optionally intramolecular crosslinks as well, arising from the formation of covalent bonds. Entanglement is another example of non-covalent bonding that may result after inter-reaction between two or more reactive groups. Covalent bonding between two reactive groups may be direct in which case an atom in reactive group is directly bound to an atom in the other reactive group or it may be indirect through a linking group. Noncovalent bonds include ionic (electrostatic) bonds, hydrogen bonds, or the association of hydrophobic molecular segments, which may be the same or different. A crosslinked matrix may, in addition to covalent bonds, also include such intermolecular and/or intramolecular noncovalent bonds.

When referring to polymers, the terms "hydrophilic" and "hydrophobic" are generally defined in terms of an HLB value, i.e., a hydrophilic lipophilic balance. A high HLB value indicates a hydrophilic compound, while a low HLB value characterizes a hydrophobic compound. HLB values are well known in the art, and generally range from 1 to 18. Preferred multifunctional compound cores are hydrophilic, although as long as the multifunctional compound as a whole contains at least one hydrophilic component, crosslinkable hydrophobic components may also be present.

The term "effective amount" refers to the amount of an agent or composition that provides the effect desired. The actual amount that is determined to be an effective amount will vary depending on factors such as the size, general health and condition, sex and age of the patient and can be more readily determined by the caregiver. The term "in situ" as used herein means at the site of administration. Thus, agents and compositions described can be delivered, injected, or otherwise applied to a specific site within a patient's body, such as a diverticulum.

The term "aqueous medium" includes solutions, suspensions, dispersions, colloids, and the like containing water. The term "aqueous environment" means an environment containing an aqueous medium. Similarly, the term "dry environment" means an environment that does not contain an aqueous medium.

The terms "active agent," "biologically active agent," "therapeutic agent," "pharmacologically active agent," and "drug" are used interchangeably herein to refer to a chemical material or compound suitable for administration to a patient and that induces a desired effect. The terms include agents that are therapeutically effective as well as prophylactically effective. Also included are derivatives and analogs of those compounds or classes of compounds specifically mentioned that also induce the desired effect.

As discussed above, the present invention provides compositions, implants, and methods for treating diverticular disease. Described in more detail below are therapeutic agents; compositions and implants for delivering the therapeutic agents; and methods for treating diverticulitis using the agents and compositions discussed herein.

Therapeutic Agents

Numerous therapeutic agents (also referred to herein as 'therapeutic agents' or 'drugs') have been identified that can be used to induce scarring and closure of a diverticula. The agent may be formulated with one or more other materials, e.g., a polymeric carrier, which formulations are discussed below. Many suitable therapeutic agents are specifically identified herein, and others may be readily determined based upon in vitro and in vivo (animal) models such as those provided in the Examples. Therapeutic agents that promote fibrosis can be identified through in vivo models such as the rat carotid artery model. One or more therapeutic agents may be introduced into a host for treatment of diverticular disease. A host may be a mammal, which may be a human (such as a patient or subject in need of treatment or a non-human mammal. Exemplary non-human mammals include, but are not limited to, a non-human primate, a rodent (e.g., rat, mouse, rabbit, hamster), a cat, dog, horse, pig, bovine, sheep, or goat. A host in need of treatment is a host who has developed or is at risk for developing a diverticular disease.

Fibrosis-Inducing Agents

Within one embodiment of the invention, a fibrosis-inducing pharmacologic agent or an implant adapted to include or to release an agent that induces fibrosis is administered onto or into diverticula. Thus, in one embodiment, a medical implants is provided that comprises at least one of (i) a fibrosis-inducing agent (fibrosing agent) and (ii) a composition that comprises a fibrosis-inducing agent. When placed within diverticula, the fibrosing agent is capable of inducing fibrosis formation that would otherwise not occur. In another embodiment, methods are provided for inducing a fibrosis in a diverticulum and for treating a diverticular disease, wherein a fibrosis-inducing agent and/or an implant/composition that comprises a fibrosis-inducing agent, are placed into a host (e.g., a mammal) having diverticula.

As discussed in further detail herein, a therapeutic agent includes a fibrosis-inducing agent that is a diverticular wall irritant, for example, talcum powder, metallic beryllium and oxides thereof, copper, silk, coated silk sutures, uncoated silk sutures, virgin silk, degummed silk, saracin, silica, crystalline silicates, talc, quartz dust, and ethanol; a component of extracellular matrix; fibronectin, collagen, fibrin, or fibrinogen. A fibrosis-inducing agent may also be poly (ethylene terephthalate (Dacron), polylysine, poly(ethylene-co-vinylacetate), chitosan, N-carboxybutylchitosan, an RGD protein, or a polymer of vinyl chloride. Therapeutic agents include adhesives, such as cyanoacrylates and crosslinked poly(ethylene glycol)—methylated collagen and may also include an inflammatory cytokine (e.g., TGFβ, PDGF, VEGF, bFGF, TNFα, NGF, GM-CSF, IGF-a, IL-1, IL-8, IL-6, and growth hormone); connective tissue growth factor (CTGF); a bone morphogenic protein (BMP) (e.g., BMP-2, BMP-3, BMP-4, BMP-5, BMP-6, or BMP-7); and bleomycin or an analogue or derivative thereof. A fibrosis-inducing agent also includes a proliferative agent that stimulates cellular proliferation, for example, dexamethasone, isotretinoin, 17-β-estradiol, estradiol, diethylstibesterol, cyclosporine A, a/1-trans retinoic acid (ATRA), and analogues and derivatives thereof.

In one embodiment, the fibrosis or adhesion-inducing agent suitable for use in the treatment of diverticula is silk. Silk refers to a fibrous protein, and may be obtained from a number of sources, typically spiders and silkworms. Typical silks contain about 75% of actual fiber, referred to as fibroin, and about 35% sericin, which is a gummy protein that holds the filaments together. Silk filaments are generally very fine and long—as much as 300–900 meters long. There are several species of domesticated silkworm that are used in commercial silk production, however, *Bombyx mori* is the most common, and most silk comes from this source. Other suitable silkworms include *Philosamia cynthia ricini, Antheraea yamamai, Antheraea pernyi*, and *Antheraea mylitta*. Spider silk is relatively more difficult to obtain, however, recombinant techniques hold promise as a means to obtain spider silk at economical prices (see, e.g., U.S. Pat. Nos. 6,268,169; 5,994,099; 5,989,894; and 5,728,810, which are exemplary only). Biotechnology has allowed researchers to develop other sources for silk production, including animals (e.g., goats) and vegetables (e.g., potatoes). Silk from any of these sources may be used in the present invention.

A commercially available silk protein is available from Croda, Inc., of Parsippany, N.J., and is sold under the trade names CROSILK LIQUID (silk amino acids), CROSILK 10,000 (hydrolyzed silk), CROSILK POWDER (powdered silk), and CROSILKQUAT (cocodiammonium hydroxypropyl silk amino acid). Another example of a commercially available silk protein is SERICIN, available from Pentapharm, LTD, a division of Kordia, BV, of the Netherlands. Further details of such silk protein mixtures can be found in U.S. Pat. No. 4,906,460, to Kim, et al., assigned to Sorenco. Silk useful in the present invention includes natural (raw) silk, hydrolyzed silk, and modified silk, i.e., silk that has undergone a chemical, mechanical, or vapor treatment, e.g., acid treatment or acylation (see, e.g., U.S. Pat. No. 5,747, 015).

Raw silk is typically twisted into a strand sufficiently strong for weaving or knitting. Four different types of silk thread may be produced by this procedure: organzine, crepe, tram and thrown singles. Organzine is a thread made by giving the raw silk a preliminary twist in one direction and then twisting two of these threads together in the opposite direction. Crepe is similar to organzine but is twisted to a much greater extent. Twisting in only one direction two or more raw silk threads makes tram. Thrown singles are individual raw silk threads that are twisted in only one direction. Any of these types of silk threads may be used in the present invention.

The silk used in the present invention may be in any suitable form that allows the silk to be joined with the medical implant applied to the diverticula, for example, the silk may be in thread or powder-based forms. The silk can be prepared in the powdered form by several different methods. For example the silk can be milled (e.g., cryomill) into a powdered form. Alternatively the silk can be dissolved in a suitable solvent (e.g., HFIP or 9M LiBr) and then sprayed (electrospray, spray dry) or added to a non-solvent to produce a powder. Furthermore, the silk may have any molecular weight, where various molecular weights are typically obtained by the hydrolysis of natural silk, where the extent and harshness of the hydrolysis conditions determines the product molecular weight. For example, the silk may have an average (number or weight) molecular weight of about 200 to 5,000. See, e.g., JP-B-59-29199 (examined Japanese patent publication) for a description of conditions that may be used to hydrolyze silk.

A discussion of silk may be found in the following documents, which are exemplary only, Hinman, M. B., et al. "Synthetic spider silk: a modular fibre" *Trends in Biotechnology*, 2000, 18(9) 374–379; Vollrath, F. and Knight, D. P. "Liquid crystalline spinning of spider silk" *Nature*, 2001, 410(6828) 541–548; and Hayashi, C. Y., et al. "Hypotheses that correlate the sequence, structure, and mechanical properties of spider silk proteins" *Int. J. Biol. Macromolecules*, 1999, 24(2-3), 265–270; and U.S. Pat. No. 6,427,933.

The silk may be virgin silk, partially degummed, or degummed silk. The silk can also further comprise a coating. The coating may be a silicone-based coating, a wax based coating, or a degradable polymer based coating.

In another embodiment, the fibrosis-inducing agent is a fibroin protein, or a fragment or fragments thereof. In a certain embodiment, the fibroin protein may be a synthetic analogue that is made and that has one or more of the known repeat sequences of the fibroin protein.

In another embodiment, the fibrosing agent is sarecin. Sarecin is a component of virgin silk that can be used to assist in the induction of a fibrotic response.

Other representative examples of fibrosis and adhesion-inducing agents (fibrosing agents) suitable for administration to diverticula include irritants (e.g., talc, talcum powder, copper, metallic beryllium (or its oxides), wool (e.g., animal wool, wood wolol, and synthetic wool), cotton, quartz dust, silica, crystalline silicates), polymers (e.g., polylysine, polyurethanes, poly(ethylene terephthalate), polytetrafluoroethylene (PTFE), poly(alkylcyanoacrylates), and poly(ethylene-co-vinylacetate)); polymers of vinyl chloride; peptides with high lysine content; growth factors and inflammatory cytokines involved in angiogenesis, fibroblast migration, fibroblast proliferation, ECM synthesis and tissue remodeling, such as epidermal growth factor (EGF) family, transforming growth factor-α (TGF-α), transforming growth factor-β (TGF-β-1, TGF-β-2, TGF-β-3, platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor—PIGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNFα), nerve growth factor (NGF), interferon-α, interferon-β, histamine, endothelin-1, angiotensin II, growth hormone (GH), and synthetic peptides, analogues or derivatives of these factors are also suitable for release from specific implants described herein.

Other examples of fibrosing agents include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see, e.g., U.S. Pat. No. 5,997,895), and tissue adhesives, such as cyanoacrylate and crosslinked poly(ethylene glycol)-methylated collagen compositions, such as described below. Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) *Science:* 242 (4885); 1528–1534.

As described above, one fibrosis-inducing agent is a wool. The term "wool" refers to an entangled mass of fibers without any ordered arrangement, while the term "fiber" refers to a particle with a length to diameter ratio ("aspect ratio") of at least about 3:1 and roughly parallel edges.

Wool that may be used in the compositions and methods described herein induces an enhanced fibrotic response between the medical implant and the tissue adjacent to the in vivo medical implant. In other words, absent the wool, the medical implant would generate a "normal" adhesion between the adjacent tissue and the medical implant, while in the presence of the wool, the same medical implant is capable of generating an enhanced adhesion (e.g., via an enhanced matrix deposition response to the presence of the wool).

Wool useful as a fibrosis inducing agent may be obtained or prepared from natural sources (e.g., animal wool and wood wool). Alternatively, it may be artificially synthesized (e.g., polymeric wool and mineral wool).

"Animal wool" refers to animal hair fibers, typically derived from the fleece of sheep or lamb, goat (e.g., Angora and Cashmere), camel, alpaca, llama, vicuna, or the like. Animal wool is a dead tissue that has a complex morphological and chemical structure, which make it unique among textile fibers. Morphologically, wool fibers are biological composites, with each component having a different physical and chemical composition. Wool fibers are generally composed of three different types of spindle-shaped cortical cells surrounded by a sheath of overlapping, rectangular cell known as the cuticle, which forms the external layer of the fiber. Approximately 90% of the cortical cell type is made up of longitudinally arrayed intermediate filaments with accompanying matrix. The remainder includes membranes and remnants from the nucleus and cytoplasm.

Animal wool fibers exhibit a range of diameters, lengths, and crimp (i.e., a measure of fiber curvature), which allows the wool fibers to entrap air. Animal wool is also hygroscopic and is able to absorb and desorb large amounts of water as the relative humidity surrounding the fiber changes. Furthermore, animal wool liberates heat if it absorbs water. These properties contribute to animal wool's extraordinary insulating quality.

Animal wool belongs to a family of proteins called a-keratins, which also include materials such as hooves, horns, nails, claws, and beak. A characteristic feature of a-keratins (also referred to as "hard" keratins) is a higher concentration of sulfur than "soft" keratins, such as those in the skin. Clean animal wool contains about 82% keratinous proteins that are high in sulfur content, and about 17% of the fiber is protein with a relatively low sulfur content (<3%). The sulfur in wool occurs in the form of the amino acid cysteine. Due to the high cysteine content, animal wool is highly cross-linked by disulfide bonds that render it essentially insoluble. It is estimated that animal wool contains about 170 different types of polypeptides varying in relative molecular mass from below 10,000 to greater than 50,000. The groups of proteins that constitute animal wool are not uniformly distributed throughout the fiber but are aggregated within various regions. Animal wool also contains about 1% non-proteinaceous material that consists mainly of free and structural lipids and polysaccharide materials, trace elements, and pigments (e.g., melanin).

Animal wool is usually harvested from animals by annual shearing. Thus, the fiber length is determined largely by the rate of growth, which in turn depends on both genetic and environmental factors. For instance, typical merino fibers are 50–125 mm long and have irregular crimp (curvature). Animal wool fibers exhibit a range of diameters, which also depend on both genetics and environment. For example, coarse wool fibers generally have a diameter of 25–70 mm, while fine merino fibers typically have a diameter of 10–25 mm.

Another example of a naturally derived wool is wood wool, which is a specially prepared, non-compressed wood fiber frequently used in surgical dressings and packaging materials. Wood wool fibers also can be obtained from pine needles.

Although wool is usually associated with fibers derived from natural sources, a variety of synthetic wool is also available. Synthetic wool includes, for example, mineral wools, such as glass wool, stone wool, and slag wool, and wool made from polymeric materials. Mineral wool may be formed, for example, from a molten, inorganic material such as glass, stone, or slag that is spun into a fiber-like structure. Inorganic rock or slag is the main component (typically 98%) of stone wool. The remaining 2% organic content is generally a thermosetting resin binder (an adhesive) and a small amount of oil. Glass wool products usually contain about 95% inorganic material. Glass wool is made from sand or recycled glass, limestone, and soda ash, which are the same ingredients used for familiar glass objects such as window panes or glass bottles. Glass fiber may, additionally, include a small amount of boron. Stone wool can be made from volcanic rock, typically basalt or dolomite. Slag wool is made from blast furnace slag (waste).

A discussion of wool may be found in the following documents, which are exemplary only: *Encyclopedia of Polymer Science and Technology*, John Wiley & Sons, Inc. (2003); Dowling and Sparrow, TIBS 16:115–118 (1991); Powman, *J. Chromatogr. B* 787:63–76 (2003); Hearle, *Intl. J. Biol. Macromol.* 27:123–38 (2000); and Vuyst et al., *Eur. Resp. J.* 8:2149–73 (1995).

In certain embodiments, wool fibers have an average length of about, or at least about, 1, 2, 3, 4, 5, 6, 7, 8, 9, 10, 15, 20, 25, 30, 35, 40, 45, 50 mm or longer. In certain embodiments, the lengths of wool fibers are in a range of about 1–5 mm, 5–10 mm, 10–50 mm, 50–100 mm, 1–10 mm, 1–50 mm, or 1–100 mm. In certain embodiments, wool fibers have an average diameter of about, or at least about, 1, 2, 3, 4, 5, 6, 7, 8, 9, 10, 15, 20, 25, 30, 35, 40, 45, or 50 mm. In certain embodiments, the diameters of wool fibers are in a range of about 1–3 mm, 3–5 mm, 5–10 mm, 10–50 mm, 1–10 mm, or 1–50 mm. In certain embodiments, the average length to diameter ratio of wool fibers is 3:1, 4:1, 5:1, 6:1, 7:1, 8:1, 9:1, 10:1 or larger.

In certain embodiments, wool may be further processed into other forms or shapes, for example, sheet, powder, thread, braid, filament, fiber, film, foam, and the like. In certain embodiments, the wool is further processed into threads or powder. In certain other embodiments, the wool is further processed into the form of a spiral or coil.

Wool may be used alone or may be used in combination with a medical implant, such as described herein. In certain embodiments, wool may be used in combination with one or more of other fibrosis inducing agents described herein. Wool may be secured to a medical implant by any of a number of methods. Suitable methods include, without limitation, interweaving the wool into the implant, interweaving the wool into the implant structure; attaching the wool to the implant via knotting or suturing it around the implant structure; attaching the wool to the medical implant by means of an adhesive; and using one or more sutures to "sew" the wool onto the medical implant. In one aspect, a plurality of separated wool braids or threads is attached to the medical implant.

In one embodiment, the wool is secured only to the outside of the medical implant. In another embodiment, the wool is secured to distal regions of the medical implant. The wool may be attached to the implant portion of the medical implant, or it may be attached to the implant portion of the medical implant, or it may be attached to both the implant and implant portions of the medical implant.

The wool threads can be located on the implant in various configurations that may result in either partial or complete coverage of the exterior of the implant. The threads could be attached around the ends of the implant. The wool threads can be attached in bands along the medical implant. The attachment could be in a vertical, horizontal, or diagonal manner. Depending on the specific design of the medical implant, the polymeric thread(s) can be attached to either the implant component or the implant component of the medical implant. Alternatively, or in addition, the wool thread may be allowed to extend some distance from the medical implant. For example, in certain embodiments, only one end of the wool threads may be secured to the medical implant, thereby allowing the other end of the thread to extend away from the implant. Alternatively, both ends of the thread may be secured to a medical implant, however, the mid-portion of the thread is not secured to the medical implant, and the ends of the thread are secured at a sufficiently short distance from one another that the mid-portion is free to extend away from the medical implant.

In another embodiment, the ends of the wool threads can be attached to the medical implant, and/or one or more points along the wool thread can be attached to the medical implant. In yet another embodiment, the ends of the wool thread are not attached to the medical implant. Rather, one or more points along the wool thread are attached to the medical implant. In yet another embodiment, the wool thread(s) can be made into a preformed structure (e.g., mesh, looped bundle, and the like) that is then attached to the medical implant.

Other representative examples of fibrosis-inducing agents suitable for the induction of fibrosis within a divertiuculum include crosslinked compositions that comprise amino-functional groups. For example, amino-functionalized polyethylene glycol (e.g., 4-armed tetra-amino PEG [10k]) can be reacted with a 4-armed NHS functionalized PEG (e.g., pentaerythritol poly(ethylene glycol)ether tetra-succinimidyl glutarate) under basic buffer conditions. In another example a 4-armed thiol functionalized PEG (e.g., pentaerythritol poly(ethylene glycol)ether tetra-thiol) can be substituted for the 4-arm amino-functionalized PEG such that the amount of amino functional groups in the final composition can be varied. These reagents can be mixed at the time of application to provide an in situ forming crosslinked hydrogel. These reagents could be premixed to produce the crosslinked material. The material can be made in various forms such as rods, tubes, films, meshes, screens, threads, fibers, slabs, or spheres. The crosslinked material could also be milled to produce a particulate material. These materials can be dried (e.g., air, vacuum, freeze-dried) and used as a dry powdered material. Alternatively the materials can be hydrated just prior to application. These materials can further comprise one of the fibrosis-inducing agents described herein.

Other representative examples of fibrosis-inducing agents of use in the management of diverticular disease include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291.

In separate embodiments, the agent is a diverticular vessel wall irritant; the fibrosing agent is or comprises silk; the fibrosing agent is or comprises silkworm silk; the fibrosing agent is or comprises spider silk; the fibrosing agent is or comprises recombinant silk; the fibrosing agent is or comprises raw silk; the fibrosing agent is or comprises hydrolyzed silk; the fibrosing agent is or comprises acid-treated silk; the fibrosing agent is or comprises acylated silk; the fibrosing agent is in the form of strands; the fibrosing agent is in the form of tufts; the fibrosing agent is in the form of microparticulates; the fibrosing agent is or comprises mineral particles; the fibrosing agent is or comprises talc; the fibrosing agent is or comprises chitosan; the fibrosing agent is or comprises polylysine; the fibrosing agent is or comprises fibronectin; the fibrosing agent is or comprises bleomycin; the fibrosing agent is or comprises CTGF; the fibrosing agent is in the form of a thread, or is in contact with a thread. Optionally, the thread is biodegradable (e.g., it comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester); or the thread is non-biodegradable (e.g., it comprises a material selected from the group consisting of polyester, polyurethane, silicone, polyethylene, polypropylene, polystyrene, polyacrylate, polymethacrylate, poly-acrylics, polymethacrylics, and silk); the thread is coated with a polymer, the thread is coated with a pharmaceutical agent that induces a fibrotic response in the patient, the thread is coated with a pharmaceutical agent that induces an osteogenic response in the patient; the composition further comprises an agent that promotes bone growth. The agent that promotes bone growth is a bone morphogenic protein or the agent that promotes bone growth is an osteogenic growth factor (e.g., transforming growth factor, platelet-derived growth factor, and fibroblast growth factor); the composition further comprises a pharmaceutical agent that induces sclerosis (a sclerosant, e.g., a sclerosant is selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol, or the sclerosant may be a surfactant); the composition further comprises an inflammatory cytokine (e.g., an inflammatory cytokine selected from the group consisting of TGFβ, PDGF, VEGF, bFGF, TNFα, NGF, GM-CSF, IGF-a, IL-1, IL-1-β, IL-8, IL-6, and growth hormone); the composition further comprises an agent that stimulates cell proliferation (e.g., a cell proliferation agent selected from the group consisting of dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof); the composition further comprises a bulking agent; the composition further comprises a sealant; the composition further comprises a polymeric carrier; the composition further comprises a resorbable ceramic; the composition further comprises a contrast agent; the composition further comprises a thread; the composition is in the form of a tuft; the composition is in the form of a gel; the composition is in the form of a paste; the composition is in the form of a spray; the composition is in the form of an aerosol; the composition is in the form of a suspension; the composition is in the form of an emulsion or microemulsion; the composition is in the form of a microsphere; the composition is in the form of a microparticulate; the composition is in the form of a solid implant.

Within various embodiments of the invention, an implant or composition may include an agent that promotes fibrosis and a second composition or compound which acts to have an inhibitory effect on pathological processes in or around the treatment site. Representative examples of agents which can inhibit pathological processes (e.g., inflammation associated with diverticultits) within the diverticula treatment site include, but not limited to, the following classes of compounds: anti-inflammatory agents (e.g., dexamethasone, cortisone, fludrocortisone, prednisone, prednisolone, 6α-methylprednisolone, triamcinolone, and betamethasone); matrix metalloproteinase (MMP) inhibitors (e.g., marimistat, batimistat, TIMP's representative examples of which are included in U.S. Pat. Nos. 5,665,777; 5,985,911; 6,288,261; 5,952,320; 6,441,189; 6,235,786; 6,294,573; 6,294,539; 6,563,002; 6,071,903; 6,358,980; 5,852,213; 6,124,502; 6,160,132; 6,197,791; 6,172,057; 6,288,086; 6,342,508; 6,228,869; 5,977,408; 5,929,097; 6,498,167; 6,534,491; 6,548,524; 5,962,481; 6,197,795; 6,162,814; 6,441,023; 6,444,704; 6,462,073; 6,162,821; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 5,861,436; 5,691,382; 5,763,621; 5,866,717; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 5,861,436; 5,691,382; 5,763,621; 5,866,717; 5,902,791; 5,962,529; 6,017,889; 6,022,873; 6,022,898; 6,103,739; 6,127,427; 6,258,851; 6,310,084; 6,358,987; 5,872,152; 5,917,090; 6,124,329; 6,329,373; 6,344,457; 5,698,706; 5,872,146; 5,853,623; 6,624,144; 6,462,042; 5,981,491; 5,955,435; 6,090,840; 6,114,372; 6,566,384; 5,994,293; 6,063,786; 6,469,020; 6,118,001; 6,187,924; 6,310,088; 5,994,312; 6,180,611; 6,110,896; 6,380,253; 5,455,262; 5,470,834; 6,147,114; 6,333,324; 6,489,324; 6,362,183; 6,372,758; 6,448,250; 6,492,367; 6,380,258; 6,583,299; 5,239,078; 5,892,112; 5,773,438; 5,696,147; 6,066,662; 6,600,057; 5,990,158; 5,731,293; 6,277,876; 6,521,606; 6,168,807; 6,506,414; 6,620,813; 5,684,152; 6,451,791; 6,476,027; 6,013,649; 6,503,892; 6,420,427; 6,300,514; 6,403,644; 6,177,466; 6,569,899; 5,594,006; 6,417,229; 5,861,510; 6,156,798; 6,387,931; 6,350,907; 6,090,852; 6,458,822; 6,509,337; 6,147,061; 6,114,568; 6,118,016; 5,804,593; 5,847,153; 5,859,061; 6,194,451; 6,482,827; 6,638,952; 5,677,282; 6,365,630; 6,130,254; 6,455,569; 6,057,369; 6,576,628; 6,110,924; 6,472,396; 6,548,667; 5,618,844; 6,495,578; 6,627,411; 5,514,716; 5,256,657; 5,773,428; 6,037,472; 6,579,890; 5,932,595; 6,013,792; 6,420,415; 5,532,265; 5,639,746; 5,672,598; 5,830,915; 6,630,516; 5,324,634; 6,277,061; 6,140,099; 6,455,570; 5,595,885; 6,093,398; 6,379,667; 5,641,636; 5,698,404; 6,448,058; 6,008,220; 6,265,432; 6,169,103; 6,133,304; 6,541,521; 6,624,196; 6,307,089; 6,239,288; 5,756,545; 6,020,366; 6,117,869; 6,294,674; 6,037,361; 6,399,612; 6,495,568; 6,624,177; 5,948,780; 6,620,835; 6,284,513; 5,977,141; 6,153,612; 6,297,247; 6,559,142; 6,555,535; 6,350,885; 5,627,206; 5,665,764; 5,958,972; 6,420,408; 6,492,422; 6,340,709; 6,022,948; 6,274,703; 6,294,694; 6,531,499; 6,465,508; 6,437,177; 6,376,665; 5,268,384; 5,183,900; 5,189,178; 6,511,993; 6,617,354; 6,331,563; 5,962,466; 5,861,427; 5,830,869; and 6,087,359), cytokine inhibitors (chlorpromazine, mycophenolic acid, rapamycin, 1α-hydroxy vitamin $D_3$), IMPDH (inosine monophosplate dehydrogenase) inhibitors (e.g., mycophenolic acid, ribaviran, aminothiadiazole, thiophenfurin, tiazofurin, viramidine) (Representative examples are included in U.S. Pat. Nos. 5,536,747; 5,807,876; 5,932,600; 6,054,472; 6,128,582; 6,344,465; 6,395,763; 6,399,773; 6,420,403; 6,479,628; 6,498,178; 6,514,979; 6,518,291; 6,541,496; 6,596,747; 6,617,323; and 6,624,184, U.S. Patent Application Nos. 2002/0040022A1, 2002/0052513A1, 2002/0055483A1, 2002/0068346A1, 2002/0111378A1, 2002/0111495A1, 2002/0123520A1, 2002/0143176A1, 2002/0147160A1, 2002/0161038A1, 2002/0173491A1, 2002/0183315A1, 2002/0193612A1, 2003/0027845A1, 2003/0068302A1, 2003/0105073A1, 2003/0130254A1, 2003/0143197A1, 2003/0144300A1, 2003/0166201A1, 2003/0181497A1, 2003/0186974A1, 2003/0186989A1, and 2003/0195202A1, and PCT Publication Nos. WO 00/24725A1, WO 00/25780A1, WO 00/26197A1, WO 00/51615A1, WO 00/56331A1, WO 00/73288A1, WO 01/00622A1, WO 01/66706A1, WO 01/79246A2, WO 01/81340A2, WO 01/85952A2, WO 02/16382A1, WO 02/18369A2, WO 02/051814A1, WO 02/057287A2, WO 02/057425A2, WO 02/060875A1, WO 02/060896A1, WO 02/060898A1, WO 02/068058A2, WO 03/020298A1, WO 03/037349A1, WO 03/039548A1, WO 03/045901A2, WO 03/047512A2, WO 03/053958A1, WO 03/055447A2, WO 03/059269A2, WO 03/063573A2, WO 03/087071 A1, WO 99/001545A1, WO 97/40028A1, WO 97/41211A1, WO 98/40381A1, and WO 99/55663A1), p38 MAP kinase inhibitors (MAPK) (e.g., GW-2286, CGP-52411, BIRB-798, SB220025, RO-320–1195, RWJ-67657, RWJ-68354, SCIO-469) (Representative examples are included in U.S. Pat. Nos. 6,300,347; 6,316,464; 6,316,466; 6,376,527; 6,444,696; 6,479,507; 6,509,361; 6,579,874, and 6,630,485, and U.S. Patent Application Publication Nos. 2001/0044538A1, 2002/0013354A1, 2002/0049220A1, 2002/0103245A1, 2002/0151491 A1, 2002/0156114A1, 2003/0018051A1, 2003/0073832A1, 2003/0130257A1, 2003/0130273A1, 2003/0130319A1, 2003/0139388A1, 2003/0139462A1, 2003/0149031 A1, 2003/0166647A1, and 2003/0181411A1, and PCT Publication Nos. WO 00/63204A2, WO 01/21591A1, WO 01/35959A1, WO 01/74811A2, WO 02/18379A2, WO 02/064594A2, WO 02/083622A2, WO 02/094842A2,WO 02/096426A1, WO 02/101015A2, WO 02/103000A2, WO 03/008413A1, WO 03/016248A2, WO 03/020715A1, WO 03/024899A2, WO 03/031431 A1, WO 03/040103A1, WO 03/053940A1, WO 03/053941A2, WO 03/063799A2, WO 03/079986A2, WO 03/080024A2, WO 03/082287A1, WO 97/44467A1, WO 99/01449A1, and WO 99/58523A1), and immunomodulatory agents (rapamycin, everolimus, ABT-578, azathioprine azithromycin, analogues of rapamycin, tacrolimus and derivatives thereof (e.g., EP 0184162B1 and those described in U.S. Pat. No. 6,258,823) and everolimus and derivatives thereof (e.g., U.S. Pat. No. 5,665,772). Further representative examples of sirolimus analogues and derivatives include ABT-578 and those found in PCT Publication Nos. WO 97/10502, WO 96/41807, WO 96/35423, WO 96/03430, WO 96/00282, WO 95/16691, WO 95/15328, WO 95/07468, WO 95/04738, WO 95/04060, WO 94/25022, WO 94/21644, WO 94/18207, WO 94/10843, WO 94/09010, WO 94/04540, WO 94/02485, WO 94/02137, WO 94/02136, WO 93/25533, WO 93/18043, WO 93/13663, WO 93/11130, WO 93/10122, WO 93/04680, WO 92/14737, and WO 92/05179 and in U.S. Pat. Nos. 6,342,507; 5,985,890; 5,604,234; 5,597,715; 5,583,139; 5,563,172; 5,561,228; 5,561,137; 5,541,193; 5,541,189; 5,534,632; 5,527,907; 5,484,799; 5,457,194; 5,457,182; 5,362,735; 5,324,644; 5,318,895; 5,310,903; 5,310,901; 5,258,389; 5,252,732; 5,247,076; 5,225,403; 5,221,625; 5,210,030; 5,208,241; 5,200,411; 5,198,421; 5,147,877; 5,140,018; 5,116,756; 5,109,112; 5,093,338; and 5,091,389.

Other examples of drugs that may be included in the compositions and implants of the invention include tyrosine kinase inhibitors, such as imantinib, ZK-222584, CGP-52411, CGP-53716, NVP-MK980-NX, CP-127374, CP-564959, PD-171026, PD-173956, PD-180970, SU-0879, and SKI-606. Other examples of drugs that may be included in the compositions and implants of the invention include MMP inhibitors such as nimesulide, PKF-241-466, PKF-242-484, CGS-27023A, SAR-943, primomastat, SC-77964, PNU-171829, AG-3433, PNU-142769, SU-5402, and dexlipotam. Other examples of drugs that may be included in the compositions and implants of the invention include p38 MAP kinase inhibitors such as CGH-2466 and PD-98-59. Other examples of drugs that may be included in the compositions and implants of the invention include immunosuppressants such as argyrin B, macrocyclic lactone, ADZ-62-826, CCI-779, tilomisole, amcinonide, FK-778, AVE-1726, and MDL-28842. Other examples of cytokine inhibitors include TNF-484A, PD-172084, CP-293121, CP-353164, and PD-168787. Other examples of drugs that may be included in the compositions and implants of the invention include NFKB inhibitors, such as, AVE-0547, AVE-0545, and IPL-576092. Other examples of drugs that may be included in the compositions and implants of the invention include HMGCoA reductase inhibitors, such as, pravestatin, atorvastatin, fluvastatin, dalvastatin, glenvastatin, pitavastatin, CP-83101, U-20685, apoptosis antagonist (e.g., troloxamine, TCH-346 (N-methyl-N-propargyl-10, aminomethyl-dibenzo(b,f)oxepin), caspase inhibitors (e.g., PF-5901 (benzenemethanol, alpha-pentyl-3-(2-quinolinyl-methoxy)-), and JNK inhibitor (e.g., AS-602801).

Within various embodiments, a diverticular implant or composition incorporates or is coated with a composition that promotes fibrosis, as well as a composition or compound that acts to stimulate cellular proliferation. Representative examples of agents that stimulate cellular proliferation include, pyruvic acid, naltrexone, leptin, D-glucose, insulin, amlodipine, alginate oligosaccharides, minoxidil, dexamethasone, isotretinoin (13-cis retinoic acid), 17-β-estradiol, estradiol, 1-a-25 dihydroxyvitamin $D_3$, diethylstibesterol, cyclosporine A, L-NAME (L-NG-nitroarginine methyl ester (hydrochloride)), all-trans retinoic acid (ATRA), and analogues and derivatives thereof. Other examples of agents that stimulate cellular proliferation include sphingosine 1-phosphate receptor agonist (e.g., FTY-720 (1,3-propanediol, 2-amino-2-(2-(4-octylphenyl)ethyl)-, hydrochloride; immunostimulants, such as Imupedone (methanone, [5-amino-2-(4-methyl-1-piperidinyl)phenyl](4-chlorophenyl)-, DIAPEP227 synthetic peptide (Peptor Ltd., Israel)); and nerve growth factor agonist, e.g., NG-012 (5H,9H,13H, 21H,25H,-dibenzo[k,u][1,5,9,15,19] pentaoxacyclotetracosin-5,9,13,21,25-pentone, 7,8,11,12,15,16,23,24,27,28-decahydro-2,4,18,20-tetrahydroxy-11-(hydroxymethyl)-7, 15,23,27-tetramethyl-, NG-121, SS-701 (2,2':6',2"-terpyridine, 4'-(4-methylphenyl)-, trihydrochloride, AMPAlex (piperidine, 1-(6-quinoxalinylcarbonyl), RGH-2716 (8-[4,4-bis(4-fluorophenyl)butyl]-3-(1,1-dimethyl-ethyl-4-methylene-1-oxa-3,8-diaza-spiro[4.5] decan-2-one, and TDN-345 (1-oxa-3,8-diazaspiro[4.5]decan-2-one, 8-[4, 4-bis(4-fluorophenyl)butyl]-3-(1,1-dimethylethyl)-4-methylene-).

Haemostatic Agents

For managing bleeding, including lower gastrointestinal hemorrhage, which is the result of diverticular bleeding, the diverticular implant or composition may include a fibrosing agent and a haemostatic agent (a thrombotic or clotting agent) that promotes clotting and hemostatis upon implantation of a medical implant (or composition). A haemostat or haemostatic agent is any agent that arrests chemically or mechanically the flow of blood from an open vessel. A haemostatic agent can be applied directly to a bleeding site, and the agent functions in the presence of actively flowing blood. Accordingly, a haemostatic agent may chemically or biologically arrest the flow of blood by interfering with one or more steps in the clotting cascade, such as by accelerating the clotting mechanism (e.g., COSTASIS). The increased clotting then serves as a physical barrier to the flow of blood. Alternatively a haemostatic agent may in a more direct manner mechanically or physically block the flow of blood (e.g., COSEAL) and thus may be referred to as a sealant (an agent used to prevent leakage of liquids gases or solids). A haemostatic agent may be applied or claped to a tissue surface to provide a barrier to the flow of blood.

Within various embodiments, a diverticular implant contains a haemostatic agent or composition comprising a haemostatic agent and/or an agent or composition that promotes fibrosis. In certain alternative embodiments, an implant is coated on one aspect with a composition that promotes fibrosis, as well as being coated with a composition or agent that is hemostatic on another aspect of the implant. Representative examples of hemostatic agents include fibrin; aminocaproic acid; tranexamic acid; aprotinin; desmopressin; vitamin K; Tisseel® and FloSeal® (which are fibrinogen-containing formulations) (Baxter Healthcare Corp., Glendale, Calif.); CrossSeal® (American Red Cross); CoSeal® (PEG-containing formulation) and CoStasis® (collagen-containing formulation) (Angiotech BioMaterials Corp., Palo Alto, Calif.); and CryoSeal® AHS (Thermogenesis, Sacramento, Calif.).

Anti-Infective Agents

In one embodiment, a composition and medical implant is provided that includes a fibrosing agent and an anti-infective agent, which reduces the likelihood of infections in medical implants. Infection is a common complication that results from the implantation of foreign bodies such as medical devices and implants into a host or patient. Foreign materials provide an ideal site for microorganisms to attach and colonize. In addition, according to non-limiting theory, the risk that a host will develop an infection may be increased as a consequence of an impairment of host defenses against infection in the microenvironment surrounding a foreign material. These factors make medical implants particularly susceptible to infection.

A composition for treating and/or managing diverticular infection (diverticulitis) may include an anti-infective agent, antibiotic, or other agent that inhibits (impairs or decreases) the growth or division rate or kills a microorganism (for example, bacteria and yeast). Diverticulitis can occur when inspissated stool, a fecalith trapped within a diverticulum, results in local infection (or abscess formation) within the diverticulum. When severe, this can lead to perforation and the formation of generalized peritonitis. Even in the management of diverticula that are not acutely infected, diverticula lumen may be sterilized such that bacteria are not contained within the developing scar tissue. This will lessen the possibility that an infection or abscess will develop at a later point in time.

An anti-infective agent refers to an agent that reduces the likelihood of an infection. An agent is demonstrated to be an active anti-infective agent toward a microorganism by assays routinely practiced by persons skilled in the art, for example, an in vitro assay determining inhibition of bacterial growth as indicated by the M.I.C. (minimimum inhibitory concentration). In certain embodiments, anti-infective agents are chemotherapeutic agents that have antimicrobial activity at low doses (e.g., anthracyclines, fluoropyrimidines, folic acid antagonists, podophylotoxins, camptothecins, hydroxyureas, and platinum complexes.

An anti-septic agent refers to an agent or substance that is capable of effective antisepsis, that is, prevention of infection by inhibiting the growth of an infectious organism without necessarily killing the organism. Representative examples of anti-septic agents include chlorhexadine, triclosan, and chloroxylenol.

Antibiotic refers to an agent that kills or inhibits the growth of microorganisms. Antibiotics may have a narrow or wide range of activity against either one or both of Gram-positive and Gram-negative organisms. Antibiotic agents can be identified through in vitro inhibition of bacterial growth as shown in the M.I.C. assay described herein. Representative examples of antibiotics include gentamicin sulfate, amikacin sulfate, kanamycin sulfate, polymyxin B, neomycin sulfate, cephazolin sodium, metronidazole, Ciprofloxacin, piperacillin, Cefoxitin, Cefepime,Azithromycin, and Trimethoprom-sulfamethoxazole.

Within various embodiments of the invention, a composition comprises, or an implant is loaded or coated with a composition that promotes fibrosis, as well as being loaded or coated with an an anti-infective agent (e.g., antibiotic, chemotherapeutic agent, and/or antiseptic agent) or a composition that includes an antibiotic (or antiseptic agent). Representative examples are provided herein of agents such as chemotherapeutic agents that can be released from a composition, and which have potent antimicrobial activity at extremely low doses. A wide variety of anti-infective agents can be used in combination with the present compositions. Suitable anti-infective agents may be readily determined by methods practiced in the art and as exemplified in the assays provided in Example 41. Described in greater detail below are several representative examples of anati-infective agents: (A) anthracyclines (e.g., doxorubicin and mitoxantrone); (B) fluoropyrimidines (e.g., 5-FU); (C) folic acid antagonists (e.g., methotrexate); (D) podophylotoxins (e.g., etoposide); (E) camptothecins; (F) hydroxyureas; and (G) platinum complexes (e.g., cisplatin).

Anti-infective agents have the capability to prevent infection, reduce the incidence of abscess formation, treat diverticulitis, and/or contribute to sterilization of the lumen of the diverticula during the scarring process. Such anti-infective agents include, but are not limited to antibiotics and anti-cancer agents. In addition, implants may be coated with antimicrobial drugs. Representative examples of implants and coating of implants with antimicrobial drugs are provided in U.S. Pat. No. 5,520,664, U.S. Pat. No. 5,709,672, U.S. Pat. No. 6,361,526, U.S. Pat. No. 6,261,271, U.S. Pat. No. 5,902,283, U.S. Pat. No. 5,624,704, and U.S. Pat. No. 5,709,672.

Anti-Infective Agents—Antibiotics

Antibiotics and combinations of antibiotics that are used by those skilled in the medical art include the following exemplary antibiotics: fourth generation penicillins such as mezlocillin and piperacillin (ureidopenicillins), carbenicillin and ticarcillin (carboxypenicillins), and analogues and derivatives thereof; first generation cephalosporins such as cephazolin, Cephazolin Sodium, Cephalexin (Keflex), Cefazolin (Ancef), Cephapirin (Cefadyl), and Cephalothin (Keflin), and analogues and derivatives thereof; Ticarcillin; second generation cephalosporins such as Cefuroxime (Ceftin (oral) and Zinocef), Cefotetan (Cefotan), and Cefoxitin (Mefoxin), and analogues and derivatives thereof; third generation cephalosporin such as Naxcel (Ceftiofur Sodium), Cefdinir (Omnicef), Cefoperazone (Cefobid), Ceftazidime (Fortaz), and Ceftriaxone (Rocephin), and Cefotaxime (Claforan), and analogues and derivatives thereof; and fourth generation cephalosporins such as Cefepime (Maxipime) and analogues and derivatives thereof; monobactams such as aztreonam and analogues and derivatives thereof; carbapenems such as imipenem, ertapenem and meropenem, and analogues and derivatives thereof. Also included are inhibitors of protein synthesis such as aminoglycosides including streptomycin, gentamicin, gentamicin sulfate, tobramycin, and amikacin, amikacin sulfate, and analogues and derivatives thereof; inhibitors of protein synthesis such as the MSL group including macrolides (Erythromycin), long acting macrolides (Azithromycin) and lincosamides (Clindamycin) and streptogramins (Syneroid), clarithromycin, kanamycin, kanamycin sulfate, and analogues and derivatives thereof. Other exemplary antibiotics include inhibitors of DNA synthesis such as the quinolones including ciprofloxacin, ofloxacin, gatifloxacin, moxifloxacin, levofloxacin, trovafloxacin, and analogues and derivatives thereof, as well as other inhibitors of DNA synthesis such as metronidazole and analogues and derivatives thereof. Other antibiotics include inhibitors of folate metabolism such as sulfonamides and trimethoprim, and analogues and derivatives thereof. Additional agents include but are not limited to cefixime, spectinomycin, tetracycline, nitrofurantoin, doxycycline, polymyxin B, neomycin, neomycin sulfate, and analogues and derivatives thereof. In certain embodiments, the anti-infective agent is gentamicin sulfate, amikacin sulfate, kanamycin sulfate, polymyxin B, neomycin sulfate, cephazolin sodium, metronidazole, ciprofloxacin, piperacillin, cefoxitin, cefepime, azithromycin, or trimethoprim-sulfamethoxazole.

Furthermore, additional therapeutic agents may be delivered in combinations. Such combinations include, by way of example, but are not limited to amoxicillin and clavulanate, ampicillin and sulbactam, trimethoprom-sulfamethoxazole, ampicillin and probenecid, amoxicillin and probenecid, penicillin G and probenecid, and penicillin and a penicillinase inhibitor.

Antibiotics described herein and used by those skilled in the medical art may be administered orally (1–2 grams per day depending upon factors such as age and/or weight and/or mass of the patient). As described herein, one or more antibiotics may also be administered parenterally or an antibiotic may be administered in a composition that includes the fibrosis agent, or may be administered in combination with an implant.

Anti-Infective Agents—Chemotherapeutic Agents

Also provided herein are agents (e.g., chemotherapeutic agents) that can be incorporated onto or into, or released from, an implant or a composition implanted within a diverticulum, and which have potent antimicrobial activity at extremely low doses. A wide variety of anti-infective agents can be used in combination with a fibrosing agent. Described in more detail below are several representative examples of chemotehrapeutic/anti-infective agents: (A) anthracyclines (e.g., doxorubicin and mitoxantrone), (B) fluoropyrimidines (e.g., 5-FU), (C) folic acid antagonists (e.g., methotrexate), (D) podophylotoxins (e.g., etoposide), (E) camptothecins, (F) hydroxyureas, and (G) platinum complexes (e.g., cisplatin).

(A) Anthracyclines

Anthracyclines have the following general structure, where the R groups may be a variety of organic groups:

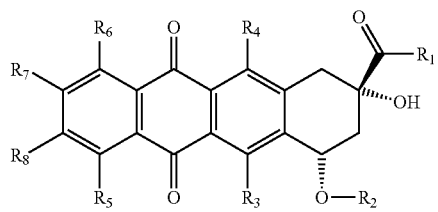

According to U.S. Pat. No. 5,594,158, suitable R groups are as follows: $R_1$ is $CH_3$ or $CH_2OH$; $R_2$ is daunosamine or H; $R_3$ and $R_4$ are independently one of OH, $NO_2$, $NH_2$, F, Cl, Br, I, CN, H or groups derived from these; $R_5$ is hydrogen, hydroxyl, or methoxy; and $R_{6-8}$ are all hydrogen. Alternatively, $R_5$ and $R_6$ are hydrogen and $R_7$ and $R_8$ are alkyl or halogen, or vice versa.

According to U.S. Pat. No. 5,843,903, $R_1$ may be a conjugated peptide. According to U.S. Pat. No. 4,296,105, $R_5$ may be an ether linked alkyl group. According to U.S. Pat. No. 4,215,062, $R_5$ may be OH or an ether linked alkyl group. $R_1$ may also be linked to the anthracycline ring by a group other than C(O), such as an alkyl or branched alkyl group having the C(O) linking moiety at its end, such as —$CH_2CH(CH_2$—X)C(O)—$R_1$, wherein X is H or an alkyl group (see, e.g., U.S. Pat. No. 4,215,062). $R_2$ may alternately be a group linked by the functional group =N—NHC(O)—Y, where Y is a group such as a phenyl or substituted phenyl ring. Alternately $R_3$ may have the following structure:

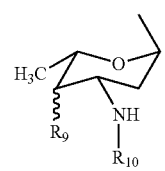

in which $R_9$ is OH either in or out of the plane of the ring, or is a second sugar moiety such as $R_3$. $R_{10}$ may be H or form a secondary amine with a group such as an aromatic group, saturated or partially saturated 5 or 6 membered heterocyclic having at least one ring nitrogen (see U.S. Pat. No. 5,843,903). Alternately, $R_{10}$ may be derived from an amino acid, having the structure —C(O)CH(NHR$_{11}$)(R$_{12}$), in which $R_{11}$ is H, or forms a $C_{3-4}$ membered alkylene with $R_{12}$. $R_{12}$ may be H, alkyl, aminoalkyl, amino, hydroxyl, mercapto, phenyl, benzyl or methylthio (see U.S. Pat. No. 4,296,105).

Exemplary anthracyclines are doxorubicin, daunorubicin, idarubicin, epirubicin, pirarubicin, zorubicin, and carubicin. Suitable compounds have the structures:

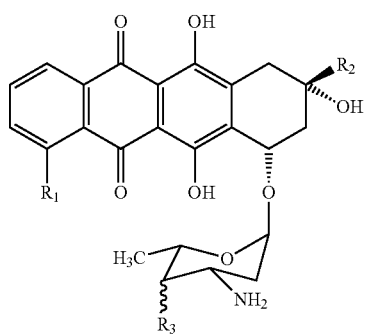

|  | $R_1$ | $R_2$ | $R_3$ |
|---|---|---|---|
| Doxorubicin: Epirubicin: | $OCH_3$ | $C(O)CH_2OH$ | OH out of ring plane |
| (4' epimer of doxorubicin) | $OCH_3$ | $C(O)CH_2OH$ | OH in ring plane |
| Daunorubicin: | $OCH_3$ | $C(O)CH_3$ | OH out of ring plane |
| Idarubicin: | H | $C(O)CH_3$ | OH out of ring plane |
| Pirarubicin: | $OCH_3$ | $C(O)CH_2OH$ | ![ring] |
| Zorubicin: | $OCH_3$ | $C(CH_3)(=N)NHC(O)C_6H_5$ | OH |
| Carubicin: | OH | $C(O)CH_3$ | OH out of ring plane |

Other suitable anthracyclines are anthramycin, mitoxantrone, menogaril, nogalamycin, aclacinomycin A, olivomycin A, chromomycin $A_3$, and plicamycin having the structures:

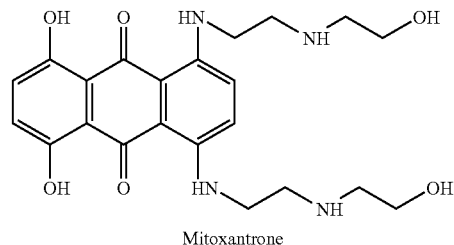
Mitoxantrone
|  | $R_1$ | $R_2$ | $R_3$ |
|---|---|---|---|
| Menogaril | H | $OCH_3$ | H |
| Nogatamycin | O-sugar | H | $COOCH_3$ |
sugar: 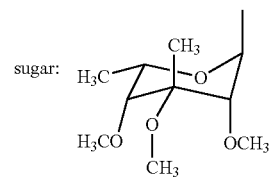
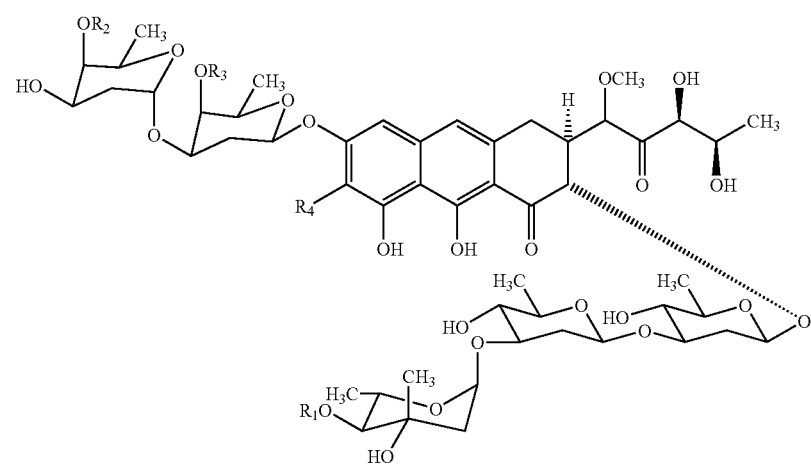
|  | $R_1$ | $R_2$ | $R_3$ | $R_4$ |
|---|---|---|---|---|
| Olivomycin A | $COCH(CH_3)_2$ | $CH_3$ | $COCH_3$ | H |
| Chromomycin $A_3$ | $COCH_3$ | $CH_3$ | $COCH_3$ | $CH_3$ |
| Plicamycin | H | H | H | $CH_3$ |

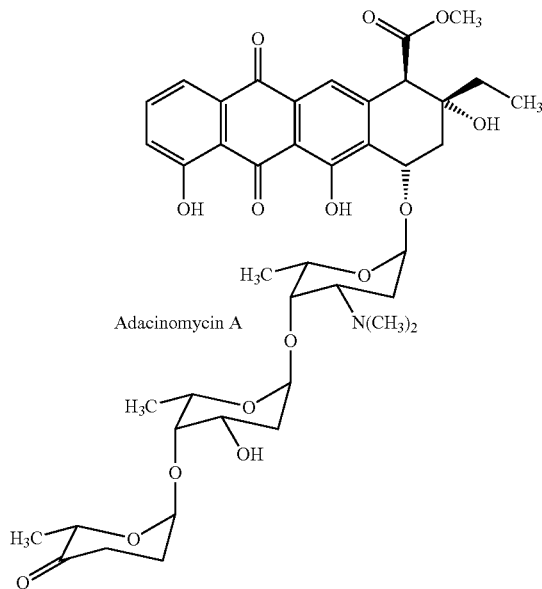

Adacinomycin A

Other representative anthracyclines include, FCE 23762, a doxorubicin derivative (Quaglia et al., *J. Liq. Chromatogr.* 17(18):3911–3923, 1994), annamycin (Zou et al., *J. Pharm. Sci.* 82(11):1151–1154, 1993), ruboxyl (Rapoport et al., *J. Controlled Release* 58(2):153–162, 1999), anthracycline disaccharide doxorubicin analogue (Pratesi et al., *Clin. Cancer Res.* 4(11):2833–2839, 1998), N-(trifluoroacetyl)doxorubicin and 4'-O-acetyl-N-(trifluoroacetyl)doxorubicin (Berube & Lepage, *Synth. Commun.* 28(6):1109–1116, 1998), 2-pyrrolinodoxorubicin (Nagy et al., *Proc. Nat'l Acad. Sci. U.S.A.* 95(4):1794–1799, 1998), disaccharide doxorubicin analogues (Arcamone et al., *J. Nat'l Cancer Inst.* 89(16):1217–1223, 1997), 4-demethoxy-7-O-[2,6-dideoxy-4-O-(2,3,6-trideoxy-3-amino-α-L-lyxo-hexopyranosyl)-α-L-lyxo-hexopyranosyl]-adriamicinone doxorubicin disaccharide analogue (Monteagudo et al., *Carbohydr. Res.* 300(1):11–16, 1997), 2-pyrrolinodoxorubicin (Nagy et al., *Proc. Nat'l Acad. Sci. U.S.A.* 94(2):652–656, 1997), morpholinyl doxorubicin analogues (Duran et al., *Cancer Chemother. Pharmacol.* 38(3):210–216, 1996), enaminomalonyl-β-alanine doxorubicin derivatives (Seitz et al., *Tetrahedron Lett.* 36(9):1413–16, 1995), cephalosporin doxorubicin derivatives (Vrudhula et al., *J. Med. Chem.* 38(8): 1380–5, 1995), hydroxyrubicin (Solary et al., *Int. J. Cancer* 58(1):85–94, 1994), methoxymorpholino doxorubicin derivative (Kuhl et al., *Cancer Chemother. Pharmacol.* 33(1):10–16, 1993), (6-maleimidocaproyl)hydrazone doxorubicin derivative (Willner et al., *Bioconjugate Chem.* 4(6): 521–7, 1993), N-(5,5-diacetoxypent-1-yl) doxorubicin (Cherif & Farquhar, *J. Med. Chem.* 35(17):3208–14, 1992), FCE 23762 methoxymorpholinyl doxorubicin derivative (Ripamonti et al., *Br. J. Cancer* 65(5):703–7, 1992), N-hydroxysuccinimide ester doxorubicin derivatives (Demant et al., *Biochim. Biophys. Acta* 1118(1):83–90, 1991), polydeoxynucleotide doxorubicin derivatives (Ruggiero et al., *Biochim. Biophys. Acta* 1129(3):294–302, 1991), morpholinyl doxorubicin derivatives (EPA 434960), mitoxantrone doxorubicin analogue (Krapcho et al., *J. Med. Chem.* 34(8):2373–80. 1991), AD198 doxorubicin analogue (Traganos et al., *Cancer Res.* 51(14):3682–9, 1991), 4-demethoxy-3'-N-trifluoroacetyldoxorubicin (Horton et al., *Drug Des. Delivery* 6(2):123–9, 1990), 4'-epidoxorubicin (Drzewoski et al., *Pol. J. Pharmacol. Pharm.* 40(2):159–65, 1988; Weenen et al., *Eur. J. Cancer Clin. Oncol.* 20(7): 919–26, 1984), alkylating cyanomorpholino doxorubicin derivative (Scudder et al., *J. Nat'l Cancer Inst.* 80(16): 1294–8, 1988), deoxydihydroiodooxorubicin (EPA 275966), adriblastin (Kalishevskaya et al., *Vestn. Mosk. Univ.,* 16(Biol. 1):21–7, 1988), 4'-deoxydoxorubicin (Schoelzel et al., *Leuk. Res.* 10(12):1455–9, 1986), 4-demethoxy-4'-o-methyldoxorubicin (Giuliani et al., *Proc. Int. Congr. Chemother.* 16:285-70–285-77, 1983), 3'-deamino-3'-hydroxydoxorubicin (Horton et al., *J. Antibiot.* 37(8):853–8, 1984), 4-demethyoxy doxorubicin analogues (Barbieri et al., *Drugs Exp. Clin. Res.* 10(2):85–90, 1984), N-L-leucyl doxorubicin derivatives (Trouet et al., Anthracyclines (*Proc. Int. Symp. Tumor Pharmacother.*), 179–81, 1983), 3'-deamino-3'-(4-methoxy-1-piperidinyl) doxorubicin derivatives (U.S. Pat. No. 4,314,054), 3'-deamino-3'-(4-mortholinyl) doxorubicin derivatives (U.S. Pat. No. 4,301,277), 4'-deoxydoxorubicin and 4'-o-methyldoxorubicin (Giuliani et al., *Int. J. Cancer* 27(1):5–13, 1981), aglycone doxorubicin derivatives (Chan & Watson, *J. Pharm. Sci.* 67(12):1748–52, 1978), SM 5887 (*Pharma Japan* 1468:20, 1995), MX-2 (*Pharma Japan* 1420:19, 1994), 4'-deoxy-13(S)-dihydro-4'-iododoxorubicin (EP 275966), morpholinyl doxorubicin derivatives (EPA 434960), 3'-deamino-3'-(4-methoxy-1-piperidinyl) doxorubicin derivatives (U.S. Pat. No. 4,314, 054), doxorubicin-14-valerate, morpholinodoxorubicin (U.S. Pat. No. 5,004,606), 3'-deamino-3'-(3"-cyano-4"-morpholinyl doxorubicin; 3'-deamino-3'-(3"-cyano-4"-morpholinyl)-13-dihydoxorubicin); (3'-deamino-3'-(3"-cyano-4"-morpholinyl) daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives (U.S. Pat. No. 4,585,859), 3'-deamino-3'-(4-methoxy-1-piperidinyl) doxorubicin derivatives (U.S. Pat. No. 4,314,054) and 3-deamino-3-(4-morpholinyl) doxorubicin derivatives (U.S. Pat. No. 4,301,277).

(B) Fluoropyrimidine Analogues

In another aspect, the therapeutic agent is a fluoropyrimidine analog, such as 5-fluorouracil, or an analogue or derivative thereof, including carmofur, doxifluridine, emitefur, tegafur, and floxuridine. Exemplary compounds have the structures:

A

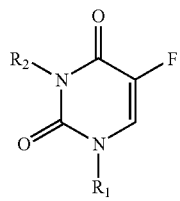

| | $R_1$ | $R_2$ |
|---|---|---|
| 5-Fluorouracil | H | H |
| Carmofur | $C(O)NH(CH_2)_5CH_3$ | H |
| Doxifluridine | $A_1$ | H |
| Floxuridine | $A_2$ | H |
| Emitefur | $CH_2OCH_2CH_3$ | B |
| Tegafur | C | H |

B

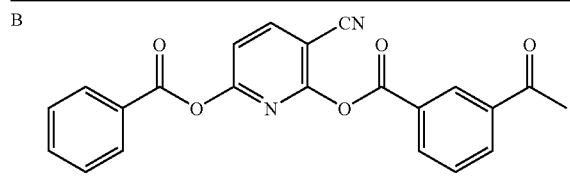

C

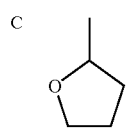

Other suitable fluoropyrimidine analogues include 5-FudR (5-fluorodeoxyuridine), or an analogue or derivative thereof, including 5-iododeoxyuridine (5-IudR), 5-bromodeoxyuridine (5-BudR), fluorouridine triphosphate (5-FUTP), and fluorodeoxyuridine monophosphate (5-dFUMP). Exemplary compounds have the structures:

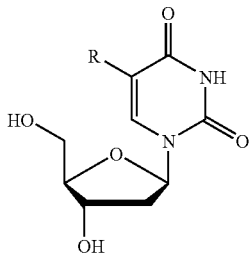

| | |
|---|---|
| 5-Fluoro-2'-deoxyuridine: | R = F |
| 5-Bromo-2'-deoxyuridine: | R = Br |
| 5-Iodo-2'-deoxyuridine: | R = I |

Other representative examples of fluoropyrimidine analogues include N3-alkylated analogues of 5-fluorouracil (Kozai et al., *J. Chem. Soc., Perkin Trans.* 1(19):3145–3146, 1998), 5-fluorouracil derivatives with 1,4-oxaheteroepane moieties (Gomez et al., *Tetrahedron* 54(43): 13295–13312, 1998), 5-fluorouracil and nucleoside analogues (Li, *Anticancer Res.* 17(1A):21–27, 1997), cis- and trans-5-fluoro-5,6-dihydro-6-alkoxyuracil (Van der Wilt et al., *Br. J. Cancer* 68(4):702–7, 1993), cyclopentane 5-fluorouracil analogues (Hronowski & Szarek, *Can. J. Chem.* 70(4):1162–9,1992), A-OT-fluorouracil (Zhang et al., *Zongguo Yiyao Gongye Zazhi* 20(11):513–15, 1989), N4-trimethoxybenzoyl-5'-deoxy-5-fluorocytidine and 5'-deoxy-5-fluorouridine (Miwa et al., *Chem. Pharm. Bull.* 38(4):998–1003, 1990), 1-hexylcarbamoyl-5-fluorouracil (Hoshi et al., *J. Pharmacobio-Dun.* 3(9):478–81, 1980; Maehara et al., *Chemotherapy (Basel)* 34(6):484–9, 1988), B-3839 (Prajda et al., *In Vivo* 2(2):151–4, 1988), uracil-1-(2-tetrahydrofuryl)-5-fluorouracil (Anai et al., *Oncology* 45(3):144–7, 1988), 1-(2'-deoxy-2'-fluoro-β-D-arabinofuranosyl)-5-fluorouracil (Suzuko et al., *Mol. Pharmacol.* 31(3):301–6, 1987), doxifluridine (Matuura et al., *Oyo Yakuri* 29(5):803–31, 1985), 5'-deoxy-5-fluorouridine (Bollag & Hartmann, *Eur. J. Cancer* 16(4):427–32, 1980), 1-acetyl-3-O-toluyl-5-fluorouracil (Okada, *Hiroshima J. Med. Sci.* 28(1):49–66, 1979), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680).

These compounds are believed to function as therapeutic agents by serving as antimetabolites of pyrimidine.

(C) Folic Acid Antagonists

In another aspect, the therapeutic agent is a folic acid antagonist, such as methotrexate or derivatives or analogues thereof, including edatrexate, trimetrexate, raltitrexed, piritrexim, denopterin, tomudex, and pteropterin. Methotrexate analogues have the following general structure:

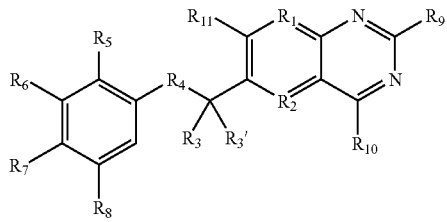

The identity of the R group may be selected from organic groups, particularly those groups set forth in U.S. Pat. Nos. 5,166,149 and 5,382,582. For example, $R_1$ may be N, $R_2$ may be N or $C(CH_3)$, $R_3$ and $R_3'$ may H or alkyl, e.g., $CH_3$, $R_4$ may be a single bond or NR, where R is H or alkyl group. $R_5$, $R_6$, and/or $R_8$ may be H, $OCH_3$, or alternately they can be halogens or hydro groups. $R_7$ is a side chain of the general structure:

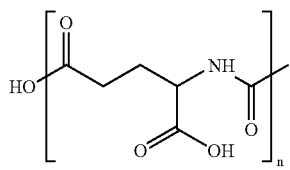

wherein n=1 for methotrexate, n=3 for pteropterin. The carboxyl groups in the side chain may be esterified or form a salt such as a $Zn^{2+}$ salt. $R_9$ and $R_{10}$ can be $NH_2$ or may be alkyl substituted.

Exemplary folic acid antagonist compounds have the structures:

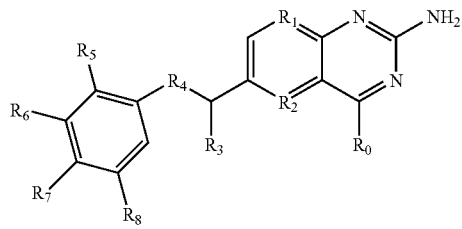

| | $R_0$ | $R_1$ | $R_2$ | $R_3$ | $R_4$ | $R_5$ | $R_6$ | $R_7$ | $R_8$ |
|---|---|---|---|---|---|---|---|---|---|
| Methotrexate | $NH_2$ | N | N | H | $N(CH_3)$ | H | H | A (n = 1) | H |
| Edatrexate | $NH_2$ | N | N | H | $CH(CH_2CH_3)$ | H | H | A (n = 1) | H |
| Trimetrexate | $NH_2$ | CH | $C(CH_3)$ | H | NH | H | $OCH_3$ | $OCH_3$ | $OCH_3$ |
| Pteropterin | OH | N | N | H | NH | H | H | A (n = 3) | H |
| Denopterin | OH | N | N | $CH_3$ | $N(CH_3)$ | H | H | A (n = 1) | H |
| Peritrexim | $NH_2$ | N | $C(CH_3)$ | H | single bond | $OCH_3$ | H | H | $OCH_3$ |

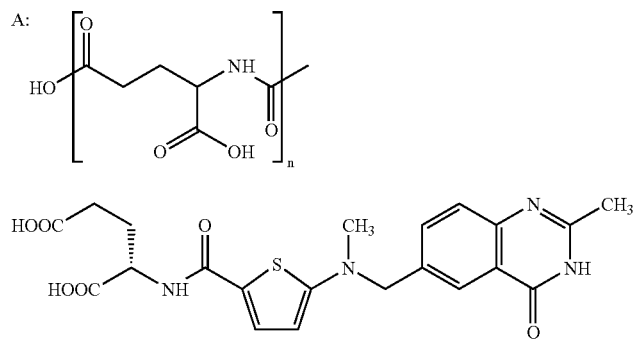

Tomudex

Other representative examples include 6-S-aminoacyloxymethyl mercaptopurine derivatives (Harada et al., *Chem. Pharm. Bull.* 43(10):793–6, 1995), 6-mercaptopurine (6-MP) (Kashida et al., *Biol. Pharm. Bull.* 18(11):1492–7, 1995), 7,8-polymethyleneimidazo-1,3,2-diazaphosphorines (Nilov et al., *Mendeleev Commun.* 2:67, 1995), azathioprine (Chifotides et al., *J. Inorg. Biochem.* 56(4):249–64, 1994), methyl-D-glucopyranoside mercaptopurine derivatives (Da Silva et al., *Eur. J. Med. Chem.* 29(2):149–52, 1994) and s-alkynyl mercaptopurine derivatives (Ratsino et al., *Khim.-Farm. Zh.* 15(8):65–7, 1981); indoline ring and a modified ornithine or glutamic acid-bearing methotrexate derivatives (Matsuoka et al., *Chem. Pharm. Bull.* 45(7):1146–1150, 1997), alkyl-substituted benzene ring C bearing methotrexate derivatives (Matsuoka et al., *Chem. Pharm. Bull.* 44(12):2287–2293, 1996), benzoxazine or benzothiazine moiety-bearing methotrexate derivatives (Matsuoka et al., *J. Med. Chem.* 40(1):105–111, 1997), 10-deazaminopterin analogues (DeGraw et al., *J. Med. Chem.* 40(3):370–376, 1997), 5-deazaminopterin and 5,10-dideazaminopterin methotrexate analogues (Piper et al., *J. Med. Chem.* 40(3):377–384, 1997), indoline moiety-bearing methotrexate derivatives (Matsuoka et al., *Chem. Pharm. Bull.* 44(7):1332–1337, 1996), lipophilic amide methotrexate derivatives (Pignatello et al., *World Meet. Pharm. Biopharm. Pharm. Technol.,* 563–4,1995), L-threo-(2S,4S)-4-fluoroglutamic acid and DL-3,3-difluoroglutamic acid-containing methotrexate analogues (Hart et al., *J. Med. Chem.* 39(1):56–65, 1996), methotrexate tetrahydroquinazoline analogue (Gangjee, et al., *J. Heterocycl. Chem.* 32(1):243–8, 1995), N-(α-aminoacyl) methotrexate derivatives (Cheung et al., *Pteridines* 3(1–2):101–2, 1992), biotin methotrexate derivatives (Fan et al., *Pteridines* 3(1–2):131–2, 1992), D-glutamic acid or D-erythrou, threo-4-fluoroglutamic acid methotrexate analogues (McGuire et al., *Biochem. Pharmacol.* 42(12):2400–3, 1991), β,γ-methano methotrexate analogues (Rosowsky et al., *Pteridines* 2(3):133–9, 1991), 10-deazaminopterin (10-EDAM) analogue (Braakhuis et al., *Chem. Biol. Pteridines, Proc. Int. Symp. Pteridines Folic Acid Deriv.,* 1027–30, 1989), γ-tetrazole methotrexate analogue (Kalman et al., *Chem. Biol. Pteridines, Proc. Int. Symp. Pteridines Folic Acid Deriv.,* 1154–7, 1989), N-(L-α-aminoacyl) methotrexate derivatives (Cheung et al., *Heterocycles* 28(2):751–8, 1989), meta and ortho isomers of aminopterin (Rosowsky et al., *J. Med. Chem.* 32(12):2582, 1989), hydroxymethylmethotrexate (DE 267495), γ-fluoromethotrexate (McGuire et al., *Cancer Res.* 49(16):4517–25, 1989), polyglutamyl methotrexate derivatives (Kumar et al., *Cancer Res.* 46(10):5020–3, 1986), gem-diphosphonate methotrexate analogues (WO 88/06158), α- and γ-substituted methotrexate analogues (Tsushima et al., *Tetrahedron* 44(17):5375–87, 1988), 5-methyl-5-deaza methotrexate analogues (U.S. Pat. No. 4,725, 687), Nδ-acyl-Nα-(4-amino-4-deoxypteroyl)-L-ornithine derivatives (Rosowsky et al., *J. Med. Chem.* 31(7):1332–7, 1988), 8-deaza methotrexate analogues (Kuehl et al., *Cancer*

Res. 48(6):1481–8, 1988), acivicin methotrexate analogue (Rosowsky et al., *J. Med. Chem.* 30(8):1463–9, 1987), polymeric platinol methotrexate derivative (Carraher et al., *Polym. Sci. Technol.* (*Plenum*), 35(*Adv. Biomed. Polym.*): 311–24, 1987), methotrexate-γ-dimyristoylphophatidyletha-nolamine (Kinsky et al., *Biochim. Biophys. Acta* 917(2): 211–18, 1987), methotrexate polyglutamate analogues (Rosowsky et al., Chem. Biol. Pteridines, Pteridines Folic Acid Deriv., Proc. Int. Symp. Pteridines Folic Acid Deriv.: Chem., Biol. Clin. Aspects: 985–8, 1986), poly-γ-glutamyl methotrexate derivatives (Kisliuk et al., Chem. Biol. Pteridines, Pteridines Folic Acid Deriv., Proc. Int. Symp. Pteridines Folic Acid Deriv.: Chem., Biol. Clin. Aspects: 989–92, 1986), deoxyuridylate methotrexate derivatives (Webber et al., Chem. Biol. Pteridines, Pteridines Folic Acid Deriv., Proc. Int. Symp. Pteridines Folic Acid Deriv.: Chem., Biol. Clin. Aspects: 659–62, 1986), iodoacetyl lysine methotrexate analogue (Delcamp et al., Chem. Biol. Pteridines, Pteridines Folic Acid Deriv., Proc. Int. Symp. Pteridines Folic Acid Deriv.: Chem., Biol. Clin. Aspects: 807–9, 1986), 2,.omega.-diaminoalkanoid acid-containing methotrexate analogues (McGuire et al., *Biochem. Pharmacol.* 35(15): 2607–13, 1986), polyglutamate methotrexate derivatives (Kamen & Winick, *Methods Enzymol.* 122 (Vitam. Coenzymes, Pt. G):339–46, 1986), 5-methyl-5-deaza analogues (Piper et al., *J. Med. Chem.* 29(6):1080–7, 1986), quinazoline methotrexate analogue (Mastropaolo et al., *J. Med. Chem.* 29(1):155–8, 1986), pyrazine methotrexate analogue (Lever & Vestal, *J. Heterocycl. Chem.* 22(1):5–6, 1985), cysteic acid and homocysteic acid methotrexate analogues (U.S. Pat. No. 4,490,529), γ-tert-butyl methotrexate esters (Rosowsky et al., *J. Med. Chem.* 28(5):660–7, 1985), fluorinated methotrexate analogues (Tsushima et al., *Heterocycles* 23(1):45–9, 1985), folate methotrexate analogue (Trombe, *J. Bacteriol.* 160(3):849–53, 1984), phosphonoglutamic acid analogues (Sturtz & Guillamot, *Eur. J. Med. Chem.—Chim. Ther.* 19(3):267–73, 1984), poly (L-lysine) methotrexate conjugates (Rosowsky et al., *J. Med. Chem.* 27(7):888–93, 1984), dilysine and trilysine methotrexate derivates (Forsch & Rosowsky, *J. Org. Chem.* 49(7):1305–9, 1984), 7-hydroxymethotrexate (Fabre et al., *Cancer Res.* 43(10):4648–52, 1983), poly-γ-glutamyl methotrexate analogues (Piper & Montgomery, *Adv. Exp. Med. Biol.,* 163 (*Folyl Antifolyl Polyglutamates*):95–100, 1983), 3',5'-dichloromethotrexate (Rosowsky & Yu, *J. Med. Chem.* 26(10):1448–52, 1983), diazoketone and chloromethylketone methotrexate analogues (Gangjee et al., *J. Pharm. Sci.* 71(6):717–19, 1982), 10-propargylaminopterin and alkyl methotrexate homologs (Piper et al., *J. Med. Chem.* 25(7): 877–80, 1982), lectin derivatives of methotrexate (Lin et al., *JNCI* 66(3):523–8, 1981), polyglutamate methotrexate derivatives (Galivan, *Mol. Pharmacol.* 17(1):105–10, 1980), halogentated methotrexate derivatives (Fox, *JNCI* 58(4): J955–8, 1977), 8-alkyl-7,8-dihydro analogues (Chaykovsky et al., *J. Med. Chem.* 20(10):J1323–7, 1977), 7-methyl methotrexate derivatives and dichloromethotrexate (Rosowsky & Chen, *J. Med. Chem.* 17(12):J1308–11, 1974), lipophilic methotrexate derivatives and 3',5'-dichloromethotrexate (Rosowsky, *J. Med. Chem.* 16(10):J1190–3, 1973), deaza amethopterin analogues (Montgomery et al., *Ann. N.Y. Acad. Sci.* 186:J227–34, 1971), MX068 (Pharma Japan, 1658:18, 1999) and cysteic acid and homocysteic acid methotrexate analogues (EPA 0142220);

These compounds are believed to act as antimetabolites of folic acid.

(D) Podophyllotoxins

In another aspect, the therapeutic agent is a Podophyllotoxin, or a derivative or an analogue thereof. Exemplary compounds of this type are etoposide or teniposide, which have the following structures:

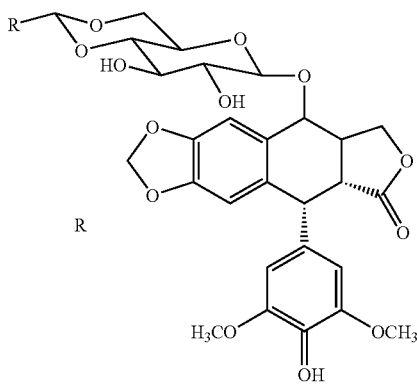

Etoposide  CH₃

Teniposide 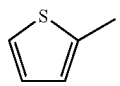

Other representative examples of podophyllotoxins include Cu(II)-VP-16 (etoposide) complex (Tawa et al., *Bioorg. Med. Chem.* 6(7):1003–1008, 1998), pyrrolecarboxamidino-bearing etoposide analogues (Ji et al., *Bioorg. Med. Chem. Lett.* 7(5):607–612, 1997), 4β-amino etoposide analogues (Hu, University of North Carolina Dissertation, 1992), γ-lactone ring-modified arylamino etoposide analogues (Zhou et al., *J. Med. Chem.* 37(2):287–92, 1994), N-glucosyl etoposide analogue (Allevi et al., *Tetrahedron Lett.* 34(45):7313–16, 1993), etoposide A-ring analogues (Kadow et al., *Bioorg. Med. Chem. Lett.* 2(1):17–22, 1992), 4'-deshydroxy-4'-methyl etoposide (Saulnier et al., *Bioorg. Med. Chem. Lett.* 2(10):1213–18, 1992), pendulum ring etoposide analogues (Sinha et al., *Eur. J. Cancer* 26(5): 590–3, 1990) and E-ring desoxy etoposide analogues (Saulnier et al., *J. Med. Chem.* 32(7):1418–20, 1989).

These compounds are believed to act as topoisomerase II inhibitors and/or DNA cleaving agents.

(E) Camptothecins

In another aspect, the therapeutic agent is camptothecin, or an analogue or derivative thereof. Camptothecins have the following general structure.

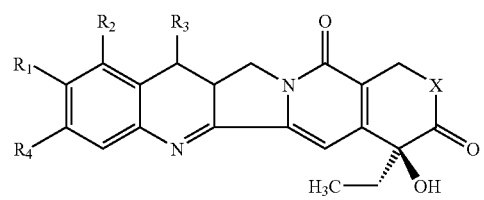

In this structure, X is typically O, but can be other groups, e.g., NH in the case of 21-lactam derivatives. $R_1$ is typically H or OH, but may be other groups, e.g., a terminally hydroxylated $C_{1-3}$ alkane. $R_2$ is typically H or an amino containing group such as $(CH_3)_2NHCH_2$, but may be other groups e.g., $NO_2$, $NH_2$, halogen (as disclosed in, e.g., U.S. Pat. No. 5,552,156) or a short alkane containing these groups. $R_3$ is typically H or a short alkyl such as $C_2H_5$. $R_4$ is typically H but may be other groups, e.g., a methylenedioxy group with $R_1$.

Exemplary camptothecin compounds include topotecan, irinotecan (CPT-11), 9-aminocamptothecin, 21-lactam-20(S)-camptothecin, 10,11-methylenedioxycamptothecin, SN-38, 9-nitrocamptothecin, 10-hydroxycamptothecin. Exemplary compounds have the structures:

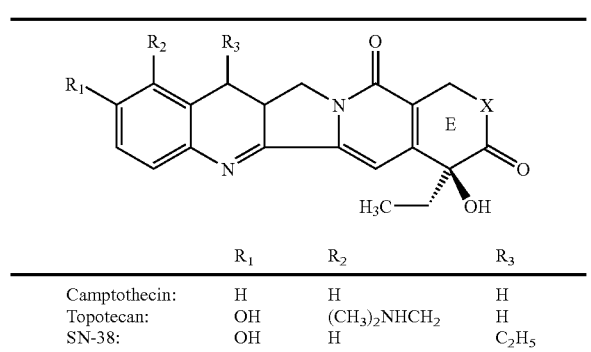

|  | $R_1$ | $R_2$ | $R_3$ |
| --- | --- | --- | --- |
| Camptothecin: | H | H | H |
| Topotecan: | OH | $(CH_3)_2NHCH_2$ | H |
| SN-38: | OH | H | $C_2H_5$ |

X: O for most analogs, NH for 21-lactam analogs

Camptothecins have the five rings shown here. The ring labeled E must be intact (the lactone rather than carboxylate form) for maximum activity and minimum toxicity.

Camptothecins are believed to function as topoisomerase I inhibitors and/or DNA cleavage agents.

(F) Hydroxyureas

The therapeutic agent of the present invention may be a hydroxyurea. Hydroxyureas have the following general structure:

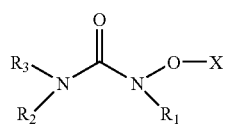

Suitable hydroxyureas are disclosed in, for example, U.S. Pat. No. 6,080,874, wherein $R_1$ is:

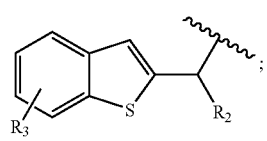

and $R_2$ is an alkyl group having 1–4 carbons and $R_3$ is one of H, acyl, methyl, ethyl, and mixtures thereof, such as a methylether.

Other suitable hydroxyureas are disclosed in, e.g., U.S. Pat. No. 5,665,768, wherein $R_1$ is a cycloalkenyl group, for example N-[3-[5-(4-fluorophenylthio)-furyl]-2-cyclopenten-1-yl]N-hydroxyurea; $R_2$ is H or an alkyl group having 1 to 4 carbons and $R_3$ is H; X is H or a cation.

Other suitable hydroxyureas are disclosed in, e.g., U.S. Pat. No. 4,299,778, wherein $R_1$ is a phenyl group substituted with one or more fluorine atoms; $R_2$ is a cyclopropyl group; and $R_3$ and X is H.

Other suitable hydroxyureas are disclosed in, e.g., U.S. Pat. No. 5,066,658, wherein $R_2$ and $R_3$ together with the adjacent nitrogen form:

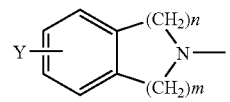

wherein m is 1 or 2, n is 0–2 and Y is an alkyl group.

In one aspect, the hydroxyurea has the structure:

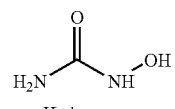

Hydroxyurea

These compounds are thought to function by inhibiting DNA synthesis.

(G) Platinum Complexes

In another aspect, the therapeutic agent is a platinum compound. In general, suitable platinum complexes may be of Pt(II) or Pt(IV) and have this basic structure:

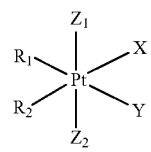

wherein X and Y are anionic leaving groups such as sulfate, phosphate, carboxylate, and halogen; $R_1$ and $R_2$ are alkyl, amine, amino alkyl may be further substituted, and are basically inert or bridging groups. For Pt(II) complexes $Z_1$ and $Z_2$ are non-existent. For Pt(IV) $Z_1$ and $Z_2$ may be anionic groups such as halogen, hydroxy, carboxylate, ester, sulfate or phosphate. See, e.g., U.S. Pat. Nos. 4,588,831 and 4,250,189.

Suitable platinum complexes may contain multiple Pt atoms. See, e.g., U.S. Pat. Nos. 5,409,915 and 5,380,897. For example bisplatinum and triplatinum complexes of the type:

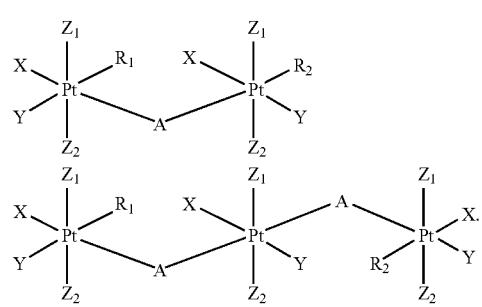

-continued

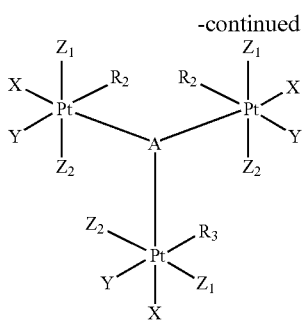

Exemplary platinum compounds are cisplatin, carboplatin, oxaliplatin, and miboplatin having the structures:

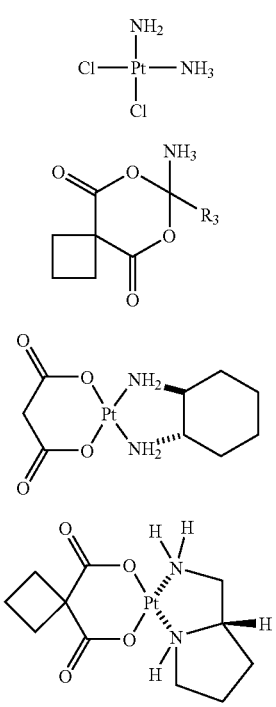

Cisplatin

Carboplatin

Oxaliplatin

Miboplatin

Other representative platinum compounds include (CPA)$_2$Pt[DOLYM] and (DACH)Pt[DOLYM] cisplatin (Choi et al., *Arch. Pharmacal Res.* 22(2):151–156, 1999), Cis-[PtCl$_2$(4,7-H-5-methyl-7-oxo]1,2,4[triazolo[1,5-a]pyrimidine)$_2$] (Navarro et al., *J. Med. Chem.* 41(3):332–338, 1998), [Pt(cis-1,4-DACH)(trans-Cl$_2$)(CBDCA)].½MeOH cisplatin (Shamsuddin et al., *Inorg. Chem.* 36(25):5969–5971, 1997), 4-pyridoxate diammine hydroxy platinum (Tokunaga et al., *Pharm. Sci.* 3(7):353–356, 1997), Pt(II) . . . Pt(II) (Pt$_2$[NHCHN(C(CH$_2$)(CH$_3$))]$_4$) (Navarro et al., *Inorg. Chem.* 35(26):7829–7835, 1996), 254-S cisplatin analogue (Koga et al., *Neurol. Res.* 18(3):244–247, 1996), o-phenylenediamine ligand bearing cisplatin analogues (Koeckerbauer & Bednarski, *J. Inorg. Biochem.* 62(4):281–298, 1996), trans, cis-[Pt(OAc)$_2$I$_2$(en)] (Kratochwil et al., *J. Med. Chem.* 39(13):2499–2507, 1996), estrogenic 1,2-diarylethylenediamine ligand (with sulfur-containing amino acids and glutathione) bearing cisplatin analogues (Bednarski, *J. Inorg. Biochem.* 62(1):75, 1996), cis-1,4-diaminocyclohexane cisplatin analogues (Shamsuddin et al., *J. Inorg. Biochem.* 61(4):291–301, 1996), 5' orientational isomer of cis-[Pt(NH$_3$)(4-amino TEMP-O){d(GpG)}] (Dunham & Lippard, *J. Am. Chem. Soc.* 117(43):10702–12, 1995), chelating diamine-bearing cisplatin analogues (Koeckerbauer & Bednarski, *J. Pharm. Sci.* 84(7):819–23, 1995), 1,2-diarylethyleneamine ligand-bearing cisplatin analogues (Otto et al., *J. Cancer Res. Clin. Oncol.* 121(1):31–8, 1995), (ethylenediamine)platinum(II) complexes (Pasini et al., *J. Chem. Soc., Dalton Trans.* 4:579–85, 1995), CI-973 cisplatin analogue (Yang et al., *Int. J. Oncol.* 5(3):597–602, 1994), cis-diaminedichloroplatinum(II) and its analogues cis-1,1-cyclobutanedicarbosylato(2R)-2-methyl-1,4-butanediamine-platinum(II) and cis-diammine(glycolato)platinum (Claycamp & Zimbrick, *J. Inorg. Biochem.* 26(4):257–67, 1986; Fan et al., *Cancer Res.* 48(11):3135–9, 1988; Heiger-Bemays et al., *Biochemistry* 29(36):8461–6, 1990; Kikkawa et al., *J. Exp. Clin. Cancer Res.* 12(4):233–40, 1993; Murray et al., *Biochemistry* 31(47):11812–17, 1992; Takahashi et al., *Cancer Chemother. Pharmacol.* 33(1):31–5, 1993), cis-amine-cyclohexylamine-dichloroplatinum(II) (Yoshida et al., *Biochem. Pharmacol.* 48(4):793–9, 1994), gem-diphosphonate cisplatin analogues (FR 2683529), (meso-1,2-bis(2,6-dichloro-4-hydroxyplenyl)ethylenediamine) dichloroplatinum(II) (Bednarski et al., *J. Med. Chem.* 35(23):4479–85, 1992), cisplatin analogues containing a tethered dansyl group (Hartwig et al., *J. Am. Chem. Soc.* 114(21):8292–3, 1992), platinum(II) polyamines (Siegmann et al., *Inorg. Met-Containing Polym. Mater.*, (*Proc. Am. Chem. Soc. Int. Symp.*), 335–61, 1990), cis-(3H)dichloro (ethylenediamine)platinum(II) (Eastman, *Anal. Biochem.* 197(2):311–15, 1991), trans-diamminedichloroplatinum(II) and cis-(Pt(NH$_3$)$_2$(N$_3$-cytosine)Cl) (Bellon & Lippard, *Biophys. Chem.* 35(2–3):179–88, 1990), 3H-cis-1,2-diaminocyclohexanedichloroplatinum(II) and 3H-cis-1,2-diaminocyclohexane-malonatoplatinum (II) (Oswald et al., *Res. Commun. Chem. Pathol. Pharmacol.* 64(1):41–58, 1989), diaminocarboxylatoplatinum (EPA 296321), trans-(D,1)-1,2-diaminocyclohexane carrier ligand-bearing platinum analogues (Wyrick & Chaney, *J. Labelled Compd. Radiopharm.* 25(4):349–57, 1988), aminoalkylaminoanthraquinone-derived cisplatin analogues (Kitov et al., *Eur. J. Med. Chem.* 23(4):381–3, 1988), spiroplatin, carboplatin, iproplatin and JM40 platinum analogues (Schroyen et al., *Eur. J. Cancer Clin. Oncol.* 24(8):1309–12, 1988), bidentate tertiary diamine-containing cisplatinum derivatives (Orbell et al., *Inorg. Chim. Acta* 152(2):125–34, 1988), platinum(II), platinum(IV) (Liu & Wang, *Shandong Yike Daxue Xuebao* 24(1):35–41, 1986), cis-diammine(1,1-cyclobutanedicarboxylato-)platinum(II) (carboplatin, JM8) and ethylenediammine-malonatoplatinum(II) (JM40) (Begg et al., *Radiother. Oncol.* 9(2):157–65, 1987), JM8 and JM9 cisplatin analogues (Harstrick et al., *Int. J. Androl.* 10(1); 139–45, 1987), (NPr4)2((PtCL4).cis-(PtCl2-(NH2Me)2)) (Brammer et al., *J. Chem. Soc., Chem. Commun.* 6:443–5, 1987), aliphatic tricarboxylic acid platinum complexes (EPA 185225), and cis-dichloro(amino acid)(tert-butylamine) platinum(II) complexes (Pasini & Bersanetti, *Inorg. Chim. Acta* 107(4):259–67, 1985). These compounds are thought to function by binding to DNA, i.e., acting as alkylating agents of DNA.

Dosing of Therapeutic Agents

As described herein, various compositions and implants may be used for treating a diverticular disease. Because medical implants and compositions are made in a variety of configurations, forms, and sizes, the exact dose of a therapeutic agent administered will vary with the implant size, surface area, design, and portions of the implant coated. In addition, the number and size of diverticula present may be considered when determining the total amount of drug and material administered to a host. However, certain principles can be applied in the application of this art. Drug dose can be calculated as a function of dose per unit area (for example, the portion of the implant being coated), total drug dose administered can be measured, and appropriate surface concentrations of active drug can be determined. Regardless of the method of application of the drug, whether in a composition or applied to the medical implant, the anticancer/anti-infective agents described herein, used alone or in combination, may be administered under the following dosing guidelines.

(a) Anthracyclines. Utilizing the anthracycline doxorubicin as an example, whether applied as a polymer coating, incorporated into the polymers which make up the implant components, or applied with or without a carrier polymer, the total dose of doxorubicin applied to the implant preferably does not exceed 25 mg (range of 0.1 μg to 25 mg). In a particularly preferred embodiment, the total amount of drug applied is in the range of 1 μg to 5 mg. The dose per unit area (i.e., the amount of drug as a function of the surface area of the portion of the implant to which drug is applied and/or incorporated) falls within the range of 0.01 μg–100 μg per mm$^2$ of surface area. In another particularly preferred embodiment, doxorubicin is applied to the diverticular surface at a dose of 0.1 μg/mm$^2$–10 μg/mm$^2$. Because different implants will release doxorubicin at differing rates, the above dosing parameters are preferably used in combination with the release rate of the drug from the implant surface such that a minimum concentration of $10^{-7}$–$10^{-4}$ M of doxorubicin is maintained on the surface. Preferably, surface drug concentrations exceed concentrations of doxorubicin known to be lethal to multiple species of bacteria and fungi (i.e., are in excess of $10^{-4}$ M) although for some embodiments lower concentrations are sufficient. In a preferred embodiment, doxorubicin is released from the surface of the implant such that anti-infective activity is maintained for a period ranging from several hours to several months. In a particularly preferred embodiment the drug is released in effective concentrations for a period ranging from 1 week–6 months. Analogues and derivatives of doxorubicin (as described previously) with similar functional activity can also be utilized for the purposes of this invention; the above dosing parameters are then adjusted according to the relative potency of the analogue or derivative as compared to the parent compound (e.g., a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the implant, or applied with or without a carrier polymer, the total dose of mitoxantrone applied preferably does not exceed 5 mg (range of 0.01 μg to 5 mg). In a particularly preferred embodiment, the total amount of drug applied is in the range of 0.1 μg to 1 mg. The dose per unit area (i.e., the amount of drug as a function of the surface area of the portion of the implant to which drug is applied and/or incorporated) falls within the range of 0.01 μg–20 μg per mm$^2$ of surface area. In a particularly preferred embodiment, mitoxantrone is applied to the diverticular surface at a dose of 0.05 μg/mm$^2$–3 μg/mm$^2$. Because different implants will release mitoxantrone at differing rates, the above dosing parameters are preferably utilized in combination with the release rate of the drug from the implant surface such that a minimum concentration of $10^{-5}$–$10^{-6}$ M of mitoxantrone is maintained. Preferably, drug concentrations on the implant surface exceed concentrations of mitoxantrone known to be lethal to multiple species of bacteria and fungi (i.e., are in excess of $10^{-5}$ M) although for some embodiments lower drug levels will be sufficient. In one embodiment, mitoxantrone is released from the surface of the implant such that anti-infective activity is maintained for a period ranging from several hours to several months. In another embodiment the drug is released in effective concentrations for a period ranging from 1 week–6 months. On the basis of the disclosure provided herein analogues and derivatives of mitoxantrone (as described previously) with similar functional activity can be used for the methods and compositions described herein; the above dosing parameters are then adjusted according to the relative potency of the analogue or derivative as compared to the parent compound (e.g., a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the implant, or applied with or without a carrier polymer, the total dose of 5-fluorouracil applied preferably does not exceed 250 mg (range of 1.0 μg to 250 mg). In a particularly preferred embodiment, the total amount of drug applied is in the range of 10 μg to 25 mg. The dose per unit area (i.e., the amount of drug as a function of the surface area of the portion of the implant to which drug is applied and/or incorporated) falls within the range of 0.1 μg–1 mg per mm$^2$ of surface area. In one embodiment, 5-fluorouracil is applied to the diverticular or implnt surface at a dose of 1.0 μg/mm$^2$–50 μg/mm$^2$. Because different implants will release 5-fluorouracil at differing rates, the above dosing parameters can be used in combination with the release rate of the drug from the implant surface such that a minimum concentration of $10^{-4}$–$10^{-7}$ M of 5-fluorouracil is maintained. Preferably, surface drug concentrations exceed concentrations of 5-fluorouracil known to be lethal to numerous species of bacteria and fungi (i.e., are in excess of $10^{-4}$ M) although for some embodiments lower drug levels will be sufficient. In another embodiment, 5-fluorouracil is released from the implant surface such that anti-infective activity is maintained for a period ranging from several hours to several months. In still another embodiment the drug is released in effective concentrations for a period ranging from 1 week–6 months. Analogues and derivatives of 5-fluorouracil (as described previously) with similar functional activity can be used. The above dosing parameters are then adjusted according to the relative potency of the analogue or derivative as compared to the parent compound (i.e., a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the implant, or applied with or without a carrier polymer, the total dose of etoposide applied preferably does not exceed 25 mg (range of 0.1 μg to 25 mg). In a particularly preferred embodiment, the total amount of drug applied is in the range of 1 μg to 5 mg. The dose per unit area (i.e., the amount of drug as a function of the surface area of the portion of the implant to which drug is applied and/or incorporated) falls within the range of 0.01 μg–100 μg per mm$^2$ of surface area.

In one embodiment, etoposide is applied to the diverticular surface at a dose of 0.1 µg/mm$^2$–10 µg/mm$^2$. The above dosing parameters should be utilized in combination with the release rate of the drug from the implant surface such that a concentration of 10$^{-5}$–10$^{-6}$ M of etoposide is maintained. It is necessary to insure that surface drug concentrations exceed concentrations of etoposide known to be lethal to a variety of bacteria and fungi (i.e., are in excess of 10$^{-5}$ M; although for some embodiments lower drug levels will be sufficient). In one embodiment, etoposide is released from the surface of the implant such that anti-infective activity is maintained for a period ranging from several hours to several months. In another embodiment the drug is released in effective concentrations for a period ranging from 1 week–6 months. On the basis of the description provided herein analogues and derivatives of etoposide (as described previously) with similar functional activity can be used in the compositions and methods described herein. The above dosing parameters are then adjusted according to the relative potency of the analogue or derivative as compared to the parent compound (i.e., a compound twice as potent as etoposide is administered at half the above parameters, a compound half as potent as etoposide is administered at twice the above parameters, etc.).

(d) Haemostatic Agents. Utilizing CoStasis® as an exemplary hemostatic agent, whether it is applied as a polymer coating, incorporated into the polymers which make up an implant, applied as an implant, or applied to tissue, the total volume of CoStasis® delivered as an implant or from an implant or composition, or coated onto the surface of an implant or tissue, preferably does not exceed 25 mL (range of 0.2 mL to 25 mL). In one embodiment, the total amount of CoStasis® in the composition or implant is in the range of 0.5 mL to 15 mL. In another embodiment, the amount per unit area of the implant or tissue (i.e., the amount of CoStasis® as a function of the surface area of the portion of the implant or tissue to which it is applied and/or incorporated) falls within the range of 0.01 mL–5.0 mL per cm$^2$ of surface area coated. In another embodiment, CoStasis® is applied on an implant or tissue surface at a dose of 0.1 mL/cm$^2$–0.5 mL/cm$^2$ of surface area coated. Under circumstances where one or more pharmacological agents is (are) included in the composition, CoStasis® may release such pharmacologically active agent(s) at differing rates, as such, the above dosing parameters are preferably used in combination with the release rate of the drug from the composition or implant such that a minimum concentration of 0.01 nM–1000 µM of pharmacologically active agent is delivered to the tissue. In one embodiment, an agent is released from the surface of an implant such that fibrosis in the diverticulum is promoted for a period ranging from several hours to several months. In another embodiment, an agent is released from the surface of an implant such that bacterial growth is inhibited for a period ranging from several hours to several months. For example, an agent may be released in effective concentrations for a period ranging from 1 hour–30 days. The above dosing parameters of CoStasis® may be adjusted for an analogue or derivative of CoStasis® or of a component of the composition according to the relative potency of the analogue or derivative of the pharmacologically active agent as compared to the parent pharmacologically active agent (e.g., a compound twice as potent is administered at half the above parameters, a compound half as potent may be administered administered at twice the above parameters, etc.).

Utilizing Tisseel® as an exemplary hemostatic agent, whether it is applied as a polymer coating, incorporated into the polymers which make up an implant, applied as an implant, or applied to tissue, the total volume of Tisseel® delivered as an implant or from an implant or composition, or coated onto the surface of an implant or tissue, preferably does not exceed 25 mL (range of 0.2 mL to 25 mL). In one embodiment, the total amount of Tisseel® in the composition or implant is in the range of 0.5 mL to 15 mL. In another embodiment, the amount per unit area of the implant or tissue (i.e., the amount of Tisseel® as a function of the surface area of the portion of the implant or tissue to which it is applied and/or incorporated) falls within the range of 0.01 mL–5.0 mL per cm$^2$ of surface area coated. In another embodiment, Tisseel® is applied on an implant or tissue surface at a dose of 0.1 mL/cm$^2$–0.5 mL/cm$^2$ of surface area coated. Under circumstances when one or more pharmacological agents is (are) included in the composition, Tisseel® may release such pharmacologically active agent(s) at differing rates, as such, the above dosing parameters are preferably used in combination with the release rate of the drug from the composition or implant such that a minimum concentration of 0.01 nM–1000 µM of pharmacologically active agent is delivered to the tissue. In one embodiment, an agent is released from the surface of an implant such that fibrosis in the diverticulum is promoted for a period ranging from several hours to several months. In another embodiment, an agent is released from the surface of an implant such that bacterial growth is inhibited for a period ranging from several hours to several months. For example, an agent may be released in effective concentrations for a period ranging from 1 hour–30 days. The above dosing parameters of Tisseel® may be adjusted for an analogue or derivative of Tisseel® or of a component of Tisseel® according to the relative potency of the analogue or derivative of the pharmacologically active agent as compared to the parent pharmacologically active agent (e.g., a compound twice as potent is administered at half the above parameters, a compound half as potent may be administered administered at twice the above parameters, etc.).

Utilizing FloSeal® as an exemplary hemostatic agent, whether it is applied as a polymer coating, incorporated into the polymers which make up an implant, applied as an implant, or applied to tissue, the total volume of FloSeal® delivered as an implant or from an implant or composition, or coated onto the surface of an implant or tissue, preferably does not exceed 25 mL (range of 0.2 mL to 25 mL). In one embodiment, the total amount of FloSeal® in the composition or implant is in the range of 0.5 mL to 15 mL. In another embodiment, the amount per unit area of the implant or tissue (i.e., the amount of FloSeal® as a function of the surface area of the portion of the implant or tissue to which it is applied and/or incorporated) falls within the range of 0.01 mL–5.0 mL per cm$^2$ of surface area coated. In another embodiment, FloSeal® is applied on an implant or tissue surface at a dose of 0.1 mL/cm$^2$–0.5 mL/cm$^2$ of surface area coated. Under circumstances when one or more pharmacological agents is (are) included in the composition, FloSeal® may release such pharmacologically active agent(s) at differing rates, as such, the above dosing parameters are preferably used in combination with the release rate of the drug from the composition or implant such that a minimum concentration of 0.01 nM–1000 µM of pharmacologically active agent is delivered to the tissue. In one embodiment, an agent is released from the surface of an implant such that fibrosis in the diverticulum is promoted for a period ranging from several hours to several months. In another embodiment, an agent is released from the surface of an implant such that bacterial growth is inhibited for a period ranging from several hours to several months. For example, an agent may be released in effective concentrations for a period ranging from 1 hour–30 days. The above dosing parameters of FloSeal® may be adjusted for an analogue or derivative thereof according to the relative potency of the analogue or derivative of the pharmacologically active agent when compared to the parent pharmacologically active agent (e.g., a compound twice as potent is administered at half the above parameters, a compound half as potent may be administered administered at twice the above parameters, etc.). Utilizing CoSeal® as an exemplary hemostatic agent, whether it is applied as a polymer coating, incorporated into the polymers which make up an implant, applied as an implant, or applied to tissue, the total volume of CoSeal® delivered as an implant or from an implant or composition, or coated onto the surface of an implant or tissue, preferably does not exceed 30 mL (range of 0.2 mL to 30 mL). In one embodiment, the total amount of CoSeal® in the composition or implant is in the range of 0.5 mL to 15 mL. In another embodiment, the amount per unit area of the implant or tissue (i.e., the amount of CoSeal® as a function of the surface area of the portion of the implant or tissue to which it is applied and/or incorporated) falls within the range of 0.01 mL–5.0 mL per $cm^2$ of surface area coated. In another embodiment, CoSeal® is applied on an implant or tissue surface at a dose of 0.1 $mL/cm^2$–0.5 $mL/cm^2$ of surface area coated. Under circumstances when one or more pharmacological agents is (are) included in the composition, CoSeal® may release such pharmacologically active agent(s) at differing rates, as such, the above dosing parameters are preferably used in combination with the release rate of the drug from the composition or implant such that a minimum concentration of 0.01 nM–1000 μM of pharmacologically active agent is delivered to the tissue. In one embodiment, an agent is released from the surface of an implant such that fibrosis in the diverticulum is promoted for a period ranging from several hours to several months. In another embodiment, an agent is released from the surface of an implant such that bacterial growth is inhibited for a period ranging from several hours to several months. For example, an agent may be released in effective concentrations for a period ranging from 1 hour–30 days. The above dosing parameters of CoSeal® may be adjusted for a derivative or analogue of a physiologically active agent of CoSeal® according to the relative potency of the analogue or derivative of the pharmacologically active agent as compared to the parent pharmacologically active agent (e.g., a compound twice as potent is administered at half the above parameters, a compound half as potent may be administered administered at twice the above parameters, etc.).

On the basis of the disclosure provided herein, combinations of anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be used to enhance the antibacterial activity of the diverticular implant. Similarly, anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with traditional antibiotic and/or antifungal agents to enhance efficacy. In another embodiment, the anti-infective agent may be further combined with a fibrosing agent and/or hemostatic agent for the comprehensive management of acute diverticulitis.

Methods for Generating Compositions and Medical Implants that Include a Fibrosis-Inducing Agent Drug-coated, drug-impregnated, or drug containing implants are provided herein that induce adhesion or fibrosis in the diverticular, or facilitate "filling" of the diverticular sac with scar tissue or fibrotic tissue in situ. Within various embodiments, fibrosis is induced by local or regional release of specific pharmacological agents that become localized within the diverticular. Nmerous methods are available for optimizing delivery of the fibrosis-inducing agent to the diverticula, and several of these are described below.

Implants that Contain or Release Fibrosis-Inducing Agents

Medical implants as described herein contain and/or are adapted to release an agent which induces fibrosis or adhesion to the surrounding tissue. Medical implants may be adapted to have incorporated into their structure a fibrosis-inducing agent, adapted to have a surface coating of a fibrosis-inducing agent and/or adapted to release a fibrosis-inducing agent by (a) directly affixing to the implant a desired fibrosis-inducing agent or composition containing the fibrosis-inducing agent (e.g., by either spraying the medical implant with a drug and/or carrier (polymeric or non-polymeric)-drug composition to create a film or coating on all, or parts of the internal or external surface of the implant; by dipping the implant into a drug and/or carrier (polymeric or non-polymeric)-drug solution to coat all or parts of the implant; or by other covalent or non-covalent (e.g., mechanically attached via knotting or the use of an adhesive or thermal treatment, electrostatic, ionic, hydrogen bonded or hydrophobic interactions) attachment of the therapeutic agent to the implant surface); (b) by coating the medical implant with a substance such as a hydrogel which can in turn absorb the desired fibrosis-inducing agent or composition; (c) by interweaving a "thread" composed of, or coated with, the fibrosis-inducing agent into the medical implant (e.g., a polymeric strand composed of materials that induce fibrosis (e.g., silk, collagen, EVA, PLA, polyurethanes, polymerized drug compositions) or polymers which comprise and/or release a fibrosis-inducing agent from the thread); (d) by covering all, or portions of the implant with a sleeve, cover or mesh containing a fibrosis-inducing agent (i.e., a covering comprised of a fibrosis-inducing agent—polymers such as silk, collagen, EVA, PLA, polyurethanes or polymerized compositions containing fibrosis-inducing agents); (e) constructing all, or parts of the implant itself with the desired agent or composition (e.g., constructing the implant from polymers such as silk, collagen, EVA, PLA, polyurethanes or polymerized compositions of fibrosis-inducing agents); (f) otherwise impregnating the implant with the desired fibrosis-inducing agent or composition; (g) scoring (i.e., creating ridges or indentations) on all, or parts, of the implant surface to produce irritation of the tissue and ultimately fibrosis; (h) composing all, or parts, of the implant from metal alloys that induce fibrosis (e.g., copper); (i) constructing all, or parts of the implant itself from a degradable or non-degradable polymer that releases one or more fibrosis-inducing agents; (j) utilizing specialized multi-drug releasing medical implant systems (described, e.g., in U.S. Pat. No. 6,562,065; U.S. Patent Application Publication Nos. 2003/0199970 and 2003/0167085; and in PCT Publication Nos. WO 03/015664 and WO 02/32347) to deliver fibrosis-inducing agents alone or in combination.

Bulking Agents. In one embodiment, an implant is or comprises a bulking agent. A bulking agent refers to a liquid, solid or semi-solid ingredient used either alone or in combination with another material (e.g., a polymer) to partially or fully seal or fill a void (e.g., a diverticulum) or lumen within a host. A bulking agent may be applied directly into the treatment site or may be injected into the tissue immediately surrounding the treatment area. Bulking agent also refers to compound and mixtures that undergo a chemical reaction, precipitation, or crystallization in situ, which can partially or fully seal or fill a void or lumen within a host. Bulking agents can be used to increase the volume, extend, or dilute other solids. A bulking agent may have a fixed volume or may increase in volume as it comes into contact with body fluids in the host and begins to swell. Depending on the method of use, a bulking agent may be in an injectable form (e.g., solution, gel, paste, and the like) or in the form of an implant. For example, the bulking agent may be in the form of a three dimensional object, such as, a film, mesh, microsphere, bead, or another shape). In certain embodiments, the bulking agent may be combined with a polymeric composition (e.g., a gel or hydrogel) to facilitate delivery of the agent into the host.

Representative examples of bulking agents include inorganic materials such as minerals, glasses, ceramics (e.g., ground and powdered ceramics and glasses), clays, calcium carbonate, magnesium carbonate, pumice, talc, zinc oxide, hydroxyapatite, cornstarch, cellulose, wood (e.g., saw dust), naturally occurring materials such as bone, leather, horn, hair, various proteinaceous materials, such as collagen and collagen containing materials (e.g., collagen based injectable products, including those derived from non-bovine, human, or recombinant sources), polysaccharides (e.g., hyaluronic acid), and synthetic polymers (e.g., ethylene vinyl alcohol polymer implant, acrylates, methacrylates, acrylics, polydimethylsiloxane, silicone, and the like).

Bulking agents for use in treating diverticulitis may be combined with one or more fibrosis-inducing agents as described herein. Bulking agents include but are not limited to commercially available products such as collagen-based injectable products, including those derived from non-bovine, human, or recombinant sources; injectable microspheres from Artes Medical, Inc. (San Diego, Calif.); ENTERYX (ethylene vinyl alcohol polymer implant from Boston Scientific Corporation); hydroxyapatite loaded gel (COAPATITE from BioForm Medical, Inc., San Mateo, Calif.); micronized alloderm acellular matrix (CYMETRA from LifeCell Corporation, Branchburg, N.J.); non-animal stabilized hyaluronic acid (NASHA and DEFLUX from Q-Med); pyrolytic carbon-coated micro-beads in hydrogel containing beta-glucan (DURASPHERE from Carbon Medical Technologies, Inc. St. Paul, Minn. and Boston Scientific Corporation, Natick, Mass.); engineered collagen fibrils (Organogenesis, Inc., Canton, Mass.); hylan polymer (HYLAGEL URO from Genzyme); MACROPLASTIQUE (polydimethylsiloxane in hydrogel carrier) from Uroplasty, Inc. (Minneapolis, Minn.); microspheres (e.g., acrylic beads, such as those available from Biosphere Medical, Inc. Marlborough, Mass.); urethral bulking agents containing silk and elastin proteins (Protein Polymer Technologies, San Diego, Calif.); cross-linked silicon microballoon filled with biocompatible polymer (UROVIVE from American Medical Systems, Minnetonka, Minn.); and URYX bulking agent and Embolyx from Microtherapeutics, Inc., San Clemente, Calif. and Genyx Medical, Inc., Aliso Viejo, Calif. Other manufacturers of carriers suitable for use in bulking compositions include C.R. Bard, Inc. (Murray Hill, N.J.), Collagenesis, Inc. (Acton, Mass.), American Medical Systems, Mentor, Uromed Corporation (Norwood, Mass.), Boston Scientific Corporation, Johnson & Johnson (Ethicon, Inc.), Cook Group, Inc. (Bloomington, Ind.), W.L. Gore & Associates, and SURx, Inc. (Pleasonton, Calif.).

Regional and Local Delivery of Fibrosis-Inducing Agents to Diverticucla

A variety of drug-delivery technologies are available for regional and local delivery of therapeutic agents. Several of these techniques may be suitable to achieve preferentially elevated levels of fibrosis-inducing agents within the diverticula, including: (a) using drug-delivery catheters for local or regional delivery of fibrosing agents into the diverticula (typically, drug delivery catheters are advanced into tissues under endoscopic or radiological guidance until they reach the opening of the diverticula; the fibrosing agent can then be released from the catheter lumen in high local concentrations in order to deliver therapeutic doses of the drug to the diverticula); (b) drug localization techniques such as magnetic, ultrasonic or MRI-guided drug delivery; (c) chemical modification of the fibrosis-inducing drug or formulation designed to increase uptake of the agent into the diverticula (e.g., modification of the drug or formulation to include antibodies directed against damaged or healing tissue components such as macrophages, neutrophils, smooth muscle cells, fibroblasts, extracellular matrix components, fibrin, components of the clotting cascade); (d) chemical modification of the fibrosis-inducing drug or formulation designed to localize the drug to areas of bleeding or disrupted vasculature such as encapsulation of the drug into site directed liposomes; and/or (e) microparticulate silk and/or silk strands (e.g., linear, branched, and/or coiled) are also useful for directed delivery (via endoscope or guided catheter) into the diverticula; (f) injectable collagen-containing hemostatic formulations such as COSTASIS (Angiotech Pharmaceuticals, Inc., Vancouver, BC) or materials made from 4-armed thiol PEG (10K), a 4-armed NHS PEG(10K) and methylated collagen (described below), or materials made from 4-armed thiol PEG (10K), a 4-armed NHS PEG(10K) and collagen or gelatin, either alone, or loaded with a fibrosis-inducing agent and/or an anti-infective agent, applied to the diverticula; (g) sprayable in situ forming PEG-containing formulations such as COSEAL (Angiotech Pharmaceuticals, Inc., Canada), FOCALSEAL (Genzyme Corporation, Cambridge, Mass.), SPRAYGEL or DURASEAL (both from Confluent Surgical, Inc., Waltham, Mass.), either alone, or loaded with a fibrosis-inducing agent and/or an anti-infective agent and/or a hemostatic agent, applied to the diverticula; (h) fibrinogen-containing formulations such as FLOSEAL or TISSEAL (both from Baxter Healthcare Corporation; Fremont, Calif.), either alone, or loaded with a fibrosis-inducing agent and/or an anti-infective agent, applied to the diverticula; (i) hyaluronic acid-containing formulations (either non-crosslinked, crosslinked or chemically modified) such as PERLANE or RESTYLANE (both from Q-Med AB, Sweden), HYLAFORM (Inamed Corporation; Santa Barbara, Calif.), SYNVISC (Biomatrix, Inc.; Ridgefied, N.J.), SEPRAFILM or SEPRACOAT (both from Genzyme Corporation; Cambridge, Mass.) loaded with a fibrosis-inducing agent and/or an anti-infective agent and/or a hemostatic agent applied to the diverticula; (j) polymeric gels for surgical implantation such as REPEL (Life Medical Sciences, Inc.; Princeton, N.J.) or FLOWGEL (Baxter Healthcare Corporation, Deerfield, Ill.) loaded with a fibrosis-inducing agent and/or an anti-infective agent and/or a hemostatic agent applied to the diverticula; (k) surgical adhesives containing one or more cyanoacrylate monomers (e.g., methyl cyanoacrylate, ethyl cyanoacrylate, butyl cyanoacrylate, octyl cyanoacrylate, methoxypropyl cyanoacrylate) such as DERMABOND (Johnson & Johnson, Inc.), INDERMIL (United States Surgical; Norwalk, Conn.), GLUSTITCH (Blacklock Medical Products, Inc., Canada) or TISSUMEND II (Veterinary Products Laboratories; Phoenix, Ariz.), VETBOND (3M Company; St. Paul, Minn.), TISSUEMEND (TEI Biosciences, Inc.; Boston, Mass.), HISTOACRYL or HISTOACRYL BLUE (Davis & Geck; St. Louis, Mo.) and ORABASE SOOTHE-N-SEAL LIQUID PROTECTANT (Colgate-Palmolive Company; New York; N.Y.), either alone, or loaded with a fibrosis-inducing agent and/or an anti-infective agent and/or a hemostatic agent, applied to the diverticula; (l) other biocompatible tissue fillers loaded with a fibrosis-inducing agent and/or an anti-infective agent and/or a hemostatic agent, such as those made by BioCure, Inc. (Norcross, Ga.), 3M Company and Neomend, Inc. (Sunnyvale, Calif.), applied to the diverticula; (m) polysaccharide gels such as the ADCON series of gels (Gliatech, Inc.; Cleveland, Ohio) either alone, or loaded with a fibrosis-inducing agent and/or an anti-infective agent and/or a hemostatic agent, applied to the diverticula; (n) films, sponges or meshes such as INTERCEED or VICRYL mesh (Ethicon, Inc., a Johnson & Johnson Company, Somerville, N.J.), and GELFOAM (Pharmacia & Upjohn Company; Kalamazoo, Mich.) either alone, or loaded with a fibrosis-inducing agent and/or an anti-infective agent and/or a hemostatic agent, applied to the diverticula; (o) polymeric (non-crosslinked and crosslinked) strands, braids, fibers, particles, polymeric knitted, woven, non-woven or electrosprayed material (e.g., linear, branched, and/or coiled; hydrogel and non hydrogel coated) are also useful for directed delivery (via endoscope or guided catheter) into the diverticula; and (p) a hydrogel that is formed from an amino-functionalized polyethylene glycol (e.g., 4-armed tetra-amino PEG [10 k]) and a 4-armed NHS functionalized PEG (e.g., pentaerythritol poly(ethylene glycol)ether tetra-succinimidyl glutarate [10 K]). This hydrogel may further contain collagen, methylated collagen and/or gelatin. Other hydrogels can include crosslinked polysaccharides (e.g,. carboxymethyl cellulose, dextran, hyaluronic acid, chitosan, alignate etc), vinyl based crosslinked hydrogels (e.g., polyacrylates, polyacrylic acids, polymethacrylic acids, poly(hydroxyethylmethacrylate)). These hydrogels can further comprise a fibrosis-inducing agent and/or an anti-infective agent and/or a hemostatic agent, and can be applied to the diverticula.

In one embodiment, a mesh or film or other similar material may be inserted or applied to a diverticulum. This mesh, film, or similar material is capable, at least in part, to fill the diverticulum. An in-situ sealant, glue, or embolic agent may be used to maintain the position of the mesh or film in the diverticulum. In other embodiments, a fibrosis-inducing agent, an anti-infective agent, and/or a hemostatic agent, may also be used in combination with the mesh or film. The one or more agents may be applied directly to the diverticular tissue or to the mesh or film according to any of the methods described herein.

In one embodiment, the fibrosis-inducing agent may be delivered to the diverticula as a solution via a catheter inserted into the diverticula under endoscopic or radiographic guidance. The fibrosis-inducing agent can be incorporated directly into the solution to provide a homogeneous solution or dispersion. In certain embodiments, the solution is an aqueous solution. The aqueous solution may further include buffer salts, as well as viscosity modifying agents (e.g., hyaluronic acid, alginates, CMC, and the like). In another aspect of the invention, the solution can include a biocompatible solvent, such as ethanol, DMSO, glycerol, PEG-200, PEG-300 or NMP.

Sustained-Release and Coating Preparations of Fibrosis-Inducing Agents

For many of the aforementioned therapeutic agents, the fibrosis-inducing agent can be incorporated into a carrier so that therapeutic levels can be delivered locally into the diverticula for periods long enough for complete healing and fibrosis to occur (weeks to months). For example, a desired fibrosis-inducing agent may be admixed with, blended with, conjugated to, or, otherwise modified to contain a polymeric composition (which may be either biodegradable or non-biodegradable) or non-polymeric composition in order to release the fibrosis-inducing agent over a period of time. For the above embodiments, biodegradable and non-biodegradable polymers, polymer conjugates as well as non-polymeric materials can be used to accomplish the local delivery of the fibrosis-inducing agent, hemostatic agent and/or anti-infective agent into the diverticula.

Representative examples of biodegradable polymers suitable for the delivery of fibrosis-inducing agents, hemostatic agents and/or anti-infective agents into diverticula include albumin, collagen, gelatin, hyaluronic acid, aliphatic, heteroatomic and aromatic esters of hyaluronic acid, thiol containing hyaluronic acid derivatives, starch, cellulose and cellulose derivatives (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, carboxymethyl dextran, amino-dextran, polysaccharides, fibrinogen, poly(ether ester) multiblock copolymers, based on poly(ethylene glycol) and poly(butylene terephthalate), tyrosine-derived polycarbonates (e.g., U.S. Pat. No. 6,120,491), poly(hydroxyl acids), poly(D,L-lactide), poly(D,L-lactide-co-glycolide), poly(glycolide), poly(hydroxybutyrate), polydioxanone, poly(alkylcarbonate) and poly(orthoesters), polyesters, poly(hydroxyvaleric acid), polydioxanone, poly(ethylene terephthalate), poly(malic acid), poly(tartronic acid), poly(acrylamides), polyanhydrides, poly(ester-amides), poly(ester-imides), poly(ester-ureas), poly(ester-urethane-ureas), poly(anhydride-esters), poly(anhydride-imides), polyphosphazenes, poly(amino acids), poly(alkylene oxide)-poly(ester) block copolymers (e.g., X-Y, X-Y-X or Y-X-Y, where X is a polyalkylene oxide and Y is a polyester (e.g., PLGA, PLA, PCL, polydioxanone and copolymers thereof), and copolymers as well as blends thereof. (see generally, Illum, L., Davids, S. S. (eds.) "Polymers in Controlled Drug Delivery" Wright, Bristol, 1987; Arshady, *J. Controlled Release* 17:1–22, 1991; Pitt, *Int. J. Phar.* 59:173–196,1990; Holland et al., *J. Controlled Release* 4:155–0180, 1986).

Representative examples of non-degradable polymers suitable for the delivery of fibrosis-inducing agents, hemostatic agents and/or anti-infective agents into diverticula include poly(ethylene-co-vinyl acetate) ("EVA") copolymers, silicone rubber, acrylic polymers (e.g., polyacrylic acid, polymethylacrylic acid, polymethylmethacrylate, poly(butyl methacrylate)), poly(alkylcyanoacrylate) (e.g., poly(ethylcyanoacrylate), poly(butylcyanoacrylate), poly(hexylcyanoacrylate), and poly(octylcyanoacrylate)), polyethylene, polypropylene, polyamides (nylon 6,6), polyurethanes (including hydrophilic polyurethanes), poly(ester-urethanes), poly(ether-urethanes), poly(ester-urea), poly(carbonate urethane)s, polyethers (poly(ethylene oxide), poly(propylene oxide), polyoxyalkylene ether block copolymers based on ethylene oxide and propylene oxide such as PLURONICs and PLURONICs R and poly(tetramethylene glycol)), styrene-based polymers (polystyrene, poly(styrene sulfonic acid), poly(styrene)-block-poly(isobutylene)-block-poly(styrene), poly(styrene)-poly(isoprene) block copolymers], and vinyl polymers (polyvinylpyrrolidone, poly(vinyl alcohol), poly(vinyl acetate phthalate) as well as copolymers and blends thereof. Polymers may also be developed which are either anionic (e.g., alginate, carrageenan, carboxymethyl cellulose, poly(acrylamido-2-methyl propane sulfonic acid) and copolymers thereof, poly(methacrylic acid) and copolymers thereof, and poly(acrylic acid) and copolymers thereof, as well as blends thereof) or cationic (e.g., chitosan, poly-L-lysine, polyethylenimine, and poly(allyl amine) and blends thereof (see generally, Dunn et al., *J. Applied Polymer Sci.* 50:353–365, 1993; Cascone et al., *J. Materials Sci.: Materials in Medicine* 5:770–774, 1994; Shiraishi et al., *Biol. Pharm. Bull.* 16(11):1164–1168, 1993; Thacharodi and Rao, *Int'l J. Pharm.* 120:115–118, 1995; Miyazaki et al., *Int'l J. Pharm.* 118:257–263, 1995).

Particularly preferred polymeric carriers for sustained delivery of the afformentioned therapeutic agents into diverticula include poly(ethylene-co-vinyl acetate), cellulose esters (nitrocellulose), poly(hydroxymethacrylate), poly(methylmethacrylate), poly(ethylene-co-acrylic acid), poly(vinylpyrrolidone) polyurethanes (e.g., CHRONOFLEX AL and CHRONOFLEX AR (both from CardioTech International, Inc., Woburn, Mass.) and BIONATE (Polymer Technology Group, Inc., Emeryville, Calif.), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, poly(anhydride esters), poly(ester-amides), poly(ester-ureas), copolymers of poly (caprolactone) or poly (lactic acid) with a polyethylene glycol (e.g., MePEG), polymers that comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2one, poly (alkylene oxide)-poly(ester) block copolymers (e.g., X-Y, X-Y-X, Y-X-Y, R-(Y-X)$_n$, or R-(X-Y)$_n$, where X is a polyalkylene oxide (e.g., poly(ethylene glycol, poly(propylene glycol) and block copolymers of poly(ethylene oxide) and poly(propylene oxide) (e.g., PLURONIC and PLURONIC R series of polymers from BASF Corporation, Mount Olive, N.J.) and Y is a polyester, wherein the polyester may comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2one, silicone rubbers, poly(styrene)block-poly (isobutylene)-block-poly(styrene), poly(acrylate) polymers, and blends, admixtures, or co-polymers of any of the above. Other preferred polymers include collagen, poly(alkylene oxide)-based polymers, polysaccharides such as hyaluronic acid, chitosan and fucans, and copolymers of polysaccharides with degradable polymers, as well as crosslinked compositions of the above.

Other representative polymers capable of sustained localized delivery of fibrosis-inducing agents, hemostatic agents and/or anti-infective agents into diverticula include carboxylic polymers, polyacetates, polyacrylamides, polycarbonates, polyethers, substituted polyethylenes, polyvinylbutyrals, polysilanes, polyureas, polyoxides, polystyrenes, polysulfides, polysulfones, polysulfonides, polyvinylhalides, pyrrolidones, isoprene rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxies, melamines, other amino resins, phenolic polymers, and copolymers thereof, water-insoluble cellulose ester polymers (including cellulose acetate propionate, cellulose acetate, nitrocellulose, cellulose acetate butyrate, cellulose nitrate, cellulose acetate phthalate, and mixtures thereof), polyvinylpyrrolidone (pvp), polyethylene glycols, polyethylene oxides, polyvinyl alcohol, polyethers, polyhydroxyacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, nitro-cellulose, hydroxyethyl cellulose, cellulose nitrate, cellulose acetate, cellulose acetate butyrate, cellulose acetate propionate, polyacrylate, natural and synthetic elastomers, acetal, styrene polybutadiene, acrylic resin, polyvinylidene chloride, polycarbonate, homopolymers and copolymers of vinyl compounds, polyvinylchloride, and polyvinylchloride acetate.

Representative examples of patents relating to drug-delivery polymers and their preparation include PCT Publication Nos. WO 98/19713, WO 01/17575, WO 01/41821, WO 01/41822, and WO 01/15526 (as well as their corresponding U.S. applications), and U.S. Pat. Nos. 4,500,676, 4,582,865, 4,629,623, 4,636,524, 4,713,448, 4,795,741, 4,913,743, 5,069,899, 5,099,013, 5,128,326, 5,143,724, 5,153,174, 5,246,698, 5,266,563, 5,399,351, 5,525,348, 5,800,412, 5,837,226, 5,942,555, 5,997,517, 6,007,833, 6,071,447, 6,090,995, 6,106,473, 6,110,483, 6,121,027, 6,156,345, 6,214,901, 6,368,611 6,630,155, 6,528,080, RE37,950, 6,46, 1631, 6,143,314, 5,990,194, 5,792,469, 5,780,044, 5,759, 563, 5,744,153, 5,739,176, 5,733,950, 5,681,873, 5,599,552, 5,340,849, 5,278,202, 5,278,201, 6,589,549, 6,287,588, 6,201,072, 6,117,949, 6,004,573, 5,702,717, 6,413,539, and 5,714,159, 5,612,052 and U.S. Patent Application Publication Nos. 2003/0068377, 2002/0192286, 2002/0076441, and 2002/0090398.

The polymers as described herein can also be blended or copolymerized in various compositions appropriately to deliver therapeutic doses of fibrosis-inducing agents, hemostatic agents, and/or anti-infective agents to diverticula.

Polymeric carriers for fibrosis-inducing agents, hemostatic agents, and/or anti-infective agents can be fashioned in a variety of forms, with desired release characteristics and/or with specific properties. For example, polymeric carriers may be fashioned to release a therapeutic agent upon exposure to a specific triggering event such as pH (see, e.g., Heller et al., "Chemically Self-Regulated Drug Delivery Systems," in *Polymers in Medicine III*, Elsevier Science Publishers B.V., Amsterdam, 1988, pp. 175–188; Kang et al., *J. Applied Polymer Sci.* 48:343–354, 1993; Dong et al., *J. Controlled Release* 19:171–178, 1992; Dong and Hoffman, *J. Controlled Release* 15:141–152, 1991; Kim et al., *J. Controlled Release* 28:143–152, 1994; Cornejo-Bravo et al., *J. Controlled Release* 33:223–229, 1995; Wu and Lee, *Pharm. Res.* 10(10):1544–1547, 1993; Serres et al., *Pharm. Res.* 13(2):196–201, 1996; Peppas, "Fundamentals of pHand Temperature-Sensitive Delivery Systems," in Gurny et al. (eds.), *Pulsatile Drug Delivery*, Wissenschaftliche Verlagsgesellschaft mbH, Stuttgart, 1993, pp. 41–55; Doelker, "Cellulose Derivatives," 1993, in Peppas and Langer (eds.), *Biopolymers I*, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water-soluble polymer.

Likewise, fibrosis-inducing agents, hemostatic agents, and/or anti-infective agents can be delivered to diverticula via polymeric carriers which are temperature sensitive (see, e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater.* 22:167–168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater.* 22:111–112, Controlled Release Society, Inc., 1995; Johnston et al., *Pharm. Res.* 9(3):425–433, 1992; Tung, *Int'l J. Pharm.* 107:85–90, 1994; Harsh and Gehrke, *J. Controlled Release* 17:175–186, 1991; Bae et al., *Pharm. Res.* 8(4):531–537, 1991; Dinarvand and D'Emanuele, *J. Controlled Release* 36:221–227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, OR, pp. 820–821; Zhou and Smid, "Physical Hydrogels of Associative Star Polymers," Polymer Research Institute, Dept. of Chemistry, College of Environmental Science and Forestry, State Univ. of New York, Syracuse, NY, pp. 822–823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829–830; Kim et al., *Pharm. Res.* 9(3):283–290, 1992; Bae et al., *Pharm. Res.* 8(5):624–628, 1991; Kono et al., *J. Controlled Release* 30:69–75, 1994; Yoshida et al., *J. Controlled Release* 32:97–102, 1994; Okano et al., *J. Controlled Release* 36:125–133, 1995; Chun and Kim, *J. Controlled Release* 38:39–47, 1996; D'Emanuele and Dinarvand, *Int'l J. Pharm.* 118:237–242, 1995; Katono et al., *J. Controlled Release* 16:215–228, 1991; Hoffman, "Thermally Reversible Hydrogels Containing Biologically Active Species," in Migliaresi et al. (eds.), *Polymers in Medicine III*, Elsevier Science Publishers B.V., Amsterdam, 1988, pp. 161–167; Hoffman, "Applications of Thermally Reversible Polymers and Hydrogels in Therapeutics and Diagnostics," in *Third International Symposium on Recent Advances in Drug Delivery Systems*, Salt Lake City, Utah, Feb. 24–27, 1987, pp. 297–305; Gutowska et al., *J. Controlled Release* 22:95–104, 1992; Palasis and Gehrke, *J. Controlled Release* 18:1–12, 1992; Paavola et al., *Pharm. Res.* 12(12):1997–2002, 1995).

Representative examples of thermogelling polymers, and their gelatin temperature [LCST (° C.)] include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N, n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; and poly (N-ethylacrylamide), 72.0. Moreover, thermogelling polymers may be made by preparing copolymers between (among) monomers of the above, or by combining such homopolymers with other water-soluble polymers such as acrylmonomers (e.g., acrylic acid and derivatives thereof, such as methylacrylic acid, acrylate and derivatives thereof, such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, polyalkylene oxide-polyester block copolymers of the structure X-Y, Y-X-Y and X-Y-X where X is a polyalkylene oxide and Y is a biodegradable polyester (e.g., PLG-PEG-PLG) and PLURONICS such as F-127, 10–15° C.; L-122, 19° C.; L-92, 26° C.; L-81, 20° C.; and L-61, 24° C.

Representative examples of patents and patent applications relating to thermally gelling polymers and their preparation include U.S. Pat. Nos. 6,451,346; 6,201,072; 6,117,949; 6,004,573; 5,702,717; and 5,484,610; and PCT Publication Nos. WO 99/07343; WO 99/18142; WO 03/17972; WO 01/82970; WO 00/18821; WO 97/15287; WO 01/41735; WO 00/00222; and WO 00/38651.

Another representative example of a gel composition is a gel formed by the combination of a chitosan solution with glycerol phosphate.

Fibrosis-inducing agents, hemostatic agents, and/or anti-infective agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, and threads of various size, films and sprays.

Within certain embodiments, therapeutic compositions may be fashioned in any size ranging from 50 nm to 500 μm, depending upon the particular use (diverticula can occur in a variety of anatomical sites and sizes to be described below). These compositions can be in the form of microspheres (porous or non-porous), microparticles, and/or nanoparticles. These compositions can be formed, for example, by spray-drying methods, milling methods, coacervation methods, W/O (water-oil) emulsion methods, W/O/W emulsion methods, and solvent evaporation methods. In some embodiments, these compositions can include microemulsions, emulsions, liposomes and micelles. Alternatively, such compositions may also be readily applied as a "spray", which solidifies into a film or tissue surface coating at the implantation site. Such sprays may be prepared from microspheres of a wide array of sizes, including for example, from 0.1 μm to 3 μm, from 10 μm to 30 μm, and from 30 μm to 100 μm, and are ideal for delivery via the delivery port of an endoscope.

Therapeutic compositions of the present invention may also be prepared in a variety of paste or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made utilizing a variety of techniques (see, e.g., PCT Publication WO 98/24427). Other pastes may be applied as a liquid, which solidify in vivo due to dissolution of a water-soluble component of the paste and precipitation of encapsulated drug into the aqueous body environment. These pastes and gels containing fibrosis-inducing agents, hemostatic agents and/or anti-infective agents are particularly useful for application to the lumen of a divertica under radiographic or endoscopic guidance.

Within further aspects of the present invention, polymeric carriers are provided which are adapted to contain and release a hydrophobic fibrosis-inducing, hemostatic and/or anti-infective compound, and/or the carrier containing the hydrophobic compound(s), in combination with a carbohydrate, protein or polypeptide. In certain embodiments, the polymeric carrier provides sustained release for a therapeutic agent (e.g., a fibrosis-inducing agent, anti-infective agent, an antibiotic, or another type of agent) from a composition comprising the carrier and an agent. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic therapeutic compound, followed by incorporation of the matrix within the polymeric carrier. A variety of matrices can be utilized in this regard, including for example, carbohydrates and polysaccharides such as starch, cellulose, dextran, methylcellulose, sodium alginate, heparin, chitosan and hyaluronic acid and proteins or polypeptides such as albumin, collagen, fibrin, and/or gelatin. Within alternative embodiments, hydrophobic compounds may be contained within a hydrophobic core, and this core contained within a hydrophilic shell.

Within another embodiment, the polymeric carriers used to deliver therapeutic agents into the diverticula can be materials that are formed in situ. In one embodiment, the precursors can be monomers or macromers that contain unsaturated groups which can be polymerized or crosslinked. The monomers or macromers can then, for example, be injected into the diverticular sac or onto the surface of the diverticula and polymerized or crosslinked in situ using a radiation source (e.g., visible or UV light) or a free radical system (e.g., potassium persulfate and ascorbic acid or iron and hydrogen peroxide). The polymerization or crosslinking step can be performed immediately prior to, simultaneously to, or post injection of the reagents into the diverticula. Representative examples of compositions that undergo free radical polymerization or crosslinking reactions are described in WO 01/44307, WO 01/68720, WO 02/072166, WO 03/043552, WO 93/17669, and WO 00/64977, U.S. Pat. Nos. 5,900,245; 6,051,248; 6,083,524; 6,177,095; 6,201,065; 6,217,894; 6,639,014; 6,352,710; 6,410,645; 6,531,147; 5,567,435; 5,986,043; and 6,602,975, and U.S. Patent Application Publication Nos. 2002/012796, 2002/0127266, 2002/0151650, 2003/0104032, 2002/0091229, and 2003/0059906.

In another embodiment, the reagents can undergo an electrophilic-nucleophilic reaction to produce a crosslinked matrix. Polymers terminated with nucleophilic groups such as amine, sulfhydryl, hydroxyl, —$PH_2$ or CO—NH—$NH_2$ can be used as the nucleophilic reagents and polymers terminated with electrophilic groups such as succinimidyl, carboxylic acid, aldehyde, epoxide, isocyanate, vinyl, vinyl sulfone, maleimide, —S—S—($C_5H_4N$) or activated esters, such as are used in peptide synthesis can be used as the electrophilic reagents. For example, a 4-armed thiol derivatized poly(ethylene glycol) (e.g., pentaerythritol poly(ethylene glycol)ether tetra-sulfhydryl) can be reacted with a 4 armed NHS-derivatized polyethylene glycol (e.g., pentaerythritol poly(ethylene glycol)ether tetra-succinimidyl glutarate) under basic conditions (pH>about 8). Representative examples of compositions that undergo such electrophilic-nucleophilic crosslinking reactions are described, for example, in U.S. Pat. Nos. 5,752,974; 5,807,581; 5,874,500; 5,936,035; 6,051,648; 6,165,489; 6,312,725; 6,458,889; 6,495,127; 6,534,591; 6,624,245; 6,566,406; 6,610,033; 6,632,457; U.S. Patent Application Publication No. 2003/0077272A1; and co-pending patent applications entitled "Tissue Reactive Compounds and Compositions and Uses Thereof" (U.S. Ser. No. 60/437,384, filed Dec. 30, 2002, and U.S. Ser. No. 60/44,924, filed Jan. 17, 2003) and "Drug Delivery from Rapid Gelling Polymer Composition" (U.S. Ser. No. 60/437,471, filed Dec. 30, 2002, and U.S. Ser. No. 60/440,875, filed Jan. 17, 2003).

In another embodiment, the electrophilic- or nucleophilic-terminated polymers can further comprise a polymer that can enhance the mechanical and/or adhesive properties of the in situ forming compositions. This polymer can be a degradable or non-degradable polymer. For example, the polymer may be collagen or a collagen derivative, for example methylated collagen. An example of an in situ forming composition uses pentaerythritol poly(ethylene glycol)ether tetra-sulfhydryl] (4-armed thiol PEG), pentaerythritol poly(ethylene glycol)ether tetra-succinimidyl glutarate] (4-armed NHS PEG) and methylated collagen as the reactive reagents. This composition, when mixed with the appropriate buffers can produce a crosslinked hydrogel. (See, e.g., U.S. Pat. Nos. 5,874,500; 6,051,648; 6,166,130; 5,565,519 and 6,312,725).

In another embodiment, the in situ forming material polymer can be a polyester. Polyesters that can be used in in situ forming compositions include poly(hydroxyesters). In another embodiment, the polyester can comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2-one. Representative examples of these types of compositions are described in U.S. Pat. Nos. 5,874,500; 5,936,035; 6,312,725; 6,495,127 and PCT Publication Nos. WO 2004/028547.

In another embodiment, the electrophilic-terminated polymer can be partially or completely replaced by a small molecule or oligomer that comprises an electrophilic group (e.g., disuccinimidyl glutarate).

In another embodiment, the nucleophilic-terminated polymer can be partially or completely replaced by a small molecule or oligomer that comprises a nucleophilic group (e.g., dicysteine, dilysine, trilysine, etc.).

Other examples of in situ forming materials that can be used include those based on the crosslinking of proteins (described in, for example, U.S. Pat. Nos. RE38,158; 4,839, 345; 5,514,379, 5,583,114; 6,310,036; 6,458,147; 6,371, 975; U.S. Patent Application Publication Nos. 2004/0063613A1, 2002/0161399A1, and 2001/0018598A1, and PCT Publication Nos. WO 03/090683, WO 01/45761, WO 99/66964, and WO 96/03159) and those based on isocyanate or isothiocyanate capped polymers (see, e.g., PCT Publication No. WO 04/021983).

First and Second Synthetic Polymers

In one embodiment, crosslinked polymer compositions (in other words, crosslinked matrices) are prepared by reacting a first synthetic polymer containing two or more nucleophilic groups with a second synthetic polymer containing two or more electrophilic groups, where the electrophilic groups are capable of covalently binding with the nucleophilic groups. In one embodiment, the first and second polymers are each non-immunogenic. In another embodiment, the matrices are not susceptible to enzymatic cleavage by, e.g., a matrix metalloproteinase (e.g., collagenase) and are therefore expected to have greater long-term persistence in vivo than collagen-based compositions.

As used herein, the term "polymer" refers inter alia to polyalkyls, polyamino acids, polyalkyleneoxides and polysaccharides. Additionally, for external or oral use, the polymer may be polyacrylic acid or carbopol. As used herein, the term "synthetic polymer" refers to polymers that are not naturally occurring and that are produced via chemical synthesis. As such, naturally occurring proteins such as collagen and naturally occurring polysaccharides such as hyaluronic acid are specifically excluded. Synthetic collagen, and synthetic hyaluronic acid, and their derivatives, are included. Synthetic polymers containing either nucleophilic or electrophilic groups are also referred to herein as "multifunctionally activated synthetic polymers." The term "multifunctionally activated" (or, simply, "activated") refers to synthetic polymers which have, or have been chemically modified to have, two or more nucleophilic or electrophilic groups which are capable of reacting with one another (i.e., the nucleophilic groups react with the electrophilic groups) to form covalent bonds. Types of multifunctionally activated synthetic polymers include difunctionally activated, tetrafunctionally activated, and star-branched polymers.

Multifunctionally activated synthetic polymers for use in the present invention must contain at least two, more preferably, at least three, functional groups in order to form a three-dimensional crosslinked network with synthetic polymers containing multiple nucleophilic groups (i.e., "multi-nucleophilic polymers"). In other words, they must be at least difunctionally activated, and are more preferably trifunctionally or tetrafunctionally activated. If the first synthetic polymer is a difunctionally activated synthetic polymer, the second synthetic polymer must contain three or more functional groups in order to obtain a three-dimensional crosslinked network. Most preferably, both the first and the second synthetic polymer contain at least three functional groups.

Synthetic polymers containing multiple nucleophilic groups are also referred to generically herein as "multi-nucleophilic polymers." For use in the present invention, multi-nucleophilic polymers must contain at least two, more preferably, at least three, nucleophilic groups. If a synthetic polymer containing only two nucleophilic groups is used, a synthetic polymer containing three or more electrophilic groups must be used in order to obtain a three-dimensional crosslinked network.

Preferred multi-nucleophilic polymers for use in the compositions and methods of the present invention include synthetic polymers that contain, or have been modified to contain, multiple nucleophilic groups such as primary amino groups and thiol groups. Preferred multi-nucleophilic polymers include: (i) synthetic polypeptides that have been synthesized to contain two or more primary amino groups or thiol groups; and (ii) polyethylene glycols that have been modified to contain two or more primary amino groups or thiol groups. In general, reaction of a thiol group with an electrophilic group tends to proceed more slowly than reaction of a primary amino group with an electrophilic group.

In one embodiment, the multi-nucleophilic polypeptide is a synthetic polypeptide that has been synthesized to incorporate amino acid residues containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000.

Poly(lysine)s for use in the present invention preferably have a molecular weight within the range of about 1,000 to about 300,000; more preferably, within the range of about 5,000 to about 100,000; most preferably, within the range of about 8,000 to about 15,000. Poly(lysine)s of varying molecular weights are commercially available from Peninsula Laboratories, Inc. (Belmont, Calif.) and Aldrich Chemical (Milwaukee, Wis.).

Polyethylene glycol can be chemically modified to contain multiple primary amino or thiol groups according to methods set forth, for example, in Chapter 22 of Poly(ethylene Glycol) Chemistry: Biotechnical and Biomedical Applications, J. Milton Harris, ed., Plenum Press, N.Y. (1992). Polyethylene glycols which have been modified to contain two or more primary amino groups are referred to herein as "multi-amino PEGs." Polyethylene glycols which have been modified to contain two or more thiol groups are referred to herein as "multi-thiol PEGs." As used herein, the term "polyethylene glycol(s)" includes modified and or derivatized polyethylene glycol(s).

Various forms of multi-amino PEG are commercially available from Shearwater Polymers (Huntsville, Ala.) and from Huntsman Chemical Company (Utah) under the name "Jeffamine." Multi-amino PEGs useful in the present invention include Huntsman's Jeffamine diamines ("D" series) and triamines ("T" series), which contain two and three primary amino groups per molecule, respectively.

Polyamines such as ethylenediamine ($H_2N-CH_2-CH_2-NH_2$), tetramethylenediamine ($H_2N-(CH_2)_4-NH_2$), pentamethylenediamine (cadaverine) ($H_2N-(CH_2)_5-NH_2$), hexamethylenediamine ($H_2N-(CH_2)_6-NH_2$), di(2-aminoethyl)amine ($HN-(CH_2-CH_2-NH_2)_2$), and tris(2-aminoethyl)amine ($N-(CH_2-CH_2-NH_2)_3$) may also be used as the synthetic polymer containing multiple nucleophilic groups.

Synthetic polymers containing multiple electrophilic groups are also referred to herein as "multi-electrophilic polymers." For use in the present invention, the multifunctionally activated synthetic polymers must contain at least two, more preferably, at least three, electrophilic groups in order to form a three-dimensional crosslinked network with multi-nucleophilic polymers. Preferred multi-electrophilic polymers for use in the compositions of the invention are polymers which contain two or more succinimidyl groups capable of forming covalent bonds with nucleophilic groups on other molecules. Succinimidyl groups are highly reactive with materials containing primary amino ($NH_2$) groups, such as multi-amino PEG, poly(lysine), or collagen. Succinimidyl groups are slightly less reactive with materials containing thiol (SH) groups, such as multi-thiol PEG or synthetic polypeptides containing multiple cysteine residues.

As used herein, the term "containing two or more succinimidyl groups" is meant to encompass polymers which are preferably commercially available containing two or more succinimidyl groups, as well as those that must be chemically derivatized to contain two or more succinimidyl groups. As used herein, the term "succinimidyl group" is intended to encompass sulfosuccinimidyl groups and other such variations of the "generic" succinimidyl group. The presence of the sodium sulfite moiety on the sulfosuccinimidyl group serves to increase the solubility of the polymer.

Hydrophilic polymers and, in particular, various derivatized polyethylene glycols, are preferred for use in the compositions of the present invention. As used herein, the term "PEG" refers to polymers having the repeating structure $(OCH_2—CH_2)_n$. Structures for some specific, tetrafunctionally activated forms of PEG are shown in FIGS. 4 to 13 of U.S. Pat. No. 5,874,500, incorporated herein by reference. Examples of suitable PEGS include PEG succinimidyl propionate (SE-PEG), PEG succinimidyl succinamide (SSA-PEG), and PEG succinimidyl carbonate (SC-PEG). In one aspect of the invention, the crosslinked matrix is formed in situ by reacting pentaerythritol poly(ethylene glycol)ether tetra-sulfhydryl] (4-armed thiol PEG) and pentaerythritol poly(ethylene glycol)ether tetra-succinimidyl glutarate] (4-armed NHS PEG) as reactive reagents. Structures for these reactants are shown in U.S. Pat. No. 5,874,500. Each of these materials has a core with a structure that may be seen by adding ethylene oxide-derived residues to each of the hydroxyl groups in pentaerythritol, and then derivatizing the terminal hydroxyl groups (derived from the ethylene oxide) to contain either thiol groups (so as to form 4-armed thiol PEG) or N-hydroxysuccinimydyl groups (so as to form 4-armed NHS PEG), optionally with a linker group present between the ethylene oxide derived backbone and the reactive functional group, where this product is commercially available as COSEAL from Angiotech Pharmaceuticals Inc. Optionally, a group "D" may be present in one or both of these molecules, as discussed in more detail below.

As discussed above, preferred activated polyethylene glycol derivatives for use in the invention contain succinimidyl groups as the reactive group. However, different activating groups can be attached at sites along the length of the PEG molecule. For example, PEG can be derivatized to form functionally activated PEG propionaldehyde (A-PEG), or functionally activated PEG glycidyl ether (E-PEG), or functionally activated PEG-isocyanate (I-PEG), or functionally activated PEG-vinylsulfone (V-PEG).

Hydrophobic polymers can also be used to prepare the compositions of the present invention. Hydrophobic polymers for use in the present invention preferably contain, or can be derivatized to contain, two or more electrophilic groups, such as succinimidyl groups, most preferably, two, three, or four electrophilic groups. As used herein, the term "hydrophobic polymer" refers to polymers which contain a relatively small proportion of oxygen or nitrogen atoms.

Hydrophobic polymers which already contain two or more succinimidyl groups include, without limitation, disuccinimidyl suberate (DSS), bis(sulfosuccinimidyl) suberate (BS3), dithiobis(succinimidylpropionate) (DSP), bis(2-succinimidooxycarbonyloxy) ethyl sulfone (BSOCOES), and 3,3'-dithiobis(sulfosuccinimidylpropionate) (DTSPP), and their analogs and derivatives. The above-referenced polymers are commercially available from Pierce (Rockford, Ill.), under catalog Nos. 21555, 21579, 22585, 21554, and 21577, respectively.

Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing multiple nucleophilic groups.

Certain polymers, such as polyacids, can be derivatized to contain two or more functional groups, such as succinimidyl groups. Polyacids for use in the present invention include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid). Many of these polyacids are commercially available from DuPont Chemical Company (Wilmington, Del.). According to a general method, polyacids can be chemically derivatized to contain two or more succinimidyl groups by reaction with an appropriate molar amount of N-hydroxysuccinimide (NHS) in the presence of N,N'-dicyclohexylcarbodiimide (DCC).

Polyalcohols such as trimethylolpropane and di(trimethylol propane) can be converted to carboxylic acid form using various methods, then further derivatized by reaction with NHS in the presence of DCC to produce trifunctionally and tetrafunctionally activated polymers, respectively, as described in U.S. application Ser. No. 08/403,358. Polyacids such as heptanedioic acid $(HOOC—(CH_2)_5—COOH)$, octanedioic acid $(HOOC—(CH_2)_6—COOH)$, and hexadecanedioic acid $(HOOC—(CH_2)_{14}—COOH)$ are derivatized by the addition of succinimidyl groups to produce difunctionally activated polymers.

Polyamines such as ethylenediamine, tetramethylenediamine, pentamethylenediamine (cadaverine), hexamethylenediamine, bis (2-aminoethyl)amine, and tris(2-aminoethyl)amine can be chemically derivatized to polyacids, which can then be derivatized to contain two or more succinimidyl groups by reacting with the appropriate molar amounts of N-hydroxysuccinimide in the presence of DCC, as described in U.S. application Ser. No. 08/403,358. Many of these polyamines are commercially available from DuPont Chemical Company.

In a preferred embodiment, the first synthetic polymer will contain multiple nucleophilic groups (represented below as "X") and it will react with the second synthetic polymer containing multiple electrophilic groups (represented below as "Y"), resulting in a covalently bound polymer network, as follows:

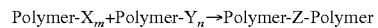

Polymer-$X_m$+Polymer-$Y_n$→Polymer-Z-Polymer wherein m≦2, n≦2, and m+n≦5;

where exemplary X groups include —$NH_2$, —SH, —OH, —$PH_2$, CO—NH—$NH_2$, etc., where the X groups may be the same or different in polymer-$X_m$;

where exemplary Y groups include —$CO_2$—$N(COCH_2)_2$, —$CO_2H$, —CHO, —$CHOCH_2$ (epoxide), —N=C=O, —$SO_2$—CH=$CH_2$, —$N(COCH)_2$ (i.e., a five-membered heterocyclic ring with a double bond present between the two CH groups), —S—S—$(C_5H_4N)$, etc., where the Y groups may be the same or different in polymer-$Y_n$; and where Z is the functional group resulting from the union of a nucleophilic group (X) and an electrophilic group (Y).

As noted above, it is also contemplated by the present invention that X and Y may be the same or different, i.e., a synthetic polymer may have two different electrophilic groups, or two different nucleophilic groups, such as with glutathione.

In one embodiment, the backbone of at least one of the synthetic polymers comprises alkylene oxide residues, e.g., residues from ethylene oxide, propylene oxide, and mixtures thereof. The term 'backbone' refers to a significant portion of the polymer.

For example, the synthetic polymer containing alkylene oxide residues may be described by the formula X-polymer-X or Y-polymer-Y, wherein X and Y are as defined above, and the term "polymer" represents —$(CH_2CH_2O)_n$— or —$(CH(CH_3)CH_2\ O)_n$— or —$(CH_2$—$CH_2$-$O)_n$—$(CH(CH_3)CH_2$—$O)_n$—. In these cases the synthetic polymer would be difunctional.

The required functional group X or Y is commonly coupled to the polymer backbone by a linking group (represented below as "Q"), many of which are known or possible. There are many ways to prepare the various functionalized polymers, some of which are listed below:

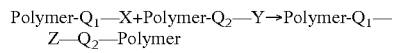

Exemplary Q groups include —O—$(CH_2)_n$—; —S—$(CH_2)_n$—; —NH—$(CH_2)_n$—; —$O_2C$—NH—$(CH_2)_n$—; —$O_2C$—$(CH_2)_n$—; —$O_2C$—$(CR^1H)_n$—; and —O—$R_2$—CO—NH—, which provide synthetic polymers of the partial structures: polymer-O—$(CH_2)_n$—(X or Y); polymer-S—$(CH_2)_n$—(X or Y); polymer-NH—$(CH_2)_n$—(X or Y); polymer-$O_2C$—NH—$(CH_2)_n$—(X or Y); polymer-$O_2C$—$(CH_2)_n$—(X or Y); polymer-$O_2C$—$(CR^1H)_n$—(X or Y); and polymer-O—$R_2$—CO—NH—(X or Y), respectively. In these structures, n=1–10, $R^1$=H or alkyl (i.e., $CH_3$, $C_2H_5$, etc.); $R^2$=$CH_2$, or CO—NH—$CH_2CH_2$; and $Q_1$ and $Q_2$ may be the same or different.

For example, when $Q_2$=$OCH_2CH_2$ (there is no $Q_1$ in this case); Y=—$CO_2$—$N(COCH_2)_2$; and X=—$NH_2$, —SH, or —OH, the resulting reactions and Z groups would be as follows:

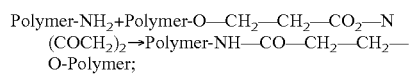

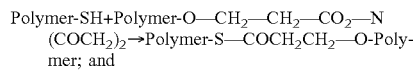

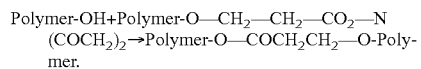

An additional group, represented below as "D", can be inserted between the polymer and the linking group, if present. One purpose of such a D group is to affect the degradation rate of the crosslinked polymer composition in vivo, for example, to increase the degradation rate, or to decrease the degradation rate. This may be useful in many instances, for example, when drug has been incorporated into the matrix, and it is desired to increase or decrease polymer degradation rate so as to influence a drug delivery profile in the desired direction. An illustration of a crosslinking reaction involving first and second synthetic polymers each having D and Q groups is shown below.

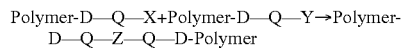

Some useful biodegradable groups "D" include polymers formed from one or more α-hydroxy acids, e.g., lactic acid, glycolic acid, and the cyclization products thereof (e.g., lactide, glycolide), ε-caprolactone, and amino acids. The polymers may be referred to as polylactide, polyglycolide, poly(co-lactide-glycolide); poly-ε-caprolactone, polypeptide (also known as poly amino acid, for example, various di- or tri-peptides) and poly(anhydride)s.

In a general method for preparing the crosslinked polymer compositions used in the context of the present invention, a first synthetic polymer containing multiple nucleophilic groups is mixed with a second synthetic polymer containing multiple electrophilic groups. Formation of a three-dimensional crosslinked network occurs as a result of the reaction between the nucleophilic groups on the first synthetic polymer and the electrophilic groups on the second synthetic polymer.

The concentrations of the first synthetic polymer and the second synthetic polymer used to prepare the compositions of the present invention will vary depending upon a number of factors, including the types and molecular weights of the particular synthetic polymers used and the desired end use application. In general, when using multi-amino PEG as the first synthetic polymer, it is preferably used at a concentration in the range of about 0.5 to about 20 percent by weight of the final composition, while the second synthetic polymer is used at a concentration in the range of about 0.5 to about 20 percent by weight of the final composition. For example, a final composition having a total weight of 1 gram (1000 milligrams) would contain between about 5 to about 200 milligrams of multi-amino PEG, and between about 5 to about 200 milligrams of the second synthetic polymer.

Use of higher concentrations of both first and second synthetic polymers will result in the formation of a more tightly crosslinked network, producing a stiffer, more robust gel. Compositions intended for use in tissue augmentation will generally employ concentrations of first and second synthetic polymer that fall toward the higher end of the preferred concentration range. Compositions intended for use as bioadhesives or in adhesion prevention do not need to be as firm and may therefore contain lower polymer concentrations.

Because polymers containing multiple electrophilic groups will also react with water, the second synthetic polymer is generally stored and used in sterile, dry form to prevent the loss of crosslinking ability due to hydrolysis which typically occurs upon exposure of such electrophilic groups to aqueous media. Processes for preparing synthetic hydrophilic polymers containing multiple electrophylic groups in sterile, dry form are set forth in U.S. Pat. No. 5,643,464. For example, the dry synthetic polymer may be compression molded into a thin sheet or membrane, which can then be sterilized using gamma or, preferably, e-beam irradiation. The resulting dry membrane or sheet can be cut to the desired size or chopped into smaller size particulates. In contrast, polymers containing multiple nucleophilic groups are generally not water-reactive and can therefore be stored in aqueous solution.

In certain embodiments, one or both of the electrophilic- or nucleophilic-terminated polymers described above can be combined with a synthetic or naturally occurring polymer. The presence of the synthetic or naturally occurring polymer may enhance the mechanical and/or adhesive properties of the in situ forming compositions. Naturally occurring polymers, and polymers derived from naturally occurring polymer that may be included in in situ forming materials include naturally occurring proteins, such as collagen, collagen derivatives (such as methylated collagen), fibrinogen, thrombin, albumin, fibrin, and derivatives of and naturally occurring polysaccharides, such as glycosaminoglycans, including deacetylated and desulfated glycosaminoglycan derivatives.

In one aspect, a composition comprising naturally-occurring protein and both of the first and second synthetic polymer as described above is used to form the crosslinked matrix according to the present invention. In one aspect, a composition comprising collagen and both of the first and second synthetic polymer as described above is used to form the crosslinked matrix according to the present invention. In one aspect, a composition comprising methylated collagen and both of the first and second synthetic polymer as described above is used to form the crosslinked matrix according to the present invention. In one aspect, a composition comprising fibrinogen and both of the first and second synthetic polymer as described above is used to form the crosslinked matrix according to the present invention. In one aspect, a composition comprising thrombin and both of the first and second synthetic polymer as described above is used to form the crosslinked matrix according to the present invention. In one aspect, a composition comprising albumin and both of the first and second synthetic polymer as described above is used to form the crosslinked matrix according to the present invention. In one aspect, a composition comprising fibrin and both of the first and second synthetic polymer as described above is used to form the crosslinked matrix according to the present invention. In one aspect, a composition comprising naturally occurring polysaccharide and both of the first and second synthetic polymer as described above is used to form the crosslinked matrix according to the present invention. In one aspect, a composition comprising glycosaminoglycan and both of the first and second synthetic polymer as described above is used to form the crosslinked matrix according to the present invention. In one aspect, a composition comprising deacetylated glycosaminoglycan and both of the first and second synthetic polymer as described above is used to form the crosslinked matrix according to the present invention. In one aspect, a composition comprising desulfated glycosaminoglycan and both of the first and second synthetic polymer as described above is used to form the crosslinked matrix according to the present invention.

In one aspect, a composition comprising naturally-occurring protein and the first synthetic polymer as described above is used to form the crosslinked matrix according to the present invention. In one aspect, a composition comprising collagen and the first synthetic polymer as described above is used to form the crosslinked matrix according to the present invention. In one aspect, a composition comprising methylated collagen and the first synthetic polymer as described above is used to form the crosslinked matrix according to the present invention. In one aspect, a composition comprising fibrinogen and the first synthetic polymer as described above is used to form the crosslinked matrix according to the present invention. In one aspect, a composition comprising thrombin and the first synthetic polymer as described above is used to form the crosslinked matrix according to the present invention. In one aspect, a composition comprising albumin and the first synthetic polymer as described above is used to form the crosslinked matrix according to the present invention. In one aspect, a composition comprising fibrin and the first synthetic polymer as described above is used to form the crosslinked matrix according to the present invention. In one aspect, a composition comprising naturally occurring polysaccharide and the first synthetic polymer as described above is used to form the crosslinked matrix according to the present invention. In one aspect, a composition comprising glycosaminoglycan and the first synthetic polymer as described above is used to form the crosslinked matrix according to the present invention. In one aspect, a composition comprising deacetylated glycosaminoglycan and the first synthetic polymer as described above is used to form the crosslinked matrix according to the present invention. In one aspect, a composition comprising desulfated glycosaminoglycan and the first synthetic polymer as described above is used to form the crosslinked matrix according to the present invention.

In one aspect, a composition comprising naturally-occurring protein and the second synthetic polymer as described above is used to form the crosslinked matrix according to the present invention. In one aspect, a composition comprising collagen and the second synthetic polymer as described above is used to form the crosslinked matrix according to the present invention. In one aspect, a composition comprising methylated collagen and the second synthetic polymer as described above is used to form the crosslinked matrix according to the present invention. In one aspect, a composition comprising fibrinogen and the second synthetic polymer as described above is used to form the crosslinked matrix according to the present invention. In one aspect, a composition comprising thrombin and the second synthetic polymer as described above is used to form the crosslinked matrix according to the present invention. In one aspect, a composition comprising albumin and the second synthetic polymer as described above is used to form the crosslinked matrix according to the present invention. In one aspect, a composition comprising fibrin and the second synthetic polymer as described above is used to form the crosslinked matrix according to the present invention. In one aspect, a composition comprising naturally occurring polysaccharide and the second synthetic polymer as described above is used to form the crosslinked matrix according to the present invention. In one aspect, a composition comprising glycosaminoglycan and the second synthetic polymer as described above is used to form the crosslinked matrix according to the present invention. In one aspect, a composition comprising deacetylated glycosaminoglycan and the second synthetic polymer as described above is used to form the crosslinked matrix according to the present invention. In one aspect, a composition comprising desulfated glycosaminoglycan and the second synthetic polymer as described above is used to form the crosslinked matrix according to the present invention.

The presence of protein or polysaccharide components which contain functional groups that can react with the functional groups on multiple activated synthetic polymers can result in formation of a crosslinked synthetic polymer-naturally occurring polymer matrix upon mixing and/or crosslinking of the synthetic polymer(s). In particular, when the naturally occurring polymer (protein or polysaccharide) also contains nucleophilic groups such as primary amino groups, the electrophilic groups on the second synthetic polymer will react with the primary amino groups on these components, as well as the nucleophilic groups on the first synthetic polymer, to cause these other components to become part of the polymer matrix. For example, lysine-rich proteins such as collagen may be especially reactive with electrophilic groups on synthetic polymers.

In one aspect, the naturally occurring protein is polymer may be collagen. As used herein, the term "collagen" or "collagen material" refers to all forms of collagen, including those which have been processed or otherwise modified and is intended to encompass collagen of any type, from any source, including, but not limited to, collagen extracted from tissue or produced recombinantly, collagen analogues, collagen derivatives, modified collagens, and denatured collagens, such as gelatin.

In general, collagen from any source may be included in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. U.S. Pat. No. 5,428,022 discloses methods of extracting and purifying collagen from the human placenta. U.S. Pat. No. 5,667,839, discloses methods of producing recombinant human collagen in the milk of transgenic animals, including transgenic cows. Collagen of any type, including, but not limited to, types I, II, III, IV, or any combination thereof, may be used in the compositions of the invention, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from Inamed Aesthetics (Santa Barbara, Calif.) at collagen concentrations of 35 mg/ml and 65 mg/ml under the trademarks ZYDERM I Collagen and ZYDERM II Collagen, respectively. Glutaraldehyde crosslinked atelopeptide fibrillar collagen is commercially available from Inamed Corporation (Santa Barbara, Calif.) at a collagen concentration of 35 mg/ml under the trademark ZYPLAST Collagen.

Collagens for use in the present invention are generally in aqueous suspension at a concentration between about 20 mg/ml to about 120 mg/ml; preferably, between about 30 mg/ml to about 90 mg/ml.

Because of its tacky consistency, nonfibrillar collagen may be preferred for use in compositions that are intended for use as bioadhesives. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is particularly preferred for use in bioadhesive compositions, as disclosed in U.S. application Ser. No. 08/476,825.

Collagens for use in the crosslinked polymer compositions of the present invention may start out in fibrillar form, then be rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids (e.g., arginine), inorganic salts (e.g., sodium chloride and potassium chloride), and carbohydrates (e.g., various sugars including sucrose).

In one aspect, the polymer may be collagen or a collagen derivative, for example methylated collagen. An example of an in situ forming composition uses pentaerythritol poly (ethylene glycol)ether tetra-sulfhydryl] (4-armed thiol PEG), pentaerythritol poly(ethylene glycol)ether tetra-succinimidyl glutarate] (4-armed NHS PEG) and methylated collagen as the reactive reagents. This composition, when mixed with the appropriate buffers can produce a crosslinked hydrogel. (See, e.g., U.S. Pat. Nos. 5,874,500; 6,051,648; 6,166,130; 5,565,519 and 6,312,725).

In another aspect, the naturally occurring polymer may be a glycosaminoglycan. Glycosaminoglycans, e.g., hyaluronic acid, contain both anionic and cationic functional groups along each polymeric chain, which can form intramolecular and/or intermolecular ionic crosslinks, and are responsible for the thixotropic (or shear thinning) nature of hyaluronic acid.

In certain aspects, the glycosaminoglycan may be derivatized. For example, glycosaminoglycans can be chemically derivatized by, e.g., deacetylation, desulfation, or both in order to contain primary amino groups available for reaction with electrophilic groups on synthetic polymer molecules. Glycosaminoglycans that can be derivatized according to either or both of the aforementioned methods include the following: hyaluronic acid, chondroitin sulfate A, chondroitin sulfate B (dermatan sulfate), chondroitin sulfate C, chitin (can be derivatized to chitosan), keratan sulfate, keratosulfate, and heparin. Derivatization of glycosaminoglycans by deacetylation and/or desulfation and covalent binding of the resulting glycosaminoglycan derivatives with synthetic hydrophilic polymers is described in further detail in commonly assigned, allowed U.S. patent application Ser. No. 08/146,843, filed Nov. 3, 1993.

In general, the collagen is added to the first synthetic polymer, then the collagen and first synthetic polymer are mixed thoroughly to achieve a homogeneous composition. The second synthetic polymer is then added and mixed into the collagen/first synthetic polymer mixture, where it will covalently bind to primary amino groups or thiol groups on the first synthetic polymer and primary amino groups on the collagen, resulting in the formation of a homogeneous crosslinked network. Various deacetylated and/or desulfated glycosaminoglycan derivatives can be incorporated into the composition in a similar manner as that described above for collagen. In addition, the introduction of hydrocolloids such as carboxymethylcellulose may promote tissue adhesion and/or swellability.

Administration of the Crosslinked Synthetic Polymer Compositions

The compositions of the present invention having two synthetic polymers may be administered before, during or after crosslinking of the first and second synthetic polymer. Certain uses, which are discussed in greater detail below, such as tissue augmentation, may require the compositions to be crosslinked before administration, whereas other applications, such as tissue adhesion, require the compositions to be administered before crosslinking has reached "equilibrium." The point at which crosslinking has reached equilibrium is defined herein as the point at which the composition no longer feels tacky or sticky to the touch.

In order to administer the composition prior to crosslinking, the first synthetic polymer and second synthetic polymer may be contained within separate barrels of a dual-compartment syringe. In this case, the two synthetic polymers do not actually mix until the point at which the two polymers are extruded from the tip of the syringe needle into the patient's tissue. This allows the vast majority of the crosslinking reaction to occur in situ, avoiding the problem of needle blockage which commonly occurs if the two synthetic polymers are mixed too early and crosslinking between the two components is already too advanced prior to delivery from the syringe needle. The use of a dual-compartment syringe, as described above, allows for the use of smaller diameter needles, which is advantageous when performing soft tissue augmentation in delicate facial tissue, such as that surrounding the eyes.

Alternatively, the first synthetic polymer and second synthetic polymer may be mixed according to the methods described above prior to delivery to the tissue site, then injected to the desired tissue site immediately (preferably, within about 60 seconds) following mixing.

In another embodiment of the invention, the first synthetic polymer and second synthetic polymer are mixed, then extruded and allowed to crosslink into a sheet or other solid form. The crosslinked solid is then dehydrated to remove substantially all unbound water. The resulting dried solid may be ground or comminuted into particulates, then suspended in a nonaqueous fluid carrier, including, without limitation, hyaluronic acid, dextran sulfate, dextran, succinylated noncrosslinked collagen, methylated noncrosslinked collagen, glycogen, glycerol, dextrose, maltose, triglycerides of fatty acids (such as corn oil, soybean oil, and sesame oil), and egg yolk phospholipid. The suspension of particulates can be injected through a small-gauge needle to a tissue site. Once inside the tissue, the crosslinked polymer particulates will rehydrate and swell in size at least five-fold.

Hydrophilic Polymer+Plurality of Crosslinkable Components

As mentioned above, the first and/or second synthetic polymers may be combined with a hydrophilic polymer, e.g., collagen or methylated collagen, to form a composition useful in the present invention. In one general embodiment, the compositions useful in the present invention include a hydrophilic polymer in combination with two or more crosslinkable components. This embodiment is described in further detail in this section.

The Hydrophilic Polymer Component:

The hydrophilic polymer component may be a synthetic or naturally occurring hydrophilic polymer. Naturally occurring hydrophilic polymers include, but are not limited to: proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen (e.g., methylated collagen) and glycosaminoglycans are preferred naturally occurring hydrophilic polymers for use herein.

In general, collagen from any source may be used in the composition of the method; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. See, e.g., U.S. Pat. No. 5,428,022, to Palefsky et al., which discloses methods of extracting and purifying collagen from the human placenta. See also U.S. Pat. No. 5,667,839, to Berg, which discloses methods of producing recombinant human collagen in the milk of transgenic animals, including transgenic cows. Unless otherwise specified, the term "collagen" or "collagen material" as used herein refers to all forms of collagen, including those that have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used; however, when collagen from a source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from McGhan Medical Corporation (Santa Barbara, Calif.) at collagen concentrations of 35 mg/ml and 65 mg/ml under the trademarks ZYDERM® I Collagen and ZYDERM® II Collagen, respectively. Glutaraldehyde-crosslinked atelopeptide fibrillar collagen is commercially available from McGhan Medical Corporation at a collagen concentration of 35 mg/ml under the trademark ZYPLAST®.

Collagens for use in the present invention are generally, although not necessarily, in aqueous suspension at a concentration between about 20 mg/ml to about 120 mg/ml, preferably between about 30 mg/ml to about 90 mg/ml.

Although intact collagen is preferred, denatured collagen, commonly known as gelatin, can also be used in the compositions of the invention. Gelatin may have the added benefit of being degradable faster than collagen.

Because of its greater surface area and greater concentration of reactive groups, nonfibrillar collagen is generally preferred. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen, propylated collagen, ethylated collagen, methylated collagen, and the like, both of which can be prepared according to the methods described in U.S. Pat. No. 4,164,559, to Miyata et al., which is hereby incorporated by reference in its entirety. Due to its inherent tackiness, methylated collagen is particularly preferred, as disclosed in U.S. Pat. No. 5,614,587 to Rhee et al.

Collagens for use in the crosslinkable compositions of the present invention may start out in fibrillar form, then be rendered nonfibrillar by the addition of one or more fiber disassembly agents. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

As fibrillar collagen has less surface area and a lower concentration of reactive groups than nonfibrillar, fibrillar collagen is less preferred. However, as disclosed in U.S. Pat. No. 5,614,587, fibrillar collagen, or mixtures of nonfibrillar and fibrillar collagen, may be preferred for use in compositions intended for long-term persistence in vivo, if optical clarity is not a requirement.

Synthetic hydrophilic polymers may also be used in the present invention. Useful synthetic hydrophilic polymers include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethyl-methacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines. It must be emphasized that the aforementioned list of polymers is not exhaustive, and a variety of other synthetic hydrophilic polymers may be used, as will be appreciated by those skilled in the art.

The Crosslinkable Components:

The compositions of the invention also comprise a plurality of crosslinkable components. Each of the crosslinkable components participates in a reaction that results in a crosslinked matrix. Prior to completion of the crosslinking reaction, the crosslinkable components provide the necessary adhesive qualities that enable the methods of the invention.

The crosslinkable components are selected so that crosslinking gives rise to a biocompatible, nonimmunogenic matrix useful in a variety of contexts including adhesion prevention, biologically active agent delivery, tissue augmentation, and other applications. The crosslinkable components of the invention comprise: a component A, which has m nucleophilic groups, wherein $m \geq 2$ and a component B, which has n electrophilic groups capable of reaction with the m nucleophilic groups, wherein $n \geq 2$ and $m+n \geq 4$. An optional third component, optional component C, which has at least one functional group that is either electrophilic and capable of reaction with the nucleophilic groups of component A, or nucleophilic and capable of reaction with the electrophilic groups of component B may also be present. Thus, the total number of functional groups present on components A, B and C, when present, in combination is $\geq 5$; that is, the total functional groups given by $m+n+p$ must be $\geq 5$, where p is the number of functional groups on component C and, as indicated, is $\geq 1$. Each of the components is biocompatible and nonimmunogenic, and at least one component is comprised of a hydrophilic polymer. Also, as will be appreciated, the composition may contain additional crosslinkable components D, E, F, etc., having one or more reactive nucleophilic or electrophilic groups and thereby participate in formation of the crosslinked biomaterial via covalent bonding to other components.

The m nucleophilic groups on component A may all be the same, or, alternatively, A may contain two or more different nucleophilic groups. Similarly, the n electrophilic groups on component B may all be the same, or two or more different electrophilic groups may be present. The functional group(s) on optional component C, if nucleophilic, may or may not be the same as the nucleophilic groups on component A, and, conversely, if electrophilic, the functional group(s) on optional component C may or may not be the same as the electrophilic groups on component B.

Accordingly, the components may be represented by the structural formulae

| (I) | $R^1(\text{-}[Q^1]_q\text{-}X)_m$ | (component A), |
|---|---|---|
| (II) | $R^2(\text{-}[Q^2]_r\text{-}Y)_n$ | (component B), and |
| (III) | $R^3(\text{-}[Q^3]_s\text{-}Fn)_p$ | (optional component C), | wherein:

$R^1$, $R^2$ and $R^3$ are independently selected from the group consisting of $C_2$ to $C_{14}$ hydrocarbyl, heteroatom-containing $C_2$ to $C_{14}$ hydrocarbyl, hydrophilic polymers, and hydrophobic polymers, providing that at least one of $R^1$, $R^2$ and $R^3$ is a hydrophilic polymer, preferably a synthetic hydrophilic polymer;

X represents one of the m nucleophilic groups of component A, and the various X moieties on A may be the same or different;

Y represents one of the n electrophilic groups of component B, and the various Y moieties on A may be the same or different;

Fn represents a functional group on optional component C;

$Q^1$, $Q^2$ and $Q^3$ are linking groups;

$m=2$, $n=2$, $m+n$ is $=4$, q, and r are independently zero or 1, and when optional component C is present, $p=1$, and s is independently zero or 1.

Reactive Groups:

X may be virtually any nucleophilic group, so long as reaction can occur with the electrophilic group Y. Analogously, Y may be virtually any electrophilic group, so long as reaction can take place with X. The only limitation is a practical one, in that reaction between X and Y should be fairly rapid and take place automatically upon admixture with an aqueous medium, without need for heat or potentially toxic or non-biodegradable reaction catalysts or other chemical reagents. It is also preferred although not essential that reaction occur without need for ultraviolet or other radiation. Ideally, the reactions between X and Y should be complete in under 60 minutes, preferably under 30 minutes. Most preferably, the reaction occurs in about 5 to 15 minutes or less.

Examples of nucleophilic groups suitable as X include, but are not limited to, —$NH_2$, —$NHR^4$, —$N(R^4)_2$, —SH, —OH, —COOH, —$C_6H_4$—OH, —$PH_2$, —$PHR^5$, —$P(R^5)_2$, —NH—$NH_2$, —CO—NH—$NH_2$, —$C_5H_4N$, etc. wherein $R^4$ and $R^5$ are hydrocarbyl, typically alkyl or monocyclic aryl, preferably alkyl, and most preferably lower alkyl. Organometallic moieties are also useful nucleophilic groups for the purposes of the invention, particularly those that act as carbanion donors. Organometallic nucleophiles are not, however, preferred. Examples of organometallic moieties include: Grignard functionalities —$R^6$MgHal wherein $R^6$ is a carbon atom (substituted or unsubstituted), and Hal is halo, typically bromo, iodo or chloro, preferably bromo; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups in the crosslinkable composition, the composition must be admixed with an aqueous base in order to remove a proton and provide an —$S^-$ or —$O^-$ species to enable reaction with an electrophile. Unless it is desirable for the base to participate in the crosslinking reaction, a nonnucleophilic base is preferred. In some embodiments, the base may be present as a component of a buffer solution. Suitable bases and corresponding crosslinking reactions are described infra in Section E.

The selection of electrophilic groups provided within the crosslinkable composition, i.e., on component B, must be made so that reaction is possible with the specific nucleophilic groups. Thus, when the X moieties are amino groups, the Y groups are selected so as to react with amino groups. Analogously, when the X moieties are sulfhydryl moieties, the corresponding electrophilic groups are sulfhydryl-reactive groups, and the like.

By way of example, when X is amino (generally although not necessarily primary amino), the electrophilic groups present on Y are amino reactive groups such as, but not limited to: (1) carboxylic acid esters, including cyclic esters and "activated" esters; (2) acid chloride groups (—CO—Cl); (3) anhydrides (—(CO)—O—(CO)—R); (4) ketones and aldehydes, including a,β-unsaturated aldehydes and ketones such as —CH=CH—CH=O and —CH=CH—C($CH_3$)=O; (5) halides; (6) isocyanate (—N=C=O); (7) isothiocyanate (—N=C=S); (8) epoxides; (9) activated hydroxyl groups (e.g., activated with conventional activating agents such as carbonyldiimidazole or sulfonyl chloride); and (10) olefins, including conjugated olefins, such as ethenesulfonyl (—$SO_2CH$=$CH_2$) and analogous functional groups, including acrylate (—$CO_2$—C=$CH_2$), methacrylate (—$CO_2$—C($CH_3$)=$CH_2$)), ethyl acrylate (—$CO_2$—C($CH_2CH_3$)=$CH_2$), and ethyleneimino (—CH=CH—C=NH). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when X is sulfhydryl, the electrophilic groups present on Y are groups that react with a sulfhydryl moiety. Such reactive groups include those that form thioester linkages upon reaction with a sulfhydryl group, such as those described in PCT Publication No. WO 00/62827 to Wallace et al. As explained in detail therein, such "sulfhydryl reactive" groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive groups that form thioester linkages, various other sulfhydryl reactive functionalities can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups; such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and a,β-unsaturated aldehydes and ketones. This class of sulfhydryl reactive groups are particularly preferred as the thioether bonds may provide faster crosslinking and longer in vivo stability.

When X is —OH, the electrophilic functional groups on the remaining component(s) must react with hydroxyl groups. The hydroxyl group may be activated as described above with respect to carboxylic acid groups, or it may react directly in the presence of base with a sufficiently reactive electrophile such as an epoxide group, an aziridine group, an acyl halide, or an anhydride.

When X is an organometallic nucleophile such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

The covalent linkages in the crosslinked structure that result upon covalent binding of specific nucleophilic components to specific electrophilic components in the crosslinkable composition include, solely by way of example, the following (the optional linking groups $Q^1$ and $Q^2$ are omitted for clarity):

TABLE

| REPRESENTATIVE NUCLEOPHILIC COMPONENT (A, optional component C element $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N(COCH$_2$) (succinimidyl carbonate terminus) | $R^1$—NH—(CO)—O—$R^2$ |
| $R^1$—SH | $R^2$—O—(CO)—O—N(COCH$_2$) | $R^1$—S—(CO)—O—$R^2$ |
| $R^1$—OH | $R^2$—O—(CO)—O—N(COCH$_2$) | $R^1$—O—(CO)—$R^2$ |
| $R^1$—$NH_2$ | $R^2$—O(CO)—CH=CH$_2$ (acrylate terminus) | $R^1$—NH—CH$_2$CH$_2$—(CO)—O—$R^2$ |
| $R^1$—SH | $R^2$—O—(CO)—CH=CH$_2$ | $R^1$—S—CH$_2$CH$_2$—(CO)—O—$R^2$ |
| $R^1$—OH | $R^2$—O—(CO)—CH=CH$_2$ | $R^1$—O—CH$_2$CH$_2$—(CO)—O—$R^2$ |
| $R^1$—$NH_2$ | $R^2$—O(CO)—(CH$_2$)$_3$—CO$_2$—N(COCH$_2$) (succinimidyl glutarate terminus) | $R^1$—NH—(CO)—(CH$_2$)$_3$—(CO)—O$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—OH | $R^2$—O(CO)—(CH$_2$)$_3$—CO$_2$—N(COCH$_2$) | $R^1$—O—(CO)—(CH$_2$)$_3$—(CO)—O$R^2$ |
| $R^1$—$NH_2$ | $R^2$—O—CH$_2$—CO$_2$—N(COCH$_2$) (succinimidyl acetate terminus) | $R^1$—NH—(CO)—CH$_2$—O$R^2$ |
| $R^1$—SH | $R^2$—O—CH$_2$—CO$_2$—N(COCH$_2$) | $R^1$—S—(CO)—CH$_2$—O$R^2$ |
| $R^1$—OH | $R^2$—O—CH$_2$—CO$_2$—N(COCH$_2$) | $R^1$—O—(CO)—CH$_2$—O$R^2$ |
| $R^1$—$NH_2$ | $R^2$—O—NH(CO)—(CH$_2$)$_2$—CO$_2$—N(COCH$_2$) (succinimidyl succinamide terminus) | $R^1$—NH—(CO)—(CH$_2$)$_2$—(CO)—NH—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—OH | $R^2$—O—NH(CO)—(CH$_2$)$_2$—CO$_2$—N(COCH$_2$) | $R^1$—O—(CO)—(CH$_2$)$_2$—(CO)—NH—O$R^2$ |

TABLE-continued

| REPRESENTATIVE NUCLEOPHILIC COMPONENT (A, optional component C element $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CH$_2$)$_2$—CHO (propionaldehyde terminus) | $R^1$—NH—(CO)—(CH$_2$)$_2$—O$R^2$ |
| $R^1$—$NH_2$ | $R^2$—O—CH$_2$—CH—CH$_2$ (glycidyl ether terminus) | $R^1$—NH—CH$_2$—CH(OH)—CH$_2$—O$R^2$ and $R^1$—N[CH$_2$—CH(OH)—CH$_2$—O$R^2$]$_2$ |
| $R^1$—$NH_2$ | $R^2$—O—(CH$_2$)$_2$—N=C=O (isocyanate terminus) | $R^1$—NH—(CO)—NH—CH$_2$—O$R^2$ |
| $R^1$—$NH_2$ | $R^2$—SO$_2$—CH=CH$_2$ (vinyl sulfone terminus) | $R^1$—NH—CH$_2$CH$_2$—SO$_2$—$R^2$ |
| $R^1$—SH | $R^2$—SO$_2$—CH=CH$_2$ | $R^1$—S—CH$_2$CH$_2$—SO$_2$—$R^2$ |

Linking Groups:

The functional groups X and Y and FN on optional component C may be directly attached to the compound core ($R^1$, $R^2$ or $R^3$ on optional component C, respectively), or they may be indirectly attached through a linking group, with longer linking groups also termed "chain extenders." In structural formulae (I), (II) and (III), the optional linking groups are represented by $Q^1$, $Q^2$ and $Q^3$, wherein the linking groups are present when q, r and s are equal to 1 (with R, X, Y, Fn, m n and p as defined previously).

Suitable linking groups are well known in the art. See, for example, International Patent Publication No. WO 97/22371. Linking groups are useful to avoid steric hindrance problems that are sometimes associated with the formation of direct linkages between molecules. Linking groups may additionally be used to link several multifunctionally activated compounds together to make larger molecules. In a preferred embodiment, a linking group can be used to alter the degradative properties of the compositions after administration and resultant gel formation. For example, linking groups can be incorporated into components A, B, or optional component C to promote hydrolysis, to discourage hydrolysis, or to provide a site for enzymatic degradation.

Examples of linking groups that provide hydrolyzable sites, include, inter alia: ester linkages; anhydride linkages, such as obtained by incorporation of glutarate and succinate; ortho ester linkages; ortho carbonate linkages such as trimethylene carbonate; amide linkages; phosphoester linkages; a-hydroxy acid linkages, such as may be obtained by incorporation of lactic acid and glycolic acid; lactone-based linkages, such as may be obtained by incorporation of caprolactone, valerolactone, ?-butyrolactone and p-dioxanone; and amide linkages such as in a dimeric, oligomeric, or poly(amino acid) segment. Examples of non-degradable linking groups include succinimide, propionic acid and carboxymethylate linkages. See, for example, PCT WO 99/07417. Examples of enzymatically degradable linkages include Leu-Gly-Pro-Ala, which is degraded by collagenase; and Gly-Pro-Lys, which is degraded by plasmin.

Linking groups can also enhance or suppress the reactivity of the various nucleophilic and electrophilic groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a carbonyl group (e.g., the reactive carbonyl of glutaryl-N-hydroxysuccinimidyl) would increase the reactivity of the carbonyl carbon with respect to an incoming nucleophile. By contrast, sterically bulky groups in the vicinity of a functional group can be used to diminish reactivity and thus coupling rate as a result of steric hindrance.

By way of example, particular linking groups and corresponding component structure are indicated in the following Table:

TABLE

| LINKING GROUP | COMPONENT STRUCTURE |
| --- | --- |
| —O—$(CH_2)_n$— | Component A: $R^1$—O—$(CH_2)_n$—X |
| | Component B: $R^2$—O—$(CH_2)_n$—Y |
| | Optional Component C: $R^3$—O—$(CH_2)_n$—Z |
| —S—$(CH_2)_n$— | Component A: $R^1$—S—$(CH_2)_n$—X |
| | Component B: $R^2$—S—$(CH_2)_n$—Y |
| | Optional Component C: $R^3$—S—$(CH_2)_n$—Z |
| —NH—$(CH_2)_n$— | Component A: $R^1$—NH—$(CH_2)_n$—X |
| | Component B: $R^2$—NH—$(CH_2)_n$—Y |
| | Optional Component C: $R^3$—NH—$(CH_2)_n$—Z |
| —O—(CO)—NH—$(CH_2)_n$— | Component A: $R^1$—O—(CO)—NH—$(CH_2)_n$—X |
| | Component B: $R^2$—O—(CO)—NH—$(CH_2)_n$—Y |
| | Optional Component C: $R^3$—O—(CO)—NH—$(CH_2)_n$—Z |
| —NH—(CO)—O—$(CH_2)_n$— | Component A: $R^1$—NH—(CO)—O—$(CH_2)_n$—X |
| | Component B: $R^2$—NH—(CO)—O—$(CH_2)_n$—Y |
| | Optional Component C: $R^3$—NH—(CO)—O—$(CH_2)_n$—Z |
| —O—(CO)—$(CH_2)_n$— | Component A: $R^1$—O—(CO)—$(CH_2)_n$—X |
| | Component B: $R^2$—O—(CO)—$(CH_2)_n$—Y |
| | Optional Component C: $R^3$—O—(CO)—$(CH_2)_n$—Z |
| —(CO)—O—$(CH_2)_n$— | Component A: $R^1$—(CO)—O—$(CH_2)_n$—X |
| | Component B: $R^2$—(CO)—O—$(CH_2)_n$—Y |
| | Optional Component C: $R^3$—(CO)—O—$(CH_2)_n$—Z |
| —O—(CO)—O—$(CH_2)_n$— | Component A: $R^1$—O—(CO)—O—$(CH_2)_n$—X |
| | Component B: $R^2$—O—(CO)—O—$(CH_2)_n$—Y |
| | Optional Component C: $R^3$—O—(CO)—O—$(CH_2)_n$—Z |
| —O—(CO)—$CHR^7$— | Component A: $R^1$—O—(CO)—$CHR^7$—X |
| | Component B: $R^2$—O—(CO)—$CHR^7$—Y |
| | Optional Component C: $R^3$—O—(CO)—$CHR^7$—Z |
| —O—$R^8$—(CO)—NH— | Component A: $R^1$—O—$R^8$—(CO)—NH—X |
| | Component B: $R^2$—O—$R^8$—(CO)—NH—Y |
| | Optional Component C: $R^3$—O—$R^8$—(CO)—NH—Z |

In the above Table, n is generally in the range of 1 to about 10, $R^7$ is generally hydrocarbyl, typically alkyl or aryl, preferably alkyl, and most preferably lower alkyl, and $R^8$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—$CH_2$).

Other general principles that should be considered with respect to linking groups are as follows: If higher molecular weight components are to be used, they preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Hydrophilic groups can be easily introduced using known chemical synthesis, so long as they do not give rise to unwanted swelling or an undesirable decrease in compressive strength. In particular, polyalkoxy segments may weaken gel strength.

The Component Core:

The "core" of each crosslinkable component is comprised of the molecular structure to which the nucleophilic or electrophilic groups are bound. Using the formulae (I) $R^1$—$[Q^1]_q$—$X)_m$, for component A, (II) $R^2$(—$[Q^2]_r$—Y)$_n$ for component B, and (III)

$R^3$(—$[Q^3]_s$—Fn)$_p$ for optional component C, the "core" groups are $R^1$, $R^2$ and $R^3$. Each molecular core of the reactive components of the crosslinkable composition is generally selected from synthetic and naturally occurring hydrophilic polymers, hydrophobic polymers, and $C_2$–$C_{14}$ hydrocarbyl groups zero to 2 heteroatoms selected from N, O and S, with the proviso that at least one of the crosslinkable components A, B, and optionally C, comprises a molecular core of a synthetic hydrophilic polymer. In a preferred embodiment, at least one of A and B comprises a molecular core of a synthetic hydrophilic polymer.

Hydrophilic Crosslinkable Components

In one aspect, the crosslinkable component(s) is (are) hydrophilic polymers. The term "hydrophilic polymer" as used herein refers to a synthetic polymer having an average molecular weight and composition effective to render the polymer "hydrophilic" as defined above. As discussed above, synthetic crosslinkable hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethyl-methacrylate), poly(hydroxyethylacrylate), poly(methylalkylsulfoxide methacrylate), poly (methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly (methyloxazoline) and poly(ethyloxazoline); and polyvinylamines. It must be emphasized that the aforementioned list of polymers is not exhaustive, and a variety of other synthetic hydrophilic polymers may be used, as will be appreciated by those skilled in the art.

The synthetic crosslinkable hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like.

Other suitable synthetic crosslinkable hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly (lysine)s of varying molecular weights are commercially available from Peninsula Laboratories, Inc. (Belmont, Calif.).

The synthetic crosslinkable hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like.

Although a variety of different synthetic crosslinkable hydrophilic polymers can be used in the present compositions, as indicated above, preferred synthetic crosslinkable hydrophilic polymers are polyethylene glycol (PEG) and polyglycerol (PG), particularly highly branched polyglycerol. Various forms of PEG are extensively used in the modification of biologically active molecules because PEG lacks toxicity, antigenicity, and immunogenicity (i.e., is biocompatible), can be formulated so as to have a wide range of solubilities, and do not typically interfere with the enzymatic activities and/or conformations of peptides. A particularly preferred synthetic crosslinkable hydrophilic polymer for certain applications is a polyethylene glycol (PEG) having a molecular weight within the range of about 100 to about 100,000 mol. wt., although for highly branched PEG, far higher molecular weight polymers can be employed—up to 1,000,000 or more—providing that biodegradable sites are incorporated ensuring that all degradation products will have a molecular weight of less than about 30,000. For most PEGs, however, the preferred molecular weight is about 1,000 to about 20,000 mol. wt., more preferably within the range of about 7,500 to about 20,000 mol. wt. Most preferably, the polyethylene glycol has a molecular weight of approximately 10,000 mol. wt.

Naturally occurring crosslinkable hydrophilic polymers include, but are not limited to: proteins such as collagen, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are examples of naturally occurring hydrophilic polymers for use herein, with methylated collagen being a preferred hydrophilic polymer.

Any of the hydrophilic polymers herein must contain, or be activated to contain, functional groups, i.e., nucleophilic or electrophilic groups, which enable crosslinking. Activation of PEG is discussed below; it is to be understood, however, that the following discussion is for purposes of illustration and analogous techniques may be employed with other polymers.

With respect to PEG, first of all, various functionalized polyethylene glycols have been used effectively in fields such as protein modification (see Abuchowski et al., Enzymes as Drugs, John Wiley & Sons: New York, N.Y. (1981) pp. 367–383; and Dreborg et al., Crit. Rev. Therap. Drug Carrier Syst. (1990) 6:315), peptide chemistry (see Mutter et al., The Peptides, Academic: New York, N.Y. 2:285–332; and Zalipsky et al., Int. J. Peptide Protein Res. (1987) 30:740), and the synthesis of polymeric drugs (see Zalipsky et al., Eur. Polym. J. (1983) 19:1177; and Ouchi et al., J. Macromol. Sci. Chem. (1987) A24:1011).

Activated forms of PEG, including multifunctionally activated PEG, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992); and Shearwater Polymers, Inc. Catalog, Polyethylene Glycol Derivatives, Huntsville, Ala. (1997–1998).

Structures for some specific, tetrafunctionally activated forms of PEG are shown in FIGS. 1 to 10 of U.S. Pat. No. 5,874,500, as are generalized reaction products obtained by reacting the activated PEGs with multi-amino PEGs, i.e., a PEG with two or more primary amino groups. The activated PEGs illustrated have a pentaerythritol (2,2-bis(hydroxymethyl)-1,3-propanediol) core. Such activated PEGs, as will be appreciated by those in the art, are readily prepared by conversion of the exposed hydroxyl groups in the PEGylated polyol (i.e., the terminal hydroxyl groups on the PEG chains) to carboxylic acid groups (typically by reaction with an anhydride in the presence of a nitrogenous base), followed by esterification with N-hydroxysuccinimide, N-hydroxysulfosuccinimide, or the like, to give the polyfunctionally activated PEG.

Hydrophobic Polymers:

The crosslinkable compositions of the invention can also include hydrophobic polymers, although for most uses hydrophilic polymers are preferred. Polylactic acid and polyglycolic acid are examples of two hydrophobic polymers that can be used. With other hydrophobic polymers, only short-chain oligomers should be used, containing at most about 14 carbon atoms, to avoid solubility-related problems during reaction.

Low Molecular Weight Components:

As indicated above, the molecular core of one or more of the crosslinkable components can also be a low molecular weight compound, i.e., a $C_2$–$C_{14}$ hydrocarbyl group containing zero to 2 heteroatoms selected from N, O, S and combinations thereof. Such a molecular core can be substituted with nucleophilic groups or with electrophilic groups.

When the low molecular weight molecular core is substituted with primary amino groups, the component may be, for example, ethylenediamine ($H_2N$—$CH_2CH_2$—$NH_2$), tetramethylenediamine ($H_2N$—$(CH_4)$—$NH_2$), pentamethylenediamine (cadaverine) ($H_2N$—$(CH_5)$—$NH_2$), hexamethylenediamine ($H_2N$—$(CH_6)$—$NH_2$), bis(2-aminoethyl) amine (HN—$[CH_2CH_2$—$NH_2]_2$), or tris(2-aminoethyl) amine (N—$[CH_2CH_2$—$NH_2]_3$).

Low molecular weight diols and polyols include trimethylolpropane, di(trimethylol propane), pentaerythritol, and diglycerol, all of which require activation with a base in order to facilitate their reaction as nucleophiles. Such diols and polyols may also be functionalized to provide di- and poly-carboxylic acids, functional groups that are, as noted earlier herein, also useful as nucleophiles under certain conditions. Polyacids for use in the present compositions include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid), all of which are commercially available and/or readily synthesized using known techniques.

Low molecular weight di- and poly-electrophiles include, for example, disuccinimidyl suberate (DSS), bis(sulfosuccinimidyl) suberate ($BS_3$), dithiobis(succinimidylpropionate) (DSP), bis(2-succinimidooxycarbonyloxy) ethyl sulfone (BSOCOES), and 3,3'-dithiobis(sulfosuccinimidylpropionate (DTSPP), and their analogs and derivatives. The aforementioned compounds are commercially available from Pierce (Rockford, Ill.). Such di- and poly-electrophiles can also be synthesized from di- and polyacids, for example by reaction with an appropriate molar amount of N-hydroxysuccinimide in the presence of DCC. Polyols such as trimethylolpropane and di(trimethylol propane) can be converted to carboxylic acid form using various known techniques, then further derivatized by reaction with NHS in the presence of DCC to produce trifunctionally and tetrafunctionally activated polymers.

Delivery Systems:

Suitable delivery systems for the homogeneous dry powder composition (containing at least two crosslinkable polymers) and the two buffer solutions may involve a multi-compartment spray device, where one or more compartments contains the powder and one or more compartments contain the buffer solutions needed to provide for the aqueous environment, so that the composition is exposed to the aqueous environment as it leaves the compartment. Many devices that are adapted for delivery of multi-component tissue sealants/hemostatic agents are well known in the art and can also be used in the practice of the present invention. Alternatively, the composition can be delivered using any type of controllable extrusion system, or it can be delivered manually in the form of a dry powder, and exposed to the aqueous environment at the site of administration.

The homogeneous dry powder composition and the two buffer solutions may be conveniently formed under aseptic conditions by placing each of the three ingredients (dry powder, acidic buffer solution and basic buffer solution) into separate syringe barrels. For example, the composition, first buffer solution and second buffer solution can be housed separately in a multiple-compartment syringe system having a multiple barrels, a mixing head, and an exit orifice. The first buffer solution can be added to the barrel housing the composition to dissolve the composition and form a homogeneous solution, which is then extruded into the mixing head. The second buffer solution can be simultaneously extruded into the mixing head. Finally, the resulting composition can then be extruded through the orifice onto a surface.

For example, the syringe barrels holding the dry powder and the basic buffer may be part of a dual-syringe system, e.g., a double barrel syringe as described in U.S. Pat. No. 4,359,049 to Redl et al. In this embodiment, the acid buffer can be added to the syringe barrel that also holds the dry powder, so as to produce the homogeneous solution. In other words, the acid buffer may be added (e.g., injected) into the syringe barrel holding the dry powder to thereby produce a homogeneous solution of the first and second components. This homogeneous solution can then be extruded into a mixing head, while the basic buffer is simultaneously extruded into the mixing head. Within the mixing head, the homogeneous solution and the basic buffer are mixed together to thereby form a reactive mixture. Thereafter, the reactive mixture is extruded through an orifice and onto a surface (e.g., tissue), where a film is formed, which can function as a sealant or a barrier, or the like. The reactive mixture begins forming a three-dimensional matrix immediately upon being formed by the mixing of the homogeneous solution and the basic buffer in the mixing head. Accordingly, the reactive mixture is preferably extruded from the mixing head onto the tissue very quickly after it is formed so that the three-dimensional matrix forms on, and is able to adhere to, the tissue.

Other systems for combining two reactive liquids are well known in the art, and include the systems described in U.S.

Pat. No. 6,454,786 to Holm et al.; U.S. Pat. No. 6,461,325 to Delmotte et al.; U.S. Pat. No. 5,585,007 to Antanavich et al.; U.S. Pat. No. 5,116,315 to Capozzi et al.; and U.S. Pat. No. 4,631,055 to Redl et al.

Storage and Handling:

Because crosslinkable components containing electrophilic groups react with water, the electrophilic component or components are generally stored and used in sterile, dry form to prevent hydrolysis. Processes for preparing synthetic hydrophilic polymers containing multiple electrophilic groups in sterile, dry form are set forth in commonly assigned U.S. Pat. No. 5,643,464 to Rhee et al. For example, the dry synthetic polymer may be compression molded into a thin sheet or membrane, which can then be sterilized using gamma or, preferably, e-beam irradiation. The resulting dry membrane or sheet can be cut to the desired size or chopped into smaller size particulates.

Components containing multiple nucleophilic groups are generally not water-reactive and can therefore be stored either dry or in aqueous solution. If stored as a dry, particulate, solid, the various components of the crosslinkable composition may be blended and stored in a single container. Admixture of all components with water, saline, or other aqueous media should not occur until immediately prior to use.

In an alternative embodiment, the crosslinking components can be mixed together in a single aqueous medium in which they are both unreactive, i.e., such as in a low pH buffer. Thereafter, they can be sprayed onto the targeted tissue site along with a high pH buffer, after which they will rapidly react and form a gel.

Suitable liquid media for storage of crosslinkable compositions include aqueous buffer solutions such as monobasic sodium phosphate/dibasic sodium phosphate, sodium carbonate/sodium bicarbonate, glutamate or acetate, at a concentration of 0.5 to 300 mM. In general, a sulfhydryl-reactive component such as PEG substituted with maleimido groups or succinimidyl esters is prepared in water or a dilute buffer, with a pH of between around 5 to 6. Buffers with pKs between about 8 and 10.5 for preparing a polysulfhydryl component such as sulfhydryl-PEG are useful to achieve fast gelation time of compositions containing mixtures of sulfhydryl-PEG and SG-PEG. These include carbonate, borate and AMPSO (3-[(1,1-dimethyl-2-hydroxyethyl)amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG.

Collagen+Fibrinogen and/or Thrombin (e.g., Costasis)

In yet another aspect, the polymer composition may include collagen in combination with fibrinogen and/or thrombin. (See, e.g., U.S. Pat. Nos. 5,290,552; 6,096,309; 5,997,811; 5,968,018, and 6,123,687). For example, an aqueous composition may include a fibrinogen and FXIII, particularly plasma, collagen in an amount sufficient to thicken the composition, thrombin in an amount sufficient to catalyze polymerization of fibrinogen present in the composition, and $Ca^{2+}$ and, optionally, an antifibrinolytic agent in amount sufficient to retard degradation of the resulting adhesive clot. The composition may be formulated as a two-part composition that may be mixed together just prior to use, in which fibrinogen/FXIII and collagen constitute the first component, and thrombin together with an antifibrinolytic agent, and $Ca^{2+}$ constitute the second component.

Plasma, which provides a source of fibrinogen, may be obtained from the patient for which the composition is to be delivered. The plasma can be used "as is" after standard preparation which includes centrifuging out cellular components of blood. Alternatively, the plasma can be further processed to concentrate the fibrinogen to prepare a plasma cryoprecipitate. The plasma cryoprecipitate can be prepared by freezing the plasma for at least about an hour at about −20° C., and then storing the frozen plasma overnight at about 4° C. to slowly thaw. The thawed plasma is centrifuged and the plasma cryoprecipitate is harvested by removing approximately four-fifths of the plasma to provide a cryoprecipitate comprising the remaining one-fifth of the plasma. Other fibrinogen/FXIII preparations may be used, such as cryoprecipitate, patient autologous fibrin sealant, fibrinogen analogs or other single donor or commercial fibrin sealant materials. Approximately 0.5 ml to about 1.0 ml of either the plasma or the plasma-cryoprecipitate provides about 1 to 2 ml of adhesive composition which is sufficient for use in middle ear surgery. Other plasma proteins (e.g., albumin, plasminogen, von Willebrands factor, Factor VIII, etc.) may or may not be present in the fibrinogen/FXII separation due to wide variations in the formulations and methods to derive them.

Collagen, preferably hypoallergenic collagen, is present in the composition in an amount sufficient to thicken the composition and augment the cohesive properties of the preparation. The collagen may be atelopeptide collagen or telopeptide collagen, e.g., native collagen. In addition to thickening the composition, the collagen augments the fibrin by acting as a macromolecular lattice work or scaffold to which the fibrin network adsorbs. This gives more strength and durability to the resulting glue clot with a relatively low concentration of fibrinogen in comparison to the various concentrated autogenous fibrinogen glue formulations (i.e., AFGs).

The form of collagen which is employed may be described as at least "near native" in its structural characteristics. It may be further characterized as resulting in insoluble fibers at a pH above 5; unless crosslinked or as part of a complex composition, e.g., bone, it will generally consist of a minor amount by weight of fibers with diameters greater than 50 nm, usually from about 1 to 25 volume % and there will be substantially little, if any, change in the helical structure of the fibrils. In addition, the collagen composition must be able to enhance gelation in the surgical adhesion composition.

A number of commercially available collagen preparations may be used. ZYDERM Collagen Implant (ZCI) has a fibrillar diameter distribution consisting of 5 to 10 nm diameter fibers at 90% volume content and the remaining 10% with greater than about 50 nm diameter fibers. ZCI is available as a fibrillar slurry and solution in phosphate buffered isotonic saline, pH 7.2, and is injectable with fine gauge needles. As distinct from ZCI, cross-linked collagen available as ZYPLAST may be employed. ZYPLAST is essentially an exogenously crosslinked (glutaraldehyde) version of ZCI. The material has a somewhat higher content of greater than about 50 nm diameter fibrils and remains insoluble over a wide pH range. Crosslinking has the effect of mimicking in vivo endogenous crosslinking found in many tissues.

Thrombin acts as a catalyst for fibrinogen to provide fibrin, an insoluble polymer and is present in the composition in an amount sufficient to catalyze polymerization of fibrinogen present in the patient plasma. Thrombin also activates FXIII, a plasma protein that catalyzes covalent crosslinks in fibrin, rendering the resultant clot insoluble. Usually the thrombin is present in the adhesive composition in concentration of from about 0.01 to about 1000 or greater NIH units (NIHu) of activity, usually about i to about 500 NIHu, most usually about 200 to about 500 NIHu. The thrombin can be from a variety of host animal sources, conveniently bovine. Thrombin is commercially available from a variety of sources including Parke-Davis, usually lyophilized with buffer salts and stabilizers in vials which provide thrombin activity ranging from about 1000 NIHu to 10,000 NIHu. The thrombin is usually prepared by reconstituting the powder by the addition of either sterile distilled water or isotonic saline. Alternately, thrombin analogs or reptile-sourced coagulants may be used.

The composition may additionally comprise an effective amount of an antifibrinolytic agent to enhance the integrity of the glue clot as the healing processes occur. A number of antifibrinolytic agents are well known and include aprotinin, C1-esterase inhibitor and ε-amino-n-caproic acid (EACA). ε-amino-n-caproic acid, the only antifibrinolytic agent approved by the FDA, is effective at a concentration of from about 5 mg/ml to about 40 mg/ml of the final adhesive composition, more usually from about 20 to about 30 mg/ml. EACA is commercially available as a solution having a concentration of about 250 mg/ml. Conveniently, the commercial solution is diluted with distilled water to provide a solution of the desired concentration. That solution is desirably used to reconstitute lyophilized thrombin to the desired thrombin concentration.

Other examples of in situ forming materials based on the crosslinking of proteins are described, e.g., in U.S. Pat. Nos. RE38,158; 4,839,345; 5,514,379, 5,583,114; 6,458,147; 6,371,975; 5,290,552; 6,096,309; U.S. Patent Application Publication Nos. 2002/0161399; 2001/0018598 and PCT Publication Nos. WO 03/090683; WO 01/45761; WO 99/66964 and WO 96/03159).

Self-Reactive Compounds

In one aspect, the therapeutic agent is released from a crosslinked matrix formed, at least in part, from a self-reactive compound. As used herein, a self-reactive compound comprises a core substituted with a minimum of three reactive groups. The reactive groups may be directed attached to the core of the compound, or the reactive groups may be indirectly attached to the compound's core, e.g., the reactive groups are joined to the core through one or more linking groups.

Each of the three reactive groups that are necessarily present in a self-reactive compound can undergo a bond-forming reaction with at least one of the remaining two reactive groups. For clarity it is mentioned that when these compounds react to form a crosslinked matrix, it will most often happen that reactive groups on one compound will reactive with reactive groups on another compound. That is, the term "self-reactive" is not intended to mean that each self-reactive compound necessarily reacts with itself, but rather that when a plurality of identical self-reactive compounds are in combination and undergo a crosslinking reaction, then these compounds will react with one another to form the matrix. The compounds are "self-reactive" in the sense that they can react with other compounds having the identical chemical structure as themselves.

The self-reactive compound comprises at least four components: a core and three reactive groups. In one embodiment, the self-reactive compound can be characterized by the formula (I), where R is the core, the reactive groups are represented by $X^1$, $X^2$ and $X^3$, and a linker (L) is optionally present between the core and a functional group.

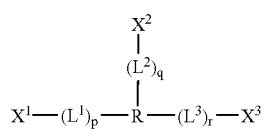

(1)

The core R is a polyvalent moiety having attachment to at least three groups (i.e., it is at least trivalent) and may be, or may contain, for example, a hydrophilic polymer, a hydrophobic polymer, an amphiphilic polymer, a $C_{2-14}$ hydrocarbyl, or a $C_{2-14}$ hydrocarbyl which is heteroatom-containing. The linking groups $L^1$, $L^2$, and $L^3$ may be the same or different. The designators p, q and r are either 0 (when no linker is present) or 1 (when a linker is present). The reactive groups $X^1$, $X^2$ and $X^3$ may be the same or different. Each of these reactive groups reacts with at least one other reactive group to form a three-dimensional matrix. Therefore $X^1$ can react with $X^2$ and/or $X^3$, $X^2$ can react with $X^1$ and/or $X^3$, $X^3$ can react with $X^1$ and/or $X^2$ and so forth. A trivalent core will be directly or indirectly bonded to three functional groups, a tetravalent core will be directly or indirectly bonded to four functional groups, etc.

Each side chain typically has one reactive group. However, the invention also encompasses self-reactive compounds where the side chains contain more than one reactive group. Thus, in another embodiment of the invention, the self-reactive compound has the formula (II):

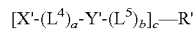

where: a and b are integers from 0–1; c is an integer from 3–12; R' is selected from hydrophilic polymers, hydrophobic polymers, amphiphilic polymers, $C_{2-14}$ hydrocarbyls, and heteroatom-containing $C_{2-14}$ hydrocarbyls; X' and Y' are reactive groups and can be the same or different; and $L^4$ and $L^5$ are linking groups. Each reactive group inter-reacts with the other reactive group to form a three-dimensional matrix. The compound is essentially non-reactive in an initial environment but is rendered reactive upon exposure to a modification in the initial environment that provides a modified environment such that a plurality of the self-reactive compounds inter-react in the modified environment to form a three-dimensional matrix. In one preferred embodiment, R is a hydrophilic polymer. In another preferred embodiment, X' is a nucleophilic group and Y' is an electrophilic group.

The following self-reactive compound is one example of a compound of formula (II):

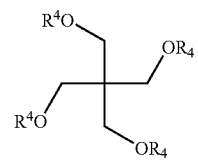

where $R^4$ has the formula:

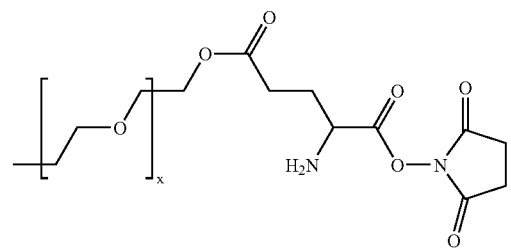

Thus, in formula (II), a and b are 1; c is 4; the core R' is the hydrophilic polymer, tetrafunctionally activated polyethylene glycol, $(C(CH_2-O-)_4$; X' is the electrophilic reac tive group, succinimidyl; Y' is the nucleophilic reactive group —CH—NH$_2$; L$^4$ is —C(O)—O—; and L$^5$ is —(CH$_2$—CH$_2$—O—CH$_2$)$_x$—CH$_2$—O—C(O)—(CH$_2$)$_2$—.
The self-reactive compounds of the invention are readily synthesized by techniques that are well known in the art. An exemplary synthesis is set forth below:
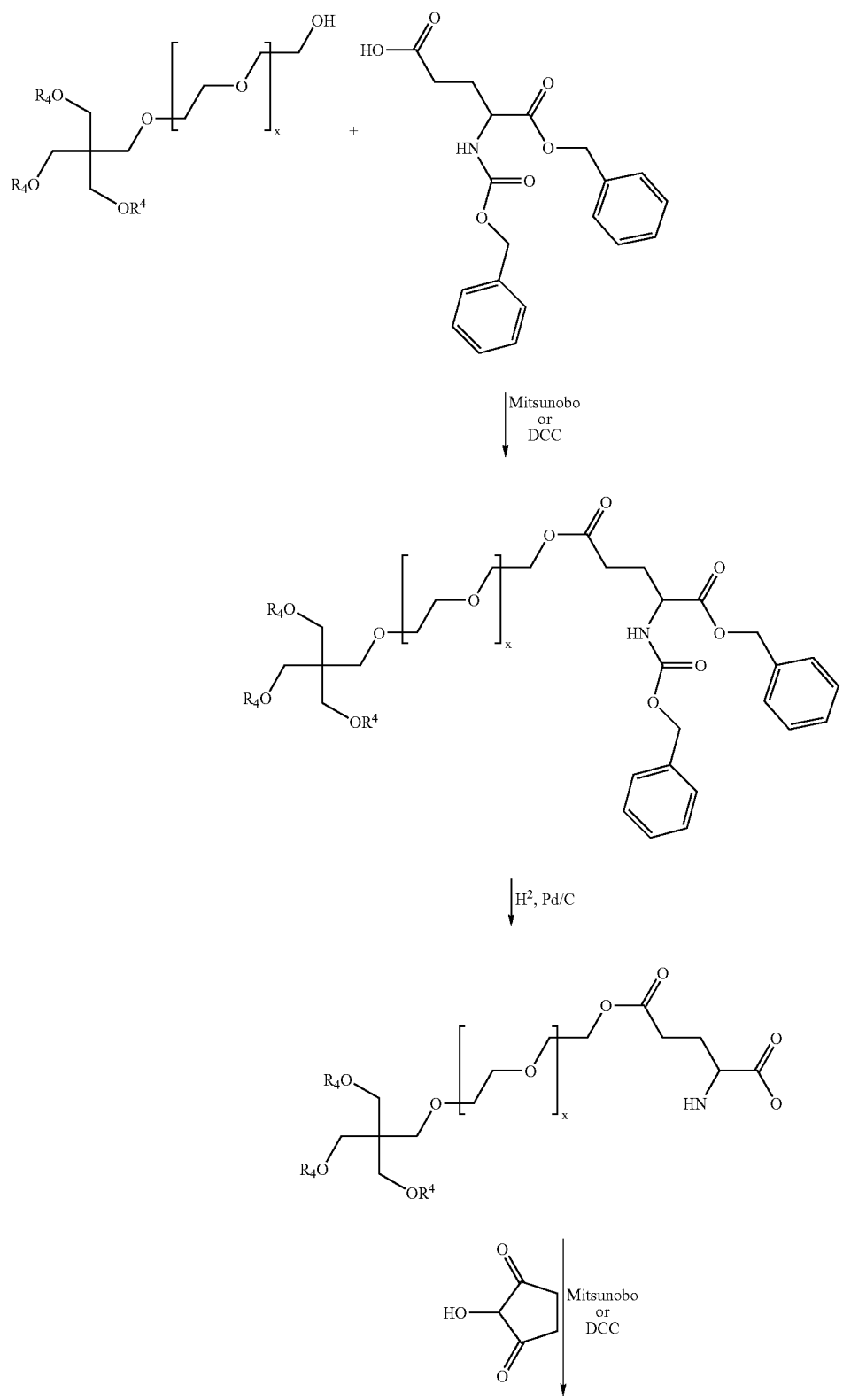

-continued

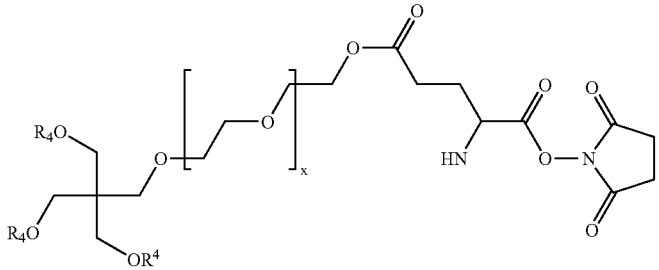

The reactive groups are selected so that the compound is essentially non-reactive in an initial environment. Upon exposure to a specific modification in the initial environment, providing a modified environment, the compound is rendered reactive and a plurality of self-reactive compounds are then able to inter-react in the modified environment to form a three-dimensional matrix. Examples of modification in the initial environment are detailed below, but include the addition of an aqueous medium, a change in pH, exposure to ultraviolet radiation, a change in temperature, or contact with a redox initiator.

The core and reactive groups can also be selected so as to provide a compound that has one of more of the following features: are biocompatible, are non-immunogenic, and do not leave any toxic, inflammatory or immunogenic reaction products at the site of administration. Similarly, the core and reactive groups can also be selected so as to provide a resulting matrix that has one or more of these features.

In one embodiment of the invention, substantially immediately or immediately upon exposure to the modified environment, the self-reactive compounds inter-react form a three-dimensional matrix. The term "substantially immediately" is intended to mean within less than five minutes, preferably within less than two minutes, and the term "immediately" is intended to mean within less than one minute, preferably within less than 30 seconds.

In one embodiment, the self-reactive compound and resulting matrix are not subject to enzymatic cleavage by matrix metalloproteinases such as collagenase, and are therefore not readily degradable in vivo. Further, the self-reactive compound may be readily tailored, in terms of the selection and quantity of each component, to enhance certain properties, e.g., compression strength, swellability, tack, hydrophilicity, optical clarity, and the like.

In one preferred embodiment, R is a hydrophilic polymer. In another preferred embodiment, X is a nucleophilic group, Y is an electrophilic group and Z is either an electrophilic or a nucleophilic group. Additional embodiments are detailed below.

A higher degree of inter-reaction, e.g., crosslinking, may be useful when a less swellable matrix is desired or increased compressive strength is desired. In those embodiments, it may be desirable to have n be an integer from 2–12. In addition, when a plurality of self-reactive compounds are utilized, the compounds may be the same or different.

A. Reactive Groups

Prior to use, the self-reactive compound is stored in an initial environment that insures that the compound remain essentially non-reactive until use. Upon modification of this environment, the compound is rendered reactive and a plurality of compounds will then inter-react to form the desired matrix. The initial environment, as well as the modified environment, is thus determined by the nature of the reactive groups involved.

The number of reactive groups can be the same or different. However, in one embodiment of the invention, the number of reactive groups are approximately equal. As used in this context, the term "approximately" refers to a 2:1 to 1:2 ratio of moles of one reactive group to moles of a different reactive groups. A 1:1:1 molar ratio of reactive groups is generally preferred.

In general, the concentration of the self-reactive compounds in the modified environment, when liquid in nature, will be in the range of about 1 to 50 wt %, generally about 2 to 40 wt %. The preferred concentration of the compound in the liquid will depend on a number of factors, including the type of compound (i.e., type of molecular core and reactive groups), its molecular weight, and the end use of the resulting three-dimensional matrix. For example, use of higher concentrations of the compounds, or using highly functionalized compounds, will result in the formation of a more tightly crosslinked network, producing a stiffer, more robust gel. As such, compositions intended for use in tissue augmentation will generally employ concentrations of self-reactive compounds that fall toward the higher end of the preferred concentration range. Compositions intended for use as bioadhesives or in adhesion prevention do not need to be as firm and may therefore contain lower concentrations of the self-reactive compounds.

1) Electrophilic and Nucleophilic Reactive Groups

In one embodiment of the invention, the reactive groups are electrophilic and nucleophilic groups, which undergo a nucleophilic substitution reaction, a nucleophilic addition reaction, or both. The term "electrophilic" refers to a reactive group that is susceptible to nucleophilic attack, i.e., susceptible to reaction with an incoming nucleophilic group. Electrophilic groups herein are positively charged or electron-deficient, typically electron-deficient. The term "nucleophilic" refers to a reactive group that is electron rich, has an unshared pair of electrons acting as a reactive site, and reacts with a positively charged or electron-deficient site. For such reactive groups, the modification in the initial environment comprises the addition of an aqueous medium and/or a change in pH.

In one embodiment of the invention, X1 (also referred to herein as X) can be a nucleophilic group and X2 (also referred to herein as Y) can be an electrophilic group or vice versa, and X3 (also referred to herein as Z) can be either an electrophilic or a nucleophilic group.

X may be virtually any nucleophilic group, so long as reaction can occur with the electrophilic group Y and also with Z, when Z is electrophilic ($Z_{EL}$). Analogously, Y may be virtually any electrophilic group, so long as reaction can take place with X and also with Z when Z is nucleophilic ($Z_{NU}$). The only limitation is a practical one, in that reaction between X and Y, and X and $Z_{EL}$, or Y and $Z_{NU}$ should be fairly rapid and take place automatically upon admixture with an aqueous medium, without need for heat or potentially toxic or non-biodegradable reaction catalysts or other chemical reagents. It is also preferred although not essential that reaction occur without need for ultraviolet or other radiation. In one embodiment, the reactions between X and Y, and between either X and $Z_{EL}$ or Y and $Z_{NU}$, are complete in under 60 minutes, preferably under 30 minutes. Most preferably, the reaction occurs in about 5 to 15 minutes or less.

Examples of nucleophilic groups suitable as X or $Fn_{NU}$ include, but are not limited to: —$NH_2$, —$NHR^1$, —$N(R^1)_2$, —SH, —OH, —COOH, —$C_6H_4$—OH, —H, —$PH_2$, —$PHR^1$, —$P(R^1)_2$, —NH—$NH_2$, —CO—NH—$NH_2$, —$C_5H_4N$, etc. wherein $R^1$ is a hydrocarbyl group and each R1 may be the same or different. $R^1$ is typically alkyl or monocyclic aryl, preferably alkyl, and most preferably lower alkyl. Organometallic moieties are also useful nucleophilic groups for the purposes of the invention, particularly those that act as carbanion donors. Examples of organometallic moieties include: Grignard functionalities —$R^2$MgHal wherein $R^2$ is a carbon atom (substituted or unsubstituted), and Hal is halo, typically bromo, iodo or chloro, preferably bromo; and lithium-containing functionalities, typically alkyllithium groups; sodium-containing functionalities.

It will be appreciated by those of ordinary skill in the art that certain nucleophilic groups must be activated with a base so as to be capable of reaction with an electrophilic group. For example, when there are nucleophilic sulfhydryl and hydroxyl groups in the self-reactive compound, the compound must be admixed with an aqueous base in order to remove a proton and provide an —$S^-$ or —$O^-$ species to enable reaction with the electrophilic group. Unless it is desirable for the base to participate in the reaction, a non-nucleophilic base is preferred. In some embodiments, the base may be present as a component of a buffer solution. Suitable bases and corresponding crosslinking reactions are described herein.

The selection of electrophilic groups provided on the self-reactive compound, must be made so that reaction is possible with the specific nucleophilic groups. Thus, when the X reactive groups are amino groups, the Y and any $Z_{EL}$ groups are selected so as to react with amino groups. Analogously, when the X reactive groups are sulfhydryl moieties, the corresponding electrophilic groups are sulfhydryl-reactive groups, and the like. In general, examples of electrophilic groups suitable as Y or $Z_{EL}$ include, but are not limited to, —CO—Cl, —(CO)—O—(CO)—R (where R is an alkyl group), —CH=CH—CH=O and —CH=CH—C($CH_3$)=O, halo, —N=C=O, —N=C=S, —$SO_2$CH=$CH_2$, —O(CO)—C=$CH_2$, —O(CO)—C($CH_3$)=$CH_2$, —S—S—($C_5H_4N$), —O(CO)—C($CH_2CH_3$)=$CH_2$, —CH=CH—C=NH, —COOH, —(CO)O—N($COCH_2)_2$, —CHO, —(CO)O—N($COCH_2)_2$—S(O)$_2$OH, and —N($COCH)_2$.

When X is amino (generally although not necessarily primary amino), the electrophilic groups present on Y and $Z_{EL}$ are amine-reactive groups. Exemplary amine-reactive groups include, by way of example and not limitation, the following groups, or radicals thereof: (1) carboxylic acid esters, including cyclic esters and "activated" esters; (2) acid chloride groups (—CO—Cl); (3) anhydrides (—(CO)—O—(CO)—R, where R is an alkyl group); (4) ketones and aldehydes, including α,β-unsaturated aldehydes and ketones such as —CH=CH—CH=O and —CH=CH—C($CH_3$)=O; (5) halo groups; (6) isocyanate group (—N=C=O); (7) thioisocyanato group (—N=C=S); (8) epoxides; (9) activated hydroxyl groups (e.g., activated with conventional activating agents such as carbonyldiimidazole or sulfonyl chloride); and (10) olefins, including conjugated olefins, such as ethenesulfonyl (—$SO_2$CH=$CH_2$) and analogous functional groups, including acrylate (—O(CO)—C=$CH_2$), methacrylate (—O(CO)—C($CH_3$)=$CH_2$), ethyl acrylate (—O(CO)—C($CH_2CH_3$)=$CH_2$), and ethyleneimino (—CH=CH—C=NH).

In one embodiment the amine-reactive groups contain an electrophilically reactive carbonyl group susceptible to nucleophilic attack by a primary or secondary amine, for example the carboxylic acid esters and aldehydes noted above, as well as carboxyl groups (—COOH).

Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Accordingly, in one embodiment, the amine-reactive groups are selected from succinimidyl ester (—O(CO)—N($COCH_2)_2$), sulfosuccinimidyl ester (—O(CO)—N($COCH_2)_2$—S(O)$_2$OH), maleimido (—N($COCH)_2$), epoxy, isocyanato, thioisocyanato, and ethenesulfonyl.

Analogously, when X is sulfhydryl, the electrophilic groups present on Y and $Z_{EL}$ are groups that react with a sulfhydryl moiety. Such reactive groups include those that form thioester linkages upon reaction with a sulfhydryl group, such as those described in WO 00/62827 to Wallace et al. As explained in detail therein, sulfhydryl reactive groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive groups that form thioester linkages, various other sulfhydryl reactive functionalities can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups; such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and a,β-unsaturated aldehydes and ketones.

When X is —OH, the electrophilic functional groups on the remaining component(s) must react with hydroxyl When X is an organometallic nucleophilic group such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophilic or as electrophilic groups, depending on the selected reaction partner and/or the reaction conditions. For example, a carboxylic acid group can act as a nucleophilic group in the presence of a fairly strong base, but generally acts as an electrophilic group allowing nucleophilic attack at the carbonyl carbon and concomitant replacement of the hydroxyl group with the incoming nucleophilic group.

These, as well as other embodiments are illustrated below, where the covalent linkages in the matrix that result upon covalent binding of specific nucleophilic reactive groups to specific electrophilic reactive groups on the self-reactive compound include, solely by way of example, the following Table:

TABLE

| Representative Nucleophilic Group (X, $Z_{NU}$) | Representative Electrophilic Group (Y, $Z_{EL}$) | Resulting Linkage |
|---|---|---|
| —$NH_2$ | —O—(CO)—O—N($COCH_2$)$_2$ succinimidyl carbonate terminus | —NH—(CO)—O— |
| —SH | —O—(CO)—O—N($COCH_2$)$_2$ | —S—(CO)—O— |
| —OH | —O—(CO)—O—N($COCH_2$)$_2$ | —O—(CO)— |
| —$NH_2$ | —O(CO)—CH=$CH_2$ acrylate terminus | —NH—$CH_2CH_2$—(CO)—O— |
| —SH | —O—(CO)—CH=$CH_2$ | —S—$CH_2CH_2$—(CO)—O— |
| —OH | —O—(CO)—CH=$CH_2$ | —O—$CH_2CH_2$—(CO)—O— |
| —$NH_2$ | —O(CO)—$(CH_2)_3$—$CO_2$—N($COCH_2$)$_2$ succinimidyl glutarate terminus | —NH—(CO)—$(CH_2)_3$—(CO)—O |
| —SH | —O(CO)—$(CH_2)_3$—$CO_2$—N($COCH_2$)$_2$ | —S—(CO)—$(CH_2)_3$—(CO)—O— |
| —OH | —O(CO)—$(CH_2)_3$—$CO_2$—N($COCH_2$)$_2$ | —O—(CO)—$(CH_2)_3$—(CO)—O |
| —$NH_2$ | —O—$CH_2$—$CO_2$—N($COCH_2$)$_2$ succinimidyl acetate terminus | —NH—(CO)—$CH_2$—O— |
| —SH | —O—$CH_2$—$CO_2$—N($COCH_2$)$_2$ | —S—(CO)—$CH_2$—O— |
| —OH | —O—$CH_2$—$CO_2$—N($COCH_2$)$_2$ | —O—(CO)—$CH_2$—O— |
| —$NH_2$ | —O—NH(CO)—$(CH_2)_2$—$CO_2$—N($COCH_2$)$_2$ succinimidyl succinamide terminus | —NH—(CO)—$(CH_2)_2$—(CO)—NH—O— |
| —SH | —O—NH(CO)—$(CH_2)_2$—$CO_2$—N($COCH_2$)$_2$ | —S—(CO)—$(CH_2)_2$—(CO)—NH—O— |
| —OH | —O—NH(CO)—$(CH_2)_2$—$CO_2$—N($COCH_2$)$_2$ | —O—(CO)—$(CH_2)_2$—(CO)—NH—O |
| —$NH_2$ | —O—$(CH_2)_2$—CHO propionaldehyde terminus | —NH—(CO)—$(CH_2)_2$—O— |
| —$NH_2$ | 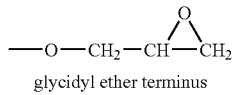 glycidyl ether terminus | —NH—$CH_2$—CH(OH)—$CH_2$—O— and —N[$CH_2$—CH(OH)—$CH_2$—O—]$_2$ |
| —$NH_2$ | —O—$(CH_2)_2$—N=C=O (isocyanate terminus) | —NH—(CO)—NH—$CH_2$—O— |
| —$NH_2$ | —$SO_2$—CH=$CH_2$ vinyl sulfone terminus | —NH—$CH_2CH_2$—$SO_2$— |
| —SH | —$SO_2$—CH=$CH_2$ | —S—$CH_2CH_2$—$SO_2$— | groups. The hydroxyl group may be activated as described above with respect to carboxylic acid groups, or it may react directly in the presence of base with a sufficiently reactive electrophilic group such as an epoxide group, an aziridine group, an acyl halide, an anhydride, and so forth.

For self-reactive compounds containing electrophilic and nucleophilic reactive groups, the initial environment typically can be dry and sterile. Since electrophilic groups react with water, storage in sterile, dry form will prevent hydrolysis. The dry synthetic polymer may be compression molded into a thin sheet or membrane, which can then be sterilized using gamma or e-beam irradiation. The resulting dry membrane or sheet can be cut to the desired size or chopped into smaller size particulates. The modification of a dry initial environment will typically comprise the addition of an aqueous medium.

In one embodiment, the initial environment can be an aqueous medium such as in a low pH buffer, i.e., having a pH less than about 6.0, in which both electrophilic and nucleophilic groups are non-reactive. Suitable liquid media for storage of such compounds include aqueous buffer solutions such as monobasic sodium phosphate/dibasic sodium phosphate, sodium carbonate/sodium bicarbonate, glutamate or acetate, at a concentration of 0.5 to 300 mM. Modification of an initial low pH aqueous environment will typically comprise increasing the pH to at least pH 7.0, more preferably increasing the pH to at least pH 9.5.

In another embodiment the modification of a dry initial environment comprises dissolving the self-reactive compound in a first buffer solution having a pH within the range of about 1.0 to 5.5 to form a homogeneous solution, and (ii) adding a second buffer solution having a pH within the range of about 6.0 to 11.0 to the homogeneous solution. The buffer solutions are aqueous and can be any pharmaceutically acceptable basic or acid composition. The term "buffer" is used in a general sense to refer to an acidic or basic aqueous solution, where the solution may or may not be functioning to provide a buffering effect (i.e., resistance to change in pH upon addition of acid or base) in the compositions of the present invention. For example, the self-reactive compound can be in the form of a homogeneous dry powder. This powder is then combined with a buffer solution having a pH within the range of about 1.0 to 5.5 to form a homogeneous acidic aqueous solution, and this solution is then combined with a buffer solution having a pH within the range of about 6.0 to 11.0 to form a reactive solution. For example, 0.375 grams of the dry powder can be combined with 0.75 grams of the acid buffer to provide, after mixing, a homogeneous solution, where this solution is combined with 1.1 grams of the basic buffer to provide a reactive mixture that substantially immediately forms a three-dimensional matrix.

Acidic buffer solutions having a pH within the range of about 1.0 to 5.5, include by way of illustration and not limitation, solutions of: citric acid, hydrochloric acid, phosphoric acid, sulfuric acid, AMPSO (3-[(1,1-dimethyl-2-hydroxyethyl)amino]2-hydroxy-propane-sulfonic acid), acetic acid, lactic acid, and combinations thereof. In a preferred embodiment, the acidic buffer solution, is a solution of citric acid, hydrochloric acid, phosphoric acid, sulfuric acid, and combinations thereof. Regardless of the precise acidifying agent, the acidic buffer preferably has a pH such that it retards the reactivity of the nucleophilic groups on the core. For example, a pH of 2.1 is generally sufficient to retard the nucleophilicity of thiol groups. A lower pH is typically preferred when the core contains amine groups as the nucleophilic groups. In general, the acidic buffer is an acidic solution that, when contacted with nucleophilic groups, renders those nucleophilic groups relatively non-nucleophilic.

An exemplary acidic buffer is a solution of hydrochloric acid, having a concentration of about 6.3 mM and a pH in the range of 2.1 to 2.3. This buffer may be prepared by combining concentrated hydrochloric acid with water, i.e., by diluting concentrated hydrochloric acid with water. Similarly, this buffer A may also be conveniently prepared by diluting 1.23 grams of concentrated hydrochloric acid to a volume of 2 liters, or diluting 1.84 grams of concentrated hydrochloric acid to a volume to 3 liters, or diluting 2.45 grams of concentrated hydrochloric acid to a volume of 4 liters, or diluting 3.07 grams concentrated hydrochloric acid to a volume of 5 liters, or diluting 3.68 grams of concentrated hydrochloric acid to a volume to 6 liters. For safety reasons, the concentrated acid is preferably added to water.

Basic buffer solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic buffer solution is a solution of carbonate salts, phosphate salts, and combinations thereof.

In general, the basic buffer is an aqueous solution that neutralizes the effect of the acidic buffer, when it is added to the homogeneous solution of the compound and first buffer, so that the nucleophilic groups on the core regain their nucleophilic character (that has been masked by the action of the acidic buffer), thus allowing the nucleophilic groups to inter-react with the electrophilic groups on the core.

An exemplary basic buffer is an aqueous solution of carbonate and phosphate salts. This buffer may be prepared by combining a base solution with a salt solution. The salt solution may be prepared by combining 34.7 g of monobasic sodium phosphate monohydrate, 49.3 g of sodium carbonate monohydrate, and sufficient water to provide a solution volume of 2 liter. Similarly, a 6 liter solution may be prepared by combining 104.0 g of monobasic sodium phosphate monohydrate, 147.94 g of sodium carbonate monohydrate, and sufficient water to provide 6 liter of the salt solution. The basic buffer may be prepared by combining 7.2 g of sodium hydroxide with 180.0 g of water. The basic buffer is typically prepared by adding the base solution as needed to the salt solution, ultimately to provide a mixture having the desired pH, e.g., a pH of 9.65 to 9.75.

In general, the basic species present in the basic buffer should be sufficiently basic to neutralize the acidity provided by the acidic buffer, but should not be so nucleophilic itself that it will react substantially with the electrophilic groups on the core. For this reason, relatively "soft" bases such as carbonate and phosphate are preferred in this embodiment of the invention.

To illustrate the preparation of a three-dimensional matrix of the present invention, one may combine an admixture of the self-reactive compound with a first, acidic, buffer (e.g., an acid solution, e.g., a dilute hydrochloric acid solution) to form a homogeneous solution. This homogeneous solution is mixed with a second, basic, buffer (e.g., a basic solution, e.g., an aqueous solution containing phosphate and carbonate salts) whereupon the reactive groups on the core of the self-reactive compound substantially immediately inter-react with one another to form a three-dimensional matrix.

2) Redox Reactive Groups

In one embodiment of the invention, the reactive groups are vinyl groups such as styrene derivatives, which undergo a radical polymerization upon initiation with a redox initiator. The term "redox" refers to a reactive group that is susceptible to oxidation-reduction activation. The term "vinyl" refers to a reactive group that is activated by a redox initiator, and forms a radical upon reaction. X, Y and Z can be the same or different vinyl groups, for example, methacrylic groups.

For self-reactive compounds containing vinyl reactive groups, the initial environment typically will be an aqueous environment. The modification of the initial environment involves the addition of a redox initiator.

3) Oxidative Coupling Reactive Groups

In one embodiment of the invention, the reactive groups undergo an oxidative coupling reaction. For example, X, Y and Z can be a halo group such as chloro, with an adjacent electron-withdrawing group on the halogen-bearing carbon (e.g., on the "L" linking group). Exemplary electron-withdrawing groups include nitro, aryl, and so forth.

For such reactive groups, the modification in the initial environment comprises a change in pH. For example, in the presence of a base such as KOH, the self-reactive compounds then undergo a de-hydro, chloro coupling reaction, forming a double bond between the carbon atoms, as illustrated below:

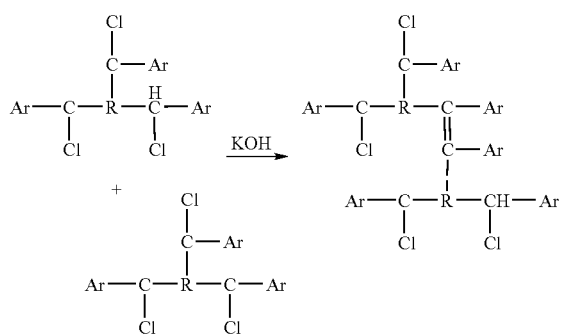

For self-reactive compounds containing oxidative coupling reactive groups, the initial environment typically can be can be dry and sterile, or a non-basic medium. The modification of the initial environment will typically comprise the addition of a base.

4) Photoinitiated Reactive Groups

In one embodiment of the invention, the reactive groups are photoinitiated groups. For such reactive groups, the modification in the initial environment comprises exposure to ultraviolet radiation.

In one embodiment of the invention, X can be an azide ($-N_3$) group and Y can be an alkyl group such as $-CH(CH_3)_2$ or vice versa. Exposure to ultraviolet radiation will then form a bond between the groups to provide for the following linkage: $-NH-C(CH_3)_2-CH_2-$. In another embodiment of the invention, X can be a benzophenone ($-(C_6H_4)-C(O)-(C_6H_5)$) group and Y can be an alkyl group such as $-CH(CH_3)_2$ or vice versa. Exposure to ultraviolet radiation will then form a bond between the groups to provide for the following linkage:

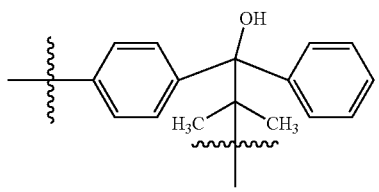

For self-reactive compounds containing photoinitiated reactive groups, the initial environment typically will be in an ultraviolet radiation-shielded environment. This can be for example, storage within a container that is impermeable to ultraviolet radiation.

The modification of the initial environment will typically comprise exposure to ultraviolet radiation.

5) Temperature-Sensitive Reactive Groups

In one embodiment of the invention, the reactive groups are temperature-sensitive groups, which undergo a thermo-chemical reaction. For such reactive groups, the modification in the initial environment thus comprises a change in temperature. The term "temperature-sensitive" refers to a reactive group that is chemically inert at one temperature or temperature range and reactive at a different temperature or temperature range.

In one embodiment of the invention, X, Y, and Z are the same or different vinyl groups.

For self-reactive compounds containing reactive groups that are temperature-sensitive, the initial environment typically will be within the range of about 10 to 30° C.

The modification of the initial environment will typically comprise changing the temperature to within the range of about 20 to 40° C.

B. Linking Groups

The reactive groups may be directly attached to the core, or they may be indirectly attached through a linking group, with longer linking groups also termed "chain extenders." In the formula (I) shown above, the optional linker groups are represented by $L^1$, $L^2$, and $L^3$, wherein the linking groups are present when p, q and r are equal to 1.

Suitable linking groups are well known in the art. See, for example, WO 97/22371 to Rhee et al. Linking groups are useful to avoid steric hindrance problems that can sometimes associated with the formation of direct linkages between molecules. Linking groups may additionally be used to link several self-reactive compounds together to make larger molecules. In one embodiment, a linking group can be used to alter the degradative properties of the compositions after administration and resultant gel formation. For example, linking groups can be used to promote hydrolysis, to discourage hydrolysis, or to provide a site for enzymatic degradation.

Examples of linking groups that provide hydrolyzable sites, include, inter alia: ester linkages; anhydride linkages, such as those obtained by incorporation of glutarate and succinate; ortho ester linkages; ortho carbonate linkages such as trimethylene carbonate; amide linkages; phosphoester linkages; a-hydroxy acid linkages, such as those obtained by incorporation of lactic acid and glycolic acid; lactone-based linkages, such as those obtained by incorporation of caprolactone, valerolactone, ?-butyrolactone and p-dioxanone; and amide linkages such as in a dimeric, oligomeric, or poly(amino acid) segment. Examples of non-degradable linking groups include succinimide, propionic acid and carboxymethylate linkages. See, for example, WO 99/07417 to Coury et al. Examples of enzymatically degradable linkages include Leu-Gly-Pro-Ala, which is degraded by collagenase; and Gly-Pro-Lys, which is degraded by plasmin.

Linking groups can also be included to enhance or suppress the reactivity of the various reactive groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a carbonyl group (e.g., the reactive carbonyl of glutaryl-N-hydroxysuccinimidyl) would increase the reactivity of the carbonyl carbon with respect to an incoming nucleophilic group. By contrast, sterically bulky groups in the vicinity of a reactive group can be used to diminish reactivity and thus reduce the coupling rate as a result of steric hindrance.

By way of example, particular linking groups and corresponding formulas are indicated in the following Table:

TABLE

| Linking group | Component structure |
|---|---|
| —O—$(CH_2)_x$— | —O—$(CH_2)_x$—X<br>—O—$(CH_2)_x$—Y<br>—O—$(CH_2)_x$—Z |
| —S—$(CH_2)_x$— | —S—$(CH_2)_x$—X<br>—S—$(CH_2)_x$—Y<br>—S—$(CH_2)_x$—Z |
| —NH—$(CH_2)_x$— | —NH—$(CH_2)_x$—X<br>—NH—$(CH_2)_x$—Y<br>—NH—$(CH_2)_x$—Z |
| —O—(CO)—NH—$(CH_2)_x$— | —O—(CO)—NH—$(CH_2)_x$—X<br>—O—(CO)—NH—$(CH_2)_x$—Y<br>—O—(CO)—NH—$(CH_2)_x$—Z |
| —NH—(CO)—O—$(CH_2)_x$— | —NH—(CO)—O—$(CH_2)_x$—X<br>—NH—(CO)—O—$(CH_2)_x$—Y<br>—NH—(CO)—O—$(CH_2)_x$—Z |
| —O—(CO)—$(CH_2)_x$— | —O—(CO)—$(CH_2)_x$—X<br>—O—(CO)—$(CH_2)_x$—Y<br>—O—(CO)—$(CH_2)_x$—Z |
| —(CO)—O—$(CH_2)_x$— | —(CO)—O—$(CH_2)_n$—X<br>—(CO)—O—$(CH_2)_n$—Y<br>—(CO)—O—$(CH_2)_n$—Z |
| —O—(CO)—O—$(CH_2)_x$— | —O—(CO)—O—$(CH_2)_x$—X<br>—O—(CO)—O—$(CH_2)_x$—Y<br>—O—(CO)—O—$(CH_2)_x$—Z |
| —O—(CO)—$CHR^2$— | —O—(CO)—$CHR^2$—X<br>—O—(CO)—$CHR^2$—Y<br>—O—(CO)—$CHR^2$—Z |
| —O—$R^3$—(CO)—NH— | —O—$R^3$—(CO)—NH—X<br>—O—$R^3$—(CO)—NH—Y<br>—O—$R^3$—(CO)—NH—Z |

In the above Table, x is generally in the range of 1 to about 10; $R^2$ is generally hydrocarbyl, typically alkyl or aryl, preferably alkyl, and most preferably lower alkyl; and $R^3$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—$CH_2$).

Other general principles that should be considered with respect to linking groups are as follows. If a higher molecular weight self-reactive compound is to be used, it will preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Hydrophilic groups can be easily introduced using known chemical synthesis, so long as they do not give rise to unwanted swelling or an undesirable decrease in compressive strength. In particular, polyalkoxy segments may weaken gel strength.

C. The Core

The "core" of each self-reactive compound is comprised of the molecular structure to which the reactive groups are bound. The molecular core can a polymer, which includes synthetic polymers and naturally occurring polymers. In one embodiment, the core is a polymer containing repeating monomer units. The polymers can be hydrophilic, hydrophobic, or amphiphilic. The molecular core can also be a low molecular weight components such as a $C_{2-14}$ hydrocarbyl or a heteroatom-containing $C_{2-14}$ hydrocarbyl. The heteroatom-containing $C_{2-14}$ hydrocarbyl can have 1 or 2 heteroatoms selected from N, O and S. In a preferred embodiment, the self-reactive compound comprises a molecular core of a synthetic hydrophilic polymer.

1) Hydrophilic Polymers

As mentioned above, the term "hydrophilic polymer" as used herein refers to a polymer having an average molecular weight and composition that naturally renders, or is selected to render the polymer as a whole "hydrophilic." Preferred polymers are highly pure or are purified to a highly pure state such that the polymer is or is treated to become pharmaceutically pure. Most hydrophilic polymers can be rendered water soluble by incorporating a sufficient number of oxygen (or less frequently nitrogen) atoms available for forming hydrogen bonds in aqueous solutions.

Synthetic hydrophilic polymers may be homopolymers, block copolymers including di-block and tri-block copolymers, random copolymers, or graft copolymers. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments preferably degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like. Other biodegradable segments that may form part of the hydrophilic polymer core include polyesters such as polylactide, polyethers such as polyalkylene oxide, polyamides such as a protein, and polyurethanes. For example, the core of the self-reactive compound can be a diblock copolymer of tetrafunctionally activated polyethylene glycol and polylactide.

Synthetic hydrophilic polymers that are useful herein include, but are not limited to: polyalkylene oxides, particularly polyethylene glycol (PEG) and poly(ethylene oxide)-poly(propylene oxide) copolymers, including block and random copolymers; polyols such as glycerol, polyglycerol (PG) and particularly highly branched polyglycerol, propylene glycol; poly(oxyalkylene)-substituted diols, and poly(oxyalkylene)-substituted polyols such as mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; poly(acrylic acids) and analogs and copolymers thereof, such as polyacrylic acid per se, polymethacrylic acid, poly(hydroxyethylmethacrylate), poly(hydroxyethylacrylate), poly(methylalkylsulfoxide methacrylates), poly(methylalkylsulfoxide acrylates) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), poly(N-isopropyl-acrylamide), and copolymers thereof; poly(olefinic alcohols) such as poly (vinyl alcohols) and copolymers thereof; poly(N-vinyl lactams) such as poly(vinyl pyrrolidones), poly(N-vinyl caprolactams), and copolymers thereof; polyoxazolines, including poly(methyloxazoline) and poly(ethyloxazoline); and polyvinylamines; as well as copolymers of any of the foregoing. It must be emphasized that the aforementioned list of polymers is not exhaustive, and a variety of other synthetic hydrophilic polymers may be used, as will be appreciated by those skilled in the art.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif.).

Although a variety of different synthetic hydrophilic polymers can be used in the present compounds, preferred synthetic hydrophilic polymers are PEG and PG, particularly highly branched PG. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred synthetic hydrophilic polymer for certain applications is a PEG having a molecular weight within the range of about 100 to about 100,000, although for highly branched PEG, far higher molecular weight polymers can be employed, up to 1,000,000 or more, providing that biodegradable sites are incorporated ensuring that all degradation products will have a molecular weight of less than about 30,000. For most PEGs, however, the preferred molecular weight is about 1,000 to about 20,000, more preferably within the range of about 7,500 to about 20,000. Most preferably, the polyethylene glycol has a molecular weight of approximately 10,000.

Naturally occurring hydrophilic polymers include, but are not limited to: proteins such as collagen, fibronectin, albumins, globulins, fibrinogen, fibrin and thrombin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

Unless otherwise specified, the term "collagen" as used herein refers to all forms of collagen, including those, which have been processed or otherwise modified. Thus, collagen from any source may be used in the compounds of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. For example, U.S. Pat. No. 5,428,022 to Palefsky et al. discloses methods of extracting and purifying collagen from the human placenta, and U.S. Pat. No. 5,667,839 to Berg discloses methods of producing recombinant human collagen in the milk of transgenic animals, including transgenic cows. Non-transgenic, recombinant collagen expression in yeast and other cell lines) is described in U.S. Pat. No. 6,413,742 to Olsen et al., U.S. Pat. No. 6,428,978 to Olsen et al., and U.S. Pat. No. 6,653,450 to Berg et al.

Collagen of any type, including, but not limited to, types I, II, III, IV, or any combination thereof, may be used in the compounds of the invention, although type I is generally preferred. Either atelopeptide or telopeptide-containing collagen may be used; however, when collagen from a natural source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the invention, although previously crosslinked collagen may be used.

Collagens for use in the present invention are generally, although not necessarily, in aqueous suspension at a concentration between about 20 mg/ml to about 120 mg/ml, preferably between about 30 mg/ml to about 90 mg/ml. Although intact collagen is preferred, denatured collagen, commonly known as gelatin, can also be used. Gelatin may have the added benefit of being degradable faster than collagen.

Nonfibrillar collagen is generally preferred for use in compounds of the invention, although fibrillar collagens may also be used. The term "nonfibrillar collagen" refers to any modified or unmodified collagen material that is in substantially nonfibrillar form, i.e., molecular collagen that is not tightly associated with other collagen molecules so as to form fibers. Typically, a solution of nonfibrillar collagen is more transparent than is a solution of fibrillar collagen. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559 to Miyata et al. Methylated collagen, which contains reactive amine groups, is a preferred nucleophile-containing component in the compositions of the present invention. In another aspect, methylated collagen is a component that is present in addition to first and second components in the matrix-forming reaction of the present invention. Methylated collagen is described in, for example, in U.S. Pat. No. 5,614,587 to Rhee et al.

Collagens for use in the compositions of the present invention may start out in fibrillar form, then can be rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Fibrillar collagen is less preferred for use in the compounds of the invention. However, as disclosed in U.S. Pat. No. 5,614,587 to Rhee et al., fibrillar collagen, or mixtures of nonfibrillar and fibrillar collagen, may be preferred for use in compounds intended for long-term persistence in vivo.

2) Hydrophobic Polymers

The core of the self-reactive compound may also comprise a hydrophobic polymer, including low molecular weight polyfunctional species, although for most uses hydrophilic polymers are preferred. Generally, "hydrophobic polymers" herein contain a relatively small proportion of oxygen and/or nitrogen atoms. Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing, for example, multiple nucleophilic groups. Thus, use of short-chain oligomers can avoid solubility-related problems during reaction. Polylactic acid and polyglycolic acid are examples of two particularly suitable hydrophobic polymers.

3) Amphiphilic Polymers

Generally, amphiphilic polymers have a hydrophilic portion and a hydrophobic (or lipophilic) portion. The hydrophilic portion can be at one end of the core and the hydrophobic portion at the opposite end, or the hydrophilic and hydrophobic portions may be distributed randomly (random copolymer) or in the form of sequences or grafts (block copolymer) to form the amphiphilic polymer core of the self-reactive compound. The hydrophilic and hydrophobic portions may include any of the aforementioned hydrophilic and hydrophobic polymers.

Alternately, the amphiphilic polymer core can be a hydrophilic polymer that has been modified with hydrophobic moieties (e.g., alkylated PEG or a hydrophilic polymer modified with one or more fatty chains), or a hydrophobic polymer that has been modified with hydrophilic moieties (e.g., "PEGylated" phospholipids such as polyethylene glycolated phospholipids).

4) Low Molecular Weight Components

As indicated above, the molecular core of the self-reactive compound can also be a low molecular weight compound, defined herein as being a $C_{2-14}$ hydrocarbyl or a heteroatom-containing $C_{2-14}$ hydrocarbyl, which contains 1 to 2 heteroatoms selected from N, O, S and combinations thereof. Such a molecular core can be substituted with any of the reactive groups described herein.

Alkanes are suitable $C_{2-14}$ hydrocarbyl molecular cores. Exemplary alkanes, for substituted with a nucleophilic primary amino group and a Y electrophilic group, include, ethyleneamine ($H_2N$—$CH_2CH_2$—Y), tetramethyleneamine ($H_2N$—$(CH_4)$—Y), pentamethyleneamine ($H_2N$—$(CH_5)$—Y), and hexamethyleneamine ($H_2N$—$(CH_6)$—Y).

Low molecular weight diols and polyols are also suitable $C_{2-14}$ hydrocarbyls and include trimethylolpropane, di(trimethylol propane), pentaerythritol, and diglycerol. Polyacids are also suitable $C_{2-14}$ hydrocarbyls, and include trimethylolpropane-based tricarboxylic acid, di(trimethylol propane)-based tetracarboxylic acid, heptanedioic acid, octanedioic acid (suberic acid), and hexadecanedioic acid (thapsic acid).

Low molecular weight di- and poly-electrophiles are suitable heteroatom-containing $C_{2-14}$ hydrocarbyl molecular cores. These include, for example, disuccinimidyl suberate (DSS), bis(sulfosuccinimidyl) suberate ($BS_3$), dithiobis(succinimidylpropionate) (DSP), bis(2-succinimidooxycarbonyloxy) ethyl sulfone (BSOCOES), and 3,3'-dithiobis(sulfosuccinimidylpropionate) (DTSPP), and their analogs and derivatives.

In one embodiment of the invention, the self-reactive compound of the invention comprises a low-molecular weight material core, with a plurality of acrylate moieties and a plurality of thiol groups.

D. Preparation

The self-reactive compounds are readily synthesized to contain a hydrophilic, hydrophobic or amphiphilic polymer core or a low molecular weight core, functionalized with the desired functional groups, i.e., nucleophilic and electrophilic groups, which enable crosslinking. For example, preparation of a self-reactive compound having a polyethylene glycol (PEG) core is discussed below. However, it is to be understood that the following discussion is for purposes of illustration and analogous techniques may be employed with other polymers.

With respect to PEG, first of all, various functionalized PEGs have been used effectively in fields such as protein modification (see Abuchowski et al., Enzymes as Drugs, John Wiley & Sons: New York, N.Y. (1981) pp. 367–383; and Dreborg et al. (1990) Crit. Rev. Therap. Drug Carrier Syst. 6:315), peptide chemistry (see Mutter et al., The Peptides, Academic: New York, N.Y. 2:285–332; and Zalipsky et al. (1987) Int. J. Peptide Protein Res. 30:740), and the synthesis of polymeric drugs (see Zalipsky et al. (1983) Eur. Polym. J. 19:1177; and Ouchi et al. (1987) J. Macromol. Sci. Chem. A24:1011).

Functionalized forms of PEG, including multi-functionalized PEG, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992).

Multi-functionalized forms of PEG are of particular interest and include, PEG succinimidyl glutarate, PEG succinimidyl propionate, succinimidyl butylate, PEG succinimidyl acetate, PEG succinimidyl succinamide, PEG succinimidyl carbonate, PEG propionaldehyde, PEG glycidyl ether, PEG-isocyanate, and PEG-vinylsulfone. Many such forms of PEG are described in U.S. Pat. Nos. 5,328,955 and 6,534,591, both to Rhee et al. Similarly, various forms of multi-amino PEG are commercially available from sources such as PEG Shop, a division of SunBio of South Korea (www.sunbio.com), Nippon Oil and Fats (Yebisu Garden Place Tower, 20–3 Ebisu 4-chome, Shibuya-ku, Tokyo), Nektar Therapeutics (San Carlos, California, formerly Shearwater Polymers, Huntsville, Ala.) and from Huntsman's Performance Chemicals Group (Houston, Tex.) under the name Jeffamine® polyoxyalkyleneamines. Multi-amino PEGs useful in the present invention include the Jeffamine diamines ("D" series) and triamines ("T" series), which contain two and three primary amino groups per molecule. Analogous poly(sulfhydryl) PEGs are also available from Nektar Therapeutics, e.g., in the form of pentaerythritol poly(ethylene glycol) ether tetra-sulfhydryl (molecular weight 10,000). These multi-functionalized forms of PEG can then be modified to include the other desired reactive groups.

Reaction with succinimidyl groups to convert terminal hydroxyl groups to reactive esters is one technique for preparing a core with electrophilic groups. This core can then be modified include nucleophilic groups such as primary amines, thiols, and hydroxyl groups. Other agents to convert hydroxyl groups include carbonyldiimidazole and sulfonyl chloride. However, as discussed herein, a wide variety of electrophilic groups may be advantageously employed for reaction with corresponding nucleophilic groups. Examples of such electrophilic groups include acid chloride groups; anhydrides, ketones, aldehydes, isocyanate, isothiocyanate, epoxides, and olefins, including conjugated olefins such as ethenesulfonyl (—$SO_2CH=CH_2$) and analogous functional groups.

Other in Situ Crosslinking Materials

Numerous other types of in situ forming materials may be used in combination with an anti-scarring agent in accordance with the invention. The in situ forming material may be a biocompatible crosslinked polymer that is formed from water soluble precursors having electrophilic and nucleophilic groups capable of reacting and crosslinking in situ (see, e.g., U.S. Pat. No. 6,566,406). The in situ forming material may be hydrogel that may be formed through a combination of physical and chemical crosslinking processes, where physical crosslinking is mediated by one or more natural or synthetic components that stabilize the hydrogel-forming precursor solution at a deposition site for a period of time sufficient for more resilient chemical crosslinks to form (see, e.g., U.S. Pat. No. 6,818,018). The in situ forming material may be formed upon exposure to an aqueous fluid from a physiological environment from dry hydrogel precursors (see, e.g., U.S. Pat. No. 6,703,047). The in situ forming material may be a hydrogel matrix that provides controlled release of relatively low molecular weight therapeutic species by first dispersing or dissolving the therapeutic species within relatively hydrophobic rate modifying agents to form a mixture; the mixture is formed into microparticles that are dispersed within bioabsorbable hydrogels, so as to release the water soluble therapeutic agents in a controlled fashion (see, e.g., 6,632,457). The in situ forming material may be a multi-component hydrogel system (see, e.g., U.S. Pat. No. 6,379,373). The in situ forming material may be a multi-arm block copolymer that includes a central core molecule, such as a residue of a polyol, and at least three copolymer arms covalently attached to the central core molecule, each copolymer arm comprising an inner hydrophobic polymer segment covalently attached to the central core molecule and an outer hydrophilic polymer segment covalently attached to the hydrophobic polymer segment, wherein the central core molecule and the hydrophobic polymer segment define a hydrophobic core region (see, e.g., U.S. Pat. No. 6,730,334). The in situ forming material may include a gel-forming macromer that includes at least four polymeric blocks, at least two of which are hydrophobic and at least one of which is hydrophilic, and including a crosslinkable group (see, e.g., U.S. Pat. No. 6,639,014). The in situ forming material may be a water-soluble macromer that includes at least one hydrolysable linkage formed from carbonate or dioxanone groups, at least one water-soluble polymeric block, and at least one polymerizable group (see, e.g., U.S. Pat. No. 6,177,095). The in situ forming material may comprise polyoxyalkylene block copolymers that form weak physical crosslinks to provide gels having a paste-like consistency at physiological temperatures. (See, e.g., U.S. Pat. No. 4,911,926). The in situ forming material may be a thermoirreversible gel made from polyoxyalkylene polymers and ionic polysaccharides (see, e.g., U.S. Pat. No. 5,126,141). The in situ forming material may be a gel forming composition that includes chitin derivatives (see, e.g., U.S. Pat. No. 5,093,319), chitosan-coagulum (see, e.g., U.S. Pat. No. 4,532,134), or hyaluronic acid (see, e.g., U.S. Pat. No. 4,141,973). The in situ forming material may be an in situ modification of alginate (see, e.g., U.S. Pat. No. 5,266,326). The in situ forming material may be formed from ethylenically unsaturated water soluble macromers that can be crosslinked in contact with tissues, cells, and bioactive molecules to form gels (see, e.g., U.S. Pat. No. 5,573,934). The in situ forming material may include urethane prepolymers used in combination with an unsaturated cyano compound containing a cyano group attached to a carbon atom, such as cyano(meth)acrylic acids and esters thereof (see, e.g., U.S. Pat. No. 4,740,534). The in situ forming material may be a biodegradable hydrogel that polymerizes by a photoinitiated free radical polymerization from water soluble macromers (see, e.g., U.S. Pat. No. 5,410,016). The in situ forming material may be formed from a two component mixture including a first part comprising a serum albumin protein in an aqueous buffer having a pH in a range of about 8.0–11.0, and a second part comprising a water-compatible or water-soluble bifunctional crosslinking agent. (see, e.g., U.S. Pat. No. 5,583,114).

In another aspect, in situ forming materials that can be used include those based on the crosslinking of proteins. For example, the in situ forming material may be a biodegradable hydrogel composed of a recombinant or natural human serum albumin and poly(ethylene) glycol polymer solution whereby upon mixing the solution cross-links to form a mechanical non-liquid covering structure which acts as a sealant. See e.g., U.S. Pat. Nos. 6,458,147 and 6,371,975. The in situ forming material may be composed of two separate mixtures based on fibrinogen and thrombin that are dispensed together to form a biological adhesive when intermixed either prior to or on the application site to form a fibrin sealant. See e.g., U.S. Pat. No. 6,764,467. The in situ forming material may be composed of ultrasonically treated collagen and albumin which form a viscous material that develops adhesive properties when crosslinked chemically with glutaraldehyde and amino acids or peptides. See e.g., U.S. Pat. No. 6,310,036. The in situ forming material may be a hydrated adhesive gel composed of an aqueous solution consisting essentially of a protein having amino groups at the side chains (e.g., gelatin, albumin) which is crosslinked with an N-hydroxyimidoester compound. See e.g., U.S. Pat. No. 4,839,345. The in situ forming material may be a hydrogel prepared from a protein or polysaccharide backbone (e.g., albumin or polymannuronic acid) bonded to a cross-linking agent (e.g., polyvalent derivatives of polyethylene or polyalkylene glycol). See e.g., U.S. Pat. No. 5,514,379. The in situ forming material may be composed of a polymerizable collagen composition that is applied to the tissue and then exposed to an initiator to polymerize the collagen to form a seal over a wound opening in the tissue. See e.g., U.S. Pat. No. 5,874,537. The in situ forming material may be a two component mixture composed of a protein (e.g., serum albumin) in an aqueous buffer having a pH in the range of about 8.0–11.0 and a water-soluble bifunctional polyethylene oxide type crosslinking agent, which transforms from a liquid to a strong, flexible bonding composition to seal tissue in situ. See e.g., U.S. Pat. Nos. 5,583,114 and RE38158 and PCT Publication No. WO 96/03159. The in situ forming material may be composed of a protein, a surfactant, and a lipid in a liquid carrier, which is crosslinked by adding a crosslinker and used as a sealant or bonding agent in situ. See e.g., U.S. Patent Application No. 2004/0063613A1 and PCT Publication Nos. WO 01/45761 and WO 03/090683. The in situ forming material may be composed of two enzyme-free liquid components that are mixed by dispensing the components into a catheter tube deployed at the vascular puncture site, wherein, upon mixing, the two liquid components chemically cross-link to form a mechanical non-liquid matrix that seals a vascular puncture site. See e.g., U.S. Patent Application Nos. 2002/0161399A1 and 2001/0018598A1. The in situ forming material may be a cross-linked albumin composition composed of an albumin preparation and a carbodiimide preparation which are mixed under conditions that permit crosslinking of the albumin for use as a bioadhesive or sealant. See e.g., PCT Publication No. WO 99/66964. The in situ forming material may be composed of collagen and a peroxidase and hydrogen peroxide, such that the collagen is crosslinked to from a semi-solid gel that seals a wound. See e.g., PCT Publication No. WO 01/35882.

In another aspect, in situ forming materials that can be used include those based on isocyanate or isothiocyanate capped polymers. For example, the in situ forming material may be composed of isocyanate-capped polymers that are liquid compositions which form into a solid adhesive coating by in situ polymerization and crosslinking upon contact with body fluid or tissue. See e.g., PCT Publication No. WO 04/021983. The in situ forming material may be a moisture-curing sealant composition composed of an active isocyanato-terminated isocyanate prepolymer containing a polyol component with a molecular weight of 2,000 to 20,000 and an isocyanurating catalyst agent. See e.g., U.S. Pat. No. 5,206,331.

In another embodiment, the reagents can undergo an electrophilic-nucleophilic reaction to produce a crosslinked matrix. Polymers containing and/or terminated with nucleophilic groups such as amine, sulfhydryl, hydroxyl, $-PH_2$ or $CO-NH-NH_2$ can be used as the nucleophilic reagents and polymers containing and/or terminated with electrophilic groups such as succinimidyl, carboxylic acid, aldehyde, epoxide, isocyanate, vinyl, vinyl sulfone, maleimide, $-S-S-(C_5H_4N)$ or activated esters, such as are used in peptide synthesis can be used as the electrophilic reagents. For example, a 4-armed thiol derivatized poly(ethylene glycol) (e.g., pentaerythritol poly(ethylene glycol)ether tetra-sulfhydryl) can be reacted with a 4 armed NHS-derivatized polyethylene glycol (e.g., pentaerythritol poly (ethylene glycol)ether tetra-succinimidyl glutarate) under basic conditions (pH>about 8). Representative examples of compositions that undergo such electrophilic-nucleophilic crosslinking reactions are described, for example, in U.S. Pat. Nos. 5,752,974; 5,807,581; 5,874,500; 5,936,035; 6,051,648; 6,165,489; 6,312,725; 6,458,889; 6,495,127; 6,534,591; 6,624,245; 6,566,406; 6,610,033; 6,632,457; and PCT Application Publication Nos. WO 04/060405 and WO 04/060346.

In another embodiment, the electrophilic- or nucleophilic-terminated polymers can further comprise a polymer that can enhance the mechanical and/or adhesive properties of the in situ forming compositions. This polymer can be a degradable or non-degradable polymer. For example, the polymer may be collagen or a collagen derivative, for example methylated collagen. An example of an in situ forming composition uses pentaerythritol poly(ethylene glycol)ether tetra-sulfhydryl) (4-armed thiol PEG), pentaerythritol poly(ethylene glycol)ether tetra-succinimidyl glutarate) (4-armed NHS PEG) and methylated collagen as the reactive reagents. This composition, when mixed with the appropriate buffers can produce a crosslinked hydrogel. (See, e.g., U.S. Pat. Nos. 5,874,500; 6,051,648; 6,166,130; 5,565,519 and 6,312,725).

In another embodiment, the reagents that can form a covalent bond with the tissue to which it is applied may be used. Polymers containing and/or terminated with electrophilic groups such as succinimidyl, aldehyde, epoxide, isocyanate, vinyl, vinyl sulfone, maleimide, $-S-S-(C_5H_4N)$ or activated esters, such as are used in peptide synthesis may be used as the reagents. For example, a 4 armed NHS-derivatized polyethylene glycol (e.g., pentaerythritol poly (ethylene glycol)ether tetra-succinimidyl glutarate) may be applied to the tissue in the solid form or in a solution form. In the preferred embodiment, the 4 armed NHS-derivatized polyethylene glycol is applied to the tissue under basic conditions (pH>about 8). Other representative examples of compositions of this nature that may be used are disclosed in PCT Application Publication No. WO 04/060405 and WO 04/060346, and U.S. patent application Ser. No. 10/749,123.

In another embodiment, the in situ forming material polymer can be a polyester. Polyesters that can be used in in situ forming compositions include poly(hydroxyesters). In another embodiment, the polyester can comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2one. Representative examples of these types of compositions are described in U.S. Pat. Nos. 5,874,500; 5,936,035; 6,312,725; 6,495,127 and PCT Publication Nos. WO 2004/028547.

In another embodiment, the electrophilic-terminated polymer can be partially or completely replaced by a small molecule or oligomer that comprises an electrophilic group (e.g., disuccinimidyl glutarate).

In another embodiment, the nucleophilic-terminated polymer can be partially or completely replaced by a small molecule or oligomer that comprises a nucleophilic group (e.g., dicysteine, dilysine, trilysine, etc.).

Other examples of in situ forming materials that can be used include those based on the crosslinking of proteins (described in, for example, U.S. Pat. Nos. RE38158; 4,839, 345; 5,514,379, 5,583,114; 6,310,036; 6,458,147; 6,371, 975; US Patent Application Publication Nos. 2004/0063613A1, 2002/0161399A1, and 2001/0018598A1, and PCT Publication Nos. WO 03/090683, WO 01/45761, WO 99/66964, and WO 96/03159) and those based on isocyanate or isothiocyanate capped polymers (see, e.g., PCT Publication No. WO 04/021983).

Other examples of in situ forming materials that are of particular interest in the treatment of diverticula, both alone and in combination with the therapeutic agents described previously, can include reagents that comprise one or more cyanoacrylate groups. These reagents can be used to prepare a poly(alkylcyanoacrylate) or poly(carboxyalkylcyanoacrylate) (e.g., poly(methylcyanoacrylate) poly(ethylcyanoacrylate), poly(butylcyanoacrylate), poly(isobutylcyanoacrylate), poly(hexylcyanoacrylate), poly(methoxypropylcyanoacrylate), and poly(octylcyanoacrylate)) as well as copolymers and mixtures of these. Specific examples of blends include blends of ethyl cyanoacrylate and methoxypropyl acrylate, methoxyproypl cyanoacrylate and octyl cyanoacrylate and methoxybutyl cyanoacrylate and butyl cyanoacrylate. Examples of commercially available cyanoacrylates that can be used include DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT.

In another embodiment, the cyanoacrylate compositions can further comprise additives to stabilize the reagents or alter the rate of reaction of the cyanoacrylate, alter the flexibility of the finally cured polymer, or alter the viscosity of the product. For example, a trimethylene carbonate based polymer or an oxalate polymer of poly(ethylene glycol) or a ε-caprolactone based copolymer (linear, branched, triaxial, terta-axial) can be mixed with a 2-alkoxyalkylcyanoacrylate (e.g., 2-methoxypropylcyanoacrylate). Examples of stabilizers include sulfur dioxide ($SO_2$) or polyphosphoric acid. Representative examples of these compositions are described in U.S. Pat. Nos. 5,350,798 and 6,299,631.

In another embodiment, the cyanoacrylate composition can be prepared by capping heterochain polymers with a cyanoacrylate group. The cyanoacrylate-capped heterochain polymer preferably has at least two cyanoacrylate ester groups per chain. The heterochain polymer can comprise an absorbable poly(ester), poly(ester-carbonate), poly(ether-carbonate) and poly(ether-ester). The poly(ether-ester)s described in U.S. Pat. Nos. 5,653,992 and 5,714,159 can also be used as the heterochain polymers. A triaxial poly(ε-caprolactone-co-trimethylene carbonate) is an example of a poly(ester-carbonate) that can be used. The heterochain polymer may be a polyether. Examples of polyethers that can be used include poly(ethylene glycol), poly(propylene glycol) and block copolymers of poly(ethylene glycol) and poly(propylene glycol) (e.g., PLURONICS group of polymers including but not limited to PLURONIC F127 or F68). Representative examples of these compositions are described in U.S. Pat. No. 6,699,940.

Within another aspect of the invention, the biologically active fibrosis-inducing agent, anti-infective, and/or hemostatic agent can be delivered with a non-polymeric compound (e.g., a carrier). These non-polymeric carriers can include sucrose derivatives (e.g., sucrose acetate isobutyrate, sucrose oleate), sterols such as cholesterol, stigmasterol, β-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols, calcium phosphate, sintered and unscintered hydoxyapatite, zeolites; and combinations and mixtures thereof.

Representative examples of patents relating to non-polymeric delivery systems and the preparation include U.S. Pat. Nos. 5,736,152; 5,888,533; 6,120,789; 5,968,542; and 5,747,058.

Within certain embodiments of the invention, the therapeutic compositions are provided that include (i) a fibrosis-inducing agent and/or (ii) an anti-infective agent. The therapeutic compositions may include one or more additional therapeutic agents (such as described above), for example, a hemostatic agent. Other agents that may be combined with the therapeutic compositions include, e.g., anti-inflammation agents, matrix metalloproteinase inhibitors, cytokine inhibitors, IMPDH inhibitors, immunomodulatory agents, tyrosine inhibitors, p38 MAP kinase inhibitors, NFKβ inhibitors, HMGCoA reductase inhibitors, apoptosis antagonist, caspase inhibitors, and JNK inhibitors.

In one aspect, the present invention provides compositions comprising i) a fibrosing agent and ii) a polymer or a compound that forms a crosslinked polymer in situ. The following are some, but by no means all, of the preferred fibrosis-inducing agents and classes of fibrosis-inducing agents that may be included in the inventive compositions:

1a. A fibrosing agent that promotes cell regeneration.
2a. A fibrosing agent that promotes angiogenesis.
3a. A fibrosing agent that promotes fibroblast migration.
4a. A fibrosing agent that promotes fibroblast proliferation.
5a. A fibrosing agent that promotes deposition of extracellular matrix.
6a. A fibrosing agent that promotes tissue remodeling.
7a. A fibrosing agent that is a diverticular wall irritant.
8a. A fibrosing agent that is silk (such as silkworm silk, spider silk, recombinant silk, raw silk, hydrolyzed silk, acid-treated silk, and acylated silk)
9a. A fibrosing agent that is talc.
10a. A fibrosing agent that is chitosan.
11a. A fibrosing agent that is polylysine.
12a. A fibrosing agent that is fibronectin.
13a. A fibrosing agent that is bleomycin or an analogue or derivative thereof.
14a. A fibrosing agent that is connective tissue growth factor (CTGF).
15a. A fibrosing agent that is metallic beryllium or an oxide thereof.
16a. A fibrosing agent that is copper.

17a. A fibrosing agent that is saracin.
18a. A fibrosing agent that is silica.
19a. A fibrosing agent that is crystalline silicates.
20a. A fibrosing agent that is quartz dust.
21a. A fibrosing agent that is talcum powder.
22a. A fibrosing agent that is ethanol.
23a. A fibrosing agent that is a component of extracellular matrix.
24a. A fibrosing agent that is collagen.
25a. A fibrosing agent that is fibrin.
26a. A fibrosing agent that is fibrinogen.
27a. A fibrosing agent that is poly(ethylene terephthalate).
28a. A fibrosing agent that is poly(ethylene-co-vinylacetate).
29a. A fibrosing agent that is N-carboxybutylchitosan.
30a. A fibrosing agent that is an RGD protein.
31a. A fibrosing agent that is a polymer of vinyl chloride.
32a. A fibrosing agent that is cyanoacrylate.
33a. A fibrosing agent that is crosslinked poly(ethylene glycol)-methylated collagen.
34a. A fibrosing agent that is an inflammatory cytokine.
35a. A fibrosing agent that is TGFβ.
36a. A fibrosing agent that is PDGF.
37a. A fibrosing agent that is VEGF.
38a. A fibrosing agent that is TNFa.
39a. A fibrosing agent that is NGF.
40a. A fibrosing agent that is GM-CSF.
41a. A fibrosing agent that is IGF-a.
42a. A fibrosing agent that is IL-1
43a. A fibrosing agent is IL-8.
44a. A fibrosing agent is IL-6.
45a. A fibrosing agent that is a growth hormone.
46a. A fibrosing agent that is a bone morphogenic protein.
47a. A fibrosing agent that is a cell proliferative agent.
48a. A fibrosing agent that is dexamethasone.
49a. A fibrosing agent that is isotretinoin.
50a. A fibrosing agent that is 17-β-estradiol.
51a. A fibrosing agent that is estradiol.
52a. A fibrosing agent that is diethylstibesterol.
53a. A fibrosing agent that is cyclosporine A.
54a. A fibrosing agent that is all-trans retinoic acid or an analogue or derivative thereof.
55a. A fibrosing agent that is wool (including animal wool, wood wool, and mineral wool).
56a. A fibrosing agent that is cotton.
57a. A fibrosing agent that is bFGF.
58a. A fibrosing agent that is polyurethane.
59a. A fibrosing agent that is polytetrafluoroethylene.
60a. A fibrosing agent that is poly(alkylcyanoacrylate).
61a. A fibrosing agent that is activin.
62a. A fibrosing agent that is angiopoietin.
63a. A fibrosing agent that is insulin-like growth factor (IGF).
64a. A fibrosing agent that is hepatocyte growth factor (HGF).
65a. A fibrosing agent that is a colony-stimulating factor (CSF).
66a. A fibrosing agent that is erythropoietin.
67a. A fibrosing agent that is an interferon.
68a. A fibrosing agent that is endothelin-1.
69a. A fibrosing agent that is angiotensin ll.
70a. A fibrosing agent that is bromocriptine.
71a. A fibrosing agent that is methylsergide.
72a. A fibrosing agent that is fibrosin.
73a. A fibrosing agent that is fibrin.
74a. A fibrosing agent that is an adhesive glycoprotein.
75a. A fibrosing agent that is a proteoglycan.
76a. A fibrosing agent that is hyaluronan.
77a. A fibrosing agent that is secreted protein acidic and rich in cysteine (SPARC).
78a. A fibrosing agent that is a thrombospondin.
79a. A fibrosing agent that is tenacin.
80a. A fibrosing agent that is a cell adhesion molecule.
81a. A fibrosing agent that is an inhibitor of matrix metalloproteinase.
82a. A fibrosing agent that is a tissue inhibitor of matrix metalloproteinase.
83a. A fibrosing agent that is methotrexate.
84a. A fibrosing agent that is carbon tetrachloride.
85a. A fibrosing agent that is thioacetamide.

As mentioned above, the present invention provides compositions comprising each of the foregoing 86 (i.e., 1a through 85a) listed fibrosing agents or classes of fibrosing agents, with each of the following 98 (i.e., 1b through 97b) polymers and compounds:

1b. A crosslinked polymer.
2b. A polymer that reacts with mammalian tissue.
3b. A polymer that is a naturally occurring polymer.
4b. A polymer that is a protein.
5b. A polymer that is a carbohydrate.
6b. A polymer that is biodegradable.
7b. A polymer that is crosslinked and biodegradable.
8b. A polymer that nonbiodegradable.
9b. Collagen.
10b. Methylated collagen.
11b. Fibrinogen.
12b. Thrombin.
13b. Albumin.
14b. Plasminogen.
15b. von Willebrands factor.
16b. Factor VIII.
17b. Hypoallergenic collagen.
18b. Atelopeptidic collagen.
19b. Telopeptide collagen.
20b. Crosslinked collagen.
21b. Aprotinin.
22b. Gelatin.
23b. A protein conjugate.
24b. A gelatin conjugate.
25b. Hyaluronic acid.
26b. A hyaluronic acid derivative.
27b. A synthetic polymer.
28b. A polymer formed from reactants comprising a synthetic isocyanate-containing compound.
29b. A synthetic isocyanate-containing compound.
30b. A polymer formed from reactants comprising a synthetic thiol-containing compound.
31b. A synthetic thiol-containing compound.
32b. A polymer formed from reactants comprising a synthetic compound containing at least two thiol groups.
33b. A synthetic compound containing at least two thiol groups.
34b. A polymer formed from reactants comprising a synthetic compound containing at least three thiol groups.
35b. A synthetic compound containing at least three thiol groups.
36b. A polymer formed from reactants comprising a synthetic compound containing at least four thiol groups.
37b. A synthetic compound containing at least four thiol groups.
38b. A polymer formed from reactants comprising a synthetic amino-containing compound.
39b. A synthetic amino-containing compound.

40b. A polymer formed from reactants comprising a synthetic compound containing at least two amino groups.

41b. A synthetic compound containing at least two amino groups.

42b. A polymer formed from reactants comprising a synthetic compound containing at least three amino groups.

43b. A synthetic compound containing at least three amino groups.

44b. A polymer formed from reactants comprising a synthetic compound containing at least four amino groups.

45b. A synthetic compound containing at least four amino groups.

46b. A polymer formed from reactants comprising a synthetic compound comprising a carbonyl-oxygen-succinimidyl group.

47b. A synthetic compound comprising a carbonyl-oxygen-succinimidyl group.

48b. A polymer formed from reactants comprising a synthetic compound comprising at least two carbonyl-oxygen-succinimidyl groups.

49b. A synthetic compound comprising at least two carbonyl-oxygen-succinimidyl groups.

50b. A polymer formed from reactants comprising a synthetic compound comprising at least three carbonyl-oxygen-succinimidyl groups.

51b. A synthetic compound comprising at least three carbonyl-oxygen-succinimidyl groups.

52b. A polymer formed from reactants comprising a synthetic compound comprising at least four carbonyl-oxygen-succinimidyl groups.

53b. A synthetic compound comprising at least four carbonyl-oxygen-succinimidyl groups.

54b. A polymer formed from reactants comprising a synthetic polyalkylene oxide-containing compound.

55b. A synthetic polyalkylene oxide-containing compound.

56b. A polymer formed from reactants comprising a synthetic compound comprising both polyalkylene oxide and biodegradable polyester blocks.

57b. A synthetic compound comprising both polyalkylene oxide and biodegradable polyester blocks.

58b. A polymer formed from reactants comprising a synthetic polyalkylene oxide-containing compound having reactive amino groups.

59b. A synthetic polyalkylene oxide-containing compound having reactive amino groups.

60b. A polymer formed from reactants comprising a synthetic polyalkylene oxide-containing compound having reactive thiol groups.

61b. A synthetic polyalkylene oxide-containing compound having reactive thiol groups.

62b. A polymer formed from reactants comprising a synthetic polyalkylene oxide-containing compound having reactive carbonyl-oxygen-succinimidyl groups.

63b. A synthetic polyalkylene oxide-containing compound having reactive carbonyl-oxygen-succinimidyl groups.

64b. A polymer formed from reactants comprising a synthetic compound comprising a biodegradable polyester block.

65b. A synthetic compound comprising a biodegradable polyester block.

66b. A polymer formed from reactants comprising a synthetic polymer formed in whole or part from lactic acid or lactide.

67b. A synthetic polymer formed in whole or part from lactic acid or lactide.

68b. A polymer formed from reactants comprising a synthetic polymer formed in whole or part from glycolic acid or glycolide.

69b. A synthetic polymer formed in whole or part from glycolic acid or glycolide.

70b. A polymer formed from reactants comprising polylysine.

71b. Polylysine.

72b. A polymer formed from reactants comprising (a) protein and (b) a compound comprising a polyalkylene oxide portion.

73b. A polymer formed from reactants comprising (a) protein and (b) polylysine.

74b. A polymer formed from reactants comprising (a) protein and (b) a compound having at least four thiol groups.

75b. A polymer formed from reactants comprising (a) protein and (b) a compound having at least four amino groups.

76b. A polymer formed from reactants comprising (a) protein and (b) a compound having at least four carbonyl-oxygen-succinimide groups.

77b. A polymer formed from reactants comprising (a) protein and (b) a compound having a biodegradable region formed from reactants selected from lactic acid, lactide, glycolic acid, glycolide, and epsilon-caprolactone.

78b. A polymer formed from reactants comprising (a) collagen and (b) a compound comprising a polyalkylene oxide portion.

79b. A polymer formed from reactants comprising (a) collagen and (b) polylysine.

80b. A polymer formed from reactants comprising (a) collagen and (b) a compound having at least four thiol groups.

81b. A polymer formed from reactants comprising (a) collagen and (b) a compound having at least four amino groups.

82b. A polymer formed from reactants comprising (a) collagen and (b) a compound having at least four carbonyl-oxygen-succinimide groups.

83b. A polymer formed from reactants comprising (a) collagen and (b) a compound having a biodegradable region formed from reactants selected from lactic acid, lactide, glycolic acid, glycolide, and epsilon-caprolactone.

84b. A polymer formed from reactants comprising (a) methylated collagen and (b) a compound comprising a polyalkylene oxide portion.

85b. A polymer formed from reactants comprising (a) methylated collagen and (b) polylysine.

86b. A polymer formed from reactants comprising (a) methylated collagen and (b) a compound having at least four thiol groups.

87b. A polymer formed from reactants comprising (a) methylated collagen and (b) a compound having at least four amino groups.

88b. A polymer formed from reactants comprising (a) methylated collagen and (b) a compound having at least four carbonyl-oxygen-succinimide groups.

89b. A polymer formed from reactants comprising (a) methylated collagen and (b) a compound having a biodegradable region formed from reactants selected from lactic acid, lactide, glycolic acid, glycolide, and epsilon-caprolactone.

90b. A polymer formed from reactants comprising hyaluronic acid.

91b. A polymer formed from reactants comprising a hyaluronic acid derivative.

92b. A polymer formed from reactants comprising pentaerythritol poly(ethylene glycol)ether tetra-sulfhydryl of number average molecular weight between 3,000 and 30,000.

93b. Pentaerythritol poly(ethylene glycol)ether tetra-sulfhydryl of number average molecular weight between 3,000 and 30,000.

94b. A polymer formed from reactants comprising pentaerythritol poly(ethylene glycol)ether tetra-amino of number average molecular weight between 3,000 and 30,000.

95b. Pentaerythritol poly(ethylene glycol)ether tetra-amino of number average molecular weight between 3,000 and 30,000.

96b. A polymer formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

97b. A mixture of (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

As mentioned above, the present invention provides compositions comprising each of the foregoing 86 (1a through 85a) listed fibrosing agents or classes of fibrosing agents, with each of the foregoing 98 (1b through 97b) polymers and compounds: Thus, in separate aspects, the invention provides 86 times 98=8,428 described compositions. In other words, each of the following is a distinct aspect of the present invention:

1a+1b; 1a+2b; 1a+3b; 1a+4b; 1a+5b; 1a+6b; 1a+7b; 1a+8b; 1a+9b; 1a+10b 1a+11b; 1a+12b; 1a+13b; 1a+14b; 1a+15b; 1a+16b; 1a+17b; 1a+18b; 1a+19b; 1a+20b; 1a+21b; 1a+22b; 1a+23b; 1a+24b; 1a+25b; 1a+26b; 1a+27b; 1a+28b; 1a+29b; 1a+30b; 1a+31b; 1a+32b; 1a+33b; 1a+34b; 1a+35b; 1a+36b; 1a+37b; 1a+38b; 1a+39b; 1a+40b; 1a+41b; 1a+42b; 1a+43b; 1a+44b; 1a+45b; 1a+46b; 1a+47b; 1a+48b; 1a+49b; 1a+50b; 1a+51b; 1a+52b; 1a+53b; 1a+54b; 1a+55b; 1a+55b; 1a+57b; 1a+58b; 1a+59b; 1a+60b; 1a+61b; 1a+62b; 1a+63b; 1a+64b; 1a+65b; 1a+66b; 1a+67b; 1a+68b; 1a+69b; 1a+70b; 1a+71b; 1a+72b; 1a+73b; 1a+74b; 1a+75b; 1a+76b; 1a+77b; 1a+78b; 1a+79b; 1a+80b; 1a+81b; 1a+82b; 1a+83b; 1a+84b; 1a+85b; 1a+86b; 1a+87b; 1a+88b; 1a+89b; 1a+90b; 1a+91b; 1a+92b; 1a+93b; 1a+94b; 1a+95b; 1a+96b; 1a+97b; 2a+1b; 2a+2b; 2a+3b; 2a+4b; 2a+5b; 2a+6b; 2a+7b; 2a+8b; 2a+9b; 2a+10b; 2a+11b; 2a+12b; 2a+13b; 2a+14b; 2a+15b; 2a+16b; 2a+17b; 2a+18b; 2a+19b; 2a+20b; 2a+21b; 2a+22b; 2a+23b; 2a+24b; 2a+25b; 2a+26b; 2a+27b; 2a+28b; 2a+29b; 2a+30b; 2a+31b; 2a+32b; 2a+33b; 2a+34b; 2a+35b; 2a+36b; 2a+37b; 2a+38b; 2a+39b; 2a+40b; 2a+41b; 2a+42b; 2a+43b; 2a+44b; 2a+45b; 2a+46b; 2a+47b; 2a+48b; 2a+49b; 2a+50b; 2a+51b; 2a+52b; 2a+53b; 2a+54b; 2a+55b; 2a+55b; 2a+57b; 2a+58b; 2a+59b; 2a+60b; 2a+61b; 2a+62b; 2a+63b; 2a+64b; 2a+65b; 2a+66b; 2a+67b; 2a+68b; 2a+69b; 2a+70b; 2a+71b; 2a+72b; 2a+73b; 2a+74b; 2a+75b; 2a+76b; 2a+77b; 2a+78b; 2a+79b; 2a+80b; 2a+81b; 2a+82b; 2a+83b; 2a+84b; 2a+85b; 2a+86b; 2a+87b; 2a+88b; 2a+89b; 2a+90b; 2a+91b; 2a+92b; 2a+93b; 2a+94b; 2a+95b; 2a+96b; 2a+97b; 3a+22b; 3a+23b; 3a+24b; 3a+25b; 3a+26b; 3a+27b; 3a+28b; 3a+29b; 3a+30b; 3a+31b; 3a+32b; 3a+33b; 3a+34b; 3a+35b; 3a+36b; 3a+37b; 3a+38b; 3a+39b; 3a+40b; 3a+41b; 3a+42b; 3a+43b; 3a+44b; 3a+45b; 3a+46b; 3a+47b; 3a+48b; 3a+49b; 3a+50b; 3a+51b; 3a+52b; 3a+53b; 3a+54b; 3a+55b; 3a+55b; 3a+57b; 3a+58b; 3a+59b; 3a+60b; 3a+61b; 3a+62b; 3a+63b; 3a+64b; 3a+65b; 3a+66b; 3a+67b; 3a+68b; 3a+69b; 3a+70b; 3a+71b; 3a+72b; 3a+73b; 3a+74b; 3a+75b; 3a+76b; 3a+77b; 3a+78b; 3a+79b; 3a+80b; 3a+81b; 3a+82b; 3a+83b; 3a+84b; 3a+85b; 3a+86b; 3a+87b; 3a+88b; 3a+89b; 3a+90b; 3a+91b; 3a+92b; 3a+93b; 3a+94b; 3a+95b; 3a+96b; 3a+97b; 3a+98b; 3a+99b; 4a+14b; 4a+15b; 4a+16b; 4a+17b; 4a+18b; 4a+19b; 4a+20b; 4a+21b; 4a+22b; 4a+23b; 4a+24b; 4a+25b; 4a+26b; 4a+27b; 4a+28b; 4a+29b; 4a+30b; 4a+31b; 4a+32b; 4a+33b; 4a+34b; 4a+35b; 4a+36b; 4a+37b; 4a+38b; 4a+39b; 4a+40b; 4a+41b; 4a+42b; 4a+43b; 4a+44b; 4a+45b; 4a+46b; 4a+47b; 4a+48b; 4a+49b; 4a+50b; 4a+51b; 4a+52b; 4a+53b; 4a+54b; 4a+55b; 4a+55b; 4a+56b; 4a+57b; 4a+59b; 4a+60b; 4a+61b; 4a+62b; 4a+63b; 4a+64b; 4a+65b; 4a+66b; 4a+67b; 4a+68b; 4a+69b; 4a+70b; 4a+71b; 4a+72b; 4a+73b; 4a+74b; 4a+75b; 4a+76b; 4a+77b; 4a+78b; 4a+79b; 4a+80b; 4a+81b; 4a+82b; 4a+83b; 4a+84b; 4a+85b; 4a+86b; 4a+87b; 4a+88b; 4a+89b; 4a+90b; 4a+91b; 4a+92b; 4a+93b; 4a+94b; 4a+95b; 4a+96b; 4a+97b; 5a+12b; 5a+13b; 5a+14b; 5a+15b; 5a+16b; 5a+17b; 5a+18b; 5a+19b; 5a+20b; 5a+21b; 5a+22b; 5a+23b; 5a+24b; 5a+25b; 5a+26b; 5a+27b; 5a+28b; 5a+29b; 5a+30b; 5a+31b; 5a+32b; 5a+33b; 5a+34b; 5a+35b; 5a+36b; 5a+37b; 5a+38b; 5a+39b; 5a+40b; 5a+41b; 5a+42b; 5a+43b; 5a+44b; 5a+45b; 5a+46b; 5a+47b; 5a+48b; 5a+49b; 5a+50b; 5a+51b; 5a+52b; 5a+53b; 5a+54b; 5a+55b; 5a+55b; 5a+57b; 5a+58b; 5a+59b; 5a+60b; 5a+61b; 5a+62b; 5a+63b; 5a+64b; 5a+65b; 5a+66b; 5a+67b; 5a+68b; 5a+69b; 5a+70b; 5a+71b; 5a+72b; 5a+73b; 5a+74b; 5a+75b; 5a+76b; 5a+77b; 5a+78b; 5a+79b; 5a+80b; 5a+81b; 5a+82b; 5a+83b; 5a+84b; 5a+85b; 5a+86b; 5a+87b; 5a+88b; 5a+89b; 5a+90b; 5a+91b; 5a+92b; 5a+93b; 5a+94b; 5a+95b; 5a+96b; 5a+97b; 6a+1b; 6a+2b; 6a+3b; 6a+4b; 6a+5b; 6a+6b; 6a+7b; 6a+8b; 6a+9b; 6a+10b; 6a+11b; 6a+12b; 6a+13b; 6a+14b; 6a+15b; 6a+16b; 6a+17b; 6a+18b; 6a+19b; 6a+20b; 6a+21b; 6a+22b; 6a+23b; 6a+24b; 6a+25b; 6a+26b; 6a+27b; 6a+28b; 6a+29b; 6a+30b; 6a+31b; 6a+32b; 6a+33b; 6a+34b; 6a+35b; 6a+36b; 6a+37b; 6a+38b; 6a+39b; 6a+40b; 6a+41b; 6a+42b; 6a+43b; 6a+44b; 6a+45b; 6a+46b; 6a+47b; 6a+48b; 6a+49b; 6a+50b; 6a+51b; 6a+52b; 6a+53b; 6a+54b; 6a+55b; 6a+55b; 6a+57b; 6a+58b; 6a+59b; 6a+60b; 6a+61b; 6a+62b; 6a+63b; 6a+64b; 6a+65b; 6a+66b; 6a+67b; 6a+68b; 6a+69b; 6a+70b; 6a+71b; 6a+72b; 6a+73b; 6a+74b; 6a+75b; 6a+76b; 6a+77b; 6a+78b; 6a+79b; 6a+80b; 6a+81b; 6a+82b; 6a+83b; 6a+84b; 6a+85b; 6a+86b; 6a+87b; 6a+88b; 6a+89b; 6a+90b; 6a+91b; 6a+92b; 6a+93b; 6a+94b; 6a+95b; 6a+96b; 6a+97b; 7a+1b; 7a+2b; 7a+3b; 7a+4b; 7a+5b; 7a+6b; 7a+7b; 7a+8b; 7a+9b; 7a+10b; 7a+11b; 7a+12b; 7a+13b; 7a+14b; 7a+15b; 7a+16b; 7a+17b; 7a+18b; 7a+19b; 7a+20b; 7a+21b; 7a+22b; 7a+23b; 7a+24b; 7a+25b; 7a+26b; 7a+27b; 7a+28b; 7a+29b; 7a+30b; 7a+31b; 7a+32b; 7a+33b; 7a+34b; 7a+35b; 7a+36b; 7a+37b; 7a+38b; 7a+39b; 7a+40b; 7a+41b; 7a+42b; 7a+43b; 7a+44b; 7a+45b; 7a+46b; 7a+47b; 7a+48b; 7a+49b; 7a+50b; 7a+51b; 7a+52b; 7a+53b; 7a+54b; 7a+55b; 7a+55b; 7a+57b; 7a+58b; 7a+59b; 7a+60b; 7a+61b;

7a+62b; 7a+63b; 7a+64b; 7a+65b; 7a+66b; 7a+67b; 7a+68b; 7a+69b; 7a+70b; 7a+71b; 7a+72b; 7a+73b; 7a+74b; 7a+75b; 7a+76b; 7a+77b; 7a+78b; 7a+79b; 7a+80b; 7a+81b; 7a+82b; 7a+83b; 7a+84b; 7a+85b; 7a+86b; 7a+87b; 7a+88b; 7a+89b; 7a+90b; 7a+91b; 7a+92b; 7a+93b; 7a+94b; 7a+95b; 7a+96b; 7a+97b; 8a+12b; 8a+13b; 8a+14b; 8a+15b; 8a+16b; 8a+17b; 8a+18b; 8a+19b; 8a+20b; 8a+21b; 8a+22b; 8a+23b; 8a+24b; 8a+25b; 8a+26b; 8a+27b; 8a+28b; 8a+29b; 8a+30b; 8a+31b; 8a+32b; 8a+33b; 8a+34b; 8a+35b; 8a+36b; 8a+37b; 8a+38b; 8a+39b; 8a+40b; 8a+41b; 8a+42b; 8a+43b; 8a+44b; 8a+45b; 8a+46b; 8a+47b; 8a+48b; 8a+49b; 8a+50b; 8a+51b; 8a+52b; 8a+53b; 8a+54b; 8a+55b; 8a+55b; 8a+57b; 8a+58b; 8a+59b; 8a+60b; 8a+61b; 8a+62b; 8a+63b; 8a+64b; 8a+65b; 8a+66b; 8a+67b; 8a+68b; 8a+69b; 8a+70b; 8a+71b; 8a+72b; 8a+73b; 8a+74b; 8a+75b; 8a+76b; 8a+77b; 8a+78b; 8a+79b; 8a+80b; 8a+81b; 8a+82b; 8a+83b; 8a+84b; 8a+85b; 8a+86b; 8a+87b; 8a+88b; 8a+89b; 8a+90b; 8a+91b; 8a+92b; 8a+93b; 8a+94b; 8a+95b; 8a+96b; 8a+97b; 9a+1b; 9a+2b; 9a+3b; 9a+4b; 9a+5b; 9a+6b; 9a+7b; 9a+8b; 9a+9b; 9a+10b; 9a+11b; 9a+12b; 9a+13b; 9a+14b; 9a+15b; 9a+16b; 9a+17b; 9a+18b; 9a+19b; 9a+20b; 9a+21b; 9a+22b; 9a+23b; 9a+24b; 9a+25b; 9a+26b; 9a+27b; 9a+28b; 9a+29b; 9a+30b; 9a+31b; 9a+32b; 9a+33b; 9a+34b; 9a+35b; 9a+36b; 9a+37b; 9a+38b; 9a+39b; 9a+40b; 9a+41b; 9a+42b; 9a+43b; 9a+44b; 9a+45b; 9a+46b; 9a+47b; 9a+48b; 9a+49b; 9a+50b; 9a+51b; 9a+52b; 9a+53b; 9a+54b; 9a+55b; 9a+56b; 9a+57b; 9a+58b; 9a+59b; 9a+60b; 9a+61b; 9a+62b; 9a+63b; 9a+64b; 9a+65b; 9a+66b; 9a+67b; 9a+68b; 9a+69b; 9a+70b; 9a+71b; 9a+72b; 9a+73b; 9a+74b; 9a+75b; 9a+76b; 9a+77b; 9a+78b; 9a+79b; 9a+80b; 9a+81b; 9a+82b; 9a+83b; 9a+84b; 9a+85b; 9a+86b; 9a+87b; 9a+88b; 9a+89b; 9a+90b; 9a+91b; 9a92b; 9a+93b; 9a+94b; 9a+95b; 9a+96b; 9a+97b; 10a+1b; 10a+2b; 10a+3b; 10a+4b; 10a+5b; 10a+6b; 10a+7b; 10a+8b; 10a+9b; 10a+10b; 10a+11b; 10a+12b; 10a+13b; 10a+14b; 10a+15b; 10a+16b; 10a+17b; 10a+18b; 10a+19b; 10a+20b; 10a+21b; 10a+22b; 10a+23b; 10a+24b; 10a+25b; 10a+26b; 10a+27b; 10a+28b; 10a+29b; 10a+30b; 10a+31b; 10a+32b; 10a+33b; 10a+34b; 10a+35b; 10a+36b; 10a+37b; 10a+38b; 10a+39b; 10a+40b; 10a+41b; 10a+42b; 10a+43b; 10a+44b; 10a+45b; 10a+46b; 10a+47b; 10a+48b; 10a+49b; 10a+50b; 10a+51b; 10a+52b; 10a+53b; 10a+54b; 10a+55b; 10a+55b; 10a+57b; 10a+58b; 10a+59b; 10a+60b; 10a+61b; 10a+62b; 10a+63b; 10a+64b; 10a+65b; 10a+66b; 10a+67b; 10a+68b; 10a+69b; 10a+70b; 10a+71b; 10a+72b; 10a+73b; 10a+74b; 10a+75b; 10a+76b; 10a+77b; 10a+78b; 10a+79b; 10a+80b; 10a+81b; 10a+82b; 10a+83b; 10a+84b; 10a+85b; 10a+86b; 10a+87b; 10a+88b; 10a+89b; 10a+90b; 10a+91b; 10a+92b; 10a+93b; 10a+94b; 10a+95b; 10a+96b; 10a+97b; 11a+1b; 11a+2b; 11a+3b; 11a+4b; 11a+5b; 11a+6b; 11a+7b; 11a+8b; 11a+9b; 11a+10b; 11a+11b; 11a+12b; 11a+13b; 11a+14b; 11a+15b; 11a+16b; 11a+17b; 11a+18b; 11a+19b; 11a+20b; 11a+21b; 11a+22b; 11a+23b; 11a+24b; 11a+25b; 11a+26b; 11a+27b; 1a+28b; 11a+29b; 11a+30b; 11a+31b; 11a+32b; 11a+33b; 11a+34b; 11a+35b; 11a+36b; 11a+37b; 11a+38b; 11a+39b; 11a+40b; 11a+41b; 11a+42b; 11a+43b; 11a+44b; 11a+45b; 11a+46b; 11a+47b; 11a+48b; 11a+49b; 11a+50b; 11a+51b; 11a+52b; 11a+53b; 11a+54b; 11a+55b; 11a+55b; 11a+57b; 11a+58b; 11a+59b; 11a+60b; 11a+61b; 11a+62b; 11a+63b; 11a+64b; 11a+65b; 11a+66b; 11a+67b; 11a+68b; 11a+69b; 11a+70b; 11a+71b; 11a+72b; 11a+73b; 11a+74b; 11a+75b; 11a+76b; 11a+77b; 11a+78b; 11a+79b; 11a+80b; 11a+81b; 11a+82b; 11a+83b; 11a+84b; 11a+85b; 11a+86b; 11a+87b; 11a+88b; 11a+89b; 11a+90b; 11a+91b; 11a+92b; 11a+93b; 11a+94b; 11a+95b; 11a+96b; 11a+97b; 12a+1b; 12a+2b; 12a+3b; 12a+4b; 12a+5b; 12a+6b; 12a+7b; 12a+8b; 12a+9b; 12a+10b; 12a+11b; 12a+12b; 12a+13b; 12a+14b; 12a+15b; 12a+16b; 12a+17b; 12a+18b; 12a+19b; 12a+20b; 12a+21b; 12a+22b; 12a+23b; 12a+24b; 12a+25b; 12a+26b; 12a+27b; 12a+28b; 12a+29b; 12a+30b; 12a+31b; 12a+32b; 12a+33b; 12a+34b; 12a+35b; 12a+36b; 12a+37b; 12a+38b; 12a+39b; 12a+40b; 12a+41b; 12a+42b; 12a+43b; 12a+44b; 12a+45b; 12a+46b; 12a+47b; 12a+48b; 12a+49b; 12a+50b; 12a+51b; 12a+52b; 12a+53b; 12a+54b; 12a+55b; 12a+55b; 12a+57b; 12a+58b; 12a+59b; 12a+60b; 12a+61b; 12a+62b; 12a+63b; 12a+64b; 12a+65b; 12a+66b; 12a+67b; 12a+68b; 12a+69b; 12a+70b; 12a+71b; 12a+72b; 12a+73b; 12a+74b; 12a+75b; 12a+76b; 12a+77b; 12a+78b; 12a+79b; 12a+80b; 12a+81b; 12a+82b; 12a+83b; 12a+84b; 12a+85b; 12a+86b; 12a+87b; 12a+88b; 12a+89b; 12a+90b; 12a+91b; 12a+92b; 12a+93b; 12a+94b; 12a+95b; 12a+96b; 12a+97b; 13a+1b; 13a+2b; 13a+3b; 13a+4b; 13a+5b; 13a+6b; 13a+7b; 13a+8b; 13a+9b; 13a+10b; 13a+11b; 13a+12b; 13a+13b; 13a+14b; 13a+15b; 13a+16b; 13a+17b; 13a+18b; 13a+19b; 13a+20b; 13a+21b; 13a+22b; 13a+23b; 13a+24b; 13a+25b; 13a+26b; 13a+27b; 13a+28b; 13a+29b; 13a+30b; 13a+31b; 13a+32b; 13a+33b; 13a+34b; 13a+35b; 13a+36b; 13a+37b; 13a+38b; 13a+39b; 13a+40b; 13a+41b; 13a+42b; 13a+43b; 13a+44b; 13a+45b; 13a+46b; 13a+47b; 13a+48b; 13a+49b; 13a+50b; 13a+51b; 13a+52b; 13a+53b; 13a+54b; 13a+55b; 13a+55b; 13a+57b; 13a+58b; 13a+59b; 13a+60b; 13a+61b; 13a+62b; 13a+63b; 13a+64b; 13a+65b; 13a+66b; 13a+67b; 13a+68b; 13a+69b; 13a+70b; 13a+71b; 13a+72b; 13a+73b; 13a+74b; 13a+75b; 13a+76b; 13a+77b; 13a+78b; 13a+79b; 13a+80b; 13a+81b; 13a+82b; 13a+83b; 13a+84b; 13a+85b; 13a+86b; 13a+87b; 13a+88b; 13a+89b; 13a+90b; 13a+91b; 13a+92b; 13a+93b; 13a+94b; 13a+95b; 13a+96b; 13a+97b; 14a+1b; 14a+2b; 14a+3b; 14a+4b; 14a+5b; 14a+6b; 14a+7b; 14a+8b; 14a+9b; 14a+10b; 14a+11b; 14a+12b; 14a+13b; 14a+14b; 14a+15b; 14a+16b; 14a+17b; 14a+18b; 14a+19b; 14a+20b; 14a+21b; 14a+22b; 14a+23b; 14a+24b; 14a+25b; 14a+26b; 14a+27b; 14a+28b; 14a+29b; 14a+30b; 14a+31b; 14a+32b; 14a+33b; 14a+34b; 14a+35b; 14a+36b; 14a+37b; 14a+38b; 14a+39b; 14a+40b; 14a+41b; 14a+42b; 14a+43b; 14a+44b; 14a+45b; 14a+46b; 14a+47b; 14a+48b; 14a+49b; 14a+50b; 14a+51b; 14a+52b; 14a+53b; 14a+54b; 14a+55b; 14a+55b; 14a+57b; 14a+58b; 14a+59b; 14a+60b; 14a+61b; 14a+62b; 14a+63b; 14a+64b; 14a+65b; 14a+66b; 14a+67b; 14a+68b; 14a+69b; 14a+70b; 14a+71b; 14a+72b; 14a+73b; 14a+74b; 14a+72b; 14a+73b; 14a+77b; 14a+78b; 14a+79b; 14a+80b; 14a+81b; 14a+82b; 14a+83b; 14a+84b; 14a+85b; 14a+86b; 14a+87b; 14a+88b; 14a+89b; 14a+90b; 14a+91b; 14a+92b; 14a+93b; 14a+94b; 14a+95b; 14a+96b; 14a+97b; 15a+1b; 15a+2b; 15a+3b; 15a+4b; 15a+5b; 15a+6b; 15a+7b; 15a+8b; 15a+9b; 15a+10b; 15a+11b; 15a+12b; 15a+13b; 15a+14b; 15a+15b; 15a+16b; 15a+17b; 15a+18b; 15a+19b; 15a+20b; 15a+21b; 15a+22b; 15a+23b; 15a+24b; 15a+25b; 15a+26b; 15a+27b; 15a+28b; 15a+29b; 15a+30b; 15a+31b; 15a+32b; 15a+33b; 15a+34b; 15a+35b; 15a+36b; 15a+37b; 15a+38b; 15a+39b; 15a+40b; 15a+41b; 15a+42b; 15a+43b; 15a+44b; 15a+45b; 15a+46b; 15a+47b; 15a+48b; 15a+49b; 15a+50b; 15a+51b; 15a+52b; 15a+53b; 15a+54b; 15a+55b; 15a+55b; 15a+57b; 15a+58b; 15a+59b; 15a+60b; 15a+61b; 15a+62b;

15a+63b; 15a+64b; 15a+65b; 15a+66b; 15a+67b; 15a+68b; 15a+69b; 15a+70b; 15a+71b; 15a+72b; 15a+73b; 15a+74b; 15a+75b; 15a+76b; 15a+77b; 15a+78b; 15a+79b; 15a+80b; 15a+81b; 15a+82b; 15a+83b; 15a+84b; 15a+85b; 15a+86b; 15a+87b; 15a+88b; 15a+89b; 15a+90b; 15a+91b; 15a+92b; 15a+93b; 15a+94b; 15a+95b; 15a+96b; 15a+97b; 16a+1b; 16a+2b; 16a+3b; 16a+4b; 16a+5b; 16a+6b; 16a+7b; 16a+8b; 16a+9b; 16a+10b; 16a+11b; 16a+12b; 16a+13b; 16a+14b; 16a+15b; 16a+16b; 16a+17b; 16a+18b; 16a+19b; 16a+20b; 16a+21b; 16a+22b; 16a+23b; 16a+24b; 16a+25b; 16a+26b; 16a+27b; 16a+28b; 16a+29b; 16a+30b; 16a+31b; 16a+32b; 16a+33b; 16a+34b; 16a+35b; 16a+36b; 16a+37b; 16a+38b; 16a+39b; 16a+40b; 16a+41b; 16a+42b; 16a+43b; 16a+44b; 16a+45b; 16a+46b; 16a+47b; 16a+48b; 16a+49b; 16a+50b; 16a+51b; 16a+52b; 16a+53b; 16a+54b; 16a+55b; 16a+55b; 16a+57b; 16a+58b; 16a+59b; 16a+60b; 16a+61b; 16a+62b; 16a+63b; 16a+64b; 16a+65b; 16a+66b; 16a+67b; 16a+68b; 16a+69b; 16a+70b; 16a+71b; 16a+72b; 16a+73b; 16a+74b; 16a+75b; 16a+76b; 16a+77b; 16a+78b; 16a+79b; 16a+80b; 16a+81b; 16a+82b; 16a+83b; 16a+84b; 16a+85b; 16a+86b; 16a+87b; 16a+88b; 16a+89b; 16a+90b; 16a+91b; 16a+92b; 16a+93b; 16a+94b; 16a+95b; 16a+96b; 16a+97b; 17a+1b; 17a+2b; 17a+3b; 17a+4b; 17a+5b; 17a+6b; 17a+7b; 17a+8b; 17a+9b; 17a+10b; 17a+11b; 17a+12b; 17a+13b; 17a+14b; 17a+15b; 17a+16b; 17a+17b; 17a+18b; 17a+19b; 17a+20b; 17a+21b; 17a+22b; 17a+23b; 17a+24b; 17a+25b; 17a+26b; 17a+27b; 17a+28b; 17a+29b; 17a+30b; 17a+31b; 17a+32b; 17a+33b; 17a+34b; 17a+35b; 17a+36b; 17a+37b; 17a+38b; 17a+39b; 17a+40b; 17a+41b; 17a+42b; 17a+43b; 17a+44b; 17a+45b; 17a+46b; 17a+47b; 17a+48b; 17a+49b; 17a+50b; 17a+51b; 17a+52b; 17a+53b; 17a+54b; 17a+55b; 17a+55b; 17a+57b; 17a+58b; 17a+59b; 17a+60b; 17a+61b; 17a+62b; 17a+63b; 17a+64b; 17a+65b; 17a+66b; 17a+67b; 17a+68b; 17a+69b; 17a+70b; 17a+71b; 17a+72b; 17a+73b; 17a+74b; 17a+75b; 17a+76b; 17a+77b; 17a+78b; 17a+79b; 17a+80b; 17a+81b; 17a+82b; 17a+83b; 17a+84b; 17a+85b; 17a+86b; 17a+87b; 17a+88b; 17a+89b; 17a+90b; 17a+91b; 17a+92b; 17a+93b; 17a+94b; 17a+95b; 17a+96b; 17a+97b; 18a+1b; 18a+2b; 18a+3b; 18a+4b; 18a+5b; 18a+6b; 18a+7b; 18a+8b; 18a+9b; 18a+10b; 18a+11b; 18a+12b; 18a+13b; 18a+14b; 18a+15b; 18a+16b; 18a+17b; 18a+18b; 18a+19b; 18a+20b; 18a+21b; 18a+22b; 18a+23b; 18a+24b; 18a+25b; 18a+26b; 18a+27b; 18a+28b; 18a+29b; 18a+30b; 18a+31b; 18a+32b; 18a+33b; 18a+34b; 18a+35b; 18a+36b; 18a+37b; 18a+38b; 18a+39b; 18a+40b; 18a+41b; 18a+42b; 18a+43b; 18a+44b; 18a+45b; 18a+46b; 18a+47b; 18a+48b; 18a+49b; 18a+50b; 18a+51b; 18a+52b; 18a+53b; 18a+54b; 18a+55b; 18a+55b; 18a+57b; 18a+58b; 18a+59b; 18a+60b; 18a+61b; 18a+62b; 18a+63b; 18a+64b; 18a+65b; 18a+66b; 18a+67b; 18a+68b; 18a+69b; 18a+70b; 18a+71b; 18a+72b; 18a+73b; 18a+74b; 18a+75b; 18a+76b; 18a+77b; 18a+78b; 18a+79b; 18a+80b; 18a+81b; 18a+82b; 18a+83b; 18a+84b; 18a+85b; 18a+86b; 18a+87b; 18a+88b; 18a+89b; 18a+90b; 18a+91b; 18a+92b; 18a+93b; 18a+94b; 18a+95b; 18a+96b; 18a+97b; 19a+1b; 19a+2b; 19a+3b; 19a+4b; 19a+5b; 19a+6b; 19a+7b; 19a+8b; 19a+9b; 19a+10b; 19a+11b; 19a+12b; 19a+13b; 19a+14b; 19a+15b; 19a+16b; 19a+17b; 19a+18b; 19a+19b; 19a+20b; 19a+21b; 19a+22b; 19a+23b; 19a+24b; 19a+25b; 19a+26b; 19a+27b; 19a+28b; 19a+29b; 19a+30b; 19a+31b; 19a+32b; 19a+33b; 19a+34b; 19a+35b; 19a+36b; 19a+37b; 19a+38b; 19a+39b; 19a+40b; 19a+41b; 19a+42b; 19a+43b; 19a+44b; 19a+45b; 19a+46b; 19a+47b; 19a+48b; 19a+49b; 19a+50b; 19a+51b; 19a+52b; 19a+53b; 19a+54b; 19a+55b; 19a+55b; 19a+57b; 19a+58b; 19a+59b; 19a+60b; 19a+61b; 19a+62b; 19a+63b; 19a+64b; 19a+65b; 19a+66b; 19a+67b; 19a+68b; 19a+69b; 19a+70b; 19a+71b; 19a+72b; 19a+73b; 19a+74b; 19a+75b; 19a+76b; 19a+77b; 19a+78b; 19a+79b; 19a+80b; 19a+81b; 19a+82b; 19a+83b; 19a+84b; 19a+85b; 19a+86b; 19a+87b; 19a+88b; 19a+89b; 19a+90b; 19a+91b; 19a+92b; 19a+93b; 19a+94b; 19a+95b; 19a+96b; 19a+97b; 20a+1b; 20a+2b; 20a+3b; 20a+4b; 20a+5b; 20a+6b; 20a+7b; 20a+8b; 20a+9b; 20a+10b; 20a+11b; 20a+12b; 20a+13b; 20a+14b; 20a+15b; 20a+16b; 20a+17b; 20a+18b; 20a+19b; 20a+20b; 20a+21b; 20a+22b; 20a+23b; 20a+24b; 20a+25b; 20a+26b; 20a+27b; 20a+28b; 20a+29b; 20a+30b; 20a+31b; 20a+32b; 20a+33b; 20a+34b; 20a+35b; 20a+36b; 20a+37b; 20a+38b; 20a+39b; 20a+40b; 20a+41b; 20a+42b; 20a+43b; 20a+44b; 20a+45b; 20a+46b; 20a+47b; 20a+48b; 20a+49b; 20a+50b; 20a+51b; 20a+52b; 20a+53b; 20a+54b; 20a+55b; 20a+55b; 20a+57b; 20a+58b; 20a+59b; 20a+60b; 20a+61b; 20a+62b; 20a+63b; 20a+64b; 20a+65b; 20a+66b; 20a+67b; 20a+68b; 20a+69b; 20a+70b; 20a+71b; 20a+72b; 20a+73b; 20a+74b; 20a+75b; 20a+76b; 20a+77b; 20a+78b; 20a+79b; 20a+80b; 20a+81b; 20a+82b; 20a+83b; 20a+84b; 20a+85b; 20a+86b; 20a+87b; 20a+88b; 20a+89b; 20a+90b; 20a+91b; 20a+92b; 20a+93b; 20a+94b; 20a+95b; 20a+96b; 20a+97b; 21a+1b; 21a+2b; 21a+3b; 21a+4b; 21a+5b; 21a+6b; 21a+7b; 21a+8b; 21a+9b; 21a+10b; 21a+11b; 21a+12b; 21a+13b; 21a+14b; 21a+15b; 21a+16b; 21a+17b; 21a+18b; 21a+19b; 21a+20b; 21a+21b; 21a+22b; 21a+23b; 21a+24b; 21a+25b; 21a+26b; 21a+27b; 21a+28b; 21a+29b; 21a+30b; 21a+31b; 21a+32b; 21a+33b; 21a+34b; 21a+35b; 21a+36b; 21a+37b; 21a+38b; 21a+39b; 21a+40b; 21a+41b; 21a+42b; 21a+43b; 21a+44b; 21a+45b; 21a+46b; 21a+47b; 21a+48b; 21a+49b; 21a+50b; 21a+51b; 21a+52b; 21a+53b; 21a+54b; 21a+55b; 21a+55b; 21a+57b; 21a+58b; 21a+59b; 21a+60b; 21a+61b; 21a+62b; 21a+63b; 21a+64b; 21a+65b; 21a+66b; 21a+67b; 21a+68b; 21a+69b; 21a+70b; 21a+71b; 21a+72b; 21a+73b; 21a+74b; 21a+75b; 21a+76b; 21a+77b; 21a+78b; 21a+79b; 21a+80b; 21a+81b; 21a+82b; 21a+83b; 21a+84b; 21a+85b; 21a+86b; 21a+87b; 21a+88b; 21a+89b; 21a+90b; 21a+91b; 21a+92b; 21a+93b; 21a+94b; 21a+95b; 21a+96b; 21a+97b; 22a+1b; 22a+2b; 22a+3b; 22a+4b; 22a+5b; 22a+6b; 22a+7b; 22a+8b; 22a+9b; 22a+10b; 22a+11b; 22a+12b; 22a+13b; 22a+14b; 22a+15b; 22a+16b; 22a+17b; 22a+18b; 22a+19b; 22a+20b; 22a+21b; 22a+22b; 22a+23b; 22a+24b; 22a+25b; 22a+26b; 22a+27b; 22a+28b; 22a+29b; 22a+30b; 22a+31b; 22a+32b; 22a+33b; 22a+34b; 22a+35b; 22a+36b; 22a+37b; 22a+38b; 22a+39b; 22a+40b; 22a+41b; 22a+42b; 22a+43b; 22a+44b; 22a+45b; 22a+46b; 22a+47b; 22a+48b; 22a+49b; 22a+50b; 22a+51b; 22a+52b; 22a+53b; 22a+54b; 22a+55b; 22a+55b; 22a+57b; 22a+58b; 22a+59b; 22a+60b; 22a+61b; 22a+62b; 22a+63b; 22a+64b; 22a+65b; 22a+66b; 22a+67b; 22a+68b; 22a+69b; 22a+70b; 22a+71b; 22a+72b; 22a+73b; 22a+74b; 22a+75b; 22a+76b; 22a+77b; 22a+78b; 22a+79b; 22a+80b; 22a+81b; 22a+82b; 22a+83b; 22a+84b; 22a+85b; 22a+86b; 22a+87b; 22a+88b; 22a+89b; 22a+90b; 22a+91b; 22a+92b; 22a+93b; 22a+94b; 22a+95b; 22a+96b; 22a+97b; 23a+1b; 23a+2b; 23a+3b; 23a+4b; 23a+5b; 23a+6b; 23a+7b; 23a+8b; 23a+9b; 23a+10b; 23a+11b; 23a+12b; 23a+13b; 23a+14b; 23a+15b; 23a+16b; 23a+17b; 23a+18b; 23a+19b; 23a+20b; 23a+21b; 23a+22b; 23a+23b; 23a+24b; 23a+25b; 23a+26b; 23a+27b; 23a+28b; 23a+29b; 23a+30b; 23a+31b; 23a+32b; 23a+33b;

23a+34b; 23a+35b; 23a+36b; 23a+37b; 23a+38b; 23a+39b; 23a+40b; 23a+41b; 23a+42b; 23a+43b; 23a+44b; 23a+45b; 23a+46b; 23a+47b; 23a+48b; 23a+49b; 23a+50b; 23a+51b; 23a+52b; 23a+53b; 23a+54b; 23a+55b; 23a+55b; 23a+57b; 23a+58b; 23a+59b; 23a+60b; 23a+61b; 23a+62b; 23a+63b; 23a+64b; 23a+65b; 23a+66b; 23a+67b; 23a+68b; 23a+69b; 23a+70b; 23a+71b; 23a+72b; 23a+73b; 23a+74b; 23a+75b; 23a+76b; 23a+77b; 23a+78b; 23a+79b; 23a+80b; 23a+81b; 23a+82b; 23a+83b; 23a+84b; 23a+85b; 23a+86b; 23a+87b; 23a+88b; 23a+89b; 23a+90b; 23a+91b; 23a+92b; 23a+93b; 23a+94b; 23a+95b; 23a+96b; 23a+97b; 24a+1b; 24a+2b; 24a+3b; 24a+4b; 24a+5b; 24a+6b; 24a+7b; 24a+8b; 24a+9b; 24a+10b; 24a+11b; 24a+12b; 24a+13b; 24a+14b; 24a+15b; 24a+16b; 24a+17b; 24a+18b; 24a+19b; 24a+20b; 24a+21b; 24a+22b; 24a+23b; 24a+24b; 24a+25b; 24a+26b; 24a+27b; 24a+28b; 24a+29b; 24a+30b; 24a+31b; 24a+32b; 24a+33b; 24a+34b; 24a+35b; 24a+36b; 24a+37b; 24a+38b; 24a+39b; 24a+40b; 24a+41b; 24a+42b; 24a+43b; 24a+44b; 24a+45b; 24a+46b; 24a+47b; 24a+48b; 24a+49b; 24a+50b; 24a+51b; 24a+52b; 24a+53b; 24a+54b; 24a+55b; 24a+55b; 24a+57b; 24a+58b; 24a+59b; 24a+60b; 24a+61b; 24a+62b; 24a+63b; 24a+64b; 24a+65b; 24a+66b; 24a+67b; 24a+68b; 24a+69b; 24a+70b; 24a+71b; 24a+72b; 24a+73b; 24a+74b; 24a+75b; 24a+76b; 24a+77b; 24a+78b; 24a+79b; 24a+80b; 24a+81b; 24a+82b; 24a+83b; 24a+84b; 24a+85b; 24a+86b; 24a+87b; 24a+88b; 24a+89b; 24a+90b; 24a+91b; 24a+92b; 24a+93b; 24a+94b; 24a+95b; 24a+96b; 24a+97b; 25a+1b; 25a+2b; 25a+3b; 25a+4b; 25a+5b; 25a+6b; 25a+7b; 25a+8b; 25a+9b; 25a+10b; 25a+11b; 25a+12b; 25a+13b; 25a+14b; 25a+15b; 25a+16b; 25a+17b; 25a+18b; 25a+19b; 25a+20b; 25a+21b; 25a+22b; 25a+23b; 25a+24b; 25a+25b; 25a+26b; 25a+27b; 25a+28b; 25a+29b; 25a+30b; 25a+31b; 25a+32b; 25a+33b; 25a+34b; 25a+35b; 25a+36b; 25a+37b; 25a+38b; 25a+39b; 25a+40b; 25a+41b; 25a+42b; 25a+43b; 25a+44b; 25a+45b; 25a+46b; 25a+47b; 25a+48b; 25a+49b; 25a+50b; 25a+51b; 25a+52b; 25a+53b; 25a+54b; 25a+55b; 25a+55b; 25a+57b; 25a+58b; 25a+59b; 25a+60b; 25a+61b; 25a+62b; 25a+63b; 25a+64b; 25a+65b; 25a+66b; 25a+67b; 25a+68b; 25a+69b; 25a+70b; 25a+71b; 25a+72b; 25a+73b; 25a+74b; 25a+75b; 25a+76b; 25a+77b; 25a+78b; 25a+79b; 25a+80b; 25a+81b; 25a+82b; 25a+82b; 25a+83b; 25a+85b; 25a+86b; 25a+87b; 25a+88b; 25a+89b; 25a+90b; 25a+91b; 25a+92b; 25a+93b; 25a+94b; 25a+95b; 25a+96b; 25a+97b; 26a+1b; 26a+2b; 26a+3b; 26a+4b; 26a+5b; 26a+6b; 26a+7b; 26a+8b; 26a+9b; 26a+10b; 26a+11b; 26a+12b; 26a+13b; 26a+14b; 26a+15b; 26a+16b; 26a+17b; 26a+18b; 26a+19b; 26a+20b; 26a+21b; 26a+22b; 26a+23b; 26a+24b; 26a+25b; 26a+26b; 26a+27b; 26a+28b; 26a+29b; 26a+30b; 26a+31b; 26a+32b; 26a+33b; 26a+34b; 26a+35b; 26a+36b; 26a+37b; 26a+38b; 26a+39b; 26a+40b; 26a+41b; 26a+42b; 26a+43b; 26a+44b; 26a+45b; 26a+46b; 26a+47b; 26a+48b; 26a+49b; 26a+50b; 26a+51b; 26a+52b; 26a+53b; 26a+54b; 26a+55b; 26a+55b; 26a+57b; 26a+58b; 26a+59b; 26a+60b; 26a+61b; 26a+62b; 26a+63b; 26a+64b; 26a+65b; 26a+66b; 26a+67b; 26a+68b; 26a+69b; 26a+70b; 26a+71b; 26a+72b; 26a+73b; 26a+74b; 26a+75b; 26a+76b; 26a+77b; 26a+78b; 26a+79b; 26a+80b; 26a+81b; 26a+82b; 26a+83b; 26a+84b; 26a+85b; 26a+86b; 26a+87b; 26a+88b; 26a+89b; 26a+90b; 26a+91b; 26a+92b; 26a+93b; 26a+94b; 26a+95b; 26a+96b; 26a+97b; 27a+1b; 27a+2b; 27a+3b; 27a+4b; 27a+5b; 27a+6b; 27a+7b; 27a+8b; 27a+9b; 27a+10b; 27a+11b; 27a+12b; 27a+13b; 27a+14b; 27a+15b; 27a+16b; 27a+17b; 27a+18b; 27a+19b; 27a+20b; 27a+21b; 27a+22b; 27a+23b; 27a+24b; 27a+25b; 27a+26b; 27a+27b; 27a+28b; 27a+29b; 27a+30b; 27a+31b; 27a+32b; 27a+33b; 27a+34b; 27a+35b; 27a+36b; 27a+37b; 27a+38b; 27a+39b; 27a+40b; 27a+41b; 27a+42b; 27a+43b; 27a+44b; 27a+45b; 27a+46b; 27a+47b; 27a+48b; 27a+49b; 27a+50b; 27a+51b; 27a+52b; 27a+53b; 27a+54b; 27a+55b; 27a+55b; 27a+57b; 27a+58b; 27a+59b; 27a+60b; 27a+61b; 27a+62b; 27a+63b; 27a+64b; 27a+65b; 27a+66b; 27a+67b; 27a+68b; 27a+69b; 27a+70b; 27a+71b; 27a+72b; 27a+73b; 27a+74b; 27a+75b; 27a+76b; 27a+77b; 27a+78b; 27a+79b; 27a+80b; 27a+81b; 27a+82b; 27a+83b; 27a+84b; 27a+85b; 27a+86b; 27a+87b; 27a+88b; 27a+89b; 27a+90b; 27a+91b; 27a+92b; 27a+93b; 27a+94b; 27a+95b; 27a+96b; 27a+97b; 28a+1b; 28a+2b; 28a+3b; 28a+4b; 28a+5b; 28a+6b; 28a+7b; 28a+8b; 28a+9b; 28a+10b; 28a+11b; 28a+12b; 28a+13b; 28a+14b; 28a+15b; 28a+16b; 28a+17b; 28a+18b; 28a+19b; 28a+20b; 28a+21b; 28a+22b; 28a+23b; 28a+24b; 28a+25b; 28a+26b; 28a+27b; 28a+28b; 28a+29b; 28a+30b; 28a+31b; 28a+32b; 28a+33b; 28a+34b; 28a+35b; 28a+36b; 28a+37b; 28a+38b; 28a+39b; 28a+40b; 28a+41b; 28a+42b; 28a+43b; 28a+44b; 28a+45b; 28a+46b; 28a+47b; 28a+48b; 28a+49b; 28a+50b; 28a+51b; 28a+52b; 28a+53b; 28a+54b; 28a+55b; 28a+55b; 28a+57b; 28a+58b; 28a+59b; 28a+60b; 28a+61b; 28a+62b; 28a+63b; 28a+64b; 28a+65b; 28a+66b; 28a+67b; 28a+68b; 28a+69b; 28a+70b; 28a+71b; 28a+72b; 28a+73b; 28a+74b; 28a+75b; 28a+76b; 28a+77b; 28a+78b; 28a+79b; 28a+80b; 28a+81b; 28a+82b; 28a+83b; 28a+84b; 28a+85b; 28a+86b; 28a+87b; 28a+88b; 28a+89b; 28a+90b; 28a+91b; 28a+92b; 28a+93b; 28a+94b; 28a+95b; 28a+96b; 28a+97b; 29a+1b; 29a+2b; 29a+3b; 29a+4b; 29a+5b; 29a+6b; 29a+7b; 29a+8b; 29a+9b; 29a+10b; 29a+11b; 29a+12b; 29a+13b; 29a+14b; 29a+15b; 29a+16b; 29a+17b; 29a+18b; 29a+19b; 29a+20b; 29a+21b; 29a+22b; 29a+23b; 29a+24b; 29a+25b; 29a+26b; 29a+27b; 29a+28b; 29a+29b; 29a+30b; 29a+31b; 29a+32b; 29a+33b; 29a+34b; 29a+35b; 29a+36b; 29a+37b; 29a+38b; 29a+39b; 29a+40b; 29a+41b; 29a+42b; 29a+43b; 29a+44b; 29a+45b; 29a+46b; 29a+47b; 29a+48b; 29a+49b; 29a+50b; 29a+51b; 29a+52b; 29a+53b; 29a+54b; 29a+55b; 29a+55b; 29a+57b; 29a+58b; 29a+59b; 29a+60b; 29a+61b; 29a+62b; 29a+63b; 29a+64b; 29a+65b; 29a+66b; 29a+67b; 29a+68b; 29a+69b; 29a+70b; 29a+71b; 29a+72b; 29a+73b; 29a+74b; 29a+75b; 29a+76b; 29a+77b; 29a+78b; 29a+79b; 29a+80b; 29a+81b; 29a+82b; 29a+83b; 29a+84b; 29a+85b; 29a+86b; 29a+87b; 29a+88b; 29a+89b; 29a+90b; 29a+91b; 29a+92b; 29a+93b; 29a+94b; 29a+95b; 29a+96b; 29a+97b; 30a+1b; 30a+2b; 30a+3b; 30a+4b; 30a+5b; 30a+6b; 30a+7b; 30a+8b; 30a+9b; 30a+10b; 30a+11b; 30a+12b; 30a+13b; 30a+14b; 30a+15b; 30a+16b; 30a+17b; 30a+18b; 30a+19b; 30a+20b; 30a+21b; 30a+22b; 30a+23b; 30a+24b; 30a+25b; 30a+26b; 30a+27b; 30a+28b; 30a+29b; 30a+30b; 30a+31b; 30a+32b; 30a+33b; 30a+34b; 30a+35b; 30a+36b; 30a+37b; 30a+38b; 30a+39b; 30a+40b; 30a+41b; 30a+42b; 30a+43b; 30a+44b; 30a+45b; 30a+46b; 30a+47b; 30a+48b; 30a+49b; 30a+50b; 30a+51b; 30a+52b; 30a+53b; 30a+54b; 30a+55b; 30a+55b; 30a+57b; 30a+58b; 30a+59b; 30a+60b; 30a+61b; 30a+62b; 30a+63b; 30a+64b; 30a+65b; 30a+66b; 30a+67b; 30a+68b; 30a+69b; 30a+70b; 30a+71b; 30a+72b; 30a+73b; 30a+74b; 30a+75b; 30a+76b; 30a+77b; 30a+78b; 30a+79b; 30a+80b; 30a+81b; 30a+82b; 30a+83b; 30a+84b; 30a+85b; 30a+86b; 30a+87b; 30a+88b; 30a+89b; 30a+90b; 30a+91b; 30a+92b; 30a+93b; 30a+94b; 30a+95b; 30a+96b; 30a+97b; 31a+1b; 31a+2b; 31a+3b; 31a+4b;

31a+5b; 31a+6b; 31a+7b; 31a+8b; 31a+9b; 31a+10b; 31a+11b; 31a+12b; 31a+13b; 31a+14b; 31a+15b; 31a+16b; 31a+17b; 31a+18b; 31a+19b; 31a+20b; 31a+21b; 31a+22b; 31a+23b; 31a+24b; 31a+25b; 31a+26b; 31a+27b; 31a+28b; 31a+29b; 31a+30b; 31a+31b; 31a+32b; 31a+33b; 31a+34b; 31a+35b; 31a+36b; 31a+37b; 31a+38b; 31a+39b; 31a+40b; 31a+41b; 31a+42b; 31a+43b; 31a+44b; 31a+45b; 31a+46b; 31a+47b; 31a+48b; 31a+49b; 31a+50b; 31a+51b; 31a+52b; 31a+53b; 31a+54b; 31a+55b; 31a+55b; 31a+57b; 31a+58b; 31a+59b; 31a+60b; 31a+61b; 31a+62b; 31a+63b; 31a+64b; 31a+65b; 31a+66b; 31a+67b; 31a+68b; 31a+69b; 31a+70b; 31a+71b; 31a+72b; 31a+73b; 31a+74b; 31a+75b; 31a+76b; 31a+77b; 31a+78b; 31a+79b; 31a+80b; 31a+81b; 31a+82b; 31a+83b; 31a+84b; 31a+85b; 31a+86b; 31a+87b; 31a+88b; 31a+89b; 31a+90b; 31a+91b; 31a+92b; 31a+93b; 31a+94b; 31a+95b; 31a+96b; 31a+97b; 32a+1b; 32a+2b; 32a+3b; 32a+4b; 32a+5b; 32a+6b; 32a+7b; 32a+8b; 32a+9b; 32a+10b; 32a+11b; 32a+12b; 32a+13b; 32a+14b; 32a+15b; 32a+16b; 32a+17b; 32a+18b; 32a+19b; 32a+20b; 32a+21b; 32a+22b; 32a+23b; 32a+24b; 32a+25b; 32a+26b; 32a+27b; 32a+28b; 32a+29b; 32a+30b; 32a+31b; 32a+32b; 32a+33b; 32a+34b; 32a+35b; 32a+36b; 32a+37b; 32a+38b; 32a+39b; 32a+40b; 32a+41b; 32a+42b; 32a+43b; 32a+44b; 32a+45b; 32a+46b; 32a+47b; 32a+48b; 32a+49b; 32a+50b; 32a+51b; 32a+52b; 32a+53b; 32a+54b; 32a+55b; 32a+55b; 32a+57b; 32a+58b; 32a+59b; 32a+60b; 32a+61b; 32a+62b; 32a+63b; 32a+64b; 32a+65b; 32a+66b; 32a+67b; 32a+68b; 32a+69b; 32a+70b; 32a+71b; 32a+72b; 32a+73b; 32a+74b; 32a+75b; 32a+76b; 32a+77b; 32a+78b; 32a+79b; 32a+80b; 32a+81b; 32a+82b; 32a+83b; 32a+84b; 32a+85b; 32a+86b; 32a+87b; 32a+88b; 32a+89b; 32a+90b; 32a+91b; 32a+92b; 32a+93b; 32a+94b; 32a+95b; 32a+96b; 32a+97b; 33a+1b; 33a+2b; 33a+3b; 33a+4b; 33a+5b; 33a+6b; 33a+7b; 33a+8b; 33a+9b; 33a+10b; 33a+11b; 33a+12b; 33a+13b; 33a+14b; 33a+15b; 33a+16b; 33a+17b; 33a+18b; 33a+19b; 33a+20b; 33a+21b; 33a+22b; 33a+23b; 33a+24b; 33a+25b; 33a+26b; 33a+27b; 33a+28b; 33a+29b; 33a+30b; 33a+31b; 33a+32b; 33a+33b; 33a+34b; 33a+35b; 33a+36b; 33a+37b; 33a+38b; 33a+39b; 33a+40b; 33a+41b; 33a+42b; 33a+43b; 33a+44b; 33a+45b; 33a+46b; 33a+47b; 33a+48b; 33a+49b; 33a+50b; 33a+51b; 33a+52b; 33a+53b; 33a+54b; 33a+55b; 33a+55b; 33a+57b; 33a+58b; 33a+59b; 33a+60b; 33a+61b; 33a+62b; 33a+63b; 33a+64b; 33a+65b; 33a+66b; 33a+67b; 33a+68b; 33a+69b; 33a+70b; 33a+71b; 33a+72b; 33a+73b; 33a+74b; 33a+75b; 33a+76b; 33a+77b; 33a+78b; 33a+79b; 33a+80b; 33a+81b; 33a+82b; 33a+83b; 33a+84b; 33a+85b; 33a+86b; 33a+87b; 33a+88b; 33a+89b; 33a+90b; 33a+91b; 33a+92b; 33a+93b; 33a+94b; 33a+95b; 33a+96b; 33a+97b; 34a+1b; 34a+2b; 34a+3b; 34a+4b; 34a+5b; 34a+6b; 34a+7b; 34a+8b; 34a+9b; 34a+10b; 34a+11b; 34a+12b; 34a+13b; 34a+14b; 34a+15b; 34a+16b; 34a+17b; 34a+18b; 34a+19b; 34a+20b; 34a+21b; 34a+22b; 34a+23b; 34a+24b; 34a+25b; 34a+26b; 34a+27b; 34a+28b; 34a+29b; 34a+30b; 34a+31b; 34a+32b; 34a+33b; 34a+34b; 34a+35b; 34a+36b; 34a+37b; 34a+38b; 34a+39b; 34a+40b; 34a+41b; 34a+42b; 34a+43b; 34a+44b; 34a+45b; 34a+46b; 34a+47b; 34a+48b; 34a+49b; 34a+50b; 34a+51b; 34a+52b; 34a+53b; 34a+54b; 34a+55b; 34a+55b; 34a+57b; 34a+58b; 34a+59b; 34a+60b; 34a+61b; 34a+62b; 34a+63b; 34a+64b; 34a+65b; 34a+66b; 34a+67b; 34a+68b; 34a+69b; 34a+70b; 34a+71b; 34a+72b; 34a+73b; 34a+74b; 34a+75b; 34a+76b; 34a+77b; 34a+78b; 34a+79b; 34a+80b; 34a+81b; 34a+82b; 34a+83b; 34a+84b; 34a+85b; 34a+86b; 34a+87b; 34a+88b; 34a+89b; 34a+90b; 34a+91b; 34a+92b; 34a+93b; 34a+94b; 34a+95b; 34a+96b; 34a+97b; 35a+1b; 35a+2b; 35a+3b; 35a+4b; 35a+5b; 35a+6b; 35a+7b; 35a+8b; 35a+9b; 35a+10b; 35a+11b; 35a+12b; 35a+13b; 35a+14b; 35a+15b; 35a+16b; 35a+17b; 35a+18b; 35a+19b; 35a+20b; 35a+21b; 35a+22b; 35a+23b; 35a+24b; 35a+25b; 35a+26b; 35a+27b; 35a+28b; 35a+29b; 35a+30b; 35a+31b; 35a+32b; 35a+33b; 35a+34b; 35a+35b; 35a+36b; 35a+37b; 35a+38b; 35a+39b; 35a+40b; 35a+41b; 35a+42b; 35a+43b; 35a+44b; 35a+45b; 35a+46b; 35a+47b; 35a+48b; 35a+49b; 35a+50b; 35a+51b; 35a+52b; 35a+53b; 35a+54b; 35a+55b; 35a+55b; 35a+57b; 35a+58b; 35a+59b; 35a+60b; 35a+61b; 35a+62b; 35a+63b; 35a+64b; 35a+65b; 35a+66b; 35a+67b; 35a+68b; 35a+69b; 35a+70b; 35a+71b; 35a+72b; 35a+73b; 35a+74b; 35a+75b; 35a+76b; 35a+77b; 35a+78b; 35a+79b; 35a+80b; 35a+81b; 35a+82b; 35a+83b; 35a+84b; 35a+85b; 35a+86b; 35a+87b; 35a+88b; 35a+89b; 35a+90b; 35a+91b; 35a+92b; 35a+93b; 35a+94b; 35a+95b; 35a+96b; 35a+97b; 36a+1b; 36a+2b; 36a+3b; 36a+4b; 36a+5b; 36a+6b; 36a+7b; 36a+8b; 36a+9b; 36a+10b; 36a+11b; 36a+12b; 36a+13b; 36a+14b; 36a+15b; 36a+16b; 36a+17b; 36a+18b; 36a+19b; 36a+20b; 36a+21b; 36a+22b; 36a+23b; 36a+24b; 36a+25b; 36a+26b; 36a+27b; 36a+28b; 36a+29b; 36a+30b; 36a+31b; 36a+32b; 36a+33b; 36a+34b; 36a+35b; 36a+36b; 36a+37b; 36a+38b; 36a+39b; 36a+40b; 36a+41b; 36a+42b; 36a+43b; 36a+44b; 36a+45b; 36a+46b; 36a+47b; 36a+48b; 36a+49b; 36a+50b; 36a+51b; 36a+52b; 36a+53b; 36a+54b; 36a+55b; 36a+55b; 36a+57b; 36a+58b; 36a+59b; 36a+60b; 36a+61b; 36a+62b; 36a+63b; 36a+64b; 36a+65b; 36a+66b; 36a+67b; 36a+68b; 36a+69b; 36a+70b; 36a+71b; 36a+72b; 36a+73b; 36a+74b; 36a+75b; 36a+76b; 36a+77b; 36a+78b; 36a+79b; 36a+80b; 36a+81b; 36a+82b; 36a+83b; 36a+84b; 36a+85b; 36a+86b; 36a+87b; 36a+88b; 36a+89b; 36a+90b; 36a+91b; 36a+92b; 36a+93b; 36a+94b; 36a+95b; 36a+96b; 36a+97b; 37a+1b; 37a+2b; 37a+3b; 37a+4b; 37a+5b; 37a+6b; 37a+7b; 37a+8b; 37a+9b; 37a+10b; 37a+11b; 37a+12b; 37a+13b; 37a+14b; 37a+15b; 37a+16b; 37a+17b; 37a+18b; 37a+19b; 37a+20b; 37a+21b; 37a+22b; 37a+23b; 37a+24b; 37a+25b; 37a+26b; 37a+27b; 37a+28b; 37a+29b; 37a+30b; 37a+31b; 37a+32b; 37a+33b; 37a+34b; 37a+35b; 37a+36b; 37a+37b; 37a+38b; 37a+39b; 37a+40b; 37a+41b; 37a+42b; 37a+43b; 37a+44b; 37a+45b; 37a+46b; 37a+47b; 37a+48b; 37a+49b; 37a+50b; 37a+51b; 37a+52b; 37a+53b; 37a+54b; 37a+55b; 37a+55b; 37a+57b; 37a+58b; 37a+59b; 37a+60b; 37a+61b; 37a+62b; 37a+63b; 37a+64b; 37a+65b; 37a+66b; 37a+67b; 37a+68b; 37a+69b; 37a+70b; 37a+71b; 37a+72b; 37a+73b; 37a+74b; 37a+75b; 37a+76b; 37a+77b; 37a+78b; 37a+79b; 37a+80b; 37a+81b; 37a+82b; 37a+83b; 37a+84b; 37a+85b; 37a+86b; 37a+87b; 37a+88b; 37a+89b; 37a+90b; 37a+91b; 37a+92b; 37a+93b; 37a+94b; 37a+95b; 37a+96b; 37a+97b; 38a+1b; 38a+2b; 38a+3b; 38a+4b; 38a+5b; 38a+6b; 38a+7b; 38a+8b; 38a+9b; 38a+10b; 38a+11b; 38a+12b; 38a+13b; 38a+14b; 38a+15b; 38a+16b; 38a+17b; 38a+18b; 38a+19b; 38a+20b; 38a+21b; 38a+22b; 38a+23b; 38a+24b; 38a+25b; 38a+26b; 38a+27b; 38a+28b; 38a+29b; 38a+30b; 38a+31b; 38a+32b; 38a+33b; 38a+34b; 38a+35b; 38a+36b; 38a+37b; 38a+38b; 38a+39b; 38a+40b; 38a+41b; 38a+42b; 38a+43b; 38a+44b; 38a+45b; 38a+46b; 38a+47b; 38a+48b; 38a+49b; 38a+50b; 38a+51b; 38a+52b; 38a+53b; 38a+54b; 38a+55b; 38a+55b; 38a+57b; 38a+58b; 38a+59b; 38a+60b; 38a+61b; 38a+62b; 38a+63b; 38a+64b; 38a+65b; 38a+66b; 38a+67b; 38a+68b; 38a+69b; 38a+70b; 38a+71b; 38a+

72b; 38a+73b; 38a+74b; 38a+75b; 38a+76b; 38a+77b; 38a+78b; 38a+79b; 38a+80b; 38a+81b; 38a+82b; 38a+83b; 38a+84b; 38a+85b; 38a+86b; 38a+87b; 38a+88b; 38a+89b; 38a+90b; 38a+91b; 38a+92b; 38a+93b; 38a+94b; 38a+95b; 38a+96b; 38a+97b; 39a+1b; 39a+2b; 39a+3b; 39a+4b; 39a+5b; 39a+6b; 39a+7b; 39a+8b; 39a+9b; 39a+10b; 39a+11b; 39a+12b; 39a+13b; 39a+14b; 39a+15b; 39a+16b; 39a+17b; 39a+18b; 39a+19b; 39a+20b; 39a+21b; 39a+22b; 39a+23b; 39a+24b; 39a+25b; 39a+26b; 39a+27b; 39a+28b; 39a+29b; 39a+30b; 39a+31b; 39a+32b; 39a+33b; 39a+34b; 39a+35b; 39a+36b; 39a+37b; 39a+38b; 39a+39b; 39a+40b; 39a+41b; 39a+42b; 39a+43b; 39a+44b; 39a+45b; 39a+46b; 39a+47b; 39a+48b; 39a+49b; 39a+50b; 39a+51b; 39a+52b; 39a+53b; 39a+54b; 39a+55b; 39a+55b; 39a+57b; 39a+58b; 39a+59b; 39a+60b; 39a+61b; 39a+62b; 39a+63b; 39a+64b; 39a+65b; 39a+66b; 39a+67b; 39a+68b; 39a+69b; 39a+70b; 39a+71b; 39a+72b; 39a+73b; 39a+74b; 39a+75b; 39a+76b; 39a+77b; 39a+78b; 39a+79b; 39a+80b; 39a+81b; 39a+82b; 39a+83b; 39a+84b; 39a+85b; 39a+86b; 39a+87b; 39a+88b; 39a+89b; 39a+90b; 39a+91b; 39a+92b; 39a+93b; 39a+94b; 39a+95b; 39a+96b; 39a+97b; 40a+1b; 40a+2b; 40a+3b; 40a+4b; 40a+5b; 40a+6b; 40a+7b; 40a+8b; 40a+9b; 40a+10b; 40a+11b; 40a+12b; 40a+13b; 40a+14b; 40a+15b; 40a+16b; 40a+17b; 40a+18b; 40a+19b; 40a+20b; 40a+21b; 40a+22b; 40a+23b; 40a+24b; 40a+25b; 40a+26b; 40a+27b; 40a+28b; 40a+29b; 40a+30b; 40a+31b; 40a+32b; 40a+33b; 40a+34b; 40a+35b; 40a+36b; 40a+37b; 40a+38b; 40a+39b; 40a+40b; 40a+41b; 40a+42b; 40a+43b; 40a+44b; 40a+45b; 40a+46b; 40a+47b; 40a+48b; 40a+49b; 40a+50b; 40a+51b; 40a+52b; 40a+53b; 40a+54b; 40a+55b; 40a+55b; 40a+57b; 40a+58b; 40a+59b; 40a+60b; 40a+61b; 40a+62b; 40a+63b; 40a+64b; 40a+65b; 40a+66b; 40a+67b; 40a+68b; 40a+69b; 40a+70b; 40a+71b; 40a+72b; 40a+73b; 40a+74b; 40a+75b; 40a+76b; 40a+77b; 40a+78b; 40a+79b; 40a+80b; 40a+81b; 40a+82b; 40a+83b; 40a+84b; 40a+85b; 40a+86b; 40a+87b; 40a+88b; 40a+89b; 40a+90b; 40a+91b; 40a+92b; 40a+93b; 40a+94b; 40a+95b; 40a+96b; 40a+97b; 41a+1b; 41a+2b; 41a+3b; 41a+4b; 41a+5b; 41a+6b; 41a+7b; 41a+8b; 41a+9b; 41a+10b; 41a+11b; 41a+12b; 41a+13b; 41a+14b; 41a+15b; 41a+16b; 41a+17b; 41a+18b; 41a+19b; 41a+20b; 41a+21b; 41a+22b; 41a+23b; 41a+24b; 41a+25b; 41a+26b; 41a+27b; 41a+28b; 41a+29b; 41a+30b; 41a+31b; 41a+32b; 41a+33b; 41a+34b; 41a+35b; 41a+36b; 41a+37b; 41a+38b; 41a+39b; 41a+40b; 41a+41b; 41a+42b; 41a+43b; 41a+44b; 41a+45b; 41a+46b; 41a+47b; 41a+48b; 41a+49b; 41a+50b; 41a+51b; 41a+52b; 41a+53b; 41a+54b; 41a+55b; 41a+55b; 41a+57b; 41a+58b; 41a+59b; 41a+60b; 41a+61b; 41a+62b; 41a+63b; 41a+64b; 41a+65b; 41a+66b; 41a+67b; 41a+68b; 41a+69b; 41a+70b; 41a+71b; 41a+72b; 41a+73b; 41a+74b; 41a+75b; 41a+76b; 41a+77b; 41a+78b; 41a+79b; 41a+80b; 41a+81b; 41a+82b; 41a+83b; 41a+84b; 41a+85b; 41a+86b; 41a+87b; 41a+88b; 41a+89b; 41a+90b; 41a+91b; 41a+92b; 41a+93b; 41a+94b; 41a+95b; 41a+96b; 41a+97b; 42a+1b; 42a+2b; 42a+3b; 42a+4b; 42a+5b; 42a+6b; 42a+7b; 42a+8b; 42a+9b; 42a+10b; 42a+11b; 42a+12b; 42a+13b; 42a+14b; 42a+15b; 42a+16b; 42a+17b; 42a+18b; 42a+19b; 42a+20b; 42a+21b; 42a+22b; 42a+23b; 42a+24b; 42a+25b; 42a+26b; 42a+27b; 42a+28b; 42a+29b; 42a+30b; 42a+31b; 42a+32b; 42a+33b; 42a+34b; 42a+35b; 42a+36b; 42a+37b; 42a+38b; 42a+39b; 42a+40b; 42a+41b; 42a+42b; 42a+43b; 42a+44b; 42a+45b; 42a+46b; 42a+47b; 42a+48b; 42a+49b; 42a+50b; 42a+51b; 42a+52b; 42a+53b; 42a+54b; 42a+55b; 42a+55b; 42a+57b; 42a+58b; 42a+59b; 42a+60b; 42a+61b; 42a+62b; 42a+63b; 42a+64b; 42a+65b; 42a+66b; 42a+67b; 42a+68b; 42a+69b; 42a+70b; 42a+71b; 42a+72b; 42a+73b; 42a+74b; 42a+75b; 42a+76b; 42a+77b; 42a+78b; 42a+79b; 42a+80b; 42a+81b; 42a+82b; 42a+83b; 42a+84b; 42a+85b; 42a+86b; 42a+87b; 42a+88b; 42a+89b; 42a+90b; 42a+91b; 42a+92b; 42a+93b; 42a+94b; 42a+95b; 42a+96b; 42a+97b; 43a+1b; 43a+2b; 43a+3b; 43a+4b; 43a+5b; 43a+6b; 43a+7b; 43a+8b; 43a+9b; 43a+10b; 43a+11b; 43a+12b; 43a+13b; 43a+14b; 43a+15b; 43a+16b; 43a+17b; 43a+18b; 43a+19b; 43a+20b; 43a+21b; 43a+22b; 43a+23b; 43a+24b; 43a+25b; 43a+26b; 43a+27b; 43a+28b; 43a+29b; 43a+30b; 43a+31b; 43a+32b; 43a+33b; 43a+34b; 43a+35b; 43a+36b; 43a+37b; 43a+38b; 43a+39b; 43a+40b; 43a+41b; 43a+42b; 43a+43b; 43a+44b; 43a+45b; 43a+46b; 43a+47b; 43a+48b; 43a+49b; 43a+50b; 43a+51b; 43a+52b; 43a+53b; 43a+54b; 43a+55b; 43a+55b; 43a+57b; 43a+58b; 43a+59b; 43a+60b; 43a+61b; 43a+62b; 43a+63b; 43a+64b; 43a+65b; 43a+66b; 43a+67b; 43a+68b; 43a+69b; 43a+70b; 43a+71b; 43a+72b; 43a+73b; 43a+74b; 43a+75b; 43a+76b; 43a+77b; 43a+78b; 43a+79b; 43a+80b; 43a+81b; 43a+82b; 43a+83b; 43a+84b; 43a+85b; 43a+86b; 43a+87b; 43a+88b; 43a+89b; 43a+90b; 43a+91b; 43a+92b; 43a+93b; 43a+94b; 43a+95b; 43a+96b; 43a+97b; 44a+1b; 44a+2b; 44a+3b; 44a+4b; 44a+5b; 44a+6b; 44a+7b; 44a+8b; 44a+9b; 44a+10b; 44a+11b; 44a+12b; 44a+13b; 44a+14b; 44a+15b; 44a+16b; 44a+17b; 44a+18b; 44a+19b; 44a+20b; 44a+21b; 44a+22b; 44a+23b; 44a+24b; 44a+25b; 44a+26b; 44a+27b; 44a+28b; 44a+29b; 44a+30b; 44a+31b; 44a+32b; 44a+33b; 44a+34b; 44a+35b; 44a+36b; 44a+37b; 44a+38b; 44a+39b; 44a+40b; 44a+41b; 44a+42b; 44a+43b; 44a+44b; 44a+45b; 44a+46b; 44a+47b; 44a+48b; 44a+49b; 44a+50b; 44a+51b; 44a+52b; 44a+53b; 44a+54b; 44a+55b; 44a+55b; 44a+57b; 44a+58b; 44a+59b; 44a+60b; 44a+61b; 44a+62b; 44a+63b; 44a+64b; 44a+65b; 44a+66b; 44a+67b; 44a+68b; 44a+69b; 44a+70b; 44a+71b; 44a+72b; 44a+73b; 44a+74b; 44a+75b; 44a+76b; 44a+77b; 44a+78b; 44a+79b; 44a+80b; 44a+81b; 44a+82b; 44a+83b; 44a+84b; 44a+85b; 44a+86b; 44a+87b; 44a+88b; 44a+89b; 44a+90b; 44a+91b; 44a+92b; 44a+93b; 44a+94b; 44a+95b; 44a+96b; 44a+97b; 45a+1b; 45a+2b; 45a+3b; 45a+4b; 45a+5b; 45a+6b; 45a+7b; 45a+8b; 45a+9b; 45a+10b; 45a+11b; 45a+12b; 45a+13b; 45a+14b; 45a+15b; 45a+16b; 45a+17b; 45a+18b; 45a+19b; 45a+20b; 45a+21b; 45a+22b; 45a+23b; 45a+24b; 45a+25b; 45a+26b; 45a+27b; 45a+28b; 45a+29b; 45a+30b; 45a+31b; 45a+32b; 45a+33b; 45a+34b; 45a+35b; 45a+36b; 45a+37b; 45a+38b; 45a+39b; 45a+40b; 45a+41b; 45a+42b; 45a+43b; 45a+44b; 45a+45b; 45a+46b; 45a+47b; 45a+48b; 45a+49b; 45a+50b; 45a+51b; 45a+52b; 45a+53b; 45a+54b; 45a+55b; 45a+55b; 45a+57b; 45a+58b; 45a+59b; 45a+60b; 45a+61b; 45a+62b; 45a+63b; 45a+64b; 45a+65b; 45a+66b; 45a+67b; 45a+68b; 45a+69b; 45a+70b; 45a+71b; 45a+72b; 45a+73b; 45a+74b; 45a+75b; 45a+76b; 45a+77b; 45a+78b; 45a+79b; 45a+80b; 45a+81b; 45a+82b; 45a+83b; 45a+84b; 45a+85b; 45a+86b; 45a+87b; 45a+88b; 45a+89b; 45a+90b; 45a+91b; 45a+92b; 45a+93b; 45a+94b; 45a+95b; 45a+96b; 45a+97b; 46a+1b; 46a+2b; 46a+3b; 46a+4b; 46a+5b; 46a+6b; 46a+7b; 46a+8b; 46a+9b; 46a+10b; 46a+11b; 46a+12b; 46a+13b; 46a+14b; 46a+15b; 46a+16b; 46a+17b; 46a+18b; 46a+19b; 46a+20b; 46a+21b; 46a+22b; 46a+23b; 46a+24b; 46a+25b; 46a+26b; 46a+27b; 46a+28b; 46a+29b; 46a+30b; 46a+31b; 46a+32b; 46a+33b; 46a+34b; 46a+35b; 46a+36b; 46a+37b; 46a+38b; 46a+39b; 46a+40b; 46a+41b; 46a+42b; 46a+43b;

46a+44b; 46a+45b; 46a+46b; 46a+47b; 46a+48b; 46a+49b; 46a+50b; 46a+51b; 46a+52b; 46a+53b; 46a+54b; 46a+55b; 46a+55b; 46a+57b; 46a+58b; 46a+59b; 46a+60b; 46a+61b; 46a+62b; 46a+63b; 46a+64b; 46a+65b; 46a+66b; 46a+67b; 46a+68b; 46a+69b; 46a+70b; 46a+71b; 46a+72b; 46a+73b; 46a+74b; 46a+75b; 46a+76b; 46a+77b; 46a+78b; 46a+79b; 46a+80b; 46a+81b; 46a+82b; 46a+83b; 46a+84b; 46a+85b; 46a+86b; 46a+87b; 46a+88b; 46a+89b; 46a+90b; 46a+91b; 46a+92b; 46a+93b; 46a+94b; 46a+95b; 46a+96b; 46a+97b; 47a+1b; 47a+2b; 47a+3b; 47a+4b; 47a+5b; 47a+6b; 47a+7b; 47a+8b; 47a+9b; 47a+10b; 47a+11b; 47a+12b; 47a+13b; 47a+14b; 47a+15b; 47a+16b; 47a+17b; 47a+18b; 47a+19b; 47a+20b; 47a+21b; 47a+22b; 47a+23b; 47a+24b; 47a+25b; 47a+26b; 47a+27b; 47a+28b; 47a+29b; 47a+30b; 47a+31b; 47a+32b; 47a+33b; 47a+34b; 47a+35b; 47a+36b; 47a+37b; 47a+38b; 47a+39b; 47a+40b; 47a+41b; 47a+42b; 47a+43b; 47a+44b; 47a+45b; 47a+46b; 47a+47b; 47a+48b; 47a+49b; 47a+50b; 47a+51b; 47a+52b; 47a+53b; 47a+54b; 47a+55b; 47a+55b; 47a+57b; 47a+58b; 47a+59b; 47a+60b; 47a+61b; 47a+62b; 47a+63b; 47a+64b; 47a+65b; 47a+66b; 47a+67b; 47a+68b; 47a+69b; 47a+70b; 47a+71b; 47a+72b; 47a+73b; 47a+74b; 47a+75b; 47a+76b; 47a+77b; 47a+78b; 47a+79b; 47a+80b; 47a+81b; 47a+82b; 47a+83b; 47a+84b; 47a+85b; 47a+86b; 47a+87b; 47a+88b; 47a+89b; 47a+90b; 47a+91b; 47a+92b; 47a+93b; 47a+94b; 47a+95b; 47a+96b; 47a+97b; 48a+1b; 48a+2b; 48a+3b; 48a+4b; 48a+5b; 48a+6b; 48a+7b; 48a+8b; 48a+9b; 48a+10b; 48a+11b; 48a+12b; 48a+13b; 48a+14b; 48a+15b; 48a+16b; 48a+17b; 48a+18b; 48a+19b; 48a+20b; 48a+21b; 48a+22b; 48a+23b; 48a+24b; 48a+25b; 48a+26b; 48a+27b; 48a+28b; 48a+29b; 48a+30b; 48a+31b; 48a+32b; 48a+33b; 48a+34b; 48a+35b; 48a+36b; 48a+37b; 48a+38b; 48a+39b; 48a+40b; 48a+41b; 48a+42b; 48a+43b; 48a+44b; 48a+45b; 48a+46b; 48a+47b; 48a+48b; 48a+49b; 48a+50b; 48a+51b; 48a+52b; 48a+53b; 48a+54b; 48a+55b; 48a+55b; 48a+57b; 48a+58b; 48a+59b; 48a+60b; 48a+61b; 48a+62b; 48a+63b; 48a+64b; 48a+65b; 48a+66b; 48a+67b; 48a+68b; 48a+69b; 48a+70b; 48a+71b; 48a+72b; 48a+73b; 48a+74b; 48a+75b; 48a+76b; 48a+77b; 48a+78b; 48a+79b; 48a+80b; 48a+81b; 48a+82b; 48a+83b; 48a+84b; 48a+85b; 48a+86b; 48a+87b; 48a+88b; 48a+89b; 48a+90b; 48a+91b; 48a+92b; 48a+93b; 48a+94b; 48a+95b; 48a+96b; 48a+97b; 49a+1b; 49a+2b; 49a+3b; 49a+4b; 49a+5b; 49a+6b; 49a+7b; 49a+8b; 49a+9b; 49a+10b; 49a+11b; 49a+12b; 49a+13b; 49a+14b; 49a+15b; 49a+16b; 49a+17b; 49a+18b; 49a+19b; 49a+20b; 49a+21b; 49a+22b; 49a+23b; 49a+24b; 49a+25b; 49a+26b; 49a+27b; 49a+28b; 49a+29b; 49a+30b; 49a+31b; 49a+32b; 49a+33b; 49a+34b; 49a+35b; 49a+36b; 49a+37b; 49a+38b; 49a+39b; 49a+40b; 49a+41b; 49a+42b; 49a+43b; 49a+44b; 49a+45b; 49a+46b; 49a+47b; 49a+48b; 49a+49b; 49a+50b; 49a+51b; 49a+52b; 49a+53b; 49a+54b; 49a+55b; 49a+55b; 49a+57b; 49a+58b; 49a+59b; 49a+60b; 49a+61b; 49a+62b; 49a+63b; 49a+64b; 49a+65b; 49a+66b; 49a+67b; 49a+68b; 49a+69b; 49a+70b; 49a+71b; 49a+72b; 49a+73b; 49a+74b; 49a+75b; 49a+76b; 49a+77b; 49a+78b; 49a+79b; 49a+80b; 49a+81b; 49a+82b; 49a+83b; 49a+84b; 49a+85b; 49a+86b; 49a+87b; 49a+88b; 49a+89b; 49a+90b; 49a+91b; 49a+92b; 49a+93b; 49a+94b; 49a+95b; 49a+96b; 49a+97b; 50a+1b; 50a+2b; 50a+3b; 50a+4b; 50a+5b; 50a+6b; 50a+7b; 50a+8b; 50a+9b; 50a+10b; 50a+11b; 50a+12b; 50a+13b; 50a+14b; 50a+15b; 50a+16b; 50a+17b; 50a+18b; 50a+19b; 50a+20b; 50a+21b; 50a+22b; 50a+23b; 50a+24b; 50a+25b; 50a+26b; 50a+27b; 50a+28b; 50a+29b; 50a+30b; 50a+31b; 50a+32b; 50a+33b; 50a+34b; 50a+35b; 50a+36b; 50a+37b; 50a+38b; 50a+39b; 50a+40b; 50a+41b; 50a+42b; 50a+43b; 50a+44b; 50a+45b; 50a+46b; 50a+47b; 50a+48b; 50a+49b; 50a+50b; 50a+51b; 50a+52b; 50a+53b; 50a+54b; 50a+55b; 50a+55b; 50a+57b; 50a+58b; 50a+59b; 50a+60b; 50a+61b; 50a+62b; 50a+63b; 50a+64b; 50a+65b; 50a+66b; 50a+67b; 50a+68b; 50a+69b; 50a+70b; 50a+71b; 50a+72b; 50a+73b; 50a+74b; 50a+75b; 50a+76b; 50a+77b; 50a+78b; 50a+79b; 50a+80b; 50a+81b; 50a+82b; 50a+83b; 50a+84b; 50a+85b; 50a+86b; 50a+87b; 50a+88b; 50a+89b; 50a+90b; 50a+91b; 50a+92b; 50a+93b; 50a+94b; 50a+95b; 50a+96b; 50a+97b; 51a+1b; 51a+2b; 51a+3b; 51a+4b; 51a+5b; 51a+6b; 51a+7b; 51a+8b; 51a+9b; 51a+10b; 51a+11b; 51a+12b; 51a+13b; 51a+14b; 51a+15b; 51a+16b; 51a+17b; 51a+18b; 51a+19b; 51a+20b; 51a+21b; 51a+22b; 51a+23b; 51a+24b; 51a+25b; 51a+26b; 51a+27b; 51a+28b; 51a+29b; 51a+30b; 51a+31b; 51a+32b; 51a+33b; 51a+34b; 51a+35b; 51a+36b; 51a+37b; 51a+38b; 51a+39b; 51a+40b; 51a+41b; 51a+42b; 51a+43b; 51a+44b; 51a+45b; 51a+46b; 51a+47b; 51a+48b; 51a+49b; 51a+50b; 51a+51b; 51a+52b; 51a+53b; 51a+54b; 51a+55b; 51a+55b; 51a+57b; 51a+58b; 51a+59b; 51a+60b; 51a+61b; 51a+62b; 51a+63b; 51a+64b; 51a+65b; 51a+66b; 51a+67b; 51a+68b; 51a+69b; 51a+70b; 51a+71b; 51a+72b; 51a+73b; 51a+74b; 51a+75b; 51a+76b; 51a+77b; 51a+78b; 51a+79b; 51a+80b; 51a+81b; 51a+82b; 51a+83b; 51a+84b; 51a+85b; 51a+86b; 51a+87b; 51a+88b; 51a+89b; 51a+90b; 51a+91b; 51a+92b; 51a+93b; 51a+94b; 51a+95b; 51a+96b; 51a+97b; 52a+1b; 52a+2b; 52a+3b; 52a+4b; 52a+5b; 52a+6b; 52a+7b; 52a+8b; 52a+9b; 52a+10b; 52a+11b; 52a+12b; 52a+13b; 52a+14b; 52a+15b; 52a+16b; 52a+17b; 52a+18b; 52a+19b; 52a+20b; 52a+21b; 52a+22b; 52a+23b; 52a+24b; 52a+25b; 52a+26b; 52a+27b; 52a+28b; 52a+29b; 52a+30b; 52a+31b; 52a+32b; 52a+33b; 52a+34b; 52a+35b; 52a+36b; 52a+37b; 52a+38b; 52a+39b; 52a+40b; 52a+41b; 52a+42b; 52a+43b; 52a+44b; 52a+45b; 52a+46b; 52a+47b; 52a+48b; 52a+49b; 52a+50b; 52a+51b; 52a+52b; 52a+53b; 52a+54b; 52a+55b; 52a+55b; 52a+57b; 52a+58b; 52a+59b; 52a+60b; 52a+61b; 52a+62b; 52a+63b; 52a+64b; 52a+65b; 52a+66b; 52a+67b; 52a+68b; 52a+69b; 52a+70b; 52a+71b; 52a+72b; 52a+73b; 52a+74b; 52a+75b; 52a+76b; 52a+77b; 52a+78b; 52a+79b; 52a+80b; 52a+81b; 52a+82b; 52a+83b; 52a+84b; 52a+85b; 52a+86b; 52a+87b; 52a+88b; 52a+89b; 52a+90b; 52a+91b; 52a+92b; 52a+93b; 52a+94b; 52a+95b; 52a+96b; 52a+97b; 53a+1b; 53a+2b; 53a+3b; 53a+4b; 53a+5b; 53a+6b; 53a+7b; 53a+8b; 53a+9b; 53a+10b; 53a+11b; 53a+12b; 53a+13b; 53a+14b; 53a+15b; 53a+16b; 53a+17b; 53a+18b; 53a+19b; 53a+20b; 53a+21b; 53a+22b; 53a+23b; 53a+24b; 53a+25b; 53a+26b; 53a+27b; 53a+28b; 53a+29b; 53a+30b; 53a+31b; 53a+32b; 53a+33b; 53a+34b; 53a+35b; 53a+36b; 53a+37b; 53a+38b; 53a+39b; 53a+40b; 53a+41b; 53a+42b; 53a+43b; 53a+44b; 53a+45b; 53a+46b; 53a+47b; 53a+48b; 53a+49b; 53a+50b; 53a+51b; 53a+52b; 53a+53b; 53a+54b; 53a+55b; 53a+55b; 53a+57b; 53a+58b; 53a+59b; 53a+60b; 53a+61b; 53a+62b; 53a+63b; 53a+64b; 53a+65b; 53a+66b; 53a+67b; 53a+68b; 53a+69b; 53a+70b; 53a+71b; 53a+72b; 53a+73b; 53a+74b; 53a+75b; 53a+76b; 53a+77b; 53a+78b; 53a+79b; 53a+80b; 53a+81b; 53a+82b; 53a+83b; 53a+84b; 53a+85b; 53a+86b; 53a+87b; 53a+88b; 53a+89b; 53a+90b; 53a+91b; 53a+92b; 53a+93b; 53a+94b; 53a+95b; 53a+96b; 53a+97b; 54a+1b; 54a+2b; 54a+3b; 54a+4b; 54a+5b; 54a+6b; 54a+7b; 54a+8b; 54a+9b; 54a+10b; 54a+11b; 54a+12b; 54a+13b; 54a+14b; 54a+

15b; 54a+16b; 54a+17b; 54a+18b; 54a+19b; 54a+20b; 54a+21b; 54a+22b; 54a+23b; 54a+24b; 54a+25b; 54a+26b; 54a+27b; 54a+28b; 54a+29b; 54a+30b; 54a+31b; 54a+32b; 54a+33b; 54a+34b; 54a+35b; 54a+36b; 54a+37b; 54a+38b; 54a+39b; 54a+40b; 54a+41b; 54a+42b; 54a+43b; 54a+44b; 54a+45b; 54a+46b; 54a+47b; 54a+48b; 54a+49b; 54a+50b; 54a+51b; 54a+52b; 54a+53b; 54a+54b; 54a+55b; 54a+55b; 54a+57b; 54a+58b; 54a+59b; 54a+60b; 54a+61b; 54a+62b; 54a+63b; 54a+64b; 54a+65b; 54a+66b; 54a+67b; 54a+68b; 54a+69b; 54a+70b; 54a+71b; 54a+72b; 54a+73b; 54a+74b; 54a+75b; 54a+76b; 54a+77b; 54a+78b; 54a+79b; 54a+80b; 54a+81b; 54a+82b; 54a+83b; 54a+84b; 54a+85b; 54a+86b; 54a+87b; 54a+88b; 54a+89b; 54a+90b; 54a+91b; 54a+92b; 54a+93b; 54a+94b; 54a+95b; 54a+96b; 54a+97b; 55a+1b; 55a+2b; 55a+3b; 55a+4b; 55a+5b; 55a+6b; 55a+7b; 55a+8b; 55a+9b; 55a+10b; 55a+11b; 55a+12b; 55a+13b; 55a+14b; 55a+15b; 55a+16b; 55a+17b; 55a+18b; 55a+19b; 55a+20b; 55a+21b; 55a+22b; 55a+23b; 55a+24b; 55a+25b; 55a+26b; 55a+27b; 55a+28b; 55a+29b; 55a+30b; 55a+31b; 55a+32b; 55a+33b; 55a+34b; 55a+35b; 55a+36b; 55a+37b; 55a+38b; 55a+39b; 55a+40b; 55a+41b; 55a+42b; 55a+43b; 55a+44b; 55a+45b; 55a+46b; 55a+47b; 55a+48b; 55a+49b; 55a+50b; 55a+51b; 55a+52b; 55a+53b; 55a+54b; 55a+55b; 55a+55b; 55a+57b; 55a+58b; 55a+59b; 55a+60b; 55a+61b; 55a+62b; 55a+63b; 55a+64b; 55a+65b; 55a+66b; 55a+67b; 55a+68b; 55a+69b; 55a+70b; 55a+71b; 55a+72b; 55a+73b; 55a+74b; 55a+75b; 55a+76b; 55a+77b; 55a+78b; 55a+79b; 55a+80b; 55a+81b; 55a+82b; 55a+83b; 55a+84b; 55a+85b; 55a+86b; 55a+87b; 55a+88b; 55a+89b; 55a+90b; 55a+91b; 55a+92b; 55a+93b; 55a+94b; 55a+95b; 55a+96b; 55a+97b; 56a+1b; 56a+2b; 56a+3b; 56a+4b; 56a+5b; 56a+6b; 56a+7b; 56a+8b; 56a+9b; 56a+10b; 56a+11b; 56a+12b; 56a+13b; 56a+14b; 56a+15b; 56a+16b; 56a+17b; 56a+18b; 56a+19b; 56a+20b; 56a+21b; 56a+22b; 56a+23b; 56a+24b; 56a+25b; 56a+26b; 56a+27b; 56a+28b; 56a+29b; 56a+30b; 56a+31b; 56a+32b; 56a+33b; 56a+34b; 56a+35b; 56a+36b; 56a+37b; 56a+38b; 56a+39b; 56a+40b; 56a+41b; 56a+42b; 56a+43b; 56a+44b; 56a+45b; 56a+46b; 56a+47b; 56a+48b; 56a+49b; 56a+50b; 56a+51b; 56a+52b; 56a+53b; 56a+54b; 56a+55b; 56a+55b; 56a+57b; 56a+58b; 56a+59b; 56a+60b; 56a+61b; 56a+62b; 56a+63b; 56a+64b; 56a+65b; 56a+66b; 56a+67b; 56a+68b; 56a+69b; 56a+70b; 56a+71b; 56a+72b; 56a+73b; 56a+74b; 56a+75b; 56a+76b; 56a+77b; 56a+78b; 56a+79b; 56a+80b; 56a+81b; 56a+82b; 56a+83b; 56a+84b; 56a+85b; 56a+86b; 56a+87b; 56a+88b; 56a+89b; 56a+90b; 56a+91b; 56a+92b; 56a+93b; 56a+94b; 56a+95b; 56a+96b; 56a+97b; 57a+1b; 57a+2b; 57a+3b; 57a+4b; 57a+5b; 57a+6b; 57a+7b; 57a+8b; 57a+9b; 57a+10b; 57a+11b; 57a+12b; 57a+13b; 57a+14b; 57a+15b; 57a+16b; 57a+17b; 57a+18b; 57a+19b; 57a+20b; 57a+21b; 57a+22b; 57a+23b; 57a+24b; 57a+25b; 57a+26b; 57a+27b; 57a+28b; 57a+29b; 57a+30b; 57a+31b; 57a+32b; 57a+33b; 57a+34b; 57a+35b; 57a+36b; 57a+37b; 57a+38b; 57a+39b; 57a+40b; 57a+41b; 57a+42b; 57a+43b; 57a+44b; 57a+45b; 57a+46b; 57a+47b; 57a+48b; 57a+49b; 57a+50b; 57a+51b; 57a+52b; 57a+53b; 57a+54b; 57a+55b; 57a+55b; 57a+57b; 57a+58b; 57a+59b; 57a+60b; 57a+61b; 57a+62b; 57a+63b; 57a+64b; 57a+65b; 57a+66b; 57a+67b; 57a+68b; 57a+69b; 57a+70b; 57a+71b; 57a+72b; 57a+73b; 57a+74b; 57a+75b; 57a+76b; 57a+77b; 57a+78b; 57a+79b; 57a+80b; 57a+81b; 57a+82b; 57a+83b; 57a+84b; 57a+85b; 57a+86b; 57a+87b; 57a+88b; 57a+89b; 57a+90b; 57a+91b; 57a+92b; 57a+93b; 57a+94b; 57a+95b; 57a+96b; 57a+97b; 58a+1b; 58a+2b; 58a+3b; 58a+4b; 58a+5b; 58a+6b; 58a+7b; 58a+8b; 58a+9b; 58a+10b; 58a+11b; 58a+12b; 58a+13b; 58a+14b; 58a+15b; 58a+16b; 58a+17b; 58a+18b; 58a+19b; 58a+20b; 58a+21b; 58a+22b; 58a+23b; 58a+24b; 58a+25b; 58a+26b; 58a+27b; 58a+28b; 58a+29b; 58a+30b; 58a+31b; 58a+32b; 58a+33b; 58a+34b; 58a+35b; 58a+36b; 58a+37b; 58a+38b; 58a+39b; 58a+40b; 58a+41b; 58a+42b; 58a+43b; 58a+44b; 58a+45b; 58a+46b; 58a+47b; 58a+48b; 58a+49b; 58a+50b; 58a+51b; 58a+52b; 58a+53b; 58a+54b; 58a+55b; 58a+55b; 58a+57b; 58a+58b; 58a+59b; 58a+60b; 58a+61b; 58a+62b; 58a+63b; 58a+64b; 58a+65b; 58a+66b; 58a+67b; 58a+68b; 58a+69b; 58a+70b; 58a+71b; 58a+72b; 58a+73b; 58a+74b; 58a+75b; 58a+76b; 58a+77b; 58a+78b; 58a+79b; 58a+80b; 58a+81b; 58a+82b; 58a+83b; 58a+84b; 58a+85b; 58a+86b; 58a+87b; 58a+88b; 58a+89b; 58a+90b; 58a+91b; 58a+92b; 58a+93b; 58a+94b; 58a+95b; 58a+96b; 58a+97b; 59a+1b; 59a+2b; 59a+3b; 59a+4b; 59a+5b; 59a+6b; 59a+7b; 59a+8b; 59a+9b; 59a+10b; 59a+11b; 59a+12b; 59a+13b; 59a+14b; 59a+15b; 59a+16b; 59a+17b; 59a+18b; 59a+19b; 59a+20b; 59a+21b; 59a+22b; 59a+23b; 59a+24b; 59a+25b; 59a+26b; 59a+27b; 59a+28b; 59a+29b; 59a+30b; 59a+31b; 59a+32b; 59a+33b; 59a+34b; 59a+35b; 59a+36b; 59a+37b; 59a+38b; 59a+39b; 59a+40b; 59a+41b; 59a+42b; 59a+43b; 59a+44b; 59a+45b; 59a+46b; 59a+47b; 59a+48b; 59a+49b; 59a+50b; 59a+51b; 59a+52b; 59a+53b; 59a+54b; 59a+55b; 59a+55b; 59a+57b; 59a+58b; 59a+59b; 59a+60b; 59a+61b; 59a+62b; 59a+63b; 59a+64b; 59a+65b; 59a+66b; 59a+67b; 59a+68b; 59a+69b; 59a+70b; 59a+71b; 59a+72b; 59a+73b; 59a+74b; 59a+75b; 59a+76b; 59a+77b; 59a+78b; 59a+79b; 59a+80b; 59a+81b; 59a+82b; 59a+83b; 59a+84b; 59a+85b; 59a+86b; 59a+87b; 59a+88b; 59a+89b; 59a+90b; 59a+91b; 59a+92b; 59a+93b; 59a+94b; 59a+95b; 59a+96b; 59a+97b; 60a+1b; 60a+2b; 60a+3b; 60a+4b; 60a+5b; 60a+6b; 60a+7b; 60a+8b; 60a+9b; 60a+10b; 60a+11b; 60a+12b; 60a+13b; 60a+14b; 60a+15b; 60a+16b; 60a+17b; 60a+18b; 60a+19b; 60a+20b; 60a+21b; 60a+22b; 60a+23b; 60a+24b; 60a+25b; 60a+26b; 60a+27b; 60a+28b; 60a+29b; 60a+30b; 60a+31b; 60a+32b; 60a+33b; 60a+34b; 60a+35b; 60a+36b; 60a+37b; 60a+38b; 60a+39b; 60a+40b; 60a+41b; 60a+42b; 60a+43b; 60a+44b; 60a+45b; 60a+46b; 60a+47b; 60a+48b; 60a+49b; 60a+50b; 60a+51b; 60a+52b; 60a+53b; 60a+54b; 60a+55b; 60a+55b; 60a+57b; 60a+58b; 60a+59b; 60a+60b; 60a+61b; 60a+62b; 60a+63b; 60a+64b; 60a+65b; 60a+66b; 60a+67b; 60a+68b; 60a+69b; 60a+70b; 60a+71b; 60a+72b; 60a+73b; 60a+74b; 60a+75b; 60a+76b; 60a+77b; 60a+78b; 60a+79b; 60a+80b; 60a+81b; 60a+82b; 60a+83b; 60a+84b; 60a+85b; 60a+86b; 60a+87b; 60a+88b; 60a+89b; 60a+90b; 60a+91b; 60a+92b; 60a+93b; 60a+94b; 60a+95b; 60a+96b; 60a+97b; 61a+1b; 61a+2b; 61a+3b; 61a+4b; 61a+5b; 61a+6b; 61a+7b; 61a+8b; 61a+9b; 61a+10b; 61a+11b; 61a+12b; 61a+13b; 61a+14b; 61a+15b; 61a+16b; 61a+17b; 61a+18b; 61a+19b; 61a+20b; 61a+21b; 61a+22b; 61a+23b; 61a+24b; 61a+25b; 61a+26b; 61a+27b; 61a+28b; 61a+29b; 61a+30b; 61a+31b; 61a+32b; 61a+33b; 61a+34b; 61a+35b; 61a+36b; 61a+37b; 61a+38b; 61a+39b; 61a+40b; 61a+41b; 61a+42b; 61a+43b; 61a+44b; 61a+45b; 61a+46b; 61a+47b; 61a+48b; 61a+49b; 61a+50b; 61a+51b; 61a+52b; 61a+53b; 61a+54b; 61a+55b; 61a+55b; 61a+57b; 61a+58b; 61a+59b; 61a+60b; 61a+61b; 61a+62b; 61a+63b; 61a+64b; 61a+65b; 61a+66b; 61a+67b; 61a+68b; 61a+69b; 61a+70b; 61a+71b; 61a+72b; 61a+73b; 61a+74b; 61a+75b; 61a+76b; 61a+77b; 61a+78b; 61a+79b; 61a+80b; 61a+81b; 61a+

82b; 61a+83b; 61a+84b; 61a+85b; 61a+86b; 61a+87b; 61a+88b; 61a+89b; 61a+90b; 61a+91b; 61a+92b; 61a+93b; 61a+94b; 61a+95b; 61a+96b; 61a+97b; 62a+1b; 62a+2b; 62a+3b; 62a+4b; 62a+5b; 62a+6b; 62a+7b; 62a+8b; 62a+9b; 62a+10b; 62a+11b; 62a+12b; 62a+13b; 62a+14b; 62a+15b; 62a+16b; 62a+17b; 62a+18b; 62a+19b; 62a+20b; 62a+21b; 62a+22b; 62a+23b; 62a+24b; 62a+25b; 62a+26b; 62a+27b; 62a+28b; 62a+29b; 62a+30b; 62a+31b; 62a+32b; 62a+33b; 62a+34b; 62a+35b; 62a+36b; 62a+37b; 62a+38b; 62a+39b; 62a+40b; 62a+41b; 62a+42b; 62a+43b; 62a+44b; 62a+45b; 62a+46b; 62a+47b; 62a+48b; 62a+49b; 62a+50b; 62a+51b; 62a+52b; 62a+53b; 62a+54b; 62a+55b; 62a+55b; 62a+57b; 62a+58b; 62a+59b; 62a+60b; 62a+61b; 62a+62b; 62a+63b; 62a+64b; 62a+65b; 62a+66b; 62a+67b; 62a+68b; 62a+69b; 62a+70b; 62a+71b; 62a+72b; 62a+73b; 62a+74b; 62a+75b; 62a+76b; 62a+77b; 62a+78b; 62a+79b; 62a+80b; 62a+81b; 62a+82b; 62a+83b; 62a+84b; 62a+85b; 62a+86b; 62a+87b; 62a+88b; 62a+89b; 62a+90b; 62a+91b; 62a+92b; 62a+93b; 62a+94b; 62a+95b; 62a+96b; 62a+97b; 63a+1b; 63a+2b; 63a+3b; 63a+4b; 63a+5b; 63a+6b; 63a+7b; 63a+8b; 63a+9b; 63a+10b; 63a+11b; 63a+12b; 63a+13b; 63a+14b; 63a+15b; 63a+16b; 63a+17b; 63a+18b; 63a+19b; 63a+20b; 63a+21b; 63a+22b; 63a+23b; 63a+24b; 63a+25b; 63a+26b; 63a+27b; 63a+28b; 63a+29b; 63a+30b; 63a+31b; 63a+32b; 63a+33b; 63a+34b; 63a+35b; 63a+36b; 63a+37b; 63a+38b; 63a+39b; 63a+40b; 63a+41b; 63a+42b; 63a+43b; 63a+44b; 63a+45b; 63a+46b; 63a+47b; 63a+48b; 63a+49b; 63a+50b; 63a+51b; 63a+52b; 63a+53b; 63a+54b; 63a+55b; 63a+55b; 63a+57b; 63a+58b; 63a+59b; 63a+60b; 63a+61b; 63a+62b; 63a+63b; 63a+64b; 63a+65b; 63a+66b; 63a+67b; 63a+68b; 63a+69b; 63a+70b; 63a+71b; 63a+72b; 63a+73b; 63a+74b; 63a+75b; 63a+76b; 63a+77b; 63a+78b; 63a+79b; 63a+80b; 63a+81b; 63a+82b; 63a+83b; 63a+84b; 63a+85b; 63a+86b; 63a+87b; 63a+88b; 63a+89b; 63a+90b; 63a+91b; 63a+92b; 63a+93b; 63a+94b; 63a+95b; 63a+96b; 63a+97b; 64a+1b; 64a+2b; 64a+3b; 64a+4b; 64a+5b; 64a+6b; 64a+7b; 64a+8b; 64a+9b; 64a+10b; 64a+11b; 64a+12b; 64a+13b; 64a+14b; 64a+15b; 64a+16b; 64a+17b; 64a+18b; 64a+19b; 64a+20b; 64a+21b; 64a+22b; 64a+23b; 64a+24b; 64a+25b; 64a+26b; 64a+27b; 64a+28b; 64a+29b; 64a+30b; 64a+31b; 64a+32b; 64a+33b; 64a+34b; 64a+35b; 64a+36b; 64a+37b; 64a+38b; 64a+39b; 64a+40b; 64a+41b; 64a+42b; 64a+43b; 64a+44b; 64a+45b; 64a+46b; 64a+47b; 64a+48b; 64a+49b; 64a+50b; 64a+51b; 64a+52b; 64a+53b; 64a+54b; 64a+55b; 64a+55b; 64a+57b; 64a+58b; 64a+59b; 64a+60b; 64a+61b; 64a+62b; 64a+63b; 64a+64b; 64a+65b; 64a+66b; 64a+67b; 64a+68b; 64a+69b; 64a+70b; 64a+71b; 64a+72b; 64a+73b; 64a+74b; 64a+75b; 64a+76b; 64a+77b; 64a+78b; 64a+79b; 64a+80b; 64a+81b; 64a+82b; 64a+83b; 64a+84b; 64a+85b; 64a+86b; 64a+87b; 64a+88b; 64a+89b; 64a+90b; 64a+91b; 64a+92b; 64a+93b; 64a+94b; 64a+95b; 64a+96b; 64a+97b; 65a+1b; 65a+2b; 65a+3b; 65a+4b; 65a+5b; 65a+6b; 65a+7b; 65a+8b; 65a+9b; 65a+10b; 65a+11b; 65a+12b; 65a+13b; 65a+14b; 65a+15b; 65a+16b; 65a+17b; 65a+18b; 65a+19b; 65a+20b; 65a+21b; 65a+22b; 65a+23b; 65a+24b; 65a+25b; 65a+26b; 65a+27b; 65a+28b; 65a+29b; 65a+30b; 65a+31b; 65a+32b; 65a+33b; 65a+34b; 65a+35b; 65a+36b; 65a+37b; 65a+38b; 65a+39b; 65a+40b; 65a+41b; 65a+42b; 65a+43b; 65a+44b; 65a+45b; 65a+46b; 65a+47b; 65a+48b; 65a+49b; 65a+50b; 65a+51b; 65a+52b; 65a+53b; 65a+54b; 65a+55b; 65a+55b; 65a+57b; 65a+58b; 65a+59b; 65a+60b; 65a+61b; 65a+62b; 65a+63b; 65a+64b; 65a+65b; 65a+66b; 65a+67b; 65a+68b; 65a+69b; 65a+70b; 65a+71b; 65a+72b; 65a+73b; 65a+74b; 65a+75b; 65a+76b; 65a+77b; 65a+78b; 65a+79b; 65a+80b; 65a+81b; 65a+82b; 65a+83b; 65a+84b; 65a+85b; 65a+86b; 65a+87b; 65a+88b; 65a+89b; 65a+90b; 65a+91b; 65a+92b; 65a+93b; 65a+94b; 65a+95b; 65a+96b; 65a+97b; 66a+1b; 66a+2b; 66a+3b; 66a+4b; 66a+5b; 66a+6b; 66a+7b; 66a+8b; 66a+9b; 66a+10b; 66a+11b; 66a+12b; 66a+13b; 66a+14b; 66a+15b; 66a+16b; 66a+17b; 66a+18b; 66a+19b; 66a+20b; 66a+21b; 66a+22b; 66a+23b; 66a+24b; 66a+25b; 66a+26b; 66a+27b; 66a+28b; 66a+29b; 66a+30b; 66a+31b; 66a+32b; 66a+33b; 66a+34b; 66a+35b; 66a+36b; 66a+37b; 66a+38b; 66a+39b; 66a+40b; 66a+41b; 66a+42b; 66a+43b; 66a+44b; 66a+45b; 66a+46b; 66a+47b; 66a+48b; 66a+49b; 66a+50b; 66a+51b; 66a+52b; 66a+53b; 66a+54b; 66a+55b; 66a+55b; 66a+57b; 66a+58b; 66a+59b; 66a+60b; 66a+61b; 66a+62b; 66a+63b; 66a+64b; 66a+65b; 66a+66b; 66a+67b; 66a+68b; 66a+69b; 66a+70b; 66a+71b; 66a+72b; 66a+73b; 66a+74b; 66a+75b; 66a+76b; 66a+77b; 66a+78b; 66a+79b; 66a+80b; 66a+81b; 66a+82b; 66a+83b; 66a+84b; 66a+85b; 66a+86b; 66a+87b; 66a+88b; 66a+89b; 66a+90b; 66a+91b; 66a+92b; 66a+93b; 66a+94b; 66a+95b; 66a+96b; 66a+97b; 67a+1b; 67a+2b; 67a+3b; 67a+4b; 67a+5b; 67a+6b; 67a+7b; 67a+8b; 67a+9b; 67a+10b; 67a+11b; 67a+12b; 67a+13b; 67a+14b; 67a+15b; 67a+16b; 67a+17b; 67a+18b; 67a+19b; 67a+20b; 67a+21b; 67a+22b; 67a+23b; 67a+24b; 67a+25b; 67a+26b; 67a+27b; 67a+28b; 67a+29b; 67a+30b; 67a+31b; 67a+32b; 67a+33b; 67a+34b; 67a+35b; 67a+36b; 67a+37b; 67a+38b; 67a+39b; 67a+40b; 67a+41b; 67a+42b; 67a+43b; 67a+44b; 67a+45b; 67a+46b; 67a+47b; 67a+48b; 67a+49b; 67a+50b; 67a+51b; 67a+52b; 67a+53b; 67a+54b; 67a+55b; 67a+55b; 67a+57b; 67a+58b; 67a+59b; 67a+60b; 67a+61b; 67a+62b; 67a+63b; 67a+64b; 67a+65b; 67a+66b; 67a+67b; 67a+68b; 67a+69b; 67a+70b; 67a+71b; 67a+72b; 67a+73b; 67a+74b; 67a+75b; 67a+76b; 67a+77b; 67a+78b; 67a+79b; 67a+80b; 67a+81b; 67a+82b; 67a+83b; 67a+84b; 67a+85b; 67a+86b; 67a+87b; 67a+88b; 67a+89b; 67a+90b; 67a+91b; 67a+92b; 67a+93b; 67a+94b; 67a+95b; 67a+96b; 67a+97b; 68a+1b; 68a+2b; 68a+3b; 68a+4b; 68a+5b; 68a+6b; 68a+7b; 68a+8b; 68a+9b; 68a+10b; 68a+11b; 68a+12b; 68a+13b; 68a+14b; 68a+15b; 68a+16b; 68a+17b; 68a+18b; 68a+19b; 68a+20b; 68a+21b; 68a+22b; 68a+23b; 68a+24b; 68a+25b; 68a+26b; 68a+27b; 68a+28b; 68a+29b; 68a+30b; 68a+31b; 68a+32b; 68a+33b; 68a+34b; 68a+35b; 68a+36b; 68a+37b; 68a+38b; 68a+39b; 68a+40b; 68a+41b; 68a+42b; 68a+43b; 68a+44b; 68a+45b; 68a+46b; 68a+47b; 68a+48b; 68a+49b; 68a+50b; 68a+51b; 68a+52b; 68a+53b; 68a+54b; 68a+55b; 68a+55b; 68a+57b; 68a+58b; 68a+59b; 68a+60b; 68a+61b; 68a+62b; 68a+63b; 68a+64b; 68a+65b; 68a+66b; 68a+67b; 68a+68b; 68a+69b; 68a+70b; 68a+71b; 68a+72b; 68a+73b; 68a+74b; 68a+75b; 68a+76b; 68a+77b; 68a+78b; 68a+79b; 68a+80b; 68a+81b; 68a+82b; 68a+83b; 68a+84b; 68a+85b; 68a+86b; 68a+87b; 68a+88b; 68a+89b; 68a+90b; 68a+91b; 68a+92b; 68a+93b; 68a+94b; 68a+95b; 68a+96b; 68a+97b; 69a+1b; 69a+2b; 69a+3b; 69a+4b; 69a+5b; 69a+6b; 69a+7b; 69a+8b; 69a+9b; 69a+10b; 69a+11b; 69a+12b; 69a+13b; 69a+14b; 69a+15b; 69a+16b; 69a+17b; 69a+18b; 69a+19b; 69a+20b; 69a+21b; 69a+22b; 69a+23b; 69a+24b; 69a+25b; 69a+26b; 69a+27b; 69a+28b; 69a+29b; 69a+30b; 69a+31b; 69a+32b; 69a+33b; 69a+34b; 69a+35b; 69a+36b; 69a+37b; 69a+38b; 69a+39b; 69a+40b; 69a+41b; 69a+42b; 69a+43b; 69a+44b; 69a+45b; 69a+46b; 69a+47b; 69a+48b; 69a+49b; 69a+50b; 69a+51b; 69a+52b; 69a+53b;

69a+54b; 69a+55b; 69a+55b; 69a+57b; 69a+58b; 69a+59b; 69a+60b; 69a+61b; 69a+62b; 69a+63b; 69a+64b; 69a+65b; 69a+66b; 69a+67b; 69a+68b; 69a+69b; 69a+70b; 69a+71b; 69a+72b; 69a+73b; 69a+74b; 69a+75b; 69a+76b; 69a+77b; 69a+78b; 69a+79b; 69a+80b; 69a+81b; 69a+82b; 69a+83b; 69a+84b; 69a+85b; 69a+86b; 69a+87b; 69a+88b; 69a+89b; 69a+90b; 69a+91b; 69a+92b; 69a+93b; 69a+94b; 69a+95b; 69a+96b; 69a+97b; 70a+b; 70a+2b; 70a+3b; 70a+4b; 70a+5b; 70a+6b; 70a+7b; 70a+8b; 70a+9b; 70a+10b; 70a+11b; 70a+12b; 70a+13b; 70a+14b; 70a+15b; 70a+16b; 70a+17b; 70a+18b; 70a+19b; 70a+20b; 70a+21b; 70a+22b; 70a+23b; 70a+24b; 70a+25b; 70a+26b; 70a+27b; 70a+28b; 70a+29b; 70a+30b; 70a+31b; 70a+32b; 70a+33b; 70a+34b; 70a+35b; 70a+36b; 70a+37b; 70a+38b; 70a+39b; 70a+40b; 70a+41b; 70a+42b; 70a+43b; 70a+44b; 70a+45b; 70a+46b; 70a+47b; 70a+48b; 70a+49b; 70a+50b; 70a+51b; 70a+52b; 70a+53b; 70a+54b; 70a+55b; 70a+55b; 70a+57b; 70a+58b; 70a+59b; 70a+60b; 70a+61b; 70a+62b; 70a+63b; 70a+64b; 70a+65b; 70a+66b; 70a+67b; 70a+68b; 70a+69b; 70a+70b; 70a+71b; 70a+72b; 70a+73b; 70a+74b; 70a+75b; 70a+76b; 70a+77b; 70a+78b; 70a+79b; 70a+80b; 70a+81b; 70a+82b; 70a+83b; 70a+84b; 70a+85b; 70a+86b; 70a+87b; 70a+88b; 70a+89b; 70a+90b; 70a+91b; 70a+92b; 70a+93b; 70a+94b; 70a+95b; 70a+96b; 70a+97b; 71a+1b; 71a+2b; 71a+3b; 71a+4b; 71a+5b; 71a+6b; 71a+7b; 71a+8b; 71a+9b; 71a+10b; 71a+11b; 71a+12b; 71a+13b; 71a+14b; 71a+15b; 71a+16b; 71a+17b; 71a+18b; 71a+19b; 71a+20b; 71a+21b; 71a+22b; 71a+23b; 71a+24b; 71a+25b; 71a+26b; 71a+27b; 71a+28b; 71a+29b; 71a+30b; 71a+31b; 71a+32b; 71a+33b; 71a+34b; 71a+35b; 71a+36b; 71a+37b; 71a+38b; 71a+39b; 71a+40b; 71a+41b; 71a+42b; 71a+43b; 71a+44b; 71a+45b; 71a+46b; 71a+47b; 71a+48b; 71a+49b; 71a+50b; 71a+51b; 71a+52b; 71a+53b; 71a+54b; 71a+55b; 71a+55b; 71a+57b; 71a+58b; 71a+59b; 71a+60b; 71a+61b; 71a+62b; 71a+63b; 71a+64b; 71a+65b; 71a+66b; 71a+67b; 71a+68b; 71a+69b; 71a+70b; 71a+71b; 71a+72b; 71a+73b; 71a+74b; 71a+75b; 71a+76b; 71a+77b; 71a+78b; 71a+79b; 71a+80b; 71a+81b; 71a+82b; 71a+83b; 71a+84b; 71a+85b; 71a+86b; 71a+87b; 71a+88b; 71a+89b; 71a+90b; 71a+91b; 71a+92b; 71a+93b; 71a+94b; 71a+95b; 71a+96b; 71a+97b; 72a+1b; 72a+2b; 72a+3b; 72a+4b; 72a+5b; 72a+6b; 72a+7b; 72a+8b; 72a+9b; 72a+10b; 72a+11b; 72a+12b; 72a+13b; 72a+14b; 72a+15b; 72a+16b; 72a+17b; 72a+18b; 72a+19b; 72a+20b; 72a+21b; 72a+22b; 72a+23b; 72a+24b; 72a+25b; 72a+26b; 72a+27b; 72a+28b; 72a+29b; 72a+30b; 72a+31b; 72a+32b; 72a+33b; 72a+34b; 72a+35b; 72a+36b; 72a+37b; 72a+38b; 72a+39b; 72a+40b; 72a+41b; 72a+42b; 72a+43b; 72a+44b; 72a+45b; 72a+46b; 72a+47b; 72a+48b; 72a+49b; 72a+50b; 72a+51b; 72a+52b; 72a+53b; 72a+54b; 72a+55b; 72a+55b; 72a+57b; 72a+58b; 72a+59b; 72a+60b; 72a+61b; 72a+62b; 72a+63b; 72a+64b; 72a+65b; 72a+66b; 72a+67b; 72a+68b; 72a+69b; 72a+70b; 72a+71b; 72a+72b; 72a+73b; 72a+74b; 72a+75b; 72a+76b; 72a+77b; 72a+78b; 72a+79b; 72a+80b; 72a+81b; 72a+82b; 72a+83b; 72a+84b; 72a+85b; 72a+86b; 72a+87b; 72a+88b; 72a+89b; 72a+90b; 72a+91b; 72a+92b; 72a+93b; 72a+94b; 72a+95b; 72a+96b; 72a+97b; 73a+1b; 73a+2b; 73a+3b; 73a+4b; 73a+5b; 73a+6b; 73a+7b; 73a+8b; 73a+9b; 73a+10b; 73a+11b; 73a+12b; 73a+13b; 73a+14b; 73a+15b; 73a+16b; 73a+17b; 73a+18b; 73a+19b; 73a+20b; 73a+21b; 73a+22b; 73a+23b; 73a+24b; 73a+25b; 73a+26b; 73a+27b; 73a+28b; 73a+29b; 73a+30b; 73a+31b; 73a+32b; 73a+33b; 73a+34b; 73a+35b; 73a+36b; 73a+37b; 73a+38b; 73a+39b; 73a+40b; 73a+41b; 73a+42b; 73a+43b; 73a+44b; 73a+45b; 73a+46b; 73a+47b; 73a+48b; 73a+49b; 73a+50b; 73a+51b; 73a+52b; 73a+53b; 73a+54b; 73a+55b; 73a+55b; 73a+57b; 73a+58b; 73a+59b; 73a+60b; 73a+61b; 73a+62b; 73a+63b; 73a+64b; 73a+65b; 73a+66b; 73a+67b; 73a+68b; 73a+69b; 73a+70b; 73a+71b; 73a+72b; 73a+73b; 73a+74b; 73a+75b; 73a+76b; 73a+77b; 73a+78b; 73a+79b; 73a+80b; 73a+81b; 73a+82b; 73a+83b; 73a+84b; 73a+85b; 73a+86b; 73a+87b; 73a+88b; 73a+89b; 73a+90b; 73a+91b; 73a+92b; 73a+93b; 73a+94b; 73a+95b; 73a+96b; 73a+97b; 74a+1b; 74a+2b; 74a+3b; 74a+4b; 74a+5b; 74a+6b; 74a+7b; 74a+8b; 74a+9b; 74a+10b; 74a+11b; 74a+12b; 74a+13b; 74a+14b; 74a+15b; 74a+16b; 74a+17b; 74a+18b; 74a+19b; 74a+20b; 74a+21b; 74a+22b; 74a+23b; 74a+24b; 74a+25b; 74a+26b; 74a+27b; 74a+28b; 74a+29b; 74a+30b; 74a+31b; 74a+32b; 74a+33b; 74a+34b; 74a+35b; 74a+36b; 74a+37b; 74a+38b; 74a+39b; 74a+40b; 74a+41b; 74a+42b; 74a+43b; 74a+44b; 74a+45b; 74a+46b; 74a+47b; 74a+48b; 74a+49b; 74a+50b; 74a+51b; 74a+52b; 74a+53b; 74a+54b; 74a+55b; 74a+55b; 74a+57b; 74a+58b; 74a+59b; 74a+60b; 74a+61b; 74a+62b; 74a+63b; 74a+64b; 74a+65b; 74a+66b; 74a+67b; 74a+68b; 74a+69b; 74a+70b; 74a+71b; 74a+72b; 74a+73b; 74a+74b; 74a+75b; 74a+76b; 74a+77b; 74a+78b; 74a+79b; 74a+80b; 74a+81b; 74a+82b; 74a+83b; 74a+84b; 74a+85b; 74a+86b; 74a+87b; 74a+88b; 74a+89b; 74a+90b; 74a+91b; 74a+92b; 74a+93b; 74a+94b; 74a+95b; 74a+96b; 74a+97b; 75a+1b; 75a+2b; 75a+3b; 75a+4b; 75a+5b; 75a+6b; 75a+7b; 75a+8b; 75a+9b; 75a+10b; 75a+11b; 75a+12b; 75a+13b; 75a+14b; 75a+15b; 75a+16b; 75a+17b; 75a+18b; 75a+19b; 75a+20b; 75a+21b; 75a+22b; 75a+23b; 75a+24b; 75a+25b; 75a+26b; 75a+27b; 75a+28b; 75a+29b; 75a+30b; 75a+31b; 75a+32b; 75a+33b; 75a+34b; 75a+35b; 75a+36b; 75a+37b; 75a+38b; 75a+39b; 75a+40b; 75a+41b; 75a+42b; 75a+43b; 75a+44b; 75a+45b; 75a+46b; 75a+47b; 75a+48b; 75a+49b; 75a+50b; 75a+51b; 75a+52b; 75a+53b; 75a+54b; 75a+55b; 75a+55b; 75a+57b; 75a+58b; 75a+59b; 75a+60b; 75a+61b; 75a+62b; 75a+63b; 75a+64b; 75a+65b; 75a+66b; 75a+67b; 75a+68b; 75a+69b; 75a+70b; 75a+71b; 75a+72b; 75a+73b; 75a+74b; 75a+75b; 75a+76b; 75a+77b; 75a+78b; 75a+79b; 75a+80b; 75a+81b; 75a+82b; 75a+83b; 75a+84b; 75a+85b; 75a+86b; 75a+87b; 75a+88b; 75a+89b; 75a+90b; 75a+91b; 75a+92b; 75a+93b; 75a+94b; 75a+95b; 75a+96b; 75a+97b; 76a+1b; 76a+2b; 76a+3b; 76a+4b; 76a+5b; 76a+6b; 76a+7b; 76a+8b; 76a+9b; 76a+10b; 76a+11b; 76a+12b; 76a+13b; 76a+14b; 76a+15b; 76a+16b; 76a+17b; 76a+18b; 76a+19b; 76a+20b; 76a+21b; 76a+22b; 76a+23b; 76a+24b; 76a+25b; 76a+26b; 76a+27b; 76a+28b; 76a+29b; 76a+30b; 76a+31b; 76a+32b; 76a+33b; 76a+34b; 76a+35b; 76a+36b; 76a+37b; 76a+38b; 76a+39b; 76a+40b; 76a+41b; 76a+42b; 76a+43b; 76a+44b; 76a+45b; 76a+46b; 76a+47b; 76a+48b; 76a+49b; 76a+50b; 76a+51b; 76a+52b; 76a+53b; 76a+54b; 76a+55b; 76a+55b; 76a+57b; 76a+58b; 76a+59b; 76a+60b; 76a+61b; 76a+62b; 76a+63b; 76a+64b; 76a+65b; 76a+66b; 76a+67b; 76a+68b; 76a+69b; 76a+70b; 76a+71b; 76a+72b; 76a+73b; 76a+74b; 76a+75b; 76a+76b; 76a+77b; 76a+78b; 76a+79b; 76a+80b; 76a+81b; 76a+82b; 76a+83b; 76a+84b; 76a+85b; 76a+86b; 76a+87b; 76a+88b; 76a+89b; 76a+90b; 76a+91b; 76a+92b; 76a+93b; 76a+94b; 76a+95b; 76a+96b; 76a+97b; 77a+1b; 77a+2b; 77a+3b; 77a+4b; 77a+5b; 77a+6b; 77a+7b; 77a+8b; 77a+9b; 77a+10b; 77a+11b; 77a+12b; 77a+13b; 77a+14b; 77a+15b; 77a+16b; 77a+17b; 77a+18b; 77a+19b; 77a+20b; 77a+21b; 77a+22b; 77a+23b; 77a+24b; 77a+

25b; 77a+26b; 77a+27b; 77a+28b; 77a+29b; 77a+30b; 77a+31b; 77a+32b; 77a+33b; 77a+34b; 77a+35b; 77a+36b; 77a+37b; 77a+38b; 77a+39b; 77a+40b; 77a+41b; 77a+42b; 77a+43b; 77a+44b; 77a+45b; 77a+46b; 77a+47b; 77a+48b; 77a+49b; 77a+50b; 77a+51b; 77a+52b; 77a+53b; 77a+54b; 77a+55b; 77a+55b; 77a+57b; 77a+58b; 77a+59b; 77a+60b; 77a+61b; 77a+62b; 77a+63b; 77a+64b; 77a+65b; 77a+66b; 77a+67b; 77a+68b; 77a+69b; 77a+70b; 77a+71b; 77a+72b; 77a+73b; 77a+74b; 77a+75b; 77a+76b; 77a+77b; 77a+78b; 77a+79b; 77a+80b; 77a+81b; 77a+82b; 77a+83b; 77a+84b; 77a+85b; 77a+86b; 77a+87b; 77a+88b; 77a+89b; 77a+90b; 77a+91b; 77a+92b; 77a+93b; 77a+94b; 77a+95b; 77a+96b; 77a+97b; 78a+1b; 78a+2b; 78a+3b; 78a+4b; 78a+5b; 78a+6b; 78a+7b; 78a+8b; 78a+9b; 78a+10b; 78a+11b; 78a+12b; 78a+13b; 78a+14b; 78a+15b; 78a+16b; 78a+17b; 78a+18b; 78a+19b; 78a+20b; 78a+21b; 78a+22b; 78a+23b; 78a+24b; 78a+25b; 78a+26b; 78a+27b; 78a+28b; 78a+29b; 78a+30b; 78a+31b; 78a+32b; 78a+33b; 78a+34b; 78a+35b; 78a+36b; 78a+37b; 78a+38b; 78a+39b; 78a+40b; 78a+41b; 78a+42b; 78a+43b; 78a+44b; 78a+45b; 78a+46b; 78a+47b; 78a+48b; 78a+49b; 78a+50b; 78a+51b; 78a+52b; 78a+53b; 78a+54b; 78a+55b; 78a+55b; 78a+57b; 78a+58b; 78a+59b; 78a+60b; 78a+61b; 78a+62b; 78a+63b; 78a+64b; 78a+65b; 78a+66b; 78a+67b; 78a+68b; 78a+69b; 78a+70b; 78a+71b; 78a+72b; 78a+73b; 78a+74b; 78a+75b; 78a+76b; 78a+77b; 78a+78b; 78a+79b; 78a+80b; 78a+81b; 78a+82b; 78a+83b; 78a+84b; 78a+85b; 78a+86b; 78a+87b; 78a+88b; 78a+89b; 78a+90b; 78a+91b; 78a+92b; 78a+93b; 78a+94b; 78a+95b; 78a+96b; 78a+97b; 79a+1b; 79a+2b; 79a+3b; 79a+4b; 79a+5b; 79a+6b; 79a+7b; 79a+8b; 79a+9b; 79a+10b; 79a+11b; 79a+12b; 79a+13b; 79a+14b; 79a+15b; 79a+16b; 79a+17b; 79a+18b; 79a+19b; 79a+20b; 79a+21b; 79a+22b; 79a+23b; 79a+24b; 79a+25b; 79a+26b; 79a+27b; 79a+28b; 79a+29b; 79a+30b; 79a+31b; 79a+32b; 79a+33b; 79a+34b; 79a+35b; 79a+36b; 79a+37b; 79a+38b; 79a+39b; 79a+40b; 79a+41b; 79a+42b; 79a+43b; 79a+44b; 79a+45b; 79a+46b; 79a+47b; 79a+48b; 79a+49b; 79a+50b; 79a+51b; 79a+52b; 79a+53b; 79a+54b; 79a+55b; 79a+55b; 79a+57b; 79a+58b; 79a+59b; 79a+60b; 79a+61b; 79a+62b; 79a+63b; 79a+64b; 79a+65b; 79a+66b; 79a+67b; 79a+68b; 79a+69b; 79a+70b; 79a+71b; 79a+72b; 79a+73b; 79a+74b; 79a+75b; 79a+76b; 79a+77b; 79a+78b; 79a+79b; 79a+80b; 79a+81b; 79a+82b; 79a+83b; 79a+84b; 79a+85b; 79a+86b; 79a+87b; 79a+88b; 79a+89b; 79a+90b; 79a+91b; 79a+92b; 79a+93b; 79a+94b; 79a+95b; 79a+96b; 79a+97b; 80a+1b; 80a+2b; 80a+3b; 80a+4b; 80a+5b; 80a+6b; 80a+7b; 80a+8b; 80a+9b; 80a+10b; 80a+11b; 80a+12b; 80a+13b; 80a+14b; 80a+15b; 80a+16b; 80a+17b; 80a+18b; 80a+19b; 80a+20b; 80a+21b; 80a+22b; 80a+23b; 80a+24b; 80a+25b; 80a+26b; 80a+27b; 80a+28b; 80a+29b; 80a+30b; 80a+31b; 80a+32b; 80a+33b; 80a+34b; 80a+35b; 80a+36b; 80a+37b; 80a+38b; 80a+39b; 80a+40b; 80a+41b; 80a+42b; 80a+43b; 80a+44b; 80a+45b; 80a+46b; 80a+47b; 80a+48b; 80a+49b; 80a+50b; 80a+51b; 80a+52b; 80a+53b; 80a+54b; 80a+55b; 80a+55b; 80a+57b; 80a+58b; 80a+59b; 80a+60b; 80a+61b; 80a+62b; 80a+63b; 80a+64b; 80a+65b; 80a+66b; 80a+67b; 80a+68b; 80a+69b; 80a+70b; 80a+71b; 80a+72b; 80a+73b; 80a+74b; 80a+75b; 80a+76b; 80a+77b; 80a+78b; 80a+79b; 80a+80b; 80a+81b; 80a+82b; 80a+83b; 80a+84b; 80a+85b; 80a+86b; 80a+87b; 80a+88b; 80a+89b; 80a+90b; 80a+91b; 80a+92b; 80a+93b; 80a+94b; 80a+95b; 80a+96b; 80a+97b; 81a+1b; 81a+2b; 81a+3b; 81a+4b; 81a+5b; 81a+6b; 81a+7b; 81a+8b; 81a+9b; 81a+10b; 81a+11b; 81a+12b; 81a+13b; 81a+14b; 81a+15b; 81a+16b; 81a+17b; 81a+18b; 81a+19b; 81a+20b; 81a+21b; 81a+22b; 81a+23b; 81a+24b; 81a+25b; 81a+26b; 81a+27b; 81a+28b; 81a+29b; 81a+30b; 81a+31b; 81a+32b; 81a+33b; 81a+34b; 81a+35b; 81a+36b; 81a+37b; 81a+38b; 81a+39b; 81a+40b; 81a+41b; 81a+42b; 81a+43b; 81a+44b; 81a+45b; 81a+46b; 81a+47b; 81a+48b; 81a+49b; 81a+50b; 81a+51b; 81a+52b; 81a+53b; 81a+54b; 81a+55b; 81a+55b; 81a+57b; 81a+58b; 81a+59b; 81a+60b; 81a+61b; 81a+62b; 81a+63b; 81a+64b; 81a+65b; 81a+66b; 81a+67b; 81a+68b; 81a+69b; 81a+70b; 81a+71b; 81a+72b; 81a+73b; 81a+74b; 81a+75b; 81a+76b; 81a+77b; 81a+78b; 81a+79b; 81a+80b; 81a+81b; 81a+82b; 81a+83b; 81a+84b; 81a+85b; 81a+86b; 81a+87b; 81a+88b; 81a+89b; 81a+90b; 81a+91b; 81a+92b; 81a+93b; 81a+94b; 81a+95b; 81a+96b; 81a+97b; 82a+1b; 82a+2b; 82a+3b; 82a+4b; 82a+5b; 82a+6b; 82a+7b; 82a+8b; 82a+9b; 82a+10b; 82a+11b; 82a+12b; 82a+13b; 82a+14b; 82a+15b; 82a+16b; 82a+17b; 82a+18b; 82a+19b; 82a+20b; 82a+21b; 82a+22b; 82a+23b; 82a+24b; 82a+25b; 82a+26b; 82a+27b; 82a+28b; 82a+29b; 82a+30b; 82a+31b; 82a+32b; 82a+33b; 82a+34b; 82a+35b; 82a+36b; 82a+37b; 82a+38b; 82a+39b; 82a+40b; 82a+41b; 82a+42b; 82a+43b; 82a+44b; 82a+45b; 82a+46b; 82a+47b; 82a+48b; 82a+49b; 82a+50b; 82a+51b; 82a+52b; 82a+53b; 82a+54b; 82a+55b; 82a+55b; 82a+57b; 82a+58b; 82a+59b; 82a+60b; 82a+61b; 82a+62b; 82a+63b; 82a+64b; 82a+65b; 82a+66b; 82a+67b; 82a+68b; 82a+69b; 82a+70b; 82a+71b; 82a+72b; 82a+73b; 82a+74b; 82a+75b; 82a+76b; 82a+77b; 82a+78b; 82a+79b; 82a+80b; 82a+81b; 82a+82b; 82a+83b; 82a+84b; 82a+85b; 82a+86b; 82a+87b; 82a+88b; 82a+89b; 82a+90b; 82a+91b; 82a+92b; 82a+93b; 82a+94b; 82a+95b; 82a+96b; 82a+97b; 83a+1b; 83a+2b; 83a+3b; 83a+4b; 83a+5b; 83a+6b; 83a+7b; 83a+8b; 83a+9b; 83a+10b; 83a+11b; 83a+12b; 83a+13b; 83a+14b; 83a+15b; 83a+16b; 83a+17b; 83a+18b; 83a+19b; 83a+20b; 83a+21b; 83a+22b; 83a+23b; 83a+24b; 83a+25b; 83a+26b; 83a+27b; 83a+28b; 83a+29b; 83a+30b; 83a+31b; 83a+32b; 83a+33b; 83a+34b; 83a+35b; 83a+36b; 83a+37b; 83a+38b; 83a+39b; 83a+40b; 83a+41b; 83a+42b; 83a+43b; 83a+44b; 83a+45b; 83a+46b; 83a+47b; 83a+48b; 83a+49b; 83a+50b; 83a+51b; 83a+52b; 83a+53b; 83a+54b; 83a+55b; 83a+55b; 83a+57b; 83a+58b; 83a+59b; 83a+60b; 83a+61b; 83a+62b; 83a+63b; 83a+64b; 83a+65b; 83a+66b; 83a+67b; 83a+68b; 83a+69b; 83a+70b; 83a+71b; 83a+72b; 83a+73b; 83a+74b; 83a+75b; 83a+76b; 83a+77b; 83a+78b; 83a+79b; 83a+80b; 83a+81b; 83a+82b; 83a+83b; 83a+84b; 83a+85b; 83a+86b; 83a+87b; 83a+88b; 83a+89b; 83a+90b; 83a+91b; 83a+92b; 83a+93b; 83a+94b; 83a+95b; 83a+96b; 83a+97b; 84a+1b; 84a+2b; 84a+3b; 84a+4b; 84a+5b; 84a+6b; 84a+7b; 84a+8b; 84a+9b; 84a+10b; 84a+11b; 84a+12b; 84a+13b; 84a+14b; 84a+15b; 84a+16b; 84a+17b; 84a+18b; 84a+19b; 84a+20b; 84a+21b; 84a+22b; 84a+23b; 84a+24b; 84a+25b; 84a+26b; 84a+27b; 84a+28b; 84a+29b; 84a+30b; 84a+31b; 84a+32b; 84a+33b; 84a+34b; 84a+35b; 84a+36b; 84a+37b; 84a+38b; 84a+39b; 84a+40b; 84a+41b; 84a+42b; 84a+43b; 84a+44b; 84a+45b; 84a+46b; 84a+47b; 84a+48b; 84a+49b; 84a+50b; 84a+51b; 84a+52b; 84a+53b; 84a+54b; 84a+55b; 84a+55b; 84a+57b; 84a+58b; 84a+59b; 84a+60b; 84a+61b; 84a+62b; 84a+63b; 84a+64b; 84a+65b; 84a+66b; 84a+67b; 84a+68b; 84a+69b; 84a+70b; 84a+71b; 84a+72b; 84a+73b; 84a+74b; 84a+75b; 84a+76b; 84a+77b; 84a+78b; 84a+79b; 84a+80b; 84a+81b; 84a+82b; 84a+83b; 84a+84b; 84a+85b; 84a+86b; 84a+87b; 84a+88b; 84a+89b; 84a+90b; 84a+91b; 84a+

92b; 84a+93b; 84a+94b; 84a+95b; 84a+96b; 84a+97b; 85a+1b; 85a+2b; 85a+3b; 85a+4b; 85a+5b; 85a+6b; 85a+7b; 85a+8b; 85a+9b; 85a+10b; 85a+11b; 85a+12b; 85a+13b; 85a+14b; 85a+15b; 85a+16b; 85a+17b; 85a+18b; 85a+19b; 85a+20b; 85a+21b; 85a+22b; 85a+23b; 85a+24b; 85a+25b; 85a+26b; 85a+27b; 85a+28b; 85a+29b; 85a+30b; 85a+31b; 85a+32b; 85a+33b; 85a+34b; 85a+35b; 85a+36b; 85a+37b; 85a+38b; 85a+39b; 85a+40b; 85a+41b; 85a+42b; 85a+43b; 85a+44b; 85a+45b; 85a+46b; 85a+47b; 85a+48b; 85a+49b; 85a+50b; 85a+51b; 85a+52b; 85a+53b; 85a+54b; 85a+55b; 85a+55b; 85a+57b; 85a+58b; 85a+59b; 85a+60b; 85a+61b; 85a+62b; 85a+63b; 85a+64b; 85a+65b; 85a+66b; 85a+67b; 85a+68b; 85a+69b; 85a+70b; 85a+71b; 85a+72b; 85a+73b; 85a+74b; 85a+75b; 85a+76b; 85a+77b; 85a+78b; 85a+79b; 85a+80b; 85a+81b; 85a+82b; 85a+83b; 85a+84b; 85a+85b; 85a+86b; 85a+87b; 85a+88b; 85a+89b; 85a+90b; 85a+91b; 85a+92b; 85a+93b; 85a+94b; 85a+95b; 85a+96b; and 85a+97b.

As described above, the fibrosing agent can be coated onto an implant or a portion of an implant using the polymeric coatings described above. This can be accomplished, for example, by dipping, spraying, electrospinning, painting or by vacuum deposition. In addition to the coating compositions and methods described above, there are various other coating compositions and methods that are known in the art. Representative examples of these coating compositions and methods are described in U.S. Pat. Nos. 6,610,016; 6,358,557; 6,306,176; 6,110,483; 6,106,473; 5,997,517; 5,800,412; 5,525,348; 5,331,027; 5,001,009; 6,562,136; 6,406,754; 6,344,035; 6,254,921; 6,214,901; 6,077,698; 6,603,040; 6,278,018; 6,238,799; 6,096,726; 5,766,158; 5,599,576; 4,119,094; 4,100,309; 6,599,558; 6,369,168; 6,521,283; 6,497,916; 6,251,964; 6,225,431; 6,087,462; 6,083,257; 5,739,237; 5,739,236; 5,705,583; 5,648,442; 5,645,883; 5,556,710; 5,496,581; 4,689,386; 6,214,115; 6,090,901; 6,599,448; 6,054,504; 4,987,182; 4,847,324; and 4,642,267, U.S. Patent Application Publication Nos. 2003/0129130; 2001/0026834; 2003/0190420; 2001/0000785; 2003/0059631; 2003/0190405; 2002/0146581; 2003/020399; 2003/0129130, 2001/0026834; 2003/0190420; 2001/0000785; 2003/0059631; 2003/0190405; 2002/0146581; and 2003/020399, and PCT Publication Nos. WO 02/055121; WO 01/57048; WO 01/52915; and WO 01/01957.

Within another aspect of the invention, the biologically active fibrosing, hemostatic and/or anti-infective agent(s) can be delivered with a non-polymeric agent into the diverticula. Examples of non-polymeric agents include sucrose derivatives (e.g., sucrose acetate isobutyrate, sucrose oleate), sterols such as cholesterol, stigmasterol, beta-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols, calcium phosphate, sintered and unscintered hydoxyapatite, zeolites; and combinations and mixtures thereof.

Representative examples of patents relating to non-polymeric delivery systems and their preparation include U.S. Pat. Nos. 5,736,152; 5,888,533; 6,120,789; 5,968,542; and 5,747,058.

Other carriers that may likewise be utilized to contain and deliver fibrosis-inducing agents, hemostatic agents, and/or anti-infective agents described herein include: hydroxypropyl cyclodextrin (Cserhati and Hollo, *Int. J. Pharm.* 108: 69–75, 1994), liposomes (see, e.g., Sharma et al., *Cancer Res.* 53:5877–5881, 1993; Sharma and Straubinger, *Pharm. Res.* 11(60):889–896, 1994; WO 93/18751; U.S. Pat. No. 5,242,073), liposome/gel (WO 94/26254), nanocapsules (Bartoli et al., *J. Microencapsulation* 7(2):191–197, 1990), micelles (Alkan-Onyuksel et al., *Pharm. Res.* 11(2):206–212, 1994), nanoparticles (Violante and Lanzafame PAACR), nanoparticles—modified (U.S. Pat. No. 5,145,684), nanoparticles (surface modified) (U.S. Pat. No. 5,399,363), micelle (surfactant) (U.S. Pat. No. 5,403,858), synthetic phospholipid compounds (U.S. Pat. No. 4,534,899), gas borne dispersion (U.S. Pat. No. 5,301,664), liquid emulsions, foam, spray, gel, lotion, cream, ointment, dispersed vesicles, particles or droplets solid- or liquid-aerosols, microemulsions (U.S. Pat. No. 5,330,756), polymeric shell (nano- and micro-capsule) (U.S. Pat. No. 5,439,686), emulsions (Tarr et al., *Pharm Res.* 4: 62–165, 1987), nanospheres (Hagan et al., *Proc. Intern. Symp. Control Rel. Bioact Mater.* 22, 1995; Kwon et al., *Pharm Res.* 12(2): 192–195; Kwon et al., *Pharm Res.* 10(7):970–974; Yokoyama et al., *J. Contr. Rel.* 32:269–277, 1994; Gref et al., *Science* 263:1600–1603, 1994; Bazile et al., *J. Pharm. Sci.* 84:493–498, 1994) and implants (U.S. Pat. No. 4,882, 168, Jampel et al., *Invest. Ophthalm. Vis. Science* 34(11): 3076–3083, 1993; Walter et al., *Cancer Res.* 54:22017–2212, 1994).

Within another embodiment, the fibrosis-inducing agent, hemostatic agent, and/or anti-infective agent can further comprise a secondary carrier. The secondary carrier can be in the form of microspheres (e.g., PLGA, PLLA, PDLLA, PCL, gelatin, polydioxanone, poly(alkylcyanoacrylate)), nanospheres (e.g., PLGA, PLLA, PDLLA, PCL, gelatin, polydioxanone, poly(alkylcyanoacrylate)), liposomes, emulsions, microemulsions, micelles (e.g., SDS, block copolymers of the form X-Y, X-Y-X or Y-X-Y, where X is a poly(alkylene oxide) or an alkyl ether thereof and Y is a polyester (e.g., PLGA, PLLA, PDLLA, PCL, polydioxanone)), zeolites or cyclodextrins.

Within another embodiment, these therapeutic agent/secondary carrier compositions can be a) incorporated directly into or onto a biomaterial implant, b) incorporated into an injectable solution, or c) incorporated into a gel or viscous solution, d) incorporated into the composition used for coating the implant, or e) incorporated into or onto the implant following coating of the implant with a coating composition.

For example, therapeutic agent-loaded PLGA microspheres may be incorporated into a polyurethane coating solution, which is then incorporated into an implant. In yet another example, the implant can be coated with a polyurethane and then allowed to partially dry such that the surface is still tacky. A particulate form of the fibrosis-inducing agent or fibrosis-inducing agent/secondary carrier can then be applied to all or a portion of the tacky coating after which the implant is dried. In addition to coating the implant with one or more of the therapeutic agents described herein, the agent can be mixed with the materials that are used to make the implant such that the agent is incorporated into the implant.

In yet another example, an implant can be coated with any one of the coatings described above. A thermal treatment process can then be used to soften the coating, after which the fibrosis-inducing agent or the fibrosis-inducing agent/ secondary carrier is applied to the entire implant or to a portion of the implant (e.g., outer surface).

In one embodiment, fibrosis-inducing agents, hemostatic agents, and/or anti-infective agents can be incorporated directly into the formulation to produce a suspension or a solution (e.g., silk powder, bleomycin) or it can be incorporated into a secondary carrier (e.g., micelles, liposomes, micropsheres, microparticles, nanospheres, micropaticulates, emulsions and/or microemulations) that is then incorporated into a bulking composition (e.g., fibrin, collagen, PEG, cyanoacrylate, or a mixture thereof). In another embodiment, the therapeutic agent can be electrostatically or covalently bound to one or more of the polymeric components of the in-situ forming composition.

In another embodiment, the therapuetic agent can be incorporated into a bulking agent during the manufacture of the agent. For example, silk powder can be added as a reagent during the manufacture of microspheres that are used as bulking agents.

Within another aspect of the invention, a coated implant that promotes an in vivo fibrotic reaction is further coated with a compound or composition which delays the release of and/or activity of the fibrosis-inducing agent. Representative examples of such agents include biologically inert materials such as gelatin, PLGA/MePEG film, PLA, polyurethanes, silicone rubbers, surfactants, lipids, or polyethylene glycol, as well as biologically active materials such as heparin (e.g., to induce coagulation).

For example, in one embodiment of the invention, the active agent on the implant is top-coated with a physical barrier. Such barriers can include non-degradable materials or biodegradable materials such as gelatin, PLGA/MePEG film, PLA, polyethylene glycol, or the like. In one embodiment, the rate of diffusion of the therapeutic agent in the barrier coat is slower that the rate of diffusion of the therapeutic agent in the coating layer. In the case of PLGA/ MePEG, once the PLGA/MePEG becomes exposed to bodily fluids, the MePEG can dissolve out of the PLGA, leaving channels through the PLGA to an underlying layer containing the fibrosis-inducing agent (e.g., silk or cyclosporine A), which can then diffuse into the vessel wall and initiate its biological activity.

In another embodiment of the invention, for example, a particulate form of the active agent (e.g., silk or cyclosporine A) may be coated onto the implant using a polymer (e.g., PLG, PLA, or polyurethane). A second polymer, that dissolves slowly or degrades (e.g., MePEG-PLGA or PLG) and that does not contain the active agent, may be coated over the first layer. Once the top layer dissolves or degrades, it exposes the under coating, which allows the active agent to be exposed to the treatment site or to be released from the coating.

Within another aspect of the invention, the outer layer of the coated implant, which induces an in vivo fibrotic, hemostatic and/or anti-infective response, is further treated to crosslink the outer layer of the coating. This can be accomplished by subjecting the coated implant to a plasma treatment process. The degree of crosslinking and nature of the surface modification can be altered by changing the RF power setting, the location with respect to the plasma, the duration of treatment as well as the gas composition introduced into the plasma chamber.

Protection of a biologically active surface can also be utilized by coating the implant surface with an inert molecule that prevents access to the active site through steric hindrance, or by coating the surface with an inactive form of the therapeutic agent, which is later activated. For example, the implant can be coated with an enzyme, which causes either release of the fibrosis-inducing agent or activates the fibrosis-inducing agent.

In another strategy, the implant can be coated with an inactive form of the fibrosis-inducing agent, hemostatic agent and/or anti-infective agent, which is then activated once the implant is deployed. Such activation may be achieved by injecting another material into the diverticula after the implant (as described below) is deployed or after the fibrosis-inducing agent has been administered to the treatment area (via, e.g., injections, spray, wash, drug delivery catheters or balloons). For example, the implant may be coated with an inactive form of the fibrosis-inducing agent. Once the implant is deployed, the activating substance is injected or applied into or onto the treatment site where the inactive form of the fibrosis-inducing agent has been applied.

For example, a implant may be coated with a biologically active fibrosis-inducing agent, hemostatic agent, and/or anti-infective agent in the usual manner. The outer surface containing the active therapeutic agents(s) may then be covered (e.g., coated) with polyethylene glycol. The PEG and the therapeutic agent containing coating may be bonded through the formulation of a bond between reactive groups on the two layers. For example, an ester bond may be formed using a condensation reaction. Prior to the deployment of the implant, an esterase is injected into the treatment site around the outside of the implant. The esterase can cleave the bond between the ester and the therapeutic agent, thereby allowing the agent to initiate fibrosis (fibrosis-inducing agent), hemostasis (hemostatic agent), and/or inhibition of bacterial growth (anti-infective agent).

Within certain embodiments of the invention, the therapeutic compositions may also comprise additional ingredients such as surfactants (e.g., PLURONICS, such as F-127, L-122, L-101, L-92, L-81, and L-61), anti-inflammatory agents, preservatives, and/or anti-oxidants.

Within certain embodiments of the invention, the therapeutic agent or carrier can also comprise radio-opaque, echogenic materials and magnetic resonance imaging (MRI) responsive materials (i.e., MRI contrast agents) to aid in visualization of the implant under ultrasound, fluoroscopy and/or MRI. For example, a therapeutic implant may be made with or coated with a composition which is echogenic or radiopaque (e.g., made with echogenic or radiopaque with materials such as powdered tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodamide, lypophylic agents, iodipamide and ioglycamic acid or, by the addition of microspheres or bubbles which present an acoustic interface). Visualization of an implant by ultrasonic imaging may be achieved using an echogenic coating. Echogenic coatings are described in, e.g., U.S. Pat. Nos. 6,106,473 and 6,610,016. For visualization under MRI, contrast agents (e.g., gadolinium (III) chelates or iron oxide compounds) may be incorporated into or onto the implant, such as, as a component in a coating or within the void volume of the implant (e.g., within a lumen, reservoir, or within the structural material used to form the implant). In some embodiments, a diverticular implant may include radio-opaque or MRI visible markers (e.g., bands) that may be used to orient and guide the implant during the implantation procedure.

Medical implants may, alternatively, or in addition, be visualized under visible light, using fluorescence, or by other spectroscopic means. Visualization agents that can be included for this purpose include dyes, pigments, and other colored agents that can improve visualization during endoscopic deployment. In one aspect, the medical implant may further include a colorant to improve visualization of the implant in vivo and/or ex vivo. Frequently, implants can be difficult to visualize upon insertion, especially at the margins of implant. A coloring agent can be incorporated into a diverticular implant to reduce or eliminate the incidence or severity of this problem. The coloring agent provides a unique color, increased contrast, or unique fluorescence characteristics to the implant. In one aspect, a solid implant is provided that includes a colorant such that it is readily visible (under visible light or using a fluorescence technique) and easily differentiated from its implant site. In another aspect, a colorant can be included in a liquid or semi-solid composition. For example, a single component of a two component mixture may be colored, such that when combined ex-vivo or in-vivo, the mixture is sufficiently colored.

The coloring agent may be, for example, an endogenous compound (e.g., an amino acid or vitamin) or a nutrient or food material and may be a hydrophobic or a hydrophilic compound. Preferably, the colorant has a very low or no toxicity at the concentration used. Also preferred are colorants that are safe and normally enter the body through absorption such as β-carotene. Representative examples of colored nutrients (under visible light) include fat soluble vitamins such as Vitamin A (yellow); water soluble vitamins such as Vitamin B12 (pink-red) and folic acid (yellow-orange); carotenoids such as β-carotene (yellow-purple) and lycopene (red). Other examples of coloring agents include natural product (berry and fruit) extracts such as anthrocyanin (purple) and saffron extract (dark red). The coloring agent may be a fluorescent or phosphorescent compound such as α-tocopherolquinol (a Vitamin E derivative) or L-tryptophan. Derivatives, analogues, and isomers of any of the above colored compounds also may be used. The method for incorporating a colorant into an implant or therapeutic composition may be varied depending on the properties of and the desired location for the colorant. For example, a hydrophobic colorant may be selected for hydrophobic matrices. The colorant may be incorporated into a carrier matrix, such as micelles. Further, the pH of the environment may be controlled to further control the color and intensity.

In one aspect, the composition of the present invention include one or more coloring agents, also referred to as dyestuffs, which will be present in an effective amount to impart observable coloration to the composition, e.g., the gel. Examples of coloring agents include dyes suitable for food such as those known as F. D. & C. dyes and natural coloring agents such as grape skin extract, beet red powder, beta carotene, annato, carmine, turmeric, paprika, and so forth. Derivatives, analogues, and isomers of any of the above colored compound also may be used. The method for incorporating a colorant into an implant or therapeutic composition may be varied depending on the properties of and the desired location for the colorant. For example, a hydrophobic colorant may be selected for hydrophobic matrices. The colorant may be incorporated into a carrier matrix, such as micelles. Further, the pH of the environment may be controlled to further control the color and intensity.

In one aspect, the compositions of the present invention include one or more preservatives or bacteriostatic agents, present in an effective amount to preserve the composition and/or inhibit bacterial growth in the composition, for example, bismuth tribromophenate, methyl hydroxybenzoate, bacitracin, ethyl hydroxybenzoate, propyl hydroxybenzoate, erythromycin, chlorocresol, benzalkonium chlorides, and the like. Additional examples of the preservative include paraoxybenzoic acid esters, chlorobutanol, benzyl alcohol, phenethyl alcohol, dehydroacetic acid, sorbic acid, and the like. In one aspect, the compositions of the present invention include one or more bactericidal (also known as bacteriacidal) agents.

In one aspect, the compositions of the present invention include one or more antioxidants, present in an effective amount. Examples of the antioxidant include sulfites, alpha-tocopherol and ascorbic acid.

Within related aspects of the present invention, implants and compositions are provided, which release an agent which induces fibrosis, hemostasis and/or anti-infective activity in vivo upon deployment of the implant or administration of the composition. In certain aspects, the therapeutic agent or composition that comprises the therapeutic agent is delivered locally or regionally to the treatment site from the composition.

Within certain aspects of the present invention, the therapeutic composition are preferably biocompatible, and release one or more fibrosing agents, hemostatic agents and/or anti-infective agents over a period of several hours, days, or months.

The implants of the present invention may be configured to release the fibrosis-inducing agent, hemostatic agent and/or anti-infective agent at one or more phases, the one or more phases having similar or different performance (e.g., release) profiles. The therapeutic agent may be made available to the tissue at amounts which may be sustainable, intermittent, or continuous; in one or more phases; and/or rates of delivery; effective to increase or promote any one or more components of fibrosis (or scarring), hemostasis or infection control.

Thus, the release rate may be programmed to impact fibrosis (or scarring), hemostasis (clotting) and/or infection by releasing the fibrosis inducing (scarring), hemostatic and/or anti-infective agent at a time such that at least one of the components of fibrosis, hemostasis and/or infection control is promoted or increased. Moreover, the predetermined release rate may reduce agent loading and/or concentration as well as potentially providing minimal drug washout and thus, increases efficiency of drug effect. In one embodiment, the rate of release may provide a sustainable level of the therapeutic agent to the treatment site. In another embodiment, the rate of release is substantially constant. The rate may decrease and/or increase over time, and it may optionally include a substantially non-release period. The release rate may comprise a plurality of rates. In an embodiment, the plurality of release rates may include rates selected from the group consisting of substantially constant, decreasing, increasing, and substantially non-releasing.

The total amount of fibrosis-inducing agent, hemostatic agent, and/or anti-infective agent made available on, in or near the diverticula may be in an amount ranging from about 0.01 µg (micrograms) to about 2500 mg (milligrams). Generally, the fibrosis-inducing, hemostatic, and/or anti-infective agent may be in the amount ranging from 0.01 µg to about 10 µg; or from 10 µg to about 1 mg; or from 1 mg to about 10 mg; or from 10 mg to about 100 mg; or from 100 mg to about 500 mg; or from 500 mg to about 2500 mg.

The surface amount of fibrosis-inducing agent, hemostatic agent, and/or anti-infective agent on, in or near the diverticula may be in an amount ranging from less than 0.01 µg to about 250 µg per $mm^2$ of surface area. Generally, the therapeutic agent may be in the amount ranging from less than 0.01 $µg/mm^2$; or from 0.01 µg to about 10 $µg/mm^2$; or from 10 µg to about 25 $µg/mm^2$; or from 25 µg to about 250 $µg/mm^2$.

The fibrosis-inducing agent, hemostatic agent, and/or anti-infective agent that is on, in or near the diverticula may be released from the composition and/or implant in a time period that may be measured from the time of implantation, which ranges from about less than 1 day to about 180 days. Generally, the release time may also be from about less than 1 day to about 7 days; from 7 days to about 14 days; from 14 days to about 28 days; from 28 days to about 56 days; from 56 days to about 90 days; from 90 days to about 180 days.

In one aspect, "quick release" or "burst" therapeutic compositions are provided that release greater than 10%, 20%, or 25% (w/v) of a fibrosis-inducing agent, hemostatic agent, and/or anti-infective agent over a period of 7 to 10 days. Such "quick release" compositions should, within certain embodiments, be capable of releasing therapeutic levels (where applicable) of a desired fibrosing, hemostatic, and/or anti-infective agent. Within other embodiments, "slow release" therapeutic compositions are provided that release less than 1% (w/v) of a fibrosis-inducing agent, hemostatic agent, and/or anti-infective agent over a period of 7 to 10 days. Within other embodiments therapeutic compositions are provided that release either less than 1% (w/v) of a therapeutic agent over a period longer than 10 days or do not release the therapeutic composition at all, but maintain the composition for a very long period of time such as for the entire duration of the diverticular healing process in the body.

The amount of therapeutic agent released from the composition and/or implant as a function of time may be determined based on the in vitro release characteristics of the agent from the composition. The in vitro release rate may be determined by placing the fibrosis-inducing agent (scarring), hemostatic agent, and/or anti-infective agent within the composition or implant in an appropriate buffer such as 0.1M phosphate buffer (pH 7.4)) at 37° C. Samples of the buffer solution are then periodically removed for analysis by either HPLC or by gravimetric means, and the buffer is replaced to avoid any saturation effects.

Based on the in vitro release rates, the release of fibrosis-inducing agent, hemostatic agent, and/or anti-infective agent per day may range from about 0.0001 µg (micrograms) to about 2500 mg (milligrams). Generally, the therapeutic agent that may be released in a day may be in the amount ranging from 0.0001 to 0.01 µg; 0.01 µg to about 10 µg; or from 10 µg to about 1 mg; or from 1 mg to about 10 mg; or from 10 mg to about 100 mg; or from 100 mg to about 500 mg; or from 500 mg to about 2500 mg. In one embodiment, the fibrosis-inducing agent, hemostatic agent, and/or anti-infective agent is made available to the diverticular tissue in a constant but substantially unchanging manner so that the agent remains at the tissue essentially permanently. In another embodiment, the therapeutic agent is made available to the susceptible diverticular tissue in a sustained and/or controlled manner which results in increased efficiency and/or efficacy. Further, the release rates may vary during either or both of the initial and subsequent release phases. There may also be additional phase(s) for release of the same substance(s) and/or different substance(s).

In one embodiment, the release rate of the fibrosis-inducing agent, hemostatic agent, and/or anti-infective agent may be classed as zero order, first order, or a combination of zero and first order.

Further, therapeutic compositions of the present invention preferably have a stable shelf-life for at least several months and capable of being produced and maintained under sterile conditions. The composition may be sterile either by preparing them under aseptic environment and/or they may be terminally sterilized using methods available in the art. Many pharmaceuticals are manufactured to be sterile and this criterion is defined by the USP XXII <1211>. The term "USP" refers to U.S. Pharmacopeia (see www.usp.org, Rockville, Md.). Sterilization may be accomplished by a number of means accepted in the industry and listed in the USP XXII <1211>, including gas sterilization, ionizing radiation or, when appropriate, filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. Sterilization may also occur by terminally using gamma radiation or electron beam sterilization methods. Filtration may be accomplished using a filter with suitable pore size, for example 0.22 µm and of a suitable material, for instance polytetrafluoroethylene (e.g., TEFLON). A combination of these methods may also be used to prepare the composition in the sterile form.

In another aspect, the agents, compositions, and implants of the present invention are contained in a container that allows them to be used for their intended purpose. Properties of the container that are important are a volume of empty space to allow for the addition of a constitution medium, such as water or other aqueous medium, e.g., saline, acceptable light transmission characteristics in order to prevent light energy from damaging the composition in the container (refer to USP XXII <661>), an acceptable limit of extractables within the container material (refer to USP XXII), an acceptable barrier capacity for moisture (refer to USP XXII <671>) or oxygen. In the case of oxygen penetration, this may be controlled by including in the container, a positive pressure of an inert gas, such as high purity nitrogen, or a noble gas, such as argon.

Typical materials used to make containers for pharmaceuticals include USP Type I through III and Type NP glass (refer to USP XXII <661>), polyethylene, TEFLON, silicone, and gray-butyl rubber. For parenterals, USP Types I to III glass and polyethylene are preferred.

In certain embodiments fibrosis inducing agents, hemostatic agents, anti-infective agents or derivatives and analogues thereof as described herein, can be used to create variations of the above compositions. In addition, the therapeutic agent(s) may be used in a composition with a polymyer carrier as described herein or without polymer carrier.

Other agents which may be incorporated into or onto the implant or released from the implant include extracellular matrix components such as fibrous structural proteins (e.g., fibrillar collagens, nonfibrillar collagen and elastins), adhesive glycoproteins (e.g., laminin and fibronectin), proteoglycans (e.g., heparin sulphate, chondroitin sulphate, dermatan sulphate), hyaluronan (e.g., hyaluronic acid), secreted protein acidic and rich in cysteine (SPARC), thrombospondins, tenacin, inhibitors of matrix metalloproteinases (e.g., TIMPs and synthetic TIMPs such as marimistat, batimistat, doxycycline, tetracycline, minocycline, TROCADE, Ro-1130830, CGS 27023A, BMS-275291) and polylysine. Growth factors and inflammatory cytokines involved in angiogenesis, fibroblast migration, fibroblast proliferation, ECM synthesis and tissue remodeling such as epidermal growth factor (EGF) family, transforming growth factor-$\alpha$ (TGF-$\alpha$), transforming growth factor-$\beta$ (TGF-$\beta$-1, TGF-$\beta$-2, TGF-$\beta$-3), platelet-derived growth factor (PDGF), fibroblast growth factor (acidic—aFGF; and basic—bFGF), bone morphogenic proteins, activins, vascular endothelial growth factor (VEGF, VEGF-B, VEGF-C, placental growth factor—PIGF), angiopoietins, insulin-like growth factors (IGF), hepatocyte hrowth factor (HGF), connective tissue growth factor (CTGF), myeloid colony-stimulating factors (CSFs), granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, IL-6), tumor necrosis factor-$\alpha$ (TNF$\alpha$), nerve growth factor (NGF), interferon-$\alpha$, interferon-$\beta$, and growth hormone (GH) are also suitable for incorporation and release from specific diverticular implants. Other agents which may be coated onto or released by the diverticular implant include adhesives such as cyanoacrylate or materials made from 4-armed thiol PEG (10K), a 4-armed NHS PEG (10K) and methylated collagen.

Devices for Treating or Preventing Diverticular Disease

In certain embodiments, medical implants are provided that comprise at least one of (i) a fibrosis-inducing agent and (ii) a composition that comprises a fibrosis-inducing agent. Within another embodiment, a fibrosis-inducing pharmacologic agent, an implant adapted to include or to release an agent that induces fibrosis (through one or more of the mechanisms described herein), an anti-infective agent, and/or a haemostatic agent are administered onto or into diverticula. When placed within diverticula, the fibrosing agent is present to induce fibrosis formation that would otherwise not occur. The fibrosis-inducing, pharmacologic agent and/or an implant/composition that comprises a fibrosis-inducing agent (and/or an anti-infective agent and/or a haemostatic agent) are introduced into a into a host (human or non-human mammal) with diverticula according to methods described herein, such that the agent causes the formation of fibrosis within the diverticula, which fibrosis would otherwise not occur in the absence of the agent.

Also provided herein are devices for gaining access to the lumen of the diverticula and for administering fibrosis-inducing therapy. The lumen of the body passageway can be accessed via an endoscope (e.g., colonoscope, gastroscope, ERCP, bronchoscope, cystoscope etc.) or under radiographic (x-ray, fluoroscopy, ultrasound, CT scanning, MRI scanning, PET scanning or other imaging modality) guidance. Upon visualizing the opening of the diverticula into the lumen of the passageway, a variety of specialized catheters may be used for the delivery of the previously therapeutic agents and compositions described herein. These devices all have lumens that enable the localized delivery of fibrosis-inducing agents, hemostatic agents, and/or anti-infective agents into the lumen of diverticula, which may be effected either under direct vision (endoscopy) or radiographic guidance.

Catheters

Numerous intravascular catheters (catheter containing one or more lumens suitable for the intravascular delivery of aqueous, microparticulate, fluid, or gel formulations into the bloodstream, the vascular wall, plaque, or an aneurysm sac) may be used for direct, site-specific drug delivery (e.g., microinjector catheters, catheters placed within or immediately adjacent to the target tissue), regional drug delivery (i.e., catheters placed in an artery that supplies the target organ or tissue), or systemic drug delivery (i.e., intra-arterial and intravenous catheters placed in the peripheral circulation). For example, catheters and balloon catheters suitable for use can deliver fibrosing agents from an end orifice, through one or more side ports, through a microporous outer structure, or through direct injection into the desired tissue or vascular location.

A variety of catheters are available for regional or localized drug-delivery. Intravascular balloon and non-balloon catheters for delivering drugs are described, for example, in U.S. Pat. Nos. 5,180,366; 5,171,217; 5,049,132; 5,021,044; 6,592,568; 5,304,121; 5,295,962; 5,286,254; 5,254,089; 5,112,305; PCT Publication Nos. WO 93/08866, WO 92/11890, and WO 92/11895; and Riessen et al., *JACC* 23: 1234–1244 (1994); Kandarpa K. *J. Vasc. Interv. Radio.* 11 (suppl.): 419–423 (2000); and Yang, X. *Imaging of Vascular Gene Therapy* 228:36–49 (2003).

In addition, numerous physical interventions described herein such as the application of thermal energy (heat or cryotherapy), cautery, electricity, RF energy, laser, radioactivity, ultrasound, balloon inflation, physical abrasion, etc., will have the added benefit of wounding the luminal surface of the diverticula to initiate the healing/scarring cascade that may or may not be further amplified by the concurrent administration of a fibrosis-inducing agent. Although virtually any delivery catheter of the correct length, flexibility, and lumen size could be used in the delivery of therapeutic agents in and around diverticula, the following devices are non-limiting examples of catheters that may be used for treating diverticular disease.

Drug Delivery Catheters. A variety of drug delivery catheters may be used, or that may be adapted for use, for delivery of an agent or composition comprising the agent into a host. A catheter is advanced through the side port of the endoscope (or under radiographic guidance) until is enters the lumen of the diverticula. The fibrosis-inducing agent or implant can then be administered into the lumen of the diverticula via the catheter. Examples of drug delivery catheters include diffusion catheters, infusion catheters, and direct injection catheters. The drug delivery catheter may be an energy-enabled drug delivery system, such as an electroporation, ultrasound, laser light, or other energy-based delivery system that activates a drug and/or accelerates the delivery of the drug into a tissue (e.g., a diverticular surface).

Representative examples of drug delivery catheters include balloon catheters, such as the CHANNEL and TRANSPORT balloon catheters from Boston Scientific Corporation (Natick, Mass.) and Stack Perfusion Coronary Dilitation catheters from Advanced Cardiovascular Systems, Inc. (Santa Clara, Calif.). Other examples of drug delivery catheters include infusion catheters, such as the CRESCENDO coronary infusion catheter available from Cordis Corporation (Miami Lakes, Fla.), the Cragg-McNamara Valved Infusion Catheter available from Microtherapeutics, Inc. (San Clemente, Calif.), the DISPATCH catheter from Boston Scientific Corporation, the GALILEO Centering Catheter from Guidant Corporation (Houston, Tex.), and infusion sleeve catheters, such as the INFUSASLEEVE catheter from LocalMed, Inc. (Sunnyvale, Calif.). Infusion sleeve catheters are described in, e.g., U.S. Pat. Nos. 5,318,531; 5,336,178; 5,279,565; 5,364,356; 5,772,629; 5,810,767; and 5,941,868. Catheters that mechanically or electrically enhance drug delivery include, for example, pressure driven catheters (e.g., needle injection catheters having injector ports, such as the INFILTRATOR catheter available from InterVentional Technologies, Inc. (San Diego, Calif.)) (see, e.g., U.S. Pat. No. 5,354,279) and ultrasonically assisted (phonophoresis) and iontophoresis catheters (see, e.g., Singh, J., et al. (1989) Drug Des. Deliv. 4:1–12 and U.S. Pat. Nos. 5,362,309; 5,318,014; 5,315,998; 5,304,120; 5,282,785; and 5,267,985).

RF (radiofrequency) Ablation Catheters. A variety of catheters that deliver energy may be used, or may be adapted for use, in for treating diverticular disease. Radiofrequency ablation is a procedure by which high frequence energy is delivered into tissue. Either of two types of RF ablation may be used: temperature control or fluid-cooled ablation. A carefully controlled amount of energy is delivered to the surface of the diverticulum such that the surface is disrupted (but not enough to cause perforation of the diverticula) or injured enough to initiate (or stimulate) the healing response. Such a device may be used alone to induce fibrosis or may be used in combination with administration of a fibrosis-inducing agent or implant into the lumen of the diverticula. Exemplary RF ablation catheters include catheters manufactured by Medtronic, Minneapolis, Minn. (e.g., RF CONTACTR (Dual-Curve Series; RFENHANCR(SC) Series; RF CONDUCTR (MC) Series; RF MARINR (MC) Series; and 5F RF MARINR(SC) Series) and Boston Scientific Corp., Natick, Mass. (e.g., BLAZER II XP; BLAZER II HTD; POLARIS T temperature ablation catheter; CHILLI Cooled ablation catheter; CHILLI RPM cooled ablation catheter; STEEROCATH-T temperature ablation catheter; and EPT-1000XP).

Thermal Energy Catheters. A variety of catheters that deliver thermal energy (heat, microwaves, cryotherapy) (see, e.g., UROLOGIX Transurethral Thermal Therapy (T3), Urologix, Inc., Minneapolis, Minn.; Neya et al., Circulation 91:2445–53 (1995)) may be used, or that may be adapted for use, for treating diverticular disease as described herein. A carefully controlled amount of thermal energy is delivered to the surface of the diverticulum such that the surface is disrupted (but not enough to cause perforation of the diverticula) or injured sufficiently to initiate (or stimulate) the healing response. A thermal energy catheter may be used alone to induce fibrosis or may be used in combination with administration of a fibrosis-inducing agent or implant into the lumen of the diverticula. Examples of thermal energy catheters include SPINECATH Intradiscal Catheter and AUTHERM Decompression Catheter (Smith & Nephew, Inc., Andover, Mass.) and include cryoablation devices (those that apply extremely low temperatures to tissues) such as CRYOCOR (CryoCor, Inc., San Diego, Calif.); CLOSURE (VNUS Medical Technologies, Inc., San Jose, Calif.); and FREEZOR and CRYOTHERAPY (CryoCath Technologies, Inc., Kirkland, Quebec).

Laser Devices. A variety of catheters that deliver laser light energy may be used, or may be adapted for use, for treatment of diverticular disease. A carefully controlled amount of light energy is delivered to the surface of the diverticulum such that the surface is disrupted, but not enough to cause perforation of the diverticula, or injured sufficiently to initiate (stimulate or promote) the healing response (see, e.g., Capon et al., Am. J. Clin. Dermatol. 4:1–12 (2003); Reddy, J. Clin. Laser Med. Surg. 22:141–50 (2004); Vladimirov et al., Biochemistry (Moscow) 69:81–90 (2004); Schindl, et al., J. Investig. Med. 48:312–26 (2000)). This device may be used alone to induce fibrosis, or may be used in combination with administration of a fibrosis-inducing agent or implant into the lumen of the diverticula. Examples of catheters that deliver laser energy include CLIRPATH (Spectranetics, Corp., Colorado Springs, Colo.) and Trimedyne laser catheter (Trimedyne, Inc., Irvine, Calif.; see, e.g., U.S. Pat. No. 5,496,309); an argon or Nd:YAG laser (see, e.g., Hunter, Surg. Clin. North Am. 69(6):1147–66 (1989).

Radioactivity and Brachytherapy Devices. A variety of catheters and implants that deliver radioactive energy may be used, or that may be adapted for use, for treating diverticular disease. A carefully controlled amount of radioactivity energy is delivered to the surface of the diverticulum such that the surface is disrupted (but not enough to cause perforation of the diverticula) or injured sufficiently to initiate (or stimulate or promote) the healing response. This intervention can be used alone to induce fibrosis, or in combination with administration of a fibrosis-inducing agent or implant into the lumen of the diverticula. Radioactivity at low doses stimulates the healing and fibrosis response (see, e.g., Vladimirov et al., supra; Hill et al., Int. J. Radiat. Oncol. Biol. Phys. 49:353–65 (2001); Rodemann et al., Radiother. Oncol. 35:83–90 (1995); O'Sullivan et al., Semin. Radiat. Oncol. 13:274–89 (2003); Schindl, et al., supra); Conlon et al., J. Clin. Periodontol. 23:492–96 (1996), making permanent and degradable local sources of radiation particularly useful for the practice of this embodiment.

Any one of several radionuclides used for intravascular brachytherapy may be applied to diverticula (see, e.g., Nath et al., Cardiovasc. Radiat. Med. 5:88–96 (2004); von Neumann-Cosel, Phys. Med. Biol. 48:1855–62 (2003); Lehmann et al., J. Appl. Clin. Med. Phys. 4:58–63 (2003); Yue et al., Cardiovasc. Radiat Med. 5:142–50 (2004)). Systems and catheters for delivering radioactivity to a tissue are available to persons skilled in the art (see, e.g., Guglielmi detachable coils (Qureshi et al., Neurosurg. Focus 10: Preview of J. Neurosurg. 94:880–85 (2001)); wire source, balloon source (see, e.g., Lehmann et al., supra); balloon catheter as described herein). Commercially available products that may be used to deliver therapeutic compositions to a diverticulum include beta radiation catheters such as the BETA-CATH System from Novoste Corporation (Atlanta, Ga.); the GALILEO Intravascular Radiotherapy System from Guidant Corporation (Indianapolis, Ind.); and gamma radiation catheters such as the CHECKMATE System from Johnson & Johnson Corporation (New Brunswick, N.J.). Other radioactivity and brachytherapy devices that may be used or adapted for use according to the methods described herein include the GammaMedplus from Varian Medical Systems (Charlottesville, Va.), which is used in the MAMMOSITE RTS device from North Shore Medical Accelerator, PC, Smithtown, N.Y.) and brachytherapy seeds for implantation such as the I-PLANT High Activity $^{125}$Iodine Seeds (Implant Sciences Corporation, Wakefield, Mass.).

Balloon Catheters. A variety of balloon catheters may be used for treatment of diverticular disease. A balloon catheter is delivered into the lumen of the diverticulum and carefully expanded such that the surface of the diverticulum is disrupted (but not enough to cause perforation of the diverticula) or injured enough to initiate (or stimulate) the healing response. This intervention can be used alone to induce fibrosis, or in combination with administration of a fibrosis-inducing agent or implant into the lumen of the diverticula. Representative examples of drug delivery catheters include balloon catheters, such as the CHANNEL and TRANSPORT balloon catheters from Boston Scientific Corporation (Natick, Mass.) and Stack Perfusion Coronary Dilitation catheters from Advanced Cardiovascular Systems, Inc. (Santa Clara, Calif.).

The balloon catheter systems that can be used include systems in which the balloon can be inflated at the desired location where the desired fibrosis-inducing agents can be delivered through holes that are located in the balloon wall. Other balloon catheters that can be used include systems that have a plurality of holes that are located between two balloons. The system can be guided into the desired location such that the inflatable balloon components are located on either side of the specific site that is to be treated. The balloons can then be inflated to isolate the treatment area. The compositions containing the fibrosing agent are then injected into the isolated area through the plurality of holes between the two balloons. Representative examples of these types of drug delivery balloons are described in U.S. Pat. Nos. 5,087,244; 6,623,452; 5,397,307; 4,636,195; and 4,994,033.

Ultrasonic Catheters. A variety of catheters that deliver ultrasonic energy may be used for treatment of diverticular disease. A carefully controlled amount of sound energy is delivered to the surface of the diverticulum such that the surface is disrupted (but not enough to cause perforation of the diverticula) or injured sufficiently to initiate (or stimulate) the healing response. This intervention can be used alone to induce fibrosis, or in combination with administration of a fibrosis-inducing agent or implant into the lumen of the diverticula. Examples of ultrasonic catheters and systems that may be used include but are not limited to those described by Martin et al., *IEEE Transactions on Sonics and Ultrasonics Supp.* 27:277 (1980); Gage Applied Technologies, Lachine, Quebec (e.g., COMPUSCOPE (CS) 8500); U.S. Pat. No. 4,602,633; U.S. Pat. No. 4,692,139; Atar et al., *Echocardiography—J. Cardiovasc. Ultrasound Allied Tech.* 18:233–37 (2001); Horiuchi et al., *J. Endourology* 19:130–32 (2005); Dick et al., *Investigative Radiology* 33:85–90 (19985); (see also, e.g., Rasor Consulting Group, Los Gatos, Calif.). See also, e.g., U.S. Pat. Nos. 6,723,064; 6,689,086; 6,623,444; 6,592,520; 6,296,619; and 6,527,759. Representative examples of ultrasonic catheters include IVUS catheters, diagnostic catheters, and delivery catheters, and commercially available ultrasonic catheters such as the ACUNAV catheter from Siemens, the ViewMate Catheter from EPMedSystems, and the EAGLE EYE GOLD catheter from Volcano Therapeutics.

Physical Abrasion/Denudation of the Diverticular Surface. A variety of catheters that abraid the surface of the tissues they contact may be used for treatment of diverticular disease. The surface of the diverticulum is mechanically disrupted such that the surface is abraded (but not enough to cause perforation of the diverticula) or injured sufficiently to initiate (or stimulate or promote) the healing response. This intervention can be used on its own to induce fibrosis, or in combination with administration of a fibrosis-inducing agent or implant into the lumen of the diverticula. An example of such a device is a rotoblade, which is a high-speed spinning device. Atherectomy is a procedure that removes plaque from the arteries supplying blood to the heart muscle. Devices used for atherectory include a laser catheter or a rotating shaver ("burr" device on the end of a catheter), which may be used or adapted for use for treatment of a diverticular disease (see also, e.g., dissectional catheterectomy catheters that shave off tissue).

Representative examples of devices for abrading diverticular surfaces include those used in atherectomy procedures. An atherectomy device typically has a small mechanically driven tool that either shaves, cuts, or breaks a tissue (typically a fatty deposit such as a plaque) into small particles to remove the blockage from the inside of a blood vessel (e.g. an artery). After being shaved from the artery wall, this plaque is stored safely in the tip of the catheter and removed from the body. Atherectomy devices for vascular application may be used as is or be adapted or modified for use in the present invention.

In another embodiment, the atherectomy device may be a rotational or directional atherectomy device. Rotational atherectomy is a minimally invasive treatment that is sometimes used to pulverize hardened plaque within a coronary artery. During rotational atherectomy, a high-speed rotating device (referred to as a a "rotoblade" or "rotablator") that connects to the end of a catheter is used to grind away material at the treatment site. In some embodiments, an atherectomy catheter may include a rotating cutter and a collecting chamber for debris.

Several rotational and directional atherectomy devices are commercially available. For example, rotational atherectomy devices include the ROTOBLATOR Rotational Atherectomy System from Boston Scientific Corporation (Natick Mass.) and the directional atherectomy devices such as the FLEXI-CUT and FX miniRAIL cutting balloon devices from Guidant Corporation.

In one aspect, the atherectomy device may be an atherectomy catheter. The atherectomy catheter may be, for example, a 9-F Simpson directional atherectomy catheter (see, e.g., Zeller et al., *Endovasc. Ther.* 11(6):676–85 (2004) or Schechter et al., *J. Vasc. Interv. Radiol* (1993) 4(6): 819–24.

Representative example of atherectomy catheters and devices which may be used or adapted for use in the practice of the methods described herein include, without limitation, those described in U.S. Pat. Nos. 5,087,265; 5,423,846; 6,001,112; 5,865,844; 5,156,610; 5,356,418; 6,482,216; 5,312,427; 6,428,551; 5,030,201; 6,503,261, and 6,596,005.

Exemplary devices that may be used or adapted for use to abrade and/or denude a diverticular surface include commercially available products such as the SILVERHAWK plaque excision device from FoxHollow Technologies, Inc. (Redwood City, Calif.), laser catheters such as the CLIR-PATH line of excimer laser catheters from Spectranetics (Colorado Springs, Colo.) and the atherectomy devices from ev3 Inc., Johnson & Johnson/Cordis Corporation, Pathway Medical Technologies, Possis Medical Inc., Lumend (Redwood City, Calif.), Intraluminal Therapeutics (Carlsbad, Calif.), Flowcardia (Sunnyvale, Calif.), Corazon Technologies (Menlo Park, Calif.), and Medtronic Inc. (Minneapolis, Minn.).

Another method for abrading a diverticular surface is via an "endoscopic scalpel." Endoscopic instrumentation and methods are described in, e.g., International Application Publication Nos. WO 96/25107A1, WO 04/064623A2, WO 01/06943A1, WO 03/096871A2, and U.S. Pat. Nos. 6,482, 219; 6,277,135; 6,165,184; and 4,539,976.

Additional examples of devices that may be used to abrade the diverticular tissue surface are described in International Application Publication Nos. WO 01/89370A2, and WO 01/166018A1.

In another embodiment, an endoluminal paving device may be used to physically abrade or denude a diverticular surface. Endoluminal paving devices may be used, for example, to inject into a diverticulum via a catheter a polymer which is in the form of a liquid, but hardens at body temperature to seal the diverticular cavity. The polymer may be, for example, a gel, such as a hydrogel, or another type of polymer adapted for delivering a fibrosing agent to a diverticulum. Various endoluminal paving compositions and procedures are described (see, e.g., Slepian M. J., Semin. Interv. Cardiol. 1996 March; 1(1):103–16; Slepian M J., Cardiol. Clin. 1994 November; 12(4):715–37; International Application Publication Nos. WO 90/01969A1, WO 04/087065A2, WO 91/12846A1; and U.S. Pat. Nos. 5,749, 922; 5,328,471; and 5,749,915. Although versions of the above catheters have been describe for the practice of other therapeutic modalities, modifying these devices for use in gaining access to, and delivering treatment to, diverticula is an embodiment contemplated herein. In many cases these interventions alone may be sufficient or can be used in combination with a fibrosis-inducing agent, hemostatic agent, and/or anti-infective agent.

In additional embodiments, for each of the aforementioned devices combined with each of the aforementioned agents, it is, for each combination, independently disclosed that the agent may be present in a composition along with a polymer. In one embodiment, the polymer is biodegradable. In another embodiment, the polymer is non-biodegradable. Other features and characteristics of the polymer, which may be included with every combination of device and agent described above, are set forth in greater detail herein.

In addition to implants and fibrosis-inducing compositions for the treatment of diverticular disease, methods are also provided. For example, for each of the aforementioned implants, and for each possible combinations of an implant with a fibrosis-inducing agent, methods are provided wherein a specified implant is introduced into an animal (a human (patient or subject) or non-human mammal, which includes but is not limited to a rabbit, rat, mouse, hamster, dog, non-human primate, cat, goat, pig, sheep, goat, horse, bovine), advanced to the site of a diverticula, and a specified physical intervention (physical disruption of the luminal surface of the diverticula as described previously), and/or administration of a fibrosis-inducing agent or composition induces fibrosis within the diverticula that would otherwise not occur. Each of the implants identified herein may be a "specified implant."

In certain embodiments, a medical implant may be modified by attaching fibers (threads) to the surface of the implant. The fibers may be polymeric and/or may be formed of or coated with a fibrosing material, such as silk. For example, the threads may be formed from a silk suture material. The presence of the threads can result in an enhanced cellular and/or extracellular matrix response to the exterior of the implant. The threads can be attached to the implant by using any one or a combination of the following methods, including use of an adhesive, thermal welding, stitching, wrapping, weaving, knotting, and the like. The threads can be coated with a material that delays the time it takes for the thread material to come into contact with the surrounding tissue and blood, thus allowing placement of the implant without concern of thrombotic events due to the presence of the polymeric threads. Examples of materials that can be used to prepare coatings capable of degrading or dissolving upon implantation include gelatin, polyesters (e.g., PLGA, PLA, MePEG-PLGA, PLGA-PEG-PLGA, and blends thereof), lipids, fatty acids, sugar esters, nucleic acid esters, polyanhydrides, polyorthoesters, and PVA. The coating may further contain a fibrosing agent and/or a biologically active agent that may, for example, reduce the probability of an immediate thrombotic event (e.g., heparin, hydrophobic quaternary amine heparin complexes, and the like). In addition to the polymeric threads, all or a portion of the implant may be coated with a polymeric carrier that contains a fibrosis-inducing agent.

The fibers (threads) may further comprise a coating or composition that is affected by an applied magnetic field. For example, an implant may be coated with polymeric threads that are coated, contain, or are formed from a fibrosing agent (e.g., silk suture). A magnetic field can be applied to the coated implant to orient and align the polymeric fibers relative to each other and the surface of the implant to increase the surface area of the fibers exposed to biological mediators that would stimulate a fibrotic reaction. The magnetically active component can be associated with the polymeric fiber using a variety of methods. The magnetically active component may be incorporated during manufacture of the fiber, for example, by incorporating a magnetically active material such as magnetite into a polymer feed prior to extrusion of the polymeric fiber. The magnetically active component can be coated onto the entire fiber or a portion of the fiber using, for example, an adhesive or a polymeric coating. The polymeric fiber (or a portion thereof) can be heated or plasticized with a solvent and then rolled in the magnetically active component, such that the magnetic material protrudes above the surface of the fiber or is embedded into the surface of the fiber.

The threads (either with or without a magnetic component) may be attached to the implant in various configurations that can result in either partial or complete coverage of the exterior of the implant. The polymeric threads may be affixed to the ends of an implant or to the central portion of an implant, and the attachment may be in a vertical, horizontal, or diagonal manner.

Systemic, Regional and Local Delivery of Fibrosis-Inducing Agents

A variety of drug-delivery technologies are available for systemic, regional, and local delivery of therapeutic agents. Several of these techniques may be suitable to achieve preferentially elevated levels of fibrosis-inducing agents in the vicinity of the medical implant, including (a) using drug-delivery catheters for local, regional, or systemic delivery of fibrosing agents to the tissue surrounding the implant (typically, drug delivery catheters are advanced through the circulation or inserted directly into tissues under endoscopic or radiographic guidance until they reach the desired anatomical location; the fibrosing agent can then be released from the catheter lumen in high local concentrations in order to deliver therapeutic doses of the drug to the tissue surrounding the implant); (b) drug localization techniques such as magnetic, ultrasonic, or MRI-guided drug delivery; (c) chemical modification of the fibrosis-inducing drug or formulation designed to increase uptake of the agent into damaged tissues (e.g., modification of the drug or formulation to include antibodies directed against damaged or healing tissue components such as macrophages, neutrophils, smooth muscle cells, fibroblasts, extracellular matrix components, neovascular tissue); (d) chemical modification of the fibrosis-inducing drug or formulation designed to localize the drug to areas of bleeding or disrupted vasculature such as encapsulation of the drug into site directed liposomes; and/or (e) direct injection of the fibrosis-inducing agent, for example under endoscopic vision.

Infiltration of Fibrosis-Inducing Agents into the Tissue Surrounding an Implant

Alternatively, the tissue cavity into which the implant is placed can be treated with a fibrosis-inducing agent prior to, during, or after the implantation procedure. This can be accomplished in several ways including (a) topical application of the fibrosing agent into the anatomical space where the implant can be placed (particularly useful for this embodiment is the use of polymeric carriers which release the fibrosing agent over a period ranging from several hours to several weeks; fluids, suspensions, emulsions, microemulsions, microspheres, pastes, gels, microparticulates, sprays, aerosols, solid implants and other formulations which release a fibrosing agent can be delivered into the region where the implant can be inserted via specialized delivery catheters or other applicators); (b) microparticulate silk and/or silk strands (e.g., linear, branched, and/or coiled) are also useful for directed delivery into the implantation site; (c) sprayable collagen-containing formulations such as COSTASIS (Angiotech Pharmaceuticals, Inc., Vancouver, BC) or materials made from 4-armed thiol PEG (10K), a 4-armed NHS PEG (10K) and methylated collagen (described herein), or materials made from 4-armed thiol PEG (10K), a 4-armed NHS PEG (10K) and collagen or gelatin, either alone, or loaded with a fibrosis-inducing agent, applied to the implantation site (or the implant surface); (d) sprayable in situ forming PEG-containing formulations such as COSEAL (Angiotech Pharmaceuticals, Inc., Canada), FOCALSEAL (Genzyme Corporation, Cambridge, Mass.), SPRAYGEL or DURASEAL (both from Confluent Surgical, Inc., Waltham, Mass.), either alone, or loaded with a fibrosis-inducing agent, applied to the implantation site (or the implant surface); (e) fibrinogen-containing formulations such as FLOSEAL or TISSEAL (both from Baxter Healthcare Corporation; Fremont, Calif.), either alone, or loaded with a fibrosis-inducing agent, applied to the implantation site (or the implant surface); (f) hyaluronic acid-containing formulations (either non-crosslinked, crosslinked or chemically modified) such as PERLANE or RESTYLANE (both from Q-Med AB, Sweden), HYLAFORM (Inamed Corporation; Santa Barbara, Calif.), SYNVISC (Biomatrix, Inc.; Ridgefied, N.J.), SEPRAFILM or SEPRACOAT (both from Genzyme Corporation; Cambridge, Mass.) loaded with a fibrosis with a fibrosis-inducing agent applied to the implantation site (or the implant surface); (g) polymeric gels for surgical implantation such as REPEL (Life Medical Sciences, Inc.; Princeton, N.J.) or FLOWGEL (Baxter Healthcare Corporation, Deerfield, Ill.) loaded with a fibrosis-inducing agent applied to the implantation site (or the implant surface); (h) orthopedic "cements" used to hold prostheses and tissues in place loaded with a fibrosis-inducing agent applied to the implantation site (or the implant surface), such as OSTEOBOND (Zimmer, Inc., Warsaw, Ind.), LVC (Wright Medical Technology, Inc., Arlington, Tenn.), SIMPLEX P (Stryker Corporation, Kalamazoo, Mich.), PALACOS (Smith & Nephew PLC Corporation, United Kingdom), and ENDURANCE (Johnson & Johnson, Inc., New Brunswick, N.J.); (i) surgical adhesives containing one or more cyanoacrylate monomers (e.g., methyl cyanoacrylate, ethyl cyanoacrylate, butyl cyanoacrylate, octyl cyanoacrylate, methoxypropyl cyanoacrylate) such as DERMABOND (Johnson & Johnson, Inc.), INDERMIL (United States Surgical; Norwalk, Conn.), GLUSTITCH (Blacklock Medical Products, Inc., Canada) or TISSUMEND II (Veterinary Products Laboratories; Phoenix, Ariz.), VETBOND (3M Company; St. Paul, Minn.), TISSUEMEND (TEI Biosciences, Inc.; Boston, Mass.), HISTOACRYL or HISTOACRYL BLUE (Davis & Geck; St. Louis, Mo.) and ORABASE SOOTHE-N-SEAL LIQUID PROTECTANT (Colgate-Palmolive Company; New York; N.Y.), either alone, or loaded with a fibrosis-inducing agent, applied to the implantation site (or the implant surface); (j) implants containing hydroxyapatite (or synthetic bone material such as calcium sulfate, VITOSS and CORTOSS (both from Orthovita, Inc., Malvern, Pa.)) loaded with a fibrosis-inducing agent applied to the implantation site (or the implant surface); (k) other biocompatible tissue fillers loaded with a fibrosis-inducing agent, such as those made by BioCure, Inc. (Norcross, Ga.), 3M Company and Neomend, Inc. (Sunnyvale, Calif.), loaded with a fibrosis-inducing agent applied to the implantation site (or the implant surface); (l) polysaccharide gels such as the ADCON series of gels (Gliatech, Inc.; Cleveland, Ohio); (m) films, sponges or meshes such as INTERCEED or VICRYL mesh (Ethicon, Inc., a Johnson & Johnson Company, Somerville, N.J.), and GELFOAM (Pharmacia & Upjohn Company; Kalamazoo, Mich.) loaded with a fibrosis-inducing agent applied to the implantation site (or the implant surface); (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads), and (o) compositions that enhance osteointegration and/or osteogenesis, including materials composed of beta-tricalcium phosphate (e.g., VITOSS, PROOSTEON 500R made by E-Interpore-Cross International), hydroxyapatite or $Ca_{10}(PO_4)_6OH$ (e.g., OSTEOGRAF made by Ceramed Denta, Inc., Lakewood, Colo.), calcium carbonate or $CaCO_3$, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J., NORIAN SRS made by Synthes-Strates, Switzerland), as well as synthetic bone fillers (e.g., CORTOSS and processed bone fillers, e.g., BIOOSS made by Geistlich Biomaterials, Inc., Switzerland). Representative examples of these materials are described in U.S. Pat. Nos. 3,929,971; 4,861,733; 6,527,810; 4,772,468; 4,882, 149; 5,167,961; 6,576,015; 4,839,215; 5,614,206; 5,807, 567; 6,030,636; 6,652,887; 6,206,957; 6,485,754; 4,347, 234; 4,291,013; 5,129,905; 5,336,264; 5,569,442; 5,571, 493; 5,683,667; 5,709,742; 5,820,632; 5,658,332; 5,681, 872; 5,914,356; 5,939,039; 6,325,987; 6,383,519; 6,458, 162; 6,736,799; 6,521,246; and 6,709,744.

In one embodiment, the fibrosis-inducing agent may be delivered as a solution. The fibrosis-inducing agent can be incorporated directly into the solution to provide a homogeneous solution or dispersion. In certain embodiments, the solution is an aqueous solution. The aqueous solution may further include buffer salts, as well as viscosity modifying agents (e.g., hyaluronic acid, alginates, CMC, and the like). In another aspect of the invention, the solution can include a biocompatible solvent, such as ethanol, DMSO, glycerol, PEG-200, PEG-300 or NMP.

In certain embodiments, a method for inducing fibrosis within a diverticulm for treating a diverticular disease comprises irrigation (lavage, cleansing) of the diverticulum and surrounding tissues. Prior to introducing a fibrosing agent, composition, or implant, the diverticulum may be irrigated to cleanse or remove particulate matter, cells, tissues, fecal matter (for GI diverticulum), microorganisms, and the like, which are undesirable to retain in a diverticulum that is being sealed or closed. Such methods for irrigating, cleansing, and rinsing tissue or organs are routinely practiced by persons skilled in the medical art in preparation of a site for a medical procedure. Any one or all solutions used for irrigating a diverticulum may contain one or more anti-infective agents, such as an antibiotic, antiseptic, or other anti-infective agent described herein and used by a person skilled in the art. Cleansing or irrigating a diverticulum with an anti-infective agent acts to prevent or treat an infection and/or to minimize dissemination of microorganisms. One or more solutions may be applied in one or more irrigation steps, for example, which steps may include washing to remove undesired matter, disinfecting the site, and rinsing with a solution, the composition of which is the same as the composition for delivering the fibrosing agent, composition, or implant.

In certain embodiments, a haemostatic agent or composition comprising a haemostatic agent (e.g., COSTASIS) or sealant, may also be included in an irrigating solution. A polymer or carrier polymer may be combined with a haemostatic agent. A haemostatic agent or a composition comprising a haemostatic agent, which may also include a polymer or carrier polymer, may be applied to the diverticulum or tissue surrounding the diverticulum to control bleeding at the site of the diverticulum and to induce scarring.

Also as described in greater detail herein, methods for inducing fibrosis in the diverticulum and/or treating a host who has a diverticular disease may also include a diagnostic step. To determine or confirm the presence of a diverticulum in a host, the site within the body is examined by methods such as endoscopy or radiographic analysis. Endoscopy permits direct visualization of the target tissue to confirm the presence of a diverticum and to guide accurate placement of an implant or composition. Endoscopes are used to allow direct visualization in a minimally invasive fashion (i.e., not requiring open surgery) by inserting a small camera into the body via an orifice (mouth, anus) or a small incision. Any endoscopic technology may be used but a particular endoscope may be better suited for a particular tissue or site within the body. Examples of endoscopes include flexible endoscopes, rigid endoscopes, gastroscopes, ERCP, bronchoscopes, proctoscopes, angioscopes, and colonoscopes.

Alternatively, diagnosis may include radiographic analysis. Imaging technology is used to allow manipulation and intervention in a minimally invasive fashion (i.e., not requiring open surgery). Several imaging technologies are available for such use in the methods described herein. The choice of technology may be determined in part on the tissue being treated. Representative examples of imaging technology include x-ray, angiography, MRI, CT scanning, ultrasound, PET scanning, and nuclear medicine scanning.

Methods for Treating or Preventing Diverticular Disease

Methods are also provided herein for treatment of diverticular disease. Accordingly, for each of the aforementioned implants and for each of the aforementioned combinations of the implants, compositions, or implants with the fibrosis-inducing agents, methods are provided whereby a specified implant is introduced into a mammal, and advanced to the site of a diverticula. A specified physical intervention (physical disruption of the luminal surface of the diverticula as described herein) and/or administration of a fibrosis-inducing agent or composition within the diverticula may induce fibrosis that would otherwise not occur.

Also provided herein are methods for treating patients undergoing surgical, endoscopic or minimally invasive therapies where a medical implant is placed as part of the procedure. As described herein, it should be understood that "induces fibrosis" refers to a statistically significant increase (or clinically significant increase) in the amount of scar tissue around the implant or an improvement in the incorporation of the implant into the surrounding tissue and not to a permanent prohibition of any complications or failures of the implant.

Diagnosis of diverticular disease may be made by barium enema, which can outline radiographically the extent and severity of the diverticula. Typical radiological findings are sacculations with retained contrast and colonic spasm. Often the entire colon is affected, but the left and the sigmoid colon is most often affected. However, most bleeding diverticula occur on the right side of the body. Endoscopic examination can rule out concomitant lesions, and rigid sigmoidoscopy usually does not advance past the rectosigmoid junction. Colonoscopy allows for the differentiation from diverticular diseaseas, angiodysplasia or carcinoma. It also allows for direct visualization of the active bleeding site, which is ultimately found in up to 85% of patients with this technique. Colonoscopic interventions allow for direct visualization of the bleeding site and electrocoagulation of the site or irrigation with epinepherine. It also allows for the identification of other concomitant disease.

The compositions and implants provided herein may be delivered to the site of a diverticulum (e.g., via a catheter inserted through the sideport of a colonoscope for placement in the diverticulum) to treat infection, induce hemostasis, and/or to permanently to scar the diverticulum shut. The compositions may be delivered into the diverticulum directly or into tissue surrounding the diverticulum (e.g., by injection or via a catheter). In one embodiment, a fibrosing agent and/or an anti-infective agent may be combined with a haemostatic agent or loaded into a haemostatic composition to arrest bleeding or scar the diverticula shut. Representative examples of haemostatic agents and haemostatic compositions are described herein and include polymers (carrier polymers) e.g., CT3 (a composition comprising electrophilic and nucleophilic PEG derivatives and methylated collagen from Angiotech BioMaterials Corp., Palo Alto, Calif.) and commercially available surgical sealants, such as sprayable collagen-containing formulations, which include COSTASIS (Angiotech BioMaterials Corp.); sprayable PEG-containing formulations such as COSEAL or ADHIBIT (Angiotech BioMaterials Corp.); and fibrinogen-containing formulations such as FLOSEAL or TISSEAL (both from Baxter Healthcare Corporation, Fremont, Calif.); GELFOAM (Pharmacia & Upjohn Company, Kalamazoo, Mich.); and AVITINE (CR Bard, Inc., Plano, Tex.).

In one embodiment, the compositions may be in the form of sustained-release preparations (e.g., injectable compositions, sprays, and gels). Applicators and kits including the instant compositions for use in the treatment of diverticulitis also are provided. In another embodiment, the fibrosis-inducing agent and/or infective agent can be added to a cyanoacrylate adhesive that is then delivered to the diverticuli (such as described herein via a catheter using a colonoscope.

In certain embodiments, a fibrosis-inducing (scarring) agent, haemostatic agent, and/or infective agent (and compositions comprising one or more of these agents) can be included in a polymeric sealant spray, which solidifies into a film or coating to promote fibrosis and seal diverticuli. The spray, which includes a tissue adherent polymer containing a fibrosis-inducing agent, haemostatic agent, and/or infective agent may be prepared from microspheres as described above.

Numerous polymeric and non-polymeric carrier systems that can be used are described herein. These compositions can further comprise one or more fibrosis-inducing agents to promote the formation of granulation tissue. These compositions can further comprise one or more hemostatic agents to promote clotting and/or one or more anti-infective agents to prevent infection. For the in situ forming compositions, one or more fibrosis-inducing agent, haemostatic agent, and/or infective agent can be incorporated directly into the formulation to produced a suspension or a solution (e.g., silk powder, bleomycin) or the agent(s) can be incorporated into a secondary carrier (e.g., micelles, liposomes, micropsheres, microparticles, nanospheres, micropaticulates, emulsions and/or microemulations) that are then incorporated into the in situ-forming compositions. In another embodiment, the fibrosis-inducing agent, haemostatic agent, and/or infective agent can be electrostatically or covalently bound to one or more of the polymeric components of the in situ-forming composition.

In another embodiment, the fibrosis-inducing agent, haemostatic agent, and/or infective agent can be incorporated directly or via a secondary carrier into a gel or thermogel (e.g., hyaluronic acid, PLURONIC F127, polyester-PEG-polyester [PLGA-PEG-PLGA]. These gels can be applied to the treatment site prior or after the application of a sealant.

In another embodiment, the fibrosis-inducing agent, haemostatic agent, and/or infective agent can be incorporated into a biodegradable or dissolvable film or mesh that is then applied to the treatment site. An in situ-forming composition can then be sprayed over the film, thereby sealing the diverticulum and the film or mesh to the treatment site.

In another embodiment, the in situ sealant can be applied to the diverticuli after which a biodegradable or dissolvable film or mesh that comprises a fibrosis-inducing agent, haemostatic agent, and/or infective agent is applied to the treatment area. Exemplary materials for the manufacture of these films or meshes are hyaluronic acid (crosslinked or non-crosslinked), cellulose derivatives (e.g., hydroxypropyl cellulose), and crosslinked poly(ethylene glycol).

In another embodiment, the fibrosis-inducing agent, haemostatic agent, and/or infective agent can be an injectable form that can be injected directly into the diverticulum (treatment site) or tissue surrounding the treatment site. The fibrosis-inducing agent, haemostatic agent, and/or infective agent can be incorporated directly into the formulation to produce a suspension or a solution (e.g., silk powder, or bleomycin) or it can be incorporated into a secondary carrier (e.g., micelles, liposomes, micropsheres, microparticles, nanospheres, micropaticulates, emulsions and/or microemulations) that is then incorporated into the in situ-forming compositions. In another embodiment, the fibrosis-inducing agent, haemostatic agent, and/or infective agent can be electrostatically or covalently bound to one or more of the polymeric components of the in-situ forming composition. These injectable compositions can further comprise a polymer to enhance the viscosity of the solution. Polymers that can be used include hyaluronic acid, CMC, PLURONICs F127 as well as gels (normal and thermo gels) of the form X-Y, X-Y-X, or Y-X-Y where X is a degradable polyester and Y is a polyalkylene oxide, prefereably polyethylene glycol or the mono-methyl ether thereof. In another embodiment, the injectable formulation can further comprise a biocompatible solvent. These can include ethanol, DMSO, NMP, poly(ethylene glycol)-200, and/or poly(ethylene glycol)-300.

In another embodiment, the fibrosis-inducing agent may be in the form of a fiber, braid, coil, thread, monofilament fiber, or multifilament fiber that is introduced directly into the treatment site via a catheter or an endoscopic delivery device. For example, a silk braid can be delivered directly into the diverticulum.

In another embodiment, the fibrosis-inducing agent can be coated onto or incorporated into a polymeric fiber, braid, coil, thread, monofilament fiber, or multifilament fiber that is introduced directly into the treatment site via a catheter or an endoscopic delivery device. For example, a silk fiber can be incorporated into a Dacron braid that is then delivered directly into the diverticulum.

As described herein, potentially any adhesion or fibrosis-inducing agent described herein may be used alone, or in combination, in the practice of this embodiment. Exemplary fibrosing agents for use in compositions for treating diverticultis include talc, silk, chitosan, polylysine, fibroncectin, bleomycin, and CTFG, as well as analogues and derivatives of the aforementioned. Also as described herein, any fibrosis-inducing agent may be used with any of the numerous anti-infective agents known in the art and described herein, and any fibrosis-inducing agent may be used with any of the numerous haemostatic agents known in the art and described in detail herein. Any haemostatic agent may also be used with any anti-infective agent.

A variety of compositions and implants are described for the treatment of diverticulitis. As implants (e.g., compositions and devices) are made in a variety of configurations, forms, and sizes, the exact dose administered will vary with implant size, surface area, and design. However, certain principles can be applied in the application of this art. Drug dose can be calculated as a function of dose per unit area (of the portion of the implant being coated), total drug dose administered can be measured and appropriate surface concentrations of active drug can be determined. Regardless of the method of application or incorporation of the drug into implant or composition, the exemplary fibrosing agents, used alone or in combination with an anti-infective agent or haemostatic agent, may be administered under the following dosing guidelines.

Utilizing talc as an exemplary fibrosis-inducing agent, whether it is applied as a polymer coating, incorporated into the polymers which make up an implant, or applied with or without a polymeric carrier, the total dose of talc delivered from an implant or composition, or coated onto the surface of an implant, preferably does not exceed 100 mg (range of 1 µg to 100 mg). In one embodiment, the total amount of talc released from the composition or implant is in the range of 10 µg to 50 mg. The dose per unit area of the implant (i.e., the dosage of talc as a function of the surface area of the portion of the implant to which drug is applied and/or incorporated) falls within the range of 0.05 µg–10 µg per $mm^2$ of surface area coated. In another embodiment, talc is applied to an implant surface at a dose (amount) of 0.05 µg/$mm^{2-10}$ µg/$mm^2$ of surface area coated. As specific (polymeric and non-polymeric) drug delivery vehicles and specific implants release talc at differing rates, the above dosing parameters may be utilized in combination with the release rate of the drug from the composition or implant such that a minimum concentration of 0.01 nM–1000 µM of talc is delivered to the tissue. In another embodiment, talc is released from the surface of an implant such that fibrosis in the diverticulum is promoted for a period ranging from several hours to several months. For example, talc may be released in effective concentrations for a period ranging from 1 hour–30 days. Analogues and derivatives of talc (as described previously) with similar functional activity may also be utilized in the compositions and methods described herein; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied as a polymer coating, incorporated into the polymers which make up an implant, or applied with or without a polymeric carrier, the total dose of silk delivered from an implant or composition, or coated onto the surface of an implant, preferably not exceed 100 mg (range of 1 µg to 100 mg). In one embodiment, the total amount of silk released from the composition or implant is in the range of 10 µg to 50 mg. The dose per unit area of the implant (i.e., the dosage of silk as a function of the surface area of the portion of the implant to which drug is applied and/or incorporated) falls within the range of 0.05 µg–10 µg per $mm^2$ of surface area coated. In another embodiment, silk is applied to an implant surface at a dose of 0.05 $\mu g/mm^{2-10}$ $\mu g/mm^2$ of surface area coated. As specific (polymeric and non-polymeric) drug delivery vehicles and specific implants release silk at differing rates, the above dosing parameters may be utilized in combination with the release rate of the drug from the composition or implant such that a minimum concentration of 0.01 nM 1000 µM of silk is delivered to the tissue. In one embodiment, silk is released from the surface of an implant such that fibrosis in the diverticulum is promoted for a period ranging from several hours to several months. For example, silk may be released in effective concentrations for a period ranging from 1 hour–30 days. Analogues and derivatives of silk (as described previously) with similar functional activity can be utilized in the compositions and methods described herein; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied as a polymer coating, incorporated into the polymers which make up an implant, or applied with or without a polymeric carrier, the total dose of chitosan delivered from an implantor composition, or coated onto the surface of an implant, preferably does not exceed 100 mg (range of 1 µg to 100 mg). In one embodiment, the total amount of chitosan released from the composition or implant is in the range of 10 µg to 50 mg. The dose per unit area of the implant (i.e., the dosage of chitosan as a function of the surface area of the portion of the implant to which drug is applied and/or incorporated) is then within the range of 0.05 µg–10 µg per $mm^2$ of surface area coated. In another embodiment, chitosan is applied to an implant surface at a dose of 0.05 $\mu g/mm^{2-10}$ $\mu g/mm^2$ of surface area coated. As specific (polymeric and non-polymeric) drug delivery vehicles and specific implants will release chitosan at differing rates, the above dosing parameters may be utilized in combination with the release rate of the drug from the composition or implant such that a minimum concentration of 0.01 nM–1000 µM of chitosan is delivered to the tissue. In one embodiment, chitosan is released from the surface of an implant such that fibrosis in the diverticulum is promoted for a period ranging from several hours to several months. For example, chitosan may be released in effective concentrations for a period ranging from 1 hour–30 days. Analogues and derivatives of chitosan (as described previously) with similar functional activity can be utilized in the compositions and methods described herein; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied as a polymer coating, incorporated into the polymers which make up an implant, or applied with or without a polymeric carrier, the total dose of polylysine delivered from an implant or composition, or coated onto the surface of an implant, preferably does not exceed 100 mg (range of 1 µg to 100 mg). In one embodiment, the total amount of polylysine released from the composition or implant is in the range of 10 µg to 50 mg. The dose per unit area of the implant (i.e., the dosage of polylysine as a function of the surface area of the portion of the implant to which drug is applied and/or incorporated) then falls within the range of 0.05 µg–10 µg per $mm^2$ of surface area coated. In another embodiment, polylysine is applied to an implant surface at a dose of 0.05 $\mu g/mm^{2-10}$ $\mu g/mm^2$ of surface area coated. As specific (polymeric and non-polymeric) drug delivery vehicles and specific implants release polylysine at differing rates, the above dosing parameters may be utilized in combination with the release rate of the drug from the composition or implant such that a minimum concentration of 0.01 nM to 1000 µM of polylysine is delivered to the tissue. In one embodiment, polylysine is released from the surface of an implant such that fibrosis in the diverticulum is promoted for a period ranging from several hours to several months. For example, polylysine may be released in effective concentrations for a period ranging from 1 hour–30 days. Analogues and derivatives of polylysine (as described previously) with similar functional activity can be utilized for the compositions and methods described herein; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied as a polymer coating, incorporated into the polymers which make up an implant, or applied with or without a polymeric carrier, the total dose of fibronectin delivered from an implant or composition, or coated onto the surface of an implant, preferably does not exceed 100 mg (range of 1 µg to 100 mg). In one embodiment, the total amount of fibronectin released from the composition or implant is in the range of 10 µg to 50 mg. The dose per unit area of the implant (i.e., the dosage of fibronectin as a function of the surface area of the portion of the implant to which drug is applied and/or incorporated) then falls within the range of 0.05 µg–10 µg per $mm^2$ of surface area coated. In another embodiment, fibronectin is applied to an implant surface at a dose of 0.05 $\mu g/mm^{2-10}$ $\mu g/mm^2$ of surface area coated. As specific (polymeric and non-polymeric) drug delivery vehicles and specific implants will release fibronectin at differing rates, the above dosing parameters may be utilized in combination with the release rate of the drug from the composition or implant such that a minimum concentration of 0.01 nM 1000 µM of fibronectin is delivered to the tissue. In one embodiment, fibronectin is released from the surface of an implant such that fibrosis in the diverticulum is promoted for a period ranging from several hours to several months. For example, fibronectin may be released in effective concentrations for a period ranging from 1 hour–30 days. Analogues and derivatives of fibronectin (as described previously) with similar functional activity may also be utilized for the compositions and methods described herein; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied as a polymer coating, incorporated into the polymers which make up an implant, or applied with or without a polymeric carrier, the total dose of bleomycin delivered from an implant or composition, or coated onto the surface of an implant, preferably does not exceed 100 mg (range of 0.01 µg to 100 mg). In one embodiment, the total amount of bleomycin released from the composition or implant is in the range of 0.10 µg to 50 mg. The dose per unit area of the implant (i.e., the dosage of bleomycin as a function of the surface area of the portion of the implant to which drug is applied and/or incorporated) then falls within the range of 0.005 µg–10 µg per $mm^2$ of surface area coated. In another embodiment, bleomycin is preferably applied to an implant surface at a dose of 0.005 µg/$mm^{2-10}$ µg/$mm^2$ of surface area coated. As specific (polymeric and non-polymeric) drug delivery vehicles and specific implants will release bleomycin at differing rates, the above dosing parameters is utilized in combination with the release rate of the drug from the composition or implant such that a minimum concentration of 0.001 nM 1000 µM of bleomycin is delivered to the tissue. In one embodiment, bleomycin is released from the surface of an implant such that fibrosis in the diverticulum is promoted for a period ranging from several hours to several months. For example, bleomycin may be released in effective concentrations for a period ranging from 1 hour–30 days. Analogues and derivatives of bleomycin (as described previously) with similar functional activity can be utilized for the compositions and methods described herein; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTFG as an exemplary fibrosis-inducing agent, whether it is applied as a polymer coating, incorporated into the polymers which make up an implant, or applied with or without a polymeric carrier, the total dose of CTFG delivered from an implant or composition, or coated onto the surface of an implant, preferably does not exceed 100 mg (range of 0.01 µg to 100 mg). In one embodiment, the total amount of CTFG released from the composition or implant is in the range of 0.10 µg to 50 mg. The dose per unit area of the implant (i.e., the dosage of CTFG as a function of the surface area of the portion of the implant to which drug is applied and/or incorporated) then falls within the range of 0.005 µg–10 µg per $mm^2$ of surface area coated. In another embodiment, CTFG is applied to an implant surface at a dose of 0.005 µg/$mm^{2-10}$ µg/$mm^2$ of surface area coated. As specific (polymeric and non-polymeric) drug delivery vehicles and specific implants will release CTFG at differing rates, the above dosing parameters may be utilized in combination with the release rate of the drug from the composition or implant such that a minimum concentration of 0.001 nM 1000 µM of CTFG is delivered to the tissue. In one embodiment, CTFG is released from the surface of an implant such that fibrosis in the diverticulum is promoted for a period ranging from several hours to several months. For example, CTFG may be released in effective concentrations for a period ranging from 1 hour–30 days.

Analogues and derivatives of CTFG (as described previously) with similar functional activity can be utilized for compositions and methods described herein; the above dosing parameters are then adjusted according to the relative potency of the analogue or derivative as compared to the parent compound (e.g., a compound twice as potent as CTFG is administered at half the above parameters, a compound half as potent as CTFG is administered at twice the above parameters, etc.).

Agents which are tissue irritants such tissue as silk, silica, bleomycin, neomycin, talcum powder, metallic beryllium, and copper are particularly suitable for the practice of this invention. Other agents which may be incorporated into or onto the implant (e.g., a device) or released from the implant include extracellular matrix components such as fibrous structural proteins (e.g., fibrillar collagens, nonfibrillar collagen and elastins), adhesive glycoproteins (e.g., laminin and fibronectin), proteoglycans (e.g., heparin sulphate, chondroitin sulphate, dermatan sulphate), hyaluronan (e.g., hyaluronic acid), Secreted Protein Acidic and Rich in Cysteine (SPARC), Thrombospondins, Tenacin, Inhibitors of Matrix Metalloproteinases (e.g., TIMPs and synthetic TIMPs such as MARIMISTAT, BATIMISTAT, Doxycycline, Tetracycline, Minocycline, TROCADE, Ro-1130830, CGS 27023A, BMS-275291) and polylysine. Growth factors and inflammatory cytokines involved in angiogenesis, fibroblast migration, fibroblast proliferation, ECM synthesis and tissue remodeling such as Epidermal Growth Factor (EGF) Family, Transforming Growth Factor-α (TGF-α), Transforming Growth Factor-β (TGF-β-1, TGF-β-2, TGF-β-3), Platelet-derived Growth Factor (PDGF), Fibroblast Growth Factor (acidic—aFGF; and basic—bFGF), Bone Morphogenic Proteins, Activins, Vascular Endothelial Growth Factor (VEGF, VEGF-B, VEGF-C, Placental Growth Factor—PlGF), Angiopoietins, Insulin-like Growth Factors (IGF), Hepatocyte Growth Factor (HGF), Connective Tissue Growth Factor (CTGF), Myeloid Colony-stimulating Factors (CSFs), Granulocyte-Macrophage Colony-stimulating Factors (GM-CSF), Granulocyte Colony-stimulating Factor (G-CSF), Macrophage Colony-stimulating Factor (M-CSF), Erythropoietin, Interleukins (particularly IL-1, IL-8, IL-6), Tumor Necrosis Factor-α (TNFα), Nerve Growth Factor (NGF), Interferon-α, Interferon-β, and growth hormone (GH) are also suitable for release from specific implants described herein. Other agents that may be coated onto or released by the implant include adhesives such as cyanoacrylate or CT3.

Within related aspects of the present invention, implants, implantable tissue bulking agents, and other compositions are provided, wherein the implant releases an agent that induces fibrosis in vivo. "Release of an agent" refers to any statistically significant presence of the agent, or a subcomponent thereof, which has disassociated from the implant and/or remains active on the surface of (or within) the implant. Within yet other aspects of the present invention, methods are provided for manufacturing an implant, comprising the step of coating (e.g., spraying, dipping, wrapping, or administering drug through) an implant. Additionally, the implant can be constructed so that the implant itself is comprised of materials that induce fibrosis in or around the implant. A wide variety of implants may be utilized for the methods and compositions described herein, depending on the site and nature of treatment desired.

Within various embodiments, the implant is further coated with a composition or compound, which delays the onset of activity of the fibrosis-inducing agent for a period of time after implantation. Representative examples of such agents include heparin, PLGA/MePEG, PLA, and polyethylene glycol. Within further embodiments the fibrosis-inducing implant is activated before, during, or after deployment (e.g., an inactive agent on the implant is first activated to one that induces or accelerates an in vivo fibrotic reaction).

Any of the previously described fibrosis inducing agents, or derivatives and analogues thereof, can be utilized to create variations of the above compositions. The agent may also be used in a composition with or without a polymer carrier and that any one or more of the carriers described herein may be used in a composition with a fibrosing agent, anti-infective agent, and/or haemostatic agent.

Methods for Treating Diverticular Disease

Also provided by the present invention are methods for treating patients undergoing surgical, endoscopic, or minimally invasive therapies wherein a therapeutic agent or implant is delivered into a diverticula. Diverticular disease is a condition whereby there is herniation of the mucosa and submucosa of a hollow organ, such as the gastrointestinal (GI) tract, urinary tract or repiratory tract, which produces outpouchings through the muscular wall of the body passageway. Although diverticula can occur in any tubular organ, diverticular disease is of greatest clinical relevance in the lower GI tract (large bowel or colon) where it can cause life threatening inflammation and infection (diverticulitis) or bleeding (lower GI hemorrhage). Several specific clinical conditions, for example, diverticular disease including diverticulosis and diverticulitis, colonic diverticulosis, acute diverticulitis, GI hemorrhage, diverticular hemorrhage, appendicitis, Zenker's diverticulum (esophageal), Meckel's diverticulitis (small bowel abnormality), small bowel diverticulum, gastric diverticulum, and urinary diverticulum for which diverticula can be treated using the agents, formulations, and implants, described herein are described in greater detail below.

By way of example, a method to treat diverticular bleeding and thus to treat or prevent a diverticular disease in a host, such as a patient, may include the following. A patient exhibiting symptoms of a diverticular disease (e.g., abdominal pain and lower GI bleeding) may undergo either a physical or radiographic examination (e.g., X-ray, ultrasound, or a CT scan) or both to determine the extent of the diverticular disease. Once the patient is diagnosed with diverticular disease, a patient may be treated using the methods and compositions described herein immediately to induce fibrosis within the diverticulum to stop the bleeding or, alternatively, after the acute episode has subsided (e.g., any time up to about 6 weeks) to prevent the recurrence of a new bleed. To treat or prevent diverticular bleeding, a patient may be administered intravenous sedation (e.g., midazolam with either demerol or fentanyl) and then placed on the patient's left side. For example, when a colonic diverticulum is diagnosed and treated an end viewing colonoscope is advanced through the colon to inspect the entire bowel visually, identifying sites of diverticular disease and bleeding. Once the bleeding site(s) and pertinent diverticula are identified, a spray tip delivery catheter is introduced through the biopsy portal of the colonoscope. A variety of delivery catheters are described herein and used in the medical art.

The implant or composition(s) may be delivered to the diverticulum to induce fibrosis and to stop bleeding. For example, a spray tip catheter includes a syringe portion configured to contain the components of a multi-component therapy. The multi-component therapy (see description of kits herein) includes an in situ forming hemostatic composition (e.g., VITAGEL from Orthovita, Inc. (Malvern, Pa.), COSTASIS from Angiotech Pharmaceuticals, Inc. (Vancouver, BC)) and a mixing portion. The syringe portion is configured to combine and mix the components of the composition just prior to delivery into the diverticulum. Examples of mixing and dispensing devices that can be used in this procedure are described in a co-pending application PCT/US2004/037450. One or more components of the composition may also include a vasoconstrictive agent (e.g. epinephrine). The spray tip catheter is delivered to the treatment site through the portal of the colonoscope and manipulated to position the syringe tip inside the diverticulum or at the orifice of the diverticulum. The spray tip catheter plunger is pushed, activating the syringe, and delivering the composition to the diverticulum. Subsequent cross-linking of the composition occludes the lumen or orifice of the diverticulum, resulting in control of the bleeding.

In another embodiment, the method for treating a diverticular disease in a patient diagnosed with a diverticular disease, the following exemplary method may be performed. A patient is administered intravenous sedation (e.g., midazolam with either demerol or fentanyl) and then placed on their left side. When, for example, when treating colonic diverticular disease, an end viewing colonoscope is advanced through the colon to inspect the entire bowel visually and to locate diverticular openings in the bowel lumen. Once the opening(s) is identified, a sclerosing needle is advanced through the portal of the colonoscope. The needle is attached to a syringe that is loaded with an irrigation solution (e.g., saline), which can include an antiseptic agent (e.g., chlorhexadine), an antibiotic agent (e.g., gentamicin sulfate or doxycyline), and/or any other anti-infective agent (which are described herein), such as a chemotherapeutic agent with anti-microbial activity (e.g., 5-fluorouracil, doxorubicin, mitoxantrone, methotrexate, or etoposide), to eliminate bowel flora, including anaerobes and aerobes present in the diverticulum. The needle is advanced through the biopsy portal to the opening of the affected diverticulum. The diverticulum is gently irrigated with the irrigation solution. Once the diverticulum is cleared of debris (cells, fecal matter) the needle in the biopsy portal is replaced with a spray tip delivery catheter. The spray tip delivery catheter is used to deliver a multi-component in situ forming composition to the diverticulum, as described herein. Subsequent cross-linking of the composition partially or completely occludes the lumen or orifice of the diverticulum, thereby decreasing the probability of bleeding, infection, or inflammation.

Colonic Diverticulosis

Diverticulosis of the large bowel is an acquired condition that is extrememly common in the Western World. The incidence of diverticulosis increases with age—affecting 30% of people over the age of 60 and over 50% of people over the age of 80. Since the incidence of diverticulosis continues to increase, it is a significant healthcare problem for which very few new treatments have been developed.

Colonic diverticula are pouches of mucosa that protrude through the colonic musculature. Typically, the mucosa escapes through defects in the muscle where the vasa recta (the arteries that supply blood to the mucosa) penetrate through the colonic musculature. Diagnosis of diverticular disease can often be made by CT scan or by barium enema, which can outline radiographically the extent and severity of the diverticula. Typical radiological findings are sacculations with retained contrast and colonic spasm. Often the entire colon is affected, but the majority of diverticula occur in the sigmoid colon (95%), while right-sided diverticula (cecum and acending colon) are less common (6–7% of cases). Most patients with diverticulosis remain symptom-free, but 10–20% will develop complications such as infection (diverticulitits), fistulas (abnormal communication between 2 organs—most often between the colon and the bladder), bowel obstruction or hemorrhage. If symptomatic, the current treatment of diverticular disease involves open surgical resection of the affected segment of the colon; the methods described herein provide minimally-invasive treatments that can be performed as an alternative to surgery.

Acute Diverticulitis

In acute diverticulitis, without wishing to be bound by theory, a small fragment of stool (a fecalith) may become trapped within a diverticulum, which causes thinning of the diverticular wall and produces a localized (and contained) microperforation with infection and inflammation at the site of perforation. In some cases, the infection can progress to peridiverticular abscess formation, phlegmon, abdominal or pelvic abscess formation, and/or generalized peritonitis if free perforation occurs. Patients are characteristically treated with broad spectrum oral or intravenous antibiotics, but the localized nature of the disease lends itself well to the administration of the therapeutic interventions described herein, in conjunction with or alternatively to antibiotic treatment alone.

Colonoscopy (or in some cases CT scan, ultrasound, or other imaging technology) is used to identify the diverticula that has become infected. A catheter (several examples are described herein) is advanced through the side port of the endoscope (or under radiographic guidance) until is enters the lumen of the diverticula. Depending upon the catheter used, the luminal surface of the diverticulum may be disrupted by abrasion or the application of energy (RF, thermal, laser, ultrasound etc. as described herein) to facilitate healing and fibrosis. In cases in which the diverticulum is extremely inflamed and friable, these catheters are preferably not used because they will increase the risk of perforation; under these circumstances the therapeutic agent(s) may be administered via a single or multi-lumen drug-delivery catheter. The diverticulum is then infiltrated with an anti-infective agent and/or a fibrosis-inducing agent to treat the infection and/or encourage fibrosis and permanent filling/closure of the diverticulum. As described previously, it may also be beneficial to deliver the therapeutic agents in a sustained release preparation (or implant delivered into the lumen of the diverticulum) to fully treat the infection and promote complete healing of the diverticululm. Formulations that release the therapeutic agents for a minimum of 7 days, and preferably for 30–60 days and beyond, are particularly effective for this embodiment. In instances in which hemorrhage or risk or of hemorrhage is evident, a hemostatic agent may also be used in addition to the anti-infective or fibrosis-inducing agent(s).

In one embodiment, the fibrosis-inducing agent, anti-infective agent, and/or hemostatic may be delivered to the diverticulum through an abdominal endoscopic approach. In this embodiment, an endoscope is inserted into the abdomen (typically via the umbilicus) as part of a standard abdominal endoscopic procedure. The diverticulum is located, and an injection device that is delivered via the sideport of the endoscope pierces the outer wall of diverticulum such that it enters the lumen. The therapeutic agent(s) or composition is then injected via a catheter into the lumen of the diverticulum. Due to the risk of rupture, this method may be reserved for cases for which colonoscopy cannot be conducted.

Diverticular Hemorrhage

Diverticular bleeding occurs in 5–15% of patients who have diverticulosis, and in many (up to one third), the bleeding is substantial enough to cause cardiovascular instabllity. The precise cause of diverticular hemorrhage is unknown, but the close anatomic association of the diverticulum to the vasa recta is thought to be important. According to non-limiting theory, the site of the hemiations may be the same as the site of penetration of a nutrient artery, and the local inflammation of diverticulitis causes erosion of the artery wall. This approximation of the neck of the sack of the diverticulum and the arterial supply may be the reason for the massive hemorrhages observed in patients with diverticulosis. The average age of a patient at the time of diverticular hemorrhage is 65. As a result, mortality and morbidity is high (10% to 20%), in part due to patient comorbidity with other conditions such as cardiac, pulmonary, renal disease.

Diagnosis is made by barium enema, which can radiographically outline the extent and severity of the diverticula present. The right colon is the most common source of bleeding and is the cause in 48% to 90% of patients. Emergency angiography is appropriate for patients with brisk bleeding (0.5 ml–1.0 ml/min). Evaluation begins with examination of the mesenteric artery (because right colon bleeds are most common) and followed by examination of the inferior mesenteric artery and the celiac artery. Angiography not only has a high predictive value, but it also enables the detection of other causes of GI hemorrhage such as angiodysplasia, tumors or diffuse mucosal bleeds. Angiography can also be used therapeutically for the introduction of vasospastic substances or selective embolization. Risks associated with vasospastic substances include a re-bleeding rate of 50% in patients after withdrawal of the therapy, decreased coronary perfusion, hypertension and cardiac arrythmias; embolization can sometimes stop the bleeding but it is associated with colon infarctions. Nuclear scanning with technetium is used diagnostically in the detection of the source of slow bleeds (i.e. when the rate of bleeding is less than 0.1 ml/min).

Generally diverticular bleeds are massive, painless, and self limiting. Patients are treated supportively with volume resuscitation, correction of coagulation abnormalities, and transfusion if required. Patients frequently require multiple blood transfusions and the average patient receives 7.6 Units of packed cells per episode of bleeding. Fortunately, diverticular bleeding stops spontaneously in 70 to 95% of cases by using supportive measures only. Generally, bleeding stops in 99% of patients if they require less than 4 Units of blood within the first 24 hours. Approximately 15% of patients will continue to be unstable despite aggressive resuscitation and will require surgery in an to attempt to stop the bleeding, but this is associated with a very high mortality rate (14% to 38%). Unfortunately, recurrent episodes of hemorrhage requiring a second hospital admission are also common and occur in 25% of patients who have had a previous diverticular hemorrhage. After a second bleeding episode, the risk of recurrence increases further to the point where the chance of a having a third hemorrhage increases to over 50%. Thus, a significant need exists for a therapy that can be used acutely to control bleeding, as well as a need for a treatment that reduces the risk that a patient will suffer a subsequent hemorrhage.

Endoscopic examination can determine the presence of concomitant lesions such as malignancy and angiodysplasia. Colonoscopy allows for direct visualization of the active bleeding site, which is ultimately found in up to 85% of patients with this technique. Colonoscopic interventions allow for direct visualization of the bleeding site, electrocoagulation of the bleeding site, irrigation of the area with epinephrine and identification of other concomitant disease. For the purposes of the methods described herein, colonoscopy (or in some cases CT scan, ultrasound, or other imaging technology) is used to identify the diverticula that is the source of the bleeding. A specialized catheter (described in a previous section) is advanced through the side port of the endoscope (or under radiographic guidance) until it enters the lumen of the diverticula where the hemorrhage originates. Depending upon the catheter used, the luminal surface of the diverticulum may be disrupted by abrasion or the application of energy (RF, thermal, laser, ultrasound etc. as described herein) to facilitate thrombosis and initiate healing and fibrosis. In instances in which the diverticulum is extremely inflamed and friable, these catheters are preferably not used because they will increase the risk of perforation; under these circumstances the therapeutic agent(s) may be administered via a single or multi-lumen drug-delivery catheter. The diverticulum is then infiltrated with a hemostatic agent alone or in combination with a fibrosis-inducing agent to encourage fibrosis and permanent filling/closure of the diverticulum and/or an anti-infective agent to treat or prevent infection. As described previously, it may also be beneficial to deliver the therapeutic agents in a sustained release preparation (or implant delivered into the lumen of the diverticulum) to fully treat the hemorrhage, promote complete healing of the diverticululm, and/or reduce the incidence of infection. Formulations that release the therapeutic agents for a minimum of 7 days, and preferably for 30–60 days and longer, are particularly effective for this embodiment. The ideal implant not only induces hemostasis in the management of acute bleeding, but is capable of inducing permanent healing and fibrosis, thereby reducing the risk and incidence of subsequent (recurrent) hemorrhage.

Minimally-Invasive Treatment of Appendicitis

Although not a true diverticula, the appendix is similar in many ways and suitable for treatment using the compositions, implants and methods of the present invention. The appendix is a blind-ended pouch off of the cecum that usually causes no clinical problems. However, like a diverticulum, the neck of the appendix can become obstructed by a fecalith, causing thinning of the appendix wall and producing a localized (and contained) microperforation with infection and inflammation at the site of perforation (acute appendicitis). In some cases, the infection can progress to abscess formation and/or generalized peritonitis if free perforation occurs (perforated appendix). Acute appendicitis, with or without perforation, is a medical emergency that requires surgical removal of the appendix.

Minimally-invasive treatment of appendicitis is conducted in the same manner as described previously for diverticulitis. Briefly, colonoscopy (or in some cases CT scan, ultrasound, or other imaging technology) is used to locate the appendix in the cecum. A specialized catheter (described in the previous section) is advanced through the side port of the endoscope (or under radiographic guidance) until it enters the lumen of the appendix. Depending upon the catheter used, the luminal surface of the appendix may be disrupted by abrasion or the application of energy (RF, thermal, laser, ultrasound etc. as described above) to facilitate healing and fibrosis. In cases where the appendix appears thinned or is friable, these catheters are preferably not be used because they will increase the risk of perforation; under these circumstances the therapeutic agent(s) are administered via a single or multi-lumen drug-delivery catheter. The appendix is then infused with a fibrosis-inducing agent or composition to encourage fibrosis and permanent filling/closure of the appendix. In cases of acute appendicitis, an anti-infective agent (with or without a hemostatic agent) should also be delivered as part of the treatment. As described previously, it may also be beneficial to deliver the therapeutic agents in a sustained release preparation (or implant) into the lumen of the appendix to promote complete healing. Formulations that release the therapeutic agents for a minimum of 7 days, and preferably for 30 to 60 days and beyond, are particularly effective for this embodiment.

Although classically described as occurring in the large bowel, it should be noted that diverticula may occur in any tubular body organ such as other segments of the gastrointestinal tract, the respiratory tract, and the urinary tract. As described for colonic diverticulum above, these diverticular diseases can be treated with minimally-invasive, locally delivered, fibrosis-inducing agents, anti-infective agents, and/or hemostatic agents and compositions comprising one or more of these agents. Examples of non-colonic diverticular diseases include, but are not limited to, the following.

In one embodiment, the fibrosis-inducing agent, anti-infective agent, and/or hemostatic can be delivered to the diverticulum or appendix through an abdominal endoscopic approach. In this embodiment, an endoscope is inserted into the abdomen (typically via the umbilicus) as part of a standard abdominal endoscopic procedure. The appendix or diverticulum is located, and an injection device that is delivered via the sideport of the endoscope pierces the outer wall of the appendix or diverticulum such that it enters the lumen. The therapeutic agent(s) or composition is then injected via a catheter into the lumen of the diverticulum or appendix. Due to the risk of rupture, this method may be reserved for cases for which colonoscopy cannot be conducted.

Treatment of Intra-Abdominal and Pelvic Abscesses

In another embodiment, compositions and methods are provided for accessing and treating intra-abdominal and pelvic abscesses. Using CT or ultrasonic guidance, a needle may be used to cannulate the abscess. The needle may include an echogenic coating to enhance visibility. The contents of the abscess may then be drained through a syringe, attached to the needle. The abscess may be irrigated with a solution that includes an anti-infective such as an antibiotic to treat any infection associated with the abscess. After the abscess has been cannulated, a composition that includes a fibrosing agent as described herein may be delivered into the abscess to seal and fill and to seal off the abscess. In one embodiment, the composition is an in situ forming polymer (e.g., COSTASIS). In another embodiment, the composition is an adhesive (e.g., CT3 or a cyanoacrylate, which are described herein). An anti-infective agent (e.g., an antibiotic or chemotherapeutic agent) may be included in the fibrosing composition to prevent the recurrence of infection at the treatment site.

Esophageal (Zenker's) Diverticulum

Zenker's Diverticulum is a diverticular pouch created by hemeation of the pharangeal mucosa through a defect in the muscular coat (hemeation through Killian's dehiscence which is bound by the thyropharangeus muscle and the cricopharangeus muscle). Zenker's Diverticulum can enlarge; compress the esophagus, and cause dysphagia (difficulty swallowing and eating), regurgitation of undigested food following meals, aspiration, and cough.

Although often treated conservatively, in some patients the symptoms are severe enough that the diverticulum must be surgically corrected. Typically, this is accomplished through an open surgical approach with the patient under general anesthetic. The pouch is identified beneath the stemomastoid muscle, the neck of the pouch is transected, the entire pouch is removed, and the defect in the pharynx closed with sutures.

Alternatively, a Zenker's Diverticulum can be accessed endoluminally using endoscopy. According to the methods described herein, injectable compositions that include a bulking or filling agent and a fibrosing agent may be directly injected into a Zenker's Diverticulum. While the patient (host) is under general anesthesia or sedation, a bivalved esophageal speculum is inserted such that the anterior blade is positioned in the esophageal lumen and the posterior blade is placed in the pouch. An endoscope can be advanced into the lumen of the diverticulum allowing the pouch to be visualized and thoroughly irrigated to remove any contents. Once the diverticulum has been fully visualized and prepared, a fibrosis-inducing agent, anti-infective agent, and/or a haemostatic agent, or composition of same, (and/or a polymer and/or a bulking agent) can be infiltrated into the lumen of the diverticulum via a sideport of the endoscope. As described previously, a suitable injectable material containing a fibrosis-inducing agent is injected into the diverticulum (alone or in combination with polymeric carrier, which may be in the form of, for example, a gel, paste, or spray) in order to enhance scarring and permanently close the Zenker's Diverticulum (for example, without wishing to be bound by theory, by inducing the production of fibrous tissue that fills and closes the diverticular sac), such that the patient's dysphagia is diminished or relieved. Suitable therapeutic agents, polymers, and formulations for the practice of this method are the same as those described previously for diverticulitis.

Meckel's Diverticulitis

Meckel's diverticulum (a persistence of an embryonic structure—the omphalomesenteric duct) is the most common small bowel congenital abnormality. It occurs in 2% of the population and is found 60 cm from the ileocecal valve in the terminal ileum. When inflamed and infected, Meckel's diverticulum mimics appendicitis clinically and often presents in young children (2 years of age). In some patients the symptoms are severe enough that the diverticulum must be surgically removed—particularly if it causes GI bleeding. Typically, this is accomplished through an open abdominal surgical approach under general anesthetic where the diverticulum is identified, the neck of the pouch is transected, the entire pouch is removed, and the defect in the ileum closed with sutures.

Alternatively, a Meckel's Diverticulum can be accessed endoluminally using endoscopy. According to the methods and compositions described herein, injectable compositions that include a fibrosing agent, a hemostatic agent, and/or an anti-infective agent may be directly injected into a Meckel's Diverticulum. While a patient is under general anesthesia or sedation, an endoscope can be advanced into the lumen of the diverticulum, allowing the pouch to be visualized and then thoroughly irrigated to remove any contents. Once the diverticulum has been fully visualized and prepared, a fibrosis-inducing, anti-infective and/or hemostatic composition (and/or a polymer and/or a bulking agent) can be infiltrated or introduced into the lumen of the diverticulum via a sideport of the endoscope. As described previously, a suitable injectable material containing a fibrosis-inducing agent, anti-infective agent, and/or hemostatic agent is injected into the diverticulum (alone or in combination with a bulking agent or a polymeric carrier, which may be in the form, for example, of a gel, paste, or spray) in order to enhance scarring and permanently close the Meckel's Diverticulum (e.g., by inducing the production of fibrous tissue which fills and closes the diverticular sac), such that the patient's symptoms are relieved. Suitable therapeutic agents, polymers, and formulations for the practice of this method are the same as those described previously for diverticulitis.

Small Bowel Diverticulum

Small bowel diverticulosis is thought to be relatively uncommon (1% of the population) and most patients are asymptomatic. However, small bowel diverticual can produce life-threatening complications when symptomatic. Duodenal diverticula are the most common, are usually solitary, and tend to occur in the second portion of the duodenum. Jejunoileal diverticula tend to be multiple and most are found in the proximal jejunum. When the diverticula become obstructed and inflamed, the symptoms mimic pancreatitis or cholecystitis, and in some cases perforation can occur. Operative treatment is risky and not generally indicated due to the high incidence of pancreatobiliary complications (biliary duct damage, pancreatitis, etc).

Alternatively, a small bowel diverticulum endoluminally can be accessed using endoscopy (ERCP). According to the methods and compositions described herein, injectable compositions that include a fibrosing agent, a hemostatic agent, and/or an anti-infective agent may be directly injected into a small bowel diverticulum. When a patient is under general anesthesia or sedation, an endoscope can be advanced into the lumen of the diverticulum, allowing the pouch to be visualized and thoroughly irrigated to remove any contents. Once the diverticulum has been fully visualized and prepared, a fibrosis-inducing, anti-infective and/or hemostatic composition can be infiltrated into the lumen of the diverticulum via a sideport of the endoscope. As described previously, a suitable injectable material containing a fibrosis-inducing agent, anti-infective agent, and/or hemostatic agent is injected into the diverticulum (alone or in combination with a bulking agent and/or a polymer or polymeric carrier, which may be in the form, for example of a gel, paste, or spray) in order to enhance scarring and permanently close the small bowel diverticulum (e.g., by inducing the production of fibrous tissue which fills and closes the diverticular sac), such that the patient's symptoms are relieved. Suitable therapeutic agents, polymers, and formulations for the practice of this method are the same as those described previously for diverticulitis.

Gastric Diverticulum

Gastric diverticula are uncommon and most are asymptomatic. However, gastric diverticula can produce complications such as hemorrhage, obstruction, and perforation when symptomatic.

Alternatively, a gastric diverticulum may be accessed endoluminally using a gastroscope. According to the methods and compositions described herein, injectable compositions that include a fibrosing agent, a hemostatic agent, and/or an anti-infective agent may be directly injected into a gastric diverticulum. When a patient is under general anesthesia or sedation, a gastroscope can be advanced into the lumen of the diverticulum, allowing the pouch to be visualized and thoroughly irrigated to remove any contents. Once the diverticulum has been fully visualized and prepared, a fibrosis-inducing, anti-infective and/or hemostatic composition can be infiltrated into the lumen of the diverticulum via a sideport of the endoscope. As described previously, a suitable injectable material containing a fibrosis-inducing agent, anti-infective agent and/or hemostatic agent is injected into the diverticulum (alone or in combination with a bulking agent and/or a polymer or polymeric carrier, which may be in the form, for example of a gel, paste, or spray) in order to enhance scarring and permanently close the gastric diverticulum (e.g., by inducing the production of fibrous tissue which fills and closes the diverticular sac), such that the patient's symptoms are relieved. Suitable therapeutic agents, polymers and formulations for the practice of this method are the same as those described previously for diverticulitis.

Urinary Diverticulum

Urinary diverticula are common (particularly in the bladder, occasionally in the ureters) and most are asymptomatic. However, urinary diverticula can produce complications such as hemorrhage, obstruction, and perforation when symptomatic.

Alternatively, a urinary diverticulum can be accessed endoluminally using cystoscopy. According to the methods and compositions described herein, injectable compositions that include a fibrosing agent, a hemostatic agent, and/or an anti-infective agent may be directly injected into a urinary diverticulum. When a patienet is under general anesthesia or sedation, a cystoscope can be advanced into the lumen of the diverticulum, allowing the pouch to be visualized and thoroughly irrigated to remove any contents. Once the diverticulum has been fully visualized and prepared, a fibrosis-inducing, anti-infective and/or hemostatic composition can be infiltrated into the lumen of the diverticulum via a sideport of the endoscope. As described previously, a suitable injectable material containing a fibrosis-inducing agent, anti-infective agent and/or hemostatic agent is injected into the diverticulum (alone or in combination with a bulking agent and/or a polymer or polymeric carrier, which may be in the form, for example of a gel, paste, or spray) in order to enhance scarring and permanently close the urinary diverticulum (e.g., by inducing the production of fibrous tissue which fills and closes the diverticular sac), such that the patient's symptoms are relieved. Suitable therapeutic agents, polymers, and formulations for the practice of this method are the same as those described previously for diverticulitis.

Elective Treatment of Diverticula

As described previously, diverticulosis is an extremely common condition that can be easily diagnosed with routine diagnostic tests such as barium enema or colonoscopy. Also, most patients with symptomatic diverticulitis or GI hemorrhage from diverticular disease are often initially treated with non-surgical, non-curative treatments, for example, systemic antibiotics for treatment of diverticulitis, and adminstration of fluids, transfusion, and supportive care for GI hemorrhage. Patients with established symptomatic diverticular disease are also at an increased risk for subsequent complications. For example, 25% of patients who have had a previous diverticular hemorrhage will have a second one, while the chance of a having a third hemorrhage is over 50%. Therefore, a large number of patients have an established diverticular disease and are at risk for developing significant complications from their disease. At present, the only preventative therapy available to these patients is elective resection of the affected portion of the colon. Not only is this an extremely invasive procedure, but many patients who would benefit from surgical resection of their diverticula are often not surgical candidates because of age, frailty as a result of blood loss, or other concurrent medical conditions. Therefore, surgical resection of the segment of the colon containing the diverticula is a therapy that is not applicable to many patients. Thus, a significant need exists for a minimally-invasive, curative therapy that can be used as a preventative treatment in diverticulosis patients to reduce the risk of subsequent complications (such as repeat hemorrhage).

The methods, compositions, agents, and implants described herein are suitable for preventative management of diverticulosis. The methods described herein may be performed while a patient is under light sedation (i.e., it does not require general anesthesia) and the methods are minimally-invasive (e.g., colonoscopy or radiographic guidance), making the methods suitable for patients who are not surgical candidates. Also, the therapeutic agents or drug-impregnated implants (or biomaterials) that induce adhesion or fibrosis in the walls of the diverticula facilitate "filling" of the diverticula in situ, thus, obliterating the lumen of the diverticula and reducing the risk that subsequent complications will develop (infection or hemorrhage). The addition of anti-infective agents and/or hemostatic agents can further increase the efficacy of the procedure depending upon the clinical circumstances. Permanent closure and scarring of the diverticula may be curative in many patients (i.e., by eliminating the diverticular sac where infection, inflammation, or and/or hemorrhage can occur) and may have an efficacy such that an alternative approach to open surgical resection (and its complications) is provided.

Elective diverticular treatment is conducted in the same manner as described for diverticulitis and hemorrhage. Briefly, colonoscopy (or in some cases CT scan, ultrasound, or other imaging technology) is used to identify the diverticula. A catheter as described herein is advanced through the side port of the endoscope (or under radiographic guidance) until it enters the lumen of the diverticula. Depending upon the catheter used, the luminal surface of the diverticulum may be disrupted by abrasion or the application of energy (RF, thermal, laser, ultrasound etc. as described above) to facilitate healing and fibrosis. In instances in which the diverticulum appears thinned or is poorly visualized, these catheters are preferably not used because they will increase the risk of perforation. Under these circumstances the therapeutic agent(s) may be administered via a single or multi-lumen drug-delivery catheter. The diverticulum is then infused with a fibrosis-inducing agent or composition to encourage fibrosis and permanent filling/closure of the diverticulum. In some cases an anti-infective agent and/or a hemostatic agent may be delivered as part of the treatment. As described previously, it may also be beneficial to deliver the therapeutic agents in a sustained release preparation (or implant) into the lumen of the diverticulum to promote complete healing. Formulations that release the therapeutic agents for a minimum of 7 days, and preferably for 30 to 60 days and beyond, are particularly effective for this embodiment.

Kits for Delivering Agents and Compositions

In one embodiment, the agents (such as a fibrosing agent) and compositions described herein are packaged in kits, which are used for introducing or delivering an anti-fibrosing agent into a diverticulum. The kit may include buffer solutions, as well as written or otherwise illustrated instructions for use. A typical kit for use in medical applications, comprises: (a) a homogeneous dry powder composition comprised of: (i) a first component having a core substituted with m nucleophilic groups, where m=2; and (ii) a second component having a core substituted with n electrophilic groups, where n=2 and m+n>4; wherein the nucleophilic and electrophilic groups are non-reactive in a dry environment but are rendered reactive upon exposure to an aqueous environment such that the components inter-react in the aqueous environment to form a three-dimensional matrix; (b) a first buffer solution having a pH within the range of about 1.0 to 5.5; and (c) a second buffer solution having a pH within the range of about 6.0 to 11.0; wherein each component is packaged separately and admixed immediately prior to use. Prior to use, each component preferably remains in a separate sterile package.

In another embodiment, the kit may further comprise a delivery system that will allow the composition to be delivered as a spray. The spray can be generated by manually mixing the components and passing them through a spray nozzle. The spray generation can also be accomplished by using a flow of gas (for example, air, nitrogen, carbon dioxide).

In one embodiment, the kit includes a delivery system for the compositions described herein. Delivery devices that may be included in the kits include a multi-component syringe device and/or a pressurized delivery devices as described herein.

In another embodiment of the kit, a multi-component syringe device is included in the kit. As described herein, the multi-component spray device may be a multiple-compartment syringe system having multiple barrels, a mixing head, and an exit orifice, wherein the dry powder composition, the first buffer, and the second buffer are housed separately in the multiple-compartment syringe system.

In another embodiment of the kit, a pressurized delivery device is included in the kit. As previously described, the pressurized delivery device of the present invention includes a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet.

Kits contemplated under the present invention are not limited to the devices described herein and may also include any other suitable delivery device known in the art of drug delivery.

In certain embodiments, a therapeutic agent, such as a fibrosing agent, is included in a kit for delivering such an active agent into a host, particularly within a diverticulum of a host. The fibrosing agent may be mixed with the components to form a homogeneous mixture or the fibrosing agent may be packaged separately. The kit as described herein may be used in the treatment of a diverticular disease. In one embodiment, the mixture of the therapeutic agent(s) with the components is a homogeneous mixture. Whether packaged together or separately, each of the components and the fibrosing agent should be in sterile packages prior to use.

The kit may be used in the methods described herein, which entail applying the composition to the damaged tissue or organ to seal gastrointestinal tract, esophageal tissue, or pancreatic tissue to stop or minimize the leakage of fecal (GI tract) or tissue contents. The kit may also be used to seal urinary tract (e.g., bladder or urethra) to stop or minimize the leakage of urine. The compositions can be used 1) by applying them to the surface of one tissue and then a second tissue may be rapidly pressed against the first tissue or 2) by bringing the tissues in close juxtaposition and then applying the compositions. In addition, the compositions can be used to fill spaces in soft and hard tissues that are created by disease or surgery.

Therefore, one embodiment of the invention is a method of sealing tissue of a patient comprising the steps of: (a) providing a composition as described herein; (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution to form a mixture; and (c) placing the mixture into contact with tissue and allowing a three-dimensional matrix to form and seal the tissue. In another embodiment, the compositions can be applied in conjunction with an implanted medical device such that it prevents the leakage of gases, liquids or solids from the device or from the device-tissue interface.

Thus, in certain embodiments, the composition is combined with a fibrosing agent to further enhance the properties of the sealant or adhesive. In one embodiment, a fibrosing (i.e., scarring) agent can be included in a polymeric sealant spray that solidifies into a film or coating to promote fibrosis and seal air leaks. Exemplary fibrosing agents, which are described herein in detail, include talc, silk, wool, chitosan, polylysine, fibronectin, bleomycin, and connective tissue growth factor (CTGF), as well as analogues and derivatives of the aforementioned.

Pharmaceutically Acceptable Carrier

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier or excipient known to those of ordinary skill in the art may be employed in the pharmaceutical compositions described herein. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration.

A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose.

Pharmaceutical compositions may be administered in a manner appropriate to the disease to be treated (or prevented) as determined by persons skilled in the medical arts. As described herein, an appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose is chosen that is sufficient to prevent, delay the onset of, or diminish the severity of a diverticular disease. Optimal doses may generally be determined using experimental models and/or clinical trials. The optimal dose may depend upon the body mass, weight, or blood volume of the patient.

Delivery Systems

Multi-Compartment Devices

Suitable delivery systems for the homogeneous dry powder composition and the two buffer solutions may involve a multi-compartment device, where one or more compartments contain the powder and one or more compartments contain the buffer solutions needed to provide for the aqueous environment, so that the composition is exposed to the aqueous environment as it leaves the compartment. Many devices that are adapted for delivery of multi-component tissue sealants/hemostatic agents are well known in the art and can also be used in the practice of the present invention. Alternatively, the composition can be delivered using any type of controllable extrusion system, or it can be delivered manually in the form of a dry powder, and exposed to the aqueous environment at the site of administration.

The homogeneous dry powder composition and the two buffer solutions may be conveniently formed under aseptic conditions by placing each of the three ingredients (dry powder, acidic buffer solution and basic buffer solution) into separate syringe barrels. For example, the composition, first buffer solution and second buffer solution can be housed separately in a multiple-compartment syringe system having a multiple barrels, a mixing head, and an exit orifice. The first buffer solution can be added to the barrel housing the composition to dissolve the composition and form a homogeneous solution, which is then extruded into the mixing head. The second buffer solution can be simultaneously extruded into the mixing head. Finally, the resulting composition can then be extruded through the orifice onto a surface.

For example, the syringe barrels holding the dry powder and the basic buffer may be part of a dual-syringe system, e.g., a double barrel syringe as described in U.S. Pat. No. 4,359,049 to Redl et al. In this embodiment, the acid buffer can be added to the syringe barrel that also holds the dry powder, so as to produce the homogeneous solution. In other words, the acid buffer may be added (e.g., injected) into the syringe barrel holding the dry powder to thereby produce a homogeneous solution of the first and second components. This homogeneous solution can then be extruded into a mixing head, while the basic buffer is simultaneously extruded into the mixing head. Within the mixing head, the homogeneous solution and the basic buffer are mixed together to thereby form a reactive mixture. Thereafter, the reactive mixture is extruded through an orifice and onto a surface (e.g., tissue), where a film is formed, which can function as a sealant or a barrier, or the like. The reactive mixture begins forming a three-dimensional matrix immediately upon being formed by the mixing of the homogeneous solution and the basic buffer in the mixing head. Accordingly, the reactive mixture is preferably extruded from the mixing head onto the tissue very quickly after it is formed so that the three-dimensional matrix forms on, and is able to adhere to, the tissue.

Other systems for combining two reactive liquids are well known in the art, and include the systems described in U.S. Pat. No. 6,454,786 to Holm et al.; U.S. Pat. No. 6,461,325 to Delmotte et al.; U.S. Pat. No. 5,585,007 to Antanavich et al.; U.S. Pat. No. 5,116,315 to Capozzi et al.; U.S. Pat. No. 4,631,055 to Redl et al.; and U.S. Patent Application Publication No. 2004/0068266 to Delmotte.

Pressurized Delivery Devices

Other delivery systems for dispensing the multicomponent compositions of the invention may include pressurized delivery devices, examples of which are described in commonly owned co-pending U.S. patent application Ser. No. 10/957,493, filed on Oct. 1, 2004, and entitled "Mixing and Dispensing Fluid Components of a Multicomponent Composition." Such a pressurized delivery device may include a diffuser surface having an outlet extending therethrough that is positioned downstream from a plurality of inlets. While at least one inlet is adapted to communicate with a source of a pressurized carrier fluid, each of a plurality of inlets is adapted to communicate with a source of a different fluid component. Using this device, the dry powder solution is premixed with the first buffer to form a homogeneous solution as previously described and this solution is subsequently communicated with a first fluid component. The second fluid component will communicate with the second buffer solution previously described. Once the diffuser surface receives fluid components from the inlets, each received fluid component is pushed toward the outlet for mixing and dispensing therethrough by the pressurized carrier fluid, typically a gas such as air, from the carrier fluid inlet. The diffuser surface and the inlets may represent components of a mixing nozzle.

In general, there are two categories of gas enhanced nozzles for dispensing reactive components of a multicomponent composition—those that involve internal mixing and those that involve external mixing. When the diffuser surface is a part of a nozzle, the nozzle may be considered an internal-mixing nozzle. Unlike other internal-mixing technologies, the internal-mixing nozzle of the pressurized delivery device of the present invention provides several features that serve individually and collectively to eliminate clogging. For example, a diffuser surface typically has a shape effective to direct and maintain each received fluid component in a different flow path on the diffuser surface toward the outlet for mixing therein and dispensing therethrough. Due to the minimal residence time of the mixture within the nozzle, reactive components do not have time to set and clog the nozzle before the mixture is forced out of the nozzle by the pressurized carrier fluid. In addition, the outlet may be aligned with any or all of the carrier fluid inlets that may be present in the nozzle to direct the pressurized carrier fluid in a manner that enhances fluid component mixing and to expel the mixture in a jet like manner. As the orientation of the diffuser surface relative to the inlets affects the performance of the device, the diffuser surface may be permanently affixed or immobilized with respect to the inlets; however, when the diffuser surface is detachable from the inlets, the nozzle may be disassembled to facilitate cleaning and/or replacement of parts. For example, the diffuser surface may be replaceable/and or disposable. Nevertheless, when the pressurized delivery device of the present invention has diffuser surface that is detachable from the inlets, the device may be constructed to allow assembly of the components in only configurations that align the diffuser surface to the inlets such that the performance of the device is optimized.

In general, any of a number of carrier fluids may be employed with the pressurized delivery device of the present invention. For example, the carrier fluid may be gaseous and/or liquid in nature. Typically, however, the carrier fluid is chemically inert with respect to the fluid components. Suitable inert gases include, without limitation, air, carbon dioxide, nitrogen, argon, helium, gaseous perfluorinated alkanes and ethers, gaseous chlorofluorocarbons and the like. Suitable inert liquids include, without limitation, polysiloxanes, perfluroinated polyethers, and the like. Pressurized air represents an economical and practical carrier fluid for use with the pressurized delivery device. Equipment associated with pressurized air is well known in the art and may include pressurized tanks or cylinders as well as compressors. In some instances, one or more check valves, e.g., one-way valves, may be provided to prevent back flow of fluid component resulting from pressure buildup associated with the use of the pressurized delivery device. Such check valves may be positioned upstream from the diffuser surface, e.g., within lumens associated with the inlets. Such check valves are particularly useful when inlet lumens are short, e.g., about 2 to about 5 centimeters in length, because the potential for back flow tends to be inversely proportional to the length of the lumens; however, check valves may be employed with longer lumens as well.

The portions of the device that contact multicomponent composition and the fluid components thereof are preferably inert and repellant to the materials contacted. Thus, portions of the device that contact the fluids in operation are selected according to what is appropriate for the particular fluids. For example, the device or components thereof may be made from a plastic such as polycarbonates, polyurethane, polyesters, acrylics, ABS polymers, polysulfone, and the like. Adhesion inhibiting coatings such as polysiloxanes, perfluorinated polymers, and the like may be used as well. Thus, the diffuser surface is typically inert and optionally repelling to the fluid components. Similar, lumen surfaces that may contact the fluid components or the carrier fluid are typically inert and optionally repelling to the corresponding fluid as well.

The pressurized delivery device of the present invention is particularly useful for dispensing multicomponent compositions. While some gaseous components may be used, the pressurized delivery device is particularly useful for liquids. Thus, at least one fluid component is usually a liquid. Often, each fluid component includes a liquid. For example, the pressurized delivery device is useful to dispense composition such as fluid mixtures, wherein the mixing of a plurality of fluids results in an increase in viscosity sufficient to impair mixture flow. Such compositions may be formed from fluid components that are chemically reactive with respect to each other. In some instances, a crosslinking agent may be provided.

In practice, then, a diffuser surface having an outlet extending therethrough such that the diffuser surface is downstream from a plurality of fluid component inlets and at least one carrier fluid inlet. A different fluid component is directed from each of the fluid component inlets toward the diffuser surface. In some instances, fluid components are directed at substantially the same flow rate toward the diffuser surface. Altematively, the fluid components are directed at different flow rates toward the diffuser surface. Typically, the flow rate of the carrier fluid is higher than that for the fluid components. The diffuser surface maintains and directs each received fluid component in a different flow path toward the outlet. Pressurized carrier fluid from the at least one carrier fluid inlet is also directed through the outlet, thereby mixing the fluid components present at the outlet and dispensing the composition through the outlet.

The present invention, in various aspects, provides the following itemized embodiments.

1. A method of treating a diverticular disease, comprising introducing into a diverticulum in a host, a therapeutically effective amount of a fibrosing agent or a composition comprising a fibrosing agent, wherein the fibrosing agent induces a fibrotic response within the diverticulum, thereby treating diverticular disease in the host.

2. The method of item 1 wherein the diverticular disease is diverticulosis.

3. The method of item 1 wherein the diverticular disease is diverticulitis.

4. The method of item 1 wherein the diverticular disease is colonic diverticulosis.

5. The method of item 1 wherein the diverticular disease is diverticular hemorrhage.

6. The method of item 1 wherein the diverticular disease is Zenker's (esophageal) Diverticulum.

7. The method of item 1 wherein the diverticular disease is Meckel's Diverticulum.

8. The method of item 1 wherein the diverticular disease is small bowel diverticulosis.

9. The method of item 1 wherein the diverticular disease is gastric diverticulosis.

10. The method of item 1 wherein the diverticular disease is urinary tract diverticulosis.

11. The method of item 1 wherein the fibrosing agent promotes regeneration.

12. The method of item 1 wherein the fibrosing agent promotes fibrosis and promotes regeneration.

13. The method of item 1 wherein the fibrosing agent promotes angiogenesis.

14. The method of item 1 wherein the fibrosing agent promotes fibroblast migration.

15. The method of item 1 wherein the fibrosing agent promotes fibroblast proliferation.

16. The method of item 1 wherein the fibrosing agent promotes deposition of extracellular matrix (ECM).

17. The method of item 1 wherein the fibrosing agent promotes tissue remodeling.

18. The method of item 1 wherein the fibrosing agent is a diverticular wall irritant.

19. The method of item 1 wherein the fibrosing agent is or comprises silk.

20. The method of item 1 wherein the fibrosing agent is or comprises silkworm silk.

21. The method of item 1 wherein the fibrosing agent is or comprises spider silk.

22. The method of item 1 wherein the fibrosing agent is or comprises recombinant silk.

23. The method of item 1 wherein the fibrosing agent is or comprises raw silk.

24. The method of item 1 wherein the fibrosing agent is or comprises hydrolyzed silk.

25. The method of item 1 wherein the fibrosing agent is or comprises acid-treated silk.

26. The method of item 1 wherein the fibrosing agent is or comprises acylated silk.

27. The method of item 1 wherein the fibrosing agent is in the form of strands.

28. The method of item 1 wherein the fibrosing agent is in the form of tufts.

29. The method of item 1 wherein the fibrosing agent is or comprises mineral particles.

30. The method of item 1 wherein the fibrosing agent is or comprises chitosan.

31. The method of item 1 wherein the fibrosing agent is or comprises polylysine.

32. The method of item 1 wherein the fibrosing agent is or comprises fibronectin.

33. The method of item 1 wherein the fibrosing agent is or comprises bleomycin.

34. The method of item 1 wherein the fibrosing agent is or comprises CTGF.

35. The method of item 1 wherein the fibrosing agent is or comprises a wool.

36. The method of item 1 wherein the fibrosing agent is or comprises an animal wool.

37. The method of item 1 wherein the fibrosing agent is or comprises a wood wool.

38. The method of item 1 wherein the fibrosing agent is or comprises a synthetic wool.

39. The method of item 1 wherein the fibrosing agent is in the form of a thread, or is in contact with a thread.

40. The method of item 39 wherein the thread is biodegradable.

41. The method of item 40 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

42. The method of item 39 wherein the thread is non-biodegradable.

43. The method of item 42 wherein the non-biodegradable thread comprises a material selected from the group consisting of polyester, polyurethane, silicone, polyethylene, polypropylene, polystyrene, polyacrylate, polymethacrylate, and silk.

44. The method of item 39 wherein the thread is coated with a polymer.

45. The method of item 39 wherein the thread is coated with a pharmaceutical agent that induces a fibrotic response in the host.

46. The method of item 1 wherein the fibrosing agent is in the form of a particulate.

47. The method of item 46 wherein the particulate is a biodegradable particulate.

48. The method of item 47 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

49. The method of item 46 wherein the particulate is a non-biodegradable particulate.

50. The method of item 49 wherein the non-biodegradable particulate comprises a material selected from the group consisting of polyester, polyurethane, silicone, polyethylene, polypropylene, polystyrene, polyacrylate, polymethacrylate, and silk.

51. The method of item 46 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

52. The method of item 46 wherein the particulate is coated with a polymer.

53. The method of item 46 wherein the particulate is coated with a pharmaceutical agent that induces a fibrotic response in the host.

54. The method of item 46 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

55. The method of item 1 wherein the composition comprises a growth factor.

56. The method of item 55 wherein the growth factor is selected from a transforming growth factor, a platelet-derived growth factor, and a fibroblast growth factor.

57. The method of item 1 wherein the composition further comprises a polymer.

58. The method of item 1 wherein the composition further comprises a polymer, and the polymer is, or comprises, a copolymer.

59. The method of item 1 wherein the composition further comprises a polymer, and the polymer is, or comprises, a block copolymer.

60. The method of item 1 wherein the composition further comprises a polymer, and the polymer is, or comprises, a random copolymer.

61. The method of item 1 wherein the composition further comprises a polymer, and the polymer is, or comprises, a biodegradable polymer.

62. The method of item 1 wherein the composition further comprises a polymer, and the polymer is, or comprises, a non-biodegradable polymer.

63. The method of item 1 wherein the composition further comprises a polymer, and the polymer is, or comprises, a hydrophilic polymer.

64. The method of item 1 wherein the composition further comprises a polymer, and the polymer is, or comprises, a hydrophobic polymer.

65. The method of item 1 wherein the composition further comprises a polymer, and the polymer is, or comprises, a polymer having hydrophilic domains.

66. The method of item 1 wherein the composition further comprises a polymer, and the polymer is, or comprises, a polymer having hydrophobic domains.

67. The method of item 1 wherein the composition further comprises a polymer, and the polymer is, or comprises, a non-conductive polymer.

68. The method of item 1 wherein the composition further comprises a polymer, and the polymer is, or comprises, an elastomer.

69. The method of item 1 wherein the composition further comprises a polymer, and the polymer is, or comprises, a hydrogel.

70. The method of item 1 wherein the composition further comprises a polymer, and the polymer is, or comprises, a silicone polymer.

71. The method of item 1 wherein the composition further comprises a polymer, and the polymer is, or comprises, a hydrocarbon polymer.

72. The method of item 1 wherein the composition further comprises a polymer, and the polymer is, or comprises, a styrene-derived polymer.

73. The method of item 1 wherein the composition further comprises a polymer, and the polymer is, or comprises, a butadiene-derived polymer.

74. The method of item 1 wherein the composition further comprises a polymer, and the polymer is, or comprises, a macromer.

75. The method of item 1 wherein the composition further comprises a polymer, and the polymer is, or comprises, a poly(ethylene glycol).

76. The method of item 1 wherein the composition further comprises a polymer, and the polymer is, or comprises, a collagen or a derivative thereof.

77. The method of item 1 wherein the composition further comprises a polymer, and the polymer is, or comprises, a methylated collagen.

78. The method of item 1 wherein the composition further comprises a polymer composition, wherein the polymer composition comprises a collagen or a derivative thereof and a fibrinogen.

79. The method of item 1 wherein the composition further comprises a polymer composition, wherein the polymer composition comprises a collagen or a derivative thereof and a thrombin.

80. The method of item 1 wherein the composition further comprises a polymer composition, wherein the polymer composition comprises (a) a collagen or a derivative thereof; (b) a fibrinogen; and (c) a thrombin.

81. The method of item 1 wherein the composition further comprises a polymer composition, wherein the polymer composition comprises a methylated collagen and a poly (ethylene glycol) or a derivative thereof.

82. The method of item 1 wherein the composition further comprises a haemostatic agent that comprises a collagen polymer.

83. The method of item 1 wherein the composition further comprises a haemostatic agent that comprises a collagen polymer, wherein the haemostatic agent is CT3.

84. The method of item 1 wherein the composition further comprises a haemostatic agent that comprises a collagen polymer, wherein the haemostatic agent is COSTASIS.

85. The method of item 1 wherein the composition further comprises a haemostatic agent that comprises a poly(ethylene glycol).

86. The method of item 1 wherein the composition further comprises a haemostatic agent, wherein the haemostatic agent is COSEAL, TISSEAL, or FLOSEAL.

87. The method of item 1 wherein the composition further comprises a haemostatic agent that comprises fibrin.

88. The method of item 1 wherein the composition comprises a polymer, and the polymer is, or comprises, an amorphous polymer.

89. The method of item 1 wherein the composition comprises a polymer, and the polymer is, or comprises, a cyanoacrylate.

90. The method of item 89, wherein the cyanoacrylate is selected from methyl cyanoacrylate, ethyl cyanoacrylate, butyl cyanoacrylate, octyl cyanoacrylate, and methoxypropyl cyanoacrylate.

91. The method of item 1 wherein the composition comprises a polymer, and the polymer is, or comprises, a poly(alkylcyanoacrylate).

92. The method of item 91, wherein the poly(alkylcyanoacrylate) is selected from poly(methylcyanoacrylate), poly(ethylcyanoacrylate), poly(butylcyanoacrylate), poly(isobutylcyanoacrylate), poly(hexylcyanoacrylate), and poly(octylcyanoacrylate).

93. The method of item 1 wherein the composition comprises a polymer, and the polymer is, or comprises, a poly(carboxyalkylcyanoacrylate).

94. The method of item 93 wherein the poly(carboxyalkylcyanoacrylate) is poly(methoxypropylcyanoacrylate).

95. The method of item 57 wherein the polymer is crosslinked.

96. The method of item 57 wherein the polymer reacts with mammalian tissue.

97. The method of item 57 wherein the polymer is a naturally occurring polymer.

98. The method of item 57 wherein the polymer is protein.

99. The method of item 57 wherein the polymer is carbohydrate.

100. The method of item 57 wherein the polymer is crosslinked and biodegradable.

101. The method of item 1 wherein the composition comprises a fibrinogen.

102. The method of item 1 wherein the composition comprises a thrombin.

103. The method of item 1 wherein the composition comprises a calcium salt.

104. The method of item 1 wherein the composition comprises an antifibronolytic agent.

105. The method of item 1 wherein the composition comprises a fibrinogen analog.

106. The method of item 1 wherein the composition comprises an albumin.

107. The method of item 1 wherein the composition comprises a plasminogen.

108. The method of item 1 wherein the composition comprises a von Willebrands factor.

109. The method of item 1 wherein the composition comprises a Factor VIII.

110. The method of item 1 wherein the composition comprises a hypoallergenic collagen.

111. The method of item 1 wherein the composition comprises atelopeptide collagen.

112. The method of item 1 wherein the composition comprises a crosslinked collagen.

113. The method of item 1 wherein the composition comprises an aprotinin.

114. The method of item 1 wherein the composition comprises an epsilon-amino-n-caproic acid.

115. The method of item 1 wherein the composition comprises a gelatin.

116. The method of item 1 wherein the composition comprises a protein conjugate.

117. The method of item 1 wherein the composition comprises a gelatin conjugate.

118. The method of item 1 wherein the composition comprises a hyaluronic acid.

119. The method of item 1 wherein the composition comprises a hyaluronic acid derivative.

120. The method of item 1 wherein the composition comprises a synthetic polymer.

121. The method of item 57 wherein the polymer is formed from reactants comprising a synthetic isocyanate-containing compound.

122. The method of item 1 wherein the composition comprises a synthetic isocyanate-containing compound.

123. The method of item 57 wherein the polymer is formed from reactants comprising a synthetic thiol-containing compound.

124. The method of item 1 wherein the composition comprises a synthetic thiol-containing compound.

125. The method of item 57 wherein the polymer is formed from reactants comprising a synthetic compound containing at least two thiol groups.

126. The method of item 1 wherein the composition comprises a synthetic compound containing at least two thiol groups.

127. The method of item 57 wherein the polymer is formed from reactants comprising a synthetic compound containing at least three thiol groups.

128. The method of item 1 wherein the composition comprises a synthetic compound containing at least three thiol groups.

129. The method of item 57 wherein the polymer is formed from reactants comprising a synthetic compound containing at least four thiol groups.

130. The method of item 1 wherein the composition comprises a synthetic compound containing at least four thiol groups.

131. The method of item 57 wherein the polymer is formed from reactants compnsing a synthetic amino-containing compound.

132. The method of item 1 wherein the composition comprises a synthetic amino-containing compound.

133. The method of item 57 wherein the polymer is formed from reactants comprising a synthetic compound containing at least two amino groups.

134. The method of item 1 wherein the composition comprises a synthetic compound containing at least two amino groups.

135. The method of item 57 wherein the polymer is formed from reactants comprising a synthetic compound containing at least three amino groups.

136. The method of item 1 wherein the composition comprises a synthetic compound containing at least three amino groups.

137. The method of item 57 wherein the polymer is formed from reactants comprising a synthetic compound containing at least four amino groups.

138. The method of item 1 wherein the composition comprises a synthetic compound containing at least four amino groups.

139. The method of item 57 wherein the polymer is formed from reactants comprising a synthetic compound comprising a carbonyl-oxygen-succinimidyl group.

140. The method of item 1 wherein the composition comprises a synthetic compound comprising a carbonyl-oxygen-succinimidyl group.

141. The method of item 57 wherein the polymer is formed from reactants comprising a synthetic compound comprising at least two carbonyl-oxygen-succinimidyl groups.

142. The method of item 1 wherein the composition comprises a synthetic compound comprising at least two carbonyl-oxygen-succinimidyl groups.

143. The method of item 57 wherein the polymer is formed from reactants comprising a synthetic compound comprising at least three carbonyl-oxygen-succinimidyl groups.

144. The method of item 1 wherein the composition comprises a synthetic compound comprising at least three carbonyl-oxygen-succinimidyl groups.

145. The method of item 57 wherein the polymer is formed from reactants comprising a synthetic compound comprising at least four carbonyl-oxygen-succinimidyl groups.

146. The method of item 1 wherein the composition comprises a synthetic compound comprising at least four carbonyl-oxygen-succinimidyl groups.

147. The method of item 57 wherein the polymer is formed from reactants comprising a synthetic polyalkylene oxide-containing compound.

148. The method of item 1 wherein the composition comprises a synthetic polyalkylene oxide-containing compound.

149. The method of item 57 wherein the polymer is formed from reactants comprising a synthetic compound comprising both polyalkylene oxide and biodegradable polyester blocks.

150. The method of item 1 wherein the composition comprises a synthetic compound comprising both polyalkylene oxide and biodegradable polyester blocks.

151. The method of item 57 wherein the polymer is formed from reactants comprising a synthetic polyalkylene oxide-containing compound having reactive amino groups.

152. The method of item 1 wherein the composition comprises synthetic polyalkylene oxide-containing compound having reactive amino groups.

153. The method of item 57 wherein the polymer is formed from reactants comprising a synthetic polyalkylene oxide-containing compound having reactive thiol groups.

154. The method of item 1 wherein the composition comprises synthetic polyalkylene oxide-containing compound having reactive thiol groups.

155. The method of item 57 wherein the polymer is formed from reactants comprising a synthetic polyalkylene oxide-containing compound having reactive carbonyl-oxygen-succinimidyl groups.

156. The method of item 1 wherein the composition comprises a synthetic polyalkytene oxide-containing compound having reactive carbonyl-oxygen-succinimidyl groups.

157. The method of item 57 wherein the polymer is formed from reactants comprising a synthetic compound comprising a biodegradable polyester block.

158. The method of item 1 wherein the composition comprises a synthetic compound comprising a biodegradable polyester block.

159. The method of item 57 wherein the polymer is formed from reactants comprising a synthetic polymer formed in whole or part from lactic acid or lactide.

160. The method of item 1 wherein the composition comprises a synthetic polymer formed in whole or part from lactic acid or lactide.

161. The method of item 57 wherein the polymer is formed from reactants comprising a synthetic polymer formed in whole or part from glycolic acid or glycolide.

162. The method of item 1 wherein the composition comprises a synthetic polymer formed in whole or part from glycolic acid or glycolide.

163. The method of item 57 wherein the polymer is formed from reactants comprising polylysine.

164. The method of item 1 wherein the composition comprises polylysine.

165. The method of item 57 wherein the polymer is formed from reactants comprising (a) protein and (b) a compound comprising a potyalkylene oxide portion.

166. The method of item 1 wherein the composition comprises (a) protein and (b) a compound comprising a polyalkylene oxide portion.

167. The method of item 57 wherein the polymer is formed from reactants comprising (a) protein and (b) polylysine.

168. The method of item 1 wherein the composition comprises (a) protein and (b) potylysine.

169. The method of item 57 wherein the polymer is formed from reactants comprising (a) protein and (b) a compound having at least four thiol groups.

170. The method of item 1 wherein the composition comprises (a) protein and (b) a compound having at least four thiol groups.

171. The method of item 57 wherein the polymer is formed from reactants comprising (a) protein and (b) a compound having at least four amino groups.

172. The method of item 1 wherein the composition comprises (a) protein and (b) a compound having at least four amino groups.

173. The method of item 57 wherein the polymer is formed from reactants comprising (a) protein and (b) a compound having at least four carbonyl-oxygen-succinimide groups.

174. The method of item 1 wherein the composition comprises (a) protein and (b) a compound having at least four carbonyl-oxygen-succinimide groups.

175. The method of item 57 wherein the polymer is formed from reactants comprising (a) protein and (b) a compound having a biodegradable region formed from reactants selected from lactic acid, lactide, glycolic acid, glycolide, and epsilon-caprolactone.

176. The method of item 1 wherein the composition comprises (a) protein and (b) a compound having a biodegradable region formed from reactants selected from lactic acid, lactide, glycolic acid, glycolide, and epsilon-caprolactone.

177. The method of item 57 wherein the polymer is formed from reactants comprising (a) collagen and (b) a compound comprising a polyalkylene oxide portion.

178. The method of item 1 wherein the composition comprises (a) collagen and (b) a compound comprising a polyalkylene oxide portion.

179. The method of item 57 wherein the polymer is formed from reactants comprising (a) collagen and (b) polylysine.

180. The method of item 1 wherein the composition comprises (a) collagen and (b) polylysine.

181. The method of item 57 wherein the polymer is formed from reactants comprising (a) collagen and (b) a compound having at least four thiol groups.

182. The method of item 1 wherein the composition comprises (a) collagen and (b) a compound having at least four thiol groups.

183. The method of item 57 wherein the polymer is formed from reactants comprising (a) collagen and (b) a compound having at least four amino groups.

184. The method of item 1 wherein the composition comprises (a) collagen and (b) a compound having at least four amino groups.

185. The method of item 57 wherein the polymer is formed from reactants comprising (a) collagen and (b) a compound having at least four carbonyl-oxygen-succinimide groups.

186. The method of item 1 wherein the composition comprises (a) collagen and (b) a compound having at least four carbonyl-oxygen-succinimide groups.

187. The method of item 57 wherein the polymer is formed from reactants comprising (a) collagen and (b) a compound having a biodegradable region formed from reactants selected from lactic acid, lactide, glycolic acid, glycolide, and epsilon-caprolactone.

188. The method of item 1 wherein the composition comprises (a) collagen and (b) a compound having a biodegradable region formed from reactants selected from lactic acid, lactide, glycolic acid, glycolide, and epsilon-caprolactone.

189. The method of item 57 wherein the polymer is formed from reactants comprising (a) methylated collagen and (b) a compound comprising a polyalkylene oxide portion.

190. The method of item 1 wherein the composition comprises (a) methylated collagen and (b) a compound comprising a polyalkylene oxide portion.

191. The method of item 57 wherein the polymer is formed from reactants comprising (a) methylated collagen and (b) polylysine.

192. The method of item 1 wherein the composition comprises (a) methylated collagen and (b) polylysine.

193. The method of item 57 wherein the polymer is formed from reactants comprising (a) methylated collagen and (b) a compound having at least four thiol groups.

194. The method of item 1 wherein the composition comprises (a) methylated collagen and (b) a compound having at least four thiol groups.

195. The method of item 57 wherein the polymer is formed from reactants comprising (a) methylated collagen and (b) a compound having at least four amino groups.

196. The method of item 1 wherein the composition comprises (a) methylated collagen and (b) a compound having at least four amino groups.

197. The method of item 57 wherein the polymer is formed from reactants comprising (a) methylated collagen and (b) a compound having at least four carbonyl-oxygen-succinimide groups.

198. The method of item 1 wherein the composition comprises (a) methylated collagen and (b) a compound having at least four carbonyl-oxygen-succinimide groups.

199. The method of item 57 wherein the polymer is formed from reactants comprising (a) methylated collagen and (b) a compound having a biodegradable region formed from reactants selected from lactic acid, lactide, glycolic acid, glycolide, and epsilon-caprolactone.

200. The method of item 1 wherein the composition comprises (a) methylated collagen and (b) a compound having a biodegradable region formed from reactants selected from lactic acid, lactide, glycolic acid, glycolide, and epsilon-caprolactone.

201. The method of item 57 wherein the polymer is formed from reactants comprising hyaluronic acid.

202. The method of item 1 wherein the composition comprises hyaluronic acid.

203. The method of item 57 wherein the polymer is formed from reactants comprising a hyaluronic acid derivative.

204. The method of item 1 wherein the composition comprises a hyaluronic acid derivative.

205. The method of item 57 wherein the polymer is formed from reactants comprising pentaerythritol poly(ethylene glycol)ether tetra-sulfhydryl of number average molecular weight between 3,000 and 30,000.

206. The method of item 1 wherein the composition comprises pentaerythritol poly(ethylene glycol)ether tetra-sulfhydryl of number average molecular weight between 3,000 and 30,000.

207. The method of item 57 wherein the polymer is formed from reactants comprising pentaerythritol poly(ethylene glycol)ether tetra-amino of number average molecular weight between 3,000 and 30,000.

208. The method of item 1 wherein the composition comprises pentaerythritol poly(ethylene glycol)ether tetra-amino of number average molecular weight between 3,000 and 30,000.

209. The method of item 57 wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

210. The method of item 1 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

211. The method of item 1 wherein the composition comprises a colorant.

212. The method of item 1 wherein the composition is sterile.

213. The method of item 1 wherein the composition further comprises a second pharmaceutically active agent.

214. The method of item 1 wherein the composition further comprises an anti-inflammatory agent.

215. The method of item 1 wherein the composition further comprises an agent that inhibits infection.

216. The method of item 1 wherein the composition further comprises an anthracycline.

217. The method of item 1 wherein the composition further comprises doxorubicin.

218. The method of item 1 wherein the composition further comprises mitoxantrone.

219. The method of item 1 wherein the composition further comprises a fluoropyrimidine.

220. The method of item 1 wherein the composition further comprises 5-fluorouracil (5-FU).

221. The method of item 1 wherein the composition further comprises a folic acid antagonist.

222. The method of item 1 wherein the composition further comprises methotrexate.

223. The method of item 1 wherein the composition further comprises a podophylotoxin.

224. The method of item 1 wherein the composition further comprises etoposide.

225. The method of item 1 wherein the composition further comprises camptothecin.

226. The method of item 1 wherein the composition further comprises a hydroxyurea.

227. The method of item 1 wherein the composition further comprises a platinum complex.

228. The method of item 1 wherein the composition further comprises cisplatin.

229. The method of item 1 wherein the composition further comprises an anti-infective agent.

230. The method of item 1 wherein the composition further comprises an anti-infective agent, wherein the anti-infective agent is an antibiotic.

231. The method of item 1 wherein the composition further comprises an anti-infective agent, wherein the anti-infective agent is doxycycline.

232. The method of item 1 wherein the composition further comprises an anti-infective agent, wherein the anti-infective agent is metronidazole.

233. The method of item 1 wherein the composition further comprises an anti-infective agent, wherein the anti-infective agent is trimethoprim-sulfamethoxazote.

234. The method of item 1 wherein the composition further comprises an anti-infective agent, wherein the anti-infective agent is a fourth generation penicillin.

235. The method of item 1 wherein the composition further comprises an anti-infective agent, wherein the anti-infective agent is a fourth generation penicillin selected from a ureidopenicillin and a carboxypenicillin, or an analogue or derivative thereof.

236. The method of item 1 wherein the composition further comprises an anti-infective agent, wherein the anti-infective agent is a fourth generation penicillin selected from mezlocillin, piperacillin, carbenicillin, and ticarcillin.

237. The method of item 1 wherein the composition further comprises an anti-infective agent, wherein the anti-infective agent is a first generation cephalosporin.

238. The method of item 1 wherein the composition further comprises an anti-infective agent, wherein the anti-infective agent is a first generation cephalosporin selected from cephazolin sodium, cephalexin, cefazolin, cephapirin, and cephalothin.

239. The method of item 1 wherein the composition further comprises an anti-infective agent, wherein the anti-infective agent is a carboxypenicillin.

240. The method according to item 601 wherein the carboxypenicillin is ticarcillin.

241. The method of item 1 wherein the composition further comprises an anti-infective agent, wherein the anti-infective agent is a second generation cephalosporin.

242. The method of item 1 wherein the composition further comprises an anti-infective agent, wherein the anti-infective agent is a second generation cephalosporin selected from cefuroxime, cefotetan, and cefoxitin.

243. The method of item 1 wherein the composition further comprises an anti-infective agent, wherein the anti-infective agent is a third generation cephalosporin.

244. The method of item 1 wherein the composition further comprises an anti-infective agent, wherein the anti-infective agent is a third generation cephalosporin selected from naxcel, Cefdinir, cefoperazone, ceftazidime, ceftriaxone, and cefotaxime.

245. The method of item 1 wherein the composition further comprises an anti-infective agent, wherein the anti-infective agent is a fourth generation cephalosporin.

246. The method of item 245 wherein the fourth generation cephalosporin is cefepime.

247. The method of item 1 wherein the composition further comprises an anti-infective agent, wherein the anti-infective agent is a monobactam.

248. The method of item 247 wherein the monobactam is aztreonam.

249. The method of item 1 wherein the composition further comprises an anti-infective agent, wherein the anti-infective agent is a carbapenem.

250. The method of item 1 wherein the composition further comprises an anti-infective agent, wherein the anti-infective agent is a carbapenem selected from imipenem, ertapenem and meropenem.

251. The method of item 1 wherein the composition further comprises an anti-infective agent, wherein the anti-infective agent is an aminoglycoside.

252. The method of item 1 wherein the composition further comprises an anti-infective agent, wherein the anti-infective agent is an aminoglycoside selected from streptomycin, gentamicin, tobramycin, and amikacin.

253. The method of item 1 wherein the composition further comprises an anti-infective agent, wherein the anti-infective agent is an MSL group member selected from a macrolide, a long acting macrolide, a lincosamide, and a streptogramin.

254. The method of item 1 wherein the composition further comprises an anti-infective agent, wherein the anti-infective agent is an MSL group member selected from Erythromycin, Azithromycin, Clindamycin, Syneroid, clarithromycin, and kanamycin sulfate.

255. The method of item 1 wherein the composition further comprises an anti-infective agent, wherein the anti-infective agent is a quinolone.

256. The method of item 1 wherein the composition further comprises an anti-infective agent, wherein the anti-infective agent is a quinolone selected from ciprofloxacin, ofloxacin, gatifloxacin, moxifloxacin, levofloxacin, and trovafloxacin.

257. The method of item 1 wherein the composition further comprises an anti-infective agent, wherein the anti-infective agent is a DNA synthesis inhibitor.

258. The method of item 257 wherein the DNA synthesis inhibitor is metronidazole.

259. The method of item 1 wherein the composition further comprises an anti-infective agent, wherein the anti-infective agent is a sulfonamide.

260. The method of item 259 wherein the sulfonamide is trimethoprim.

261. The method of item 1 wherein the composition further comprises an anti-infective agent, wherein the anti-infective agent is selected from cefixime, spectinomycin, tetracycline, nitrofurantoin, polymyxin B, and neomycin sulfate.

262. The method of item 1 wherein the composition further comprises a visualization agent.

263. The method of item 1 wherein the composition further comprises a visualization agent, and the visualization agent is a radiopaque material, wherein the radiopaque material comprises a metal, a halogenated compound, or a barium-containing compound.

264. The method of item 1 wherein the composition further comprises a visualization agent, and the visualization agent is, or comprises, barium, tantalum, or technetium.

265. The method of item 1 wherein the composition further comprises a visualization agent, and the visualization agent is, or comprises, an MRI responsive material or an echogenic material.

266. The method of item 1 wherein the composition further comprises a visualization agent, and the visualization agent is, or comprises, a gadolinium chelate.

267. The method of item 1 wherein the composition further comprises a visualization agent, and the visualization agent is, or comprises, iron, magnesium, manganese, copper, or chromium.

268. The method of item 1 wherein the composition further comprises a visualization agent, and the visualization agent is, or comprises, iron oxide compound.

269. The method of item 1 wherein the composition further comprises a visualization agent, and the visualization agent is, or comprises, a dye, pigment, or colorant.

270. The method of item 1 wherein the fibrosing agent is released in effective concentrations from the composition comprising the fibrosing agent by diffusion over a period ranging from the time of administration to about 90 days.

271. The method of item 1 wherein the fibrosing agent is released in effective concentrations from the composition comprising the fibrosing agent by erosion of the composition over a period ranging from the time of administration to about 90 days.

272. The method of item 1 wherein the composition further comprises an inflammatory cytokine.

273. The method of item 1 wherein the composition further comprises an agent that stimulates cell proliferation.

274. The method of item 1 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

275. The method of item 1 wherein the composition further comprises a polymeric carrier.

276. The method of item 1 wherein the composition is in the form of a gel, paste, or spray.

277. The method of item 1 wherein the composition is in the form of a mesh or film.

278. The method of item 1 wherein the fibrosing agent is delivered from a device, and the device delivers the fibrosing agent into the diverticulum.

279. The method of item 1 wherein the fibrosing agent is delivered from an implant, wherein the implant is or comprises a microsphere.

280. The method of item 1 wherein the fibrosing agent is delivered from an implant, wherein the implant is or comprises a mesh.

281. The method of item 1 wherein the fibrosing agent is delivered from an implant, wherein the implant is or comprises a film.

282. The method of item 1 wherein the fibrosing agent is delivered from a device, wherein the device is a catheter.

283. The method of item 1 wherein the fibrosing agent is delivered from a device, wherein the device is a drug delivery catheter.

284. The method of item 1 wherein the fibrosing agent is delivered from a device, wherein the device is a radiofrequencey ablation catheter.

285. The method of item 1 wherein the fibrosing agent is delivered from a device, wherein the device is a temperature ablation catheter.

286. The method of item 1 wherein the fibrosing agent is delivered from a device, wherein the device is a thermal energy catheter.

287. The method of item 1 wherein the fibrosing agent is delivered from a device, wherein the device is a cryoablation catheter.

288. The method of item 1 wherein the fibrosing agent is delivered from a device, wherein the device is a laser catheter.

289. The method of item 1 wherein the fibrosing agent is delivered from a device, wherein the device is a radioactivity-delivering catheter.

290. The method of item 1 wherein the fibrosing agent is delivered from a device, wherein the device is a balloon catheter.

291. The method of item 1 wherein the fibrosing agent is delivered from a device, wherein the device is an ultrasonic energy-delivering catheter.

292. The method of item 1 wherein the fibrosing agent is delivered from a device, wherein the device is a rotation atherectomy device.

293. The method of item 1 wherein the fibrosing agent is delivered from a device, wherein the device is a rotation atherectomy device that is a rotoblade.

294. The method of item 1 wherein the fibrosing agent is delivered from a device, wherein the device is a tissue abrasion device.

295. The method of item 1 wherein the fibrosing agent is delivered from a device, wherein the device is an atherectomy device.

296. The method of item 1 wherein the fibrosing agent is delivered from a device, wherein the device is an atherectomy catheter.

297. The method of item 1 wherein the fibrosing agent is delivered from a device, wherein the device is an endoscopic scalpel.

298. The method of item 1 wherein the fibrosing agent is introduced by delivery from a device, wherein the device further comprises a coating, and the coating comprises the fibrosing agent.

299. The method of item 1 wherein the fibrosing agent is introduced by delivery from a device, wherein the device further comprises a coating, and the coating is disposed on a surface of the device.

300. The method of item 1 wherein the fibrosing agent is introduced by delivery from a device, wherein the device further comprises a coating, and wherein the coating directly contacts the device.

301. The method of item 1 wherein the fibrosing agent is introduced by delivery from a device, wherein the device further comprises a coating, and wherein the coating indirectly contacts the device.

302. The method of item 1 wherein the fibrosing agent is introduced by delivery from a device, wherein the device further comprises a coating, and wherein the coating partially covers the device.

303. The method of item 1 wherein the fibrosing agent is introduced by delivery from a device, wherein the device further comprises a coating, and wherein the coating completely covers the device.

304. The method of item 1 wherein the fibrosing agent is introduced by delivery from a device, wherein the fibrosing agent is located within pores or holes of the device.

305. The method of item 1 wherein the fibrosing agent is introduced by delivery from a device, wherein the fibrosing agent is located within a channel, lumen, or divet of the device.

306. The method of item 1 wherein the fibrosing agent is introduced by delivery from a device, wherein the device further comprises an echogenic material.

307. The method of item 1 wherein the fibrosing agent is introduced by delivery from a device, wherein the device further comprises an echogenic material, and wherein the echogenic material is in the form of a coating.

308. The method of item 1 wherein the fibrosing agent is introduced by delivery from a device, wherein the device is sterile.

309. The method of item 1 wherein the agent is introduced by delivery from a device, wherein the fibrosing agent is released into tissue in the vicinity of the device after deployment of the device.

310. The method of item 1 wherein the fibrosing agent is introduced by delivery from a device, wherein the fibrosing agent is released into tissue in the vicinity of the device after deployment of the device, and wherein the tissue is connective tissue.

311. The method of item 1 wherein the fibrosing agent is introduced by delivery from a device, wherein the fibrosing agent is released into tissue in the vicinity of the device after deployment of the device, and wherein the tissue is muscle tissue.

312. The method of item 1 wherein the fibrosing agent is introduced by delivery from a device, wherein the fibrosing agent is released into tissue in the vicinity of the device after deployment of the device, and wherein the tissue is nerve tissue.

313. The method of item 1 wherein the fibrosing agent is introduced by delivery from a device, wherein the fibrosing agent is released into tissue in the vicinity of the device after deployment of the device, and wherein the tissue is epithelium tissue.

314. The method of item 1 wherein the fibrosing agent is introduced by delivery from a device, wherein the fibrosing agent is released in effective concentrations from the device over a period ranging from the time of deployment of the device to about 1 year.

315. The method of item 1 wherein the fibrosing agent is introduced by delivery from a device, wherein the fibrosing agent is released in effective concentrations from the device over a period ranging from about 1 month to 6 months.

316. The method of item 1 wherein the fibrosing agent is introduced by delivery from a device, and wherein the fibrosing agent is released in effective concentrations from the device over a period ranging from about 1–90 days.

317. The method of item 1 wherein the fibrosing agent is introduced by delivery from a device, and wherein the fibrosing agent is released in effective concentrations from the device at a constant rate.

318. The method of item 1 wherein the fibrosing agent is introduced by delivery from a device, and wherein the fibrosing agent is released in effective concentrations from the device at an increasing rate.

319. The method of item 1 wherein the fibrosing agent is introduced by delivery from a device, and wherein the agent is released in effective concentrations from the device at a decreasing rate.

320. The method of item 1 wherein the fibrosing agent is about 0.01 µg to about 10 µg.

321. The method of item 1 wherein the fibrosing agent is about 10 µg to about 10 mg.

322. The method of item 1 wherein the fibrosing agent is about 10 mg to about 250 mg.

323. The method of item 1 wherein the fibrosing agent is about 250 mg to about 1000 mg.

324. The method of item 1 wherein the fibrosing agent is about 1000 mg to about 2500 mg.

325. The method of item 1 wherein the fibrosing agent is introduced by delivery from an implant, and wherein a surface of the implant comprises less than 0.01 µg of the fibrosing agent per mm$^2$ of implant surface to which the agent is applied.

326. The method of item 1 wherein the fibrosing agent is introduced by delivery from an implant, and wherein a surface of the implant comprises about 0.01 µg to about 1 µg of the fibrosing agent per mm$^2$ of implant surface to which the agent is applied.

327. The method of item 1 wherein the fibrosing agent is introduced by delivery from an implant, and wherein a surface of the implant comprises about 1 µg to about 10 µg of the fibrosing agent per mm$^2$ of implant surface to which the agent is applied.

328. The method of item 1 wherein the fibrosing agent is introduced by delivery from an implant, and wherein a surface of the implant comprises about 10 µg to about 250 µg of the fibrosing agent per mm$^2$ of implant surface to which the agent is applied.

329. The method of item 1 wherein the fibrosing agent is introduced by delivery from an implant, and wherein a surface of the implant comprises about 250 µg to about 1000 µg of the fibrosing agent of fibrosing agent per mm$^2$ of implant surface to which the fibrosing agent is applied.

330. The method of item 1 wherein the fibrosing agent is introduced by delivery from an implant, and wherein a surface of the implant comprises about 1000 µg to about 2500 µg of the fibrosing agent per mm$^2$ of implant surface to which the agent is applied.

331. The method of item 1 wherein the fibrosing agent is introduced by delivery from an implant, wherein the implant further comprises a coating, and wherein the coating is a uniform coating.

332. The method of item 1 wherein the fibrosing agent is introduced by delivery from an implant, wherein the implant further comprises a coating, and wherein the coating is a non-uniform coating.

333. The method of item 1 wherein the fibrosing agent is introduced by delivery from an implant, wherein the implant further comprises a coating, and wherein the coating is a discontinuous coating.

334. The method of item 1 wherein the fibrosing agent is introduced by delivery from an implant, wherein the implant further comprises a coating, and wherein the coating is a patterned coating.

335. The method of item 1 wherein the fibrosing agent is introduced by delivery from an implant, wherein the implant further comprises a coating, and wherein the coating has a thickness of 100 µm or less.

336. The method of item 1 wherein the fibrosing agent is introduced by delivery from an implant, wherein the implant further comprises a coating, and wherein the coating has a thickness of 10 µm or less.

337. The method of item 1 wherein the fibrosing agent is introduced by delivery from an implant, wherein the implant further comprises a coating, and wherein the coating adheres to the surface of the implant upon deployment of the implant.

338. The method of item 1 wherein the fibrosing agent is introduced by delivery from an implant, wherein the implant further comprises a coating, and wherein the coating is stable at room temperature for a period of at least 1 year.

339. The method of item 1 wherein the fibrosing agent is introduced by delivery from an implant, wherein the implant further comprises a coating, and wherein the fibrosing agent is present in the coating in an amount ranging between about 0.0001% to about 1% by weight.

340. The method of item 1 wherein the fibrosing agent is introduced by delivery from an implant, wherein the implant further comprises a coating, and wherein the fibrosing agent is present in the coating in an amount ranging between about 1% to about 10% by weight.

341. The method of item 1 wherein the fibrosing agent is introduced by delivery from an implant, wherein the implant further comprises a coating, and wherein the fibrosing agent is present in the coating in an amount ranging between about 10% to about 25% by weight.

342. The method of item 1 wherein the fibrosing agent is introduced by delivery from an implant, wherein the implant further comprises a coating, and wherein the fibrosing agent is present in the coating in an amount ranging between about 25% to about 70% by weight.

343. The method of item 1 wherein the fibrosing agent is introduced by delivery from an implant, wherein the implant further comprises a coating, and wherein the coating comprises a polymer.

344. The method of item 1 wherein the fibrosing agent is introduced by delivery from an implant, wherein the implant comprises a first coating having a first composition and a second coating having a second composition.

345. The method of item 1 wherein the fibrosing agent is introduced by delivery from an implant, wherein the implant comprises a first coating having a first composition and a second coating having a second composition, wherein the first composition and the second composition are different.

346. The method of item 1 wherein the fibrosing agent or the composition comprising the fibrosing agent is injected or sprayed into the diverticulum.

347. The method of item 1 wherein the fibrosing agent or the composition comprising the fibrosing agent is injected or sprayed onto a tissue or into a tissue surrounding the diverticulum.

348. The method of item 1 wherein the composition further comprises a bulking agent.

349. The method of item 1 wherein the composition is a sealant.

350. The method of item 1 wherein the composition is a haemostatic agent.

351. The method of item 1 wherein the composition further comprises a bulking agent, wherein the bulking agent comprises microspheres.

352. The method of item 1 wherein the composition further comprises a bulking agent, wherein the bulking agent comprises a hydroxyapatite loaded gel.

353. The method of item 1 wherein the composition further comprises a bulking agent, wherein the bulking agent comprises a micronized alloderm acellular matrix.

354. The method of item 1 wherein the composition further comprises a bulking agent, wherein the bulking agent comprises hyaluronic acid.

355. The method of item 1 wherein the composition further comprises a bulking agent, wherein the bulking agent comprises micro-beads in a hydrogel.

356. The method of item 1 wherein the composition further comprises a bulking agent, wherein the bulking agent comprises a hylan polymer.

357. The method of item 1 wherein the composition further comprises a bulking agent, wherein the bulking agent comprises a silicon microballoon and biocompatible polymer.

358. The method of item 1 further comprising visualizing the presence of a diverticulum.

359. The method of item 358 wherein visualizing the presence of a diverticulum comprising endoscopy.

360. The method of item 358 wherein visualizing the presence of a diverticulum comprising radiographic imaging.

361. The method of item 1 further comprising irrigating of the diverticulum with an irrigation solution prior to introducing the fibrosing agent.

362. The method of item 361 wherein the irrigation solution comprises (a) an anti-infective agent or (b) an antiseptic agent or (c) an anti-infective agent and an antiseptic agent.

363. A method for inducing fibrosis in a diverticulum of a host in need thereof, comprising introducing a composition into the diverticulum of the host, said composition comprising a fibrosing agent, wherein the agent induces fibrosis within the diverticulum.

364. The method of item 363 wherein inducing fibrosis in a diverticulum prevents or treats a diverticular disease.

365. The method of item 364 wherein the diverticular disease is diverticulitis.

366. The method of item 364 wherein the diverticular disease is diverticulosis.

367. The method of item 364 wherein the diverticular disease is diverticular hemorrhage.

368. The method of item 364 wherein the diverticular disease is Zenker's (esophageal) Diverticulum.

369. The method of item 364 wherein the diverticular disease is Meckel's Diverticulum.

370. The method of item 364 wherein the diverticular disease is small bowel diverticulosis.

371. The method of item 364 wherein the diverticular disease is gastric diverticulosis or urinary tract diverticulosis.

372. The method of item 364 wherein the diverticular disease is colonic diverticulosis.

373. The method of item 363 wherein the fibrosing agent promotes regeneration.

374. The method of item 363 wherein the fibrosing agent promotes fibrosis and promotes regeneration.

375. The method of item 363 wherein the fibrosing agent promotes angiogenesis.

376. The method of item 363 wherein the fibrosing agent promotes fibroblast migration.

377. The method of item 363 wherein the fibrosing agent promotes fibroblast proliferation.

378. The method of item 363 wherein the fibrosing agent promotes deposition of extracellular matrix (ECM).

379. The method of item 363 wherein the fibrosing agent promotes tissue remodeling.

380. The method of item 363 wherein the fibrosing agent is a diverticular wall irritant.

381. The method of item 363 wherein the fibrosing agent is or comprises silk.

382. The method of item 363 wherein the fibrosing agent is or comprises silkworm silk.

383. The method of item 363 wherein the fibrosing agent is or comprises spider silk.

384. The method of item 363 wherein the fibrosing agent is or comprises recombinant silk.

385. The method of item 363 wherein the fibrosing agent is or comprises raw silk.

386. The method of item 363 wherein the fibrosing agent is or comprises hydrolyzed silk.

387. The method of item 363 wherein the fibrosing agent is or comprises acid-treated silk.

388. The method of item 363 wherein the fibrosing agent is or comprises acylated silk.

389. The method of item 363 wherein the fibrosing agent is in the form of strands.

390. The method of item 363 wherein the fibrosing agent is in the form of tufts.

391. The method of item 363 wherein the fibrosing agent is or comprises mineral particles.

392. The method of item 363 wherein the fibrosing agent is or comprises chitosan.

393. The method of item 363 wherein the fibrosing agent is or comprises polylysine.

394. The method of item 363 wherein the fibrosing agent is or comprises fibronectin.

395. The method of item 363 wherein the fibrosing agent is or comprises bleomycin.

396. The method of item 363 wherein the fibrosing agent is or comprises CTGF.

397. The method of item 363 wherein the fibrosing agent is or comprises a wool.

398. The method of item 363 wherein the fibrosing agent is or comprises an animal wool.

399. The method of item 363 wherein the fibrosing agent is or comprises a wood wool.

400. The method of item 363 wherein the fibrosing agent is or comprises a synthetic wool.

401. The method of item 363 wherein the fibrosing agent is in the form of a thread, or is in contact with a thread.

402. The method of item 401 wherein the thread is biodegradable.

403. The method of item 402 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

404. The method of item 401 wherein the thread is non-biodegradable.

405. The method of item 404 wherein the non-biodegradable thread comprises a material selected from the group consisting of polyester, polyurethane, silicone, polyethylene, polypropylene, polystyrene, polyacrylate, polymethacrylate, and silk.

406. The method of item 401 wherein the thread is coated with a polymer.

407. The method of item 401 wherein the thread is coated with a pharmaceutical agent that induces a fibrotic response in the host.

408. The method of item 363 wherein the fibrosing agent is in the form of a particulate.

409. The method of item 408 wherein the particulate is a biodegradable particulate.

410. The method of item 409 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

411. The method of item 408 wherein the particulate is a non-biodegradable particulate.

412. The method of item 411 wherein the non-biodegradable particulate comprises a material selected from the group consisting of polyester, polyurethane, silicone, polyethylene, polypropylene, polystyrene, polyacrylate, polymethacrylate, and silk.

413. The method of item 408 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

414. The method of item 408 wherein the particulate is coated with a polymer.

415. The method of item 408 wherein the particulate is coated with a pharmaceutical agent that induces a fibrotic response in the host.

416. The method of item 408 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

417. The method of item 363 wherein the composition comprises a growth factor.

418. The method of item 417 wherein the growth factor is selected from a transforming growth factor, a platelet-derived growth factor, and a fibroblast growth factor.

419. The method of item 363 wherein the composition further comprises a polymer.

420. The method of item 363 wherein the composition further comprises a polymer, and the polymer is, or comprises, a copolymer.

421. The method of item 363 wherein the composition further comprises a polymer, and the polymer is, or comprises, a block copolymer.

422. The method of item 363 wherein the composition further comprises a polymer, and the polymer is, or comprises, a random copolymer.

423. The method of item 363 wherein the composition further comprises a polymer, and the polymer is, or comprises, a biodegradable polymer.

424. The method of item 363 wherein the composition further comprises a polymer, and the polymer is, or comprises, a non-biodegradable polymer.

425. The method of item 363 wherein the composition further comprises a polymer, and the polymer is, or comprises, a hydrophilic polymer.

426. The method of item 363 wherein the composition further comprises a polymer, and the polymer is, or comprises, a hydrophobic polymer.

427. The method of item 363 wherein the composition further comprises a polymer, and the polymer is, or comprises, a polymer having hydrophilic domains.

428. The method of item 363 wherein the composition further comprises a polymer, and the polymer is, or comprises, a polymer having hydrophobic domains.

429. The method of item 363 wherein the composition further comprises a polymer, and the polymer is, or comprises, a non-conductive polymer.

430. The method of item 363 wherein the composition further comprises a polymer, and the polymer is, or comprises, an elastomer.

431. The method of item 363 wherein the composition further comprises a polymer, and the polymer is, or comprises, a hydrogel.

432. The method of item 363 wherein the composition further comprises a polymer, and the polymer is, or comprises, a silicone polymer.

433. The method of item 363 wherein the composition further comprises a polymer, and the polymer is, or comprises, a hydrocarbon polymer.

434. The method of item 363 wherein the composition further comprises a polymer, and the polymer is, or comprises, a styrene-derived polymer.

435. The method of item 363 wherein the composition further comprises a polymer, and the polymer is, or comprises, a butadiene-derived polymer.

436. The method of item 363 wherein the composition further comprises a polymer, and the polymer is, or comprises, a macromer.

437. The method of item 363 wherein the composition further comprises a polymer, and the polymer is, or comprises, a poly(ethylene glycol).

438. The method of item 363 wherein the composition further comprises a polymer, and the polymer is, or comprises, a collagen or a derivative thereof.

439. The method of item 363 wherein the composition further comprises a polymer, and the polymer is, or comprises, a methylated collagen.

440. The method of item 363 wherein the composition further comprises a polymer composition, wherein the polymer composition comprises a collagen or a derivative thereof and fibrinogen.

441. The method of item 363 wherein the composition further comprises a polymer composition, wherein the polymer composition comprises a collagen or a derivative thereof and thrombin.

442. The method of item 363 wherein the composition further comprises a polymer composition, wherein the polymer composition comprises (a) a collagen or a derivative thereof; (b) fibrinogen; and (c) thrombin.

443. The method of item 363 wherein the composition further comprises a polymer composition, wherein the polymer composition comprises a methylated collagen and a poly(ethylene glycol) or a derivative thereof.

444. The method of item 363 wherein the composition further comprises a haemostatic agent that comprises a collagen polymer.

445. The method of item 363 wherein the composition further comprises a haemostatic agent that comprises a collagen polymer, wherein the haemostatic agent is CT3.

446. The method of item 363 wherein the composition further comprises a haemostatic agent that comprises a collagen polymer, wherein the haemostatic agent is COSTASIS.

447. The method of item 363 wherein the composition further comprises a haemostatic agent that comprises a poly(ethylene glycol).

448. The method of item 363 wherein the composition further comprises a haemostatic agent, wherein the haemostatic agent is COSEAL, TISSEAL, OR FLOSEAL.

449. The method of item 363 wherein the composition further comprises a haemostatic agent that comprises fibrin.

450. The method of item 363 wherein the composition comprises a polymer, and the polymer is, or comprises, an amorphous polymer.

451. The method of item 363 wherein the composition comprises a polymer, and the polymer is, or comprises, a cyanoacrylate.

452. The method of item 451, wherein the cyanoacrylate is selected from methyl cyanoacrylate, ethyl cyanoacrylate, butyl cyanoacrylate, octyl cyanoacrylate, and methoxypropyl cyanoacrylate.

453. The method of item 363 wherein the composition comprises a polymer, and the polymer is, or comprises, a poly(alkylcyanoacrylate).

454. The method of item 453, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

455. The method of item 363 wherein the composition comprises a polymer, and the polymer is, or comprises, a poly(carboxyalkylcyanoacrylate).

456. The method of item 455 wherein the poly(carboxyatkylcyanoacrylate) is poly(methoxypropylcyanoacrylate).

457. The method of item 419 wherein the polymer is crosslinked.

458. The method of item 419 wherein the polymer reacts with mammalian tissue.

459. The method of item 419 wherein the polymer is a naturally occurring polymer.

460. The method of item 419 wherein the polymer is a protein.

461. The method of item 419 wherein the polymer is a carbohydrate.

462. The method of item 419 wherein the polymer is crosslinked and biodegradable.

463. The method of item 363 wherein the composition comprises a fibrinogen.

464. The method of item 363 wherein the composition comprises a thrombin.

465. The method of item 363 wherein the composition comprises a calcium salt.

466. The method of item 363 wherein the composition comprises an antifibronolytic agent.

467. The method of item 363 wherein the composition comprises a fibrinogen analog.

468. The method of item 363 wherein the composition comprises an albumin.

469. The method of item 363 wherein the composition comprises a plasminogen.

470. The method of item 363 wherein the composition comprises a von Willebrands factor.

471. The method of item 363 wherein the composition comprises a Factor VIII.

472. The method of item 363 wherein the composition comprises a hypoallergenic collagen.

473. The method of item 363 wherein the composition comprises atelopeptide collagen.

474. The method of item 363 wherein the composition comprises a crosslinked collagen.

475. The method of item 363 wherein the composition comprises an aprotinin.

476. The method of item 363 wherein the composition comprises an epsilon-amino-n-caproic acid.

477. The method of item 363 wherein the composition comprises a gelatin.

478. The method of item 363 wherein the composition comprises a protein conjugate.

479. The method of item 363 wherein the composition comprises a gelatin conjugate.

480. The method of item 363 wherein the composition comprises a hyaluronic acid.

481. The method of item 363 wherein the composition comprises a hyaluronic acid derivative.

482. The method of item 363 wherein the composition comprises a synthetic polymer.

483. The method of item 419 wherein the polymer is formed from reactants comprising a synthetic isocyanate-containing compound.

484. The method of item 363 wherein the composition comprises a synthetic isocyanate-containing compound.

485. The method of item 419 wherein the polymer is formed from reactants comprising a synthetic thiol-containing compound.

486. The method of item 363 wherein the composition comprises a synthetic thiol-containing compound.

487. The method of item 419 wherein the polymer is formed from reactants comprising a synthetic compound containing at least two thiol groups.

488. The method of item 363 wherein the composition comprises a synthetic compound containing at least two thiol groups.

489. The method of item 419 wherein the polymer is formed from reactants comprising a synthetic compound containing at least three thiol groups.

490. The method of item 363 wherein the composition comprises a synthetic compound containing at least three thiol groups.

491. The method of item 419 wherein the polymer is formed from reactants comprising a synthetic compound containing at least four thiol groups.

492. The method of item 363 wherein the composition comprises a synthetic compound containing at least four thiol groups.

493. The method of item 419 wherein the polymer is formed from reactants comprising a synthetic amino-containing compound.

494. The method of item 363 wherein the composition comprises a synthetic amino-containing compound.

495. The method of item 419 wherein the polymer is formed from reactants comprising a synthetic compound containing at least two amino groups.

496. The method of item 363 wherein the composition comprises a synthetic compound containing at least two amino groups.

497. The method of item 419 wherein the polymer is formed from reactants comprising a synthetic compound containing at least three amino groups.

498. The method of item 363 wherein the composition comprises a synthetic compound containing at least three amino groups.

499. The method of item 419 wherein the polymer is formed from reactants comprising a synthetic compound containing at least four amino groups.

500. The method of item 363 wherein the composition comprises a synthetic compound containing at least four amino groups.

501. The method of item 419 wherein the polymer is formed from reactants comprising a synthetic compound comprising a carbonyl-oxygen-succinimidyl group.

502. The method of item 363 wherein the composition comprises a synthetic compound comprising a carbonyl-oxygen-succinimidyl group.

503. The method of item 419 wherein the polymer is formed from reactants comprising a synthetic compound comprising at least two carbonyl-oxygen-succinimidyl groups.

504. The method of item 363 wherein the composition comprises a synthetic compound comprising at least two carbonyl-oxygen-succinimidyl groups.

505. The method of item 419 wherein the polymer is formed from reactants comprising a synthetic compound comprising at least three carbonyl-oxygen-succinimidyl groups.

506. The method of item 363 wherein the composition comprises a synthetic compound comprising at least three carbonyl-oxygen-succinimidyl groups.

507. The method of item 419 wherein the polymer is formed from reactants comprising a synthetic compound comprising at least four carbonyl-oxygen-succinimidyl groups.

508. The method of item 363 wherein the composition comprises a synthetic compound comprising at least four carbonyl-oxygen-succinimidyl groups.

509. The method of item 419 wherein the polymer is formed from reactants comprising a synthetic polyalkylene oxide-containing compound.

510. The method of item 363 wherein the composition comprises a synthetic polyalkylene oxide-containing compound.

511. The method of item 419 wherein the polymer is formed from reactants comprising a synthetic compound comprising both polyalkylene oxide and biodegradable polyester blocks.

512. The method of item 363 wherein the composition comprises a synthetic compound comprising both polyalkylene oxide and biodegradable polyester blocks.

513. The method of item 419 wherein the polymer is formed from reactants comprising a synthetic polyalkylene oxide-containing compound having reactive amino groups.

514. The method of item 363 wherein the composition comprises synthetic polyalkylene oxide-containing compound having reactive amino groups.

515. The method of item 419 wherein the polymer is formed from reactants comprising a synthetic polyalkylene oxide-containing compound having reactive thiol groups.

516. The method of item 363 wherein the composition comprises synthetic polyalkylene oxide-containing compound having reactive thiol groups.

517. The method of item 419 wherein the polymer is formed from reactants comprising a synthetic polyalkylene oxide-containing compound having reactive carbonyl-oxygen-succinimidyl groups.

518. The method of item 363 wherein the composition comprises a synthetic polyalkylene oxide-containing compound having reactive carbonyl-oxygen-succinimidyl groups.

519. The method of item 419 wherein the polymer is formed from reactants comprising a synthetic compound comprising a biodegradable polyester block.

520. The method of item 363 wherein the composition comprises a synthetic compound comprising a biodegradable polyester block.

521. The method of item 419 wherein the polymer is formed from reactants comprising a synthetic polymer formed in whole or part from lactic acid or lactide.

522. The method of item 363 wherein the composition comprises a synthetic polymer formed in whole or part from lactic acid or lactide.

523. The method of item 419 wherein the polymer is formed from reactants comprising a synthetic polymer formed in whole or part from glycolic acid or glycolide.

524. The method of item 363 wherein the composition comprises a synthetic polymer formed in whole or part from glycolic acid or glycolide.

525. The method of item 419 wherein the polymer is formed from reactants comprising polylysine.

526. The method of item 363 wherein the composition comprises polylysine.

527. The method of item 419 wherein the polymer is formed from reactants comprising (a) protein and (b) a compound comprising a polyalkylene oxide portion.

528. The method of item 363 wherein the composition comprises (a) protein and (b) a compound comprising a polyalkylene oxide portion.

529. The method of item 419 wherein the polymer is formed from reactants comprising (a) protein and (b) polylysine.

530. The method of item 363 wherein the composition comprises (a) protein and (b) polylysine.

531. The method of item 419 wherein the polymer is formed from reactants comprising (a) protein and (b) a compound having at least four thiol groups.

532. The method of item 363 wherein the composition comprises (a) protein and (b) a compound having at least four thiol groups.

533. The method of item 419 wherein the polymer is formed from reactants comprising (a) protein and (b) a compound having at least four amino groups.

534. The method of item 363 wherein the composition comprises (a) protein and (b) a compound having at least four amino groups.

535. The method of item 419 wherein the polymer is formed from reactants comprising (a) protein and (b) a compound having at least four carbonyl-oxygen-succinimide groups.

536. The method of item 363 wherein the composition comprises (a) protein and (b) a compound having at least four carbonyl-oxygen-succinimide groups.

537. The method of item 419 wherein the polymer is formed from reactants comprising (a) protein and (b) a compound having a biodegradable region formed from reactants selected from lactic acid, lactide, glycolic acid, glycolide, and epsilon-caprolactone.

538. The method of item 363 wherein the composition comprises (a) protein and (b) a compound having a biodegradable region formed from reactants selected from lactic acid, lactide, glycolic acid, glycolide, and epsilon-caprolactone.

539. The method of item 419 wherein the polymer is formed from reactants comprising (a) collagen and (b) a compound comprising a polyalkylene oxide portion.

540. The method of item 363 wherein the composition comprises (a) collagen and (b) a compound comprising a polyalkylene oxide portion.

541. The method of item 419 wherein the polymer is formed from reactants comprising (a) collagen and (b) polylysine.

542. The method of item 363 wherein the composition comprises (a) collagen and (b) polylysine.

543. The method of item 419 wherein the polymer is formed from reactants comprising (a) collagen and (b) a compound having at least four thiol groups.

544. The method of item 363 wherein the composition comprises (a) collagen and (b) a compound having at least four thiol groups.

545. The method of item 419 wherein the polymer is formed from reactants comprising (a) collagen and (b) a compound having at least four amino groups.

546. The method of item 363 wherein the composition comprises (a) collagen and (b) a compound having at least four amino groups.

547. The method of item 419 wherein the polymer is formed from reactants comprising (a) collage.n and (b) a compound having at least four carbonyl-oxygen-succinimide groups.

548. The method of item 363 wherein the composition comprises (a) collagen and (b) a compound having at least four carbonyl-oxygen-succinimide groups.

549. The method of item 419 wherein the polymer is formed from reactants comprising (a) collagen and (b) a compound having a biodegradable region formed from reactants selected from lactic acid, lactide, glycolic acid, glycolide, and epsilon-caprolactone.

550. The method of item 363 wherein the composition comprises (a) collagen and (b) a compound having a biodegradable region formed from reactants selected from lactic acid, lactide, glycolic acid, glycolide, and epsilon-caprolactone.

551. The method of item 419 wherein the polymer is formed from reactants comprising (a) methylated collagen and (b) a compound comprising a polyalkylene oxide portion.

552. The method of item 363 wherein the composition comprises (a) methylated collagen and (b) a compound comprising a polyalkylene oxide portion.

553. The method of item 419 wherein the polymer is formed from reactants comprising (a) methylated collagen and (b) polylysine.

554. The method of item 363 wherein the composition comprises (a) methylated collagen and (b) polylysine.

555. The method of item 419 wherein the polymer is formed from reactants comprising (a) methylated collagen and (b) a compound having at least four thiol groups.

556. The method of item 363 wherein the composition comprises (a) methylated collagen and (b) a compound having at least four thiol groups.

557. The method of item $^{419}$ wherein the polymer is formed from reactants comprising (a) methylated collagen and (b) a compound having at least four amino groups.

558. The method of item 363 wherein the composition comprises (a) methylated collagen and (b) a compound having at least four amino groups.

559. The method of item 419 wherein the polymer is formed from reactants comprising (a) methylated collagen and (b) a compound having at least four carbonyl-oxygen-succinimide groups.

560. The method of item 363 wherein the composition comprises (a) methylated collagen and (b) a compound having at least four carbonyl-oxygen-succinimide groups.

561. The method of item 419 wherein the polymer is formed from reactants comprising (a) methylated collagen and (b) a compound having a biodegradable region formed from reactants selected from lactic acid, lactide, glycolic acid, glycolide, and epsilon-caprolactone.

562. The method of item 363 wherein the composition comprises (a) methylated collagen and (b) a compound having a biodegradable region formed from reactants selected from lactic acid, lactide, glycolic acid, glycolide, and epsilon-caprolactone.

563. The method of item 419 wherein the polymer is formed from reactants comprising hyaluronic acid.

564. The method of item 363 wherein the composition comprises hyaluronic acid.

565. The method of item 419 wherein the polymer is formed from reactants comprising a hyaluronic acid derivative.

566. The method of item 363 wherein the composition comprises a hyaluronic acid derivative.

567. The method of item 419 wherein the polymer is formed from reactants comprising pentaerythritol poly(ethylene glycol)ether tetra-sulfhydryl of number average molecular weight between 3,000 and 30,000.

568. The method of item 363 wherein the composition comprises pentaerythritol poly(ethylene glycol)ether tetra-sulfhyd ryl of number average molecular weight between 3,000 and 30,000.

569. The method of item 419 wherein the polymer is formed from reactants comprising pentaerythritol poly(ethylene glycol)ether tetra-amino of number average molecular weight between 3,000 and 30,000.

570. The method of item 363 wherein the composition comprises pentaerythritol poly(ethylene glycol)ether tetra-amino of number average molecular weight between 3,000 and 30,000.

571. The method of item 419 wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

572. The method of item 363 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

573. The method of item 363 wherein the composition comprises a colorant.

574. The method of item 363 wherein the composition is sterile.

575. The method of item 363 wherein the composition further comprises a second pharmaceutically active agent.

576. The method of item 363 wherein the composition further comprises an anti-inflammatory agent.

577. The method of item 363 wherein the composition further comprises an agent that inhibits infection.

578. The method of item 363 wherein the composition further comprises an anthracycline.

579. The method of item 363 wherein the composition further comprises doxorubicin.

580. The method of item 363 wherein the composition further comprises mitoxantrone.

581. The method of item 363 wherein the composition further comprises a fluoropyrimidine.

582. The method of item 363 wherein the composition further comprises 5-fluorouracil (5-FU).

583. The method of item 363 wherein the composition further comprises a folic acid antagonist.

584. The method of item 363 wherein the composition further comprises methotrexate.

585. The method of item 363 wherein the composition further comprises a podophylotoxin.

586. The method of item 363 wherein the composition further comprises etoposide.

587. The method of item 363 wherein the composition further comprises camptothecin.

588. The method of item 363 wherein the composition further comprises a hydroxyurea.

589. The method of item 363 wherein the composition further comprises a platinum complex.

590. The method of item 363 wherein the composition further comprises cisplatin.

591. The method of item 363 wherein the composition further comprises an anti-infective agent.

592. The method of item 363 wherein the composition further comprises an anti-infective agent, wherein the anti-infective agent is an antibiotic.

593. The method of item 363 wherein the composition further comprises an anti-infective agent, wherein the anti-infective agent is doxycycline.

594. The method of item 363 wherein the composition further comprises an anti-infective agent, wherein the anti-infective agent is metronidazole.

595. The method of item 363 wherein the composition further comprises an anti-infective agent, wherein the anti-infective agent is trimethoprim-sulfamethoxazole.

596. The method of item 363 wherein the composition further comprises an anti-infective agent, wherein the anti-infective agent is a fourth generation penicillin.

597. The method of item 363 wherein the composition further comprises an anti-infective agent, wherein the anti-infective agent is a fourth generation penicillin selected from a ureidopenicillin and a carboxypenicillin, or an analogue or derivative thereof.

598. The method of item 363 wherein the composition further comprises an anti-infective agent, wherein the anti-infective agent is a fourth generation penicillin selected from meziocillin, piperacillin, carbenicillin, and ticarcillin.

599. The method of item 363 wherein the composition further comprises an anti-infective agent, wherein the anti-infective agent is a first generation cephalosporin.

600. The method of item 363 wherein the composition further comprises an anti-infective agent, wherein the anti-infective agent is a first generation cephalosporin selected from cephazolin sodium, cephalexin, cefazolin, cephapirin, and cephalothin.

601. The method of item 363 wherein the composition further comprises an anti-infective agent, wherein the anti-infective agent is a carboxypenicillin.

602. The method according to item 239 wherein the carboxypenicillin is ticarcillin.

603. The method of item 363 wherein the composition further comprises an anti-infective agent, wherein the anti-infective agent is a second generation cephalosporin.

604. The method of item 363 wherein the composition further comprises an anti-infective agent, wherein the anti-infective agent is a second generation cephalosporin selected from cefuroxime, cefotetan, and cefoxitin.

605. The method of item 363 wherein the composition further comprises an anti-infective agent, wherein the anti-infective agent is a third generation cephalosporin.

606. The method of item 363 wherein the composition further comprises an anti-infective agent, wherein the anti-infective agent is a third generation cephalosporin selected from naxcel, Cefdinir, cefoperazone, ceftazidime, ceftriaxone,and cefotaxime.

607. The method of item 363 wherein the composition further comprises an anti-infective agent, wherein the anti-infective agent is a fourth generation cephalosporin.

608. The method of item 602 wherein the fourth generation cephalosporin is cefepime.

609. The method of item 363 wherein the composition further comprises an anti-infective agent, wherein the anti-infective agent is a monobactam.

610. The method of item 609 wherein the monobactam is azireonam.

611. The method of item 363 wherein the composition further comprises an anti-infective agent, wherein the anti-infective agent is a carbapenem.

612. The method of item 363 wherein the composition further comprises an anti-infective agent, wherein the anti-infective agent is a carbapenem selected from imipenem, ertapenem and meropenem.

613. The method of item 363 wherein the composition further comprises an anti-infective agent, wherein the anti-infective agent is an aminoglycoside.

614. The method of item 363 wherein the composition further comprises an anti-infective agent, wherein the anti-infective agent is an aminoglycoside selected from streptomycin, gentamicin, tobramycin, and amikacin.

615. The method of item 363 wherein the composition further comprises an anti-infective agent, wherein the anti-infective agent is an MSL group member selected from a macrolide, a long acting macrolide, a lincosamide, and a streptogramin.

616. The method of item 363 wherein the composition further comprises an anti-infective agent, wherein the anti-infective agent is an MSL group member selected from Erythromycin, Azithromycin, Clindamycin, Syneroid, clarithromycin, and kanamycin sulfate.

617. The method of item 363 wherein the composition further comprises an anti-infective agent, wherein the anti-infective agent is a quinolone.

618. The method of item 363 wherein the composition further comprises an anti-infective agent, wherein the anti-infective agent is a quinolone selected from ciprofloxacin, ofloxacin, gatifloxacin, moxifloxacin, levofloxacin, and trovafloxacin.

619. The method of item 363 wherein the composition further comprises an anti-infective agent, wherein the anti-infective agent is a DNA synthesis inhibitor.

620. The method of item 619 wherein the DNA synthesis inhibitor is metronidazole.

621. The method of item 363 wherein the composition further comprises an anti-infective agent, wherein the anti-infective agent is a sulfonamide.

622. The method of item 621 wherein the sulfonamide is trimethoprim.

623. The method of item 363 wherein the composition further comprises an anti-infective agent, wherein the anti-infective agent is selected from cefixime, spectinomycin, tetracycline, nitrofurantoin, polymyxin B, and neomycin sulfate.

624. The method of item 363 wherein the composition further comprises a visualization agent.

625. The method of item 363 wherein the composition further comprises a visualization agent, and the visualization agent is a radiopaque material, wherein the radiopaque material comprises a metal, a halogenated compound, or a barium-containing compound.

626. The method of item 363 wherein the composition further comprises a visualization agent, and the visualization agent is, or comprises, barium, tantalum, or technetium.

627. The method of item 363 wherein the composition further comprises a visualization agent, and the visualization agent is, or comprises, an MRI responsive material or an echogenic material.

628. The method of item 363 wherein the composition further comprises a visualization agent, and the visualization agent is, or comprises, a gadolinium chelate.

629. The method of item 363 wherein the composition further comprises a visualization agent, and the visualization agent is, or comprises, iron, magnesium, manganese, copper, or chromium.

630. The method of item 363 wherein the composition further comprises a visualization agent, and the visualization agent is, or comprises, iron oxide compound.

631. The method of item 363 wherein the composition further comprises a visualization agent, and the visualization agent is, or comprises, a dye, pigment, or colorant.

632. The method of item 363 wherein the fibrosing agent is released in effective concentrations from the composition comprising the fibrosing agent by diffusion over a period ranging from the time of administration to about 90 days.

633. The method of item 363 wherein the fibrosing agent is released in effective concentrations from the composition comprising the fibrosing agent by erosion of the composition over a period ranging from the time of administration to about 90 days.

634. The method of item 363 wherein the composition further comprises an inflammatory cytokine.

635. The method of item 363 wherein the composition further comprises an agent that stimulates cell proliferation.

636. The method of item 363 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

637. The method of item 363 wherein the composition further comprises a polymeric carrier.

638. The method of item 363 wherein the composition is in the form of a gel, paste, or spray.

639. The method of item 363 wherein the composition is in the form of a mesh or film.

640. The method of item 363 wherein the fibrosing agent is delivered from a device, and the device delivers the fibrosing agent into the diverticulum.

641. The method of item 363 wherein the fibrosing agent is delivered from an implant, wherein the implant is or comprises a microsphere.

642. The method of item 363 wherein the fibrosing agent is delivered from an implant, wherein the implant is or comprises a mesh.

643. The method of item 363 wherein the fibrosing agent is delivered from an implant, wherein the implant is or comprises a film.

644. The method of item 363 wherein the fibrosing agent is delivered from a device, wherein the device is a catheter.

645. The method of item 363 wherein the fibrosing agent is delivered from a device, wherein the device is a drug delivery catheter.

646. The method of item 363 wherein the fibrosing agent is delivered from a device, wherein the device is a radiofrequencey ablation catheter.

647. The method of item 363 wherein the fibrosing agent is delivered from a device, wherein the device is a temperature ablation catheter.

648. The method of item 363 wherein the fibrosing agent is delivered from a device, wherein the device is a thermal energy catheter.

649. The method of item 363 wherein the fibrosing agent is delivered from a device, wherein the device is a cryoablation catheter.

650. The method of item 363 wherein the fibrosing agent is delivered from a device, wherein the device is a laser catheter.

651. The method of item 363 wherein the fibrosing agent is delivered from a device, wherein the device is a radioactivity-delivenng catheter.

652. The method of item 363 wherein the fibrosing agent is delivered from a device, wherein the device is a balloon catheter.

653. The method of item 363 wherein the fibrosing agent is delivered from a device, wherein the device is an ultrasonic energy-delivenng catheter.

654. The method of item 363 wherein the fibrosing agent is delivered from a device, wherein the device is a rotation atherectomy device.

655. The method of item 363 wherein the fibrosing agent is delivered from a device, wherein the device is a rotation atherectomy device that is a rotoblade.

656. The method of item 363 wherein the fibrosing agent is delivered from a device, wherein the device is a tissue abrasion device.

657. The method of item 363 wherein the fibrosing agent is delivered from a device, wherein the device is an atherectomy device.

658. The method of item 363 wherein the fibrosing agent is delivered from a device, wherein the device is an atherectomy catheter.

659. The method of item 363 wherein the fibrosing agent is delivered from a device, wherein the device is an endoscopic scalpel.

660. The method of item 363 wherein the fibrosing agent is introduced by delivery from a device, wherein the device further comprises a coating, and the coating comprises the fibrosing agent.

661. The method of item 363 wherein the fibrosing agent is introduced by delivery from a device, wherein the device further comprises a coating, and the coating is disposed on a surface of the device.

662. The method of item 363 wherein the fibrosing agent is introduced by delivery from a device, wherein the device further comprises a coating, and wherein the coating directly contacts the device.

663. The method of item 363 wherein the fibrosing agent is introduced by delivery from a device, wherein the device further comprises a coating, and wherein the coating indirectly contacts the device.

664. The method of item 363 wherein the fibrosing agent is introduced by delivery from a device, wherein the device further comprises a coating, and wherein the coating partially covers the device.

665. The method of item 363 wherein the fibrosing agent is introduced by delivery from a device, wherein the device further comprises a coating, and wherein the coating completely covers the device.

666. The method of item 363 wherein the fibrosing agent is introduced by delivery from a device, wherein the fibrosing agent is located within pores or holes of the device.

667. The method of item 363 wherein the fibrosing agent is introduced by delivery from a device, wherein the fibrosing agent is located within a channel, lumen, or divet of the device.

668. The method of item 363 wherein the fibrosing agent is introduced by delivery from a device, wherein the device further comprises an echogenic material.

669. The method of item 363 wherein the fibrosing agent is introduced by delivery from a device, wherein the device further comprises an echogenic material, and wherein the echogenic material is in the form of a coating.

670. The method of item 363 wherein the agent is introduced by delivery from a device, wherein the device is sterile.

671. The method of item 363 wherein the agent is introduced by delivery from a device, wherein the fibrosing agent is released into tissue in the vicinity of the device after deployment of the device.

672. The method of item 363 wherein the agent is introduced by delivery from a device, wherein the fibrosing agent is released into tissue in the vicinity of the device after deployment of the device, and wherein the tissue is connective tissue.

673. The method of item 363 wherein the agent is introduced by delivery from a device, wherein the fibrosing agent is released into tissue in the vicinity of the device after deployment of the device, and wherein the tissue is muscle tissue.

674. The method of item 363 wherein the agent is introduced by delivery from a device, wherein the fibrosing agent is released into tissue in the vicinity of the device after deployment of the device, and wherein the tissue is nerve tissue.

675. The method of item 363 wherein the agent is introduced by delivery from a device, wherein the fibrosing agent is released into tissue in the vicinity of the device after deployment of the device, and wherein the tissue is epithelium tissue.

676. The method of item 363 wherein the agent is introduced by delivery from a device, wherein the fibrosing agent is released in effective concentrations from the device over a period ranging from the time of deployment of the device to about 1 year.

677. The method of item 363 wherein the agent is introduced by delivery from a device, wherein the fibrosing agent is released in effective concentrations from the device over a period ranging from about 1 month to 6 months.

678. The method of item 363 wherein the agent is introduced by delivery from a device, and wherein the fibrosing agent is released in effective concentrations from the device over a period ranging from about 1–90 days.

679. The method of item 363 wherein the agent is introduced by delivery from a device, and wherein the fibrosing agent is released in effective concentrations from the device at a constant rate.

680. The method of item 363 wherein the fibrosing agent is introduced by delivery from a device, and wherein the fibrosing agent is released in effective concentrations from the device at an increasing rate.

681. The method of item 363 wherein the fibrosing agent is introduced by delivery from a device, and wherein the agent is released in effective concentrations from the device at a decreasing rate.

682. The method of item 363 wherein the composition comprises about 0.01 µg to about 10 µg of the fibrosing agent.

683. The method of item 363 wherein the composition comprises about 10 µg to about 10 mg of the fibrosing agent.

684. The method of item 363 wherein the composition comprises about 10 mg to about 250 mg of the fibrosing agent.

685. The method of item 363 wherein the composition comprises about 250 mg to about 1000 mg of the fibrosing agent.

686. The method of item 363 wherein the composition comprises about 1000 mg to about 2500 mg of the fibrosing agent.

687. The method of item 363 wherein the fibrosing agent is introduced by delivery from an implant, and wherein a surface of the implant comprises less than 0.01 µg of the fibrosing agent per mm$^2$ of implant surface to which the agent is applied.

688. The method of item 363 wherein the fibrosing agent is introduced by delivery from an implant, and wherein a surface of the implant comprises about 0.01 µg to about 1 µg of the fibrosing agent per mm$^2$ of implant surface to which the agent is applied.

689. The method of item 363 wherein the fibrosing agent is introduced by delivery from an implant, and wherein a surface of the implant comprises about 1 µg to about 10 µg of the fibrosing agent per mm$^2$ of implant surface to which the agent is applied.

690. The method of item 363 wherein the fibrosing agent is introduced by delivery from an implant, and wherein a surface of the implant comprises about 10 µg to about 250 µg of the fibrosing agent per mm$^2$ of implant surface to which the agent is applied.

691. The method of item 363 wherein the agent is introduced by delivery from an implant, and wherein a surface of the implant comprises about 250 µg to about 1000 µg of the fibrosing agent of fibrosing agent per mm$^2$ of implant surface to which the fibrosing agent is applied.

692. The method of item 363 wherein the agent is introduced by delivery from an implant, and wherein a surface of the implant comprises about 1000 µg to about 2500 µg of the fibrosing agent per mm$^2$ of implant surface to which the agent is applied.

693. The method of item 363 wherein the agent is introduced by delivery from an implant, wherein the implant further comprises a coating, and wherein the coating is a uniform coating.

694. The method of item 363 wherein the agent is introduced by delivery from an implant, wherein the implant further comprises a coating, and wherein the coating is a non-uniform coating.

695. The method of item 363 wherein the agent is introduced by delivery from an implant, wherein the implant further comprises a coating, and wherein the coating is a discontinuous coating.

696. The method of item 363 wherein the agent is introduced by delivery from an implant, wherein the implant further comprises a coating, and wherein the coating is a patterned coating.

697. The method of item 363 wherein the agent is introduced by delivery from an implant, wherein the implant further comprises a coating, and wherein the coating has a thickness of 100 µm or less.

698. The method of item 363 wherein the agent is introduced by delivery from an implant, wherein the implant further comprises a coating, and wherein the coating has a thickness of 10 µm or less.

699. The method of item 363 wherein the agent is introduced by delivery from an implant, wherein the implant further comprises a coating, and wherein the coating adheres to the surface of the implant upon deployment of the implant.

700. The method of item 363 wherein the agent is introduced by delivery from an implant, wherein the implant further comprises a coating, and wherein the coating is stable at room temperature for a period of at least 1 year.

701. The method of item 363 wherein the agent is introduced by delivery from an implant, wherein the implant further comprises a coating, and wherein the fibrosing agent is present in the coating in an amount ranging between about 0.0001% to about 1% by weight.

702. The method of item 363 wherein the agent is introduced by delivery from an implant, wherein the implant further comprises a coating, and wherein the agent is present in the coating in an amount ranging between about 1% to about 10% by weight.

703. The method of item 363 wherein the agent is introduced by delivery from an implant, wherein the implant further comprises a coating, and wherein the agent is present in the coating in an amount ranging between about 10% to about 25% by weight.

704. The method of item 363 wherein the agent is introduced by delivery from an implant, wherein the implant further comprises a coating, and wherein the fibrosing agent is present in the coating in an amount ranging between about 25% to about 70% by weight.

705. The method of item 363 wherein the agent is introduced by delivery from an implant, wherein the dev implant ice further comprises a coating, and wherein the coating comprises a polymer.

706. The method of item 363 wherein the agent is introduced by delivery from an implant, wherein the implant comprises a first coating having a first composition and a second coating having a second composition.

707. The method of item 363 wherein the agent is introduced by delivery from an implant, wherein the implant comprises a first coating having a first composition and a second coating having a second composition, wherein the first composition and the second composition are different.

708. The method of item 363 wherein the agent or the composition comprising the agent is injected or sprayed into the diverticulum.

709. The method of item 363 wherein the agent or the composition comprising the agent is injected or sprayed onto a tissue or into a tissue surrounding the diverticulum.

710. The method of item 363 wherein the composition further comprises a bulking agent.

711. The method of item 363 wherein the composition is a sealant.

712. The method of item 363 wherein the composition is a haemostatic agent.

713. The method of item 363 wherein the composition further comprises a bulking agent, wherein the bulking agent comprises microspheres.

714. The method of item 363 wherein the composition further comprises a bulking agent, wherein the bulking agent comprises a hydroxyapatite loaded gel.

715. The method of item 363 wherein the composition further comprises a bulking agent, wherein the bulking agent comprises a micronized alloderm acellular matrix.

716. The method of item 363 wherein the composition further comprises a bulking agent, wherein the bulking agent comprises hyaluronic acid.

717. The method of item 363 wherein the composition further comprises a bulking agent, wherein the bulking agent comprises micro-beads in a hydrogel.

718. The method of item 363 wherein the composition further comprises a bulking agent, wherein the bulking agent comprises a hylan polymer.

719. The method of item 363 wherein the composition further comprises a bulking agent, wherein the bulking agent comprises a silicon microballoon and biocompatible polymer.

720. The method of item 363 further comprising visualizing the presence of a diverticulum.

721. The method of item 720 wherein visualizing the presence of a diverticulum comprising endoscopy.

722. The method of item 720 wherein visualizing the presence of a diverticulum comprising radiographic imaging.

723. The method of item 363 further comprising irrigating of the diverticulum with an irrigation solution prior to introducing the fibrosing agent.

724. The method of item 723 wherein the irrigation solution comprises (a) an anti-infective agent or (b) an antiseptic agent or (c) an anti-infective agent and an antiseptic agent.

725. A composition comprising (a) a fibrosing agent and (b) a polymer or a compound that polymerizes to form a crosslinked polymer in situ.

726. The composition of item 725 wherein the fibrosing agent promotes regeneration.

727. The composition of item 725 wherein the fibrosing agent promotes fibrosis and promotes regeneration.

728. The composition of item 725 wherein the fibrosing agent promotes angiogenesis.

729. The composition of item 725 wherein the fibrosing agent promotes fibroblast migration.

730. The composition of item 725 wherein the fibrosing agent promotes fibroblast proliferation.

731. The composition of item 725 wherein the fibrosing agent promotes deposition of extracellular matrix (ECM).

732. The composition of item 725 wherein the fibrosing agent promotes tissue remodeling.

733. The composition of item 725 wherein the fibrosing agent is a diverticular wall irritant.

734. The composition of item 725 wherein the fibrosing agent is or comprises silk.

735. The composition of item 725 wherein the fibrosing agent is or comprises silkworm silk.

736. The composition of item 725 wherein the fibrosing agent is or comprises spider silk.

737. The composition of item 725 wherein the fibrosing agent is or comprises recombinant silk.

738. The composition of item 725 wherein the fibrosing agent is or comprises raw silk.

739. The composition of item 725 wherein the fibrosing agent is or comprises hydrolyzed silk.

740. The composition of item 725 wherein the fibrosing agent is or comprises acid-treated silk.

741. The composition of item 725 wherein the fibrosing agent is or comprises acylated silk.

742. The composition of item 725 wherein the fibrosing agent is in the form of strands.

743. The composition of item 725 wherein the fibrosing agent is in the form of tufts.

744. The composition of item 725 wherein the fibrosing agent is or comprises mineral particles.

745. The composition of item 725 wherein the fibrosing agent is or comprises chitosan.

746. The composition of item 725 wherein the fibrosing agent is or comprises polylysine.

747. The composition of item 725 wherein the fibrosing agent is or comprises fibronectin.

748. The composition of item 725 wherein the fibrosing agent is or comprises bleomycin.

749. The composition of item 725 wherein the fibrosing agent is or comprises CTGF.

750. The composition of item 725 wherein the fibrosing agent is or comprises a wool.

751. The composition of item 725 wherein the fibrosing agent is or comprises an animal wool.

752. The composition of item 725 wherein the fibrosing agent is or comprises a wood wool.

753. The composition of item 725 wherein the fibrosing agent is or comprises a synthetic wool.

754. The composition of item 725 wherein the fibrosing agent is in the form of a thread, or is in contact with a thread.

755. The composition of item 754 wherein the thread is biodegradable.

756. The composition of item 755 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

757. The composition of item 754 wherein the thread is non-biodegradable.

758. The composition of item 757 wherein the non-biodegradable thread comprises a material selected from the group consisting of polyester, polyurethane, silicone, polyethylene, polypropylene, polystyrene, polyacrylate, polymethacrylate, and silk.

759. The composition of item 754 wherein the thread is coated with a polymer.

760. The composition of item 754 wherein the thread is coated with a pharmaceutical agent that induces a fibrotic response in the host.

761. The composition of item 725 wherein the fibrosing agent is in the form of a particulate.

762. The composition of item 761 wherein the particulate is a biodegradable particulate.

763. The composition of item 762 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

764. The composition of item 761 wherein the particulate is a non-biodegradable particulate.

765. The composition of item 764 wherein the non-biodegradable particulate comprises a material selected from the group consisting of polyester, polyurethane, silicone, polyethylene, polypropylene, polystyrene, polyacrylate, polymethacrylate, and silk.

766. The composition of item 761 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

767. The composition of item 761 wherein the particulate is coated with a polymer.

768. The composition of item 761 wherein the particulate is coated with a pharmaceutical agent that induces a fibrotic response in the host.

769. The composition of item 761 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

770. The composition of item 725 wherein the composition comprises a growth factor.

771. The composition of item 770 wherein the growth factor is selected from a transforming growth factor, a platelet-derived growth factor, and a fibroblast growth factor.

772. The composition of any one of items 725–771, wherein the polymer is, or comprises, a copolymer.

773. The composition of any one of items 725–771, wherein the polymer is, or comprises, a block copolymer.

774. The composition of any one of items 725–771, wherein the polymer is, or comprises, a random copolymer.

775. The composition of any one of items 725–771, wherein the polymer is, or comprises, a biodegradable polymer.

776. The composition of any one of items 725–771, wherein the polymer is, or comprises, a non-biodegradable polymer.

777. The composition of any one of items 725–771, wherein the polymer is, or comprises, a hydrophilic polymer.

778. The composition of any one of items 725–771, wherein the polymer is, or comprises, a hydrophobic polymer.

779. The composition of any one of items 725–771, wherein the polymer is, or comprises, a polymer having hydrophilic domains.

780. The composition of any one of items 725–771, wherein the polymer is, or comprises, a polymer having hydrophobic domains.

781. The composition of any one of items 725–771, wherein the polymer is, or comprises, a non-conductive polymer.

782. The composition of any one of items 725–771, wherein the polymer is, or comprises, an elastomer.

783. The composition of any one of items 725–771, wherein the polymer is, or comprises, a hydrogel.

784. The composition of any one of items 725–771, wherein the polymer is, or comprises, a silicone polymer.

785. The composition of any one of items 725–771, wherein the polymer is, or comprises, a hydrocarbon polymer.

786. The composition of any one of items 725–771, wherein the polymer is, or comprises, a styrene-derived polymer.

787. The composition of any one of items 725–771, wherein the polymer is, or comprises, a butadiene-derived polymer.

788. The composition of any one of items 725–771, wherein the polymer is, or comprises, a macromer.

789. The composition of any one of items 725–771, wherein the polymer is, or comprises, a poly(ethylene glycol).

790. The composition of any one of items 725–771, wherein the polymer is, or comprises, a collagen or a derivative thereof.

791. The composition of any one of items 725–771, wherein the polymer is, or comprises, a methylated collagen.

792. The composition of any one of items 725–771, wherein the composition further comprises a polymer composition, wherein the polymer composition comprises a collagen or a derivative thereof and a fibrinogen.

793. The composition of any one of items 725–771, wherein the composition further comprises a polymer composition, wherein the polymer composition comprises a collagen or a derivative thereof and a thrombin.

794. The composition of any one of items 725–771, wherein the composition further comprises a polymer composition, wherein the polymer composition comprises (a) a collagen or a derivative thereof; (b) a fibrinogen; and (c) a thrombin.

795. The composition of any one of items 725–771, wherein the composition further comprises a polymer composition, wherein the polymer composition comprises a methylated collagen and a poly(ethylene glycol).

796. The composition of any one of items 725–771 wherein the composition further comprises a haemostatic agent that comprises a collagen polymer.

797. The composition of any one of items 725–771 wherein the composition further comprises a haemostatic agent that comprises a collagen polymer, wherein the haemostatic agent is CT3.

798. The composition of any one of items 725–771 wherein the composition further comprises a haemostatic agent that comprises a collagen polymer, wherein the haemostatic agent is COSTASIS.

799. The composition of any one of items 725–771 wherein the composition further comprises a haemostatic agent that comprises a poly(ethylene glycol).

800. The composition of any one of items 725–771, wherein the composition further comprises a haemostatic agent wherein the haemostatic agent is COSEAL, TISSEALL, or FLOSEAL.

801. The composition of any one of items 725–771, wherein the composition further comprises a haemostatic agent that comprises fibrin.

802. The composition of any one of items 725–771, wherein the polymer is, or comprises, an amorphous polymer.

803. The composition of any one of items 725–771, wherein the polymer is, or comprises, a cyanoacrylate.

804. The method of item 803, wherein the cyanoacrylate is selected from methyl cyanoacrylate, ethyl cyanoacrylate, butyl cyanoacrylate, octyl cyanoacrylate, and methoxypropyl cyanoacrylate.

805. The composition of any one of items 725–771, wherein the polymer is, or comprises, a poly(alkylcyanoacrylate).

806. The method of item 805, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

807. The composition of any one of items 725–771, wherein the polymer is, or comprises, a poly(carboxyalkylcyanoacrylate).

808. The method of item 807 wherein the poly(carboxyalkylcyanoacrylate) is poly(methoxypropylcyanoacrylate).

809. The composition of any one of items 725–771, wherein the polymer is crosslinked.

810. The composition of any one of items 725–771 wherein the polymer reacts with mammalian tissue.

811. The composition of any one of items 725–771, wherein the polymer is a naturally occurring polymer.

812. The composition of any one of items 725–771, wherein the polymer is protein.

813. The composition of any one of items 725–771, wherein the polymer is carbohydrate.

814. The composition of any one of items 725–771, wherein the polymer is crosslinked and biodegradable.

815. The composition of any one of items 725–771 wherein the composition comprises a fibnnogen.

816. The composition of any one of items 725–771 wherein the composition comprises a thrombin.

817. The composition of any one of items 725–771 wherein the composition comprises a calcium salt.

818. The composition of any one of items 725–771 wherein the composition comprises an antifibronolytic agent.

819. The composition of any one of items 725–771 wherein the composition comprises a fibrinogen analog.

820. The composition of any one of items 725–771 wherein the composition comprises an albumin.

821. The composition of any one of items 725–771 wherein the composition comprises a plasminogen.

822. The composition of any one of items 725–771 wherein the composition comprises a von Willebrands factor.

823. The composition of any one of items 725–771 wherein the composition comprises a Factor VIII.

824. The composition of any one of items 725–771 wherein the composition comprises a hypoallergenic collagen.

825. The composition of any one of items 725–771 wherein the composition comprises a telopeptide collagen.

826. The composition of any one of items 725–771 wherein the composition comprises a crosslinked collagen.

827. The composition of any one of items 725–771 wherein the composition comprises an aprotinin.

828. The composition of any one of items 725–771 wherein the composition comprises an epsilon-amino-n-caproic acid.

829. The composition of any one of items 725–771 wherein the composition comprises a gelatin.

830. The composition of any one of items 725–771 wherein the composition comprises a protein conjugate.

831. The composition of any one of items 725–771 wherein the composition comprises a gelatin conjugate.

832. The composition of any one of items 725–771 wherein the composition comprises a hyaluronic acid.

833. The composition of any one of items 725–771 wherein the composition comprises a hyaluronic acid derivative.

834. The composition of any one of items 725–771 wherein the composition comprises a synthetic polymer.

835. The composition of any one of items 725–771, wherein the polymer is formed from reactants comprising a synthetic isocyanate-containing compound.

836. The composition of any one of items 725–771 wherein the composition comprises a synthetic isocyanate-containing compound.

837. The composition of any one of items 725–771, wherein the polymer is formed from reactants comprising a synthetic thiol-containing compound.

838. The composition of any one of items 725–771 wherein the composition comprises a synthetic thiol-containing compound.

839. The composition of any one of items 725–771, wherein the polymer is formed from reactants comprising a synthetic compound containing at least two thiol groups.

840. The composition of any one of items 725–771 wherein the composition comprises a synthetic compound containing at least two thiol groups.

841. The composition of any one of items 725–771, wherein the polymer is formed from reactants comprising a synthetic compound containing at least three thiol groups.

842. The composition of any one of items 725–771 wherein the composition comprises a synthetic compound containing at least three thiol groups.

843. The composition of any one of items 725–771, wherein the polymer is formed from reactants comprising a synthetic compound containing at least four thiol groups.

844. The composition of any one of items 725–771, wherein the composition comprises a synthetic compound containing at least four thiol groups.

845. The composition of any one of items 725–771, wherein the polymer is formed from reactants comprising a synthetic amino-containing compound.

846. The composition of any one of items 725–771, wherein the composition comprises a synthetic amino-containing compound.

847. The composition of any one of items 725–771, wherein the polymer is formed from reactants comprising a synthetic compound containing at least two amino groups.

848. The composition of any one of items 725–771 wherein the composition comprises a synthetic compound containing at least two amino groups.

849. The composition of any one of items 725–771, wherein the polymer is formed from reactants comprising a synthetic compound containing at least three amino groups.

850. The composition of any one of items 725–771 wherein the composition comprises a synthetic compound containing at least three amino groups.

851. The composition of any one of items 725–771, wherein the polymer is formed from reactants comprising a synthetic compound containing at least four amino groups.

852. The composition of any one of items 725–771, wherein the composition comprises a synthetic compound containing at least four amino groups.

853. The composition of any one of items 725–771, wherein the polymer is formed from reactants comprising a synthetic compound comprising a carbonyl-oxygen-succinimidyl group.

854. The composition of any one of items 725–771 wherein the composition comprises a synthetic compound comprising a carbonyl-oxygen-succinimidyl group.

855. The composition of any one of items 725–771, wherein the polymer is formed from reactants comprising a synthetic compound comprising at least two carbonyl-oxygen-succinimidyl groups.

856. The composition of any one of items 725–771, wherein the composition comprises a synthetic compound comprising at least two carbonyl-oxygen-succinimidyl groups.

857. The composition of any one of items 725–771, wherein the polymer is formed from reactants comprising a synthetic compound comprising at least three carbonyl-oxygen-succinimidyl groups.

858. The composition of any one of items 725–771 wherein the composition comprises a synthetic compound comprising at least three carbonyl-oxygen-succinimidyl groups.

859. The composition of any one of items 725–771, wherein the polymer is formed from reactants comprising a synthetic compound comprising at least four carbonyl-oxygen-succinimidyl groups.

860. The composition of any one of items 725–771 wherein the composition comprises a synthetic compound comprising at least four carbonyl-oxygen-succinimidyl groups.

861. The composition of any one of items 725–771, wherein the polymer is formed from reactants comprising a synthetic polyalkylene oxide-containing compound.

862. The composition of any one of items 725–771 wherein the composition comprises a synthetic polyalkylene oxide-containing compound.

863. The composition of any one of items 725–771, wherein the composition further comprises a polymer, and wherein the polymer is formed from reactants comprising a synthetic compound comprising both polyalkylene oxide and biodegradable polyester blocks.

864. The composition of any one of items 725–771 wherein the composition comprises a synthetic compound comprising both polyalkylene oxide and biodegradable polyester blocks.

865. The composition of any one of items 725–771, wherein the polymer is formed from reactants comprising a synthetic polyalkylene oxide-containing compound having reactive amino groups.

866. The composition of any one of items 725–771 wherein the composition comprises synthetic polyalkylene oxide-containing compound having reactive amino groups.

867. The composition of any one of items 725–771, wherein the polymer is formed from reactants comprising a synthetic polyalkylene oxide-containing compound having reactive thiol groups.

868. The composition of any one of items 725–771 wherein the composition comprises synthetic polyalkylene oxide-containing compound having reactive thiol groups.

869. The composition of any one of items 725–771, wherein the polymer is formed from reactants comprising a synthetic polyalkylene oxide-containing compound having reactive carbonyl-oxygen-succinimidyl groups.

870. The composition of any one of items 725–771 wherein the composition comprises a synthetic polyalkylene oxide-containing compound having reactive carbonyl-oxygen-succinimidyl groups.

871. The composition of any one of items 725–771, wherein the polymer is formed from reactants comprising a synthetic compound comprising a biodegradable polyester block.

872. The composition of any one of items 725–771 wherein the composition comprises a synthetic compound comprising a biodegradable polyester block.

873. The composition of any one of items 725–771, wherein the polymer is formed from reactants comprising a synthetic polymer formed in whole or part from lactic acid or lactide.

874. The composition of any one of items 725–771 wherein the composition comprises a synthetic polymer formed in whole or part from lactic acid or lactide.

875. The composition of any one of items 725–771, wherein the polymer is formed from reactants comprising a synthetic polymer formed in whole or part from glycolic acid or glycolide.

876. The composition of any one of items 725–771 wherein the composition comprises a synthetic polymer formed in whole or part from glycolic acid or glycolide.

877. The composition of any one of items 725–771, wherein the polymer is formed from reactants comprising polylysine.

878. The composition of any one of items 725–771 wherein the composition comprises polylysine.

879. The composition of any one of items. 725–771, wherein the polymer is formed from reactants comprising (a) protein and (b) a compound comprising a polyalkylene oxide portion.

880. The composition of any one of items 725–771 wherein the composition comprises (a) protein and (b) a compound comprising a polyalkylene oxide portion.

881. The composition of any one of items 725–771, wherein the polymer is formed from reactants comprising (a) protein and (b) polylysine.

882. The composition of any one of items 725–771 wherein the composition comprises (a) protein and (b) polylysine.

883. The composition of any one of items 725–771, wherein the composition further comprises a polymer, and wherein the polymer is formed from reactants comprising (a) protein and (b) a compound having at least four thiol groups.

884. The composition of any one of items 725–771 wherein the composition comprises (a) protein and (b) a compound having at least four thiol groups.

885. The composition of any one of items 725–771, wherein the polymer is formed from reactants comprising (a) protein and (b) a compound having at least four amino groups.

886. The composition of any one of items 725–771 wherein the composition comprises (a) protein and (b) a compound having at least four amino groups.

887. The composition of any one of items 725–771, wherein the polymer is formed from reactants comprising (a) protein and (b) a compound having at least four carbonyl-oxygen-succinimide groups.

888. The composition of any one of items 725–771 wherein the composition comprises (a) protein and (b) a compound having at least four carbonyl-oxygen-succinimide groups.

889. The composition of any one of items 725–771, wherein the polymer is formed from reactants comprising (a) protein and (b) a compound having a biodegradable region formed from reactants selected from lactic acid, lactide, glycolic acid, glycolide, and epsilon-caprolactone.

890. The composition of any one of items 725–771 wherein the composition comprises (a) protein and (b) a compound having a biodegradable region formed from reactants selected from lactic acid, lactide, glycolic acid, glycolide, and epsilon-caprolactone.

891. The composition of any one of items 725–771, wherein the polymer is formed from reactants comprising (a) collagen and (b) a compound comprising a polyalkylene oxide portion.

892. The composition of any one of items 725–771 wherein the composition comprises (a) collagen and (b) a compound comprising a polyalkylene oxide portion.

893. The composition of any one of items 725–771, wherein the polymer is formed from reactants comprising (a) collagen and (b) polylysine.

894. The composition of any one of items 725–771 wherein the composition comprises (a) collagen and (b) polylysine.

895. The composition of any one of items 725–771, wherein the polymer is formed from reactants comprising (a) collagen and (b) a compound having at least four thiol groups.

896. The composition of any one of items 725–771 wherein the composition comprises (a) collagen and (b) a compound having at least four thiol groups.

897. The composition of any one of items 725–771, wherein the polymer is formed from reactants comprising (a) collagen and (b) a compound having at least four amino groups.

898. The composition of any one of items 725–771 wherein the composition comprises (a) collagen and (b) a compound having at least four amino groups.

899. The composition of any one of items 725–771, wherein the polymer is formed from reactants comprising (a) collagen and (b) a compound having at least four carbonyl-oxygen-succinimide groups.

900. The composition of any one of items 725–771 wherein the composition comprises (a) collagen and (b) a compound having at least four carbonyl-oxygen-succinimide groups.

901. The composition of any one of items 725–771, wherein the polymer is formed from reactants comprising (a) collagen and (b) a compound having a biodegradable region formed from reactants selected from lactic acid, lactide, glycolic acid, glycolide, and epsilon-caprolactone.

902. The composition of any one of items 725–771 wherein the composition comprises (a) collagen and (b) a compound having a biodegradable region formed from reactants selected from lactic acid, lactide, glycolic acid, glycolide, and epsilon-caprolactone.

903. The composition of any one of items 725–771, wherein the polymer is formed from reactants comprising (a) methylated collagen and (b) a compound comprising a polyalkylene oxide portion.

904. The composition of any one of items 725–771 wherein the composition comprises (a) methylated collagen and (b) a compound comprising a polyalkylene oxide portion.

905. The composition of any one of items 725–771, wherein the composition further comprises a polymer, and wherein the polymer is formed from reactants comprising (a) methylated collagen and (b) polylysine.

906. The composition of any one of items 725–771 wherein the composition comprises (a) methylated collagen and (b) polylysine.

907. The composition of any one of items 725–771, wherein the polymer is formed from reactants comprising (a) methylated collagen and (b) a compound having at least four thiol groups.

908. The composition of any one of items 725–771 wherein the composition comprises (a) methylated collagen and (b) a compound having at least four thiol groups.

909. The composition of any one of items 725–771, wherein the composition further comprises a polymer, and wherein the polymer is formed from reactants comprising (a) methylated collagen and (b) a compound having at least four amino groups.

910. The composition of any one of items 725–771 wherein the composition comprises (a) methylated collagen and (b) a compound having at least four amino groups.

911. The composition of any one of items 725–771, wherein the polymer is formed from reactants comprising (a) methylated collagen and (b) a compound having at least four carbonyl-oxygen-succinimide groups.

912. The composition of any one of items 725–771 wherein the composition comprises (a) methylated collagen and (b) a compound having at least four carbonyl-oxygen-succinimide groups.

913. The composition of any one of items 725–771, wherein the polymer is formed from reactants comprising (a) methylated collagen and (b) a compound having a biodegradable region formed from reactants selected from lactic acid, lactide, glycolic acid, glycolide, and epsilon-caprolactone.

914. The composition of any one of items 725–771 wherein the composition comprises (a) methylated collagen and (b) a compound having a biodegradable region formed from reactants selected from lactic acid, lactide, glycolic acid, glycolide, and epsilon-caprolactone.

915. The composition of any one of items 725–771, wherein the polymer is formed from reactants comprising hyaluronic acid.

916. The composition of any one of items 725–771 wherein the composition comprises hyaluronic acid.

917. The composition of any one of items 725–771, wherein the composition further comprises a polymer, and wherein the polymer is formed from reactants comprising a hyaluronic acid derivative.

918. The composition of any one of items 725–771 wherein the composition comprises a hyaluronic acid derivative.

919. The composition of any one of items 725–771, wherein the polymer is formed from reactants comprising pentaerythritol poly(ethylene glycol)ether tetra-sulfhydryl of number average molecular weight between 3,000 and 30,000.

920. The composition of any one of items 725–771 wherein the composition comprises pentaerythritol poly (ethylene glycol)ether tetra-sulfhydryl of number average molecular weight between 3,000 and 30,000.

921. The composition of any one of items 725–771, wherein the polymer is formed from reactants comprising pentaerythritol poly(ethylene glycol)ether tetra-amino of number average molecular weight between 3,000 and 30,000.

922. The composition of any one of items 725–771 wherein the composition comprises pentaerythritol poly (ethylene glycol)ether tetra-amino of number average molecular weight between 3,000 and 30,000.

923. The composition of any one of items 725–771, wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

924. The composition of any one of items 725–771 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

925. The composition of any one of items 725–771 wherein the composition comprises a colorant.

926. The composition of any one of items 725–771 wherein the composition is sterile.

927. The composition of any one of items 725–771, wherein the composition further comprises a second pharmaceutically active agent.

928. The composition of any one of items 725–771, wherein the composition further comprises an anti-inflammatory agent.

929. The composition of any one of items 725–771, wherein the composition further comprises an agent that inhibits infection.

930. The composition of any one of items 725–771, wherein the composition further comprises an anthracycline.

931. The composition of any one of items 725–771, wherein the composition further comprises doxorubicin.

932. The composition of any one of items 725–771 wherein the composition further comprises mitoxantrone.

933. The composition of any one of items 725–771 wherein the composition further comprises a fluoropyrimidine.

934. The composition of any one of items 725–771, wherein the composition further comprises 5-fluorouracil (5-FU).

935. The composition of any one of items 725–771, wherein the composition further comprises a folic acid antagonist.

936. The composition of any one of items 725–771, wherein the composition further comprises methotrexate.

937. The composition of any one of items 725–771, wherein the composition further comprises a podophylotoxin.

938. The composition of any one of items 725–771, wherein the composition further comprises etoposide.

939. The composition of any one of items 725–771, wherein the composition further comprises camptothecin.

940. The composition of any one of items 725–771, wherein the composition further comprises a hydroxyurea.

941. The composition of any one of items 725–771, wherein the composition further comprises a platinum complex.

942. The composition of any one of items 725–771, wherein the composition further comprises cisplatin.

943. The composition of any one of items 725–771 wherein the composition further comprises an anti-infective agent.

944. The composition of any one of items 725–771 wherein the composition further cbmprises an anti-infective agent, wherein the anti-infective agent is an antibiotic.

945. The composition of any one of items 725–771 wherein the composition further comprises an anti-infective agent, wherein the anti-infective agent is doxycycline.

946. The composition of any one of items 725–771 wherein the composition further comprises an anti-infective agent, wherein the anti-infective agent is metronidazole.

947. The composition of any one of items 725–771 wherein the composition further comprises an anti-infective agent, wherein the anti-infective agent is trimethoprim-sulfamethoxazole.

948. The composition of any one of items 725–771 wherein the composition further comprises an anti-infective agent, wherein the anti-infective agent is a fourth generation penicillin.

949. The composition of any one of items 725–771 wherein the composition further comprises an anti-infective agent, wherein the anti-infective agent is a fourth generation penicillin selected from a ureidopenicillin and a carboxypenicillin, or an analogue or derivative thereof.

950. The composition of any one of items 725–771 wherein the composition further comprises an anti-infective agent, wherein the anti-infective agent is a fourth generation penicillin selected from mezlocillin, piperacillin, carbenicillin, and ticarcillin.

951. The composition of any one of items 725–771 wherein the composition further comprises an anti-infective agent, wherein the anti-infective agent is a first generation cephalosporin.

952. The composition of any one of items 725–771 wherein the composition further comprises an anti-infective agent, wherein the anti-infective agent is a first generation cephalosporin selected from cephazolin sodium, cephalexin, cefazolin, cephapirin, and cephalothin.

953. The composition of any one of items 725–771 wherein the composition further comprises an anti-infective agent, wherein the anti-infective agent is a carboxypenicillin.

954. The composition of item 943 wherein the carboxypenicillin is ticarcillin.

955. The composition of any one of items 725–771 wherein the composition further comprises an anti-infective agent, wherein the anti-infective agent is a second generation cephalosporin.

956. The composition of any one of items 725–771 wherein the composition further comprises an anti-infective agent, wherein the anti-infective agent is a second generation cephalosporin selected from cefuroxime, cefotetan, and cefoxitin.

957. The composition of any one of items 725–771 wherein the composition further comprises an anti-infective agent, wherein the anti-infective agent is a third generation cephalosporin.

958. The composition of any one of items 725–771 wherein the composition further comprises an anti-infective agent, wherein the anti-infective agent is a third generation cephalosporin selected from naxcel, Cefdinir, cefoperazone, ceftazidime, ceftriaxone, and cefotaxime.

959. The composition of any one of items 725–771 wherein the composition further comprises an anti-infective agent, wherein the anti-infective agent is a fourth generation cephalosporin.

960. The composition of item 959 wherein the fourth generation cephalosporin is cefepime.

961. The composition of any one of items 725–771 wherein the composition further comprises an anti-infective agent, wherein the anti-infective agent is a monobactam.

962. The composition of item 961 wherein the monobactam is aztreonam.

963. The composition of any one of items 725–771 wherein the composition further comprises an anti-infective agent, wherein the anti-infective agent is a carbapenem.

964. The composition of any one of items 725–771 wherein the composition further comprises an anti-infective agent, wherein the anti-infective agent is a carbapenem selected from imipenem, ertapenem and meropenem.

965. The composition of any one of items 725–771 wherein the composition further comprises an anti-infective agent, wherein the anti-infective agent is an aminoglycoside.

966. The composition of any one of items 725–771 wherein the composition further comprises an anti-infective agent, wherein the anti-infective agent is an aminoglycoside selected from streptomycin, gentamicin, tobramycin, and amikacin.

967. The composition of any one of items 725–771 wherein the composition further comprises an anti-infective agent, wherein the anti-infective agent is an MSL group member selected from a macrolide, a long acting macrolide, a lincosamide, and a streptogramin.

968. The composition of any one of items 725–771 wherein the composition further comprises an anti-infective agent, wherein the anti-infective agent is an MSL group member selected from Erythromycin, Azithromycin, Clindamycin, Syneroid, clarithromycin, and kanamycin sulfate.

969. The composition of any one of items 725–771 wherein the composition further comprises an anti-infective agent, wherein the anti-infective agent is a quinolone.

970. The composition of any one of items 725–771 wherein the composition further comprises an anti-infective agent, wherein the anti-infective agent is a quinolone selected from ciprofloxacin, ofloxacin, gatifloxacin, moxifloxacin, levofloxacin, and trovafloxacin.

971. The composition of any one of items 725–771 wherein the composition further comprises an anti-infective agent, wherein the anti-infective agent is a DNA synthesis inhibitor.

972. The composition of item 971 wherein the DNA synthesis inhibitor is metronidazole.

973. The composition of any one of items 725–771 wherein the composition further comprises an anti-infective agent, wherein the anti-infective agent is a sulfonamide.

974. The composition of item 973 wherein the sulfonamide is trimethoprim.

975. The composition of any one of items 725–771 wherein the composition further comprises an anti-infective agent, wherein the anti-infective agent is selected from cefixime, spectinomycin, tetracycline, nitrofurantoin, polymyxin B, and neomycin sulfate 976. The composition of any one of items 725–771 wherein the composition further comprises a visualization agent.

977. The composition of any one of items 725–771 wherein the composition further comprises a visualization agent, and the visualization agent is a radiopaque material, wherein the radiopaque material comprises a metal, a halogenated compound, or a barium containing compound.

978. The composition of any one of items 725–771 wherein the composition further comprises a visualization agent, and the visualization agent is, or comprises, barium, tantalum, or technetium.

979. The composition of any one of items 725–771 wherein the composition further comprises a visualization agent, and the visualization agent is, or comprises, an MRI responsive material or an echogenic material.

980. The composition of any one of items 725–771 wherein the composition further comprises a visualization agent, and the visualization agent is, or comprises, a gadolinium chelate.

981. The composition of any one of items 725–771 wherein the composition further comprises a visualization agent, and the visualization agent is, or comprises, iron, magnesium, manganese, copper, or chromium.

982. The composition of any one of items 725–771 wherein the composition further comprises a visualization agent, and the visualization agent is, or comprises, iron oxide compound.

983. The composition of any one of items 725–771 wherein the composition further comprises a visualization agent, and the visualization agent is, or comprises, a dye, pigment, or colorant.

984. The composition of any one of items 725–771 wherein the fibrosing agent is released in effective concentrations from the composition comprising the fibrosing agent by diffusion over a period ranging from the time of administration to about 90 days.

985. The composition of any one of items 725–771 wherein the fibrosing agent is released in effective concentrations from the composition comprising the fibrosing agent by erosion of the composition over a period ranging from the time of administration to about 90 days.

986. The composition of any one of items 725–771 wherein the composition further comprises an inflammatory cytokine.

987. The composition of any one of items 725–771 wherein the composition further comprises an agent that stimulates cell proliferation.

988. The composition of any one of items 725–771 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

989. The composition of any one of items 725–771 wherein the composition further comprises a polymeric carrier.

990. The composition of any one of items 725–771 wherein the composition is in the form of a gel, paste, or spray.

991. The composition of any one of items 725–771 wherein the composition is in the form of a mesh or a film.

992. The composition of any one of items 725–771 wherein the agent or the composition comprising the agent is injected or sprayed into the diverticulum.

993. The composition of any one of items 725–771 wherein the agent or the composition comprising the agent is injected or sprayed onto a tissue or into a tissue surrounding the diverticulum.

994. The composition of any one of items 725–771 wherein the composition further comprises a bulking agent.

995. The composition of item 725–771 wherein the composition is a sealant.

996. The composition of item 725 wherein the composition is a haemostatic agent.

997. The composition of any one of items 725 wherein the composition further comprises a bulking agent, wherein the bulking agent comprises microspheres.

998. The composition of any one of items 725–771 wherein the composition further comprises a bulking agent, wherein the bulking agent comprises a hydroxyapatite loaded gel.

999. The composition of any one of items 725–771 wherein the composition further comprises a bulking agent, wherein the bulking agent comprises a micronized alloderm acellular matrix.

1000. The composition of any one of items 725–771 wherein the composition further comprises a bulking agent, wherein the bulking agent comprises hyaluronic acid.

1001. The composition of any one of items 725–771 wherein the composition further comprises a bulking agent, wherein the bulking agent comprises micro-beads in a hydrogel.

1002. The composition of any one of items 725–771 wherein the composition further comprises a bulking agent, wherein the bulking agent comprises a hylan polymer.

1003. The composition of any one of items 725–771 wherein the composition further comprises a bulking agent, wherein the bulking agent comprises a silicon microballoon and biocompatible polymer.

1004. A composition comprising a fibrosing agent and a bulking agent.

1005. The composition of item 1004 wherein the fibrosing agent promotes regeneration.

1006. The composition of item 1004 wherein the fibrosing agent promotes fibrosis and promotes regeneration.

1007. The composition of item 1004 wherein the fibrosing agent promotes angiogenesis.

1008. The composition of item 1004 wherein the fibrosing agent promotes fibroblast migration.

1009. The composition of item 1004 wherein the fibrosing agent promotes fibroblast proliferation.

1010. The composition of item 1004 wherein the fibrosing agent promotes deposition of extracellular matrix (ECM).

1011. The composition of item 1004 wherein the fibrosing agent promotes tissue remodeling.

1012. The composition of item 1004 wherein the fibrosing agent is a diverticular wall irritant.

1013. The composition of item 1004 wherein the fibrosing agent is or comprises silk.

1014. The composition of item 1004 wherein the fibrosing agent is or comprises silkworm silk.

1015. The composition of item 1004 wherein the fibrosing agent is or comprises spider silk.

1016. The composition of item 1004 wherein the fibrosing agent is or comprises recombinant silk.

1017. The composition of item 1004 wherein the fibrosing agent is or comprises raw silk.

1018. The composition of item 1004 wherein the fibrosing agent is or comprises hydrolyzed silk.

1019. The composition of item 1004 wherein the fibrosing agent is or comprises acid-treated silk.

1020. The composition of item 1004 wherein the fibrosing agent is or comprises acylated silk.

1021. The composition of item 1004 wherein the fibrosing agent is in the form of strands.

1022. The composition of item 1004 wherein the fibrosing agent is in the form of tufts.

1023. The composition of item 1004 wherein the fibrosing agent is or comprises mineral particles.

1024. The composition of item 1004 wherein the fibrosing agent is or comprises chitosan.

1025. The composition of item 1004 wherein the fibrosing agent is or comprises polylysine.

1026. The composition of item 1004 wherein the fibrosing agent is or comprises fibronectin.

1027. The composition of item 1004 wherein the fibrosing agent is or comprises bleomycin.

1028. The composition of item 1004 wherein the fibrosing agent is or comprises CTGF.

1029. The composition of item 1004 wherein the fibrosing agent is or comprises a wool.

1030. The composition of item 1004 wherein the fibrosing agent is or comprises an animal wool.

1031. The composition of item 1004 wherein the fibrosing agent is or comprises a wood wool.

1032. The composition of item 1004 wherein the fibrosing agent is or comprises a synthetic wool.

1033. The composition of item 1004 wherein the fibrosing agent is in the form of a thread, or is in contact with a thread.

1034. The composition of item 1033 wherein the thread is biodegradable.

1035. The composition of item 1034 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1036. The composition of item 1033 wherein the thread is non-biodegradable.

1037. The composition of item 1036 wherein the non-biodegradable thread comprises a material selected from the group consisting of polyester, polyurethane, silicone, polyethylene, polypropylene, polystyrene, polyacrylate, polymethacrylate, and silk.

1038. The composition of item 1033 wherein the thread is coated with a polymer.

1039. The composition of item 1033 wherein the thread is coated with a pharmaceutical agent that induces a fibrotic response in the host.

1040. The composition of item 1004 wherein the fibrosing agent is in the form of a particulate.

1041. The composition of item 1040 wherein the particulate is a biodegradable particulate.

1042. The composition of item 1041 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1043. The composition of item 1040 wherein the particulate is a non-biodegradable particulate.

1044. The composition of item 1043 wherein the non-biodegradable particulate comprises a material selected from the group consisting of polyester, polyurethane, silicone, polyethylene, polypropylene, polystyrene, polyacrylate, polymethacrylate, and silk.

1045. The composition of item 1040 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1046. The composition of item 1040 wherein the particulate is coated with a polymer.

1047. The composition of item 1040 wherein the particulate is coated with a pharmaceutical agent that induces a fibrotic response in the host.

1048. The composition of item 1040 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1049. The composition of item 1004 wherein the composition comprises a growth factor.

1050. The composition of item 1049 wherein the growth factor is selected from a transforming growth factor, a platelet-derived growth factor, and a fibroblast growth factor.

1051. The composition of any one of items 1004–1050, wherein the composition further comprises a polymer.

1052. The composition of any one of items 1004–1050, wherein the composition further comprises a polymer, and wherein the polymer is, or comprises, a copolymer.

1053. The composition of any one of items 1004–1050, wherein the composition further comprises a polymer, and wherein the polymer is, or comprises, a block copolymer.

1054. The composition of any one of items 1004–1050, wherein the composition further comprises a polymer, and wherein the polymer is, or comprises, a random copolymer.

1055. The composition of any one of items 1004–1050, wherein the composition further comprises a polymer, and wherein the polymer is, or comprises, a biodegradable polymer.

1056. The composition of any one of items 1004–1050, wherein the composition further comprises a polymer, and wherein the polymer is, or comprises, a non-biodegradable polymer.

1057. The composition of any one of items 1004–1050, wherein the composition further comprises a polymer, and wherein the polymer is, or comprises, a hydrophilic polymer.

1058. The composition of any one of items 1004–1050, wherein the composition further comprises a polymer, and wherein the polymer is, or comprises, a hydrophobic polymer.

1059. The composition of any one of items 1004–1050, wherein the composition further comprises a polymer, and wherein the polymer is, or comprises, a polymer having hydrophilic domains.

1060. The composition of any one of items 1004–1050, wherein the composition further comprises a polymer, and wherein the polymer is, or comprises, a polymer having hydrophobic domains.

1061. The composition of any one of items 1004–1050, wherein the composition further comprises a polymer, and wherein the polymer is, or comprises, a non-conductive polymer.

1062. The composition of any one of items 1004–1050, wherein the composition further comprises a polymer, and wherein the polymer is, or comprises, an elastomer.

1063. The composition of any one of items 1004–1050, wherein the composition further comprises a polymer, and wherein the polymer is, or comprises, a hydrogel.

1064. The composition of any one of items 1004–1050, wherein the composition further comprises a polymer, and wherein the polymer is, or comprises, a silicone polymer.

1065. The composition of any one of items 1004–1050, wherein the composition further comprises a polymer, and wherein the polymer is, or comprises, a hydrocarbon polymer.

1066. The composition of any one of items 1004–1050, wherein the composition further comprises a polymer, and wherein the polymer is, or comprises, a styrene-derived polymer.

1067. The composition of any one of items 1004–1050, wherein the composition further comprises a polymer, and wherein the polymer is, or comprises, a butadiene-denved polymer.

1068. The composition of any one of items 1004–1050, wherein the composition further comprises a polymer, and wherein the polymer is, or comprises, a macromer.

1069. The composition of any one of items 1004–1050, wherein the composition further comprises a polymer, and wherein the polymer is, or comprises, a poly(ethylene glycol).

1070. The composition of any one of items 1004–1050, wherein the composition further comprises a polymer, and wherein the polymer is, or comprises, a collagen or a derivative thereof.

1071. The composition of any one of items 1004–1050, wherein the composition further comprises a polymer, and wherein the polymer is, or comprises, a methylated collagen.

1072. The composition of any one of items 1004–1050, wherein the composition further comprises a polymer, and wherein the composition further comprises a polymer composition, wherein the polymer composition comprises a collagen or a derivative thereof and a fibrinogen.

1073. The composition of any one of items 1004–1050, wherein the composition further comprises a polymer, and wherein the composition further comprises a polymer composition, wherein the polymer composition comprises a collagen or a derivative thereof and a thrombin.

1074. The composition of any one of items 1004–1050, wherein the composition further comprises a polymer, and wherein the composition further comprises a polymer composition, wherein the polymer composition comprises (a) a collagen or a derivative thereof; (b) a fibrinogen; and (c) a thrombin.

1075. The composition of any one of items 1004–1050, wherein the composition further comprises a polymer, and wherein the composition further comprises a polymer composition, wherein the polymer composition comprises a methylated collagen and a poly(ethylene glycol).

1076. The composition of any one of items 1004–1050 wherein the composition further comprises a haemostatic agent that comprises a collagen polymer.

1077. The composition of any one of items 1004–1050 wherein the composition further comprises a haemostatic agent that comprises a poly(ethylene glycol).

1078. The composition of any one of items 1004–1050 wherein the composition further comprises a haemostatic agent that comprises a collagen polymer, wherein the haemostatic agent is CT3.

1079. The composition of any one of items 1004–1050 wherein the composition further comprises a haemostatic agent that comprises a collagen polymer, wherein the haemostatic agent is COSTASIS.

1080. The composition of any one of items 1004–1050, wherein the composition further comprises a haemostatic agent wherein the haemostatic agent is COSEAL, TISSEALL, or FLOSEAL.

1081. The composition of any one of items 1004–1050, wherein the composition further comprises a haemostatic agent that comprises fibrin.

1082. The composition of any one of items 1004–1050, wherein the composition further comprises a polymer, and wherein the polymer is, or comprises, an amorphous polymer.

1083. The composition of any one of items 1004–1050, wherein the composition further comprises a polymer, and wherein the polymer is, or comprises, a cyanoacrylate.

1084. The method of item 1083, wherein the cyanoacrylate is selected from methyl cyanoacrylate, ethyl cyanoacrylate, butyl cyanoacrylate, octyl cyanoacrylate, and methoxypropyl cyanoacrylate.

1085. The composition of any one of items 1004–1050, wherein the composition further comprises a polymer, and wherein the polymer is, or comprises, a poly(alkylcyanoacrylate).

1086. The method of item 1085, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

1087. The composition of any one of items 1004–1050, wherein the polymer is, or comprises, a poly(carboxyalkylcyanoacrylate).

1088. The method of item 1087 wherein the poly(carboxyalkylcyanoacrylate) is poly(methoxypropylcyanoacrylate).

1089. The composition of any one of items 1004–1050 wherein the composition further comprises a polymer, and, wherein the polymer is crosslinked 1090. The composition of any one of items 1004–1050 wherein the composition further comprises a polymer, and wherein the polymer reacts with mammalian tissue.

1091. The composition of any one of items 1004–1050, wherein the composition further comprises a polymer, and wherein the polymer is a naturally occurring polymer.

1092. The composition of any one of items 1004–1050 wherein the composition further comprises a polymer, and wherein the polymer is protein.

1093. The composition of any one of items 1004–1050 wherein the composition further comprises a polymer, and wherein the polymer is carbohydrate.

1094. The composition of any one of items 1004–1050 wherein the composition further comprises a polymer, and wherein the polymer is crosslinked and biodegradable.

1095. The composition of any one of items 1004–1050 wherein the composition comprises a fibrinogen.

1096. The composition of any one of items 1004–1050 wherein the composition comprises a thrombin.

1097. The composition of any one of items 1004–1050 wherein the composition comprises a calcium salt.

1098. The composition of any one of items 1004–1050 wherein the composition comprises an antifibronolytic agent.

1099. The composition of any one of items 1004–1050 wherein the composition comprises a fibrinogen analog.

1100. The composition of any one of items 1004–1050 wherein the composition comprises an albumin.

1101. The composition of any one of items 1004–1050 wherein the composition comprises a plasminogen.

1102. The composition of any one of items 1004–1050 wherein the composition comprises a von Willebrands factor.

1103. The composition of any one of items 1004–1050 wherein the composition comprises a Factor VIII.

1104. The composition of any one of items 1004–1050 wherein the composition comprises a hypoallergenic collagen.

1105. The composition of any one of items 1004–1050 wherein the composition comprises a telopeptide collagen.

1106. The composition of any one of items 1004–1050 wherein the composition comprises a crosslinked collagen.

1107. The composition of any one of items 1004–1050 wherein the composition comprises an aprotinin.

1108. The composition of any one of items 1004–1050 wherein the composition comprises an epsilon-amino-n-caproic acid.

1109. The composition of any one of items 1004–1050 wherein the composition comprises a gelatin.

1110. The composition of any one of items 1004–1050 wherein the composition comprises a protein conjugate.

1111. The composition of any one of items 1004–1050 wherein the composition comprises a gelatin conjugate.

1112. The composition of any one of items 1004–1050 wherein the composition comprises a hyaluronic acid.

1113. The composition of any one of items 1004–1050 wherein the composition comprises a hyaluronic acid derivative.

1114. The composition of any one of items 1004–1050 wherein the composition comprises a synthetic polymer.

1115. The composition of any one of items 1004–1050 wherein the polymer is formed from reactants comprising a synthetic isocyanate-containing compound.

1116. The composition of any one of items 1004–1050 wherein the composition comprises a synthetic isocyanate-containing compound.

1117. The composition of any one of items 1004–1050 wherein the composition further comprises a polymer, and wherein the polymer is formed from reactants comprising a synthetic thiol-containing compound.

1118. The composition of any one of items 1004–1050 wherein the composition comprises a synthetic thiol-containing compound.

1119. The composition of any one of items 1004–1050 wherein the composition further comprises a polymer, and wherein the polymer is formed from reactants comprising a synthetic compound containing at least two thiol groups.

1120. The composition of any one of items 1004–1050 wherein the composition comprises a synthetic compound containing at least two thiol groups.

1121. The composition of any one of items 1004–1050 wherein the composition further comprises a polymer, and wherein the polymer is formed from reactants comprising a synthetic compound containing at least three thiol groups.

1122. The composition of any one of items 1004–1050 wherein the composition comprises a synthetic compound containing at least three thiol groups.

1123. The composition of any one of items 1004–1050 wherein the composition further comprises a polymer, and wherein the polymer is formed from reactants comprising a synthetic compound containing at least four thiol groups.

1124. The composition of any one of items 1004–1050 wherein the composition comprises a synthetic compound containing at least four thiol groups.

1125. The composition of any one of items 1004–1050 wherein the composition further comprises a polymer, and wherein the polymer is formed from reactants comprising a synthetic amino-containing compound.

1126. The composition of any one of items 1004–1050 wherein the composition comprises a synthetic amino-containing compound.

1127. The composition of any one of items 1004–1050 wherein the composition further comprises a polymer, and wherein the polymer is formed from reactants comprising a synthetic compound containing at least two amino groups.

1128. The composition of any one of items 1004–1050 wherein the composition comprises a synthetic compound containing at least two amino groups.

1129. The composition of any one of items 1004–1050 wherein the composition further comprises a polymer, and wherein the polymer is formed from reactants comprising a synthetic compound containing at least three amino groups.

1130. The composition of any one of items 1004–1050 wherein the composition comprises a synthetic compound containing at least three amino groups.

1131. The composition of any one of items 1004–1050 wherein the composition further comprises a polymer, and wherein the polymer is formed from reactants comprising a synthetic compound containing at least four amino groups.

1132. The composition of any one of items 1004–1050 wherein the composition comprises a synthetic compound containing at least four amino groups.

1133. The composition of any one of items 1004–1050 wherein the composition further comprises a polymer, and wherein the polymer is formed from reactants comprising a synthetic compound comprising a carbonyl-oxygen-succinimidyl group.

1134. The composition of any one of items 1004–1050 wherein the composition comprises a synthetic compound comprising a carbonyl-oxygen-succinimidyl group.

1135. The composition of any one of items 1004–1050 wherein the composition further comprises a polymer, and wherein the polymer is formed from reactants comprising a synthetic compound comprising at least two carbonyl-oxygen-succinimidyl groups.

1136. The composition of any one of items 1004–1050 wherein the composition comprises a synthetic compound comprising at least two carbonyl-oxygen-succinimidyl groups.

1137. The composition of any one of items 1004–1050 wherein the composition further comprises a polymer, and wherein the polymer is formed from reactants comprising a synthetic compound comprising at least three carbonyl-oxygen-succinimidyl groups.

1138. The composition of any one of items 1004–1050 wherein the composition comprises a synthetic compound comprising at least three carbonyl-oxygen-succinimidyl groups.

1139. The composition of any one of items 1004–1050 wherein the composition further comprises a polymer, and wherein the polymer is formed from reactants comprising a synthetic compound comprising at least four carbonyl-oxygen-succinimidyl groups.

1140. The composition of any one of items 1004–1050 wherein the composition comprises a synthetic compound comprising at least four carbonyl-oxygen-succinimidyl groups.

1141. The composition of any one of items 1004–1050 wherein the composition further comprises a polymer, and wherein the polymer is formed from reactants comprising a synthetic polyalkylene oxide-containing compound.

1142. The composition of any one of items 1004–1050 wherein the composition comprises a synthetic polyalkylene oxide-containing compound.

1143. The composition of any one of items 1004–1050 wherein the composition further comprises a polymer, and wherein the composition further comprises a polymer, and wherein the polymer is formed from reactants comprising a synthetic compound comprising both polyalkylene oxide and biodegradable polyester blocks.

1144. The composition of any one of items 1004–1050 wherein the composition comprises a synthetic compound comprising both polyalkylene oxide and biodegradable polyester blocks.

1145. The composition of any one of 1004–1050 wherein the composition further comprises a polymer, and wherein the polymer is formed from reactants comprising a synthetic polyalkylene oxide-containing compound having reactive amino groups.

1146. The composition of any one of items 1004–1050 wherein the composition comprises synthetic polyalkylene oxide-containing compound having reactive amino groups.

1147. The composition of any one of items 1004–1050 wherein the composition further comprises a polymer, and wherein the polymer is formed from reactants comprising a synthetic polyalkylene oxide-containing compound having reactive thiol groups.

1148. The composition of any one of items 1004–1050 wherein the composition comprises synthetic polyalkylene oxide-containing compound having reactive thiol groups.

1149. The composition of any one of items 1004–1050 wherein the composition further comprises a polymer, and wherein the polymer is formed from reactants comprising a synthetic polyalkylene oxide-containing compound having reactive carbonyl-oxygen-succinimidyl groups.

1150. The composition of any one of items 1004–1050 wherein the composition comprises a synthetic polyalkylene oxide-containing compound having reactive carbonyl-oxygen-succinimidyl groups.

1151. The composition of any one of items 1004–1050 wherein the composition further comprises a polymer, and wherein the polymer is formed from reactants comprising a synthetic compound comprising a biodegradable polyester block.

1152. The composition of any one of items 1004–1050 wherein the composition comprises a synthetic compound comprising a biodegradable polyester block.

1153. The composition of any one of items 1004–1050 wherein the composition further comprises a polymer, and wherein the polymer is formed from reactants comprising a synthetic polymer formed in whole or part from lactic acid or lactide.

1154. The composition of any one of items 1004–1050 wherein the composition comprises a synthetic polymer formed in whole or part from lactic acid or lactide.

1155. The composition of any one of items 1004–1050 wherein the composition further comprises a polymer, and wherein the polymer is formed from reactants comprising a synthetic polymer formed in whole or part from glycolic acid or glycolide.

1156. The composition of any one of items 1004–1050 wherein the composition comprises a synthetic polymer formed in whole or part from glycolic acid or glycolide.

1157. The composition of any one of items 1004–1050 wherein the composition further comprises a polymer, and wherein the polymer is formed from reactants comprising polylysine.

1158. The composition of any one of items 1004–1050 wherein the composition comprises polylysine.

1159. The composition of any one of items 1004–1050 wherein the composition further comprises a polymer, and wherein the polymer is formed from reactants comprising (a) protein and (b) a compound comprising a polyalkylene oxide portion.

1160. The composition of any one of items 1004–1050 wherein the composition comprises (a) protein and (b) a compound comprising a polyalkylene oxide portion.

1161. The composition of any one of items 1004–1050 wherein the composition further comprises a polymer, and wherein the polymer is formed from reactants comprising (a) protein and (b) polylysine.

1162. The composition of any one of items 1004–1050 wherein the composition comprises (a) protein and (b) polylysine.

1163. The composition of any one of items 1004–1050 wherein the composition further comprises a polymer, and wherein the polymer is formed from reactants comprising (a) protein and (b) a compound having at least four thiol groups.

1164. The composition of any one of items 1004–1050 wherein the composition comprises (a) protein and (b) a compound having at least four thiol groups.

1165. The composition of any one of items 1004–1050 wherein the composition further comprises a polymer, and wherein the polymer is formed from reactants comprising (a) protein and (b) a compound having at least four amino groups.

1166. The composition of any one of items 1004–1050 wherein the composition comprises (a) protein and (b) a compound having at least four amino groups.

1167. The composition of any one of items 1004–1050 wherein the composition further comprises a polymer, and wherein the polymer is formed from reactants comprising (a) protein and (b) a compound having at least four carbonyl-oxygen-succinimide groups.

1168. The composition of any one of items 1004–1050 wherein the composition comprises (a) protein and (b) a compound having at least four carbonyl-oxygen-succinimide groups.

1169. The composition of any one of items 1004–1050 wherein the composition further comprises a polymer, and wherein the polymer is formed from reactants comprising (a) protein and (b) a compound having a biodegradable region formed from reactants selected from lactic acid, lactide, glycolic acid, glycolide, and epsilon-caprolactone.

1170. The composition of any one of items 1004–1050 wherein the composition comprises (a) protein and (b) a compound having a biodegradable region formed from reactants selected from lactic acid, lactide, glycolic acid, glycolide, and epsilon-caprolactone.

1171. The composition of any one of items 1004–1050 wherein the composition further comprises a polymer, and wherein the polymer is formed from reactants comprising (a) collagen and (b) a compound comprising a polyalkylene oxide portion.

1172. The composition of any one of items 1004–1050 wherein the composition comprises (a) collagen and (b) a compound comprising a polyalkylene oxide portion.

1173. The composition of any one of items 1004–1050 wherein the polymer is formed from reactants comprising (a) collagen and (b) polylysine.

1174. The composition of any one of items 1004–1050 wherein the composition comprises (a) collagen and (b) polylysine.

1175. The composition of any one of items 1004–1050 wherein the polymer is formed from reactants comprising (a) collagen and (b) a compound having at least four thiol groups.

1176. The composition of any one of items 1004–1050 wherein the composition comprises (a) collagen and (b) a compound having at least four thiol groups.

1177. The composition of any one of items 1004–1050 wherein the composition further comprises a polymer, and wherein the polymer is formed from reactants comprising (a) collagen and (b) a compound having at least four amino groups.

1178. The composition of any one of items 1004–1050 wherein the composition comprises (a) collagen and (b) a compound having at least four amino groups.

1179. The composition of any one of items 1004–1050 wherein the composition further comprises a polymer, and wherein the polymer is formed from reactants comprising (a) collagen and (b) a compound having at least four carbonyl-oxygen-succinimide groups.

1180. The composition of any one of items 1004–1050 wherein the composition comprises (a) collagen and (b) a compound having at least four carbonyl-oxygen-succinimide groups.

1181. The composition of any one of items 1004–1050 wherein the composition further comprises a polymer, and wherein the polymer is formed from reactants comprising (a) collagen and (b) a compound having a biodegradable region formed from reactants selected from lactic acid, lactide, glycolic acid, glycolide, and epsilon-caprolactone.

1182. The composition of any one of items 1004–1050 wherein the composition comprises (a) collagen and (b) a compound having a biodegradable region formed from reactants selected from lactic acid, lactide, glycolic acid, glycolide, and epsilon-caprolactone.

1183. The composition of any one of items 1004–1050 wherein the composition further comprises a polymer, and wherein the polymer is formed from reactants comprising (a) methylated collagen and (b) a compound comprising a polyalkylene oxide portion.

1184. The composition of any one of items 1004–1050 wherein the composition comprises (a) methylated collagen and (b) a compound comprising a polyalkylene oxide portion.

1185. The composition of any one of items 1004–1050 wherein the composition further comprises a polymer, and wherein the polymer is formed from reactants comprising (a) methylated collagen and (b) polylysine.

1186. The composition of any one of items 1004–1050 wherein the composition comprises (a) methylated collagen and (b) polylysine.

1187. The composition of any one of items 1004–1050 wherein the composition further comprises a polymer, and wherein the polymer is formed from reactants comprising (a) methylated collagen and (b) a compound having at least four thiol groups.

1188. The composition of any one of items 1004–1050 wherein the composition comprises (a) methylated collagen and (b) a compound having at least four thiol groups.

1189. The composition of any one of items 1004–1050 wherein the composition further comprises a polymer, and wherein the polymer is formed from reactants comprising (a) methylated collagen and (b) a compound having at least four amino groups.

1190. The composition of any one of items 1004–1050 wherein the composition comprises (a) methylated collagen and (b) a compound having at least four amino groups.

1191. The composition of any one of items 1004–1050 wherein the composition further comprises a polymer, and wherein the polymer is formed from reactants comprising (a) methylated collagen and (b) a compound having at least four carbonyl-oxygen-succinimide groups.

1192. The composition of any one of items 1004–1050 wherein the composition comprises (a) methylated collagen and (b) a compound having at least four carbonyl-oxygen-succinimide groups.

1193. The composition of any one of items 1004–1050 wherein the composition further comprises a polymer, and wherein the polymer is formed from reactants comprising (a) methylated collagen and (b) a compound having a biodegradable region formed from reactants selected from lactic acid, lactide, glycolic acid, glycolide, and epsilon-caprolactone.

1194. The composition of any one of items 1004–1050 wherein the composition comprises (a) methylated collagen and (b) a compound having a biodegradable region formed from reactants selected from lactic acid, lactide, glycolic acid, glycolide, and epsilon-caprolactone.

1195. The composition of any one of items 1004–1050 wherein the composition further comprises a polymer, and wherein the polymer is formed from reactants comprising hyaluronic acid.

1196. The composition of any one of items 1004–1050 wherein the composition comprises hyaluronic acid.

1197. The composition of any one of items 1004–1050 wherein the composition further comprises a polymer, and wherein the polymer is formed from reactants comprising a hyaluronic acid derivative.

1198. The composition of any one of items 1004–1050 wherein the composition comprises a hyaluronic acid derivative.

1199. The composition of any one of items 1004–1050 wherein the composition further comprises a polymer, and wherein the polymer is formed from reactants comprising pentaerythritol poly(ethylene glycol)ether tetra-sulfhydryl of number average molecular weight between 3,000 and 30,000.

1200. The composition of any one of items 1004–1050 wherein the composition comprises pentaerythritol poly(ethylene glycol)ether tetra-sulfhydryl of number average molecular weight between 3,000 and 30,000.

1201. The composition of any one of items 1004–1050 wherein the composition further comprises a polymer, and wherein the polymer is formed from reactants comprising pentaerythritol poly(ethylene glycol)ether tetra-amino of number average molecular weight between 3,000 and 30,000.

1202. The composition of any one of items 1004–1050 wherein the composition comprises pentaerythritol poly(ethylene glycol)ether tetra-amino of number average molecular weight between 3,000 and 30,000.

1203. The composition of any one of items 1004–1050 wherein the composition further comprises a polymer, and wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1204. The composition of any one of items 1004–1050 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1205. The composition of any one of items 1004–1050 wherein the composition comprises a colorant.

1206. The composition of any one of items 1004–1050 wherein the composition is sterile.

1207. The composition of any one of items 1004–1050 wherein the composition further comprises a second pharmaceutically active agent.

1208. The composition of any one of items 1004–1050 wherein the composition further comprises an anti-inflammatory agent.

1209. The composition of any one of items 1004–1050 wherein the composition further comprises an agent that inhibits infection.

1210. The composition of any one of items 1004–1050 wherein the composition further comprises an anthracycline.

1211. The composition of any one of items 1004–1050 wherein the composition further comprises doxorubicin.

1212. The composition of any one of items 1004–1050 wherein the composition further comprises mitoxantrone.

1213. The composition of any one of items 1004–1050 wherein the composition further comprises a fluoropyrimidme.

1214. The composition of any one of items 1004–1050, wherein the composition further comprises 5-fluorouracil (5-FU).

1215. The composition of any one of items 1004–1050, wherein the composition further comprises a folic acid antagonist.

1216. The composition of any one of items 1004–1050 wherein the composition further comprises methotrexate.

1217. The composition of any one of items 1004–1050 wherein the composition further comprises a podophylotoxin.

1218. The composition of any one of items 1004–1050 wherein the composition further comprises etoposide.

1219. The composition of any one of items 1004–1050 wherein the composition further comprises camptothecin.

1220. The composition of any one of items 1004–1050 wherein the composition further comprises a hydroxyurea.

1221. The composition of any one of items 1004–1050 wherein the composition further comprises a platinum complex.

1222. The composition of any one of items 1004–1050 wherein the composition further comprises cisplatin.

1223. The composition of any one of items 1004–1050 wherein the composition further comprises an anti-infective agent.

1224. The composition of any one of items 1004–1050 wherein the composition further comprises an anti-infective agent, wherein the anti-infective agent is an antibiotic.

1225. The composition of any one of items 1004–1050 wherein the composition further comprises an anti-infective agent, wherein the anti-infective agent is doxycycline.

1226. The composition of any one of items 1004–1050 wherein the composition further comprises an anti-infective agent, wherein the anti-infective agent is metronidazole.

1227. The composition of any one of items 1004–1050 wherein the composition further comprises an anti-infective agent, wherein the anti-infective agent is trimethoprim-sulfamethoxazole.

1228. The composition of any one of items 1004–1050 wherein the composition further comprises an anti-infective agent, wherein the anti-infective agent is a fourth generation penicillin.

1229. The composition of any one of items 1004–1050 wherein the composition further comprises an anti-infective agent, wherein the anti-infective agent is a fourth generation penicillin selected from a ureidopenicillin and a carboxypenicillin, or an analogue or derivative thereof.

1230. The composition of any one of items 1004–1050 wherein the composition further comprises an anti-infective agent, wherein the anti-infective agent is a fourth generation penicillin selected from meziocillin, piperacillin, carbenicillin, and ticarcillin.

1231. The composition of any one of items 1004–1050 wherein the composition further comprises an anti-infective agent, wherein the anti-infective agent is a first generation cephalosporin.

1232. The composition of any one of items 1004–1050 wherein the composition further comprises an anti-infective agent, wherein the anti-infective agent is a first generation cephalosporin selected from cephazolin sodium, cephalexin, cefazolin, cephapirin, and cephalothin.

1233. The composition of any one of items 1004–1050 wherein the composition further comprises an anti-infective agent, wherein the anti-infective agent is a carboxypenicillin.

1234. The composition of item 1233 wherein the carboxypenicillin is ticarcillin.

1235. The composition of any one of items 1004–1050 wherein the composition further comprises an anti-infective agent, wherein the anti-infective agent is a second generation cephalosporin.

1236. The composition of any one of items 1004–1050 wherein the composition further comprises an anti-infective agent, wherein the anti-infective agent is a second generation cephalosporin selected from cefuroxime, cefotetan, and cefoxitin.

1237. The composition of any one of items 1004–1050 wherein the composition further comprises an anti-infective agent, wherein the anti-infective agent is a third generation cephalosporin.

1238. The composition of any one of items 1004–1050 wherein the composition further comprises an anti-infective agent, wherein the anti-infective agent is a third generation cephalosporin selected from naxcel, Cefdinir, cefoperazone, ceftazidime, ceftriaxone,and cefotaxime.

1239. The composition of any one of items 1004–1050 wherein the composition further comprises an anti-infective agent, wherein the anti-infective agent is a fourth generation cephalosporin.

1240. The composition of item 1239 wherein the fourth generation cephalosporin is cefepime.

1241. The composition of any one of items 1004–1050 wherein the composition further comprises an anti-infective agent, wherein the anti-infective agent is a monobactam.

1242. The composition of item 1241 wherein the monobactam is aztreonam.

1243. The composition of any one of items 1004–1050 wherein the composition further comprises an anti-infective agent, wherein the anti-infective agent is a carbapenem.

1244. The composition of any one of items 1004–1050 wherein the composition further comprises an anti-infective agent, wherein the anti-infective agent is a carbapenem selected from imipenem, ertapenem and meropenem.

1245. The composition of any one of items 1004–1050 wherein the composition further comprises an anti-infective agent, wherein the anti-infective agent is an aminoglycoside.

1246. The composition of any one of items 1004–1050 wherein the composition further comprises an anti-infective agent, wherein the anti-infective agent is an aminoglycoside selected from streptomycin, gentamicin, tobramycin, and amikacin.

1247. The composition of any one of items 1004–1050 wherein the composition further comprises an anti-infective agent, wherein the anti-infective agent is an MSL group member selected from a macrolide, a long acting macrolide, a lincosamide, and a streptogramin.

1248. The composition of any one of items 1004–1050 wherein the composition further comprises an anti-infective agent, wherein the anti-infective agent is an MSL group member selected from Erythromycin, Azithromycin, Clindamycin, Syneroid, clarithromycin, and kanamycin sulfate.

1249. The composition of any one of items 1004–1050 wherein the composition further comprises an anti-infective agent, wherein the anti-infective agent is a quinolone.

1250. The composition of any one of items 1004–1050 wherein the composition further comprises an anti-infective agent, wherein the anti-infective agent is a quinolone selected from ciprofloxacin, ofloxacin, gatifloxacin, moxifloxacin, levofloxacin, and trovafloxacin.

1251. The composition of any one of items 1004–1050 wherein the composition further comprises an anti-infective agent, wherein the anti-infective agent is a DNA synthesis inhibitor.

1252. The composition of item 1251 wherein the DNA synthesis inhibitor is metronidazole.

1253. The composition of any one of items 1004–1050 wherein the composition further comprises an anti-infective agent, wherein the anti-infective agent is a sulfonamide.

1254. The composition of item 1253 wherein the sulfonamide is trimethoprim.

1255. The composition of any one of items 1004–1050 wherein the composition further comprises an anti-infective agent, wherein the anti-infective agent is selected from cefixime, spectinomycin, tetracycline, nitrofurantoin, polymyxin B, and neomycin sulfate.

1256. The composition of any one of items 1004–1050 wherein the composition further comprises a visualization agent.

1257. The composition of any one of items 1004–1050 wherein the composition further comprises a visualization agent, and the visualization agent is a radiopaque material, wherein the radiopaque material comprises a metal, a halogenated compound, or a barium containing compound.

1258. The composition of any one of items 1004–1050 wherein the composition further comprises a visualization agent, and the visualization agent is, or comprises, barium, tantalum, or technetium.

1259. The composition of any one of items 1004–1050 wherein the composition further comprises a visualization agent, and the visualization agent is, or comprises, an MRI responsive material or an echogenic material.

1260. The composition of any one of items 1004–1050 wherein the composition further comprises a visualization agent, and the visualization agent is, or comprises, a gadolinium chelate.

1261. The composition of any one of items 1004–1050 wherein the composition further comprises a visualization agent, and the visualization agent is, or comprises, iron, magnesium, manganese, copper, or chromium.

1262. The composition of any one of items 1004–1050 wherein the composition further comprises a visualization agent, and the visualization agent is, or comprises, iron oxide compound.

1263. The composition of any one of items 1004–1050 wherein the composition further comprises a visualization agent, and the visualization agent is, or comprises, a dye, pigment, or colorant.

1264. The composition of any one of items 1004–1050 wherein the fibrosing agent is released in effective concentrations from the composition comprising the fibrosing agent by diffusion over a period ranging from the time of administration to about 90 days.

1265. The composition of any one of items 1004–1050 wherein the fibrosing agent is released in effective concentrations from the composition comprising the fibrosing agent by erosion of the composition over a period ranging from the time of administration to about 90 days.

1266. The composition of any one of items 1004–1050 wherein the composition further comprises an inflammatory cytokine.

1267. The composition of any one of items 1004–1050 wherein the composition further comprises an agent that stimulates cell proliferation.

1268. The composition of any one of items 1004–1050 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

1269. The composition of any one of items 1004–1050 wherein the composition further comprises a polymeric carrier.

1270. The composition of any one of items 1004–1050 wherein the composition is in the form of a gel, paste, or spray.

1271. The composition of any one of items 1004–1050 wherein the composition is in the form of a mesh or a film.

1272. The composition of any one of items 1004–1050 wherein the agent or the composition comprising the agent is injected or sprayed into the diverticulum.

1273. The composition of any one of items 1004–1050 wherein the agent or the composition comprising the agent is injected or sprayed onto a tissue or into a tissue surrounding the diverticulum.

1274. The composition of item 1004 wherein the bulking agent is a sealant.

1275. The composition of item 1004 wherein the bulking agent is a haemostatic agent.

1276. The composition of any one of items 1004–1050 wherein the bulking agent comprises microspheres.

1277. The composition of any one of items 1004–1050 wherein the bulking agent comprises a hydroxyapatite loaded gel.

1278. The composition of any one of items 1004–1050 wherein the bulking agent comprises a micronized alloderm acellular matrix.

1279. The composition of any one of items 1004–1050 wherein the bulking agent comprises hyaluronic acid.

1280. The composition of any one of items 1004–1050 wherein the bulking agent comprises micro-beads in a hydrogel.

1281. The composition of any one of items 1004–1050 wherein the bulking agent comprises a hylan polymer.

1282. The composition of any one of items 1004–1050 wherein the bulking agent comprises a silicon microballoon and biocompatible polymer.

1283. A method of treating a diverticular disease, comprising introducing into a diverticulum in a host a composition, said composition comprising (a) a fibrosing agent and (b) a polymer or a compound that polymerizes to form a crosslinked polymer in situ, wherein the composition induces a fibrotic response within the diverticulum, thereby treating diverticular disease in the host.

1284. The method of item 1283 wherein the diverticular disease is diverticulosis.

1285. The method of item 1283 wherein the diverticular disease is diverticulitis.

1286. The method of item 1283 wherein the diverticular disease is colonic diverticulosis.

1287. The method of item 1283 wherein the diverticular disease is diverticular hemorrhage.

1288. The method of item 1283 wherein the diverticular disease is Zenker's (esophageal) Diverticulum.

1289. The method of item 1283 wherein the diverticular disease is Meckel's Diverticulum.

1290. The method of item 1283 wherein the diverticular disease is small bowel diverticulosis.

1291. The method of item 1283 wherein the diverticular disease is gastric diverticulosis.

1292. The method of item 1283 wherein the diverticular disease is urinary tract diverticulosis.

1293. The method of item 1283 wherein the fibrosing agent promotes regeneration.

1294. The method of item 1283 wherein the fibrosing agent promotes fibrosis and promotes regeneration.

1295. The method of item 1283 wherein the fibrosing agent promotes angiogenesis.

1296. The method of item 1283 wherein the fibrosing agent promotes fibroblast migration.

1297. The method of item 1283 wherein the fibrosing agent promotes fibroblast proliferation.

1298. The method of item 1283 wherein the fibrosing agent promotes deposition of extracellular matrix (ECM).

1299. The method of item 1283 wherein the fibrosing agent promotes tissue remodeling.

1300. The method of item 1283 wherein the fibrosing agent is a diverticular wall irritant.

1301. The method of item 1283 wherein the fibrosing agent is or comprises silk.

1302. The method of item 1283 wherein the fibrosing agent is or comprises silkworm silk.

1303. The method of item 1283 wherein the fibrosing agent is or comprises spider silk.

1304. The method of item 1283 wherein the fibrosing agent is or comprises recombinant silk.

1305. The method of item 1283 wherein the fibrosing agent is or comprises raw silk.

1306. The method of item 1283 wherein the fibrosing agent is or comprises hydrolyzed silk.

1307. The method of item 1283 wherein the fibrosing agent is or comprises acid-treated silk.

1308. The method of item 1283 wherein the fibrosing agent is or comprises acylated silk.

1309. The method of item 1283 wherein the fibrosing agent is in the form of strands.

1310. The method of item 1283 wherein the fibrosing agent is in the form of tufts.

1311. The method of item 1283 wherein the fibrosing agent is or comprises mineral particles.

1312. The method of item 1283 wherein the fibrosing agent is or comprises chitosan.

1313. The method of item 1283 wherein the fibrosing agent is or comprises polylysine.

1314. The method of item 1283 wherein the fibrosing agent is or comprises fibronectin.

1315. The method of item 1283 wherein the fibrosing agent is or comprises bleomycin.

1316. The method of item 1283 wherein the fibrosing agent is or comprises CTGF.

1317. The method of item 1283 wherein the fibrosing agent is or comprises a wool.

1318. The method of item 1283 wherein the fibrosing agent is or comprises an animal wool.

1319. The method of item 1283 wherein the fibrosing agent is or comprises a wood wool.

1320. The method of item 1283 wherein the fibrosing agent is or comprises a synthetic wool.

1321. The method of item 1283 wherein the fibrosing agent is in the form of a thread, or is in contact with a thread.

1322. The method of item 1321 wherein the thread is biodegradable.

1323. The method of item 1322 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1324. The method of item 1321 wherein the thread is non-biodegradable.

1325. The method of item 1324 wherein the non-biodegradable thread comprises a material selected from the group consisting of polyester, polyurethane, silicone, polyethylene, polypropylene, polystyrene, polyacrylate, polymethacrylate, and silk.

1326. The method of item 1321 wherein the thread is coated with a polymer.

1327. The method of item 1321 wherein the thread is coated with a pharmaceutical agent that induces a fibrotic response in the host.

1328. The method of item 1283 wherein the fibrosing agent is in the form of a particulate.

1329. The method of item 1328 wherein the particulate is a biodegradable particulate.

1330. The method of item 1329 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1331. The method of item 1328 wherein the particulate is a non-biodegradable particulate.

1332. The method of item 1331 wherein the non-biodegradable particulate comprises a material selected from the group consisting of polyester, polyurethane, silicone, polyethylene, polypropylene, polystyrene, polyacrylate, polymethacrylate, and silk.

1333. The method of item 1328 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1334. The method of item 1328 wherein the particulate is coated with a polymer.

1335. The method of item 1328 wherein the particulate is coated with a pharmaceutical agent that induces a fibrotic response in the host.

1336. The method of item 1328 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1337. The method of item 1283 wherein the composition comprises a growth factor.

1338. The method of item 1337 wherein the growth factor is selected from a transforming growth factor, a platelet-derived growth factor, and a fibroblast growth factor.

1339. The method of item 1283 wherein the polymer is, or comprises, a copolymer.

1340. The method of item 1283 wherein the polymer is, or comprises, a block copolymer.

1341. The method of item 1283 wherein the polymer is, or comprises, a random copolymer.

1342. The method of item 1283 wherein the polymer is, or comprises, a biodegradable polymer.

1343. The method of item 1283 wherein the polymer is, or comprises, a non-biodegradable polymer.

1344. The method of item 1283 wherein the polymer is, or comprises, a hydrophilic polymer.

1345. The method of item 1283 wherein the polymer is, or comprises, a hydrophobic polymer.

1346. The method of item 1283 wherein the polymer is, or comprises, a polymer having hydrophilic domains.

1347. The method of item 1283 wherein the polymer is, or comprises, a polymer having hydrophobic domains.

1348. The method of item 1283 wherein the polymer is, or comprises, a non-conductive polymer.

1349. The method of item 1283 wherein the polymer is, or comprises, an elastomer.

1350. The method of item 1283 wherein the polymer is, or comprises, a hydrogel.

1351. The method of item 1283 wherein the polymer is, or comprises, a silicone polymer.

1352. The method of item 1283 wherein the polymer is, or comprises, a hydrocarbon polymer.

1353. The method of item 1283 wherein the polymer is, or comprises, a styrene-derived polymer.

1354. The method of item 1283 wherein the polymer is, or comprises, a butadiene-derived polymer.

1355. The method of item 1283 the polymer is, or comprises, a macromer.

1356. The method of item 1283 wherein the polymer is, or comprises, a poly(ethylene glycol).

1357. The method of item 1283 wherein the polymer is, or comprises, a collagen or a derivative thereof.

1358. The method of item 1283 wherein the polymer is, or comprises, a methylated collagen.

1359. The method of item 1283 wherein the polymer composition comprises a collagen or a derivative thereof and a fibrinogen.

1360. The method of item 1283 wherein the polymer composition comprises a collagen or a derivative thereof and a thrombin.

1361. The method of item 1283 wherein the polymer composition comprises (a) a collagen or a derivative thereof; (b) a fibrinogen; and (c) a thrombin.

1362. The method of item 1283 wherein the polymer composition comprises a methylated collagen and a poly(ethylene glycol) or a derivative thereof.

1363. The method of item 1283 wherein the composition further comprises a haemostatic agent that comprises a collagen polymer.

1364. The method of item 1283 wherein the composition further comprises a haemostatic agent that comprises a collagen polymer, wherein the haemostatic agent is CT3.

1365. The method of item 1283 wherein the composition further comprises a haemostatic agent that comprises a collagen polymer, wherein the haemostatic agent is COSTASIS.

1366. The method of item 1283 wherein the composition further comprises a haemostatic agent that comprises a poly(ethylene glycol).

1367. The method of item 1283 wherein the composition further comprises a haemostatic agent, wherein the haemostatic agent is COSEAL, TISSEAL, OR FLOSEAL.

1368. The method of item 1283 wherein the composition further comprises a haemostatic agent that comprises fibrin.

1369. The method of item 1283 wherein the polymer is, or comprises, an amorphous polymer.

1370. The method of item 1283 wherein the polymer is, or comprises, a cyanoacrylate.

1371. The method of item 1370, wherein the cyanoacrylate is selected from methyl cyanoacrylate, ethyl cyanoacrylate, butyl cyanoacrylate, octyl cyanoacrylate, and methoxypropyl cyanoacrylate.

1372. The method of item 1283 wherein the polymer is, or comprises, a poly(alkylcyanoacrylate).

1373. The method of item 1372, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

1374. The method of item 1283 wherein the polymer is, or comprises, a poly(carboxyalkylcyanoacrylate).

1375. The method of item 1374 wherein the poly(carboxyalkylcyanoacrylate) is poly(methoxypropylcyanoacrylate).

1376. The method of item 1283 wherein the polymer is crosslinked.

1377. The method of item 1283 wherein the polymer reacts with mammalian tissue.

1378. The method of item 1283 wherein the polymer is a naturally occurring polymer.

1379. The method of item 1283 wherein the polymer is protein.

1380. The method of item 1283 wherein the polymer is carbohydrate.

1381. The method of item 1283 wherein the polymer is crosslinked and biodegradable.

1382. The method of item 1283 wherein the composition comprises a fibrinogen.

1383. The method of item 1283 wherein the composition comprises a thrombin.

1384. The method of item 1283 wherein the composition comprises a calcium salt.

1385. The method of item 1283 wherein the composition comprises an antifibrinolytic agent.

1386. The method of item 1283 wherein the composition comprises a fibrinogen analog.

1387. The method of item 1283 wherein the composition comprises an albumin.

1388. The method of item 1283 wherein the composition comprises a plasminogen.

1389. The method of item 1283 wherein the composition comprises a von Willebrands factor.

1390. The method of item 1283 wherein the composition comprises a Factor VIII.

1391. The method of item 1283 wherein the composition comprises a hypoallergenic collagen.

1392. The method of item 1283 wherein the composition comprises atelopeptide collagen.

1393. The method of item 1283 wherein the composition comprises a crosslinked collagen.

1394. The method of item 1283 wherein the composition comprises an aprotinin.

1395. The method of item 1283 wherein the composition comprises an epsilon-amino-n-caproic acid.

1396. The method of item 1283 wherein the composition comprises a gelatin.

1397. The method of item 1283 wherein the composition comprises a protein conjugate.

1398. The method of item 1283 wherein the composition comprises a gelatin conjugate.

1399. The method of item 1283 wherein the composition comprises a hyaluronic acid.

1400. The method of item 1283 wherein the composition comprises a hyaluronic acid derivative.

1401. The method of item 1283 wherein the composition comprises a synthetic polymer.

1402. The method of item 1283 wherein the polymer is formed from reactants comprising a synthetic isocyanate-containing compound.

1403. The method of item 1283 wherein the composition comprises a synthetic isocyanate-containing compound.

1404. The method of item 1283 wherein the polymer is formed from reactants comprising a synthetic thiol-containing compound.

1405. The method of item 1283 wherein the composition comprises a synthetic thiol-containing compound.

1406. The method of item 1283 wherein the polymer is formed from reactants comprising a synthetic compound containing at least two thiol groups.

1407. The method of item 1283 wherein the composition comprises a synthetic compound containing at least two thiol groups.

1408. The method of item 1283 wherein the polymer is formed from reactants comprising a synthetic compound containing at least three thiol groups.

1409. The method of item 1283 wherein the composition comprises a synthetic compound containing at least three thiol groups.

1410. The method of item 1283 wherein the polymer is formed from reactants comprising a synthetic compound containing at least four thiol groups.

1411. The method of item 1283 wherein the composition comprises a synthetic compound containing at least four thiol groups.

1412. The method of item 1283 wherein the polymer is formed from reactants comprising a synthetic amino-containing compound.

1413. The method of item 1283 wherein the composition comprises a synthetic amino-containing compound.

1414. The method of item 1283 wherein the polymer is formed from reactants comprising a synthetic compound containing at least two amino groups.

1415. The method of item 1283 wherein the composition comprises a synthetic compound containing at least two amino groups.

1416. The method of item 1283 wherein the polymer is formed from reactants comprising a synthetic compound containing at least three amino groups.

1417. The method of item 1283 wherein the composition comprises a synthetic compound containing at least three amino groups.

1418. The method of item 1283 wherein the polymer is formed from reactants comprising a synthetic compound containing at least four amino groups.

1419. The method of item 1283 wherein the composition comprises a synthetic compound containing at least four amino groups.

1420. The method of item 1283 wherein the polymer is formed from reactants comprising a synthetic compound comprising a carbonyl-oxygen-succinimidyl group.

1421. The method of item 1283 wherein the composition comprises a synthetic compound comprising a carbonyl-oxygen-succinimidyl group.

1422. The method of item 1283 wherein the polymer is formed from reactants comprising a synthetic compound comprising at least two carbonyl-oxygen-succinimidyl groups.

1423. The method of item 1283 wherein the composition comprises a synthetic compound comprising at least two carbonyl-oxygen-succinimidyl groups.

1424. The method of item 1283 wherein the polymer is formed from reactants comprising a synthetic compound comprising at least three carbonyl-oxygen-succinimidyl groups.

1425. The method of item 1283 wherein the composition comprises a synthetic compound comprising at least three carbonyl-oxygen-succinimidyl groups.

1426. The method of item 1283 wherein the polymer is formed from reactants comprising a synthetic compound comprising at least four carbonyl-oxygen-succinimidyl groups.

1427. The method of item 1283 wherein the composition comprises a synthetic compound comprising at least four carbonyl-oxygen-succinimidyl groups.

1428. The method of item 1283 wherein the polymer is formed from reactants comprising a synthetic polyalkylene oxide-containing compound.

1429. The method of item 1283 wherein the composition comprises a synthetic polyalkylene oxide-containing compound.

1430. The method of item 1283 wherein the polymer is formed from reactants comprising a synthetic compound comprising both polyalkylene oxide and biodegradable polyester blocks.

1431. The method of item 1283 wherein the composition comprises a synthetic compound comprising both polyalkylene oxide and biodegradable polyester blocks.

1432. The method of item 1283 wherein the polymer is formed from reactants comprising a synthetic polyalkylene oxide-containing compound having reactive amino groups.

1433. The method of item 1283 wherein the composition comprises synthetic polyalkylene oxide-containing compound having reactive amino groups.

1434. The method of item 1283 wherein the polymer is formed from reactants comprising a synthetic polyalkylene oxide-containing compound having reactive thiol groups.

1435. The method of item 1283 wherein the composition comprises synthetic polyalkylene oxide-containing compound having reactive thiol groups.

1436. The method of item 1283 wherein the polymer is formed from reactants comprising a synthetic polyalkylene oxide-containing compound having reactive carbonyl-oxygen-succinimidyl groups.

1437. The method of item 1283 wherein the composition comprises a synthetic polyalkylene oxide-containing compound having reactive carbonyl-oxygen-succinimidyl groups.

1438. The method of item 1283 wherein the polymer is formed from reactants comprising a synthetic compound comprising a biodegradable polyester block.

1439. The method of item 1283 wherein the composition comprises a synthetic compound comprising a biodegradable polyester block.

1440. The method of item 1283 wherein the polymer is formed from reactants comprising a synthetic polymer formed in whole or part from lactic acid or lactide.

1441. The method of item 1283 wherein the composition comprises a synthetic polymer formed in whole or part from lactic acid or lactide.

1442. The method of item 1283 wherein the polymer is formed from reactants comprising a synthetic polymer formed in whole or part from glycolic acid or glycolide.

1443. The method of item 1283 wherein the composition comprises a synthetic polymer formed in whole or part from glycolic acid or glycolide.

1444. The method of item 1283 wherein the polymer is formed from reactants comprising polylysine.

1445. The method of item 1283 wherein the composition comprises polylysine.

1446. The method of item 1283 wherein the polymer is formed from reactants comprising (a) protein and (b) a compound comprising a polyalkylene oxide portion.

1447. The method of item 1283 wherein the composition comprises (a) protein and (b) a compound comprising a polyalkylene oxide portion.

1448. The method of item 1283 wherein the polymer is formed from reactants comprising (a) protein and (b) polylysine.

1449. The method of item 1283 wherein the composition comprises (a) protein and (b) polylysine.

1450. The method of item 1283 wherein the polymer is formed from reactants comprising (a) protein and (b) a compound having at least four thiol groups.

1451. The method of item 1283 wherein the composition comprises (a) protein and (b) a compound having at least four thiol groups.

1452. The method of item 1283 wherein the polymer is formed from reactants comprising (a) protein and (b) a compound having at least four amino groups.

1453. The method of item 1283 wherein the composition comprises (a) protein and (b) a compound having at least four amino groups.

1454. The method of item 1283 wherein the polymer is formed from reactants comprising (a) protein and (b) a compound having at least four carbonyl-oxygen-succinimide groups.

1455. The method of item 1283 wherein the composition comprises (a) protein and (b) a compound having at least four carbonyl-oxygen-succinimide groups.

1456. The method of item 1283 wherein the polymer is formed from reactants comprising (a) protein and (b) a compound having a biodegradable region formed from reactants selected from lactic acid, lactide, glycolic acid, glycolide, and epsilon-caprolactone.

1457. The method of item 1283 wherein the composition comprises (a) protein and (b) a compound having a biodegradable region formed from reactants selected from lactic acid, lactide, glycolic acid, glycolide, and epsilon-caprolactone.

1458. The method of item 1283 wherein the polymer is formed from reactants comprising (a) collagen and (b) a compound comprising a polyalkylene oxide portion.

1459. The method of item 1283 wherein the composition comprises (a) collagen and (b) a compound comprising a polyalkylene oxide portion.

1460. The method of item 1283 wherein the polymer is formed from reactants comprising (a) collagen and (b) polylysine.

1461. The method of item 1283 wherein the composition comprises (a) collagen and (b) polylysine.

1462. The method of item 1283 wherein the polymer is formed from reactants comprising (a) collagen and (b) a compound having at least four thiol groups.

1463. The method of item 1283 wherein the composition comprises (a) collagen and (b) a compound having at least four thiol groups.

1464. The method of item 1283 wherein the polymer is formed from reactants comprising (a) collagen and (b) a compound having at least four amino groups.

1465. The method of item 1283 wherein the composition comprises (a) collagen and (b) a compound having at least four amino groups.

1466. The method of item 1283 wherein the polymer is formed from reactants comprising (a) collagen and (b) a compound having at least four carbonyl-oxygen-succinimide groups.

1467. The method of item 1283 wherein the composition comprises (a) collagen and (b) a compound having at least four carbonyl-oxygen-succinimide groups.

1468. The method of item 1283 wherein the polymer is formed from reactants comprising (a) collagen and (b) a compound having a biodegradable region formed from reactants selected from lactic acid, lactide, glycolic acid, glycolide, and epsilon-caprolactone.

1469. The method of item 1283 wherein the composition comprises (a) collagen and (b) a compound having a biodegradable region formed from reactants selected from lactic acid, lactide, glycolic acid, glycolide, and epsilon-caprolactone.

1470. The method of item 1283 wherein the polymer is formed from reactants comprising (a) methylated collagen and (b) a compound comprising a polyalkylene oxide portion.

1471. The method of item 1283 wherein the composition comprises (a) methylated collagen and (b) a compound comprising a polyalkylene oxide portion.

1472. The method of item 1283 wherein the polymer is formed from reactants comprising (a) methylated collagen and (b) polylysine.

1473. The method of item 1283 wherein the composition comprises (a) methylated collagen and (b) polylysine.

1474. The method of item 1283 wherein the polymer is formed from reactants comprising (a) methylated collagen and (b) a compound having at least four thiol groups.

1475. The method of item 1283 wherein the composition comprises (a) methylated collagen and (b) a compound having at least four thiol groups.

1476. The method of item 1283 wherein the polymer is formed from reactants comprising (a) methylated collagen and (b) a compound having at least four amino groups.

1477. The method of item 1283 wherein the composition comprises (a) methylated collagen and (b) a compound having at least four amino groups.

1478. The method of item 1283 wherein the polymer is formed from reactants comprising (a) methylated collagen and (b) a compound having at least four carbonyl-oxygen-succinimide groups.

1479. The method of item 1283 wherein the composition comprises (a) methylated collagen and (b) a compound having at least four carbonyl-oxygen-succinimide groups.

1480. The method of item 1283 wherein the polymer is formed from reactants comprising (a) methylated collagen and (b) a compound having a biodegradable region formed from reactants selected from lactic acid, lactide, glycolic acid, glycolide, and epsilon-caprolactone.

1481. The method of item 1283 wherein the composition comprises (a) methylated collagen and (b) a compound having a biodegradable region formed from reactants selected from lactic acid, lactide, glycolic acid, glycolide, and epsilon-caprolactone.

1482. The method of item 1283 wherein the polymer is formed from reactants comprising hyaluronic acid.

1483. The method of item 1283 wherein the composition comprises hyaluronic acid.

1484. The method of item 1283 wherein the polymer is formed from reactants comprising a hyaluronic acid derivative.

1485. The method of item 1283 wherein the composition comprises a hyaluronic acid derivative.

1486. The method of item 1283 wherein the polymer is formed from reactants comprising pentaerythritol poly(ethylene glycol)ether tetra-sulfhydryl of number average molecular weight between 3,000 and 30,000.

1487. The method of item 1283 wherein the composition comprises pentaerythritol poly(ethylene glycol)ether tetra-sulfhydryl of number average molecular weight between 3,000 and 30,000.

1488. The method of item 1283 wherein the polymer is formed from reactants comprising pentaerythritol poly(ethylene glycol)ether tetra-amino of number average molecular weight between 3,000 and 30,000.

1489. The method of item 1283 wherein the composition comprises pentaerythritol poly(ethylene glycol)ether tetra-amino of number average molecular weight between 3,000 and 30,000.

1490. The method of item 1283 wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1491. The method of item 1283 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1492. The method of item 1283 wherein the composition comprises a colorant.

1493. The method of item 1283 wherein the composition is sterile.

1494. The method of item 1283 wherein the composition further comprises a second pharmaceutically active agent.

1495. The method of item 1283 wherein the composition further comprises an anti-inflammatory agent.

1496. The method of item 1283 wherein the composition further comprises an agent that inhibits infection.

1497. The method of item 1283 wherein the composition further comprises an anthracycline.

1498. The method of item 1283 wherein the composition further comprises doxorubicin.

1499. The method of item 1283 wherein the composition further comprises mitoxantrone.

1500. The method of item 1283 wherein the composition further comprises a fluoropyrimidine.

1501. The method of item 1283 wherein the composition further comprises 5-fluorouracil (5-FU).

1502. The method of item 1283 wherein the composition further comprises a folic acid antagonist.

1503. The method of item 1283 wherein the composition further comprises methotrexate.

1504. The method of item 1283 wherein the composition further comprises a podophylotoxin.

1505. The method of item 1283 wherein the composition further comprises etoposide.

1506. The method of item 1283 wherein the composition further comprises camptothecin.

1507. The method of item 1283 wherein the composition further comprises a hydroxyurea.

1508. The method of item 1283 wherein the composition further comprises a platinum complex.

1509. The method of item 1283 wherein the composition further comprises cisplatin.

1510. The method of item 1283 wherein the composition further comprises an anti-infective agent.

1511. The method of item 1283 wherein the composition further comprises an anti-infective agent, wherein the anti-infective agent is an antibiotic.

1512. The method of item 1283 wherein the composition further comprises an anti-infective agent, wherein the anti-infective agent is doxycycline.

1513. The method of item 1283 wherein the composition further comprises an anti-infective agent, wherein the anti-infective agent is metronidazole.

1514. The method of item 1283 wherein the composition further comprises an anti-infective agent, wherein the anti-infective agent is trimethoprim-sulfamethoxazole.

1515. The method of item 1283 wherein the composition further comprises an anti-infective agent, wherein the anti-infective agent is a fourth generation penicillin.

1516. The method of item 1283 wherein the composition further comprises an anti-infective agent, wherein the anti-infective agent is a fourth generation penicillin selected from a ureidopenicillin and a carboxypenicillin, or an analogue or derivative thereof.

1517. The method of item 1283 wherein the composition further comprises an anti-infective agent, wherein the anti-infective agent is a fourth generation penicillin selected from mezlocillin, piperacillin, carbenicillin, and ticarcillin.

1518. The method of item 1283 wherein the composition further comprises an anti-infective agent, wherein the anti-infective agent is a first generation cephalosporin.

1519. The method of item 1283 wherein the composition further comprises an anti-infective agent, wherein the anti-infective agent is a first generation cephalosporin selected from cephazolin sodium, cephalexin, cefazolin, cephapirin, and cephalothin.

1520. The method of item 1283 wherein the composition further comprises an anti-infective agent, wherein the anti-infective agent is a carboxypenicillin.

1521. The method according to item 1520 wherein the carboxypenicillin is ticarcillin.

1522. The method of item 1283 wherein the composition further comprises an anti-infective agent, wherein the anti-infective agent is a second generation cephalosporin.

1523. The method of item 1283 wherein the composition further comprises an anti-infective agent, wherein the anti-infective agent is a second generation cephalosporin selected from cefuroxime, cefotetan, and cefoxitin.

1524. The method of item 1283 wherein the composition further comprises an anti-infective agent, wherein the anti-infective agent is a third generation cephalosporin.

1525. The method of item 1283 wherein the composition further comprises an anti-infective agent, wherein the anti-infective agent is a third generation cephalosporin selected from naxcel, Cefdinir, cefoperazone, ceftazidime, ceftriaxone, and cefotaxime.

1526. The method of item 1283 wherein the composition further comprises an anti-infective agent, wherein the anti-infective agent is a fourth generation cephalosporin.

1527. The method of item 1526 wherein the fourth generation cephalosporin is cefepime.

1528. The method of item 1283 wherein the composition further comprises an anti-infective agent, wherein the anti-infective agent is a monobactam.

1529. The method of item 1528 wherein the monobactam is aztreonam.

1530. The method of item 1283 wherein the composition further comprises an anti-infective agent, wherein the anti-infective agent is a carbapenem.

1531. The method of item 1283 wherein the composition further comprises an anti-infective agent, wherein the anti-infective agent is a carbapenem selected from imipenem, ertapenem and meropenem.

1532. The method of item 1283 wherein the composition further comprises an anti-infective agent, wherein the anti-infective agent is an aminoglycoside.

1533. The method of item 1283 wherein the composition further comprises an anti-infective agent, wherein the anti-infective agent is an aminoglycoside selected from streptomycin, gentamicin, tobramycin, and amikacin.

1534. The method of item 1283 wherein the composition further comprises an anti-infective agent, wherein the anti-infective agent is an MSL group member selected from a macrolide, a long acting macrolide, a lincosamide, and a streptogramin.

1535. The method of item 1283 wherein the composition further comprises an anti-infective agent, wherein the anti-infective agent is an MSL group member selected from Erythromycin, Azithromycin, Clindamycin, Syneroid, clarithromycin, and kanamycin sulfate.

1536. The method of item 1283 wherein the composition further comprises an anti-infective agent, wherein the anti-infective agent is a quinolone.

1537. The method of item 1283 wherein the composition further comprises an anti-infective agent, wherein the anti-infective agent is a quinolone selected from ciprofloxacin, ofloxacin, gatifloxacin, moxifloxacin, levofloxacin, and trovafloxacin.

1538. The method of item 1283 wherein the composition further comprises an anti-infective agent, wherein the anti-infective agent is a DNA synthesis inhibitor.

1539. The method of item 1538 wherein the DNA synthesis inhibitor is metronidazole.

1540. The method of item 1283 wherein the composition further comprises an anti-infective agent, wherein the anti-infective agent is a sulfonamide.

1541. The method of item 1540 wherein the sulfonamide is trimethoprim.

1542. The method of item 1283 wherein the composition further comprises an anti-infective agent, wherein the anti-infective agent is selected from cefixime, spectinomycin, tetracycline, nitrofurantoin, polymyxin B, and neomycin sulfate.

1543. The method of item 1283 wherein the composition further comprises a visualization agent.

1544. The method of item 1283 wherein the composition further comprises a visualization agent, and the visualization agent is a radiopaque material, wherein the radiopaque material comprises a metal, a halogenated compound, or a barium-containing compound.

1545. The method of item 1283 wherein the composition further comprises a visualization agent, and the visualization agent is, or comprises, barium, tantalum, or technetium.

1546. The method of item 1283 wherein the composition further comprises a visualization agent, and the visualization agent is, or comprises, an MRI responsive material or an echogenic material.

1547. The method of item 1283 wherein the composition further comprises a visualization agent, and the visualization agent is, or comprises, a gadolinium chelate.

1548. The method of item 1283 wherein the composition further comprises a visualization agent, and the visualization agent is, or comprises, iron, magnesium, manganese, copper, or chromium.

1549. The method of item 1283 wherein the composition further comprises a visualization agent, and the visualization agent is, or comprises, iron oxide compound.

1550. The method of item 1283 wherein the composition further comprises a visualization agent, and the visualization agent is, or comprises, a dye, pigment, or colorant.

1551. The method of item 1283 wherein the fibrosing agent is released in effective concentrations from the composition comprising the fibrosing agent by diffusion over a period ranging from the time of administration to about 90 days.

1552. The method of item 1283 wherein the fibrosing agent is released in effective concentrations from the composition comprising the fibrosing agent by erosion of the composition over a period ranging from the time of administration to about 90 days.

1553. The method of item 1283 wherein the composition further comprises an inflammatory cytokine.

1554. The method of item 1283 wherein the composition further comprises an agent that stimulates cell proliferation.

1555. The method of item 1283 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

1556. The method of item 1283 wherein the composition further comprises a polymeric carrier.

1557. The method of item 1283 wherein the composition is in the form of a gel, paste, or spray.

1558. The method of item 1283 wherein the composition is in the form of a mesh or film.

1559. The method of item 1283 wherein the fibrosing agent is delivered from a device, and the device delivers the fibrosing agent into the diverticulum.

1560. The method of item 1283 wherein the fibrosing agent is delivered from an implant, wherein the implant is or comprises a microsphere.

1561. The method of item 1283 wherein the fibrosing agent is delivered from an implant, wherein the implant is or comprises a mesh.

1562. The method of item 1283 wherein the fibrosing agent is delivered from an implant, wherein the implant is or comprises a film.

1563. The method of item 1283 wherein the fibrosing agent is delivered from a device, wherein the device is a catheter.

1564. The method of item 1283 wherein the fibrosing agent is delivered from a device, wherein the device is a drug delivery catheter.

1565. The method of item 1283 wherein the fibrosing agent is delivered from a device, wherein the device is a radiofrequencey ablation catheter.

1566. The method of item 1283 wherein the fibrosing agent is delivered from a device, wherein the device is a temperature ablation catheter.

1567. The method of item 1283 wherein the fibrosing agent is delivered from a device, wherein the device is a thermal energy catheter.

1568. The method of item 1283 wherein the fibrosing agent is delivered from a device, wherein the device is a cryoablation catheter.

1569. The method of item 1283 wherein the fibrosing agent is delivered from a device, wherein the device is a laser catheter.

1570. The method of item 1283 wherein the fibrosing agent is delivered from a device, wherein the device is a radioactivity-delivering catheter.

1571. The method of item 1283 wherein the fibrosing agent is delivered from a device, wherein the device is a balloon catheter.

1572. The method of item 1283 wherein the fibrosing agent is delivered from a device, wherein the device is an ultrasonic energy-delivering catheter.

1573. The method of item 1283 wherein the fibrosing agent is delivered from a device, wherein the device is a rotation atherectomy device.

1574. The method of item 1283 wherein the fibrosing agent is delivered from a device, wherein the device is a rotation atherectomy device that is a rotoblade.

1575. The method of item 1283 wherein the fibrosing agent is delivered from a device, wherein the device is a tissue abrasion device.

1576. The method of item 1283 wherein the fibrosing agent is delivered from a device, wherein the device is an atherectomy device.

1577. The method of item 1283 wherein the fibrosing agent is delivered from a device, wherein the device is an atherectomy catheter.

1578. The method of item 1283 wherein the fibrosing agent is delivered from a device, wherein the device is an endoscopic scalpel.

1579. The method of item 1283 wherein the fibrosing agent is introduced by delivery from a device, wherein the device further comprises a coating, and the coating comprises the fibrosing agent.

1580. The method of item 1283 wherein the fibrosing agent is introduced by delivery from a device, wherein the device further comprises a coating, and the coating is disposed on a surface of the device.

1581. The method of item 1283 wherein the fibrosing agent is introduced by delivery from a device, wherein the device further comprises a coating, and wherein the coating directly contacts the device.

1582. The method of item 1283 wherein the fibrosing agent is introduced by delivery from a device, wherein the device further comprises a coating, and wherein the coating indirectly contacts the device.

1583. The method of item 1283 wherein the fibrosing agent is introduced by delivery from a device, wherein the device further comprises a coating, and wherein the coating partially covers the device.

1584. The method of item 1283 wherein the fibrosing agent is introduced by delivery from a device, wherein the device further comprises a coating, and wherein the coating completely covers the device.

1585. The method of item 1283 wherein the fibrosing agent is introduced by delivery from a device, wherein the fibrosing agent is located within pores or holes of the device.

1586. The method of item 1283 wherein the fibrosing agent is introduced by delivery from a device, wherein the fibrosing agent is located within a channel, lumen, or divet of the device.

1587. The method of item 1283 wherein the fibrosing agent is introduced by delivery from a device, wherein the device further comprises an echogenic material.

1588. The method of item 1283 wherein the fibrosing agent is introduced by delivery from a device, wherein the device further comprises an echogenic material, and wherein the echogenic material is in the form of a coating.

1589. The method of item 1283 wherein the fibrosing agent is introduced by delivery from a device, wherein the device is sterile.

1590. The method of item 1283 wherein the agent is introduced by delivery from a device, wherein the fibrosing agent is released into tissue in the vicinity of the device after deployment of the device.

1591. The method of item 1283 wherein the fibrosing agent is introduced by delivery from a device, wherein the fibrosing agent is released into tissue in the vicinity of the device after deployment of the device, and wherein the tissue is connective tissue.

1592. The method of item 1283 wherein the fibrosing agent is introduced by delivery from a device, wherein the fibrosing agent is released into tissue in the vicinity of the device after deployment of the device, and wherein the tissue is muscle tissue.

1593. The method of item 1283 wherein the fibrosing agent is introduced by delivery from a device, wherein the fibrosing agent is released into tissue in the vicinity of the device after deployment of the device, and wherein the tissue is nerve tissue.

1594. The method of item 1283 wherein the fibrosing agent is introduced by delivery from a device, wherein the fibrosing agent is released into tissue in the vicinity of the device after deployment of the device, and wherein the tissue is epithelium tissue.

1595. The method of item 1283 wherein the fibrosing agent is introduced by delivery from a device, wherein the fibrosing agent is released in effective concentrations from the device over a period ranging from the time of deployment of the device to about 1 year.

1596. The method of item 1283 wherein the fibrosing agent is introduced by delivery from a device, wherein the fibrosing agent is released in effective concentrations from the device over a period ranging from about 1 month to 6 months.

1597. The method of item 1283 wherein the fibrosing agent is introduced by delivery from a device, and wherein the fibrosing agent is released in effective concentrations from the device over a period ranging from about 1–90 days.

1598. The method of item 1283 wherein the fibrosing agent is introduced by delivery from a device, and wherein the fibrosing agent is released in effective concentrations from the device at a constant rate.

1599. The method of item 1283 wherein the fibrosing agent is introduced by delivery from a device, and wherein the fibrosing agent is released in effective concentrations from the device at an increasing rate.

1600. The method of item 1283 wherein the fibrosing agent is introduced by delivery from a device, and wherein the agent is released in effective concentrations from the device at a decreasing rate.

1601. The method of item 1283 wherein the composition comprises about 0.01 µg to about 10 µg of the fibrosing agent.

1602. The method of item 1283 wherein the composition comprises about 10 µg to about 10 mg of the fibrosing agent.

1603. The method of item 1283 wherein the composition comprises about 10 mg to about 250 mg of the fibrosing agent.

1604. The method of item 1283 wherein the composition comprises about 250 mg to about 1000 mg of the fibrosing agent.

1605. The method of item 1283 wherein the composition comprises about 1000 mg to about 2500 mg of the fibrosing agent.

1606. The method of item 1283 wherein the fibrosing agent is introduced by delivery from an implant, and wherein a surface of the implant comprises less than 0.01 µg of the fibrosing agent per $mm^2$ of implant surface to which the agent is applied.

1607. The method of item 1283 wherein the fibrosing agent is introduced by delivery from an implant, and wherein a surface of the implant comprises about 0.01 µg to about 1 µg of the fibrosing agent per $mm^2$ of implant surface to which the agent is applied.

1608. The method of item 1283 wherein the fibrosing agent is introduced by delivery from an implant, and wherein a surface of the implant comprises about 1 µg to about 10 µg of the fibrosing agent per $mm^2$ of implant surface to which the agent is applied.

1609. The method of item 1283 wherein the fibrosing agent is introduced by delivery from an implant, and wherein a surface of the implant comprises about 10 µg to about 250 µg of the fibrosing agent per $mm^2$ of implant surface to which the agent is applied.

1610. The method of item 1283 wherein the fibrosing agent is introduced by delivery from an implant, and wherein a surface of the implant comprises about 250 µg to about 1000 µg of the fibrosing agent of fibrosing agent per $mm^2$ of implant surface to which the fibrosing agent is applied.

1611. The method of item 1283 wherein the fibrosing agent is introduced by delivery from an implant, and wherein a surface of the implant comprises about 1000 µg to about 2500 µg of the fibrosing agent per $mm^2$ of implant surface to which the agent is applied.

1612. The method of item 1283 wherein the fibrosing agent is introduced by delivery from an implant, wherein the implant further comprises a coating, and wherein the coating is a uniform coating.

1613. The method of item 1283 wherein the fibrosing agent is introduced by delivery from an implant, wherein the implant further comprises a coating, and wherein the coating is a non-uniform coating.

1614. The method of item 1283 wherein the fibrosing agent is introduced by delivery from an implant, wherein the implant further comprises a coating, and wherein the coating is a discontinuous coating.

1615. The method of item 1283 wherein the fibrosing agent is introduced by delivery from an implant, wherein the implant further comprises a coating, and wherein the coating is a patterned coating.

1616. The method of item 1283 wherein the fibrosing agent is introduced by delivery from an implant, wherein the implant further comprises a coating, and wherein the coating has a thickness of 100 µm or less.

1617. The method of item 1283 wherein the fibrosing agent is introduced by delivery from an implant, wherein the implant further comprises a coating, and wherein the coating has a thickness of 10 µm or less.

1618. The method of item 1283 wherein the fibrosing agent is introduced by delivery from an implant, wherein the implant further comprises a coating, and wherein the coating adheres to the surface of the implant upon deployment of the implant.

1619. The method of item 1283 wherein the fibrosing agent is introduced by delivery from an implant, wherein the implant further comprises a coating, and wherein the coating is stable at room temperature for a period of at least 1 year.

1620. The method of item 1283 wherein the fibrosing agent is introduced by delivery from an implant, wherein the implant further comprises a coating, and wherein the fibrosing agent is present in the coating in an amount ranging between about 0.0001% to about 1% by weight.

1621. The method of item 1283 wherein the fibrosing agent is introduced by delivery from an implant, wherein the implant further comprises a coating, and wherein the fibrosing agent is present in the coating in an amount ranging between about 1% to about 10% by weight.

1622. The method of item 1283 wherein the fibrosing agent is introduced by delivery from an implant, wherein the implant further comprises a coating, and wherein the fibrosing agent is present in the coating in an amount ranging between about 10% to about 25% by weight.

1623. The method of item 1283 wherein the fibrosing agent is introduced by delivery from an implant, wherein the implant further comprises a coating, and wherein the fibrosing agent is present in the coating in an amount ranging between about 25% to about 70% by weight.

1624. The method of item 1283 wherein the fibrosing agent is introduced by delivery from an implant, wherein the implant further comprises a coating, and wherein the coating comprises a polymer.

1625. The method of item 1283 wherein the fibrosing agent is introduced by delivery from an implant, wherein the implant comprises a first coating having a first composition and a second coating having a second composition.

1626. The method of item 1283 wherein the fibrosing agent is delivered from an implant, wherein the implant comprises a first coating having a first composition and a second coating having a second composition, wherein the first composition and the second composition are different.

1627. The method of item 1283 wherein the fibrosing agent or the composition comprising the fibrosing agent is injected or sprayed into the diverticulum.

1628. The method of item 1283 wherein the fibrosing agent or the composition comprising the fibrosing agent is injected or sprayed onto a tissue or into a tissue surrounding the diverticulum.

1629. The method of item 1283 wherein the composition further comprises a bulking agent.

1630. The method of item 1283 wherein the composition is a sealant.

1631. The method of item 1283 wherein the composition is a haemostatic agent.

1632. The method of item 1283 wherein the composition further comprises a bulking agent, wherein the bulking agent comprises microspheres.

1633. The method of item 1283 wherein the composition further comprises a bulking agent, wherein the bulking agent comprises a hydroxyapatite loaded gel.

1634. The method of item 1283 wherein the composition further comprises a bulking agent, wherein the bulking agent comprises a micronized alloderm acellular matrix.

1635. The method of item 1283 wherein the composition further comprises a bulking agent, wherein the bulking agent comprises hyaluronic acid.

1636. The method of item 1283 wherein the composition further comprises a bulking agent, wherein the bulking agent comprises micro-beads in a hydrogel.

1637. The method of item 1283 wherein the composition further comprises a bulking agent, wherein the bulking agent comprises a hylan polymer.

1638. The method of item 1283 wherein the composition further comprises a bulking agent, wherein the bulking agent comprises a silicon microballoon and biocompatible polymer.

1639. The method of item 1283 further comprising visualizing the presence of a diverticulum.

1640. The method of item 1639 wherein visualizing the presence of a diverticulum comprising endoscopy.

1641. The method of item 1639 wherein visualizing the presence of a diverticulum comprising radiographic imaging.

1642. The method of item 1283 further comprising irrigating of the diverticulum with an irrigation solution prior to introducing the fibrosing agent.

1643. The method of item 1642 wherein the irrigation solution comprises (a) an anti-infective agent or (b) an antiseptic agent or (c) an anti-infective agent and an antiseptic agent.

1644. A method for inducing fibrosis in a diverticulum of a host, comprising inserting a composition into the host, said composition comprising (a) a fibrosing agent and (b) a polymer or a compound that polymerizes to form a crosslinked polymer in situ, wherein the composition induces fibrosis in the host.

1645. The method of item 1644 wherein inducing fibrosis in a diverticulum prevents or treats a diverticular disease.

1646. The method of item 1644 wherein the diverticular disease is diverticulitis.

1647. The method of item 1644 wherein the diverticular disease is diverticulosis.

1648. The method of item 1644 wherein the diverticular disease is diverticular hemorrhage.

1649. The method of item 1644 wherein the diverticular disease is Zenker's (esophageal) Diverticulum.

1650. The method of item 1644 wherein the diverticular disease is Meckel's Diverticulum.

1651. The method of item 1644 wherein the diverticular disease is small bowel diverticulosis.

1652. The method of item 1644 wherein the diverticular disease is gastric diverticulosis or urinary tract diverticulosis.

1653. The method of item 1644 wherein the diverticular disease is colonic diverticulosis.

1654. The method of item 1644 wherein the fibrosing agent promotes regeneration.

1655. The method of item 1644 wherein the fibrosing agent promotes fibrosis and promotes regeneration.

1656. The method of item 1644 wherein the fibrosing agent promotes angiogenesis.

1657. The method of item 1644 wherein the fibrosing agent promotes fibroblast migration.

1658. The method of item 1644 wherein the fibrosing agent promotes fibroblast proliferation.

1659. The method of item 1644 wherein the fibrosing agent promotes deposition of extracellular matrix (ECM).

1660. The method of item 1644 wherein the fibrosing agent promotes tissue remodeling.

1661. The method of item 1644 wherein the fibrosing agent is a diverticular wall irritant.

1662. The method of item 1644 wherein the fibrosing agent is or comprises silk.

1663. The method of item 1644 wherein the fibrosing agent is or comprises silkworm silk.

1664. The method of item 1644 wherein the fibrosing agent is or comprises spider silk.

1665. The method of item 1644 wherein the fibrosing agent is or comprises recombinant silk.

1666. The method of item 1644 wherein the fibrosing agent is or comprises raw silk.

1667. The method of item 1644 wherein the fibrosing agent is or comprises hydrolyzed silk.

1668. The method of item 1644 wherein the fibrosing agent is or comprises acid-treated silk.

1669. The method of item 1644 wherein the fibrosing agent is or comprises acylated silk.

1670. The method of item 1644 wherein the fibrosing agent is in the form of strands.

1671. The method of item 1644 wherein the fibrosing agent is in the form of tufts.

1672. The method of item 1644 wherein the fibrosing agent is or comprises mineral particles.

1673. The method of item 1644 wherein the fibrosing agent is or comprises chitosan.

1674. The method of item 1644 wherein the fibrosing agent is or comprises polylysine.

1675. The method of item 1644 wherein the fibrosing agent is or comprises fibronectin.

1676. The method of item 1644 wherein the fibrosing agent is or comprises bleomycin.

1677. The method of item 1644 wherein the fibrosing agent is or comprises CTGF.

1678. The method of item 1644 wherein the fibrosing agent is or comprises a wool.

1679. The method of item 1644 wherein the fibrosing agent is or comprises an animal wool.

1680. The method of item 1644 wherein the fibrosing agent is or comprises a wood wool.

1681. The method of item 1644 wherein the fibrosing agent is or comprises a synthetic wool.

1682. The method of item 1644 wherein the fibrosing agent is in the form of a thread, or is in contact with a thread.

1683. The method of item 1682 wherein the thread is biodegradable.

1684. The method of item 1683 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1685. The method of item 1682 wherein the thread is non-biodegradable.

1686. The method of item 1685 wherein the non-biodegradable thread comprises a material selected from the group consisting of polyester, polyurethane, silicone, polyethylene, polypropylene, polystyrene, polyacrylate, polymethacrylate, and silk.

1687. The method of item 1682 wherein the thread is coated with a polymer.

1688. The method of item 1682 wherein the thread is coated with a pharmaceutical agent that induces a fibrotic response in the host.

1689. The method of item 1644 wherein the fibrosing agent is in the form of a particulate.

1690. The method of item 1689 wherein the particulate is a biodegradable particulate.

1691. The method of item 1690 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

1692. The method of item 1689 wherein the particulate is a non-biodegradable particulate.

1693. The method of item 1692 wherein the non-biodegradable particulate comprises a material selected from the group consisting of polyester, polyurethane, silicone, polyethylene, polypropylene, polystyrene, polyacrylate, polymethacrylate, and silk.

1694. The method of item 1689 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1695. The method of item 1689 wherein the particulate is coated with a polymer.

1696. The method of item 1689 wherein the particulate is coated with a pharmaceutical agent that induces a fibrotic response in the host.

1697. The method of item 1689 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

1698. The method of item 1644 wherein the composition comprises a growth factor.

1699. The method of item 1698 wherein the growth factor is selected from a transforming growth factor, a platelet-derived growth factor, and a fibroblast growth factor.

1700. The method of item 1644 wherein the polymer is, or comprises, a copolymer.

1701. The method of item 1644 wherein the polymer is, or comprises, a block copolymer.

1702. The method of item 1644 wherein the polymer is, or comprises, a random copolymer.

1703. The method of item 1644 wherein the polymer is, or comprises, a biodegradable polymer.

1704. The method of item 1644 wherein the polymer is, or comprises, a non-biodegradable polymer.

1705. The method of item 1644 wherein the polymer is, or comprises, a hydrophilic polymer.

1706. The method of item 1644 wherein the polymer is, or comprises, a hydrophobic polymer.

1707. The method of item 1644 wherein the polymer is, or comprises, a polymer having hydrophilic domains.

1708. The method of item 1644 wherein the polymer is, or comprises, a polymer having hydrophobic domains.

1709. The method of item 1644 wherein the polymer is, or comprises, a non-conductive polymer.

1710. The method of item 1644 wherein the polymer is, or comprises, an elastomer.

1711. The method of item 1644 wherein the polymer is, or comprises, a hydrogel.

1712. The method of item 1644 wherein the polymer is, or comprises, a silicone polymer.

1713. The method of item 1644 wherein the polymer is, or comprises, a hydrocarbon polymer.

1714. The method of item 1644 wherein the polymer is, or comprises, a styrene-derived polymer.

1715. The method of item 1644 wherein the polymer is, or comprises, a butadiene-derived polymer.

1716. The method of item 1644 the polymer is, or comprises, a macromer.

1717. The method of item 1644 wherein the polymer is, or comprises, a poly(ethylene glycol).

1718. The method of item 1644 wherein the polymer is, or comprises, a collagen or a derivative thereof.

1719. The method of item 1644 wherein the polymer is, or comprises, a methylated collagen.

1720. The method of item 1644 wherein the polymer composition comprises a collagen or a derivative thereof and a fibrinogen.

1721. The method of item 1644 wherein the polymer composition comprises a collagen or a derivative thereof and a thrombin.

1722. The method of item 1644 wherein the polymer composition comprises (a) a collagen or a derivative thereof; (b) a fibrinogen; and (c) a thrombin.

1723. The method of item 1644 wherein the polymer composition comprises a methylated collagen and a poly(ethylene glycol) or a derivative thereof.

1724. The method of item 1644 wherein the composition further comprises a haemostatic agent that comprises a collagen polymer.

1725. The method of item 1644 wherein the composition further comprises a haemostatic agent that comprises a collagen polymer, wherein the haemostatic agent is CT3.

1726. The method of item 1644 wherein the composition further comprises a haemostatic agent that comprises a collagen polymer, wherein the haemostatic agent is COSTASIS.

1727. The method of item 1644 wherein the composition further comprises a haemostatic agent that comprises a poly(ethylene glycol).

1728. The method of item 1644 wherein the composition further comprises a haemostatic agent, wherein the haemostatic agent is COSEAL, TISSEAL, OR FLOSEAL.

1729. The method of item 1644 wherein the composition further comprises a haemostatic agent that comprises fibrin.

1730. The method of item 1644 wherein the polymer is, or comprises, an amorphous polymer.

1731. The method of item 1644 wherein the polymer is, or comprises, a cyanoacrylate.

1732. The method of item 1731, wherein the cyanoacrylate is selected from methyl cyanoacrylate, ethyl cyanoacrylate, butyl cyanoacrylate, octyl cyanoacrylate, and methoxypropyl cyanoacrylate.

1733. The method of item 1644 wherein the polymer is, or comprises, a poly(alkylcyanoacrylate).

1734. The method of item 1733, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

1735. The method of item 1644 wherein the polymer is, or comprises, a poly(carboxyalkylcyanoacrylate).

1736. The method of item 1735 wherein the poly(carboxyalkylcyanoacrylate) is poly(methoxypropylcyanoacrylate).

1737. The method of item 1644 wherein the polymer is crosslinked.

1738. The method of item 1644 wherein the polymer reacts with mammalian tissue.

1739. The method of item 1644 wherein the polymer is a naturally occurring polymer.

1740. The method of item 1644 wherein the polymer is protein.

1741. The method of item 1644 wherein the polymer is carbohydrate.

1742. The method of item 1644 wherein the polymer is crosslinked and biodegradable.

1743. The method of item 1644 wherein the composition comprises a fibrinogen.

1744. The method of item 1644 wherein the composition comprises a thrombin.

1745. The method of item 1644 wherein the composition comprises a calcium salt.

1746. The method of item 1644 wherein the composition comprises an antifibrinolytic agent.

1747. The method of item 1644 wherein the composition comprises a fibrinogen analog.

1748. The method of item 1644 wherein the composition comprises an albumin.

1749. The method of item 1644 wherein the composition comprises a plasminogen.

1750. The method of item 1644 wherein the composition comprises a von Willebrands factor.

1751. The method of item 1644 wherein the composition comprises a Factor VIII.

1752. The method of item 1644 wherein the composition comprises a hypoallergenic collagen.

1753. The method of item 1644 wherein the composition comprises atelopeptide collagen.

1754. The method of item 1644 wherein the composition comprises a crosslinked collagen.

1755. The method of item 1644 wherein the composition comprises an aprotinin.

1756. The method of item 1644 wherein the composition comprises an epsilon-amino-n-caproic acid.

1757. The method of item 1644 wherein the composition comprises a gelatin.

1758. The method of item 1644 wherein the composition comprises a protein conjugate.

1759. The method of item 1644 wherein the composition comprises a gelatin conjugate.

1760. The method of item 1644 wherein the composition comprises a hyaluronic acid.

1761. The method of item 1644 wherein the composition comprises a hyaluronic acid derivative.

1762. The method of item 1644 wherein the composition comprises a synthetic polymer.

1763. The method of item 1644 wherein the polymer is formed from reactants comprising a synthetic isocyanate-containing compound.

1764. The method of item 1644 wherein the composition comprises a synthetic isocyanate-containing compound.

1765. The method of item 1644 wherein the polymer is formed from reactants comprising a synthetic thiol-containing compound.

1766. The method of item 1644 wherein the composition comprises a synthetic thiol-containing compound.

1767. The method of item 1644 wherein the polymer is formed from reactants comprising a synthetic compound containing at least two thiol groups.

1768. The method of item 1644 wherein the composition comprises a synthetic compound containing at least two thiol groups.

1769. The method of item 1644 wherein the polymer is formed from reactants comprising a synthetic compound containing at least three thiol groups.

1770. The method of item 1644 wherein the composition comprises a synthetic compound containing at least three thiol groups.

1771. The method of item 1644 wherein the polymer is formed from reactants comprising a synthetic compound containing at least four thiol groups.

1772. The method of item 1644 wherein the composition comprises a synthetic compound containing at least four thiol groups.

1773. The method of item 1644 wherein the polymer is formed from reactants comprising a synthetic amino-containing compound.

1774. The method of item 1644 wherein the composition comprises a synthetic amino-containing compound.

1775. The method of item 1644 wherein the polymer is formed from reactants comprising a synthetic compound containing at least two amino groups.

1776. The method of item 1644 wherein the composition comprises a synthetic compound containing at least two amino groups.

1777. The method of item 1644 wherein the polymer is formed from reactants comprising a synthetic compound containing at least three amino groups.

1778. The method of item 1644 wherein the composition comprises a synthetic compound containing at least three amino groups.

1779. The method of item 1644 wherein the polymer is formed from reactants comprising a synthetic compound containing at least four amino groups.

1780. The method of item 1644 wherein the composition comprises a synthetic compound containing at least four amino groups.

1781. The method of item 1644 wherein the polymer is formed from reactants comprising a synthetic compound comprising a carbonyl-oxygen-succinimidyl group.

1782. The method of item 1644 wherein the composition comprises a synthetic compound comprising a carbonyl-oxygen-succinimidyl group.

1783. The method of item 1644 wherein the polymer is formed from reactants comprising a synthetic compound comprising at least two carbonyl-oxygen-succinimidyl groups.

1784. The method of item 1644 wherein the composition comprises a synthetic compound comprising at least two carbonyl-oxygen-succinimidyl groups.

1785. The method of item 1644 wherein the polymer is formed from reactants comprising a synthetic compound comprising at least three carbonyl-oxygen-succinimidyl groups.

1786. The method of item 1644 wherein the composition comprises a synthetic compound comprising at least three carbonyl-oxygen-succinimidyl groups.

1787. The method of item 1644 wherein the polymer is formed from reactants comprising a synthetic compound comprising at least four carbonyl-oxygen-succinimidyl groups.

1788. The method of item 1644 wherein the composition comprises a synthetic compound comprising at least four carbonyl-oxygen-succinimidyl groups.

1789. The method of item 1644 wherein the polymer is formed from reactants comprising a synthetic polyalkylene oxide-containing compound.

1790. The method of item 1644 wherein the composition comprises a synthetic polyalkylene oxide-containing compound.

1791. The method of item 1644 wherein the polymer is formed from reactants comprising a synthetic compound comprising both polyalkylene oxide and biodegradable polyester blocks.

1792. The method of item 1644 wherein the composition comprises a synthetic compound comprising both polyalkylene oxide and biodegradable polyester blocks.

1793. The method of item 1644 wherein the polymer is formed from reactants comprising a synthetic polyalkylene oxide-containing compound having reactive amino groups.

1794. The method of item 1644 wherein the composition comprises synthetic polyalkylene oxide-containing compound having reactive amino groups.

1795. The method of item 1644 wherein the polymer is formed from reactants comprising a synthetic polyalkylene oxide-containing compound having reactive thiol groups.

1796. The method of item 1644 wherein the composition comprises synthetic polyalkylene oxide-containing compound having reactive thiol groups.

1797. The method of item 1644 wherein the polymer is formed from reactants comprising a synthetic polyalkylene oxide-containing compound having reactive carbonyl-oxygen-succinimidyl groups.

1798. The method of item 1644 wherein the composition comprises a synthetic polyalkylene oxide-containing compound having reactive carbonyl-oxygen-succinimidyl groups.

1799. The method of item 1644 wherein the polymer is formed from reactants comprising a synthetic compound comprising a biodegradable polyester block.

1800. The method of item 1644 wherein the composition comprises a synthetic compound comprising a biodegradable polyester block.

1801. The method of item 1644 wherein the polymer is formed from reactants comprising a synthetic polymer formed in whole or part from lactic acid or lactide.

1802. The method of item 1644 wherein the composition comprises a synthetic polymer formed in whole or part from lactic acid or lactide.

1803. The method of item 1644 wherein the polymer is formed from reactants comprising a synthetic polymer formed in whole or part from glycolic acid or glycolide.

1804. The method of item 1644 wherein the composition comprises a synthetic polymer formed in whole or part from glycolic acid or glycolide.

1805. The method of item 1644 wherein the polymer is formed from reactants comprising polylysine.

1806. The method of item 1644 wherein the composition comprises polylysine.

1807. The method of item 1644 wherein the polymer is formed from reactants comprising (a) protein and (b) a compound comprising a polyalkylene oxide portion.

1808. The method of item 1644 wherein the composition comprises (a) protein and (b) a compound comprising a polyalkylene oxide portion.

1809. The method of item 1644 wherein the polymer is formed from reactants comprising (a) protein and (b) polylysine.

1810. The method of item 1644 wherein the composition comprises (a) protein and (b) polylysine.

1811. The method of item 1644 wherein the polymer is formed from reactants comprising (a) protein and (b) a compound having at least four thiol groups.

1812. The method of item 1644 wherein the composition comprises (a) protein and (b) a compound having at least four thiol groups.

1813. The method of item 1644 wherein the polymer is formed from reactants comprising (a) protein and (b) a compound having at least four amino groups.

1814. The method of item 1644 wherein the composition comprises (a) protein and (b) a compound having at least four amino groups.

1815. The method of item 1644 wherein the polymer is formed from reactants comprising (a) protein and (b) a compound having at least four carbonyl-oxygen-succinimide groups.

1816. The method of item 1644 wherein the composition comprises (a) protein and (b) a compound having at least four carbonyl-oxygen-succinimide groups.

1817. The method of item 1644 wherein the polymer is formed from reactants comprising (a) protein and (b) a compound having a biodegradable region formed from reactants selected from lactic acid, lactide, glycolic acid, glycolide, and epsilon-caprolactone.

1818. The method of item 1644 wherein the composition comprises (a) protein and (b) a compound having a biodegradable region formed from reactants selected from lactic acid, lactide, glycolic acid, glycotide, and epsilon-caprolactone.

1819. The method of item 1644 wherein the polymer is formed from reactants comprising (a) collagen and (b) a compound comprising a polyalkylene oxide portion.

1820. The method of item 1644 wherein the composition comprises (a) collagen and (b) a compound comprising a polyalkylene oxide portion.

1821. The method of item 1644 wherein the polymer is formed from reactants comprising (a) collagen and (b) polylysine.

1822. The method of item 1644 wherein the composition comprises (a) collagen and (b) polylysine.

1823. The method of item 1644 wherein the polymer is formed from reactants comprising (a) collagen and (b) a compound having at least four thiol groups.

1824. The method of item 1644 wherein the composition comprises (a) collagen and (b) a compound having at least four thiol groups.

1825. The method of item 1644 wherein the polymer is formed from reactants comprising (a) collagen and (b) a compound having at least four amino groups.

1826. The method of item 1644 wherein the composition comprises (a) collagen and (b) a compound having at least four amino groups.

1827. The method of item 1644 wherein the polymer is formed from reactants comprising (a) collagen and (b) a compound having at least four carbonyl-oxygen-succinimide groups.

1828. The method of item 1644 wherein the composition comprises (a) collagen and (b) a compound having at least four carbonyl-oxygen-succinimide groups.

1829. The method of item 1644 wherein the polymer is formed from reactants comprising (a) collagen and (b) a compound having a biodegradable region formed from reactants selected from lactic acid, lactide, glycolic acid, glycolide, and epsilon-caprolactone.

1830. The method of item 1644 wherein the composition comprises (a) collagen and (b) a compound having a biodegradable region formed from reactants selected from lactic acid, lactide, glycolic acid, glycolide, and epsilon-caprolactone.

1831. The method of item 1644 wherein the polymer is formed from reactants comprising (a) methylated collagen and (b) a compound comprising a polyalkylene oxide portion.

1832. The method of item 1644 wherein the composition comprises (a) methylated collagen and (b) a compound comprising a polyalkylene oxide portion.

1833. The method of item 1644 wherein the polymer is formed from reactants comprising (a) methylated collagen and (b) polylysine.

1834. The method of item 1644 wherein the composition comprises (a) methylated collagen and (b) polylysine.

1835. The method of item 1644 wherein the polymer is formed from reactants comprising (a) methylated collagen and (b) a compound having at least four thiol groups.

1836. The method of item 1644 wherein the composition comprises (a) methylated collagen and (b) a compound having at least four thiol groups.

1837. The method of item 1644 wherein the polymer is formed from reactants comprising (a) methylated collagen and (b) a compound having at least four amino groups.

1838. The method of item 1644 wherein the composition comprises (a) methylated collagen and (b) a compound having at least four amino groups.

1839. The method of item 1644 wherein the polymer is formed from reactants comprising (a) methylated collagen and (b) a compound having at least four carbonyl-oxygen-succinimide groups.

1840. The method of item 1644 wherein the composition comprises (a) methylated collagen and (b) a compound having at least four carbonyl-oxygen-succinimide groups.

1841. The method of item 1644 wherein the polymer is formed from reactants comprising (a) methylated collagen and (b) a compound having a biodegradable region formed from reactants selected from lactic acid, lactide, glycolic acid, glycolide, and epsilon-caprolactone.

1842. The method of item 1644 wherein the composition comprises (a) methylated collagen and (b) a compound having a biodegradable region formed from reactants selected from lactic acid, lactide, glycolic acid, glycolide, and epsilon-caprolactone.

1843. The method of item 1644 wherein the polymer is formed from reactants comprising hyaluronic acid.

1844. The method of item 1644 wherein the composition comprises hyaluronic acid.

1845. The method of item 1644 wherein the polymer is formed from reactants comprising a hyaluronic acid derivative.

1846. The method of item 1644 wherein the composition comprises a hyaluronic acid derivative.

1847. The method of item 1644 wherein the polymer is formed from reactants comprising pentaerythritol poly(ethylene glycol)ether tetra-sulfhydryl of number average molecular weight between 3,000 and 30,000.

1848. The method of item 1644 wherein the composition comprises pentaerythritol poly(ethylene glycol)ether tetra-sulfhydryl of number average molecular weight between 3,000 and 30,000.

1849. The method of item 1644 wherein the polymer is formed from reactants comprising pentaerythritol poly(ethylene glycol)ether tetra-amino of number average molecular weight between 3,000 and 30,000.

1850. The method of item 1644 wherein the composition comprises pentaerythritol poly(ethylene glycol)ether tetra-amino of number average molecular weight between 3,000 and 30,000.

1851. The method of item 1644 wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1852. The method of item 1644 wherein the composition comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

1853. The method of item 1644 wherein the composition comprises a colorant.

1854. The method of item 1644 wherein the composition is sterile.

1855. The method of item 1644 wherein the composition further comprises a second pharmaceutically active agent.

1856. The method of item 1644 wherein the composition further comprises an anti-inflammatory agent.

1857. The method of item 1644 wherein the composition further comprises an agent that inhibits infection.

1858. The method of item 1644 wherein the composition further comprises an anthracycline.

1859. The method of item 1644 wherein the composition further comprises doxorubicin.

1860. The method of item 1644 wherein the composition further comprises mitoxantrone.

1861. The method of item 1644 wherein the composition further comprises a fluoropyrimidine.

1862. The method of item 1644 wherein the composition further comprises 5-fluorouracil (5-FU).

1863. The method of item 1644 wherein the composition further comprises a fotic acid antagonist.

1864. The method of item 1644 wherein the composition further comprises methotrexate.

1865. The method of item 1644 wherein the composition further comprises a podophylotoxin.

1866. The method of item 1644 wherein the composition further comprises etoposide.

1867. The method of item 1644 wherein the composition further comprises camptothecin.

1868. The method of item 1644 wherein the composition further comprises a hydroxyurea.

1869. The method of item 1644 wherein the composition further comprises a platinum complex.

1870. The method of item 1644 wherein the composition further comprises cisplatin.

1871. The method of item 1644 wherein the composition further comprises an anti-infective agent.

1872. The method of item 1644 wherein the composition further comprises an anti-infective agent, wherein the anti-infective agent is an antibiotic.

1873. The method of item 1644 wherein the composition further comprises an anti-infective agent, wherein the anti-infective agent is doxycycline.

1874. The method of item 1644 wherein the composition further comprises an anti-infective agent, wherein the anti-infective agent is metronidazole.

1875. The method of item 1644 wherein the composition further comprises an anti-infective agent, wherein the anti-infective agent is trimethoprim-sulfamethoxazole.

1876. The method of item 1644 wherein the composition further comprises an anti-infective agent, wherein the anti-infective agent is a fourth generation penicillin.

1877. The method of item 1644 wherein the composition further comprises an anti-infective agent, wherein the anti-infective agent is a fourth generation penicillin selected from a ureidopenicillin and a carboxypenicillin, or an analogue or derivative thereof.

1878. The method of item 1644 wherein the composition further comprises an anti-infective agent, wherein the anti-infective agent is a fourth generation penicillin selected from meziocillin, piperacillin, carbenicillin, and ticarcillin.

1879. The method of item 1644 wherein the composition further comprises an anti-infective agent, wherein the anti-infective agent is a first generation cephalosporin.

1880. The method of item 1644 wherein the composition further comprises an anti-infective agent, wherein the anti-infective agent is a first generation cephalosporin selected from cephazolin sodium, cephalexin, cefazolin, cephapirin, and cephalothin.

1881. The method of item 1644 wherein the composition further comprises an anti-infective agent, wherein the anti-infective agent is a carboxypenicillin.

1882. The method according to item 1881 wherein the carboxypenicillin is ticarcillin.

1883. The method of item 1644 wherein the composition further comprises an anti-infective agent, wherein the anti-infective agent is a second generation cephalosporin.

1884. The method of item 1644 wherein the composition further comprises an anti-infective agent, wherein the anti-infective agent is a second generation cephalosporin selected from cefuroxime, cefotetan, and cefoxitin.

1885. The method of item 1644 wherein the composition further comprises an anti-infective agent, wherein the anti-infective agent is a third generation cephalosporin.

1886. The method of item 1644 wherein the composition further comprises an anti-infective agent, wherein the anti-infective agent is a third generation cephalosporin selected from naxcel, Cefdinir, cefoperazone, ceftazidime, ceftriaxone, and cefotaxime.

1887. The method of item 1644 wherein the composition further comprises an anti-infective agent, wherein the anti-infective agent is a fourth generation cephalosporin.

1888. The method of item 1887 wherein the fourth generation cephalosporin is cefepime.

1889. The method of item 1644 wherein the composition further comprises an anti-infective agent, wherein the anti-infective agent is a monobactam.

1890. The method of item 1889 wherein the monobactam is aztreonam.

1891. The method of item 1644 wherein the composition further comprises an anti-infective agent, wherein the anti-infective agent is a carbapenem.

1892. The method of item 1644 wherein the composition further comprises an anti-infective agent, wherein the anti-infective agent is a carbapenem selected from imipenem, ertapenem and meropenem.

1893. The method of item 1644 wherein the composition further comprises an anti-infective agent, wherein the anti-infective agent is an aminoglycoside.

1894. The method of item 1644 wherein the composition further comprises an anti-infective agent, wherein the anti-infective agent is an aminoglycoside selected from streptomycin, gentamicin, tobramycin, and amikacin.

1895. The method of item 1644 wherein the composition further comprises an anti-infective agent, wherein the anti-infective agent is an MSL group member selected from a macrolide, a long acting macrolide, a lincosamide, and a streptogramin.

1896. The method of item 1644 wherein the composition further comprises an anti-infective agent, wherein the anti-infective agent is an MSL group member selected from Erythromycin, Azithromycin, Clindamycin, Syneroid, clarithromycin, and kanamycin sulfate.

1897. The method of item 1644 wherein the composition further comprises an anti-infective agent, wherein the anti-infective agent is a quinolone.

1898. The method of item 1644 wherein the composition further comprises an anti-infective agent, wherein the anti-infective agent is a quinolone selected from ciprofloxacin, ofloxacin, gatifloxacin, moxifloxacin, levofloxacin, and trovafloxacin.

1899. The method of item 1644 wherein the composition further comprises an anti-infective agent, wherein the anti-infective agent is a DNA synthesis inhibitor.

1900. The method of item 1899 wherein the DNA synthesis inhibitor is metronidazole.

1901. The method of item 1644 wherein the composition further comprises an anti-infective agent, wherein the anti-infective agent is a sulfonamide.

1902. The method of item 1901 wherein the sulfonamide is trimethoprim.

1903. The method of item 1644 wherein the composition further comprises an anti-infective agent, wherein the anti-infective agent is selected from cefixime, spectinomycin, tetracycline, nitrofurantoin, polymyxin B, and neomycin sulfate.

1904. The method of item 1644 wherein the composition further comprises a visualization agent.

1905. The method of item 1644 wherein the composition further comprises a visualization agent, and the visualization agent is a radiopaque material, wherein the radiopaque material comprises a metal, a halogenated compound, or a barium-containing compound.

1906. The method of item 1644 wherein the composition further comprises a visualization agent, and the visualization agent is, or comprises, barium, tantalum, or technetium.

1907. The method of item 1644 wherein the composition further comprises a visualization agent, and the visualization agent is, or comprises, an MRI responsive material or an echogenic material.

1908. The method of item 1644 wherein the composition further comprises a visualization agent, and the visualization agent is, or comprises, a gadolinium chelate.

1909. The method of item 1644 wherein the composition further comprises a visualization agent, and the visualization agent is, or comprises, iron, magnesium, manganese, copper, or chromium.

1910. The method of item 1644 wherein the composition further comprises a visualization agent, and the visualization agent is, or comprises, iron oxide compound.

1911. The method of item 1644 wherein the composition further comprises a visualization agent, and the visualization agent is, or comprises, a dye, pigment, or colorant.

1912. The method of item 1644 wherein the fibrosing agent is released in effective concentrations from the composition comprising the fibrosing agent by diffusion over a period ranging from the time of administration to about 90 days.

1913. The method of item 1644 wherein the fibrosing agent is released in effective concentrations from the composition comprising the fibrosing agent by erosion of the composition over a period ranging from the time of administration to about 90 days.

1914. The method of item 1644 wherein the composition further comprises an inflammatory cytokine.

1915. The method of item 1644 wherein the composition further comprises an agent that stimulates cell proliferation.

1916. The method of item 1644 wherein the composition further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

1917. The method of item 1644 wherein the composition further comprises a polymeric carrier.

1918. The method of item 1644 wherein the composition is in the form of a gel, paste, or spray.

1919. The method of item 1644 wherein the composition is in the form of a mesh or film.

1920. The method of item 1644 wherein the fibrosing agent is delivered from a device, and the device delivers the fibrosing agent into the diverticulum.

1921. The method of item 1644 wherein the fibrosing agent is delivered from an implant, wherein the implant is or comprises a microsphere.

1922. The method of item 1644 wherein the fibrosing agent is delivered from an implant, wherein the implant is or comprises a mesh.

1923. The method of item 1644 wherein the fibrosing agent is delivered from an implant, wherein the implant is or comprises a film.

1924. The method of item 1644 wherein the fibrosing agent is delivered from a device, wherein the device is a catheter.

1925. The method of item 1644 wherein the fibrosing agent is delivered from a device, wherein the device is a drug delivery catheter.

1926. The method of item 1644 wherein the fibrosing agent is delivered from a device, wherein the device is a radiofrequencey ablation catheter.

1927. The method of item 1644 wherein the fibrosing agent is delivered from a device, wherein the device is a temperature ablation catheter.

1928. The method of item 1644 wherein the fibrosing agent is delivered from a device, wherein the device is a thermal energy catheter.

1929. The method of item 1644 wherein the fibrosing agent is delivered from a device, wherein the device is a cryoablation catheter.

1930. The method of item 1644 wherein the fibrosing agent is delivered from a device, wherein the device is a laser catheter.

1931. The method of item 1644 wherein the fibrosing agent is delivered from a device, wherein the device is a radioactivity-delivering catheter.

1932. The method of item 1644 wherein the fibrosing agent is delivered from a device, wherein the device is a balloon catheter.

1933. The method of item 1644 wherein the fibrosing agent is delivered from a device, wherein the device is an ultrasonic energy-delivering catheter.

1934. The method of item 1644 wherein the fibrosing agent is delivered from a device, wherein the device is a rotation atherectomy device.

1935. The method of item 1644 wherein the fibrosing agent is delivered from a device, wherein the device is a rotation atherectomy device that is a rotoblade.

1936. The method of item 1644 wherein the fibrosing agent is delivered from a device, wherein the device is a tissue abrasion device.

1937. The method of item 1644 wherein the fibrosing agent is delivered from a device, wherein the device is an atherectomy device.

1938. The method of item 1644 wherein the fibrosing agent is delivered from a device, wherein the device is an atherectomy catheter.

1939. The method of item 1644 wherein the fibrosing agent is delivered from a device, wherein the device is an endoscopic scalpel.

1940. The method of item 1644 wherein the fibrosing agent is introduced by delivery from a device, wherein the device further comprises a coating, and the coating comprises the fibrosing agent.

1941. The method of item 1644 wherein the fibrosing agent is introduced by delivery from a device, wherein the device further comprises a coating, and the coating is disposed on a surface of the device.

1942. The method of item 1644 wherein the fibrosing agent is introduced by delivery from a device, wherein the device further comprises a coating, and wherein the coating directly contacts the device.

1943. The method of item 1644 wherein the fibrosing agent is introduced by delivery from a device, wherein the device further comprises a coating, and wherein the coating indirectly contacts the device.

1944. The method of item 1644 wherein the fibrosing agent is introduced by delivery from a device, wherein the device further comprises a coating, and wherein the coating partially covers the device.

1945. The method of item 1644 wherein the fibrosing agent is introduced by delivery from a device, wherein the device further comprises a coating, and wherein the coating completely covers the device.

1946. The method of item 1644 wherein the fibrosing agent is introduced by delivery from a device, wherein the fibrosing agent is located within pores or holes of the device.

1947. The method of item 1644 wherein the fibrosing agent is introduced by delivery from a device, wherein the fibrosing agent is located within a channel, lumen, or divet of the device.

1948. The method of item 1644 wherein the fibrosing agent is introduced by delivery from a device, wherein the device further comprises an echogenic material.

1949. The method of item 1644 wherein the fibrosing agent is introduced by delivery from a device, wherein the device further comprises an echogenic material, and wherein the echogenic material is in the form of a coating.

1950. The method of item 1644 wherein the fibrosing agent is introduced by delivery from a device, wherein the device is sterile.

1951. The method of item 1644 wherein the agent is introduced by delivery from a device, wherein the fibrosing agent is released into tissue in the vicinity of the device after deployment of the device.

1952. The method of item 1644 wherein the fibrosing agent is introduced by delivery from a device, wherein the fibrosing agent is released into tissue in the vicinity of the device after deployment of the device, and wherein the tissue is connective tissue.

1953. The method of item 1644 wherein the fibrosing agent is introduced by delivery from a device, wherein the fibrosing agent is released into tissue in the vicinity of the device after deployment of the device, and wherein the tissue is muscle tissue.

1954. The method of item 1644 wherein the fibrosing agent is introduced by delivery from a device, wherein the fibrosing agent is released into tissue in the vicinity of the device after deployment of the device, and wherein the tissue is nerve tissue.

1955. The method of item 1644 wherein the fibrosing agent is introduced by delivery from a device, wherein the fibrosing agent is released into tissue in the vicinity of the device after deployment of the device, and wherein the tissue is epithelium tissue.

1956. The method of item 1644 wherein the fibrosing agent is introduced by delivery from a device, wherein the fibrosing agent is released in effective concentrations from the device over a period ranging from the time of deployment of the device to about 1 year.

1957. The method of item 1644 wherein the fibrosing agent is introduced by delivery from a device, wherein the fibrosing agent is released in effective concentrations from the device over a period ranging from about 1 month to 6 months.

1958. The method of item 1644 wherein the fibrosing agent is introduced by delivery from a device, and wherein the fibrosing agent is released in effective concentrations from the device over a period ranging from about 1–90 days.

1959. The method of item 1644 wherein the fibrosing agent is introduced by delivery from a device, and wherein the fibrosing agent is released in effective concentrations from the device at a constant rate.

1960. The method of item 1644 wherein the fibrosing agent is introduced by delivery from a device, and wherein the fibrosing agent is released in effective concentrations from the device at an increasing rate.

1961. The method of item 1644 wherein the fibrosing agent is introduced by delivery from a device, and wherein the agent is released in effective concentrations from the device at a decreasing rate.

1962. The method of item 1644 wherein the composition comprises about 0.01 μg to about 10 μg of the fibrosing agent.

1963. The method of item 1644 wherein the composition comprises about 10 μg to about 10 mg of the fibrosing agent.

1964. The method of item 1644 wherein the composition comprises about 10 mg to about 250 mg of the fibrosing agent.

1965. The method of item 1644 wherein the composition comprises about 250 mg to about 1000 mg of the fibrosing agent.

1966. The method of item 1644 wherein the composition comprises about 1000 mg to about 2500 mg of the fibrosing agent.

1967. The method of item 1644 wherein the fibrosing agent is introduced by delivery from an implant, and wherein a surface of the implant comprises less than 0.01 μg of the fibrosing agent per mm² of implant surface to which the agent is applied.

1968. The method of item 1644 wherein the fibrosing agent is introduced by delivery from an implant, and wherein a surface of the implant comprises about 0.01 μg to about 1 μg of the fibrosing agent per mm² of implant surface to which the agent is applied.

1969. The method of item 1644 wherein the fibrosing agent is introduced by delivery from an implant, and wherein a surface of the implant comprises about 1 μg to about 10 μg of the fibrosing agent per mm² of implant surface to which the agent is applied.

1970. The method of item 1644 wherein the fibrosing agent is introduced by delivery from an implant, and wherein a surface of the implant comprises about 10 μg to about 250 μg of the fibrosing agent per mm² of implant surface to which the agent is applied.

1971. The method of item 1644 wherein the fibrosing agent is introduced by delivery from an implant, and wherein a surface of the implant comprises about 250 μg to about 1000 μg of the fibrosing agent of fibrosing agent per mm² of implant surface to which the fibrosing agent is applied.

1972. The method of item 1644 wherein the fibrosing agent is introduced by delivery from an implant, and wherein a surface of the implant comprises about 1000 μg to about 2500 μg of the fibrosing agent per mm² of implant surface to which the agent is applied.

1973. The method of item 1644 wherein the fibrosing agent is introduced by delivery from an implant, wherein the implant further comprises a coating, and wherein the coating is a uniform coating.

1974. The method of item 1644 wherein the fibrosing agent is introduced by delivery from an implant, wherein the implant further comprises a coating, and wherein the coating is a non-uniform coating.

1975. The method of item 1644 wherein the fibrosing agent is introduced by delivery from an implant, wherein the implant further comprises a coating, and wherein the coating is a discontinuous coating.

1976. The method of item 1644 wherein the fibrosing agent is introduced by delivery from an implant, wherein the implant further comprises a coating, and wherein the coating is a patterned coating.

1977. The method of item 1644 wherein the fibrosing agent is introduced by delivery from an implant, wherein the implant further comprises a coating, and wherein the coating has a thickness of 100 μm or less.

1978. The method of item 1644 wherein the fibrosing agent is introduced by delivery from an implant, wherein the implant further comprises a coating, and wherein the coating has a thickness of 10 μm or less.

1979. The method of item 1644 wherein the fibrosing agent is introduced by delivery from an implant, wherein the implant further comprises a coating, and wherein the coating adheres to the surface of the implant upon deployment of the implant.

1980. The method of item 1644 wherein the fibrosing agent is introduced by delivery from an implant, wherein the implant further comprises a coating, and wherein the coating is stable at room temperature for a period of at least 1 year.

1981. The method of item 1644 wherein the fibrosing agent is introduced by delivery from an implant, wherein the implant further comprises a coating, and wherein the fibrosing agent is present in the coating in an amount ranging between about 0.0001% to about 1% by weight.

1982. The method of item 1644 wherein the fibrosing agent is introduced by delivery from an implant, wherein the implant further comprises a coating, and wherein the fibrosing agent is present in the coating in an amount ranging between about 1% to about 10% by weight.

1983. The method of item 1644 wherein the fibrosing agent is introduced by delivery from an implant, wherein the implant further comprises a coating, and wherein the fibrosing agent is present in the coating in an amount ranging between about 10% to about 25% by weight.

1984. The method of item 1644 wherein the fibrosing agent is introduced by delivery from an implant, wherein the implant further comprises a coating, and wherein the fibrosing agent is present in the coating in an amount ranging between about 25% to about 70% by weight.

1985. The method of item 1644 wherein the fibrosing agent is introduced by delivery from an implant, wherein the implant further comprises a coating, and wherein the coating comprises a polymer.

1986. The method of item 1644 wherein the fibrosing agent is introduced by delivery from an implant, wherein the implant comprises a first coating having a first composition and a second coating having a second composition.

1987. The method of item 1644 wherein the fibrosing agent is introduced by delivery from an implant, wherein the implant comprises a first coating having a first composition and a second coating having a second composition, wherein the first composition and the second composition are different.

1988. The method of item 1644 wherein the fibrosing agent or the composition comprising the fibrosing agent is injected or sprayed into the diverticulum.

1989. The method of item 1644 wherein the fibrosing agent or the composition comprising the fibrosing agent is injected or sprayed onto a tissue or into a tissue surrounding the diverticulum.

1990. The method of item 1644 wherein the composition further comprises a bulking agent.

1991. The method of item 1664 wherein the composition is a sealant.

1992. The method of item 1664 wherein the composition is a haemostatic agent.

1993. The method of item 1644 wherein the composition further comprises a bulking agent, wherein the bulking agent comprises microspheres.

1994. The method of item 1644 wherein the composition further comprises a bulking agent, wherein the bulking agent comprises a hydroxyapatite loaded gel.

1995. The method of item 1644 wherein the composition further comprises a bulking agent, wherein the bulking agent comprises a micronized alloderm acellular matrix.

1996. The method of item 1644 wherein the composition further comprises a bulking agent, wherein the bulking agent comprises hyaluronic acid.

1997. The method of item 1644 wherein the composition further comprises a bulking agent, wherein the bulking agent comprises micro-beads in a hydrogel.

1998. The method of item 1644 wherein the composition further comprises a bulking agent, wherein the bulking agent comprises a hylan polymer.

1999. The method of item 1644 wherein the composition further comprises a bulking agent, wherein the bulking agent comprises a silicon microballoon and biocompatible polymer.

2000. The method of item 1644 further comprising visualizing the presence of a diverticulum.

2001. The method of item 2000 wherein visualizing the presence of a diverticulum comprising endoscopy.

2002. The method of item 2000 wherein visualizing the presence of a diverticulum comprising radiographic imaging.

2003. The method of item 1644 further comprising irrigating of the diverticulum with an irrigation solution prior to introducing the fibrosing agent.

2004. The method of item 2003 wherein the irrigation solution comprises (a) an anti-infective agent or (b) an antiseptic agent or (c) an anti-infective agent and an antiseptic agent.

2005. The method of item 1 wherein the composition further comprises an anti-infective agent, wherein the anti-infective agent is gentamicin sulfate.

2006. The method of item 1 wherein the composition further comprises an anti-infective agent, wherein the anti-infective agent is amikacin sulfate.

2007. The method of item 1 wherein the composition further comprises an anti-infective agent, wherein the anti-infective agent is kanamycin sulfate.

2008. The method of item 1 wherein the composition further comprises an anti-infective agent, wherein the anti-infective agent is polymyxin B.

2009. The method of item 1 wherein the composition further comprises an anti-infective agent, wherein the anti-infective agent is neomycin sulfate.

2010. The method of item 1 wherein the composition further comprises an anti-infective agent, wherein the anti-infective agent is cephazolin sodium.

2011. The method of item 1 wherein the composition further comprises an anti-infective agent, wherein the anti-infective agent is ciprofloxain.

2012. The method of item 1 wherein the composition further comprises an anti-infective agent, wherein the anti-infective agent is piperacillin.

2013. The method of item 1 wherein the composition further comprises an anti-infective agent, wherein the anti-infective agent is cefoxitin.

2014. The method of item 1 wherein the composition further comprises an anti-infective agent, wherein the anti-infective agent is cefepime.

2015. The method of item 1 wherein the composition further comprises an anti-infective agent, wherein the anti-infective agent is azithromycin.

2016. The method of item 363 wherein the composition further comprises an anti-infective agent, wherein the anti-infective agent is gentamicin sulfate.

2017. The method of item 363 wherein the composition further comprises an anti-infective agent, wherein the anti-infective agent is amikacin sulfate.

2018. The method of item 363 wherein the composition further comprises an anti-infective agent, wherein the anti-infective agent is kanamycin sulfate.

2019. The method of item 363 wherein the composition further comprises an anti-infective agent, wherein the anti-infective agent is polymyxin B.

2020. The method of item 363 wherein the composition further comprises an anti-infective agent, wherein the anti-infective agent is neomycin sulfate.

2021. The method of item 363 wherein the composition further comprises an anti-infective agent, wherein the anti-infective agent is cephazolin sodium.

2022. The method of item 363 wherein the composition further comprises an anti-infective agent, wherein the anti-infective agent is ciprofloxain.

2023. The method of item 363 wherein the composition further comprises an anti-infective agent, wherein the anti-infective agent is piperacillin.

2024. The method of item 363 wherein the composition further comprises an anti-infective agent, wherein the anti-infective agent is cefoxitin.

2025. The method of item 363 wherein the composition further comprises an anti-infective agent, wherein the anti-infective agent is cefepime.

2026. The method of item 363 wherein the composition further comprises an anti-infective agent, wherein the anti-infective agent is azithromycin.

2027. The composition of any one of items 725–771 wherein the composition further comprises an anti-infective agent, wherein the anti-infective agent is gentamicin sulfate.

2028. The composition of any one of items 725–771 wherein the composition further comprises an anti-infective agent, wherein the anti-infective agent is amikacin sulfate.

2029. The composition of any one of items 725–771 wherein the composition further comprises an anti-infective agent, wherein the anti-infective agent is kanamycin sulfate.

2030. The composition of any one of items 725–771 wherein the composition further comprises an anti-infective agent, wherein the anti-infective agent is polymyxin B.

2031. The composition of any one of items 725–771 wherein the composition further comprises an anti-infective agent, wherein the anti-infective agent is neomycin sulfate.

2032. The composition of any one of items 725–771 wherein the composition further comprises an anti-infective agent, wherein the anti-infective agent is cephazolin sodium.

2033. The composition of any one of items 725–771 wherein the composition further comprises an anti-infective agent, wherein the anti-infective agent is ciprofloxain.

2034. The composition of any one of items 725–771 wherein the composition further comprises an anti-infective agent, wherein the anti-infective agent is piperacillin.

2035. The composition of any one of items 725–771 wherein the composition further comprises an anti-infective agent, wherein the anti-infective agent is cefoxitin.

2036. The composition of any one of items 725–771 wherein the composition further comprises an anti-infective agent, wherein the anti-infective agent is cefepime.

2037. The composition of any one of items 725–771 wherein the composition further comprises an anti-infective agent, wherein the anti-infective agent is azithromycin.

2038. The composition of any one of items 1004–1050 wherein the composition further comprises an anti-infective agent, wherein the anti-infective agent is gentamicin sulfate.

2039. The composition of any one of items 1004–1050 wherein the composition further comprises an anti-infective agent, wherein the anti-infective agent is amikacin sulfate.

2040. The composition of any one of items 1004–1050 wherein the composition further comprises an anti-infective agent, wherein the anti-infective agent is kanamycin sulfate.

2041. The composition of any one of items 1004–1050 wherein the composition further comprises an anti-infective agent, wherein the anti-infective agent is polymyxin B.

2042. The composition of any one of items 1004–1050 wherein the composition further comprises an anti-infective agent, wherein the anti-infective agent is neomycin sulfate.

2043. The composition of any one of items 1004–1050 wherein the composition further comprises an anti-infective agent, wherein the anti-infective agent is cephazolin sodium.

2044. The composition of any one of items 1004–1050 wherein the composition further comprises an anti-infective agent, wherein the anti-infective agent is ciprofloxain.

2045. The composition of any one of items 1004–1050 wherein the composition further comprises an anti-infective agent, wherein the anti-infective agent is piperacillin.

2046. The composition of any one of items 1004–1050 wherein the composition further comprises an anti-infective agent, wherein the anti-infective agent is cefoxitin.

2047. The composition of any one of items 1004–1050 wherein the composition further comprises an anti-infective agent, wherein the anti-infective agent is cefepime.

2048. The composition of any one of items 1004–1050 wherein the composition further comprises an anti-infective agent, wherein the anti-infective agent is azithromycin.

2049. The method of item 1283 wherein the composition further comprises an anti-infective agent, wherein the anti-infective agent is gentamicin sulfate.

2050. The method of item 1283 wherein the composition further comprises an anti-infective agent, wherein the anti-infective agent is amikacin sulfate.

2051. The method of item 1283 wherein the composition further comprises an anti-infective agent, wherein the anti-infective agent is kanamycin sulfate.

2052. The method of item 1283 wherein the composition further comprises an anti-infective agent, wherein the anti-infective agent is polymyxin B.

2053. The method of item 1283 wherein the composition further comprises an anti-infective agent, wherein the anti-infective agent is neomycin sulfate.

2054. The method of item 1283 wherein the composition further comprises an anti-infective agent, wherein the anti-infective agent is cephazolin sodium.

2055. The method of item 1283 wherein the composition further comprises an anti-infective agent, wherein the anti-infective agent is ciprofloxain.

2056. The method of item 1283 wherein the composition further comprises an anti-infective agent, wherein the anti-infective agent is piperacillin.

2057. The method of item 1283 wherein the composition further comprises an anti-infective agent, wherein the anti-infective agent is cefoxitin.

2058. The method of item 1283 wherein the composition further comprises an anti-infective agent, wherein the anti-infective agent is cefepime.

2059. The method of item 1283 wherein the composition further comprises an anti-infective agent, wherein the anti-infective agent is azithromycin.

2060. The method of item 1644 wherein the composition further comprises an anti-infective agent, wherein the anti-infective agent is gentamicin sulfate.

2061. The method of item 1644 wherein the composition further comprises an anti-infective agent, wherein the anti-infective agent is amikacin sulfate.

2062. The method of item 1644 wherein the composition further comprises an anti-infective agent, wherein the anti-infective agent is kanamycin sulfate.

2063. The method of item 1644 wherein the composition further comprises an anti-infective agent, wherein the anti-infective agent is polymyxin B.

2064. The method of item 1644 wherein the composition further comprises an anti-infective agent, wherein the anti-infective agent is neomycin sulfate.

2065. The method of item 1644 wherein the composition further comprises an anti-infective agent, wherein the anti-infective agent is cephazolin sodium.

2066. The method of item 1644 wherein the composition further comprises an anti-infective agent, wherein the anti-infective agent is ciprofloxain.

2067. The method of item 1644 wherein the composition further comprises an anti-infective agent, wherein the anti-infective agent is piperacillin.

2068. The method of item 1644 wherein the composition further comprises an anti-infective agent, wherein the anti-infective agent is cefoxitin.

2069. The method of item 1644 wherein the composition further comprises an anti-infective agent, wherein the anti-infective agent is cefepime.

2070. The method of item 1644 wherein the composition further comprises an anti-infective agent, wherein the anti-infective agent is azithromycin.

2071. A method of making an implant comprising combining (a) a fibrosing agent; (b) a polymer, or a composition comprising a polymer; and (c) an anti-infective agent, wherein the fibrosing agent induces a fibrotic response within a diveriticulum.

2072. The method of item 2071 wherein the fibrosing agent promotes regeneration.

2073. The method of item 2071 wherein the fibrosing agent promotes fibrosis and promotes regeneration.

2074. The method of item 2071 wherein the fibrosing agent promotes angiogenesis.

2075. The method of item 2071 wherein the fibrosing agent promotes fibroblast migration.

2076. The method of item 2071 wherein the fibrosing agent promotes fibroblast proliferation.

2077. The method of item 2071 wherein the fibrosing agent promotes deposition of extracellular matrix (ECM).

2078. The method of item 2071 wherein the fibrosing agent promotes tissue remodeling.

2079. The method of item 2071 wherein the fibrosing agent is a diverticular wall irritant.

2080. The method of item 2071 wherein the fibrosing agent is or comprises silk.

2081. The method of item 2071 wherein the fibrosing agent is or comprises silkworm silk.

2082. The method of item 2071 wherein the fibrosing agent is or comprises spider silk.

2083. The method of item 2071 wherein the fibrosing agent is or comprises recombinant silk.

2084. The method of item 2071 wherein the fibrosing agent is or comprises raw silk.

2085. The method of item 2071 wherein the fibrosing agent is or comprises hydrolyzed silk.

2086. The method of item 2071 wherein the fibrosing agent is or comprises acid-treated silk.

2087. The method of item 2071 wherein the fibrosing agent is or comprises acylated silk.

2088. The method of item 2071 wherein the fibrosing agent is in the form of strands.

2089. The method of item 2071 wherein the fibrosing agent is in the form of tufts.

2090. The method of item 2071 wherein the fibrosing agent is or comprises mineral particles.

2091. The method of item 2071 wherein the fibrosing agent is or comprises chitosan.

2092. The method of item 2071 wherein the fibrosing agent is or comprises polylysine.

2093. The method of item 2071 wherein the fibrosing agent is or comprises fibronectin.

2094. The method of item 2071 wherein the fibrosing agent is or comprises bleomycin.

2095. The method of item 2071 wherein the fibrosing agent is or comprises CTGF.

2096. The method of item 2071 wherein the fibrosing agent is or comprises a wool.

2097. The method of item 2071 wherein the fibrosing agent is or comprises an animal wool.

2098. The method of item 2071 wherein the fibrosing agent is or comprises a wood wool.

2099. The method of item 2071 wherein the fibrosing agent is or comprises a synthetic wool.

2100. The method of item 2071 wherein the fibrosing agent is in the form of a thread, or is in contact with a thread.

2101. The method of item 2100 wherein the thread is biodegradable.

2102. The method of item 2101 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

2103. The method of item 2100 wherein the thread is non-biodegradable.

2104. The method of item 2103 wherein the non-biodegradable thread comprises a material selected from the group consisting of polyester, polyurethane, silicone, polyethylene, polypropylene, polystyrene, polyacrylate, polymethacrylate, and silk.

2105. The method of item 2100 wherein the thread is coated with a polymer.

2106. The method of item 2100 wherein the thread is coated with a pharmaceutical agent that induces a fibrotic response in the host.

2107. The method of item 2071 wherein the fibrosing agent is in the form of a particulate.

2108. The method of item 2107 wherein the particulate is a biodegradable particulate.

2109. The method of item 2108 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

2110. The method of item 2107 wherein the particulate is a non-biodegradable particulate.

2111. The method of item 2110 wherein the non-biodegradable particulate comprises a material selected from the group consisting of polyester, polyurethane, silicone, polyethylene, polypropylene, polystyrene, polyacrylate, polymethacrylate, and silk.

2112. The method of item 2107 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

2113. The method of item 2107 wherein the particulate is coated with a polymer.

2114. The method of item 2107 wherein the particulate is coated with a pharmaceutical agent that induces a fibrotic response in the host.

2115. The method of item 2107 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

2116. The method of item 2107 wherein the implant further comprises a growth factor.

2117. The method of item 2116 wherein the growth factor is selected from a transforming growth factor, a platelet-derived growth factor, and a fibroblast growth factor.

2118. The method of item 2071 wherein the polymer is, or comprises, a copolymer.

2119. The method of item 2071 wherein the polymer is, or comprises, a block copolymer.

2120. The method of item 2071 wherein the polymer is, or comprises, a random copolymer.

2121. The method of item 2071 wherein the polymer is, or comprises, a biodegradable polymer.

2122. The method of item 2071 wherein the polymer is, or comprises, a non-biodegradable polymer.

2123. The method of item 2071 wherein the polymer is, or comprises, a hydrophilic polymer.

2124. The method of item 2071 wherein the polymer is, or comprises, a hydrophobic polymer.

2125. The method of item 2071 wherein the polymer is, or comprises, a polymer having hydrophilic domains.

2126. The method of item 2071 wherein the polymer is, or comprises, a polymer having hydrophobic domains.

2127. The method of item 2071 wherein the polymer is, or comprises, a non-conductive polymer.

2128. The method of item 2071 wherein the polymer is, or comprises, an elastomer.

2129. The method of item 2071 wherein the polymer is, or comprises, a hydrogel.

2130. The method of item 2071 wherein the polymer is, or comprises, a silicone polymer.

2131. The method of item 2071 wherein the polymer is, or comprises, a hydrocarbon polymer.

2132. The method of item 2071 wherein the polymer is, or comprises, a styrene-derived polymer.

2133. The method of item 2071 wherein the polymer is, or comprises, a butadiene-derived polymer.

2134. The method of item 2071 the polymer is, or comprises, a macromer.

2135. The method of item 2071 wherein the polymer is, or comprises, a poly(ethylene glycol).

2136. The method of item 2071 wherein the polymer is, or comprises, a collagen or a derivative thereof.

2137. The method of item 2071 wherein the polymer is, or comprises, a methylated collagen.

2138. The method of item 2071 wherein the polymer composition comprises a collagen or a derivative thereof and a fibrinogen.

2139. The method of item 2071 wherein the polymer composition comprises a collagen or a derivative thereof and a thrombin.

2140. The method of item 2071 wherein the polymer composition comprises (a) a collagen or a derivative thereof; (b) a fibrinogen; and (c) a thrombin.

2141. The method of item 2071 wherein the polymer composition comprises a methylated collagen and a poly(ethylene glycol) or a derivative thereof.

2142. The method of item 2071 wherein the implant further comprises a haemostatic agent that comprises a collagen polymer.

2143. The method of item 2071 wherein the implant further comprises a haemostatic agent that comprises a collagen polymer, wherein the haemostatic agent is CT3.

2144. The method of item 2071 wherein the implant further comprises a haemostatic agent that comprises a collagen polymer, wherein the haemostatic agent is COSTASIS.

2145. The method of item 2071 wherein the implant further comprises a haemostatic agent that comprises a poly(ethylene glycol).

2146. The method of item 2071 wherein the implant further comprises a haemostatic agent, wherein the haemostatic agent is COSEAL, TISSEAL, OR FLOSEAL.

2147. The method of item 2071 wherein the implant further comprises a haemostatic agent that comprises fibrin.

2148. The method of item 2071 wherein the polymer is, or comprises, an amorphous polymer.

2149. The method of item 2071 wherein the polymer is, or comprises, a cyanoacrylate.

2150. The method of item 2149, wherein the cyanoacrylate is selected from methyl cyanoacrylate, ethyl cyanoacrylate, butyl cyanoacrylate, octyl cyanoacrylate, and methoxypropyl cyanoacrylate.

2151. The method of item 2071 wherein the polymer is, or comprises, a poly(alkylcyanoacrylate).

2152. The method of item 2151, wherein the poly(alkylcyanoacrylate) is selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

2153. The method of item 2071 wherein the polymer is, or comprises, a poly(carboxyalkylcyanoacrylate).

2154. The method of item 2153 wherein the poly(carboxyalkylcyanoacrylate) is poly(methoxypropylcyanoacrylate).

2155. The method of item 2071 wherein the polymer is crosslinked.

2156. The method of item 2071 wherein the polymer reacts with mammalian tissue.

2157. The method of item 2071 wherein the polymer is a naturally occurring polymer.

2158. The method of item 2071 wherein the polymer is protein.

2159. The method of item 2071 wherein the polymer is carbohydrate.

2160. The method of item 2071 wherein the polymer is crosslinked and biodegradable.

2161. The method of item 2071 wherein the implant comprises a fibrinogen.

2162. The method of item 2071 wherein the implant comprises a thrombin.

2163. The method of item 2071 wherein the implant comprises a calcium salt.

2164. The method of item 2071 wherein the implant comprises an antifibrinolytic agent.

2165. The method of item 2071 wherein the implant comprises a fibrinogen analog.

2166. The method of item 2071 wherein the implant comprises an albumin.

2167. The method of item 2071 wherein the implant comprises a plasminogen.

2168. The method of item 2071 wherein the implant comprises a von Willebrands factor.

2169. The method of item 2071 wherein the implant comprises a Factor VIII.

2170. The method of item 2071 wherein the implant comprises a hypoallergenic collagen.

2171. The method of item 2071 wherein the implant comprises atelopeptide collagen.

2172. The method of item 2071 wherein the implant comprises a crosslinked collagen.

2173. The method of item 2071 wherein the implant comprises an aprotinin.

2174. The method of item 2071 wherein the implant comprises an epsilon-amino-n-caproic acid.

2175. The method of item 2071 wherein the implant comprises a gelatin.

2176. The method of item 2071 wherein the implant comprises a protein conjugate.

2177. The method of item 2071 wherein the implant comprises a gelatin conjugate.

2178. The method of item 2071 wherein the implant comprises a hyaluronic acid.

2179. The method of item 2071 wherein the implant comprises a hyaluronic acid derivative.

2180. The method of item 2071 wherein the implant comprises a synthetic polymer.

2181. The method of item 2071 wherein the polymer is formed from reactants comprising a synthetic isocyanate-containing compound.

2182. The method of item 2071 wherein the implant comprises a synthetic isocyanate-containing compound.

2183. The method of item 2071 wherein the polymer is formed from reactants comprising a synthetic thiol-containing compound.

2184. The method of item 2071 wherein the implant comprises a synthetic thiol-containing compound.

2185. The method of item 2071 wherein the polymer is formed from reactants comprising a synthetic compound containing at least two thiol groups.

2186. The method of item 2071 wherein the implant comprises a synthetic compound containing at least two thiol groups.

2187. The method of item 2071 wherein the polymer is formed from reactants comprising a synthetic compound containing at least three thiol groups.

2188. The method of item 2071 wherein the implant comprises a synthetic compound containing at least three thiol groups.

2189. The method of item 2071 wherein the polymer is formed from reactants comprising a synthetic compound containing at least four thiol groups.

2190. The method of item 2071 wherein the implant comprises a synthetic compound containing at least four thiol groups.

2191. The method of item 2071 wherein the polymer is formed from reactants comprising a synthetic amino-containing compound.

2192. The method of item 2071 wherein the implant comprises a synthetic amino-containing compound.

2193. The method of item 2071 wherein the polymer is formed from reactants comprising a synthetic compound containing at least two amino groups.

2194. The method of item 2071 wherein the implant comprises a synthetic compound containing at least two amino groups.

2195. The method of item 2071 wherein the polymer is formed from reactants comprising a synthetic compound containing at least three amino groups.

2196. The method of item 2071 wherein the implant comprises a synthetic compound containing at least three amino groups.

2197. The method of item 2071 wherein the polymer is formed from reactants comprising a synthetic compound containing at least four amino groups.

2198. The method of item 2071 wherein the implant comprises a synthetic compound containing at least four amino groups.

2199. The method of item 2071 wherein the polymer is formed from reactants comprising a synthetic compound comprising a carbonyl-oxygen-succinimidyl group.

2200. The method of item 2071 wherein the implant comprises a synthetic compound comprising a carbonyl-oxygen-succinimidyl group.

2201. The method of item 2071 wherein the polymer is formed from reactants comprising a synthetic compound comprising at least two carbonyl-oxygen-succinimidyl groups.

2202. The method of item 2071 wherein the implant comprises a synthetic compound comprising at least two carbonyl-oxygen-succinimidyl groups.

2203. The method of item 2071 wherein the polymer is formed from reactants comprising a synthetic compound comprising at least three carbonyl-oxygen-succinimidyl groups.

2204. The method of item 2071 wherein the implant comprises a synthetic compound comprising at least three carbonyl-oxygen-succinimidyl groups.

2205. The method of item 2071 wherein the polymer is formed from reactants comprising a synthetic compound comprising at least four carbonyl-oxygen-succinimidyl groups.

2206. The method of item 2071 wherein the implant comprises a synthetic compound comprising at least four carbonyl-oxygen-succinimidyl groups.

2207. The method of item 2071 wherein the polymer is formed from reactants comprising a synthetic polyalkylene oxide-containing compound.

2208. The method of item 2071 wherein the implant comprises a synthetic polyalkylene oxide-containing compound.

2209. The method of item 2071 wherein the polymer is formed from reactants comprising a synthetic compound comprising both polyalkylene oxide and biodegradable polyester blocks.

2210. The method of item 2071 wherein the implant comprises a synthetic compound comprising both polyalkylene oxide and biodegradable polyester blocks.

2211. The method of item 2071 wherein the polymer is formed from reactants comprising a synthetic polyalkylene oxide-containing compound having reactive amino groups.

2212. The method of item 2071 wherein the implant comprises synthetic polyalkylene oxide-containing compound having reactive amino groups.

2213. The method of item 2071 wherein the polymer is formed from reactants comprising a synthetic polyalkylene oxide-containing compound having reactive thiol groups.

2214. The method of item 2071 wherein the implant comprises synthetic polyalkylene oxide-containing compound having reactive thiol groups.

2215. The method of item 2071 wherein the polymer is formed from reactants comprising a synthetic polyalkylene oxide-containing compound having reactive carbonyl-oxygen-succinimidyl groups.

2216. The method of item 2071 wherein the implant comprises a synthetic polyalkylene oxide-containing compound having reactive carbonyl-oxygen-succinimidyl groups.

2217. The method of item 2071 wherein the polymer is formed from reactants comprising a synthetic compound comprising a biodegradable polyester block.

2218. The method of item 2071 wherein the implant comprises a synthetic compound comprising a biodegradable polyester block.

2219. The method of item 2071 wherein the polymer is formed from reactants comprising a synthetic polymer formed in whole or part from lactic acid or lactide.

2220. The method of item 2071 wherein the implant comprises a synthetic polymer formed in whole or part from lactic acid or lactide.

2221. The method of item 2071 wherein the polymer is formed from reactants comprising a synthetic polymer formed in whole or part from glycolic acid or glycolide.

2222. The method of item 2071 wherein the implant comprises a synthetic polymer formed in whole or part from glycolic acid or glycolide.

2223. The method of item 2071 wherein the polymer is formed from reactants comprising polylysine.

2224. The method of item 2071 wherein the implant comprises polylysine.

2225. The method of item 2071 wherein the polymer is formed from reactants comprising (a) protein and (b) a compound comprising a polyalkylene oxide portion.

2226. The method of item 2071 wherein the implant comprises (a) protein and (b) a compound comprising a polyalkylene oxide portion.

2227. The method of item 2071 wherein the polymer is formed from reactants comprising (a) protein and (b) polylysine.

2228. The method of item 2071 wherein the implant comprises (a) protein and (b) polylysine.

2229. The method of item 2071 wherein the polymer is formed from reactants comprising (a) protein and (b) a compound having at least four thiol groups.

2230. The method of item 2071 wherein the implant comprises (a) protein and (b) a compound having at least four thiol groups.

2231. The method of item 2071 wherein the polymer is formed from reactants comprising (a) protein and (b) a compound having at least four amino groups.

2232. The method of item 2071 wherein the implant comprises (a) protein and (b) a compound having at least four amino groups.

2233. The method of item 2071 wherein the polymer is formed from reactants comprising (a) protein and (b) a compound having at least four carbonyl-oxygen-succinimide groups.

2234. The method of item 2071 wherein the implant comprises (a) protein and (b) a compound having at least four carbonyl-oxygen-succinimide groups.

2235. The method of item 2071 wherein the polymer is formed from reactants comprising (a) protein and (b) a compound having a biodegradable region formed from reactants selected from lactic acid, lactide, glycolic acid, glycolide, and epsilon-caprolactone.

2236. The method of item 2071 wherein the implant comprises (a) protein and (b) a compound having a biodegradable region formed from reactants selected from lactic acid, lactide, glycolic acid, glycolide, and epsilon-caprolactone.

2237. The method of item 2071 wherein the polymer is formed from reactants comprising (a) collagen and (b) a compound comprising a polyalkylene oxide portion.

2238. The method of item 2071 wherein the implant comprises (a) collagen and (b) a compound comprising a polyalkylene oxide portion.

2239. The method of item 2071 wherein the polymer is formed from reactants comprising (a) collagen and (b) polylysine.

2240. The method of item 2071 wherein the implant comprises (a) collagen and (b) polylysine.

2241. The method of item 2071 wherein the polymer is formed from reactants comprising (a) collagen and (b) a compound having at least four thiol groups.

2242. The method of item 2071 wherein the implant comprises (a) collagen and (b) a compound having at least four thiol groups.

2243. The method of item 2071 wherein the polymer is formed from reactants comprising (a) collagen and (b) a compound having at least four amino groups.

2244. The method of item 2071 wherein the implant comprises (a) collagen and (b) a compound having at least four amino groups.

2245. The method of item 2071 wherein the polymer is formed from reactants comprising (a) collagen and (b) a compound having at least four carbonyl-oxygen-succinimide groups.

2246. The method of item 2071 wherein the implant comprises (a) collagen and (b) a compound having at least four carbonyl-oxygen-succinimide groups.

2247. The method of item 2071 wherein the polymer is formed from reactants comprising (a) collagen and (b) a compound having a biodegradable region formed from reactants selected from lactic acid, lactide, glycolic acid, glycolide, and epsilon-caprolactone.

2248. The method of item 2071 wherein the implant comprises (a) collagen and (b) a compound having a biodegradable region formed from reactants selected from lactic acid, lactide, glycolic acid, glycolide, and epsilon-caprolactone.

2249. The method of item 2071 wherein the polymer is formed from reactants comprising (a) methylated collagen and (b) a compound comprising a polyalkylene oxide portion.

2250. The method of item 2071 wherein the implant comprises (a) methylated collagen and (b) a compound comprising a polyalkylene oxide portion.

2251. The method of item 2071 wherein the polymer is formed from reactants comprising (a) methylated collagen and (b) polylysine.

2252. The method of item 2071 wherein the implant comprises (a) methylated collagen and (b) polylysine.

2253. The method of item 2071 wherein the polymer is formed from reactants comprising (a) methylated collagen and (b) a compound having at least four thiol groups.

2254. The method of item 2071 wherein the implant comprises (a) methylated collagen and (b) a compound having at least four thiol groups.

2255. The method of item 2071 wherein the polymer is formed from reactants comprising (a) methylated collagen and (b) a compound having at least four amino groups.

2256. The method of item 2071 wherein the implant comprises (a) methylated collagen and (b) a compound having at least four amino groups.

2257. The method of item 2071 wherein the polymer is formed from reactants comprising (a) methylated collagen and (b) a compound having at least four carbonyl-oxygen-succinimide groups.

2258. The method of item 2071 wherein the implant comprises (a) methylated collagen and (b) a compound having at least four carbonyl-oxygen-succinimide groups.

2259. The method of item 2071 wherein the polymer is formed from reactants comprising (a) methylated collagen and (b) a compound having a biodegradable region formed from reactants selected from lactic acid, lactide, glycolic acid, glycolide, and epsilon-caprolactone.

2260. The method of item 2071 wherein the implant comprises (a) methylated collagen and (b) a compound having a biodegradable region formed from reactants selected from lactic acid, lactide, glycolic acid, glycolide, and epsilon-caprolactone.

2261. The method of item 2071 wherein the polymer is formed from reactants comprising hyaluronic acid.

2262. The method of item 2071 wherein the implant comprises hyaluronic acid.

2263. The method of item 2071 wherein the polymer is formed from reactants comprising a hyaluronic acid derivative.

2264. The method of item 2071 wherein the implant comprises a hyaluronic acid derivative.

2265. The method of item 2071 wherein the polymer is formed from reactants comprising pentaerythritol poly(ethylene glycol)ether tetra-sulfhydryl of number average molecular weight between 3,000 and 30,000.

2266. The method of item 2071 wherein the implant comprises pentaerythritol poly(ethylene glycol)ether tetra-sulfhydryl of number average molecular weight between 3,000 and 30,000.

2267. The method of item 2071 wherein the polymer is formed from reactants comprising pentaerythritol poly(ethylene glycol)ether tetra-amino of number average molecular weight between 3,000 and 30,000.

2268. The method of item 2071 wherein the implant comprises pentaerythritol poly(ethylene glycol)ether tetra-amino of number average molecular weight between 3,000 and 30,000.

2269. The method of item 2071 wherein the polymer is formed from reactants comprising (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

2270. The method of item 2071 wherein the implant comprises (a) a synthetic compound having a number average molecular weight between 3,000 and 30,000 and comprising a polyalkylene oxide region and multiple nucleophilic groups, and (b) a synthetic compound having a number average molecular weight between 3,000 and 30,000 and comprising a polyalkylene oxide region and multiple electrophilic groups.

2271. The method of item 2071 wherein the implant comprises a colorant.

2272. The method of item 2071 wherein the implant is sterile.

2273. The method of item 2071 wherein the implant further comprises an additional pharmaceutically active agent.

2274. The method of item 2071 wherein the implant further comprises an anti-inflammatory agent.

2275. The method of item 2071 wherein the anti-infective agent comprises an anthracycline.

2276. The method of item 2071 wherein the anti-infective agent comprises doxorubicin.

2277. The method of item 2071 wherein the anti-infective agent comprises mitoxantrone.

2278. The method of item 2071 wherein the anti-infective agent comprises a fluoropyrimidine.

2279. The method of item 2071 wherein the anti-infective agent comprises 5-fluorouracil (5-FU).

2280. The method of item 2071 wherein the anti-infective agent comprises a folic acid antagonist.

2281. The method of item 2071 wherein the anti-infective agent comprises methotrexate.

2282. The method of item 2071 wherein the anti-infective agent comprises a podophylotoxin.

2283. The method of item 2071 wherein the anti-infective agent comprises etoposide.

2284. The method of item 2071 wherein the anti-infective agent comprises camptothecin.

2285. The method of item 2071 wherein the anti-infective agent comprises a hydroxyurea.

2286. The method of item 2071 wherein the anti-infective agent comprises a platinum complex.

2287. The method of item 2071 wherein the anti-infective agent comprises cisplatin.

2288. The method of item 2071 wherein the anti-infective agent is an antibiotic.

2289. The method of item 2071 wherein the anti-infective agent is doxycycline.

2290. The method of item 2071 wherein the anti-infective agent is metronidazole.

2291. The method of item 2071 wherein the anti-infective agent is trimethoprim-sulfamethoxazole.

2292. The method of item 2071 wherein the anti-infective agent is a fourth generation penicillin.

2293. The method of item 2071 wherein the anti-infective agent is a fourth generation penicillin selected from a ureidopenicillin and a carboxypenicillin, or an analogue or derivative thereof.

2294. The method of item 2071 wherein the anti-infective agent is a fourth generation penicillin selected from meziocillin, piperacillin, carbenicillin, and ticarcillin.

2295. The method of item 2071 wherein the anti-infective agent is a first generation cephalosporin.

2296. The method of item 2071 wherein the anti-infective agent is a first generation cephalosporin selected from cephazolin sodium, cephalexin, cefazolin, cephapirin, and cephalothin.

2297. The method of item 2071 wherein the anti-infective agent is a carboxypenicillin.

2298. The method according to item 2297 wherein the carboxypenicillin is ticarcillin.

2299. The method of item 2071 wherein the anti-infective agent is a second generation cephalosporin.

2300. The method of item 2071 wherein the anti-infective agent is a second generation cephalosporin selected from cefuroxime, cefotetan, and cefoxitin.

2301. The method of item 2071 wherein the anti-infective agent is a third generation cephalosporin.

2302. The method of item 2071 wherein the anti-infective agent is a third generation cephalosporin selected from naxcel, Cefdinir, cefoperazone, ceftazidime, ceftriaxone, and cefotaxime.

2303. The method of item 2071 wherein the anti-infective agent is a fourth generation cephalosporin.

2304. The method of item 2303 wherein the fourth generation cephalosporin is cefepime.

2305. The method of item 2071 wherein the anti-infective agent is a monobactam.

2306. The method of item 2305 wherein the monobactam is aztreonam.

2307. The method of item 2071 wherein the anti-infective agent is a carbapenem.

2308. The method of item 2071 wherein the anti-infective agent is a carbapenem selected from imipenem, ertapenem and meropenem.

2309. The method of item 2071 wherein the anti-infective agent is an aminoglycoside.

2310. The method of item 2071 wherein the anti-infective agent is an aminoglycoside selected from streptomycin, gentamicin, tobramycin, and amikacin.

2311. The method of item 2071 wherein the anti-infective agent is an MSL group member selected from a macrolide, a long acting macrolide, a lincosamide, and a streptogramin.

2312. The method of item 2071 wherein the anti-infective agent is an MSL group member selected from Erythromycin, Azithromycin, Clindamycin, Syneroid, clarithromycin, and kanamycin sulfate.

2313. The method of item 2071 wherein the anti-infective agent is a quinolone.

2314. The method of item 2071 wherein the anti-infective agent is a quinolone selected from ciprofloxacin, ofloxacin, gatifloxacin, moxifloxacin, levofloxacin, and trovafloxacin.

2315. The method of item 2071 wherein the anti-infective agent is a DNA synthesis inhibitor.

2316. The method of item 2315 wherein the DNA synthesis inhibitor is metronidazole.

2317. The method of item 2071 wherein the anti-infective agent is a sulfonamide.

2318. The method of item 2317 wherein the sulfonamide is trimethoprim.

2319. The method of item 2071 the anti-infective agent is selected from cefixime, spectinomycin, tetracycline, nitrofurantoin, polymyxin B, and neomycin sulfate.

2320. The method of item 2071 wherein the anti-infective agent is gentamicin sulfate.

2321. The method of item 2071 wherein the anti-infective agent is amikacin sulfate.

2322. The method of item 2071 wherein the anti-infective agent is kanamycin sulfate.

2323. The method of item 2071 wherein the anti-infective agent is polymyxin B.

2324. The method of item 2071 wherein the anti-infective agent is neomycin sulfate.

2325. The method of item 2071 wherein the anti-infective agent is cephazolin sodium.

2326. The method of item 2071 wherein the anti-infective agent is ciprofloxain.

2327. The method of item 2071 wherein the anti-infective agent is piperacillin.

2328. The method of item 2071 wherein the anti-infective agent is cefoxitin.

2329. The method of item 2071 wherein the anti-infective agent is cefepime.

2330. The method of item 2071 wherein the anti-infective agent is azithromycin.

2331. The method of item 2071 wherein the implant further comprises a visualization agent.

2332. The method of item 2071 wherein the implant further comprises a visualization agent, and the visualization agent is a radiopaque material, wherein the radiopaque material comprises a metal, a halogenated compound, or a barium-containing compound.

2333. The method of item 2071 wherein the implant further comprises a visualization agent, and the visualization agent is, or comprises, barium, tantalum, or technetium.

2334. The method of item 2071 wherein the implant further comprises a visualization agent, and the visualization agent is, or comprises, an MRI responsive material or an echogenic material.

2335. The method of item 2071 wherein the implant further comprises a visualization agent, and the visualization agent is, or comprises, a gadolinium chelate.

2336. The method of item 2071 wherein the implant further comprises a visualization agent, and the visualization agent is, or comprises, iron, magnesium, manganese, copper, or chromium.

2337. The method of item 2071 wherein the implant further comprises a visualization agent, and the visualization agent is, or comprises, iron oxide compound.

2338. The method of item 2071 wherein the implant further comprises a visualization agent, and the visualization agent is, or comprises, a dye, pigment, or colorant.

2339. The method of item 2071 wherein the implant further comprises an inflammatory cytokine.

2340. The method of item 2071 wherein the implant further comprises an agent that stimulates cell proliferation.

2341. The method of item 2071 wherein the implant further comprises an agent that stimulates cell proliferation, wherein the proliferative agent is selected from the group consisting of dexamethasone, isotretinoin, 17-β-estradiol, estradiol, diethylstibesterol, cyclosporine A, all-trans retinoic acid (ATRA), and analogues and derivatives thereof.

2342. The method of item 2071 wherein the implant further comprises a polymeric carrier.

2343. The method of item 2071 wherein the implant is in the form of a gel, paste, or spray.

2344. The method of item 2071 wherein the implant is in the form of a mesh or film.

2345. The method of item 2071 wherein the implant is injected or sprayed into the diverticulum.

2346. The method of item 2071 wherein the implant injected or sprayed onto a tissue or into a tissue surrounding the diverticulum.

2347. The method of item 2071 wherein the implant further comprises a bulking agent.

2348. The method of item 2071 wherein the bulking agent is a sealant.

2349. The method of item 2071 wherein the bulking agent is a haemostatic agent.

2350. The method of item 2071 wherein the implant further comprises a bulking agent, wherein the bulking agent comprises microspheres.

2351. The method of item 2071 wherein the implant further comprises a bulking agent, wherein the bulking agent comprises a hydroxyapatite loaded gel.

2352. The method of item 2071 wherein the implant further comprises a bulking agent, wherein the bulking agent comprises a micronized alloderm acellular matrix.

2353. The method of item 2071 wherein the implant further comprises a bulking agent, wherein the bulking agent comprises hyaluronic acid.

2354. The method of item 2071 wherein the implant further comprises a bulking agent, wherein the bulking agent comprises micro-beads in a hydrogel.

2355. The method of item 2071 wherein the implant further comprises a bulking agent, wherein the bulking agent comprises a hylan polymer.

2356. The method of item 2071 wherein the implant further comprises a bulking agent, wherein the bulking agent comprises a silicon microballoon and biocompatible polymer.

2357. A kit for use in treating a diverticular disease, comprising: (a) a dry powder composition that comprises (i) a first component having a core substituted with m nucleophilic groups, where $m \geq 2$ and (ii) a second component having a core substituted with n electrophilic groups, where $n \geq 2$ and $m+n \geq 4$; wherein the nucleophilic and electrophilic groups are non-reactive in a dry environment but are rendered reactive upon exposure to an aqueous environment such that the componenets inter-react in the aqueous environment to form a three-dimensional composition; (b) a first buffer solution having a pH within the range of about 1.0 to 5.5; and (c) a second buffer solution having a pH within the range of about 6.0 to 11.0; and (d) a third component comprising a fibrosing agent, wherein each component is packaged separately and admixed immediately prior to use.

2358. The kit of item 2357, wherein prior to use, each component is in a separate sterile package.

2359. The kit of item 2357, further comprising a delivery device.

2360. The kit of item 2359, wherein the delivery device is a multi-component device.

2361. The kit of item 2360 wherein the device is configured to deliver the composition in the form of a spray.

2362. The kit of item 2360 wherein the device is configured to deliver the composition in the form of a gel or paste.

2363. The kit of item 2361, wherein the multi-component spray device is a multiple-compartment syringe system having multiple barrels, a mixing head, and an exit orifice.

2364. The kit of item 2357, further comprising a delivery catheter.

2365. The kit of item 2357, further comprising a delivery catheter, wherein the catheter is configured to deliver the composition to a diverticulum in a host.

2366. The kit of item 2363, wherein the dry powder composition, the first buffer solution, the second buffer solution, and the fibrosing agent are housed separately in the multiple-compartment syringe system.

2367. The kit of item 2359, wherein the delivery device is a pressurized delivery device.

2368. The kit of item 2367 wherein the pressurized delivery device comprises: (a) a plurality of fluid component inlets each adapted to communicate with a source of different fluid components; (b) at least one carrier fluid inlet adapted to communicate with a source of a pressurized carrier fluid; (c) a diffuser surface located downstream from the plurality of fluid component inlets and the at least one carrier fluid inlet; and (d) an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet.

2369. The kit of item 2368, wherein the pressurized carrier fluid is pressurized air.

2370. The kit of item 2368, wherein the fluid components are the first buffer solution and the second buffer solution.

2371. The kit of item 2357, wherein the fibrosing agent is packaged with the dry powder composition.

2372. The kit of item 2371, further comprising a pharmaceutically acceptable carrier packaged with the fibrosing agent and the dry powder composition.

2373. The kit of item 2357, wherein the fibrosing agent is packaged as a solution with the first buffer.

2374. The kit of item 2357, wherein the fibrosing agent is packaged as a solution with the second buffer.

2375. The kit of item 2357, further comprising a pharmaceutically acceptable carrier as a fourth component.

2376. The kit of item 2375, wherein the fibrosing agent is packaged with the pharmaceutically acceptable carrier.

2377. The kit of item 2357 wherein the fibrosing agent promotes regeneration.

2378. The kit of item 2357 wherein the fibrosing agent promotes fibrosis and promotes regeneration.

2379. The kit of item 2357 wherein the fibrosing agent promotes angiogenesis.

2380. The kit of item 2357 wherein the fibrosing agent promotes fibroblast migration.

2381. The kit of item 2357 wherein the fibrosing agent promotes fibroblast proliferation.

2382. The kit of item 2357 wherein the fibrosing agent promotes deposition of extracellular matrix (ECM).

2383. The kit of item 2357 wherein the fibrosing agent promotes tissue remodeling.

2384. The kit of item 2357 wherein the fibrosing agent is a diverticular wall irritant.

2385. The kit of item 2357 wherein the fibrosing agent is or comprises silk.

2386. The kit of item 2357 wherein the fibrosing agent is or comprises silkworm silk.

2387. The kit of item 2357 wherein the fibrosing agent is or comprises spider silk.

2388. The kit of item 2357 wherein the fibrosing agent is or comprises recombinant silk.

2389. The kit of item 2357 wherein the fibrosing agent is or comprises raw silk.

2390. The kit of item 2357 wherein the fibrosing agent is or comprises hydrolyzed silk.

2391. The kit of item 2357 wherein the fibrosing agent is or comprises acid-treated silk.

2392. The kit of item 2357 wherein the fibrosing agent is or comprises acylated silk.

2393. The kit of item 2357 wherein the fibrosing agent is in the form of strands.

2394. The kit of item 2357 wherein the fibrosing agent is in the form of tufts.

2395. The kit of item 2357 wherein the fibrosing agent is or comprises mineral particles.

2396. The kit of item 2357 wherein the fibrosing agent is or comprises chitosan.

2397. The kit of item 2357 wherein the fibrosing agent is or comprises polylysine.

2398. The kit of item 2357 wherein the fibrosing agent is or comprises fibronectin.

2399. The kit of item 2357 wherein the fibrosing agent is or comprises bleomycin.

2400. The kit of item 2357 wherein the fibrosing agent is or comprises CTGF.

2401. The kit of item 2357 wherein the fibrosing agent is or comprises a wool.

2402. The kit of item 2357 wherein the fibrosing agent is or comprises an animal wool.

2403. The kit of item 2357 wherein the fibrosing agent is or comprises a wood wool.

2404. The kit of item 2357 wherein the fibrosing agent is or comprises a synthetic wool.

2405. The kit of item 2357 wherein the fibrosing agent is in the form of a thread, or is in contact with a thread.

2406. The kit of item 2405 wherein the thread is biodegradable.

2407. The kit of item 2406 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

2408. The kit of item 2405 wherein the thread is non-biodegradable.

2409. The kit of item 2408 wherein the non-biodegradable thread comprises a material selected from the group consisting of polyester, polyurethane, silicone, polyethylene, polypropylene, polystyrene, polyacrylate, polymethacrylate, and silk.

2410. The kit of item 2405 wherein the thread is coated with a polymer.

2411. The kit of item 2405 wherein the thread is coated with a pharmaceutical agent that induces a fibrotic response in the host.

2412. The kit of item 2357 wherein the fibrosing agent is in the form of a particulate.

2413. The kit of item 2412 wherein the particulate is a biodegradable particulate.

2414. The kit of item 2413 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

2415. The kit of item 2412 wherein the particulate is a non-biodegradable particulate.

2416. The kit of item 2415 wherein the non-biodegradable particulate comprises a material selected from the group consisting of polyester, polyurethane, silicone, polyethylene, polypropylene, polystyrene, polyacrylate, polymethacrylate, and silk.

2417. The kit of item 2412 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

2418. The kit of item 2412 wherein the particulate is coated with a polymer.

2419. The kit of item 2412 wherein the particulate is coated with a pharmaceutical agent that induces a fibrotic response in the host.

2420. The kit of item 2412 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

2421. The kit of item 2357 wherein the third component further comprises a growth factor.

2422. The kit of item 2421 wherein the growth factor is selected from a transforming growth factor, a platelet-derived growth factor, and a fibroblast growth factor.

2423. A method of treating a diverticular disease, comprising introducing into a diverticulum in a host, a therapeutically effective amount of a fibrosing agent or a composition comprising a fibrosing agent, wherein the fibrosing agent is silk, and wherein the fibrosing agent induces a fibrotic response within the diverticulum, thereby treating diverticular disease in the host.

2424. A method of treating a diverticular disease, comprising introducing into a diverticulum in a host, a therapeutically effective amount of a fibrosing agent or a composition comprising a fibrosing agent, wherein the fibrosing agent is wool, and wherein the fibrosing agent induces a fibrotic response within the diverticulum, thereby treating diverticular disease in the host.

2425. A method of treating a diverticular disease, comprising introducing into a diverticulum in a host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer is CT3, wherein the fibrosing agent induces a fibrotic response within the diverticulum, thereby treating diverticular disease in the host.

2426. A method of treating a diverticular disease, comprising introducing into a diverticulum in a host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer COSTASIS, wherein the fibrosing agent induces a fibrotic response within the diverticulum, thereby treating diverticular disease in the host.

2427. A method of treating a diverticular disease, comprising introducing into a diverticulum in a host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer is a cyanoacrylate, wherein the fibrosing agent induces a fibrotic response within the diverticulum, thereby treating diverticular disease in the host.

2428. A method of treating a diverticular disease, comprising introducing into a diverticulum in a host, (a) a therapeutically effective amount of a fibrosing agent or a composition comprising a fibrosing agent, wherein the fibrosing agent is wool; and (b) a polymer or a compound that polymerizes to form a crosslinked polymer in situ, wherein the polymer is CT3, wherein the fibrosing agent induces a fibrotic response within the diverticulum, thereby treating diverticular disease in the host.

2429. A method of treating a diverticular disease, comprising introducing into a diverticulum in a host, (a) a therapeutically effective amount of a fibrosing agent or a composition comprising a fibrosing agent, wherein the fibrosing agent is wool; and (b) a polymer or a compound that polymerizes to form a crosslinked polymer in situ, wherein the polymer is COSTASIS, wherein the fibrosing agent induces a fibrotic response within the diverticulum, thereby treating diverticular disease in the host.

2430. A method of treating a diverticular disease, comprising introducing into a diverticulum in a host, (a) a therapeutically effective amount of a fibrosing agent or a composition comprising a fibrosing agent, wherein the fibrosing agent wool; and (b) a polymer or a compound that polymerizes to form a crosslinked polymer in situ, wherein the polymer is a cyanoacrylate, wherein the fibrosing agent induces a fibrotic response within the diverticulum, thereby treating diverticular disease in the host.

2431. The method of any one of items 2423–2430 further comprising introducing into the host an anti-infective agent.

2432. The method of item 2431 wherein the anti-infective agent is 5-fluorouracil.

2433. The method of 2431 wherein the anti-infective agent is an antibiotic.

2434. The method of item 2433 wherein the antibiotic is gentamicin sulfate.

2435. The method of item 2433 wherein the antibiotic is amikacin sulfate.

2436. The method of item 2433 wherein the antibiotic is kanamycin sulfate.

2437. The method of item 2433 wherein the antibiotic is polymyxin B.

2438. The method of item 2433 wherein the antibiotic is neomycin sulfate.

2439. The method of item 2433 wherein the antibiotic is cephazolin sodium.

2440. The method of item 2433 wherein the antibiotic is metronidazole.

2441. The method of item 2433 wherein the antibiotic is ciprofloxacin.

2442. The method of item 2433 wherein the antibiotic is piperacillin.

2443. The method of item 2433 wherein the antibiotic is cefoxitin.

2444. The method of item 2433 wherein the antibiotic is cefepime.

2445. The method of item 2433 wherein the antibiotic is azithromycin.

2446. The method of item 2433 wherein the antibiotic is trimethoprim-sulfamethoxazole.

2447. The method of any one of items 2423–2430 wherein the diverticular disease is diverticulosis.

2448. The method of any one of items 2423–2430 wherein the diverticular disease is diverticulitis.

2449. A method for inducing fibrosis in a diverticulum of a host in need thereof, comprising introducing a composition into the diverticulum of the host, said composition comprising a fibrosing agent, wherein the fibrosing agent is silk, and wherein the agent induces fibrosis within the diverticulum.

2450. A method for inducing fibrosis in a diverticulum of a host in need thereof, comprising introducing a composition into the diverticulum of the host, said composition comprising a fibrosing agent, wherein the fibrosing agent is wool, and wherein the agent induces fibrosis within the diverticulum.

2451. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer is CT3; wherein the fibrosing agent induces a fibrotic response within the diverticulum, thereby treating diverticular disease in the host.

2452. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer is COSTASIS; wherein the fibrosing agent induces a fibrotic response within the diverticulum, thereby treating diverticular disease in the host.

2453. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is silk; and (b) a polymer or a compound that polymerizes to form a crosslinked polymer in situ, wherein the polymer a cyanoacrylate, wherein the fibrosing agent induces a fibrotic response within the diverticulum, thereby treating diverticular disease in the host.

2454. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is wool; and (b) a polymer or a compound that polymerizes to form a crosslinked polymer in situ, wherein the polymer is CT3; wherein the fibrosing agent induces a fibrotic response within the diverticulum, thereby treating diverticular disease in the host.

2455. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is wool; and (b) a polymer or a compound that polymerizes to form a crosslinked polymer in situ, wherein the polymer is COSTASIS; wherein the fibrosing agent induces a fibrotic response within the diverticulum, thereby treating diverticular disease in the host.

2456. A method for inducing fibrosis in a diverticulum of a host in need thereof, comprising introducing into a diverticulum in the host, (a) a therapeutically effective amount of a fibrosing agent or a composition comprising a fibrosing agent, wherein the fibrosing agent is wool; and (b) a polymer or a compound that polymerizes to form a crosslinked polymer in situ, wherein the polymer is a cyanoacrylate, wherein the fibrosing agent induces a fibrotic response within the diverticulum, thereby treating diverticular disease in the host.

2457. The method of any one of items 2449–2456 further comprising introducing into the host an anti-infective agent.

2458. The method of item 2457 wherein the anti-infective agent is 5-fluorouracil.

2459. The method of 2457 wherein the anti-infective agent is an antibiotic.

2460. The method of item 2459 wherein the antibiotic is gentamicin sulfate.

2461. The method of item 2459 wherein the antibiotic is amikacin sulfate.

2462. The method of item 2459 wherein the antibiotic is kanamycin sulfate.

2463. The method of item 2459 wherein the antibiotic is polymyxin B.

2464. The method of item 2459 wherein the antibiotic is neomycin sulfate.

2465. The method of item 2459 wherein the antibiotic is cephazolin sodium.

2466. The method of item 2459 wherein the antibiotic is metronidazole.

2467. The method of item 2459 wherein the antibiotic is ciprofloxacin.

2468. The method of item 2459 wherein the antibiotic is piperacillin.

2469. The method of item 2459 wherein the antibiotic is cefoxitin.

2470. The method of item 2459 wherein the antibiotic is cefepime.

2471. The method of item 2459 wherein the antibiotic is azithromycin.

2472. The method of item 2459 wherein the antibiotic is trimethoprim-sulfamethoxazole.

2473. The method of any one of items 2449–2456 wherein inducing fibrosis within the diverticulum treats or presents a diverticular disease.

2474. The method of item 2473 wherein the diverticular disease is diverticulosis.

2475. The method of item 2473 wherein the diverticular disease is diverticulitis.

2476. A composition comprising silk and CT3.

2477. A composition comprising silk and COSTASIS.

2478. A composition comprising silk and a cyanoacrylate.

2479. A composition comprising wool and CT3.

2480. A composition comprising wool and COSTASIS.

2481. A composition comprising wool and a cyanoacrylate.

2482. The composition of any one of items 2476–2481 further comprising an anti-infective agent.

2483. The composition of item 2482 wherein the anti-infective agent is 5-fluorouracil.

2484. The composition of item 2482 wherein the anti-infective agent is an antibiotic.

2485. The composition of item 2484 wherein the antibiotic is gentamicin sulfate.

2486. The composition of item 2484 wherein the antibiotic is amikacin sulfate.

2487. The composition of item 2484 wherein the antibiotic is kanamycin sulfate.

2488. The composition of item 2484 wherein the antibiotic is polymyxin B.

2489. The composition of item 2484 wherein the antibiotic is neomycin sulfate.

2490. The composition of item 2484 wherein the antibiotic is cephazolin sodium.

2491. The composition of item 2484 wherein the antibiotic is metronidazole.

2492. The composition of item 2484 wherein the antibiotic is ciprofloxacin.

2493. The composition of item 2484 wherein the antibiotic is piperacillin.

2494. The composition of item 2484 wherein the antibiotic is cefoxitin.

2495. The composition of item 2484 wherein the antibiotic is cefepime.

2496. The composition of item 2484 wherein the antibiotic is azithromycin.

2497. The composition of item 2484 wherein the antibiotic is trimethoprim-sulfamethoxazole.

2498. An implant comprising silk and CT3.

2499. An implant comprising silk and COSTASIS.

2500. An implant comprising silk and a cyanoacrylate.

2501. An implant comprising wool and CT3.

2502. An implant comprising wool and COSTASIS.

2503. An implant comprising wool and a cyanoacrylate.

2504. The implant of any one of items 2498–2503 further comprising an anti-infective agent.

2505. The implant of item 2504 wherein the anti-infective agent is 5-fluorouracil.

2506. The implant of item 2504 wherein the anti-infective agent is an antibiotic.

2507. The implant of item 2506 wherein the antibiotic is gentamicin sulfate.

2508. The implant of item 2506 wherein the antibiotic is amikacin sulfate.

2509. The implant of item 2506 wherein the antibiotic is kanamycin sulfate.

2510. The implant of item 2506 wherein the antibiotic is polymyxin B.

2511. The implant of item 2506 wherein the antibiotic is neomycin sulfate.

2512. The implant of item 2506 wherein the antibiotic is cephazolin sodium.

2513. The implant of item 2506 wherein the antibiotic is metronidazole.

2514. The implant of item 2506 wherein the antibiotic is ciprofloxacin.

2515. The implant of item 2506 wherein the antibiotic is piperacillin.

2516. The implant of item 2506 wherein the antibiotic is cefoxitin.

2517. The implant of item 2506 wherein the antibiotic is cefepime.

2518. The implant of item 2506 wherein the antibiotic is azithromycin.

2519. The implant of item 2506 wherein the antibiotic is trimethoprim-sulfamethoxazole.

2520. A composition comprising a fibrosing agent, for use in a method for treating a diverticular disease, wherein the composition is introduced into a diverticulum, and wherein the fibrosing agent induces a fibrotic response within the diverticulum.

2521. A composition comprising a fibrosing agent for inducing fibrosis in a diverticulum, wherein the composition is formulated for being introduced into the diverticulum.

2522. The composition of item 2520 wherein the diverticular disease is diverticulosis or diverticulitis.

2523. The composition of either item 2520 or item 2521 wherein the fibrosing agent has at least one biological activity selected from promoting regeneration, promoting angiogenesis, promoting fibroblast proliferation, promoting deposition of extracellular matrix, promoting tissue remodeling, and promoting arterial vessel wall irritant.

2524. The composition of either item 2520 or item 2521, wherein the fibrosing agent comprises silk or wool.

2525. The composition of either item 2520 or item 2521, wherein the fibrosing agent comprises a mineral particle, chitosan, polylysine, fibronectin, bleomycin, or CTGF.

2526. The composition of either item 2520 or item 2521, wherein the fibrosing agent is (a) in the form of tufts; (b) in the form of a thread or in contact with a thread; or (c) in the form of a particulate.

2527. The composition of either item 2520 or item 2521 further comprising a polymer, or a compound that polymerizes to form a crosslinked polymer in situ.

2528. The composition according to item 2527 wherein the polymer is selected from a copolymer, a block copolymer, a random copolymer, a biodegradable copolymer, a non-biodegradable polymer, a hydrophilic polymer, a hydrophobic polymer, a polymer having hydrophilic domains, a polymer having hydrophobic domains, a non-conductive polymer, and an elastomer.

2529. The composition according to item 2527 wherein the polymer is selected from a hydrogel, a silicone polymer, a hydrocarbon polymer, a styrene-derived polymer, a butadiene-derived polymer, a macromer, and a poly(ethylene glycol).

2530. The composition of either item 2520 or item 2521 further comprising a polymer composition, wherein the polymer composition comprises at least one of (a) a collagen or a derivative thereof; (b) a fibrinogen; and (c) a thrombin.

2531. The composition of item 2527 wherein the polymer is selected from (a) a cyanoacrylate; (b) COSTASIS; and (c) CT3.

2532. The composition according to item 2531 wherein the cyanoacrylate is selected from methyl cyanoacrylate, ethyl cyanoacrylate, butyl cyanoacrylate, octyl cyanoacrylate, and methoxypropyl cyanoacrylate.

2533. The composition according to item 2531 wherein the cyanoacrylate is a poly(alkylcyanoacrylate) selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

2534. The composition according to item 2531 wherein the cyanoacrylate is a poly(carboxyalkylcyanoacrylate).

2535. The composition according to item 2535 wherein the poly(carboxyalkylcyanoacrylate) is poly(methoxypropylcyanoacrylate).

2536. The composition of either item 2520 or item 2521 wherein the composition further comprises a hemostatic agent.

2537. The composition of item 2536 wherein the hemostatic agent is selected from a collagen polymer, a poly (ethylene glycol), COSEAL, TISSEAL, FLOSEAL, and fibrin.

2538. The composition of either item 2520 or item 2521 further comprising an anti-infective agent.

2539. The composition of item 2538 wherein the anti-infective agent is selected from anthracycline, doxorubicin, mitoxantrone fluoropyrimidine, 5-fluroouracil, a folic acid antagonist, methotrexate, podophylotoxin, an etoposide, a camptothecin, a hydroxyurea, a platinum complex, and cisplatin.

2540. The composition of item 2538 wherein the anti-infective agent is an antibiotic.

2541. The composition of item 2540 wherein the antibiotic is selected from gentamicin sulfate, amikacin sulfate, kanamycin sulfate, polymyxin B, neomycin sulfate, cephazolin sodium, metronidazole, ciprofloxacin, piperacillin, cefoxitin, cefepime, azithromycin, and trimethoprim-sulfamethoxazole.

2542. The composition according to item 2520 or item 2521 further comprising a visualization agent.

2543. The composition according to item 2542 wherein the visualization agent is a radiopaque material, an echogenic material, or an MRI responsive material.

2544. The composition according to item 2520 or item 2521 wherein the composition is in the form of a spray, gel, paste, film, or mesh.

2545. A use of a composition comprising a fibrosing agent in the manufacture of a medicament for the treatment of a diverticular disease, wherein the medicament is to be introduced into a diverticulum, and wherein the medicament induces fibrosis within the diverticulum.

2546. A use of a composition comprising a fibrosing agent in the manufacture of a medicament for inducing fibrosis in a diverticulum, wherein the medicament is to be introduced into the diverticulum.

2547. The use according to either item 2545 or item 2546 wherein inducing fibrosis in a diverticulum treats or prevents a diverticular disease.

2548. The use according to item 2547 wherein the diverticular disease is diverticulitis or diverticulosis.

2549. The use according to either item 2545 or item 2546 wherein the fibrosing agent has at least one biological activity selected from promoting regeneration, promoting angiogenesis, promoting fibroblast proliferation, promoting deposition of extracellular matrix, promoting tissue remodeling, and promoting arterial vessel wall irritant.

2550. The use according to either item 2545 or item 2546, wherein the fibrosing agent comprises silk or wool.

2551. The use according to either item 2545 or item 2546, wherein the fibrosing agent comprises a mineral particle, chitosan, polylysine, fibronectin, bleomycin, or CTGF.

2552. The use according to either item 2545 or item 2546, wherein the fibrosing agent is (a) in the form of tufts; (b) in the form of a thread or in contact with a thread; or (c) in the form of a particulate.

2553. The use according to either item 2545 or item 2546 wherein the composition further comprises a polymer, or a compound that polymerizes to form a crosslinked polymer in situ.

2554. The use according to item 2553 wherein the polymer is selected from a copolymer, a block copolymer, a random copolymer, a biodegradable copolymer, a nonbiodegradable polymer, a hydrophilic polymer, a hydrophobic polymer, a polymer having hydrophilic domains, a polymer having hydrophobic domains, a non-conductive polymer, and an elastomer.

2555. The use according to item 2553 wherein the polymer is selected from a hydrogel, a silicone polymer, a hydrocarbon polymer, a styrene-derived polymer, a butadiene-derived polymer, a macromer, and a poly(ethylene glycol).

2556. The use according to either item 2545 or item 2546 wherein the composition further comprises a polymer composition, wherein the polymer composition comprises at least one of (a) a collagen or a derivative thereof; (b) a fibrinogen; and (c) a thrombin.

2557. The use according to item 2553 wherein the polymer is selected from (a) a cyanoacrylate; (b) COSTASIS; and (c) CT3.

2558. The use according to item 2557 wherein the cyanoacrylate is selected from methyl cyanoacrylate, ethyl cyanoacrylate, butyl cyanoacrylate, octyl cyanoacrylate, and methoxypropyl cyanoacrylate.

2559. The use according to item 2557 wherein the cyanoacrylate is a poly(alkylcyanoacrylate) selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

2560. The use according to item 2557 wherein the cyanoacrylate is a poly(carboxyalkylcyanoacrylate).

2561. The use according to item 2560 wherein the poly(carboxyalkylcyanoacrylate) is poly(methoxypropylcyanoacrylate).

2562. The use according to either item 2545 or item 2546 wherein the composition further comprises a hemostatic agent.

2563. The use of item 2562 wherein the hemostatic agent is selected from a collagen polymer, a poly(ethylene glycol), COSEAL, TISSEAL, FLOSEAL, and fibrin.

2564. The use according to either item 2545 or item 2546 wherein the composition further comprises an anti-infective agent.

2565. The use according to item 2564 wherein the anti-infective agent is selected from anthracycline, doxorubicin, mitoxantrone fluoropyrimidine, 5-fluroouracil, a folic acid antagonist, methotrexate, podophylotoxin, an etoposide, a camptothecin, a hydroxyurea, a platinum complex, and cisplatin.

2566. The use according to item 2564 wherein the anti-infective agent is an antibiotic.

2567. The use according to item 2567 wherein the antibiotic is selected from gentamicin sulfate, amikacin sulfate, kanamycin sulfate, polymyxin B, neomycin sulfate, cephazolin sodium, metronidazole, ciprofloxacin, piperacillin, cefoxitin, cefepime, azithromycin, and trimethoprim-sulfamethoxazole.

2568. The use according to either item 2545 or item 2546 wherein the composition further comprises a visualization agent.

2569. The use according to item 2568 wherein the visualization agent is a radiopaque material, an echogenic material, or an MRI responsive material.

2570. The use according to either item 2545 or item 2546 wherein the composition is in the form of a spray, gel, paste, film, or mesh.

2571. A composition comprising (a) a fibrosing agent and (b) a polymer or a compound that polymerizes to form a crosslinked polymer in situ.

2572. The composition according to item 2571 wherein the fibrosing agent has at least one biological activity selected from promoting regeneration, promoting angiogenesis, promoting fibroblast proliferation, promoting deposition of extracellular matrix, promoting tissue remodeling, and promoting arterial vessel wall irritant.

2573. The composition according to item 2571 wherein the fibrosing agent comprises silk or wool.

2574. The composition according to item 2571 wherein the fibrosing agent comprises a mineral particle, chitosan, polylysine, fibronectin, bleomycin, or CTGF.

2575. The composition according to item 2571 wherein the fibrosing agent is (a) in the form of tufts; (b) in the form of a thread or in contact with a thread; or (c) in the form of a particulate.

2576. The composition according to item 2571 wherein the polymer is selected from a copolymer, a block copolymer, a random copolymer, a biodegradable copolymer, a non-biodegradable polymer, a hydrophilic polymer, a hydrophobic polymer, a polymer having hydrophilic domains, a polymer having hydrophobic domains, a non-conductive polymer, and an elastomer.

2577. The composition according to item 2571 wherein the polymer is selected from a hydrogel, a silicone polymer, a hydrocarbon polymer, a styrene-derived polymer, a butadiene-derived polymer, a macromer, and a poly(ethylene glycol).

2578. The composition according to item 2571 wherein the polymer composition comprises at least one of (a) a collagen or a derivative thereof; (b) a fibrinogen; and (c) a thrombin.

2579. The composition according to item 2578 wherein the collagen is a methylated collagen.

2580. The composition according to item 2571 wherein the polymer is selected from (a) a cyanoacrylate; (b) COSTASIS; and (c) CT3.

2581. The composition according to item 2580 wherein the cyanoacrylate is selected from methyl cyanoacrylate, ethyl cyanoacrylate, butyl cyanoacrylate, octyl cyanoacrylate, and methoxypropyl cyanoacrylate.

2582. The composition according to item 2580 wherein the cyanoacrylate is a poly(alkylcyanoacrylate) selected from poly(methylcyanoacrylate) poly(ethylcyanoacrylate), poly(butylcyanoacrylate), poly(isobutylcyanoacrylate), poly(hexylcyanoacrylate), and poly(octylcyanoacrylate).

2583. The composition according to item 2580 wherein the cyanoacrylate is a poly(carboxyalkylcyanoacrylate).

2584. The composition according to item 2583 wherein the poly(carboxyalkylcyanoacrylate) is poly(methoxypropylcyanoacrylate).

2585. The composition according to item 2571 wherein the composition further comprises a hemostatic agent.

2586. The composition according to item 2585 wherein the hemostatic agent is selected from a collagen polymer, a poly(ethylene glycol), COSEAL, TISSEAL, FLOSEAL, and fibrin.

2587. The composition according to item 2571 wherein the composition further comprises an anti-infective agent.

2588. The composition according to item 2587 wherein the anti-infective agent is selected from anthracycline, doxorubicin, mitoxantrone fluoropyrimidine, 5-fluroouracil, a folic acid antagonist, methotrexate, podophylotoxin, an etoposide, a camptothecin, a hydroxyurea, a platinum complex, and cisplatin.

2589. The composition according to item 2587 wherein the anti-infective agent is an antibiotic.

2590. The composition according to item 2589 wherein the antibiotic is selected from gentamicin sulfate, amikacin sulfate, kanamycin sulfate, polymyxin B, neomycin sulfate, cephazolin sodium, metronidazole, ciprofloxacin, piperacillin, cefoxitin, cefepime, azithromycin, and trimethoprim-sulfamethoxazole.

2591. The composition according to item 2571 further comprising a bulking agent.

2592. The composition according to item 2591 wherein the bulking agent comprises microspheres, a hydroxyapatite loaded gel, micronized alloderm acellular matrix, hyaluronic acid, micro-beads in a hydrogel, a hylan polymer, a silicon microballoon and biocompatible polymer.

2593. The composition according to item 2571 further comprising a visualization agent.

2594. The composition according to item 2593 wherein the visualization agent is a radiopaque material, an echogenic material, or an MRI responsive material.

2595. The composition according to item 2571 wherein the composition is in the form of a spray, gel, paste, film, or mesh.

2596. A kit for use in treating a diverticular disease, comprising: (a) a dry powder composition that comprises (i) a first component having a core substituted with m nucleophilic groups, where $m \geq 2$ and (ii) a second component having a core substituted with n electrophilic groups, where $n \geq 2$ and $m+n \geq 4$; wherein the nucleophilic and electrophilic groups are non-reactive in a dry environment but are rendered reactive upon exposure to an aqueous environment such that the components inter-react in the aqueous environment to form a three-dimensional composition; (b) a first buffer solution having a pH within the range of about 1.0 to 5.5; and (c) a second buffer solution having a pH within the range of about 6.0 to 11.0; and (d) a third component comprising a fibrosing agent, wherein each component is packaged separately and admixed immediately prior to use.

2597. The kit of item 2596, further comprising a delivery device.

2598. The kit of item 2597 wherein the device is configured to deliver the composition in the form of a spray, a gel, or a paste.

2599. The kit of item 2596 wherein the fibrosing agent is, or comprises, silk or wool.

2600. The kit of item 2596 wherein the third component is included in (a), (b), or (c).

The following examples are offered by way of illustration, and not by way of limitation.

EXAMPLES

Example 1

Coating of Medical Implants with Fibronectin

The coating apparatus consisted of an overhead stirrer (Fisher Scientific) orientated horizontally. A stainless steel rod is attached to the chuck of the stirrer. One end of a medical implant (e.g., mesh or film) is attached to the steel rod using a drop of cyanoacrylate glue. The stirrer is then set to rotate at 30 rpm so that the whole medical implant rotates along the horizontal axis at this speed. A 1% (w/w) fibronectin (Calbiochem, San Diego, Calif.) solution in sterile water is prepared. The implant is then dipped into the solution for 2 minutes. The implant is removed from the solution and is air-dried. Once dried, the implant is removed by dissolving the cyanoacrylate glue using an acetone-soaked cotton swab.

Example 2

Coating of Medical Implants with Poly-L-Lysine

A 1% (w/w) poly-L-lysine (Sigma Aldrich, St. Louis, Mo.) solution in sterile water is prepared. A medical implant (mesh or film) is coated using the procedure described in Example 1.

Example 3

Coating of Medical Implants with N-Carboxybutyl Chitosan

A 1% (w/w) n-carboxybutyl chitosan (Carbomer, Westborough, Mass.) solution in sterile water is prepared. A medical implant (mesh or film) is coated using the procedure described in Example 1.

Example 4

Coating of Medical Implants with Bromocriptine in Poly(Ethylene Vinyl Acetate)

A 4.5% w/w solution of EVA (60/40 ratio ethylene to vinyl acetate) (Polysciences USA) is prepared in dichloromethane. Bromocriptine mesylate (Sigma Aldrich) is dissolved/suspended in this solution at 5 mg/ml. A medical implant (mesh or film) is coated using the procedure described in Example 1.

Example 5

Preparation of Inflammatory Microcrystals (Monosodium Urate Monohydrate and Calcium Pyrophosphate Dihydrate)

Monosodium urate monohydrate (MSUM) microcrystals were grown. A solution of uric acid and sodium hydroxide at 55° C. and pH 8.9 was left to stand overnight at room temperature. The crystals were rinsed several times with cold (4° C.) distilled water and dried at 60° C. for 12 hours in a circulating hot-air oven (Fisher, Isotemp).

Triclinic calcium pyrophosphate dihydrate (CPPD) crystals were prepared as follows. A 250 ml beaker containing 103 ml distilled water was heated in a water bath to 60° C., and stirred constantly with a TEFLON-coated stir bar. The stirring was slowed and 0.71 ml of concentrated hydrochloric acid and 0.32 ml of glacial acetic acid were added, followed by 0.6 g of calcium acetate. A 150 ml beaker containing 20 ml distilled water was heated to 60° C. in the water bath, and 0.6 g calcium acetate added. The rate of stir was increased in the 250 ml beaker, and 2 g of calcium acid pyrophosphate added rapidly. When the $CaH_2P_2O_7$ had nearly all dissolved, the rate of stirring was reduced for 5 minutes. Then over a period of 15 seconds, the contents of the small beaker were poured into the large beaker with vigorous stirring. In the preparation of subsequent batches, a minute amount of triclinic CPPD crystals was added to the large beaker as seed material. Stirring was discontinued, leaving a white gel. This was allowed to remain undisturbed in the cooling water bath. The pH of the supernatant was always less than 3.0. The gel collapsed as CPPD crystals formed in 24 hours. The crystals were washed in distilled water 3 times, washed in ethanol, then washed in acetone, and air dried.

Example 6

Coating of Medical Implants with Inflammatory Microcrystals (Monosodium Urate Monohydrate or Calcium Pyrophosphate Dihydrate) from EVA/DCM Solution A 4.5% w/w solution of EVA (60/40 ratio ethylene to vinyl acetate) (Polysciences) is prepared in dichloromethane. Inflammatory microcrystals (MSUM or CPPD) are ground in a pestle and mortar to a particle size of 10 to 50 micrometers and suspended in the solution at 5 mg/ml. A medical implant (mesh or film) is coated using the procedure described in Example 1.

Example 7

Coating of Medical Implants with Inflammatory Microcrystals (Monosodium Urate Monohydrate or Calcium Pyrophosphate Dihydrate)

A 4.5% w/w solution of poly (lactide co-glycolide) (85:15) (IV 0.61) (Birmingham Polymers, Birmingham, Al.) blended with methoxypolyethylene glycol 350 (MePEG 350) (Union Carbide, Danbury, Conn.) in a ratio of 80:20 w/w (PLGA:MePEG) is prepared in dichloromethane. Inflammatory microcrystals are suspended in the solution at 5 mg/ml. A medical implant (mesh or film) is coated using the procedure described in Example 1.

Example 8

Coating of Medical Implants with Angiotensin 2 Encapsulated in Polyethylene Glycol (PEG)

1.8 grams of polyethylene glycol (PEG 1475) (Union Carbide) is placed in a flat-bottomed 20 ml glass scintillation vial and warmed to 50° C. to melt the PEG in a water bath. 200 mg of glycerol (Fisher Scientific) is then added. Two mg of angiotensin 2 (Sigma Aldrich) is weighed into the vial and blended/dissolved into the melted PEG at 50° C. The vial is angled at 10 degrees in a water bath by use of a clamp. Each end of a medical implant is dipped into the molten formulation. The medical implant is then removed and cooled and stored at 4° C. until use.

Example 9

Coating of Medical Implants with Transforming Growth Factor-β(TGF-β) in Crosslinked Hyaluronic Acid A 1% solution of hyaluronic acid (HA) (sodium salt, Sigma Aldrich) in water, containing 30% glycerol (w/w to HA) (Fisher Scientific) and 8 mM 1-ethyl-3-(-3 dimethylaminopropyl) carbodiimide (EDAC) is prepared by dissolution overnight. TGF-β (Calbiochem, San Diego, Calif.) is dissolved at 0.01 mg/ml in this solution. A medical implant (mesh or film) is Coated using the procedure described in Example 1.

Example 10

Coating of Medical Implants with Fibroblast Growth Factor (FGF) in Crosslinked Chitosan A 1% solution of chitosan (Medical grade, Carbomer, Westborough, Mass.) in dilute acetic acid (pH 5), containing 30% glycerol (w/w to chitosan) (Fisher Scientific) and 0.5% glutaraldehyde (Sigma, St. Louis, Mo.) is prepared by dissolution overnight. FGF (Calbiochem, San Diego, Calif.) is dissolved at 0.01 mg/ml in this solution. A medical implant (mesh or film) is coated using the procedure described in Example 1.

Example 11

Rat Model to Assess Fibrosis Inducing Agents in Rats

The rat caecal sidewall model is used to as to assess the fibrotic-inducing capacity of formulations in viva. Sprague Dawley rats are anesthetized with halothane. Using aseptic precautions, the abdomen is opened via a midline incision. The caecum is exposed and lifted out of the abdominal cavity. The caecum is then positioned over an area of the sidewall and attached by two sutures. The fibrosis-inducing formulation, e.g., silk mesh (mesh may be made of knitted silk or a fibrosis-inducing formulation may be put onto the outside of the mesh) or a silk gel formulation, is applied over both sides of the caecum and over the peritoneal sidewall when the gel is administered, or positioned between the two tissues when the mesh is used. A further two sutures are placed to attach the caecum to the sidewall, for a total of 4 sutures, and the abdominal incision is closed in two layers. After 7 days, animals are evaluated post mortem with respect to the extent and severity of tissue reaction, which are scored both quantitatively and qualitatively. Exemplary materials that may be tested in this model include silk and talc.

Example 12

Screening Procedure for Assessment of Perimedical Implant Reaction

Large domestic rabbits are placed under general anesthetic. Using aseptic precautions, the infrarenal abdominal aorta is exposed and clamped at its superior and inferior aspects. A longitudinal arterial wall arteriotomy is performed and a 2 millimeter diameter, 1 centimeter long segment of PTFE medical implant is inserted within the aorta and the proximal and distal aspect of the medical implant is sewn so that the entire aortic blood flow is through the medical implant which is contained in the abdominal aorta in the manner of open surgical abdominal aortic repair in humans (except that no aneurysm is present in this model). The aortotomy is then surgically closed and the abdominal wound closed and the animal recovered.

The animals are randomized to receive standard PTFE medical implants or medical implants of which the middle 1 cm is coated alone circumferentially with nothing, or with an agent that induces a vessel wall reaction or adhesion between a medical implant and vessel wall alone or contained in a slow release polymer, such as polycaprolactone or polylactic acid.

The animals are sacrificed between 1 and 6 weeks post surgery, the aorta is removed en bloc and the area in relation to the medical implant is grossly examined for adhesive reaction. Any difference in morphology or histology of the vessel wall from portions of the artery which contain no medical implant, portion which contain medical implant without coating, and portion which contained medical implant with coating is noted.

Example 13

Screening Procedure for Assessment of Perigraft Reaction

A rabbit perivascular model is described for identifying irritants to vascular tissue that would be applicable as diverticular wall irritants. Large domestic rabbits are placed under general anesthetic. Using aseptic precautions, the infrarenal abdominal aorta is exposed and clamped at its superior and inferior aspects. A longitudinal arterial wall arteriotomy is performed and a 2 millimeter diameter, 1 centimeter long segment of PTFE graft is inserted within the aorta and the proximal and distal aspect of the graft is sewn so that the entire aortic blood flow is through the graft which is contained in the abdominal aorta in the manner of open surgical abdominal aortic repair in humans (except that no aneurysm is present in this model). The aortotomy is then surgically closed and the abdominal wound closed and the animal recovered.

The animals are randomized to receive standard PTFE grafts or grafts of which the middle 1 cm is coated alone circumferentially with nothing, or with an agent that induces a vessel wall reaction or adhesion between a stent graft and vessel wall alone or contained in a slow release polymer, such as polycaprolactone or polylactic acid.

The animals are sacrificed between 1 and 6 weeks post surgery, the aorta is removed en bloc and the area in relation to the graft is grossly examined for adhesive reaction. Any difference in morphology or histology of the vessel wall from portions of the artery that contain no graft, portion which contain graft without coating, and portion which contained graft with coating is noted.

Example 14

Animal Abdominal Aortic Aneurysm Model

An animal model is described for identifying biologically active or irritative substances which cause fibrosis for use as a diverticular wall irritant when placed on a polymeric material such as a stent graft. Pigs or sheep are placed under general anesthetic. Using aseptic precautions the abdominal aorta is exposed. The animal is heparinized and the aorta is cross-clamped below the renal arteries and above the bifurcation. Collaterals are temporarily controlled with vessel loops or clips that are removed upon completion of the procedure. A longitudinal aortotomy is created in the arterial aspect of the aorta, and an elliptical-shaped patch of rectus sheath from the same animal is sutured into the aortotomy to create an aneurysm. The aortic clamps from the lumbar arteries and collaterals are removed and the abdomen closed. After 30 days, the animal is re-anesthesized and the abdominal wall again opened. A cutdown is performed on the iliac artery and through this, a stent graft is positioned across the infrarenal abdominal aorta aneurysm extending from normal infrarenal abdominal aorta above to normal infrarenal abdominal aorta below the surgically created aneurysm. The device is released in a conventional way.

Animals are randomized into groups of 5, each group receiving uncoated stent grafts, stent graft containing slow release polymer alone, or stent graft containing a biologically active or irritative substance as determined by the previously mentioned screening exam. After closure of the arteriotomy and of the abdominal wound, the animal is allowed to recover. At 6 weeks and 3 months post stent graft insertion, the animal is sacrificed and the aorta removed en bloc. The infrarenal abdominal aorta is examined for evidence of histologic reaction and perigraft leaking.

Example 15

Screening Assay for Assessing the Effect of Cyclosporine A on Cell Proliferation An in vitro assay is described for determining whether a substance stimulates cell (e.g., fibroblast) proliferation (see, e.g., *In Vitro Toxicol.* (1990) 3:219; *Biotech. Histochem.* (1993) 68: 29; *Anal. Biochem.* (1993) 213:426). Primary human smooth muscle cells are cultured according to standard cell culture methods. When the cells are at at 70–90% confluency, the cells are trypsinized and replated at 600 cells/well in media in 96-well plates and allowed to attach overnight. Cyclosporine A is prepared in DMSO at a concentration of $10^{-2}$ M and then diluted in 10-fold dilutions to give a range of stock concentrations ($10^{-8}$ M to $10^{-2}$ M). Each drug dilution is diluted 1/1000 in media and added to cells to give a total volume of 200 µL/well. Each drug concentration is tested in triplicate wells. Plates containing smooth muscle cells and cyclosporine A are incubated at 37° C. for 72 hours.

To terminate the assay, the media is removed by gentle aspiration. A 1/400 dilution of CYQUANT 400X GR dye indicator (Molecular Probes, Eugene, Oreg.) is added to 1× cell lysis buffer, and 200 µl of the mixture is added to the wells of the plate. Plates are incubated at room temperature, protected from light for 3–5 minutes. Fluorescence is read in a fluorescence microplate reader at ~480 nm excitation wavelength and ~520 nm emission maxima. Activation of proliferation is determined by taking the average of triplicate wells and comparing average relative fluorescence units to the DMSO control. Data from a representative assay are shown in FIG. 1.

Figure 6:
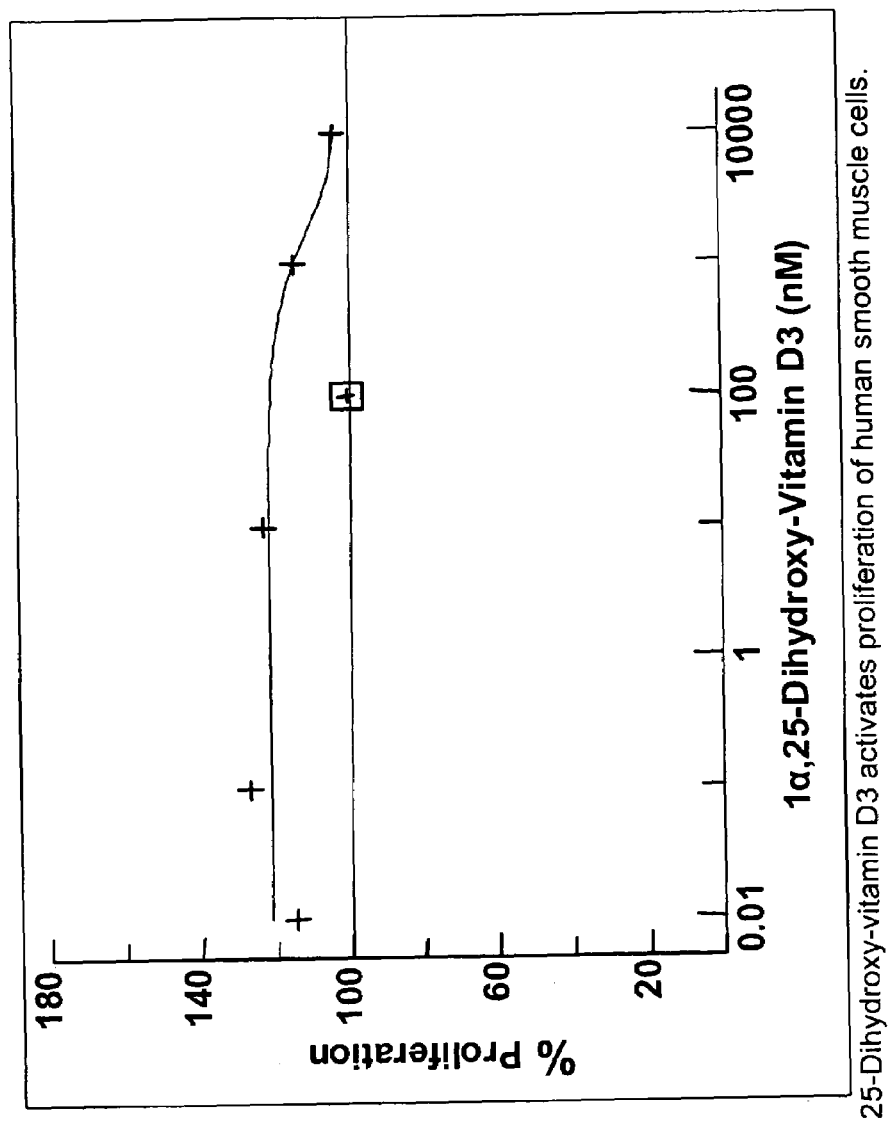
FIG. 6 is a graph showing the effect of 1a,25-dihydroxyvitamin $D_3$ on proliferation of human smooth muscle cells.

The assay was repeated for the following proliferative therapeutic agents using smooth muscle cells or human fibroblasts; data are presented in the figures as noted: dexamethasone (FIG. 2), all-trans retinoic acid (FIG. 3), isotretinoin (FIG. 4), 17-β-estradiol (FIG. 5), and 1a,25-dihydroxy-vitamin $D_3$ (FIG. 6).

Example 16

Screening Assay for Assessing the Effect of PDGF on Smooth Muscle Cell Migration An in vitro assay is described for determining whether a substance stimulates cell (e.g., fibroblast) migration. Primary human smooth muscle cells are starved of serum in smooth muscle cell basal media containing insulin and human basic fibroblast growth factor (bFGF) for 16 hours prior to the assay. For the migration assay, cells are trypsinized to remove cells from flasks, washed with migration media, and diluted to a concentration of $2-2.5 \times 10^5$ cells/ml in migration media. Migration media consists of phenol red free Dulbecco's Modified Eagle Medium (DMEM) containing 0.35% human serum albumin. A 100 µl volume of smooth muscle cells (approximately 20,000–25,000 cells) is added to the top of a Boyden chamber assembly (Chemicon QCM CHEMOTAXIS 96-well migration plate). To the bottom wells, the chemotactic agent, recombinant human platelet derived growth factor (rhPDGF-BB), is added at a concentration of 10 ng/ml in a total volume of 150

µL. Paclitaxel is prepared in DMSO at a concentration of $10^{-2}$ M and serially diluted 10-fold to give a range of stock concentrations ($10^{-8}$ M to $10^{-2}$ M). Paclitaxel is added to cells by directly adding paclitaxel DMSO stock solutions, prepared earlier, at a 1/1000 dilution, to the cells in the top chamber. Plates are incubated for 4 hours to allow cell migration.

Figure 7:
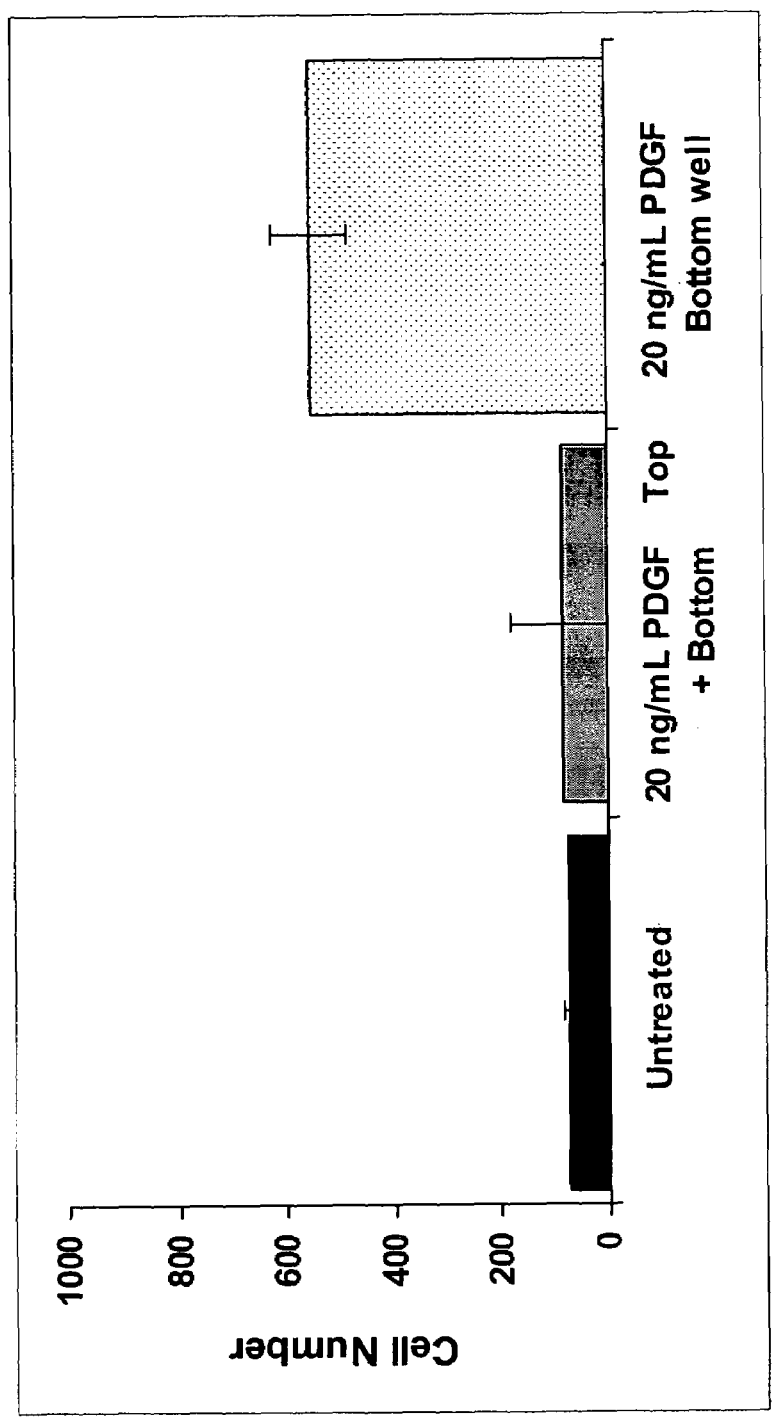
FIG. 7 is a graph showing the effect of PDGF-BB on smooth muscle cell migration.
Figure 8:
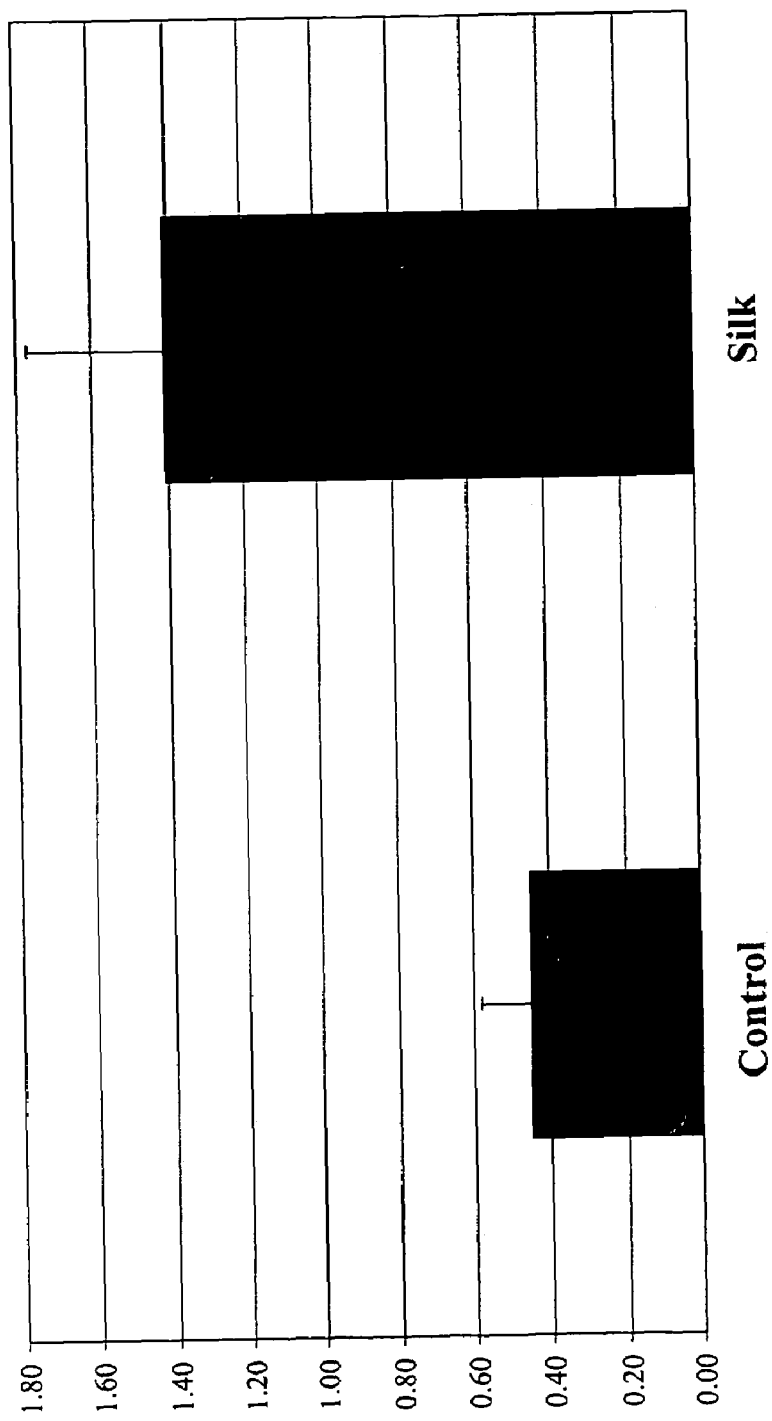
FIG. 8 is a bar graph showing the area of granulation tissue in carotid arteries exposed to silk coated perivascular polyurethane (PU) films relative to arteries exposed to uncoated PU films.

At the end of the 4 hour period, cells in the top chamber are discarded, and the smooth muscle cells attached to the underside of the filter are detached for 30 minutes at 37° C. in Cell Detachment Solution (Chemicon). Dislodged cells are lysed in lysis buffer containing the DNA binding CYQUANT GR dye and incubated at room temperature for 15 minutes. Fluorescence is read in a fluorescence microplate reader at ~480 nm excitation wavelength and ~520 nm emission maxima. Relative fluorescence units from triplicate wells are averaged after subtracting background fluorescence (control chamber without chemoattractant), and average number of cells migrating is obtained from a standard curve of smooth muscle cells serially diluted from 25,000 cells/well down to 98 cells/well. Inhibitory concentration of 50% ($IC_{50}$) is determined by comparing the average number of cells migrating in the presence of paclitaxel to the positive control (smooth muscle cell chemotaxis in response to rhPDGF-BB). The results of a representative assay are shown in FIG. 7. (See also references: *Biotechniques* 29:81 (2000); *J. Immunol. Methods* 254:85 (2001)).

Example 17

In Vivo Evaluation of Silk Coated Perivascular PU Films to Assess Scarring

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea, and the left carotid artery is exposed. A polyurethane film covered with silk strands or a control uncoated PU film is wrapped around a distal segment of the common carotid artery. The wound is closed and the animal is allowed to recover. After 28 days, the rats are sacrificed with carbon dioxide and then pressure-perfused at 100 mmHg with 10% buffered formaldehyde. Both carotid arteries are harvested and processed for histology. Serial cross-sections can be cut every 2 mm in the treated left carotid artery and at corresponding levels in the untreated right carotid artery. Sections are stained with H&E and Movat's stains to evaluate tissue growth around the carotid artery. Area of perivascular granulation tissue is quantified by computer-assisted morphometric analysis. Area of the granulation tissue was significantly higher in the silk-coated group than in the control uncoated group (see FIG. 8).

Example 18

In Vivo Evaluation of Perivascular PU Films Coated with Different Silk Suture Material to Assess Scarring A rat carotid artery model is described for determining whether a substance stimulates fibrosis. Wistar rats weighing 300 g to 400 g were anesthetized with halothane. The skin over the neck region was shaved and the skin was sterilized. A vertical incision was made over the trachea and the left carotid artery was exposed. A polyurethane film covered with silk sutures from one of three different manufacturers (3-0 Silk—Black Braided (Davis & Geck); 3-0 SOFSILK (U.S. Surgical/Davis & Geck); and 3-0 Silk—Black Braided (LIGAPAK) (Ethicon, Inc.)) was wrapped around a distal segment of the common carotid artery. (The polyurethane film can also be coated with other agents to induce fibrosis.) The wound was closed and the animal was allowed to recover.

Figure 9:
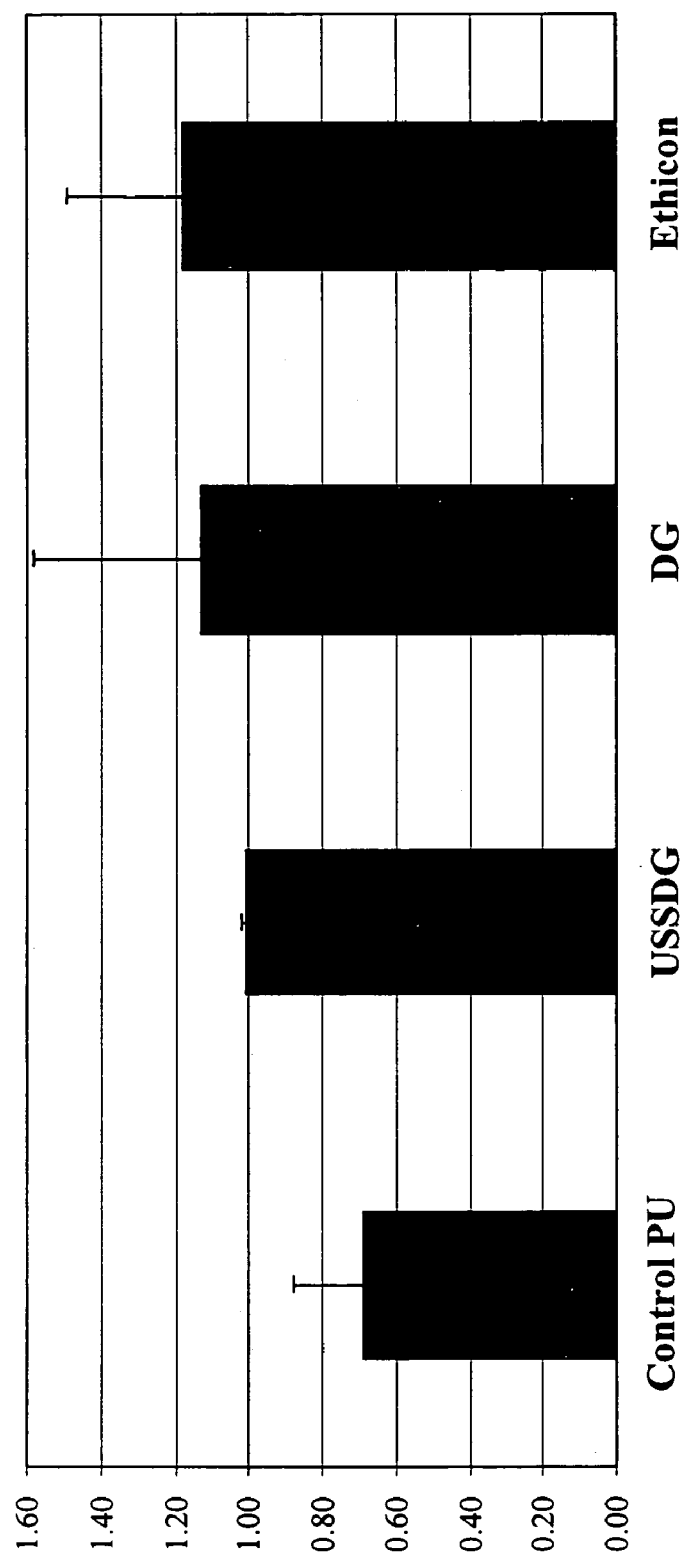
FIG. 9 is a bar graph showing the area of granulation tissue in carotid arteries exposed to silk suture coated perivascular PU films relative to arteries exposed to uncoated PU films.
Figure 10:
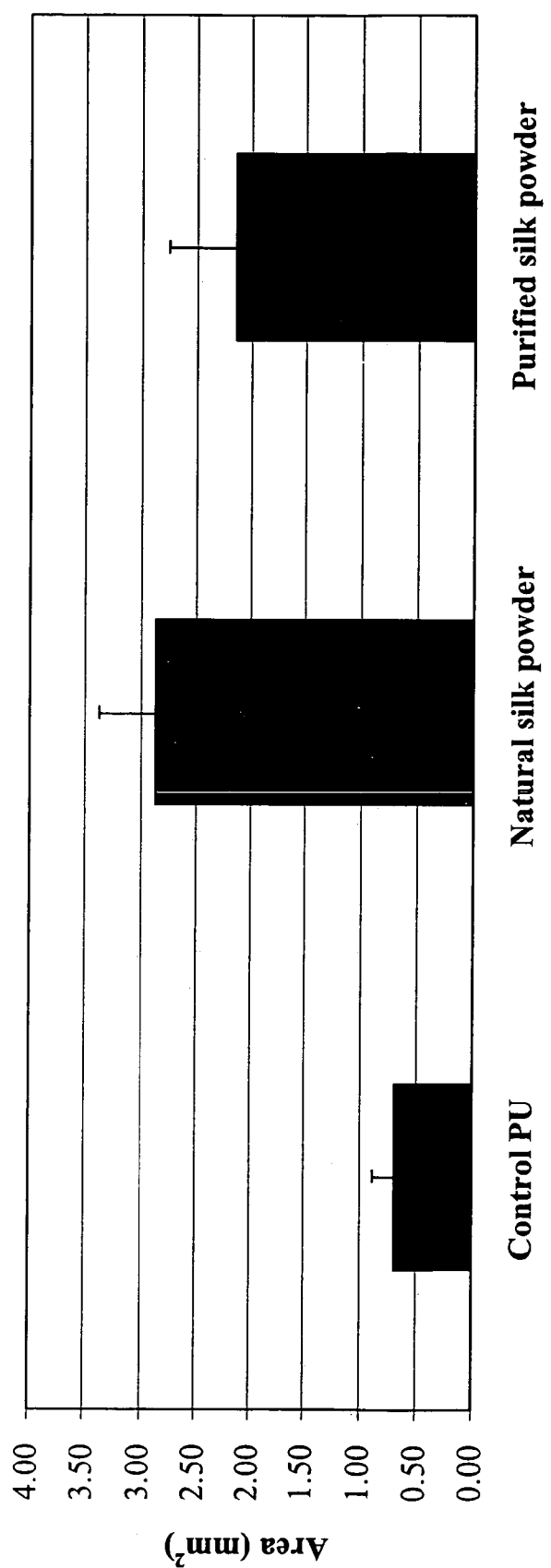
FIG. 10 is a bar graph showing the area of granulation tissue in carotid arteries exposed to natural and purified silk powder and wrapped with perivascular PU film relative to a control group in which arteries are wrapped with perivascular PU film only.
Figure 11:
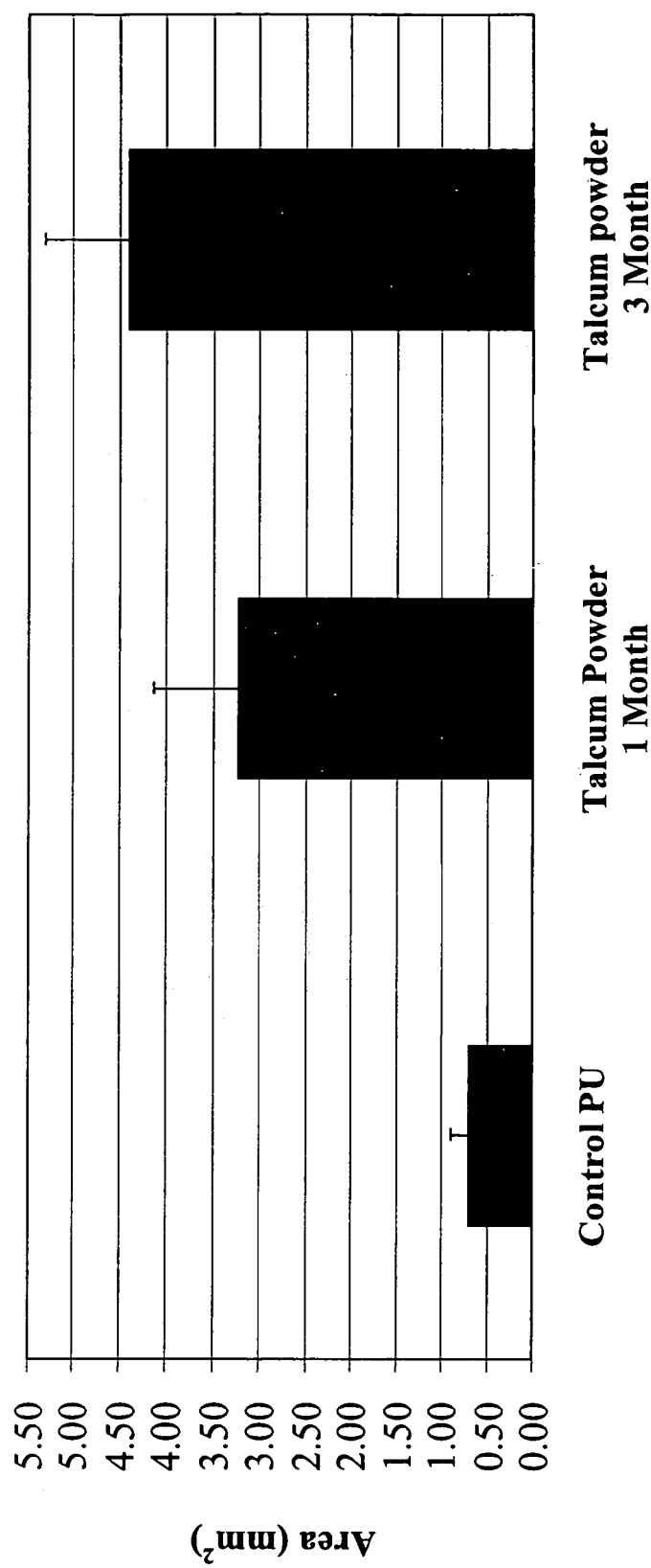
FIG. 11 is a bar graph showing the area of granulation tissue (at 1 month and 3 months) in carotid arteries sprinkled with talcum powder and wrapped with perivascular PU film relative to a control group in which arteries are wrapped with perivascular PU film only.
Figure 12:
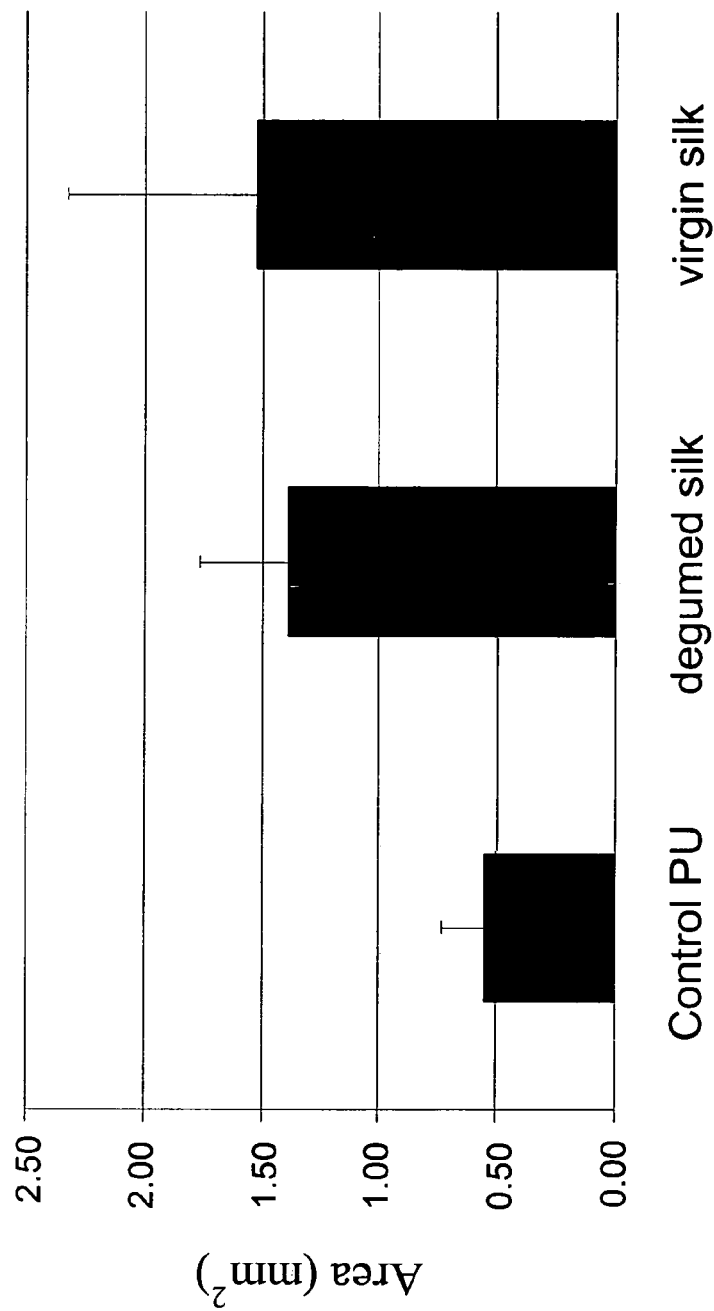
FIG. 12 is a bar graph showing indicating the area of perivascular granulation tissue quantified by computer-assisted morphometric analysis in rat carotid arteries treated with control uncoated PU films and with PU films treated with degummed and virgin silk strands. As shown in the figure, both types of silk markedly increased granulation tissue growth around the blood vessel to the same extent.
Figure 13:
FIG. 13 shows representative histology sections of rat carotid arteries treated with PU films coated with degummed and virgin silk strands. As shown in the figure, both types of silk induced a marked tissue reaction around the treated blood vessel. Movat stain, 100×.

After 28 days, the rats were sacrificed with carbon dioxide and then pressure-perfused at 100 mmHg with 10% buffered formaldehyde. Both carotid arteries were harvested and processed for histology. Serial cross-sections were cut every 2 mm in the treated left carotid artery and at corresponding levels in the untreated right carotid artery. Sections were stained with H&E and Movat's stains to evaluate tissue growth around the carotid artery. Area of perivascular granulation tissue was quantified by computer-assisted morphometric analysis. As illustrated in FIG. 9, thickness of the granulation tissue was the same in the three groups, showing that tissue proliferation around silk suture is independent of manufacturing processes.

Example 19

In Vivo Evaluation of Perivascular Silk Powder to Assess Scarring

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. Silk powder is sprinkled on the exposed artery that is then wrapped with a PU film. Natural silk powder or purified silk powder (without contaminant proteins) is used in different groups of animals. Carotids wrapped with PU films only are used as a control group. The wound is closed and the animal is allowed to recover. After 28 days, the rats are sacrificed with carbon dioxide and then pressure-perfused at 100 mmHg with 10% buffered formaldehyde. Both carotid arteries are harvested and processed for histology. Serial cross-sections are cut every 2 mm in the treated left carotid artery and at corresponding levels in the untreated right carotid artery. Sections are stained with H&E and Movat's stains to evaluate tissue growth around the carotid artery. Areas of tunica intima, tunica media, and perivascular granulation tissue are quantified by computer-assisted morphometric analysis.

In one experiment conducted on a group of six rats, the natural silk caused a severe cellular inflammation consisting mainly of a neutrophil and lymphocyte infiltrate in a fibrin network without any extracellular matrix or blood vessels in 2/6 cases. In addition, the treated arteries were seriously damaged with hypocellular media, fragmented elastic laminae and thick intimal hyperplasia. Intimal hyperplasia contained many inflammatory cells and was occlusive in 2/6 cases. This severe immune response was likely triggered by antigenic proteins coating the silk protein in this formulation. On the other end, the regenerated silk powder triggered only a mild foreign body response surrounding the treated artery. This tissue response was characterized by inflammatory cells in extracellular matrix, giant cells, and the presence of supportive blood vessels. The treated artery was intact. These results show that removing the coating proteins from natural silk prevents the immune response and promotes benign tissue growth. Degradation of the regenerated silk powder was underway in some histology sections indicating that the tissue response can likely mature and heal over time. The area of granulation tissue is presented in FIG. 10.

Example 20

In Vivo Evaluation of Perivascular Talcum Powder to Assess Scarring

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. Talcum powder is sprinkled on the exposed artery that is then wrapped with a PU film. Carotids wrapped with PU films only are used as a control group. The wound is closed and the animal is allowed to recover. After 1 or 3 months, the rats are sacrificed with carbon dioxide and then pressure-perfused at 100 mmHg with 10% buffered formaldehyde. Both carotid arteries are harvested and processed for histology. Serial cross-sections are cut every 2 mm in the treated left carotid artery and at corresponding levels in the untreated right carotid artery. Sections are stained with H&E and Movat's stains to evaluate tissue growth around the carotid artery. Thickness of tunica intima, tunica media, and perivascular granulation tissue is quantified by computer-assisted morphometric analysis.

Histopathology results and morphometric analysis showed the same local response to talcum powder at 1 month and 3 months. A large tissue reaction trapped the talcum powder at the site of application around the blood vessel. This tissue was characterized by a large number of macrophages within a dense extracellular matrix with few neutrophiles, lymphocytes, and blood vessels. The treated blood vessel appeared intact and unaffected by the treatment. Overall, this result showed that talcum powder induced a mild long-lasting fibrotic reaction that was subclinical in nature and did not harm any adjacent tissue (see FIG. 11).

Example 21

Preparation of Silk Powder

Several pieces of silk braid (Ethicon, 4-0, 638) are cut into lengths of approx 0.4 cm. These cut pieces are placed in a 100 ml round bottom flask that contains 50 ml 2M NaOH. The sample is stirred using a magnetic stirrer at room temperature for 24 h. The sample is neutralized using concentrated HCl. The neutralized contents are then dialyzed against deionized water using cellulose-based dialysis tubing (WMCO approx 3000; Spectrum). The sample is dialyzed for 48 hours with 5 water changes. The dialyzed sample is then poured into a 100 ml round bottom flask. The sample is frozen and freeze-dried to yield a fluffy powdered material.

Example 22

Preparation of Silk Powder from Silk Braid Using a Cryomill

Several pieces of silk braid (Ethicon, 4-0, 638) are cut into lengths of approx 0.4 cm. These were then milled in a cryomill (Freezermill) for 20 minutes. The powder was then passed through a 53 um stainless steel sieve. The silk powder was collected and stored in a glass vial.

Example 23

Coating of Medical Implants with a Powdered Silk/PLGA Coating

A medical implant (e.g., vicryl braid) attached to a stainless steel rod (with the aid of a bulldog clip) is attached to a Fisher overhead stirrer that is orientated vertically. The stirrer is set to rotate at 30 rpm. A 2% PLGA (9K, 50:50, Birmingham Polymers) solution (ethyl acetate) that contains the powdered silk is sprayed onto the rotating implant using an airbrush spray device. The concentration of the powdered silk in the PLGA solution is altered from 0.1% to 50%. After the spraying process, the implant is allowed to air dry for 30 minutes while still rotating. The implant is then removed from the pipette tip and is further dried under vacuum for 24 h.

Example 24

Coating of Implant with a Powdered Silk/Polyurethane Coating

A medical implant (e.g., a vicryl braid) is pushed onto a 1 ml plastic pipette tip. The open end of the pipette tip is attached to a stainless steel rod that is attached to a Fisher overhead stirrer that is orientated horizontally. The stirrer is set to rotate at 30 rpm. A 2% CHRONOFLEX AL 85A (CT Biomaterials) solution (THF) that contains powdered silk (prepared using a cryomill) is sprayed onto the rotating implant using a TLC spray device. The concentration of the powdered silk in the polyurethane solution is altered from 0.1% to 50%. After the spraying process, the implant is allowed to air dry for 30 minutes while still rotating. The implant is then removed from the pipette tip and is further dried under vacuum for 24 h.

Example 25

Top-Coating of a Coated Implant with a Degradable Coating

The coated implant from Example 24 is reattached to the overhead stirrer and is rotated at 30 rpm. A 10% 20:80 MePEG(750)-PLA block copolymer solution (acetone) is sprayed onto the rotating implant using an ILO spray device. After the spraying process, the implant is allowed to air dry for 30 minutes while still rotating. The spray coating process can be repeated until the desired thickness or uniformity of coating is obtained. The implant is then removed from the pipette tip and is further dried under vacuum for 24 h.

Example 26

Top-Coating of a Coated Implant with a Heparin-Containing Degradable Coating The coated implant from Example 24 is reattached to the overhead stirrer and is rotated at 30 rpm. A 10% 20:80 MePEG(750)-PLA block copolymer solution (acetone) that contains various amounts of a heparin benzalkonium chloride complex (PolySciences) is sprayed onto the rotating implant using an TLC spray device. After the spraying process, the implant is allowed to air dry for 30 minutes while still rotating. The spray coating process can be repeated until the desired thickness or uniformity of coating is obtained. The implant is then removed from the pipette tip and is further dried under vacuum for 24 h.

Example 27

Coating of a Coated Implant with a Heparin Coating

The coated implant from Example 24 is reattached to the overhead stirrer and is rotated at 30 rpm. A solution that contains various amounts of a heparin benzalkonium chloride complex (PolySciences) in IPA is sprayed onto the rotating implant using a TLC spray device. After the spraying process, the implant is allowed to air dry for 30 minutes while still rotating. The spray coating process can be repeated until the desired thickness or uniformity of coating is obtained. The implant is then removed from the pipette tip and is further dried under vacuum for 24 hours.

Example 28

Coating of Implant with a Powdered Silk/Cyclosporine A/Polyurethane Coating

A medical implant (e.g., a vicryl braid) is pushed onto a 1 ml plastic pipette tip. The open end of the pipette tip is attached to a stainless steel rod that is attached to a Fisher overhead stirrer that is orientated horizontally. The stirrer is set to rotate at 30 rpm. A 2% CHRONOFLEX AL 85A solution (THF) that contains the powdered silk and Cyclosporine A is sprayed onto the rotating implant using a TLC spray device. The concentration of the powdered silk in the polyurethane solution is altered from 0.1% to 50% (w/w relative to the polymer) and the concentration of the Cyclosporine A is altered from 0.1% to 10% (w/w relative to the polymer). After the spraying process, the implant is allowed to air dry for 30 minutes while still rotating. The implant is then removed from the pipette tip and is further dried under vacuum for 24 h.

Example 29

Film Impregnated with Silk Fibers

A 20% CHRONOFLEX AL 85A solution (THF) was cast onto a silicone-coated release liner. The solvent was allowed to dry. Pieces of 3-0 Silk—Black Braided (LIGAPAK) (Ethicon, Inc.) were placed on the surface of the polyurethane film. Drops of THF were then added to the surface of the polyurethane film. Using a glass scintillation vial as a roller, the silk strands were embedded into the surface of the polyurethane film.

Example 30

In Situ Forming Silk-Containing Gel (with Collagen and PEG)

Methylated collagen is prepared by the following process. Bovine corium collagen is solubilized using pepsin and purified as described in U.S. Pat. No. 4,233,360. This purified, solubilized collagen is precipitated by neutralization into 0.2 M sodium phosphate, pH 7.2. The precipitate is isolated by centrifugation to a final concentration of 70 mg/ml. The material is dried for two days and then pulverized. Dry methanol containing HCl (to 0.1 N) is added (40 ml) and stirred for four days. Collagen is separated from the acidic methanol, vacuum dried, and sterilized by irradiation. The final product is dissolved in water at a pH of 3–4.

For delivery as a gel, 10 mg of the methylated collagen, 100 mg of a tetra-functional sulfhydryl-PEG (pentaerythritol poly(ethylene glycol)ether tetra-sulfhydryl) (10,000 MW), and 100 mg of a tetra-functional succinimidyl PEG (pentaerythritol poly(ethylene glycol)ether tetra-succinimidyl glutarate) (10,000 MW) are dissolved in water at pH 3–4 to a final volume of 1 ml (first component). The second component is 1 ml of phosphate/carbonate buffer containing silk powder. The phosphate/carbonate buffer is prepared by mixing 300 mM sodium monobasic phosphate with 300 mM sodium carbonate. If required, the pH is adjusted with NaOH or HCl to achieve pH 9.6. The final molarity is approximately 117 mM phosphate and 183 mM carbonate. Various amounts (1 mg to 100 mg) of silk powder (prepared using a cryomill) are added to the phosphate/carbonate buffer. Each component is placed in a syringe and mixed and sprayed on the desired test site using a manual dual-syringe delivery system or a air-assisted dual syringe delivery system (FibriJet, Micromedics).

Example 31

Coating of the Silk Braid with a Polymer/Biological Agent—Direct Dipping

Silk braid (Ethicon, 4-0, 638) is cut into approximately 10 cm lengths. The silk braid is dipped into a chloroform solution of poly(lactide-co-glycolide) (PLGA) (9K, 50:50, Birmingham Polymers) and cyclosporine A. The concentration of the PLGA is altered from 0.1% to 20% (w/v) and concentration of the cyclosporine A in the solution is altered from 0.1% to a saturated solution. The silk braid is immersed in the PLGA/cyclosporine A solution for 5 minutes. The silk braid is then removed and air-dried. The cyclosporine A-loaded silk braid is then further dried under vacuum. The silk braid is then attached to a polyurethane film by placing the coated-braids on the polyurethane film and then pressing the film/braids in a heat press for about 10 seconds such that the coated braid is embedded in the polyurethane film.

Example 32

In Situ Forming Silk-Containing Gel (with PEG)

For delivery as a gel, 200 mg of a tetra-functional succinimidyl PEG (pentaerythritol poly(ethylene glycol) ether tetra-succinimidyl glutarate) (10,000 MW) is dissolved in water at pH 2.5 (adjusted with HCl) to a final volume of 1 ml (first component). The second component is 1 ml of phosphate/carbonate buffer that contains 200 mg of a tetra-functional amino-PEG (pentaerythritol poly(ethylene glycol)ether tetra-amino) (10,000 MW). The phosphate/carbonate buffer is prepared by mixing 300 mM sodium monobasic phosphate with 300 mM sodium carbonate. If required, the pH is adjusted with NaOH or HCl to achieve pH 9.6. The final molarity is approximately 117 mM phosphate and 183 mM carbonate. Various amounts (1 mg to 200 mg) of the silk powder are added to the acidic buffer. Each component is placed in a syringe and is sprayed on the desired test site using a manual dual-syringe delivery system or an air-assisted dual syringe delivery system (FibriJet, Micromedics).

Example 33

Cyclosporine A—Containing Coating

A 5% CHRONOFLEX AL 85A solution (chloroform) containing from 0.1% to 10% cyclosporine A is prepared. A piece PROLENE suture (Johnson & Johnson Corporation, New Brunswick, N.J.) is immersed in and then withdrawn from the coating solution. The coated sample is air-dried in the fume-hood. Samples of different coating thicknesses are prepared by repeating the dip-coating process. The coated sample is then dried under vacuum for 24 hours.

Example 34

Collagen Synthesis Assay

An in vitro assay is described for determining whether a substance promotes deposition of extracellular matrix (ECM). Normal human dermal fibroblasts are trypzanized, then re-plated in medium containing ascorbic acid-2-phosphate at 150,000 cells per well in a 12-well plate. The cells are cultured at 37° C. and 5% $CO_2$ for 2–3 weeks with media changes every three days so that they formed a 3-D matrix of cells and collagen. After 14–21 days of culture, the medium is replaced with serum free medium and the cells allowed to rest for 24 hours.

Drug is diluted in DMSO at $10^{-2}$M, then diluted 10 fold to give a range of stock concentrations from $10^{-2}$M to $10^{-8}$M. Drug is then diluted 1000 times in fresh serum free medium and added to the wells in a total volume of 3 ml per well. The plate(s) are then incubated for 72 hrs at 37° C. After 72 hrs the media is removed from the wells and put into microcentrifuge tubes and frozen at −20° C. until assayed.

The amount of collagen synthesized is measured using a Procollagen Type 1 C-Peptide (PIP) EIA kit (Takara Bio Inc., Shiga, Japan), where the amount of collagen produced is stoichiometrically represented by the amount of propeptide cleaved from the collagen when it is secreted. Anti-PIP monoclonal antibodies are immobilized on an ELISA plate, the samples added, then a second PIP monoclonal antibody conjugated to horseradish peroxidase is added to the wells and incubated. Following incubation, the wells are washed, a substrate solution is added, and the absorbance measured in a plate reader at 450 nm and compared to a standard curve of PIP (ng/ml).

Example 35

Chick Chorioallantoic Membrane ("CAM") Assay

This example describes an in vitro assay for determining whether a substance promotes angiogenesis. Fertilized, domestic chick embryos are incubated for 3 days prior to shell-less culturing. In this procedure, the egg contents are emptied by removing the shell located around the air space. The interior shell membrane is then severed and the opposite end of the shell is perforated to allow the contents of the egg to gently slide out from the blunted end. The egg contents are emptied into round-bottom sterilized glass bowls and covered with petri dish covers. These are then placed into an incubator at 90% relative humidity and 3% $CO_2$ and incubated for 3 days. (Alternatively, egg contents can remain in the shell with the opening covered with parafilm.)

The fibrosing agent is mixed at concentrations of 0.25, 0.5, 1, 5, 10, 30 μg per 10 μl aliquot of 0.5% aqueous methylcellulose. Concentrations are altered depending on the agent. Agents are mixed with other compatible materials as appropriate depending on the solubility of the agent. Ten microliter aliquots of this solution are dried on parafilm for 1 hour, forming disks 2 mm in diameter. The dried disks containing agent are then carefully placed at the growing edge of each CAM at day 6 of incubation. The day of disc placement is altered depending on the amount of angiogenesis stimulation by the agent when compared with control. Controls are obtained by placing agent-free methylcellulose disks on the CAMs over the same time course. After a 2 day exposure (day 8 of incubation) the vasculature is examined with the aid of a stereomicroscope. Liposyn II, a white opaque solution, is injected into the CAM to increase the visibility of the vascular details. The vasculature of unstained, living embryos is imaged using a Zeiss stereomicroscope that is interfaced with a video camera (Dage-MTI Inc., Michigan City, Ind.). These video signals are then displayed at 160× magnification and captured using an image analysis system (Vidas, Kontron; Etching, Germany). Image negatives are then made on a graphics recorder (Model 3000; Matrix Instruments, Orangeburg, N.Y.).

The membranes of the 8 day-old shell-less embryo are flooded with 2% glutaraldehyde in 0.1M sodium cacodylate buffer; additional fixative is injected under the CAM. After 10 minutes in situ, the CAM is removed and placed into fresh fixative for 2 hours at room temperature. The tissue is then washed overnight in cacodylate buffer containing 6% sucrose. The areas of interest are postfixed in 1% osmium tetroxide for 1.5 hours at 4° C. The tissues are then dehydrated in a graded series of ethanols, solvent exchanged with propylene oxide, and embedded in Spurr resin. Thin sections are cut with a diamond knife, placed on copper grids, stained, and examined in a Joel 1200EX electron microscope. Similarly, 0.5 mm sections are cut and stained with toluene blue for light microscopy.

At day 11 of development, chick embryos are used for the corrosion casting technique. Mercox resin (Ted Pella, Inc., Redding, Calif.) is injected into the CAM vasculature using a 30-gauge hypodermic needle. The casting material consists of 2.5 grams of Mercox CL-2B polymer and 0.05 grams of catalyst (55% benzoyl peroxide) having a 5 minute polymerization time. After injection, the plastic is allowed to sit in situ for an hour at room temperature and then overnight in an oven at 65° C. The CAM is then placed in 50% aqueous solution of sodium hydroxide to digest all organic components. The plastic casts are washed extensively in distilled water, air-dried, coated with gold/palladium, and viewed with the Philips 501B scanning electron microscope.

At day 6 of incubation, the embryo is centrally positioned to a radially expanding network of blood vessels; the CAM develops adjacent to the embryo. These growing vessels lie close to the surface and are readily visible making this system an idealized model for the study of angiogenesis. Living, unstained capillary networks of the CAM can be imaged non-invasively with a stereomicroscope.

Transverse sections through the CAM show an outer ectoderm consisting of a double cell layer, a broader mesodermal layer containing capillaries which lie subjacent to the ectoderm, adventitial cells, and an inner, single endodermal cell layer. At the electron microscopic level, the typical structural details of the CAM capillaries are demonstrated. Typically, these vessels lie in close association with the inner cell layer of ectoderm.

After 48 hours exposure to an agent at concentrations of 0.25, 0.5, 1, 5, 10, or 30 μg, each CAM is examined under living conditions with a stereomicroscope equipped with a video/computer interface to evaluate the effects on angiogenesis. This imaging setup is used at a magnification of 160× which permits the direct visualization of blood cells within the capillaries; thereby blood flow in areas of interest can be easily assessed and recorded. The change in the amount of angiogenesis is defined as an area of the CAM (measuring 2–6 mm in diameter) with increased capillary network and vascular blood flow. Throughout the experiments, zones are assessed on a 4 point gradient (Table 1). This scale represents the degree of increase in angiogenesis with maximal increase represented as a 3 on the vascular gradient scale. Scores of agents are compared with scores of controls.

Table 1

Vascular Gradient

0—no vascularity
1—some microvascular movement
2*—richly vascularized zone approximately 2 mm in diameter
3*—richly vascularized zone extending beyond the disk (6 mm in diameter)
*—indicates a positive angiogenesis response Example 36

Silk Suture Coated with Magnetically Active Particles

The end of a piece of silk 5-0 suture was immersed in a THF solution of CHRONOFLEX AL 85A polyurethane solution (about 10% w/v). The silk was removed, and the coated end was dipped into a vial containing magnetically active microparticles. The coated silk end was removed, and the particles were further embedded into the polyurethane coating by rolling the end between two fingertips. The solvent was removed by air-drying.

Example 37

Silk Suture Coated with Magnetically Active Beads

The end of a piece of silk 5-0 suture was immersed in a THF solution of CHRONOFLEX AL 85A polyurethane solution (about 10% w/v) that contained approximately 5% w/w (beads to polymer) magnetic beads. The silk was removed, and the coated end was dipped into a vial containing magnetically active microparticles. The coated silk end was removed, and the particles were further embedded into the polyurethane coating by rolling the end between two fingertips. The solvent was removed by air-drying.

Example 38

In-Vivo Evaluation of Perivascular PU Films Coated with Degummed or Virgin Silk Strands Wistar rats weighing 300 g to 400 g are anesthetized with halothane. The skin over the neck region is shaved and the skin is sterilized. A vertical incision is made over the trachea and the left carotid artery is exposed. A polyurethane film covered with degummed silk strands, virgin silk strands, or a control uncoated PU film is wrapped around a distal segment of the common carotid artery. The wound is closed and the animal is allowed to recover.

After 28 days, the rats are sacrificed with carbon dioxide and then pressure-perfused at 100 mmHg with 10% buffered formaldehyde. Both carotid arteries are harvested and processed for histology. Serial cross-sections will be cut every 2 mm in the treated left carotid artery and at corresponding levels in the untreated right carotid artery. Sections are stained with H&E and Movat's stains to evaluate tissue growth around the carotid artery. Thickness of perivascular granulation tissue is quantified by computer-assisted morphometric analysis.

Figure 14:
FIG. 14 shows representative histology sections of rat carotid arteries treated with PU films coated with degummed and virgin silk strands showing the granulation tissue that had grown around the treated vessels. The silk strands had broken down into small particles surrounded by giant cells and macrophages. The granulation tissue was highly vascularized and contained numerous inflammatory cells and fibroblasts. Extracellular matrix deposition was also extensive. H&E stain 200×.

Both types of silk markedly increased granulation tissue growth around the blood vessel to the same extent. The silk strands in both groups had broken down into small particles (approximately 30 um in diameter) scattered around the blood vessel and were surrounded by giant cells, macrophages, proteoglycan matrix, and blood vessels. These features are typical of a foreign body response. The area covered by the foreign body response was more variable in the virgin silk group than in the degummed silk group. See FIGS. 12, 13, and 14.

Example 39

Preparation of Silk Powder from Degummed Silkusing a Cryomill

Fibers of degummed silk were cut into pieces approximately 1–2 cm in length. The material was then milled to a powder using a cryomill (Spex Certiprep Freezer/Mill—Model 6850). A portion of the milled powder was then sieved through a series of different sized metal sieves to obtain silk powder of different size ranges.

Example 40

Electrospinning of Silk-Loaded Material

20% solutions of PLGA (50:50, Mw~54,000) are prepared by dissolving 2 g PLGA into 10 ml DCM. Various amounts of silk powder (25–53 µm) are added to each solution such that the silk percentage of the polymers ranges from 2% to 50%. Each solution is then loaded into a 10 ml syringe fitted with a 18 gauge needle. The syringe is then loaded into a syringe pump and 20 kV positive high voltage (by Glassman High Voltage, Inc.) is applied on the syringe needle. The grounded target drum is a rotating drum that has a diameter of about 12 cm. The syringe pump is set to pump at 25 µl per minute and the drum is rotated at approximately 250 rpm. The distance from the tip of the needle to the outside of the drum surface is about 14 cm. The rotating drum is moved from side to side during the spinning process such that the drum is virtually completely covered in the spun material. After the spinning process is completed, a razor blade is used to make a cut through the entire length of the spun material. The material is removed from the drum and is further dried in a vacuum oven for 24 hours.

Example 41

MIC (Minimum Inhibitory Concentration) Determination by Microtitre Broth Dilution Method A. MIC Assay of Various gram Negative and Positive Bacteria MIC assays were conducted essentially as described by Amsterdam, D. 1996, "Susceptibility testing of antimicrobials in liquid media," p. 52–111. In Loman, V., ed. *Antibiotics in Laboratory Medicine*, 4th ed. Williams and Wilkins, Baltimore, Md. Briefly, a variety of compounds were tested for antibacterial activity against isolates of *P. aeruginosa, K. pneumoniae, E. coli, S. epidermidus,* and *S. aureus* in the MIC (minimum inhibitory concentration) assay under aerobic conditions using 96 well polystyrene microtitre plates (Falcon 1177), and Mueller Hinton broth at 37° C. incubated for 24 h. (MHB was used for most testing except 0721 (*S. pyogenes*), which used Todd Hewitt broth, and *Haemophilus influenzae*, which used *Haemophilus* test medium (HTM)). Tests were conducted in triplicate. The results are provided below in Table 2.

and derivatives thereof; third generation cephalosporin such as Naxcel (Ceftiofur Sodium), Cefdinir (Omnicef), cefoperazone (Cefobid), ceftazidime (Fortaz), ceftriaxone (Rocephin), cefotaxime (Claforan) and analogues and derivatives thereof; fourth generation cephalosporins such as cefepime (Maxipime) and analogues and derivatives thereof; monobactams such as aztreonam and analogues and derivatives thereof; carbapenems such as imipenem, ertapenem and meropenem and analogues and derivatives thereof; inhibitors of protein synthesis such as aminoglycosides including streptomycin, gentamicin, tobramycin, and amikacin and analogues and derivatives thereof; inhibitors of protein synthesis such as the MSL group including

TABLE 2

MINIMUM INHIBITORY CONCENTRATIONS OF THERAPEUTIC AGENTS AGAINST VARIOUS GRAM NEGATIVE AND POSITIVE BACTERIA

| | Bacterial Strain | | | | | |
|---|---|---|---|---|---|---|
| Drug | *P. aeruginosa* PAE/ K799 H187 wt Gram − | *K. pneumoniae* ATCC- 13883 C238 wt Gram − | *E. coli* UB- 1005 C498 wt Gram − | *S. aureus* ATCC- 25923 C622 wt Gram + | *S. epidermidis* C621 wt Gram + | *S. pyogenes* C721 wt Gram + |
| doxorubicin | $10^{-5}$ | $10^{-6}$ | $10^{-4}$ | $10^{-5}$ | $10^{-6}$ | $10^{-7}$ |
| mitoxantrone | $10^{-5}$ | $10^{-6}$ | $10^{-5}$ | $10^{-5}$ | $10^{-5}$ | $10^{-6}$ |
| 5-fluorouracil | $10^{-5}$ | $10^{-6}$ | $10^{-6}$ | $10^{-7}$ | $10^{-7}$ | $10^{-4}$ |
| methotrexate | N | $10^{-6}$ | N | $10^{-5}$ | N | $10^{-6}$ |
| etoposide | N | $10^{-5}$ | N | $10^{-5}$ | $10^{-6}$ | $10^{-5}$ |
| camptothecin | N | N | N | N | $10^{-4}$ | N |
| hydroxyurea | $10^{-4}$ | N | N | N | N | $10^{-4}$ |
| cisplatin | $10^{-4}$ | N | N | N | N | N |
| tubercidin | N | N | N | N | N | N |
| 2-mercaptopurine | N | N | N | N | N | N |
| 6-mercaptopurine | N | N | N | N | N | N |
| Cytarabine | N | N | N | N | N | N |

MICs are presented in molar concentrations.
Wt = wild type
N = No activity

B. MIC of Antibiotic-Resistant Bacteria

Various concentrations of the following compounds, mitoxantrone, cisplatin, tubercidin, methotrexate, 5-fluorouracil, etoposide, 2-mercaptopurine, doxorubicin, 6-mercaptopurine, camptothecin, hydroxyurea and cytarabine were tested for antibacterial activity against clinical isolates of a methicillin resistant *S. aureus* and a Vancomycin-resistant pediocoocus clinical isolate in an MIC assay as described above. Compounds which showed inhibition of growth (MIC value of $<1.0\times10^{-3}$) of these resistant bacterial strains included mitoxantrone (both strains); methotrexate (vancomycin resistant pediococcus); 5-fluorouracil (both strains); etoposide (both strains); and 2-mercaptopurine (vancomycin resistant pediococcus).

Additional agents that may be tested in this assay include but are not limited to fourth generation penicillins such as mezlocillin and piperacillin (the ureidopenicillins), and carbenicillin and ticarcillin (carboxypenicillins), and analogues and derivatives thereof; first generation cephalosporins such as cephazolin sodium, cephalexin (Keflex), cefazolin (Ancef), cephapirin (Cefadyl) and cephalothin (Keflin) and analogues and derivatives thereof; Ticarcillin, second generation cephalosporins such as cefuroxime (Zinocef), cefotetan (Cefotan), and cefoxitin (Mefoxin) and analogues macrolides (Ehromycin),long acting macrolides (Azithromycin) and lincosamides (Clindamycin) and streptogramins (Syneroid), clarithromycin, kanamycin Sulfate, and analogues and derivatives thereof; inhibitors of DNA synthesis such as the quinolones including ciprofloxacin, ofloxacin, gatifloxacin, moxifloxacin, levofloxacin, trovafloxacin and analogues and derivatives thereof; inhibitors of DNA synthesis such as metronidazole and analogues and derivatives thereof; inhibitors of folate metabolism including sulfonamides and trimethoprim and analogues and derivatives thereof. Additional agents include but are not limited to cefixime, spectinomycin, tetracycline, nitrofurantoin, doxycycline, polymyxin B, neomycin sulfate, and analogues and derivatives thereof.

Example 42

Rabbit Model to Assess Fibrosis Inducing Agents

The rabbit uterine horn model is used to assess the fibrotic capacity of formulations in vivo. Mature New Zealand White (NZW) female rabbits are placed under general anesthetic. Using aseptic precautions, the abdomen is opened in two layers at the midline to expose the uterus.

Both uterine horns are lifted out of the abdominal cavity and assessed for size on the French Scale of catheters. Horns between #8 and #14 on the French Scale (2.5–4.5 mm diameter) are deemed suitable for this model. The individual horns are then opposed to the peritoneal wall and secured by two sutures placed 2 mm beyond the edges of the abraded area. The scar-inducing formulation is applied to the horns and the abdomen is closed in three layers. After 14 days, animals are evaluated post modem with the extent and severity of scarring being scored both quantitatively and qualitatively. Exemplary compounds that may be tested in this model include for example, silk and talc.

Example 43

Coating of a Vicryl Braid with Silk/PLGA

A solution of 5 g PLGA (50:50, IV=0.15, Birmingham Polymers, Inc.) is dissolved in 100 ml dichloromethane. One gram of powdered silk (25–53 μm, prepared using the cryomill as sieving as described above) is mixed into the solution. The VICRYL braid (VICRYL 2-0, Ethicon; Johnson & Johnson Corp.) is coated using the procedure described in Example 1.

Example 44

Coating of a Vicryl Braid Implant with Silk/Cyclosporine A/PLGA

A solution of 5 g PLGA (50:50, IV=0.15, Birmingham Polymers, Inc.) is dissolved in 100 ml chloroform. One gram of powdered silk (25–53 μm, prepared using the cryomill as sieving as described above) is mixed into the solution. 0.5 mg cyclosporine A is added to the solution. The VICRYL braid (VICRYL 2-0, Ethicon) is coated using the procedure described in Example 1. Other examples of fibrosing agents that may be similarly coated onto the Vicryl braid include talc, silica, starch, fibronectin, poly(ethyl cyanoacrylate), polylysine, bleomycin, and CTGF.

Example 45

Incorporation of Silk into a Surgical Mesh

A Bard Hernia Mesh (Flat Sheets, Cat # 0112680 3"×6" (7.5 cm×15 cm), DAVOL) is laid flat in a sheet of glass. Several silk sutures (PERMA-HAND Silk Suture-Taper Point, Cat: 7730G, Ethicon) are then sewn onto the mesh by inserting the needle through the mesh from one side of the mesh to the other side of the mesh. The silk is traversed through the mesh at least 4 times for each suture. The excess suture material is then cut away.

Example 46

Incorporation of Silk into a Bulking Agent

Fifty mg powdered silk (25–53 μm, prepared using the cryomill as sieving) is added to 2.5 ml of a glutaradehyde crosslinked bovine collagens solution (35 mg/ml) (CONTIGEN, CR Bard, Inc., Murray Hill, N.J.). The solution is vortexed to produce the final suspension. Other examples of fibrosing agents that may be similarly coated onto a implant include talc, silica, fibronectin, starch, poly(ethyl cyanoacrylate), polylysine, bleomycin, and CTGF.

Example 47

Incorporation of Silk into a Surgical Film Implant

A 10% solution of a 70:30 PLLA:PDLLA polymer (RESOMER LR 708, Boehringer Ingelheim, KG, Germany) is prepared by dissolving 1 g of the polymer in 10 ml DCM. One gram powdered silk (25–53 μm, prepared using the cryomill and sieving) is added to the solution. The solution is stirred for 1 hour. The solution is cast into a film on a release liner using a 40 mil casting knife. The film is dried in a forced-air oven (50° C., 3 hours) and then in a vacuum oven for 24 hours.

Example 48

Dripped-On Cyclosporine A Samples

A polyurethane (PU) (CHRONOFLEX AL 85A) is dissolved in tetrahydrofuran (THF) to form a 20% solution (20 ml). The PU film is prepared by casting the PU solution on release liner (using 40 MIL opening knife). The film is dried in a forced-air oven (50° C.) and then in a vacuum oven. The final film thickness is about 100–120 μm). Cyclosporin-A is dissolved in ethanol (500 μg/ml) to form a cyclosporin-A ethanol solution. A 50 μl aliquot of cyclosporin-A solution is dripped onto the 8×8 mm$^2$ (precut) PU film. The ethanol is evaporated in a fume hood, and the PU samples are further dried in vacuum oven.

Example 49

Encapsulated Cyclosporine A Samples

A 20% polyurethane (CHRONOFLEX AL 85A) solution in THF (2 g PU in 10 ml THE, 20 ml glass scintillation vial) is prepared. 230 μl of a 100 μg/ml cyclosporine A/chloroform solution is added to the PU solution. The solution is stirred using a magnetic stirrer for 2 hours. The PU/cyclosporine A solution is cast into a film on a release liner using a 40 mil casting knife. The film is dried in a forced-air oven (50° C.) and then in a vacuum oven. The final film thickness is about 100–120 μm.

Example 50

Release Study and Total Content Analysis for Cyclosporine A from Polyurethane Film The release of cyclosporine A from a polyurethane film is analyzed by HPLC using the following parameters.

| | |
|---|---|
| Mobile Phase | 35:65:5:0.1 (water/acetonitrile, tert-butylmethylether, phosphoric acid) |
| Wavelength | 210 nm |
| Column | ACE C18 150 × 4.6 mm 5 μm |
| Flow rate | 1.2 ml/min |
| Diluent for samples | 1:1 (acetonitrile/water) |

Standards are prepared as follows: Approximately 25 mg of cyclosporine is weighed into a 25 ml volumetric flask. A diluent (1:1 acetonitrile/water) is added to dissolve the cyclosporine. and diluent is added to achieve the correct volume. The following dilutions shown in the table below are made to obtain standards of 0.2, 0.5, 2, 5, 10, and 20 μg/ml.

| Stock solution concentration (µg/ml) | Dilution volume (ml) | Final volume (ml) | Final concentration (µg/ml) |
|---|---|---|---|
| 1000 | 8 | 10 | 800 |
| 1000 | 5 | 10 | 500 |
| 1000 | 3 | 10 | 300 |
| 1000 | 2 | 10 | 200 |
| 1000 | 1 | 10 | 100 |
| 100 | 1 | 10 | 10 |
| 500 | 1 | 10 | 50 |
| 50 | 1 | 10 | 0.5 |
| 800 | 1 | 10 | 80 |
| 80 | 1 | 10 | 0.8 |
| 200 | 1 | 10 | 20 |
| 20 | 1 | 10 | 2 |

Release Studies:

Release studies are performed as follows. A PU film is cut into 1 cm×1 cm piece, if not already this size, and weighed accurately into a 15 cm test tube. Fourteen ml of release media are dispensed into each test tube containing the sample. The sample is capped and placed on a rotator at 37° C. until the next time point. The time points are 5 hours, 1 day, 2 days, 3 days, 4 days, 5 days and then every other day after the first week until drug is not detected or until otherwise decided. At each time point, the sample is transferred into a new test tube and 14 ml of release media are added. The sample is placed back into the 37° C. oven until the next time point. The release media solution is injected at various time points directly onto the HPLC column for analysis.

Figure 15:
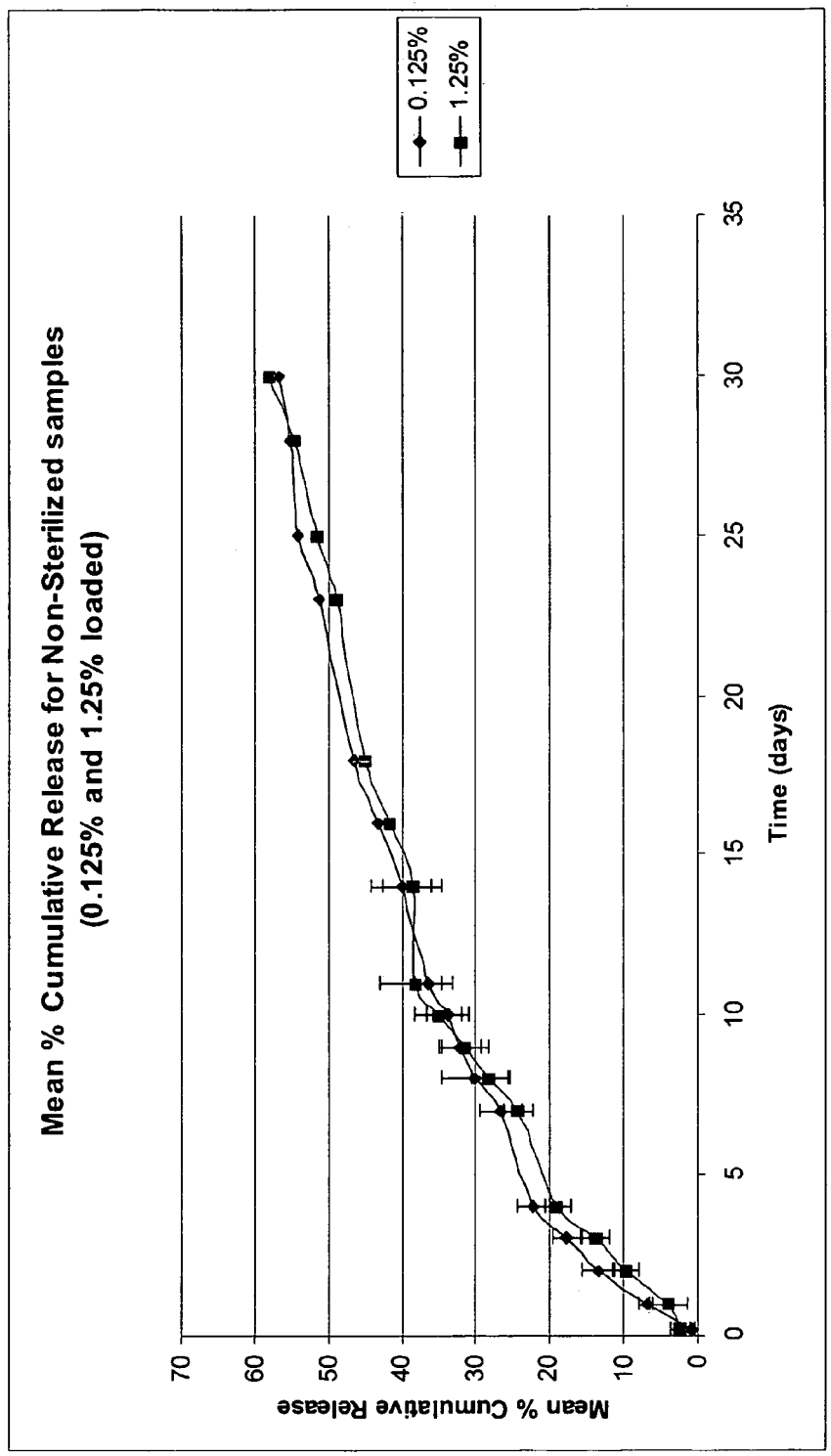
FIG. 15 shows the release profile for cyclosporine A from a polyurethane film as analyzed by HPLC.

Total Content Analysis:

A PU film is cut into 1 cm×1 cm piece, if not already this size, and weighed accurately into a 15 cm test tube. Choloform (0.5 ml) is added to each test tube and the sample is completely dissolved. Once the sample is dissolved, 6.0 ml of acetonitrile is added to each sample. The sample is capped and shaken vigorously to precipitate the polyurethane. The sample is centrifuged at 2500 rpm for 10 minutes. 5.0 ml of the supernatant is transferred into a clean test tube and dried under nitrogen at 35° C. The dried samples are reconstituted in 1.0 ml of acetonitrile and injected into the HPLC. The results of a release study for polyurethane films loaded with 1.25% and 0.125% cyclosporine are shown in FIG. 15.

Example 51

Tetra Functional Poly (Ethylene Glycol) Succinimidyl Glutarate, (PEG-SG4), Non-Gelling Formulation with Silk Powder A 1 ml syringe (syringe 1) equipped With a luer-lock mixing connector is filled With PEG-5G4 (100 mg) (Sunbio, Inc., Orinda, Calif.) and 50 mg powdered silk (Example 22). A 1 ml capped syringe (syringe 2)is filled with 0.25 ml of 6.3 mM HCl solution (pH 2.1). Al ml capped syringe (syringe 3) is filled with 0.25 ml 0.12 M monobasic sodium phosphate and 0.2 M sodium carbonate (pH 9.7) buffer. The solid contents of syringe 1 and the acidic solution of syringe 2 are mixed through a mixing connector by repeatedly transferring the contents from one syringe to the other. After complete mixing, the entire mixture is pushed into one of the syringes. The syringe containing the mixture then is attached to one inlet of an applicator (MICROMEDICS air assisted spray-applicator (Model SA-6105)). Syringe 3 containing the pH 9.7 solution is attached onto another inlet of the applicator. The formulation is applied to a tissue surface as specified by the applicator manufacturer.

Example 52

Gelling Formulation (Premix) I with Silk Powder

A 1 ml syringe (syringe 1) equipped with a luer-lock mixing connector is filled with a mixture of PEG-SG4 (50 mg) and PEG-SH4 (tetra functional poly (ethylene glycol) thiol) (50 mg) (Sunbio, Inc.) (referred to as "premix") and 50 mg powdered silk (Example 22). A 1 ml capped syringe (syringe 2) is filled with 0.25 ml of 6.3 mM HCl solution (pH 2.1). A 1 ml capped syringe (syringe 3) is filled with 0.25 ml 0.12 M monobasic sodium phosphate and 0.2 M sodium carbonate (pH 9.7) buffer. The components are mixed and applied to a tissue surface using the procedure described in Example 51.

Example 53

Tetra Functional Poly (Ethylene Glycol) Amine, (PEG-N4) Gelling Formulation

A 1 ml syringe (syringe 1) equipped with a luer-lock mixing connector is filled with PEG-SG4 (50 mg) and PEG-SH4 (tetra functional poly (ethylene glycol) thiol) (10, 25, or 40 mg) and 50 mg powdered silk (Example 22). A 1 ml capped syringe (syringe 2) is filled with 0.25 ml of 6.3 mM HCl solution (pH 2.1). A 1 ml capped syringe (syringe 3)is filled with 0.25 ml 0.12 M monobasic sodium phosphate and 0.2 M sodium carbonate (pH 9.7) buffer. A 1 ml syringe (syringe 4) equipped with luer-lock mixing connector is filled with PEG-N4 (Sunbio, Inc.) (40, 25, or 10 mg) to make a mixture (50 mg total) of PEG-SH4 (in syringe 1) and PEG-N4 (in syringe 4). The contents of syringe 1 and syringe 2 are mixed through the mixing connector by repeatedly transferring the contents from one syringe to the other. After complete mixing, all of the formulation is pushed into one of the syringes, which is then attached to one inlet of an applicator (MICROMEDICS air assisted spray-applicator (Model SA-6105)). Syringe 4 is attached to syringe 3 containing the pH 9.7 solution with a mixing connector. After complete mixing of the contents of syringe 3 and 4, the mixture is pushed into one of the syringes, which is then attached onto a second inlet of the applicator. The formulation is applied to a tissue surface as specified by the applicator manufacturer.

Example 54

Method for Treating Diverticular Bleeding

A patient exhibiting symptoms of a diverticular disease (e.g., abdominal pain and lower GI bleeding) undergoes physical and radiographic examination (e.g., X-ray, ultrasound, or a CT scan) to determine the extent of the diverticular disease. Once the patient is diagnosed with diverticular disease, a patient can be treated acutely to stop the bleeding or, after the acute episode has subsided (e.g., any time up to about 6 weeks), to prevent the recurrence of a new bleed. To treat or prevent diverticular bleeding, a patient is administered intravenous sedation (e.g., midazolam with either demerol or fentanyl) and then placed on their left side. An end viewing colonoscope is then advanced through the colon to inspect the entire bowel visually, identifying sites of diverticular disease and bleeding. Once the bleeding site(s) and pertinent diverticula are identified, a spray tip delivery catheter is introduced through the biopsy portal of the colonoscope. The spray tip catheter includes a syringe portion configured to contain the components of a multi-component in situ forming hemostatic composition (e.g., VITAGEL from Orthovita, Inc. (Malvern, Pa.) (formerly known as COSTASIS from Angiotech Pharmaceuticals, Inc. (Vancouver, BC)) and a mixing portion configured to combine and mix the components of the composition just prior to delivery into the diverticulum. Examples of mixing and dispensing devices that can be utilized in this procedure are described in, co-pending applications, entitled "Device and Method for Mixing and Dispensing Fluid Components of a Multicomponent Composition," filed Nov. 8, 2004 (PCT/US2004/037450). One or more components of the composition can include a vasoconstrictive agent (e.g. epinephrine). The spray tip catheter is delivered to the treatment site through the portal of the colonoscope and manipulated to position the syringe tip inside the diverticulum or at the orifice of the diverticulum. The spray tip catheter plunger is pushed, activating the syringe, and delivering the composition to the diverticulum. Subsequent cross-linking of the composition occludes the lumen or orifice of the diverticulum, resulting in control of the bleeding.

Example 55

Method for Treating a Diverticular Disease

Once the patient is diagnosed with a diverticular disease (via physical and radiographic examination, as described in Example 54), a patient can be treated acutely to stop bleeding (if present), after an acute bleeding episode has subsided (e.g., any time up to about 6 weeks), to prevent the recurrence of a new bleed, or prophylactically to prevent the onset of bleeding. To treat or prevent a diverticular disease, the patient is administered intravenous sedation (e.g., midazolam with either demerol or fentanyl) and then placed on their left side. An end viewing colonoscope is then advanced through the colon to inspect the entire bowel visually and to locate diverticular openings in the bowel lumen. Once the opening(s) is identified, a sclerosing needle is advanced through the portal of the colonoscope. The needle is attached to a syringe that is loaded with an irrigation solution (e.g., saline), which can include an anti-septic agent (e.g., chlorhexadine), an antibiotic agent (e.g., gentamicin sulfate or doxycyline), and/or an anti-infective agent, such as a chemotherapeutic agent with anti-microbial activity (e.g., 5-FU, 5-fluorouracil, doxorubicin, mitoxantrone, methotrexate, or etoposide), to eliminate bowel flora, anaerobes and aerobes present in the diverticulum. The needle is advanced through the biopsy portal to the opening of the affected diverticulum. The diverticulum is gently irrigated with the irrigation solution. Once the diverticulum is cleared of debris, the needle in the biopsy portal is replaced with a spray tip delivery catheter. The spray tip delivery catheter is used to deliver a multi-component in situ forming composition to the diverticulum, as described in Example 54. Subsequent cross-linking of the composition partially or completely occludes the lumen or orifice of the diverticulum, thereby decreasing the probability of bleeding, infection, or inflammation.

From the foregoing, it is appreciated that, although specific embodiments of the invention have been described herein for purposes of illustration, various modifications may be made without deviating from the spirit and scope of the invention. Accordingly, the invention is not limited except as by the appended claims.

We claim:

1. A method of treating a diverticular disease, comprising introducing into a diverticulum in a host, a therapeutically effective amount of a fibrosing agent or a composition comprising a fibrosing agent, wherein the fibrosing agent induces a fibrotic response within the diverticulum, thereby treating diverticular disease in the host, and wherein the fibrosing agent is or comprises a silk.

2. The method of claim 1 wherein the diverticular disease is diverticulosis.

3. The method of claim 1 wherein the diverticular disease is diverticulitis.

4. The method of claim 1 wherein the fibrosing agent is or comprises silkworm silk.

5. The method of claim 1 wherein the fibrosing agent is or comprises spider silk.

6. The method of claim 1 wherein the fibrosing agent is or comprises recombinant silk.

7. The method of claim 1 wherein the fibrosing agent is or comprises raw silk.

8. The method of claim 1 wherein the fibrosing agent is or comprises hydrolyzed silk.

9. The method of claim 1 wherein the fibrosing agent is or comprises acid-treated silk.

10. The method of claim 1 wherein the fibrosing agent is or comprises acylated silk.

11. The method of claim 1 wherein the fibrosing agent is in the form of strands.

12. The method of claim 1 wherein the fibrosing agent is in the form of tufts.

13. The method of claim 1 wherein the fibrosing agent is in the form of a thread, or is in contact with a thread.

14. The method of claim 1 wherein the fibrosing agent is in the form of a particulate.

15. The method of claim 1 wherein the composition further comprises a growth factor.

16. The method of claim 1 wherein the composition further comprises a polymer.

17. The method of claim 1 wherein the composition further comprises a fibrinogen.

18. The method of claim 1 wherein the composition further comprises a thrombin.

19. The method of claim 1 wherein the composition further comprises an antifibrinolytic agent.

20. The method of claim 1 wherein the composition further comprises a second pharmaceutically active agent.

21. The method of claim 1 wherein the composition further comprises an anti-inflammatory agent.

22. The method of claim 1 wherein the composition further comprises an agent that inhibits infection.

23. The method of claim 1 wherein the composition further comprises an inflammatory cytokine.

24. The method of claim 1 wherein the composition further comprises an agent that stimulates cell proliferation.

25. The method of claim 1 wherein the composition further comprises a bulking agent.

26. The method of claim 1 further comprising irrigating the diverticulum with an irrigation solution prior to introducing the fibrosing agent.

* * * * *